United States Patent
Thorpe et al.

(10) Patent No.: US 12,234,229 B2
(45) Date of Patent: Feb. 25, 2025

(54) SPHINGOSINE KINASE INHIBITOR AMIDOXIME PRODRUGS

(71) Applicants: University of Virginia Patent Foundation, Charlottesville, VA (US); Virginia Tech Intellectual Properties, Inc., Blacksburg, VA (US)

(72) Inventors: Steven Brandon Thorpe, Palmyra, VA (US); Webster L. Santos, Blacksburg, VA (US); Kevin R. Lynch, Charlottesville, VA (US)

(73) Assignees: University of Virginia Patent Foundation, Charlottesville, VA (US); Virginia Tech Intellectual Properties, Inc., Blacksburg, VA (US)

( * ) Notice: Subject to any disclaimer, the term of this patent is extended or adjusted under 35 U.S.C. 154(b) by 826 days.

(21) Appl. No.: 17/305,773

(22) Filed: Jul. 14, 2021

(65) Prior Publication Data
US 2023/0050649 A1    Feb. 16, 2023

Related U.S. Application Data

(62) Division of application No. 16/089,939, filed as application No. PCT/US2017/024852 on Mar. 29, 2017, now Pat. No. 11,180,489.

(Continued)

(51) Int. Cl.
C07D 413/14    (2006.01)
C07D 413/04    (2006.01)

(52) U.S. Cl.
CPC ......... C07D 413/14 (2013.01); C07D 413/04 (2013.01)

(58) Field of Classification Search
CPC .......................... C07D 413/14; C07D 413/04
See application file for complete search history.

(56) References Cited

U.S. PATENT DOCUMENTS

| | | | |
|---|---|---|---|
| 9,688,668 B2 | 6/2017 | Santos et al. | |
| 11,180,489 B2 * | 11/2021 | Thorpe | ........... A61P 35/00 |
| 2020/0308159 A1 | 10/2020 | Thorpe et al. | |

FOREIGN PATENT DOCUMENTS

| | | | |
|---|---|---|---|
| WO | WO-2011020116 A1 | 2/2011 | |
| WO | WO-2013119946 A1 * | 8/2013 | ........... A61P 35/00 |
| WO | WO-2017172989 A1 | 10/2017 | |

OTHER PUBLICATIONS

"U.S. Appl. No. 16/089,939, Final Office Action mailed Mar. 24, 2021", 10 pgs.

(Continued)

*Primary Examiner* — Clinton A Brooks
*Assistant Examiner* — Izabela Schmidt
(74) *Attorney, Agent, or Firm* — Schwegman Lundberg & Woessner, P.A.

(57) ABSTRACT

Sphingosine kinases are enzymes that catalyze the biosynthesis of sphingosine-1-phosphate. The invention provides prodrugs of compounds that are effective for inhibition of sphingosine kinase type 1, sphingosine kinase type 2, or both, according to formula (I) as described herein. Formula I compounds are useful in the treatment of a range of diseases wherein increasing the level of sphingosine-1-phosphate in blood is medically indicated. The invention also provides pharmaceutical compositions of Formula I compounds.

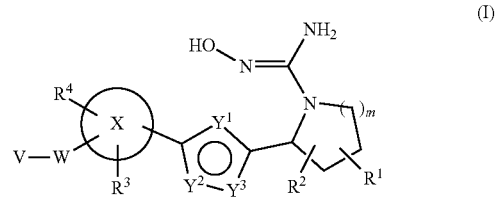

14 Claims, 2 Drawing Sheets

Related U.S. Application Data

(60) Provisional application No. 62/315,193, filed on Mar. 30, 2016.

(56) References Cited

OTHER PUBLICATIONS

"U.S. Appl. No. 16/089,939, Non Final Office Action mailed Feb. 4, 2021", 10 pgs.
"U.S. Appl. No. 16/089,939, Notice of Allowance mailed Apr. 21, 2021", 11 pgs.
"U.S. Appl. No. 16/089,939, Response filed Jan. 19, 2021 to Restriction Requirement mailed Nov. 17, 2020", 27 pgs.
"U.S. Appl. No. 16/089,939, Response filed Mar. 10, 2021 to Non Final Office Action mailed Feb. 4, 2021", 29 pgs.
"U.S. Appl. No. 16/089,939, Response filed Apr. 6, 2021 to Final Office Action mailed Mar. 24, 2021", 22 pgs.
"U.S. Appl. No. 16/089,939, Restriction Requirement mailed Nov. 17, 2020", 14 pgs.
"CID123168893", US National Library of Medicine; Database PubCHem, XP002770066, Database accession No. CID123168893, (Jan. 24, 2017).
"CID123747906", US National Library of Medicine; Database PubCHem, XP002770065, Database accession No. CID123747906, (Jan. 25, 2017).
"European Application Serial No. 17717977.7, Communication Pursuant to Article 94(3) EPC mailed Aug. 5, 2020", 6 pgs.
"European Application Serial No. 17717977.7, Communication Pursuant to Article 94(3) EPC mailed Sep. 17, 2019", 6 pgs.
"European Application Serial No. 17717977.7, Response filed 0416-20 to Communication Pursuant to Article 94(3) EPC mailed Sep. 17, 2019", 79 pgs.
"European Application Serial No. 17717977.7, Response Filed Dec. 14, 20 to Communication Pursuant to Article 94(3) EPC mailed Aug. 5, 2020", 983 pgs.
"European Application Serial No. 17717977.7, Response filed May 20, 2019 to Communication pursuant to Rules 161(1) and 162 EPC mailed Nov. 8, 2019", 73 pgs.
"International Application Serial No. PCT/US2017/024852, International Search Report mailed May 23, 2017", 6 pgs.
"International Application Serial No. PCT/US2017/024852, Written Opinion mailed May 23, 2017", 7 pgs.
"SCHEMBL15175917", US National Library of Medicine; Database PubChem, XP002770064, Database accession No. CID89741107, (Feb. 13, 2015).
"SCHEMBL15186364", US National Library of Medicine; Database PubChem, XP002770063, Database accession No. CID89750082, (Feb. 13, 2015).
Kharel, Yugesh, et al., "Sphingosine kinase type 2 inhibition elevates circulating sphingosine 1-phosphate", Biochemical Journal, 447, (Oct. 1, 2012), 2668-157.
Molly, D Congdon, et al., "Structure-Activity Relationship Studies and Molecular Modeling of Naphthalene-Based Sphingosine Kinase 2 Inhibitors", ACS Medicinal Chemistry Letters, vol. 7, No. 3, XP055285993, (Mar. 10, 2016), 229-234.
U.S. Appl. No. 16/089,939, U.S. Pat. No. 11,180,489, filed Sep. 28, 2018, Sphingosine Kinase Inhibitor Amidoxime Prodrugs.

\* cited by examiner

SPHINGOSINE KINASE INHIBITOR AMIDOXIME PRODRUGS

PRIORITY APPLICATION

This application is a divisional of U.S. patent application Ser. No. 16/089,939 (now U.S. Pat. No. 11,180,489) filed on Sep. 28, 2018, which is a U.S. national stage of International Application No. PCT/US2017/024852, filed on Mar. 29, 2017, and published as WO 2017/172989, which claims priority to U.S. Provisional Application Ser. No. 62/315,193, filed Mar. 30, 2016, the disclosure of which applications are incorporated herein in their entireties by reference.

STATEMENT OF GOVERNMENT SUPPORT

This invention was made with government support under GM106495 and GM104366 awarded by the National Institutes of Health. The government has certain rights in the invention.

BACKGROUND

Sphingosine 1-phosphate (S1P) is a lysophospholipid mediator that evokes a variety of cellular processes, including those that result in cell proliferation, cell morphology, tumor-cell invasion, endothelial cell chemotaxis, and angiogenesis. S1P mediates its effects on cellular behavior through the S1P receptors, a family of five cell surface G protein coupled receptors called S1P1, S1P2, S1P3, S1P4, and S1P5, which were formerly known as EDG-1, -3, -5, -6, and -8, respectively. In addition to the S1P receptors, S1P also activates various less well-defined intracellular targets. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and often, mitogenesis. The recent development of agonists targeting S1P receptors has provided insight regarding the role of this signaling system in physiologic homeostasis.

S1P is synthesized by the action of two enzymes, sphingosine kinase types 1 and 2 (SphK1, SphK2). These enzymes catalyze the transfer of a phosphate residue from adenosine triphosphate (ATP) to D-erythro sphingosine. SphK1 and SphK2 also catalyze the phosphorylation of reduced sphingosine (D-erythro sphinganine) and hydroxylated sphinganine (D-ribo phytosphingosine) to yield sphinganine 1-phosphate (dihydroS1P) and phytosphingosine 1-phosphate.

One example of a non-S1P agonist is the phosphorylated form of the immunomodulator, fingolimod (2-amino-2-[2-(4-octylphenyl) ethyl] propane 1,3-diol), which is an agonist of four of the five S1P receptors. Enhancing S1P tone at S1P1 influences lymphocyte trafficking by decreasing lymphocyte egress from secondary lymphoid tissues. Consistent with the role of S1P1 agonists in preventing lymphocyte egress, antagonists of some S1P1 receptors cause leakage of the lung capillary endothelium, which suggests that S1P may be involved in maintaining the integrity of the endothelial barrier in some tissue beds.

Indeed, infection and tissue injury induce a cascade of biochemical changes that trigger reactions of the immune system, collectively referred to as an inflammatory response. The evolution of this response is based, at least in part, on enhancing vascular permeability and activation of the vascular endothelium, which allows white blood cells to efficiently circulate and migrate to the damaged site, thereby increasing their chances to bind to and destroy any antigens. The vascular endothelium is then thought to be activated or inflamed. Generally, inflammation is a welcomed immune response to a variety of unexpected stimuli, and as such it exhibits rapid onset and short duration (acute inflammation). Its persistent or uncontrolled activity (chronic inflammation) has, however, detrimental effects to the body and results in the pathogenesis of several immune diseases, such as: septic shock, rheumatoid arthritis, inflammatory bowel diseases, acute lung injury, pulmonary fibrosis, and congestive heart failure, for example. Furthermore, chronic inflammation resulting from persistent tissue injury can lead to organ fibrosis, and eventually, organ failure, as is the case in idiopathic pulmonary fibrosis, end-stage renal failure, and liver cirrhosis, for example.

During vascular injury and in inflammation thrombin is also released from the blood, and it activates thrombin receptors (PA s) expressed on endothelial surface. Thrombin and thrombin receptors regulate various endothelial functions and play a role in the response of endothelial cells to vascular injury, including inducing cytoskeletal changes resulting in cell rounding. Contraction of endothelial cells leads to increased permeability and compromises in the endothelial barrier. In contrast to the edemagenic effects of thrombin, S1P may enhance endothelial cell barrier properties.

S1P has also been shown to have a direct role in modulating several important effects on cells that mediate immune functions. Platelets, monocytes and mast cells secrete S1P upon activation, promoting inflammatory cascades at the site of tissue damage. Activation of SphK is required for the signaling responses since the ability of TNF-α to induce adhesion molecule expression via activation of Nuclear Factor Kappa B (NFκB) is mimicked by S1P and is blocked by DMS. Similarly, S1P mimics the ability of TNF-α to induce the expression of cyclooxygenase-2 (COX-2) and the synthesis of prostaglandin $E_2$ ($PGE_2$), and knock-down of SphK by RNA interference blocks these responses to TNF-α. S1P is also a mediator of calcium influx during neutrophil activation by TNF-α and other stimuli, leading to the production of superoxide and other toxic radicals. Therefore, reducing the production of S1P within immune cells and their target tissues may be an effective method to treat disorders arising from oxidative stress and abnormal inflammation. Examples of such disorders include inflammatory bowel disease, arthritis, atherosclerosis, asthma, allergy, inflammatory kidney disease, circulatory shock, ischemia-reperfusion injury, post-surgical organ failure, organ transplantation, multiple sclerosis, chronic obstructive pulmonary disease, skin inflammation, periodontal disease, psoriasis and T cell-mediated diseases of immunity.

S1P also has several effects on cells that mediate immune functions. For example, platelets, monocytes, and mast cells secrete S1P upon activation, promoting inflammatory cascades. It is believed that SphK activation is required for the related signaling responses. In addition, deregulation of apoptosis in phagocytes can be an important component of chronic inflammatory diseases. S1P has been found to protect neutrophils and macrophages in response to inflammatory stresses, such as TNF-α. Additional information regarding the role of S1P and SphK in various specific inflammatory and/or autoimmune conditions can be found in U.S. Patent Application Publication No. 2008/0167352, the disclosure of which is incorporated herein. Accordingly, inhibition of the enzymatic activity of SphK (which can reduce levels of S1P) can prevent the hyperproliferation of immune cells that are important for inflammation.

S1P also has effects on vascular contractility, vascular tone, and blood pressure control. For example, the non-S1P agonist, fingolimod produces modest hypertension in patients (2-3 mmHg in 1-yr trial). In addition, it has been found that exogenous S1P elicits a marked $Ca^{2+}$— and Rho kinase-dependent pulmonary vasoconstriction in hypertensive rat lungs. Furthermore, it has been found that S1P selectively and potently constricts isolated cerebral arteries. Therefore, reducing S1P levels may be an effective method to treat disease or disorders arising from hypertension. Examples of such diseases or disorders include chronic kidney disease, pulmonary hypertension, pulmonary arterial hypertension, atherosclerosis, and stroke.

Given S1P's involvement in mediating disease pathologies associated with changes in cellular proliferation, morphology, migration, and chemotaxis, sphingosine kinases are good targets for therapeutic applications such as modulating fibrosis, tumor growth inhibition, angiogenesis, endothelial cell chemotaxis, and inflammatory and autoimmune diseases and disorders. For example, SphK1 and SphK2 have roles in affecting cell survival and proliferation. These kinases are also responsible for the equilibrium between the anti-apoptotic SU' and its pro-apoptotic metabolic precursor sphingosine and its precursor, ceramide. Thus, SphK1 and SphK2 are important drug targets.

To date, only a small number of compounds including DL-threo-dihydrosphingosine, N,N-dimethylsphingosine, and short-chain DL-erythro-sphingosine analogues, have been shown to inhibit sphingosine kinases. However, with a typical $K_I$ value in excess of 10 μM, these compounds have relatively low potency. These compounds are also neither generally selective for either SphK1 or SphK2, nor are they metabolically stable in vivo. Accordingly, these compounds are not ideally suited for addressing questions concerning SphK mediated disease states.

Traditional methods of inhibiting kinases, including sphingosine kinases, have centered on targeting the ATP binding site of the kinase, a strategy that has enjoyed moderate success. However, such methods suffer from lack of selectivity across a wide array of kinases. Additionally, the amino acid sequence of the ATP binding domain of SphK1 and SphK2 is conserved across a number of diacylglycerol (DAG) kinase family members, rendering the traditional strategy problematic because it does not discriminate among kinases. By contrast, the inhibitors in the present invention are competitive with sphingosine, not with ATP, and thus are not expected to inhibit other protein and diacylglycerol kinases.

Currently, there is a need for novel, potent, and selective agents that inhibit the sphingosine substrate-binding domain of the sphingosine kinases (e.g., human SphK1 or SphK2, or both) that have enhanced potency, selectivity, and bioavailability. In addition, there is a need in the art for identification, as well as the synthesis and use, of such compounds. The present invention satisfies these needs.

SUMMARY

One embodiment of the invention is a compound of formula (I):

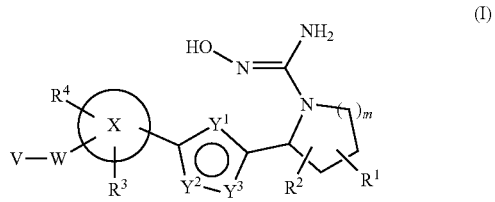

wherein
X is phenyl, indolyl, or naphthyl;
$R^1$ and $R^2$ are independently selected from the group consisting of H, OH, —($C_1$-$C_6$)alkyl-OH, halo, $NH_2$, NOH, NHOH, and CN;
or $R^1$ and $R^2$, if bound to adjacent carbon atoms, in combination with the existing carbon-carbon bond represent a double bond between the adjacent carbon atoms;
$R^3$ and $R^4$ are independently selected from the group consisting of H, ($C_1$-$C_6$)alkyl, ($C_3$-$C_8$)cycloalkyl, ($C_1$-$C_6$)haloalkyl, CN, and halo;
m=0 or 1;
W is $CH_2$, O or, NH;
V is selected from the group consisting of H, ($C_1$-$C_{10}$) alkyl, ($C_2$-$C_{12}$)alkenyl, —($C_1$-$C_{10}$)alkyl-($C_6$-$C_{10}$) aryl, —($C_2$-$C_{12}$)alkenyl-($C_6$-$C_{10}$)aryl, —($C_1$-$C_{10}$)alkyl-($C_6$-$C_{10}$)aryl-($C_1$-$C_{10}$)alkyl, —($C_1$-$C_{10}$)alkyl-($C_3$-$C_8$)cycloalkyl, —($C_1$-$C_{10}$)alkyl-heterocyclyl containing from 1 to 3 ring heteroatoms selected from N, O, and S;
wherein any aryl is optionally fused to ($C_6$-$C_{10}$)aryl, ($C_3$-$C_5$)cycloalkyl, or heterocyclyl containing from 1 to 3 ring heteroatoms selected from N, O, and S
wherein any alkyl, alkenyl, cycloalkyl, heterocyclyl, or aryl is optionally substituted by 1-4 substituents independently selected from the group consisting of F, Cl, Br, ($C_1$-$C_6$)alkyl, —O—($C_1$-$C_6$)alkyl, ($C_2$-$C_6$)alkenyl, ($C_1$-$C_6$)haloalkyl, ($C_6$-$C_{10}$)aryl, and CN;
$Y^1$, $Y^2$, and $Y^3$ are independently selected from the group consisting of C, N, NH, O, and S;
or a pharmaceutically acceptable salt thereof.

The invention also provides, in various embodiments, a subset of formula (I) compounds according to formula (II)

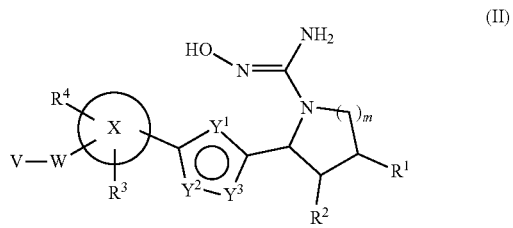

wherein:
$R^1$ and $R^2$ are H, or when m=1, one of $R^1$ and $R^2$ can be OH;

$R^3$ and $R^4$ are each independently H, $(C_1-C_4)$alkyl, cyclopropyl, $(C_1-C_2)$fluoroalkyl, cyano, or halo;

m=0 or 1;

each of $Y^1$, $Y^2$, and $Y^3$ is independently selected from the group consisting of C, N, NH, O, and S;

X is a phenyl, naphthyl, or indolyl;

W is O or $CH_2$;

V is $(C_5-C_{10})$alkyl;

or a pharmaceutically acceptable salt thereof.

In some Formula II compounds, $Y^1$ and $Y^2$ are N and $Y^3$ is O, X is phenyl, $R^1$ and $R^2$ are H, $R^3$ is trifluoromethyl, $R^4$ is H, and V is $(C_8-C_9)$alkyl.

In various embodiments, the invention provides a pharmaceutical composition comprising a compound of formula (I) and a pharmaceutically acceptable excipient.

In various embodiments, the invention provides a method of inhibiting a sphingosine kinase, comprising contacting the sphingosine kinase with an effective amount or concentration of a compound of formula (I) or an effective amount of a pharmaceutical composition comprising a compound of formula (I) in any of its embodiments. The sphingosine kinase can be sphingosine kinase type 1 or sphingosine kinase type 2. The compound of formula (I) can be a selective inhibitor of one of sphingosine kinases type 1 or type 2 relative to the other of sphingosine kinases type 1 or type 2.

In various embodiments, as described in greater detail below, the invention provides methods of treatment of various diseases in patients afflicted therewith wherein inhibition of a sphingosine kinase, for instance sphingosine kinase type 1 or type 2, is medically indicated, or wherein increasing blood plasma levels of sphingosine-1-phosphate is medically indicated, or both.

DETAILED DESCRIPTION

Figure 1A:
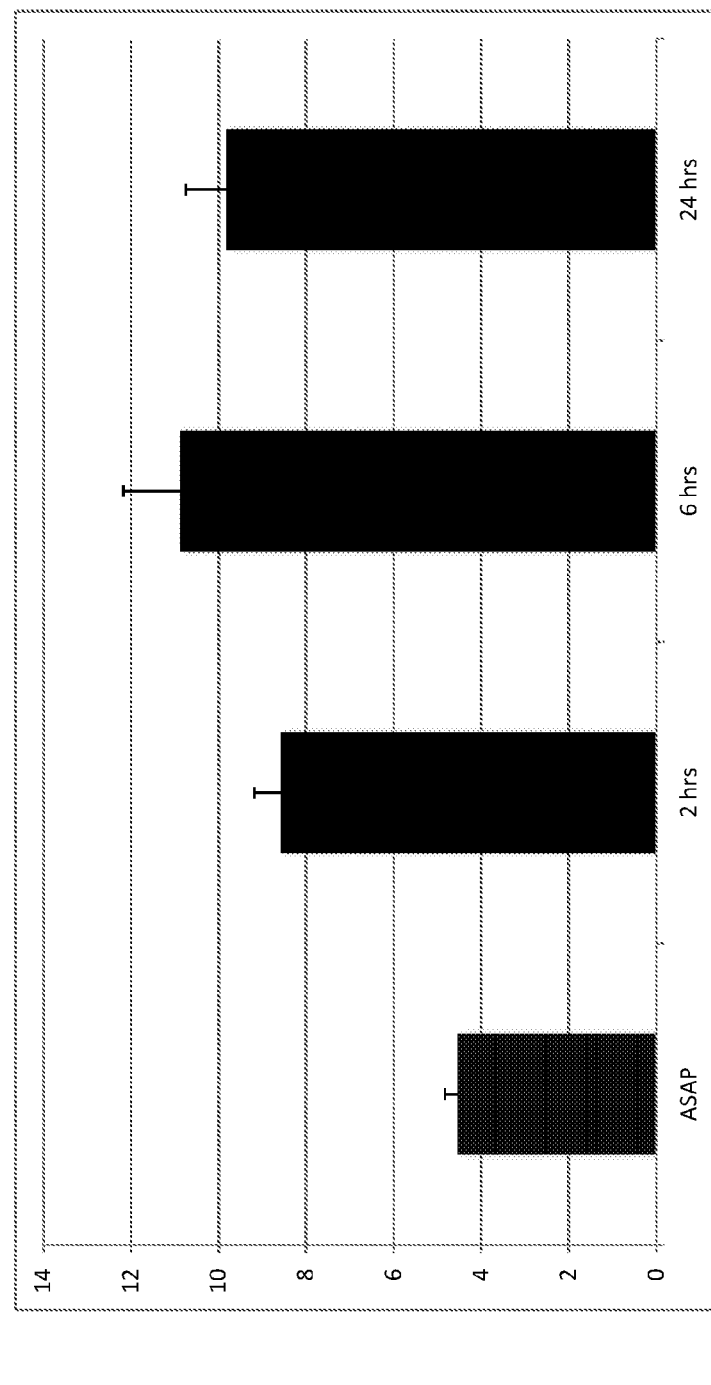
FIGS. 1A-1B. Four C57Bl/6 mice were dosed by oral gavage with 20 mg/kg of Compound 6. At the indicated times, blood was drawn, whole prepared for analysis, and the amount sphingosine 1-phosphate (S1P) was quantified by LC-MS-MS (FIG. 1A). The rise in S1P is indicative of inhibition of sphingosine kinase type 2 (SphK2). The amounts of Compound 6 (checkered) and its reduced form (i.e. Compound 6A (solid black)) was detected by LC-MS-MS in the same blood samples (FIG. 1B).

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The expression "effective amount", when used to describe therapy to an individual suffering from a disorder, refers to the quantity or concentration of a compound of the invention that is effective to inhibit or otherwise act on a sphingosine kinase in the individual's tissues wherein a sphingosine kinase, such as sphingosine kinase type 1 or sphingosine kinase type 2, is involved in the disorder, wherein such inhibition or other action occurs to an extent sufficient to produce a beneficial therapeutic effect.

The expression "effective amount", when used to describe induction of neuromuscular blockade or reversal of that blockade refers to the amount of a compound of the invention that is effective to bring about the desired effects in an individual being treated, which is adjusted based on the knowledge and discretion of the attending physician and takes into account significant medical factors.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents, or provides prophylaxis for, the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

The following abbreviations are used: sphingosine kinase ("SphK"); sphingosine kinase type 1 ("SphK1"); sphingosine kinase type 2 ("SphK2"); sphingosine ("Sph"); sphingosine 1-phosphate ("S1P"); sphinganine ("dhSph" or "H2Sph"); sphinganine 1-phosphate ("dhS1P" or "H2S1P").

The term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, is reduced.

The terms "cell," "cell line," and "cell culture" may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue is obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "detectable marker" or a "reporter molecule" is an atom or a molecule that permits the specific detection of a compound having the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

The term "disease" or "disorder" or "malcondition" are used interchangeably, and are used to refer to diseases or conditions wherein a sphingosine kinase, such as sphingosine kinase type 1 or sphingosine kinase type 2, plays a role in the biochemical mechanisms involved in the disease or malcondition or symptom(s) thereof such that a therapeutically beneficial effect can be achieved by acting on the sphingosine kinase, e.g. with an effective amount or concentration of a synthetic ligand of formula (I) of the invention. "Acting on" sphingosine kinase, or "modulating" sphingosine kinase, can include binding to sphingosine kinase and/or inhibiting the bioactivity of sphingosine kinase and/or allosterically regulating the bioactivity of sphingosine kinase in vivo. Thus, a "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "autoimmune disease" is a disease or disorder arising from and directed against an individual's own tissues. Examples of autoimmune diseases or disorders include, but are not limited to arthritis (rheumatoid arthritis, juvenile rheumatoid arthritis, osteoarthritis, psoriatic arthritis), Caplan's Syndrome, Felty's Syndrome, psoriasis, dermatitis, Sjorgren's Syndrome, Still's Disease, polymyositis/dermatomyositis, toxic epidermal necrolysis, systemic scleroderma and sclerosis, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (MBA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, anti-phospholipid antibody syndrome, allergic neuritis, Bechet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), pemphigoid bullous, pemphigus, autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-Barre' syndrome, large vessel vasculitis (including polymyalgia rheumatica and giant cell (Takayasu's) arteritis), medium vessel vasculitis (including Kawasaki's disease and polyarteritis nodosa), ankylosing spondylitis, Berger's disease (IgA nephropathy), rapidly progressive glomerulonephritis, primary biliary cirrhosis, Celiac sprue (gluten enteropathy), cryoglobulinemia, amyotrophic lateral sclerosis (ALS), coronary artery disease etc.

An "inflammatory disease" may be any autoimmune disease, as well as include, but not be limited to: ulcerative colitis, and Crohn's disease; cardiovascular diseases such as ischemic cardiac disease and heart failure; cerebrovascular diseases; kidney diseases, including glomerulonephritis, glomerular injury, nephrotic syndrome, interstitial nephritis, lupus nephritis, Goodpasture's disease, Wegener's granulomatosis, renal vasculitis, IgA nephropathy and idiopathic glomerular disease; diabetes; diabetes complications such as retinopathy, nephropathy, nerve disease, and coronary arterial disease; skin diseases, including allergic skin disease, psoriasis, atopic dermatitis, contact sensitivity and acne; obesity; nephritis; hepatitis; cancer; Alzheimer's disease; inflammatory diseases that are caused by inflammatory cytokines; skin diseases such as allergic skin diseases; chondrocalcinosis; gout; rheumatic fever and Reiter's Disease.

The term "Immune cell(s)" include, but are not limited to, lymphocytes, (including $CD4^+$ T cells, $CD8^+$ T cells, Natural Killer T cells, and B cells), mast cells, basophils, macrophaged, dendritic cells, monocytes, eosinophils, neutrophils, or any other cell type that functions within the immune system.

"Vascular permeability" refers to the capacity of small molecules (e.g., ions, water, nutrients), large molecules (e.g., proteins and nucleic acids) or even whole cells (lymphocytes on their way to the site of inflammation) to pass through a blood vessel wall. Diseases and disorders characterized by undesirable vascular permeability include, for example, edema associated with brain tumors, ascites associated with malignancies, Meigs' syndrome, lung inflammation, nephrotic syndrome, pericardial effusion and pleural effusion.

A "functional" molecule is a molecule in a form in which it exhibits a property by which it is characterized. By way of example, a functional enzyme is one that exhibits the characteristic catalytic activity by which the enzyme is characterized.

The term "inhibit" refers to the ability of a disclosed compound to reduce or impede a described function. Inhibition is by at least 10%, preferably by at least 25%, more preferably by at least 50%, even more preferably by at least 75%, and most preferably, the function is inhibited by at least 95%.

The term "selective" refers to the ability of the disclosed compounds to inhibit one of the sphingosine kinase 1 or sphingosine kinase 2 (SphK1 & SphK2) enzymes and not the other enzyme. Preferably, the selective compound will have a $K_I$ value for one enzyme that is less than, by at least an order of magnitude (e.g., a ten-fold difference), the $K_I$ value for the other enzyme or in inhibition of one of the SphK enzymes over the other enzyme.

By "chemically feasible" is meant a bonding arrangement or a compound where the generally understood rules of organic structure are not violated; for example a structure within a definition of a claim that would contain in certain situations, e.g., a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All single enantiomer, diastereomeric, and racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated as having an (R) absolute configuration, and if the descending rank of the other groups proceeds counterclockwise, the molecule is designated as having an (S) absolute configuration. In the example in the Scheme below, the Cahn-Ingold-Prelog ranking is A>B>C>D. The lowest ranking atom, D is oriented away from the viewer. The solid wedge indicates that the atom bonded thereby projects toward the viewer out of the plane of the paper, and a dashed wedge indicates that the atom bonded thereby projects away from the viewer out of the plan of the paper, i.e., the plane "of the paper" being defined by atoms A, C, and the chiral carbon atom for the (R) configuration shown below.

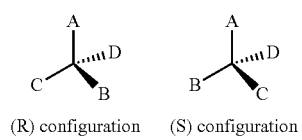

(R) configuration    (S) configuration

A carbon atom bearing the A-D atoms as shown above is known as a "chiral" carbon atom, and the position of such a carbon atom in a molecule is termed a "chiral center." Compounds of the invention may contain more than one chiral center, and the configuration at each chiral center is described in the same fashion.

There are various conventions for depicting chiral structures using solid and dashed wedges. For example, for the (R) configuration shown above, the following two depictions are equivalent:

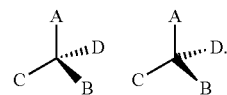

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" or "isolated enantiomer" means a compound which has been substantially purified from the corresponding optical isomer(s) of the same formula. Preferably, the isolated isomer is at least about 80%, more preferably at least 90% enantiomerically pure, even more preferably at least 98% enantiomerically pure, most preferably at least about 99% enantiomerically pure, by weight. By "enantiomeric purity" is meant the percent of the predominant enantiomer in an enantiomeric mixture of optical isomers of a compound. A pure single enantiomer has an enantiomeric purity of 100%.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Another well-known method of obtaining separate and substantially pure optical isomers is classic resolution, whereby a chiral racemic compound containing an ionized functional group, such as a protonated amine or carboxylate group, forms diastereomeric salts with an oppositely ionized chiral nonracemic additive. The resultant diastereomeric salt forms can then be separated by standard physical means, such as differential solubility, and then the chiral nonracemic additive may be either removed or exchanged with an alternate counter ion by standard chemical means, or alternatively the diastereomeric salt form may retained as a salt to be used as a therapeutic agent or as a precursor to a therapeutic agent.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

When a group is recited, wherein the group can be present in more than a single orientation within a structure resulting in more than single molecular structure, e.g., a carboxamide group C(=O)NR, it is understood that the group can be present in any possible orientation, e.g., X—C(=O)N(R)—Y or X—N(R)C(=O)—Y, unless the context clearly limits the orientation of the group within the molecular structure.

When a number of carbon atoms in a group, e.g., an alkyl, alkenyl, alkynyl, cycloalkyl, aryl, etc., is specified as a range, each individual integral number representing the number of carbon atoms is intended. For example, recitation of a ($C_1$-$C_4$)alkyl group indicates that the alkyl group can be any of methyl, ethyl, propyl, isopropyl, butyl, sec-butyl, isobutyl, or tert-butyl. It is understood that a specification of a number of carbon atoms must be an integer.

When a number of atoms in a ring is specified, e.g., a 3- to 9-membered cycloalkyl or heterocyclyl ring, the cycloalkyl or heterocyclyl ring can include any of 3, 4, 5, 6, 7, 8, or 9 atoms. A cycloalkyl ring is carbocyclic; a heterocyclyl ring can include atoms of any element in addition to carbon capable of forming two or more bonds, e.g., nitrogen, oxygen, sulfur, and the like. The number of atoms in a ring is understood to necessarily be an integer.

Alkyl groups include straight chain and branched carbon-based groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the substituent groups listed above, for example, amino, hydroxy, cyano, carboxy, nitro, thio, alkoxy, and halogen groups. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

Cycloalkyl groups are groups containing one or more carbocyclic ring including, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Cycloalkyl groups, unless otherwise specified, are unsubstituted.

Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can, if specified as such, be substituted with, for example, amino, hydroxy, cyano, carboxy, nitro, thio, alkoxy, and halogen groups. The term "cycloalkenyl" alone or in combination denotes a cyclic alkenyl group, i.e., a cycloalkyl including one or more carbon-carbon double bond.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. If specified as substituted, a carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, cyclohexenyl, cyclopentenyl, cyclohexadienyl, butadienyl, pentadienyl, and hexadienyl among others. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C($CH_3$), —C≡C($CH_2CH_3$), —$CH_2$C≡CH, —$CH_2$C≡C($CH_3$), and —$CH_2$C≡C($CH_2CH_3$) among others.

Aryl groups are cyclic aromatic hydrocarbons that do not contain heteroatoms in the ring. An aromatic compound, as is well-known in the art, is a multiply-unsaturated cyclic system that contains $4n+2$ π electrons where n is an integer. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups unless otherwise specified, are unsubstituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Heterocyclyl groups or the term "heterocyclyl" includes aromatic and non-aromatic ring compounds containing 3 or more ring members, of which one or more ring atom is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. Ring sizes can also be expressed by the total number of atoms in the ring, e.g., a 3- to 10-membered heterocyclyl group, counting both carbon and non-carbon ring atoms. A heterocyclyl ring can also include one or more double bonds. Heterocyclyl groups, unless otherwise specified, are unsubstituted. A heteroaryl ring is an embodiment of a heterocyclyl group. The term "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The term also includes polycyclic, e.g., bicyclo- and tricyclo-ring systems containing one or more heteroatom such as, but not limited to, quinuclidyl.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure, which is a multiply-unsaturated cyclic system that contains $4n+2$ π electrons, wherein n is an integer. A heteroaryl group designated as a $C_2$-heteroaryl can be a 5-ring (i.e., a 5-membered ring) with two carbon atoms and three heteroatoms, a 6-ring (i.e., a 6-membered ring) with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, thiadiazolyl, pyridinyl, pyrimidinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups, unless otherwise specified, are unsubstituted. Representative substituted heteroaryl groups can be substituted one or more times with independently selected groups such as those listed above.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by the same or differing halogen atoms, such as fluorine and/or chlorine atoms. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-di chloroethoxy, 1,3-dibromo-3,3-difluoropropoxy, perfluorobutoxy, and the like.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention. "Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. All commercially available chemicals were obtained from Aldrich, Alfa Aesare, Wako, Acros, Fisher, Fluka, Maybridge or the like and were used without further purification, except where noted. Dry solvents are obtained, for example, by passing these through activated alumina columns.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization, or chromatography, including flash column chromatography, or HPLC.

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy,* 19th Ed., 1995, or later versions thereof, incorporated by reference herein. The compositions can appear in conventional forms, for example capsules, tablets, aerosols, solutions, suspensions or topical applications.

It is within ordinary skill to evaluate any compound disclosed and claimed herein for effectiveness in inhibition of a sphingosine kinase, such as sphingosine kinase type 1 or sphingosine kinase type 2, and in the various cellular assays using the procedures described above or found in the scientific literature. Accordingly, the person of ordinary skill can prepare and evaluate any of the claimed compounds without undue experimentation.

Any compound found to be an effective inhibitor of sphingosine kinase can likewise be tested in animal models and in human clinical studies using the skill and experience of the investigator to guide the selection of dosages and treatment regimens.

In some embodiments, the invention provides a compound according to formula (I)

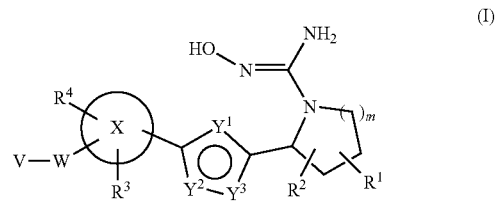

wherein
- X is phenyl, indolyl, or naphthyl;
- $R^1$ and $R^2$ are independently selected from the group consisting of H, OH, —$(C_1-C_6)$alkyl-OH, halo, $NH_2$, NOH, NHOH, and CN;
- or $R^1$ and $R^2$, if bound to adjacent carbon atoms, in combination with the existing carbon-carbon bond represent a double bond between the adjacent carbon atoms;
- $R^3$ and $R^4$ are independently selected from the group consisting of H, $(C_1-C_6)$alkyl, $(C_3-C_8)$cycloalkyl, $(C_1-C_6)$haloalkyl, CN, and halo;
- m=0 or 1;
- W is $CH_2$, O or, NH,
- V is selected from the group consisting of H, $(C_1-C_{10})$alkyl, $(C_2-C_{12})$alkenyl, —$(C_1-C_{10})$alkyl-$(C_6-C_{10})$aryl, —$(C_2-C_{12})$alkenyl-$(C_6-C_{10})$aryl, —$(C_1-C_{10})$alkyl-($C_6$-$C_{10}$)aryl-($C_1$-$C_{10}$)alkyl, —($C_1$-$C_{10}$)alkyl-($C_3$-$C_8$)cycloalkyl, —($C_1$-$C_{10}$)alkyl-heterocyclyl containing from 1 to 3 ring heteroatoms selected from N, O, and S;
wherein any aryl is optionally fused to ($C_6$-$C_{10}$)aryl, ($C_3$-$C_8$)cycloalkyl, or heterocyclyl containing from 1 to 3 ring heteroatoms selected from N, O, and S
wherein any alkyl, alkenyl, cycloalkyl, heterocyclyl, or aryl is optionally substituted by 1-4 substituents independently selected from the group consisting of F, Cl, Br, ($C_1$-$C_6$)alkyl, —O—($C_1$-$C_6$)alkyl, ($C_2$-$C_6$)alkenyl, ($C_1$-$C_6$)haloalkyl, ($C_6$-$C_{10}$)aryl, and CN;
$Y^1$, $Y^2$, and $Y^3$ are independently selected from the group consisting of C, N, NH, O, and S;
or a pharmaceutically acceptable salt thereof.

The invention also provides, in various embodiments, some formula (I) compounds that conform to formula (II):

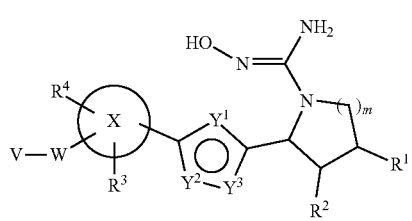

(II)

wherein:
$R^1$ and $R^2$ are H, or when m=1, one of $R^1$ and $R^2$ can be OH;
$R^3$ and $R^4$ are each independently H, ($C_1$-$C_4$)alkyl, cyclopropyl, ($C_1$-$C_2$)fluoroalkyl, cyano, or halo;
m=0 or 1;
each of $Y^1$, $Y^2$, and $Y^3$ is independently selected from the group consisting of C, N, NH, O, and S;
X is a phenyl, naphthyl, or indolyl;
W is O or $CH_2$;
V is ($C_5$-$C_{10}$)alkyl;
or a pharmaceutically acceptable salt thereof.

The invention provides in some formula I compounds wherein m is 1; and $Y^1$ is N; $Y^2$ is N and $Y^3$ is O; or $Y^2$ is O and $Y^3$ is N. Thus, the central ring in these embodiments is an oxadiazole.

In some embodiments, optionally in combination with any other embodiment, $R^1$ and $R^2$ are independently selected from the group consisting of H, OH, $CH_2OH$, F, and Cl. For instance, some formula (I) compounds provide for $R^1$ and $R^2$ as both hydrogen.

Optionally in combination with any other embodiment, some formula (I) compounds have X as phenyl and one of $R^3$ and $R^4$ as —$CF_3$. For example, in some formula (I) compounds $R^3$ is trifluoromethyl and $R^4$ is hydrogen.

Formula (II) compounds, a selection of Formula (I), also constitute various embodiments of the invention. In some Formula (II) compounds, according to some embodiments, the ring comprising $Y^1$, $Y^2$, and $Y^3$ is an oxadiazole ring. In other embodiments, the ring comprising $Y^1$, $Y^2$, and $Y^3$ is a thiadiazole ring.

In accordance with another embodiment, the invention provides Formula (II) compounds in which $R^1$ and $R^2$ are both hydrogen. In others, X is phenyl. Exemplary compounds satisfying these structural requirements are those in which m is 1 and $R^2$ is OH. In other embodiments, X is naphthyl or indolyl.

Formula I compounds are N-hydroxylated derivatives of, and in some embodiments they also are prodrugs of, SPHK1 and SPHK2 inhibitors listed below in Table 1. The compounds as shown in Table 1 are shown in the form of the salt as which they were isolated, but a compound can also be the free base form of the structure shown in Table 1, or can be a salt of that free base form other than the specific salt shown.

Table 1 below provides data with respect to the inhibitory bioactivity of the indicated exemplary compound versus human sphingosine kinase type 1 (hSPHK1) and human sphingosine kinase type 2 (hSPHK2), wherein A, B and C indicate range estimates of $K_I$ values at recombinant human SPHK1 and SPHK2; A<1 micromolar, B 1-10 micromolar, and C>10 micromolar.

TABLE 1

Exemplary Compounds and Bioactivity

| Cpd # | Structure | activity hSPHK1 | activity hSPHK2 |
|---|---|---|---|
| 1B | 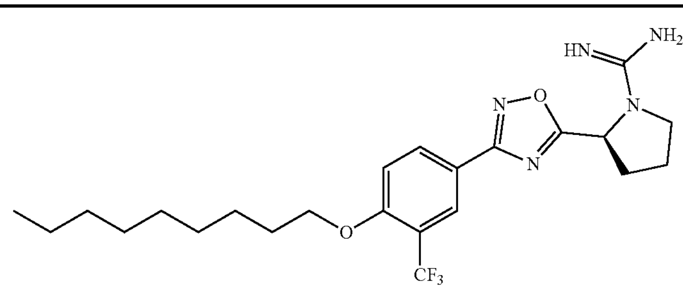 | C | A |

TABLE 1-continued
Exemplary Compounds and Bioactivity
| Cpd # | Structure | activity hSPHK1 | activity hSPHK2 |
|---|---|---|---|
| 2B | 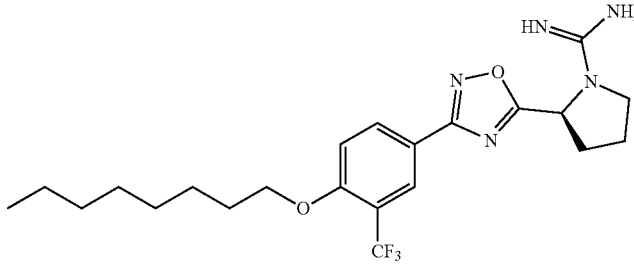 | C | A |
| 3B | 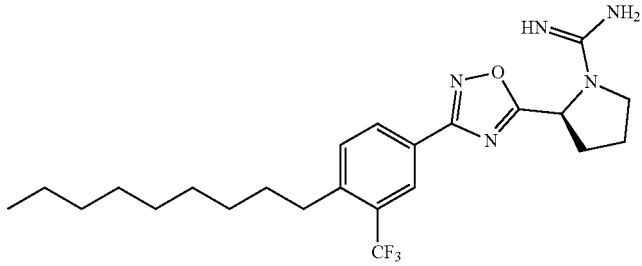 [SMILES: CCCCCCCCCc1ccc(-c2noc([C@@H]3CCCN3C(=N)N)n2)cc1C(F)(F)F] | C | A |
| 4B | 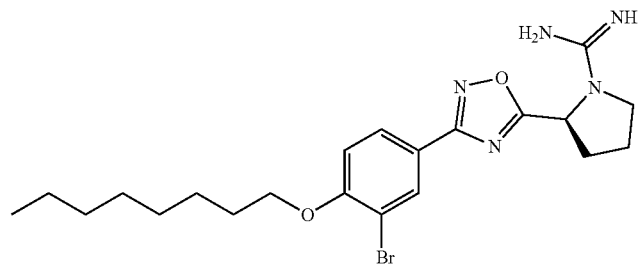 [SMILES: CCCCCCCCOc1ccc(-c2noc([C@@H]3CCCN3C(=N)N)n2)cc1Br] | C | A |
| 5B | 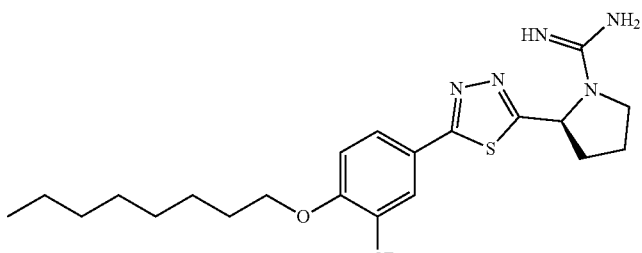 | C | A |
| 6B | 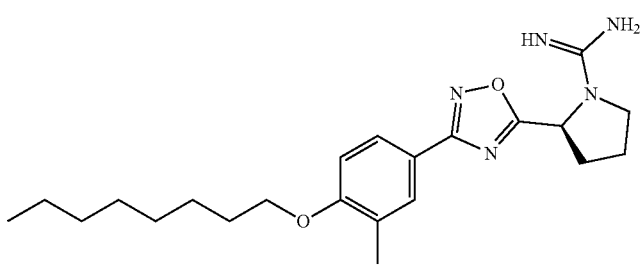 [SMILES: CCCCCCCCOc1ccc(-c2noc([C@@H]3CCCN3C(=N)N)n2)cc1C] | C | A |

TABLE 1-continued
Exemplary Compounds and Bioactivity
| Cpd # | Structure | activity hSPHK1 | activity hSPHK2 |
|---|---|---|---|
| 7B | 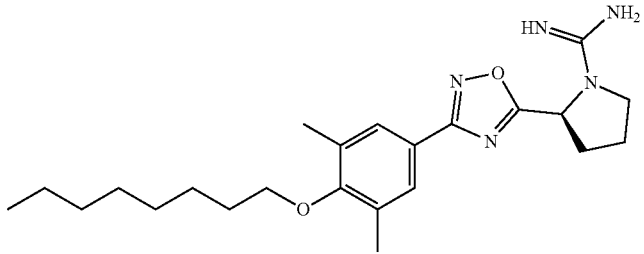 [SMILES: CCCCCCCCOc1c(C)cc(-c2noc([C@@H]3CCCN3C(=N)N)n2)cc1C] | C | A |
| 8B | 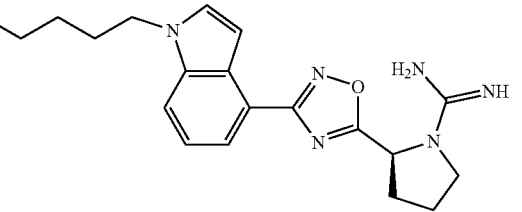 | C | A |
| 9B | 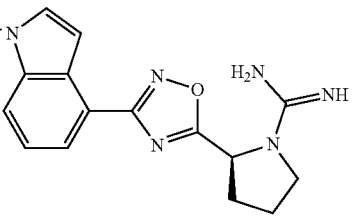 | C | A |
| 10B | 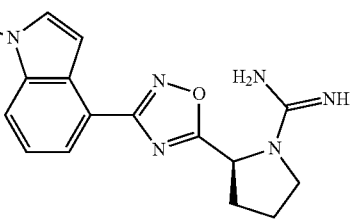 | C | A |
| 11B | 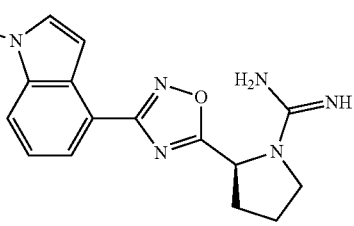 | C | A |
| 12B | 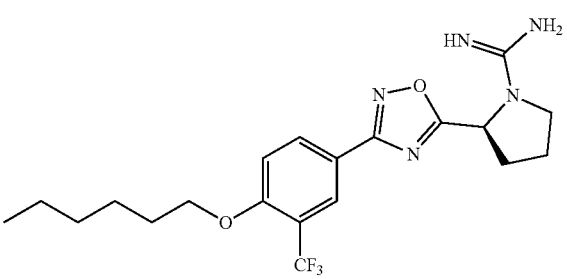 [SMILES: CCCCCCOc1ccc(-c2noc([C@@H]3CCCN3C(=N)N)n2)cc1C(F)(F)F] | B | A |

TABLE 1-continued
Exemplary Compounds and Bioactivity
| Cpd # | Structure | activity hSPHK1 | activity hSPHK2 |
|---|---|---|---|
| 13B | 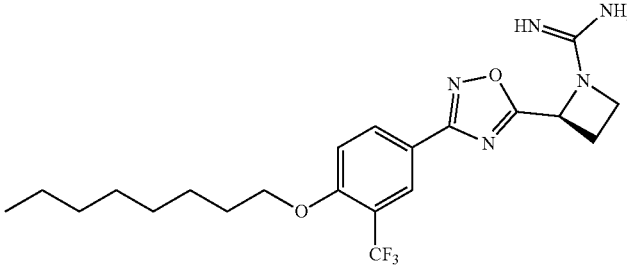 | B | A |
| 14B | 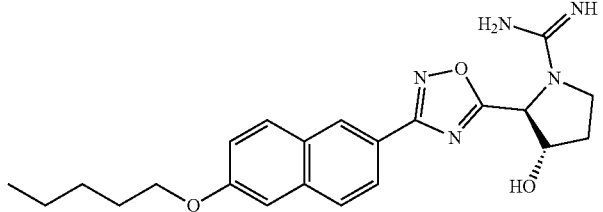 [SMILES: CCCCCOc1ccc2cc(-c3noc([C@@H]4[C@@H](O)CCN4C(=N)N)n3)ccc2c1] | A | A |
| 1A | 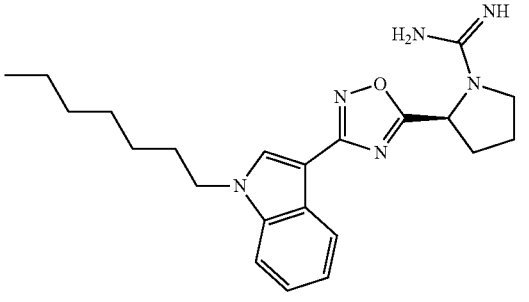 [SMILES: CCCCCCCn1cc(-c2noc([C@@H]3CCCN3C(=N)N)n2)c2ccccc21] | C | C |
| 2A | 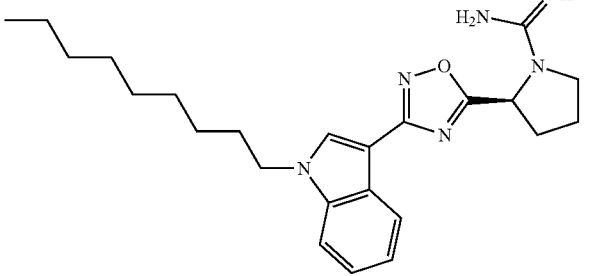 | C | C |
| 3A | 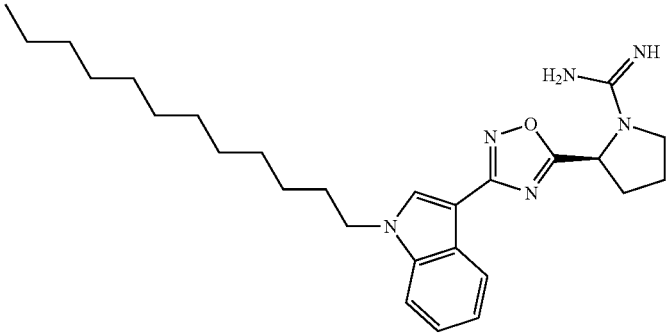 [SMILES: CCCCCCCCCCCCn1cc(-c2noc([C@@H]3CCCN3C(=N)N)n2)c2ccccc21] | B | A |

TABLE 1-continued

Exemplary Compounds and Bioactivity

| Cpd # | Structure | activity hSPHK1 | activity hSPHK2 |
|---|---|---|---|
| 4A | 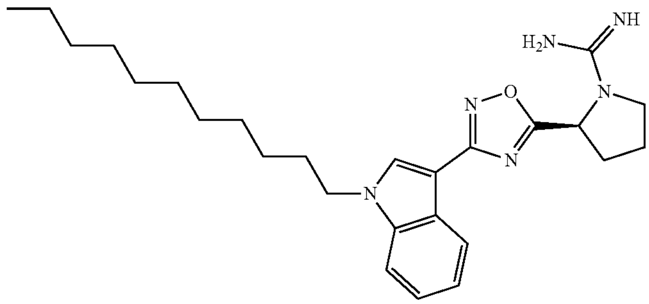 [SMILES: CCCCCCCCCCCn1cc(-c2noc([C@@H]3CCCN3C(=N)N)n2)c2ccccc21] | C | B |
| 5A | 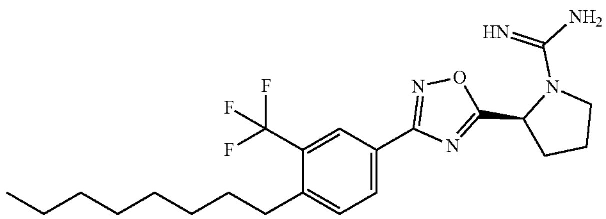 [SMILES: CCCCCCCCc1ccc(-c2noc([C@@H]3CCCN3C(=N)N)n2)cc1C(F)(F)F] | C | A |
| 6A | 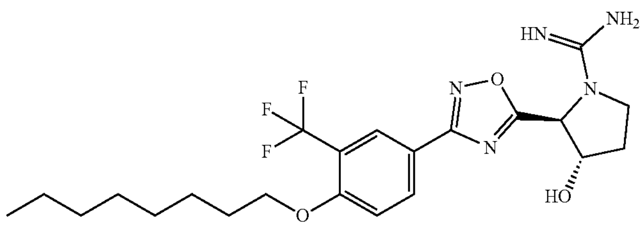 [SMILES: CCCCCCCCOc1ccc(-c2noc([C@@H]3[C@@H](O)CCN3C(=N)N)n2)cc1C(F)(F)F] | A | A |
| 7A | 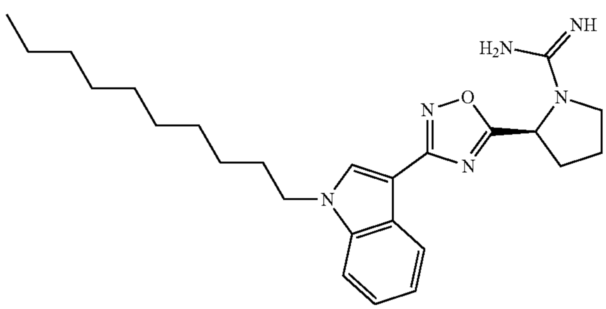 [SMILES: CCCCCCCCCCn1cc(-c2noc([C@@H]3CCCN3C(=N)N)n2)c2ccccc21] | B | A |
| 8A | 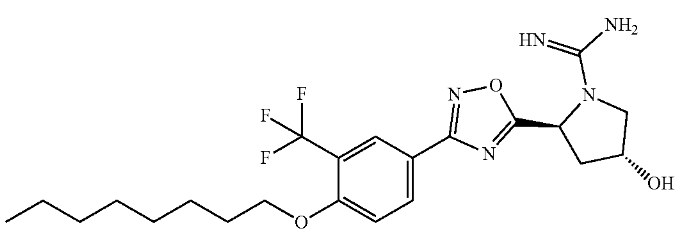 [SMILES: CCCCCCCCOc1ccc(-c2noc([C@@H]3C[C@@H](O)CN3C(=N)N)n2)cc1C(F)(F)F] | C | A |
| 9A | 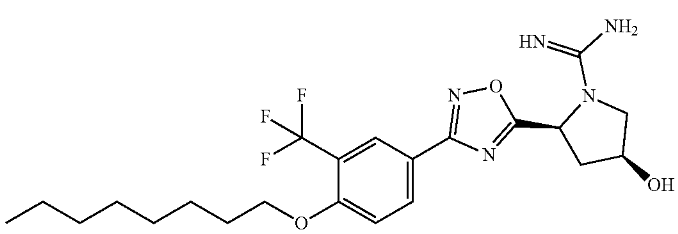 [SMILES: CCCCCCCCOc1ccc(-c2noc([C@@H]3C[C@H](O)CN3C(=N)N)n2)cc1C(F)(F)F] | C | C |

TABLE 1-continued
Exemplary Compounds and Bioactivity
| Cpd # | Structure | activity hSPHK1 | activity hSPHK2 |
|---|---|---|---|
| 10A | 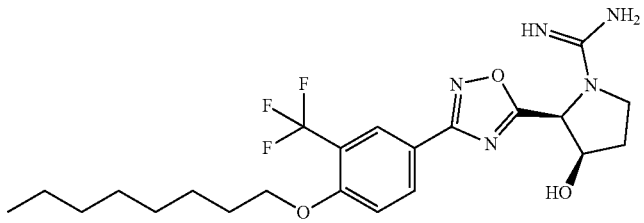 [SMILES: CCCCCCCCOc1ccc(-c2noc([C@@H]3[C@H](O)CCN3C(=N)N)n2)cc1C(F)(F)F] | C | C |
| 11A | 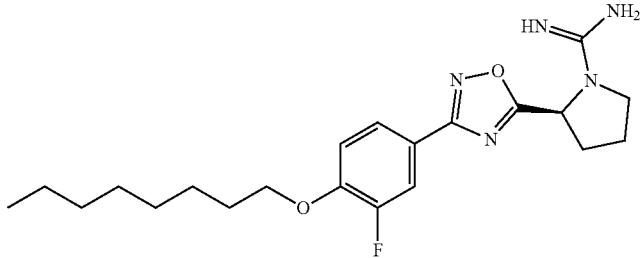 [SMILES: CCCCCCCCOc1ccc(-c2noc([C@@H]3CCCN3C(=N)N)n2)cc1F] | C | C |
| 12A | 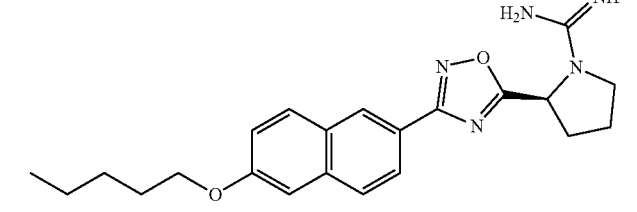 | C | C |
| 13A | 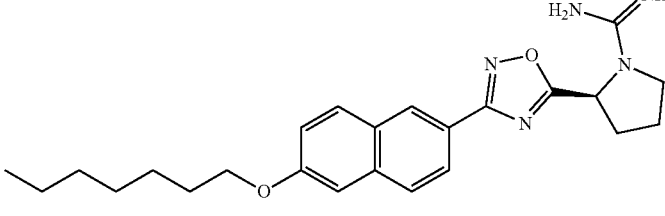 | C | B |
| 14A | 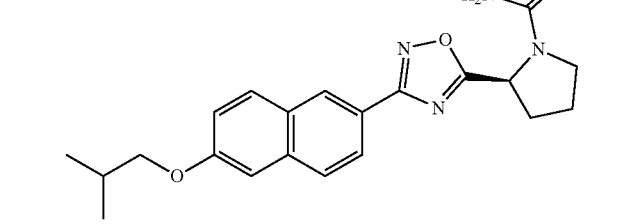 | C | C |
| 15A | 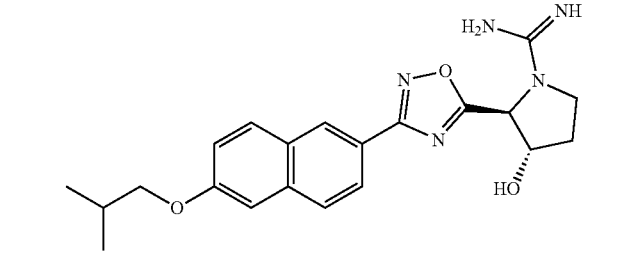 [SMILES: CC(C)COc1ccc2cc(-c3noc([C@@H]4[C@@H](O)CCN4C(=N)N)n3)ccc2c1] | B | C |

TABLE 1-continued

Exemplary Compounds and Bioactivity

| Cpd # | Structure | activity hSPHK1 | activity hSPHK2 |
|---|---|---|---|
| 16A | 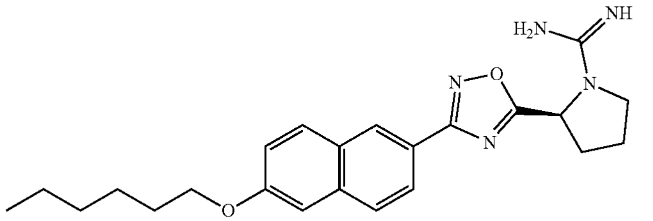 [SMILES: CCCCCCOc1ccc2cc(-c3noc([C@@H]4CCCN4C(=N)N)n3)ccc2c1] | C | C |
| 17A | 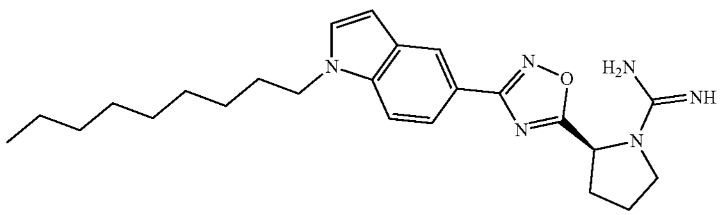 [SMILES: CCCCCCCCCn1ccc2cc(-c3noc([C@@H]4CCCN4C(=N)N)n3)ccc21] | C | A |
| 18A | 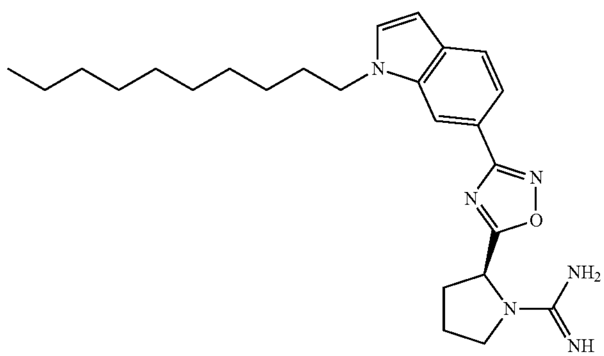 [SMILES: CCCCCCCCCCn1ccc2ccc(-c3noc([C@@H]4CCCN4C(=N)N)n3)cc21] | C | B |
| 19A | 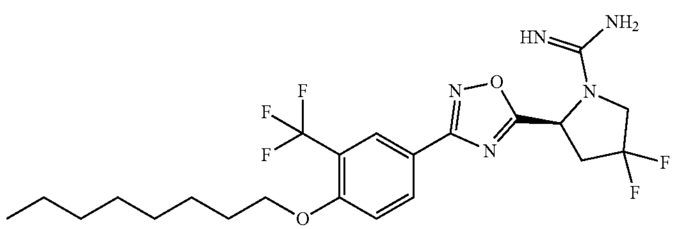 [SMILES: CCCCCCCCOc1ccc(-c2noc([C@@H]3CC(F)(F)CN3C(=N)N)n2)cc1C(F)(F)F] | C | C |
| 20A | 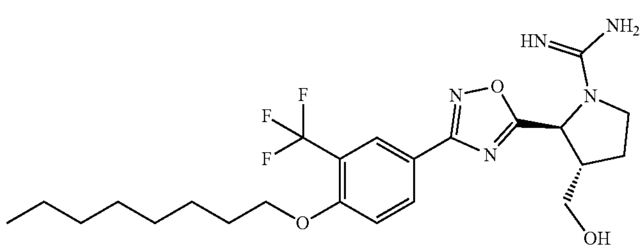 [SMILES: CCCCCCCCOc1ccc(-c2noc([C@@H]3[C@@H](CO)CCN3C(=N)N)n2)cc1C(F)(F)F] | A | A |
| 21A | 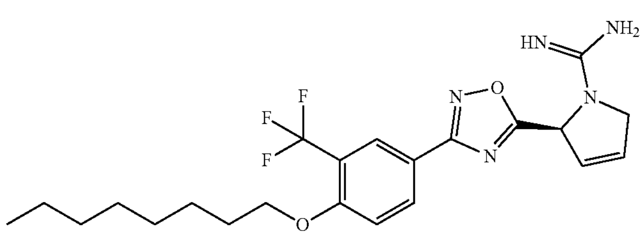 [SMILES: CCCCCCCCOc1ccc(-c2noc([C@@H]3C=CCN3C(=N)N)n2)cc1C(F)(F)F] | C | A |

TABLE 1-continued

Exemplary Compounds and Bioactivity

| Cpd # | Structure | activity hSPHK1 | activity hSPHK2 |
|---|---|---|---|
| 22A | 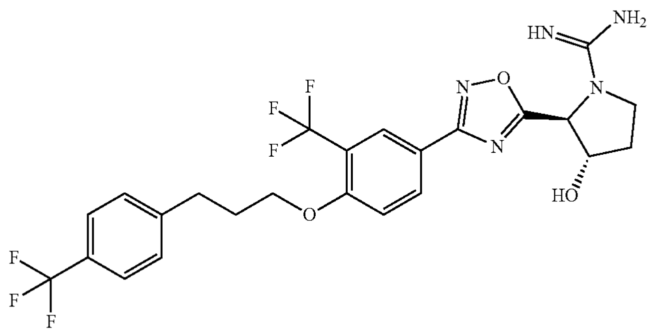 [SMILES: N=C(N)N1CC[C@H](O)[C@H]1c1nc(-c2ccc(OCCCc3ccc(C(F)(F)F)cc3)c(C(F)(F)F)c2)no1] | B | A |
| 23A | 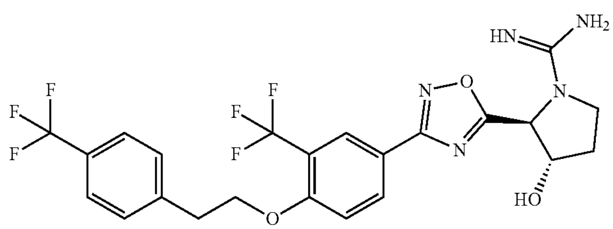 [SMILES: N=C(N)N1CC[C@H](O)[C@H]1c1nc(-c2ccc(OCCc3ccc(C(F)(F)F)cc3)c(C(F)(F)F)c2)no1] | B | A |
| 24A | 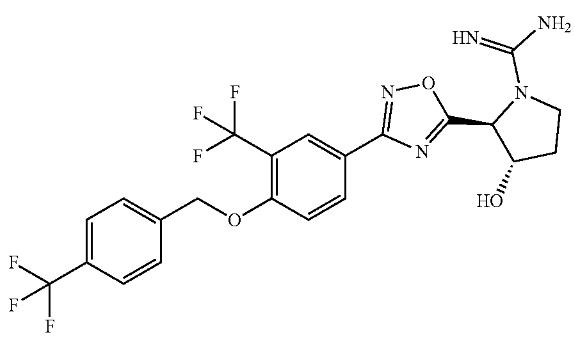 [SMILES: N=C(N)N1CC[C@H](O)[C@H]1c1nc(-c2ccc(OCc3ccc(C(F)(F)F)cc3)c(C(F)(F)F)c2)no1] | B | A |
| 25A | 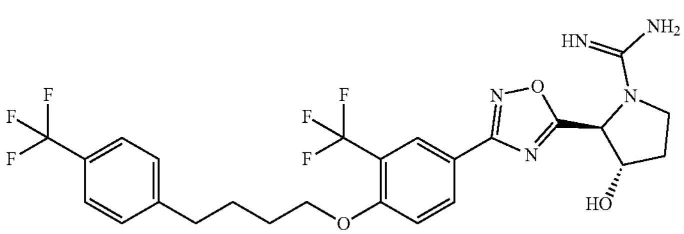 [SMILES: N=C(N)N1CC[C@H](O)[C@H]1c1nc(-c2ccc(OCCCCc3ccc(C(F)(F)F)cc3)c(C(F)(F)F)c2)no1] | A | A |
| 26A | 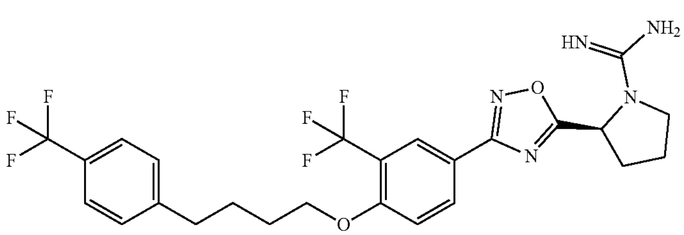 [SMILES: N=C(N)N1CCC[C@H]1c1nc(-c2ccc(OCCCCc3ccc(C(F)(F)F)cc3)c(C(F)(F)F)c2)no1] | C | A |

TABLE 1-continued

Exemplary Compounds and Bioactivity

| Cpd # | Structure | activity hSPHK1 | activity hSPHK2 |
|---|---|---|---|
| 27A | 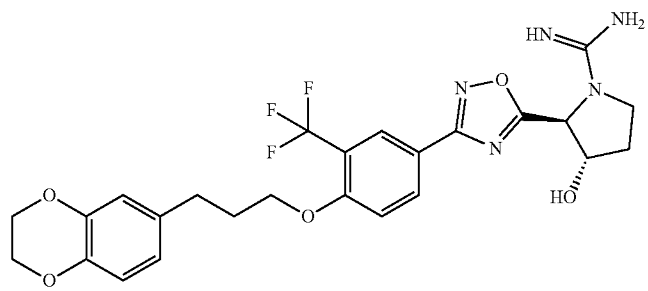 [SMILES: N=C(N)N1CC[C@H](O)[C@H]1c1nc(-c2ccc(OCCCc3ccc4c(c3)OCCO4)c(C(F)(F)F)c2)no1] | C | B |
| 28A | 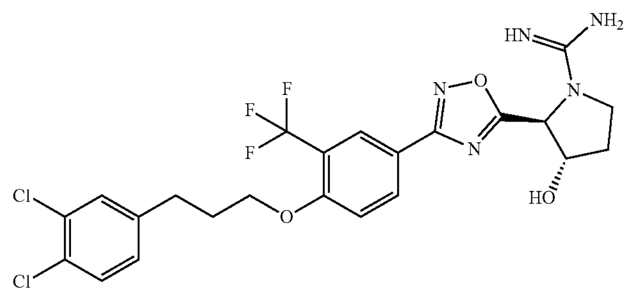 [SMILES: N=C(N)N1CC[C@H](O)[C@H]1c1nc(-c2ccc(OCCCc3ccc(Cl)c(Cl)c3)c(C(F)(F)F)c2)no1] | B | A |
| 29A | 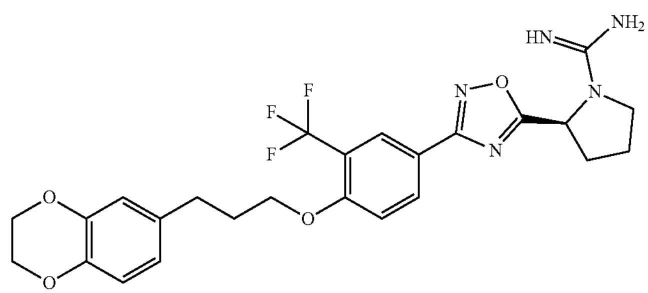 [SMILES: N=C(N)N1CCC[C@H]1c1nc(-c2ccc(OCCCc3ccc4c(c3)OCCO4)c(C(F)(F)F)c2)no1] | C | C |
| 30A | 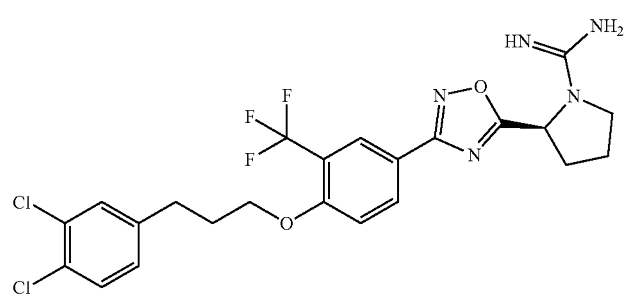 [SMILES: N=C(N)N1CCC[C@H]1c1nc(-c2ccc(OCCCc3ccc(Cl)c(Cl)c3)c(C(F)(F)F)c2)no1] | C | A |
| 31A | 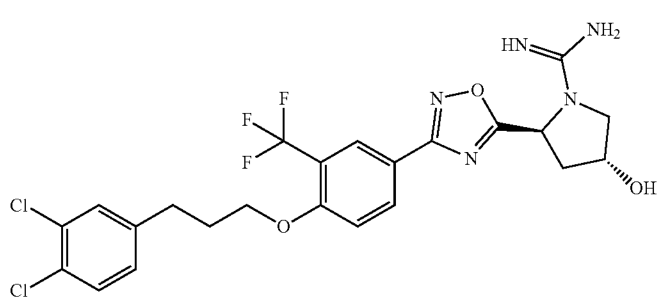 [SMILES: N=C(N)N1C[C@H](O)C[C@H]1c1nc(-c2ccc(OCCCc3ccc(Cl)c(Cl)c3)c(C(F)(F)F)c2)no1] | C | A |

TABLE 1-continued
Exemplary Compounds and Bioactivity
| Cpd # | Structure | activity hSPHK1 | activity hSPHK2 |
|---|---|---|---|
| 32A | 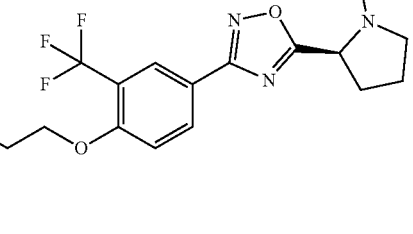 | C | A |
| 33A | 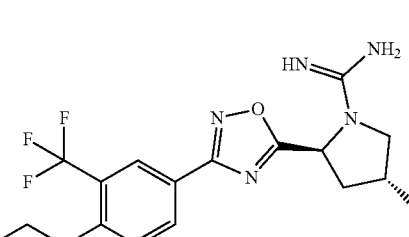 | C | A |
| 34A | 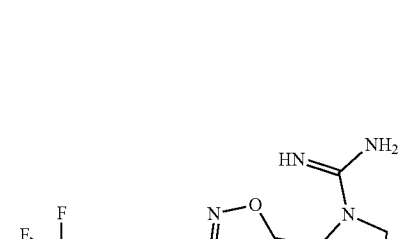 | B | A |
| 35A | 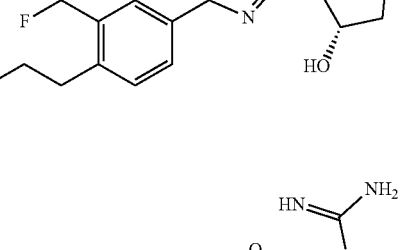 | C | A |
| 36A | 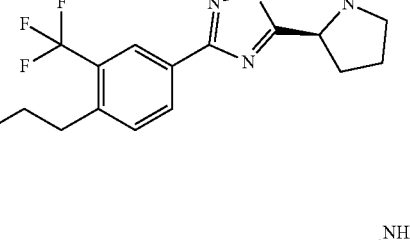 | C | A |

TABLE 1-continued
Exemplary Compounds and Bioactivity
| Cpd # | Structure | activity hSPHK1 | activity hSPHK2 |
|---|---|---|---|
| 37A | 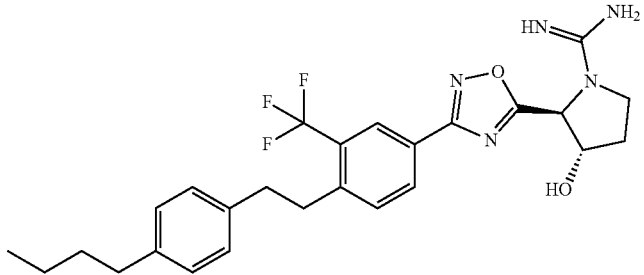 [SMILES: CCCCc1ccc(CCc2ccc(-c3noc([C@@H]4[C@@H](O)CCN4C(=N)N)n3)cc2C(F)(F)F)cc1] | B | A |
| 38A | 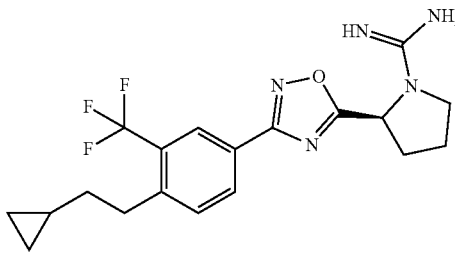 | C | B |
| 39A | 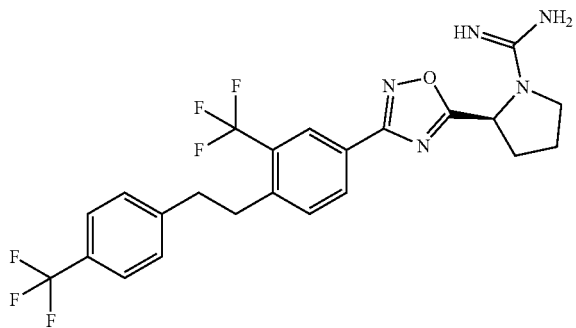 [SMILES: N=C(N)N1CCC[C@H]1c1nc(-c2ccc(CCc3ccc(C(F)(F)F)cc3)c(C(F)(F)F)c2)no1] | C | A |
| 40A | 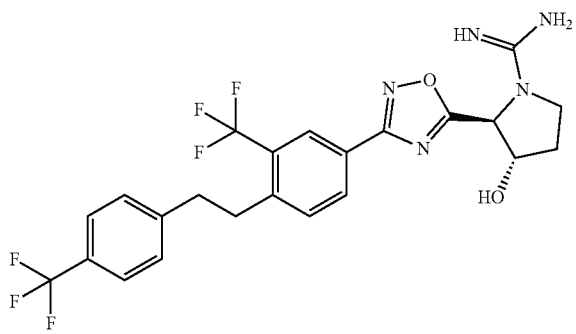 [SMILES: N=C(N)N1CC[C@H](O)[C@H]1c1nc(-c2ccc(CCc3ccc(C(F)(F)F)cc3)c(C(F)(F)F)c2)no1] | B | A |
| 41A | 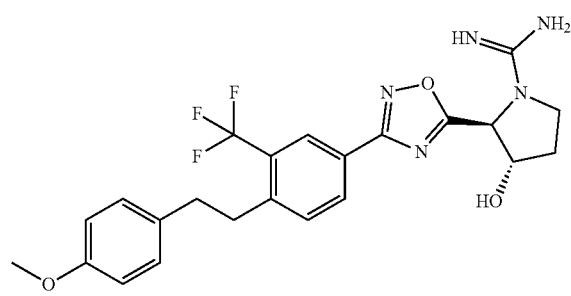 [SMILES: COc1ccc(CCc2ccc(-c3noc([C@@H]4[C@@H](O)CCN4C(=N)N)n3)cc2C(F)(F)F)cc1] | B | A |

TABLE 1-continued

Exemplary Compounds and Bioactivity

| Cpd # | Structure | activity hSPHK1 | activity hSPHK2 |
|---|---|---|---|
| 42A | 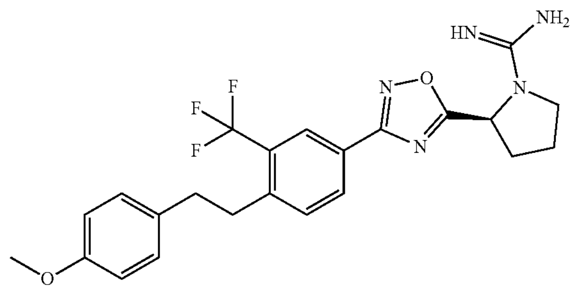 [SMILES: COc1ccc(CCc2ccc(-c3noc([C@@H]4CCCN4C(=N)N)n3)cc2C(F)(F)F)cc1] | C | A |
| 43A | 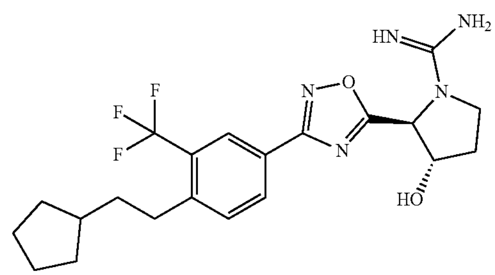 [SMILES: N=C(N)N1CC[C@H](O)[C@H]1c1nc(-c2ccc(CCC3CCCC3)c(C(F)(F)F)c2)no1] | B | A |
| 44A | 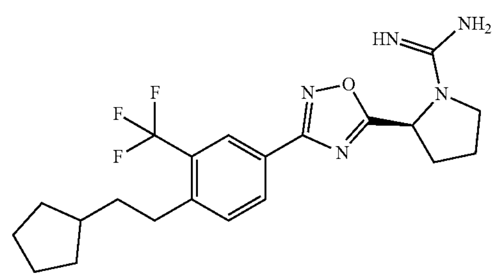 [SMILES: N=C(N)N1CCC[C@H]1c1nc(-c2ccc(CCC3CCCC3)c(C(F)(F)F)c2)no1] | C | B |
| 45A | 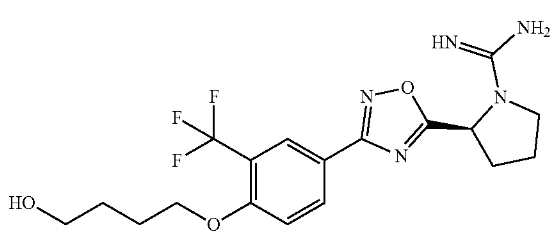 [SMILES: N=C(N)N1CCC[C@H]1c1nc(-c2ccc(OCCCCO)c(C(F)(F)F)c2)no1] | C | B |
| 46A | 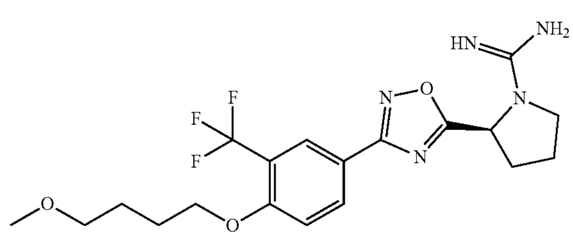 [SMILES: COCCCCOc1ccc(-c2noc([C@@H]3CCCN3C(=N)N)n2)cc1C(F)(F)F] | C | C |
| 47A | 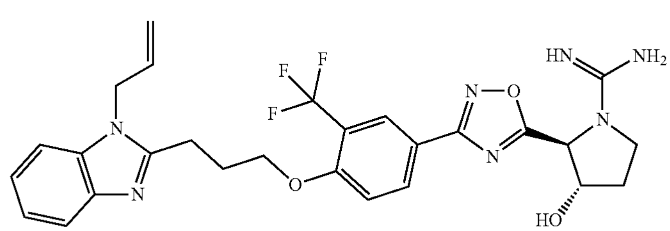 [SMILES: C=CCn1c(CCCOc2ccc(-c3noc([C@@H]4[C@@H](O)CCN4C(=N)N)n3)cc2C(F)(F)F)nc2ccccc21] | C | B |

TABLE 1-continued

Exemplary Compounds and Bioactivity

| Cpd # | Structure | activity hSPHK1 | activity hSPHK2 |
|---|---|---|---|
| 48A | 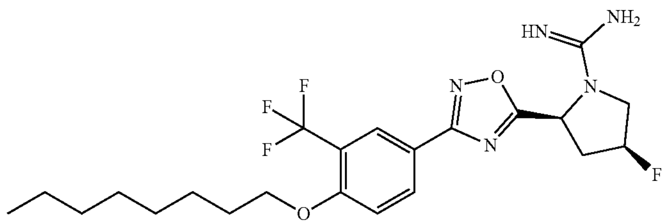 [SMILES: CCCCCCCCOc1ccc(-c2noc([C@@H]3C[C@H](F)CN3C(=N)N)n2)cc1C(F)(F)F] | C | B |
| 49A | 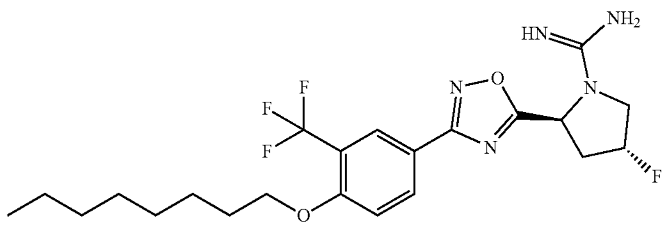 [SMILES: CCCCCCCCOc1ccc(-c2noc([C@@H]3C[C@@H](F)CN3C(=N)N)n2)cc1C(F)(F)F] | C | A |
| 50A | 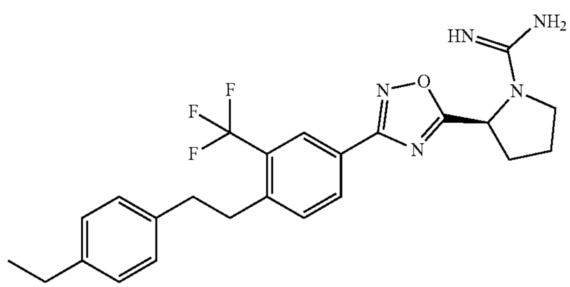 [SMILES: CCc1ccc(CCc2ccc(-c3noc([C@@H]4CCCN4C(=N)N)n3)cc2C(F)(F)F)cc1] | C | A |
| 51A | 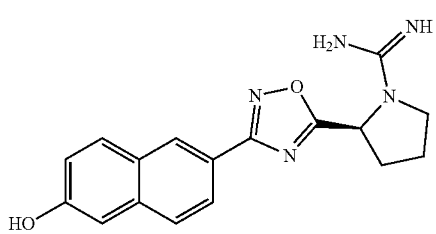 [SMILES: N=C(N)N1CCC[C@H]1c1nc(-c2ccc3cc(O)ccc3c2)no1] | C | C |
| 52A | 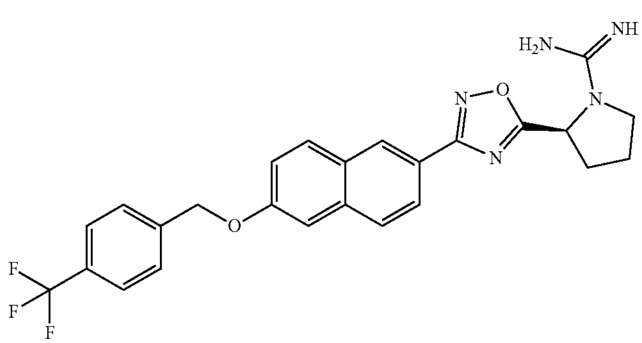 [SMILES: N=C(N)N1CCC[C@H]1c1nc(-c2ccc3cc(OCc4ccc(C(F)(F)F)cc4)ccc3c2)no1] | C | B |

TABLE 1-continued

Exemplary Compounds and Bioactivity

| Cpd # | Structure | activity hSPHK1 | activity hSPHK2 |
|---|---|---|---|
| 53A | 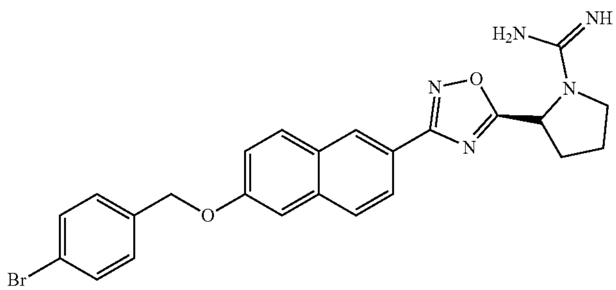 | C | B |
| 54A | 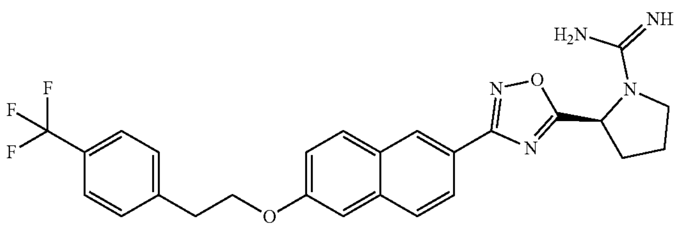 [SMILES: N=C(N)N1CCC[C@H]1c1nc(-c2ccc3cc(OCCc4ccc(C(F)(F)F)cc4)ccc3c2)no1] | C | C |
| 55A | 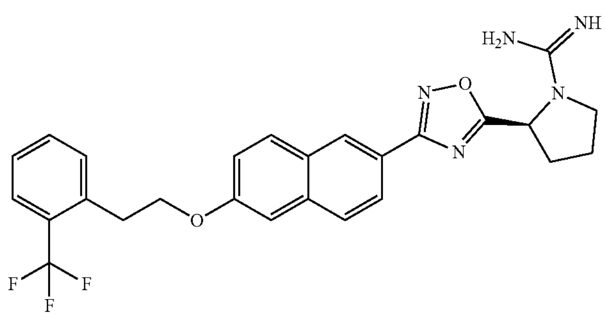 [SMILES: N=C(N)N1CCC[C@H]1c1nc(-c2ccc3cc(OCCc4ccccc4C(F)(F)F)ccc3c2)no1] | C | C |
| 56A | 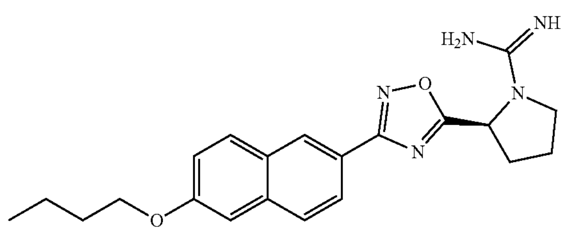 [SMILES: CCCCOc1ccc2cc(-c3noc([C@@H]4CCCN4C(=N)N)n3)ccc2c1] | C | B |
| 57A | 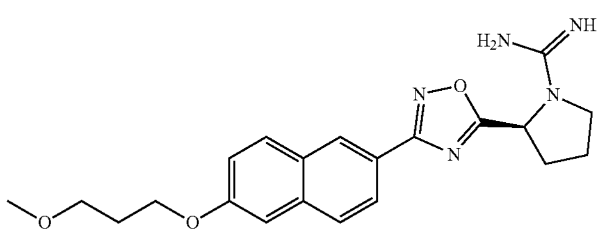 [SMILES: COCCCOc1ccc2cc(-c3noc([C@@H]4CCCN4C(=N)N)n3)ccc2c1] | C | C |

TABLE 1-continued

Exemplary Compounds and Bioactivity

| Cpd # | Structure | activity hSPHK1 | activity hSPHK2 |
|---|---|---|---|
| 58A | 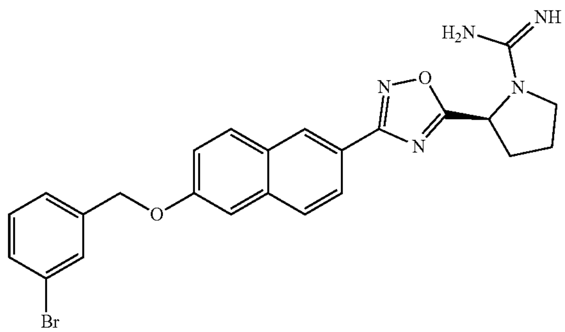 [SMILES: N=C(N)N1CCC[C@H]1c1nc(-c2ccc3cc(OCc4cccc(Br)c4)ccc3c2)no1] | C | C |
| 59A | 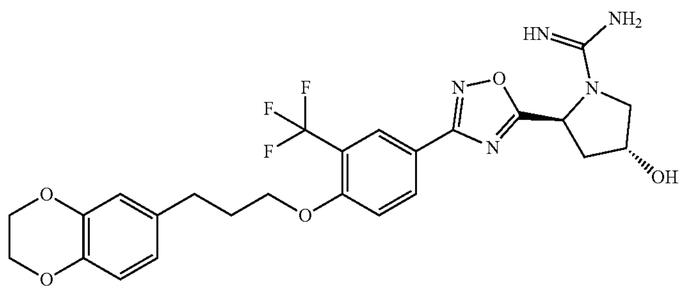 [SMILES: N=C(N)N1C[C@H](O)C[C@H]1c1nc(-c2ccc(OCCCc3ccc4c(c3)OCCO4)c(C(F)(F)F)c2)no1] | C | C |
| 60A | 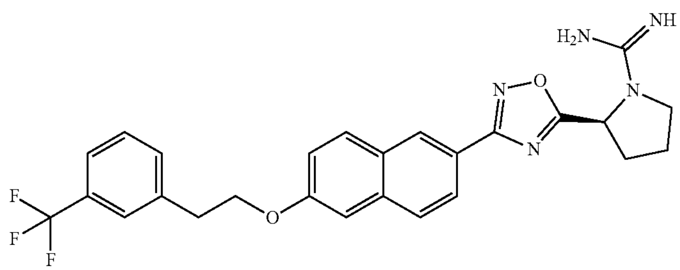 [SMILES: N=C(N)N1CCC[C@H]1c1nc(-c2ccc3cc(OCCc4cccc(C(F)(F)F)c4)ccc3c2)no1] | C | C |
| 61A | 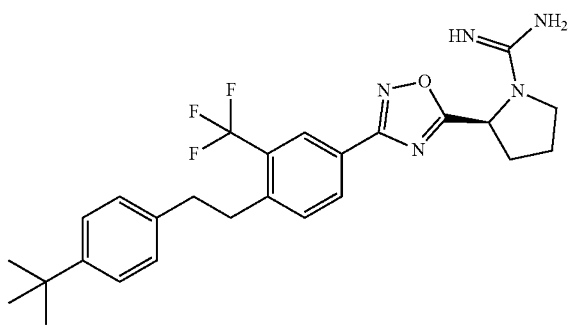 [SMILES: CC(C)(C)c1ccc(CCc2ccc(-c3noc([C@@H]4CCCN4C(=N)N)n3)cc2C(F)(F)F)cc1] | C | A |
| 62A | 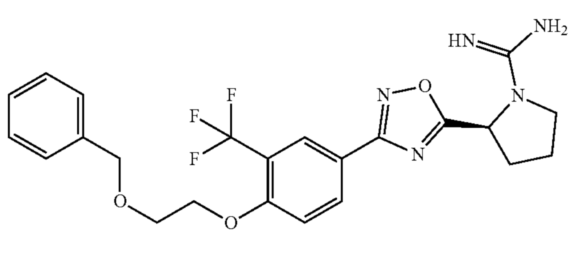 [SMILES: N=C(N)N1CCC[C@H]1c1nc(-c2ccc(OCCOCc3ccccc3)c(C(F)(F)F)c2)no1] | C | C |

TABLE 1-continued
Exemplary Compounds and Bioactivity
| Cpd # | Structure | activity hSPHK1 | activity hSPHK2 |
|---|---|---|---|
| 63A | 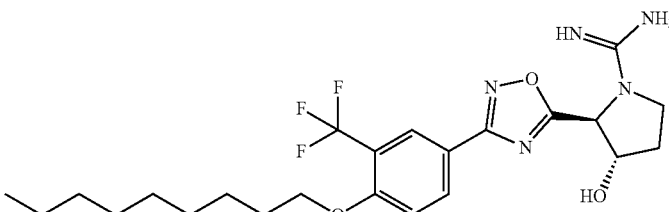 | A | A |
| 64A | 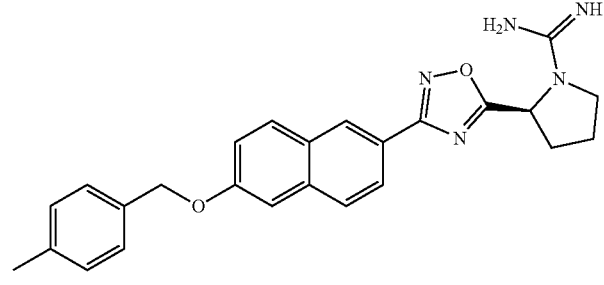 [SMILES: Cc1ccc(COc2ccc3cc(-c4noc([C@@H]5CCCN5C(=N)N)n4)ccc3c2)cc1] | C | C |
| 65A | 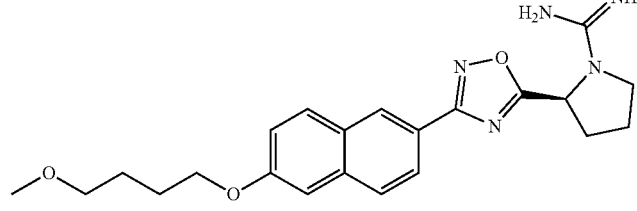 | C | C |
| 66A | 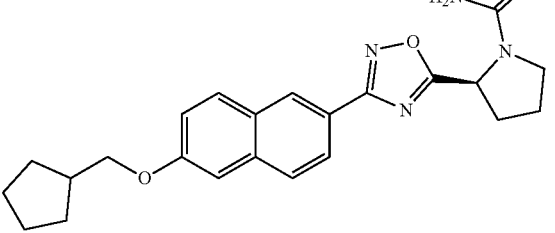 | C | C |
| 67A | 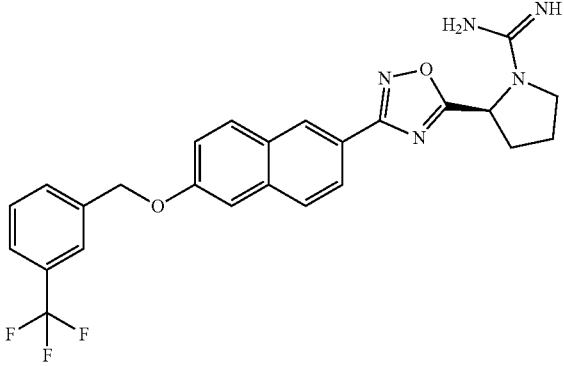 [SMILES: N=C(N)N1CCC[C@H]1c1nc(-c2ccc3cc(OCc4cccc(C(F)(F)F)c4)ccc3c2)no1] | C | B |

TABLE 1-continued

Exemplary Compounds and Bioactivity

| Cpd # | Structure | activity hSPHK1 | activity hSPHK2 |
|---|---|---|---|
| 68A | 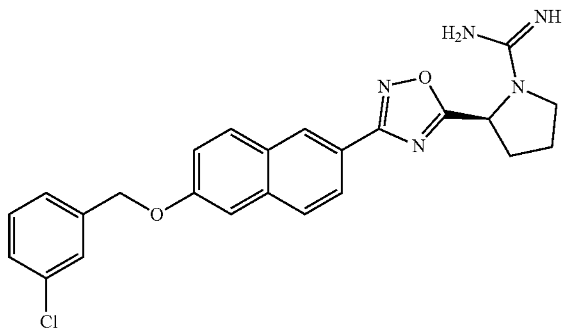 [SMILES: N=C(N)N1CCC[C@H]1c1nc(-c2ccc3cc(OCc4cccc(Cl)c4)ccc3c2)no1] | C | C |
| 69A | 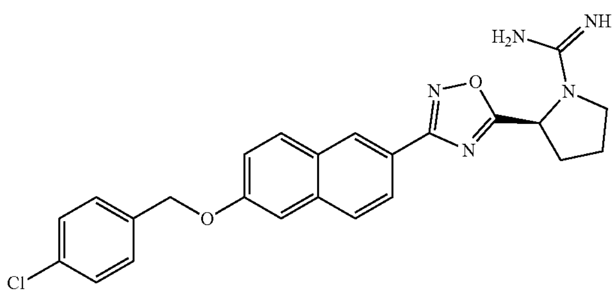 [SMILES: N=C(N)N1CCC[C@H]1c1nc(-c2ccc3cc(OCc4ccc(Cl)cc4)ccc3c2)no1] | C | C |
| 70A | 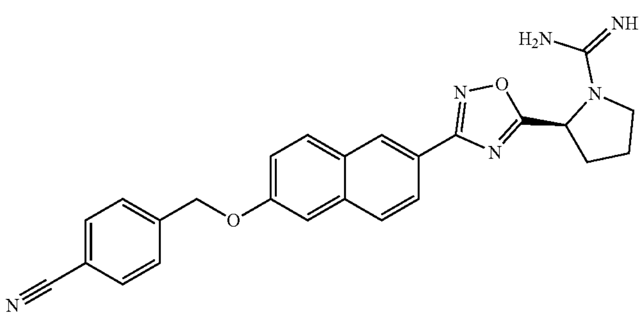 [SMILES: N#Cc1ccc(COc2ccc3cc(-c4noc([C@@H]5CCCN5C(=N)N)n4)ccc3c2)cc1] | C | B |
| 71A | 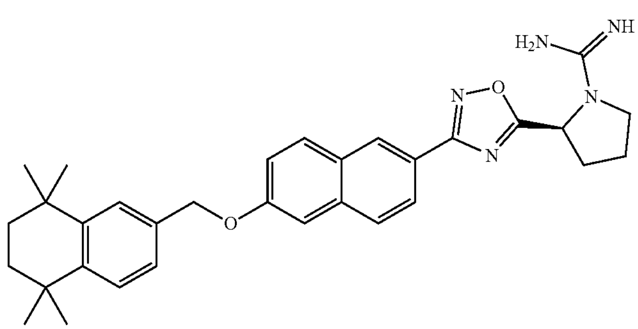 [SMILES: CC1(C)CCC(C)(C)c2cc(COc3ccc4cc(-c5noc([C@@H]6CCCN6C(=N)N)n5)ccc4c3)ccc21] | C | C |

TABLE 1-continued
Exemplary Compounds and Bioactivity
| Cpd # | Structure | activity hSPHK1 | activity hSPHK2 |
|---|---|---|---|
| 72A | 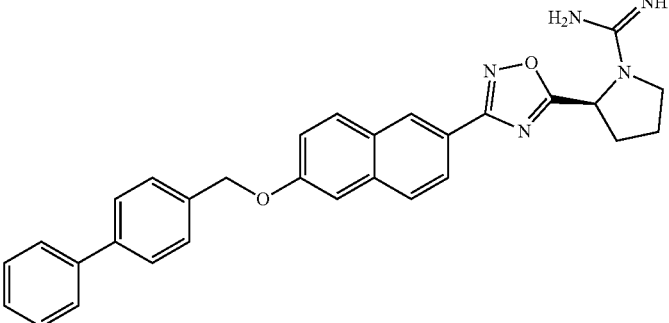 [SMILES: N=C(N)N1CCC[C@H]1c1nc(-c2ccc3cc(OCc4ccc(-c5ccccc5)cc4)ccc3c2)no1] | C | B |
| 73A | 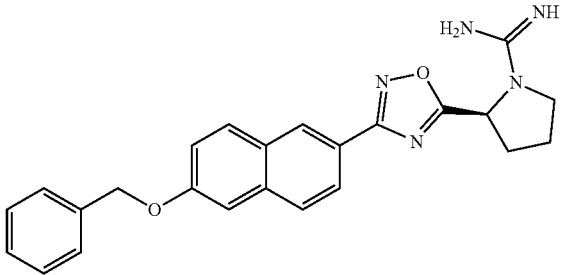 [SMILES: N=C(N)N1CCC[C@H]1c1nc(-c2ccc3cc(OCc4ccccc4)ccc3c2)no1] | C | C |
| 74A | 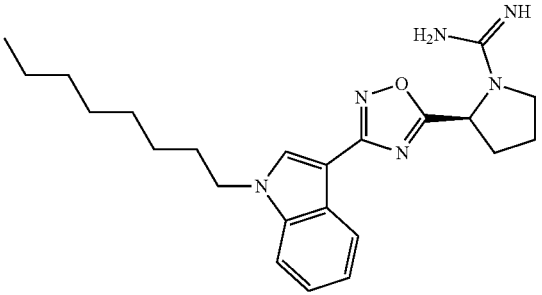 [SMILES: CCCCCCCCn1cc(-c2noc([C@@H]3CCCN3C(=N)N)n2)c2ccccc21] | C | B |
| 75A | 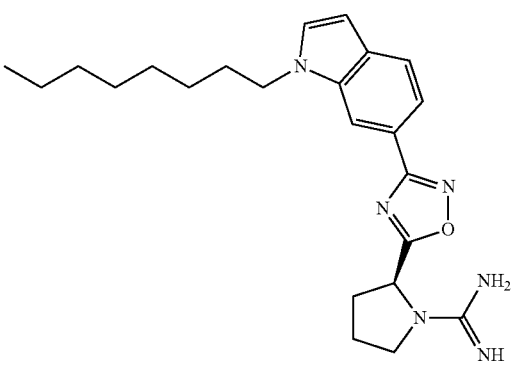 [SMILES: CCCCCCCCn1ccc2ccc(-c3noc([C@@H]4CCCN4C(=N)N)n3)cc21] | C | C |

TABLE 1-continued

Exemplary Compounds and Bioactivity

| Cpd # | Structure | activity hSPHK1 | activity hSPHK2 |
|---|---|---|---|
| 76A | 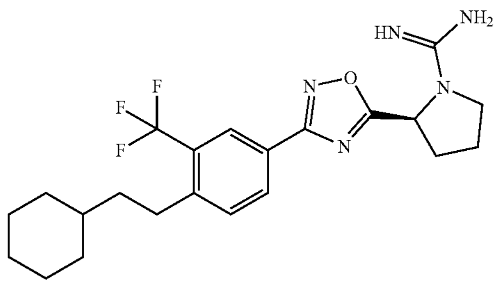 [SMILES: N=C(N)N1CCC[C@H]1c1nc(-c2ccc(CCC3CCCCC3)c(C(F)(F)F)c2)no1] | C | A |
| 77A | 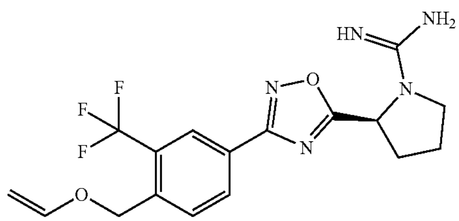 [SMILES: C=COCc1ccc(-c2noc([C@@H]3CCCN3C(=N)N)n2)cc1C(F)(F)F] | C | C |
| 78A | 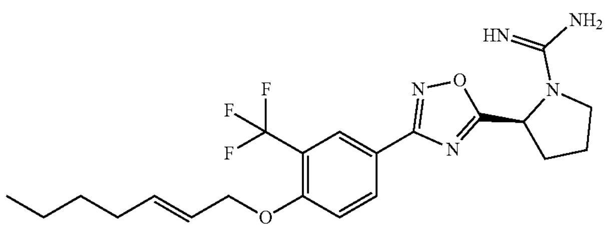 | C | A |
| 79A | 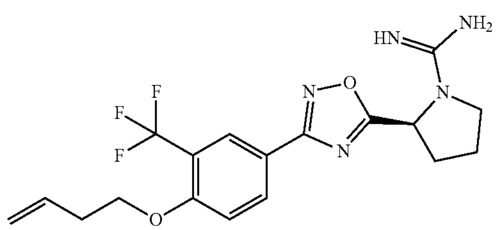 [SMILES: C=CCCOc1ccc(-c2noc([C@@H]3CCCN3C(=N)N)n2)cc1C(F)(F)F] | C | C |
| 80A | 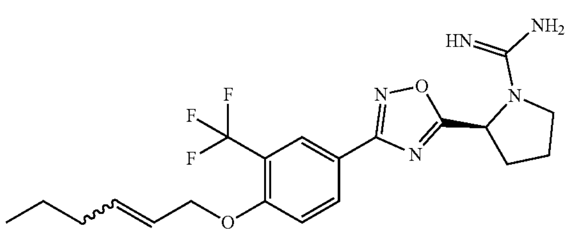 [SMILES: CCCC=CCOc1ccc(-c2noc([C@@H]3CCCN3C(=N)N)n2)cc1C(F)(F)F] | C | B |
| 81A | 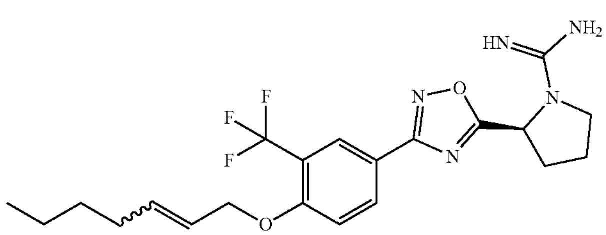 [SMILES: CCCCC=CCOc1ccc(-c2noc([C@@H]3CCCN3C(=N)N)n2)cc1C(F)(F)F] | C | A |

TABLE 1-continued
Exemplary Compounds and Bioactivity
| Cpd # | Structure | activity hSPHK1 | activity hSPHK2 |
|---|---|---|---|
| 82A | 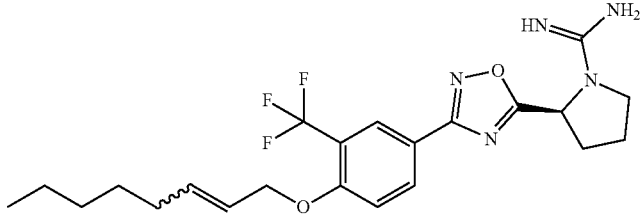 [SMILES: CCCCCC=CCOc1ccc(-c2noc([C@@H]3CCCN3C(=N)N)n2)cc1C(F)(F)F] | C | A |
| 83A | 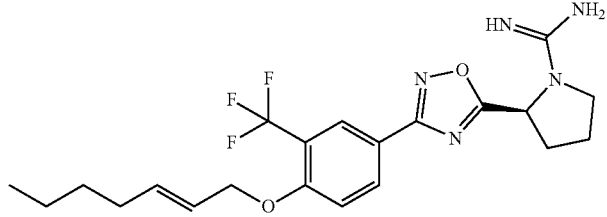 | C | A |
| 84A | 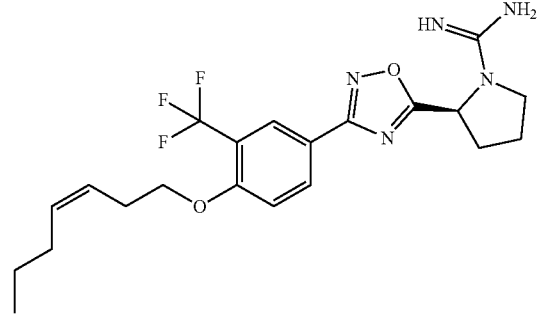 [SMILES: CCC/C=C\CCOc1ccc(-c2noc([C@@H]3CCCN3C(=N)N)n2)cc1C(F)(F)F] | C | A |
| 85A | 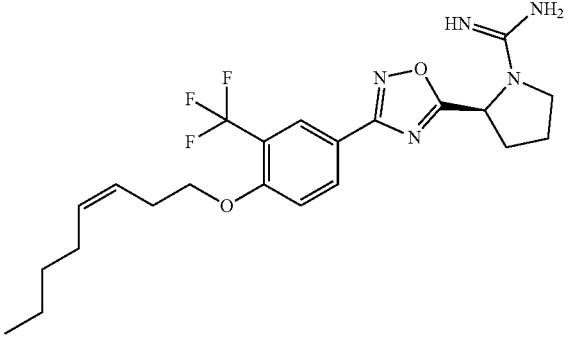 [SMILES: CCCC/C=C\CCOc1ccc(-c2noc([C@@H]3CCCN3C(=N)N)n2)cc1C(F)(F)F] | C | A |
| 86A | 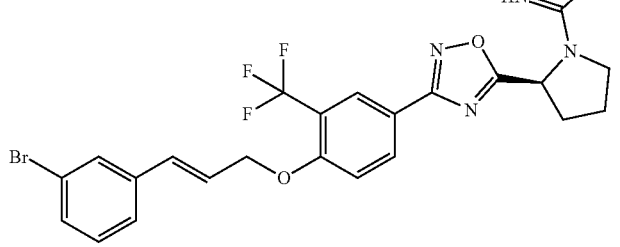 | C | A |

TABLE 1-continued

Exemplary Compounds and Bioactivity

| Cpd # | Structure | activity hSPHK1 | activity hSPHK2 |
|---|---|---|---|
| 87A | 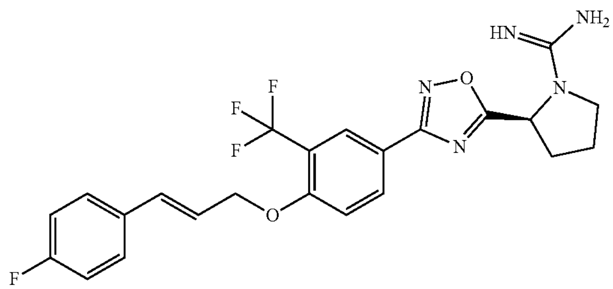 [SMILES: N=C(N)N1CCC[C@H]1c1nc(-c2ccc(OC/C=C/c3ccc(F)cc3)c(C(F)(F)F)c2)no1] | C | A |
| 88A | 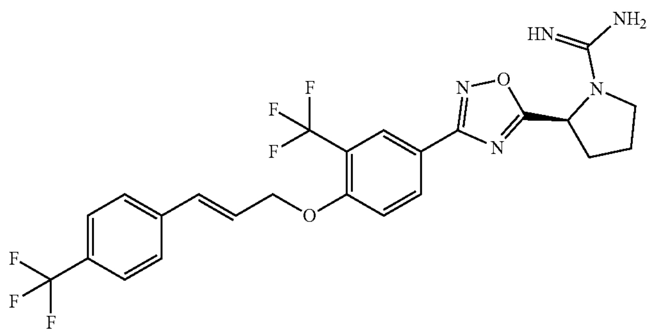 [SMILES: N=C(N)N1CCC[C@H]1c1nc(-c2ccc(OC/C=C/c3ccc(C(F)(F)F)cc3)c(C(F)(F)F)c2)no1] | C | A |
| 89A | 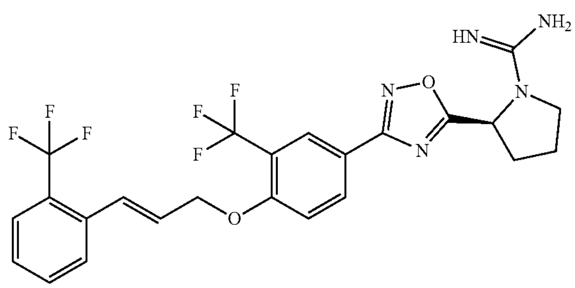 [SMILES: N=C(N)N1CCC[C@H]1c1nc(-c2ccc(OC/C=C/c3ccccc3C(F)(F)F)c(C(F)(F)F)c2)no1] | C | C |
| 90A | 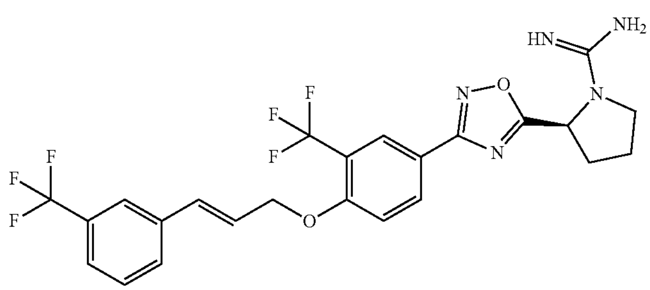 [SMILES: N=C(N)N1CCC[C@H]1c1nc(-c2ccc(OC/C=C/c3cccc(C(F)(F)F)c3)c(C(F)(F)F)c2)no1] | C | A |
| 91A | 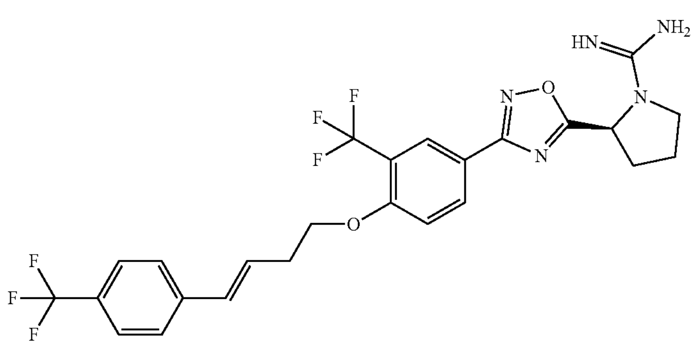 [SMILES: N=C(N)N1CCC[C@H]1c1nc(-c2ccc(OCC/C=C/c3ccc(C(F)(F)F)cc3)c(C(F)(F)F)c2)no1] | C | A |

TABLE 1-continued

Exemplary Compounds and Bioactivity

| Cpd # | Structure | activity hSPHK1 | activity hSPHK2 |
|---|---|---|---|
| 92A | 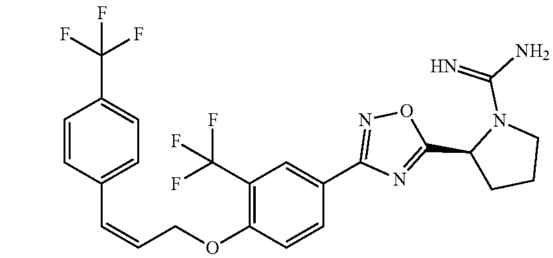 [SMILES: N=C(N)N1CCC[C@H]1c1nc(-c2ccc(OC/C=C\c3ccc(C(F)(F)F)cc3)c(C(F)(F)F)c2)no1] | C | A |
| 93A | 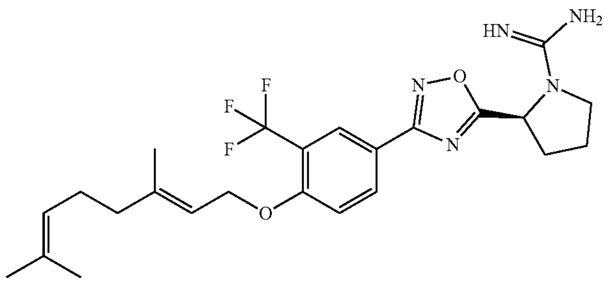 [SMILES: CC(C)=CCC/C(C)=C/COc1ccc(-c2noc([C@@H]3CCCN3C(=N)N)n2)cc1C(F)(F)F] | C | C |
| 94A | 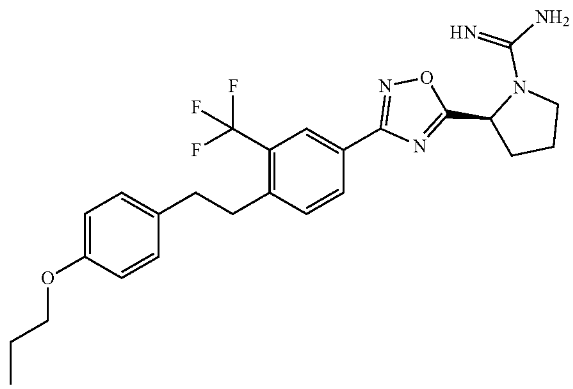 [SMILES: CCCOc1ccc(CCc2ccc(-c3noc([C@@H]4CCCN4C(=N)N)n3)cc2C(F)(F)F)cc1] | C | A |
| 95A | 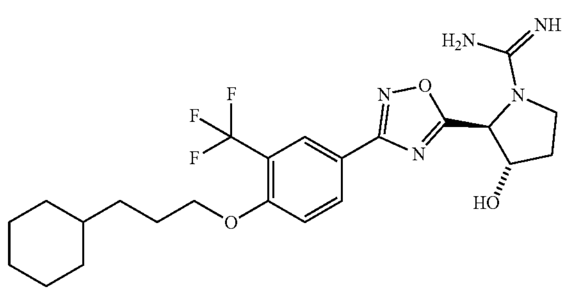 [SMILES: N=C(N)N1CC[C@H](O)[C@H]1c1nc(-c2ccc(OCCCC3CCCCC3)c(C(F)(F)F)c2)no1] | B | A |
| 96A | 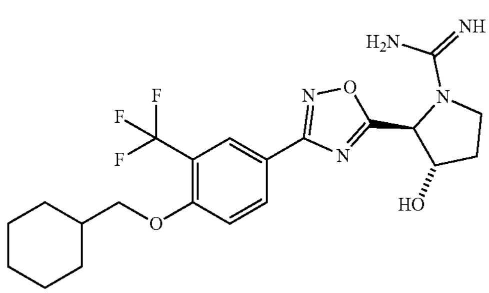 [SMILES: N=C(N)N1CC[C@H](O)[C@H]1c1nc(-c2ccc(OCC3CCCCC3)c(C(F)(F)F)c2)no1] | A | A |

Specific embodiments of the invention are Formula I compounds as shown below in Table 2.
TABLE 2
Exemplary Formula I Compounds
| Cpd. # | Structure |
|---|---|
| 1 | 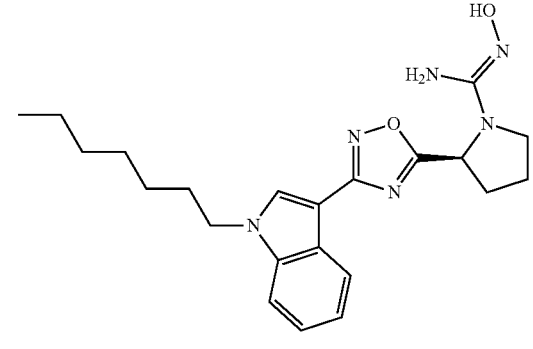 [SMILES: CCCCCCCn1cc(-c2noc([C@@H]3CCCN3/C(N)=N/O)n2)c2ccccc21] |
| 2 | 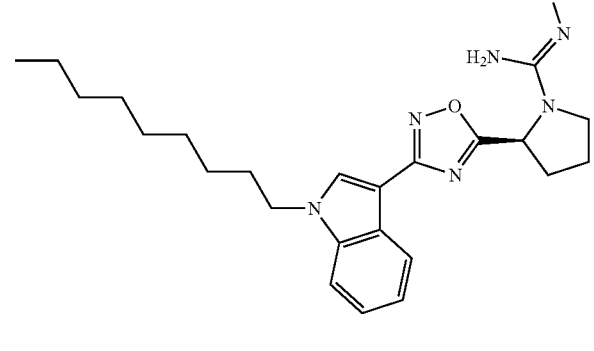 |
| 3 | 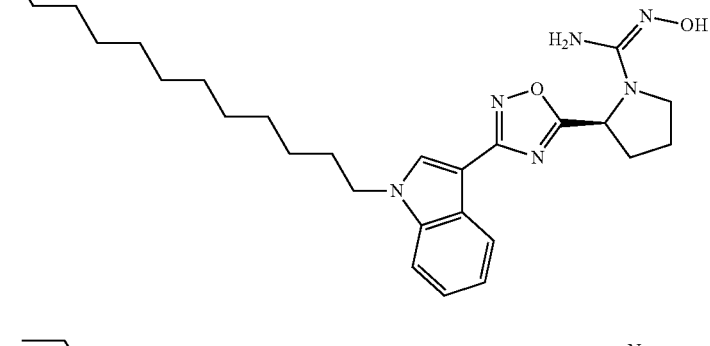 |
| 4 | 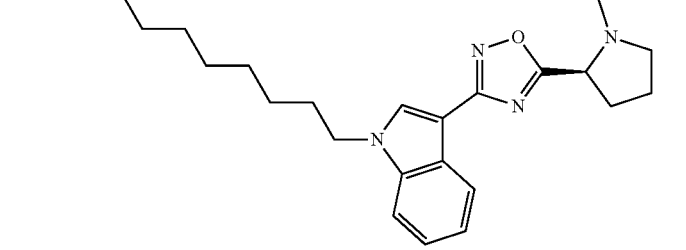 |

TABLE 2-continued
Exemplary Formula I Compounds
| Cpd. # | Structure |
|---|---|
| 5 | 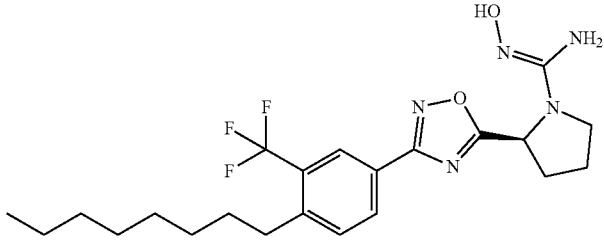 [SMILES: CCCCCCCCc1ccc(-c2noc([C@@H]3CCCN3/C(N)=N/O)n2)cc1C(F)(F)F] |
| 6 | 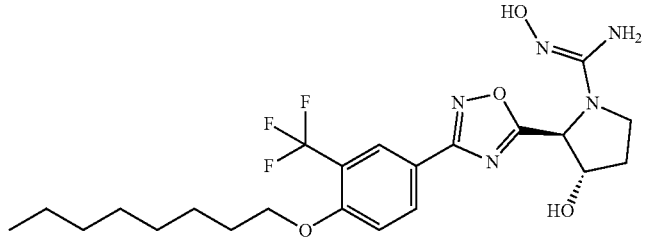 [SMILES: CCCCCCCCOc1ccc(-c2noc([C@@H]3[C@@H](O)CCN3/C(N)=N/O)n2)cc1C(F)(F)F] |
| 7 | 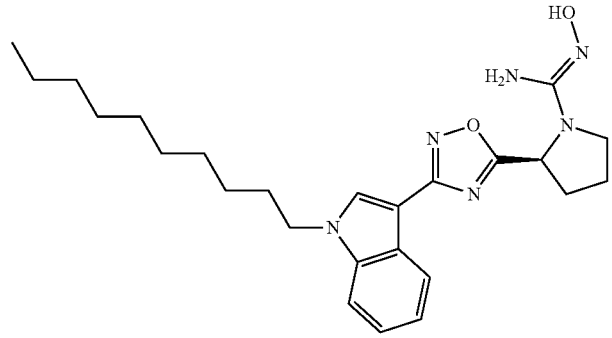 [SMILES: CCCCCCCCCCn1cc(-c2noc([C@@H]3CCCN3/C(N)=N/O)n2)c2ccccc21] |
| 8 | 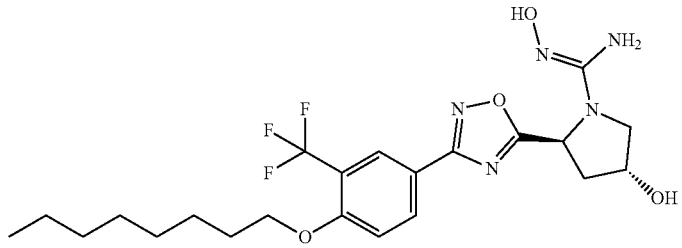 [SMILES: CCCCCCCCOc1ccc(-c2noc([C@@H]3C[C@@H](O)CN3/C(N)=N/O)n2)cc1C(F)(F)F] |
| 9 | 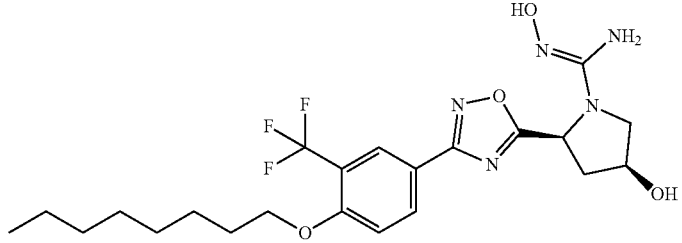 [SMILES: CCCCCCCCOc1ccc(-c2noc([C@@H]3C[C@H](O)CN3/C(N)=N/O)n2)cc1C(F)(F)F] |

TABLE 2-continued
Exemplary Formula I Compounds
| Cpd. # | Structure |
|---|---|
| 10 | 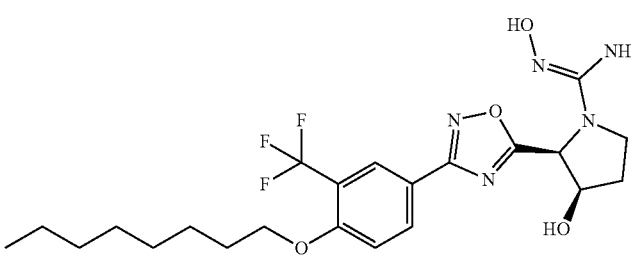 |
| 11 | 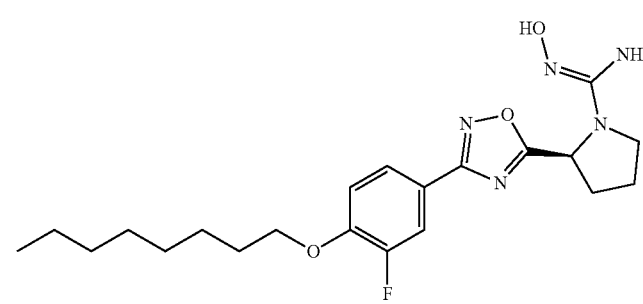 |
| 12 | 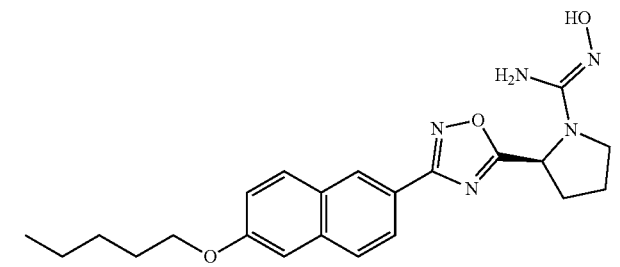 [SMILES: CCCCCOc1ccc2cc(-c3noc([C@@H]4CCCN4/C(N)=N/O)n3)ccc2c1] |
| 13 | 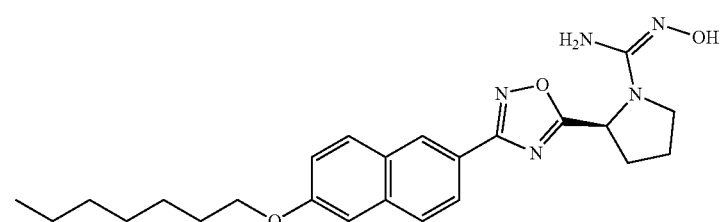 |
| 14 | 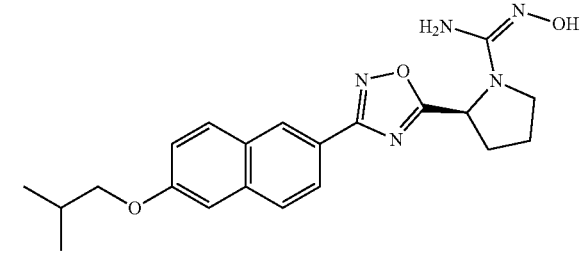 [SMILES: CC(C)COc1ccc2cc(-c3noc([C@@H]4CCCN4/C(N)=N\O)n3)ccc2c1] |

TABLE 2-continued

Exemplary Formula I Compounds

| Cpd. # | Structure |
|---|---|
| 15 | 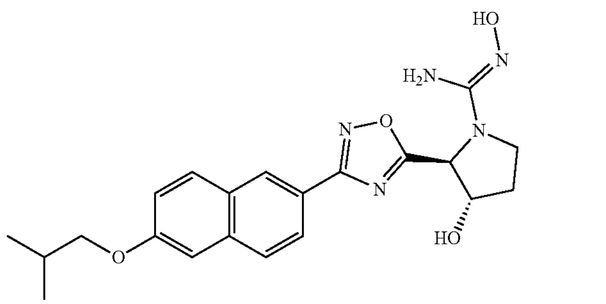 [SMILES: CC(C)COc1ccc2cc(-c3noc([C@@H]4[C@@H](O)CCN4/C(N)=N/O)n3)ccc2c1] |
| 16 | 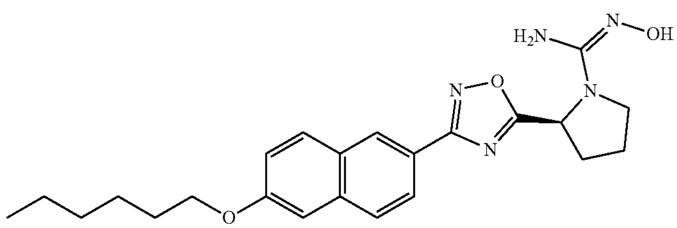 [SMILES: CCCCCCOc1ccc2cc(-c3noc([C@@H]4CCCN4/C(N)=N\O)n3)ccc2c1] |
| 17 | 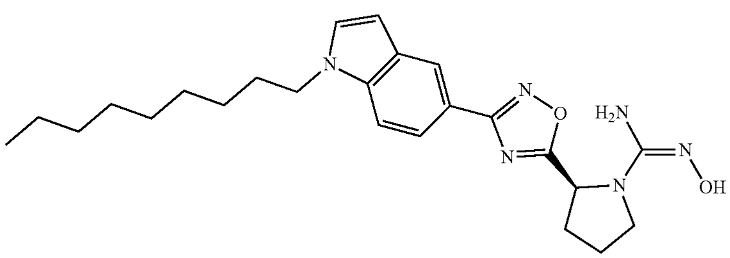 [SMILES: CCCCCCCCCn1ccc2cc(-c3noc([C@@H]4CCCN4/C(N)=N\O)n3)ccc21] |
| 18 | 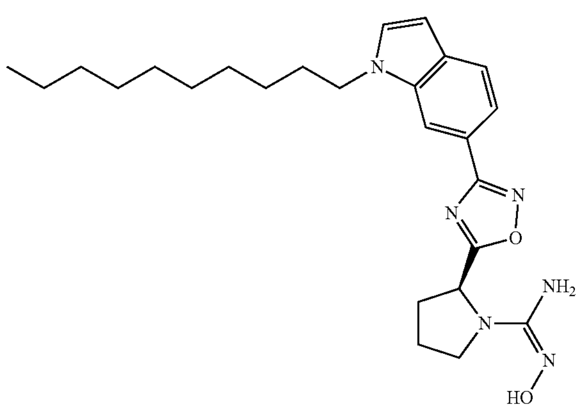 [SMILES: CCCCCCCCCCn1ccc2ccc(-c3noc([C@@H]4CCCN4/C(N)=N\O)n3)cc21] |
| 19 | 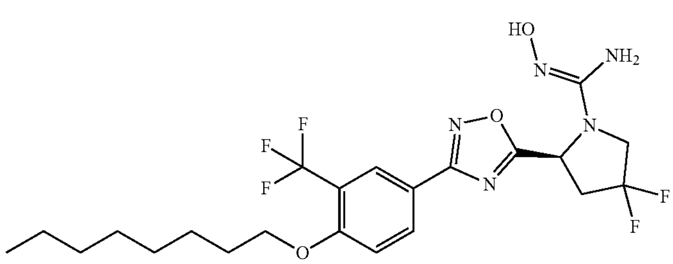 [SMILES: CCCCCCCCOc1ccc(-c2noc([C@@H]3CC(F)(F)CN3/C(N)=N/O)n2)cc1C(F)(F)F] |

TABLE 2-continued
Exemplary Formula I Compounds
| Cpd. # | Structure |
|---|---|
| 20 | 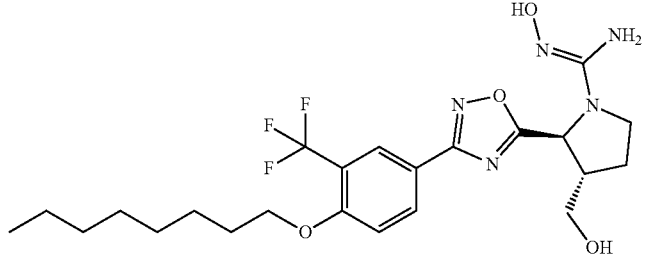 [SMILES: CCCCCCCCOc1ccc(-c2noc([C@@H]3[C@@H](CO)CCN3/C(N)=N/O)n2)cc1C(F)(F)F] |
| 21 | 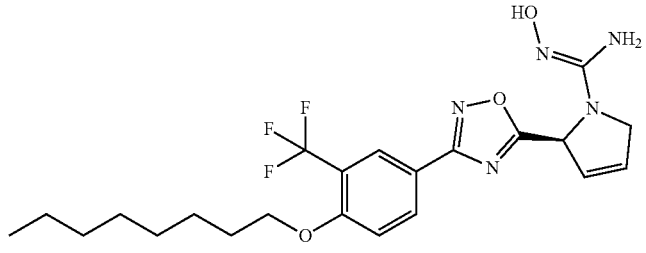 [SMILES: CCCCCCCCOc1ccc(-c2noc([C@@H]3C=CCN3/C(N)=N/O)n2)cc1C(F)(F)F] |
| 22 | 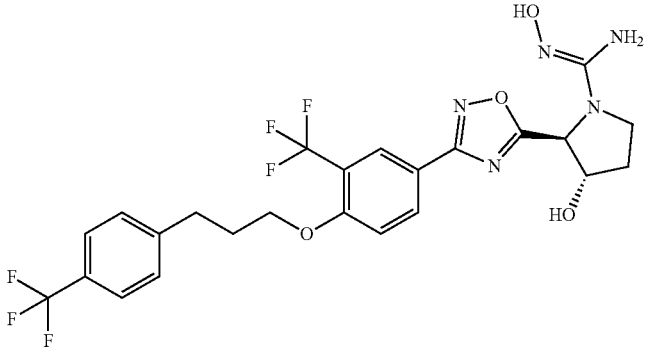 [SMILES: N/C(=N\O)N1CC[C@H](O)[C@H]1c1nc(-c2ccc(OCCCc3ccc(C(F)(F)F)cc3)c(C(F)(F)F)c2)no1] |
| 23 | 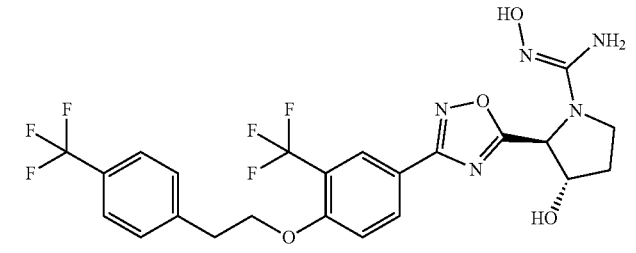 [SMILES: N/C(=N\O)N1CC[C@H](O)[C@H]1c1nc(-c2ccc(OCCc3ccc(C(F)(F)F)cc3)c(C(F)(F)F)c2)no1] |
| 24 | 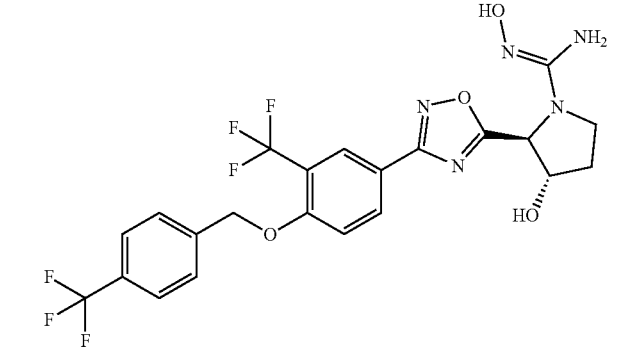 [SMILES: N/C(=N\O)N1CC[C@H](O)[C@H]1c1nc(-c2ccc(OCc3ccc(C(F)(F)F)cc3)c(C(F)(F)F)c2)no1] |

TABLE 2-continued
Exemplary Formula I Compounds
| Cpd. # | Structure |
|---|---|
| 25 | 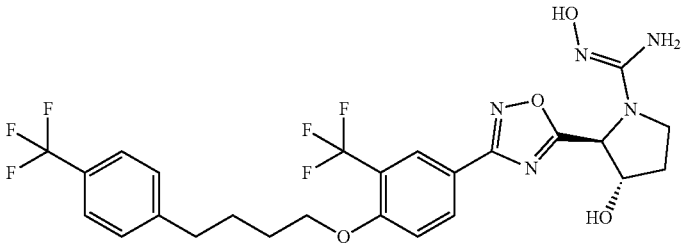 [SMILES: N/C(=N\O)N1CC[C@H](O)[C@H]1c1nc(-c2ccc(OCCCCc3ccc(C(F)(F)F)cc3)c(C(F)(F)F)c2)no1] |
| 26 | 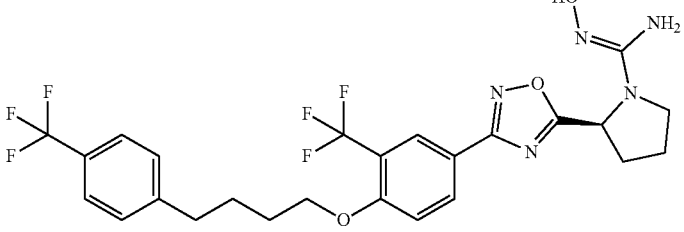 |
| 27 | 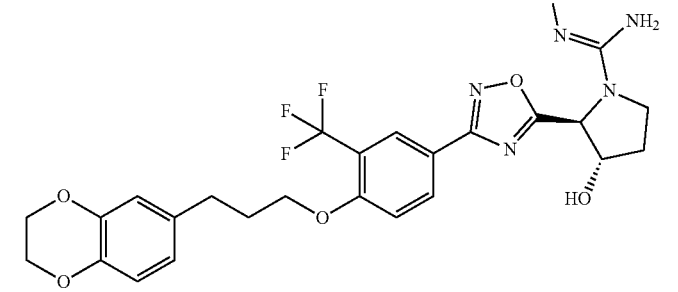 |
| 28 | 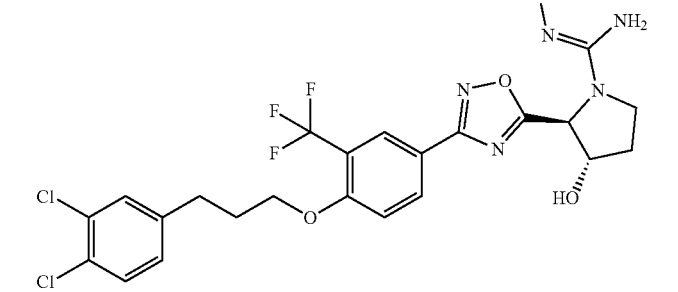 |
| 29 | 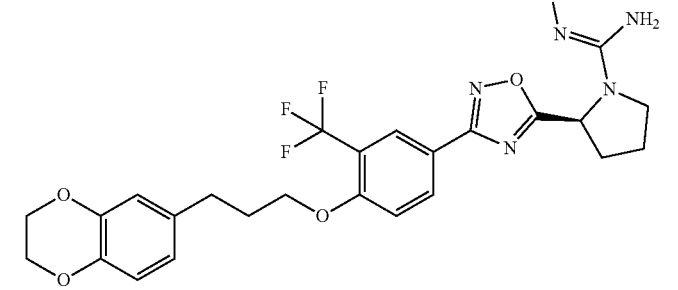 |

TABLE 2-continued
Exemplary Formula I Compounds
| Cpd. # | Structure |
|---|---|
| 30 | 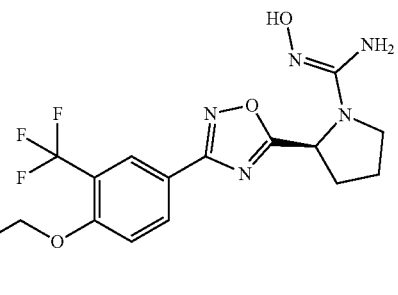 |
| 31 | 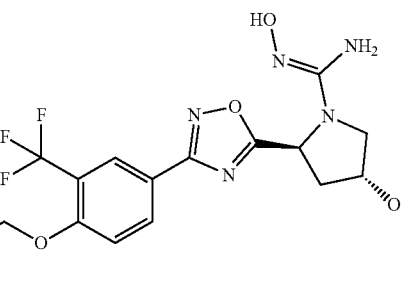 |
| 32 | 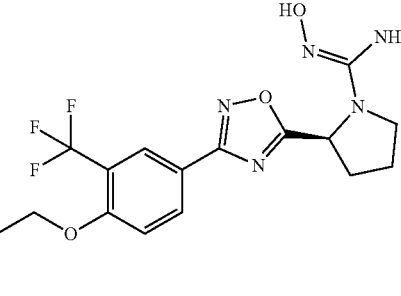 |
| 33 | 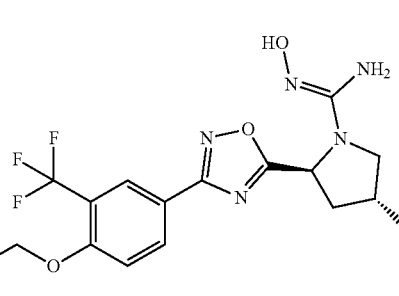 |

TABLE 2-continued
Exemplary Formula I Compounds
| Cpd. # | Structure |
|---|---|
| 34 | 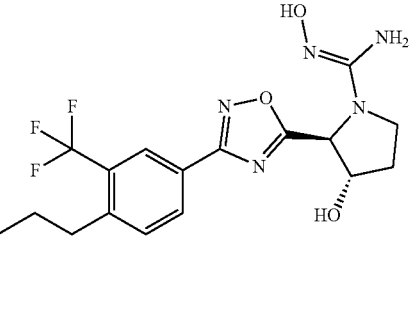 |
| 35 | 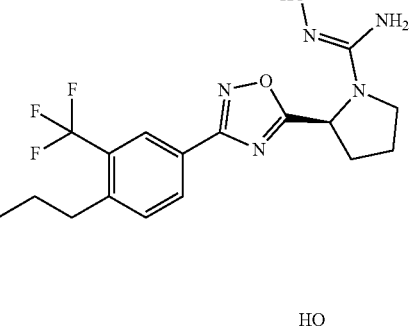 |
| 36 | 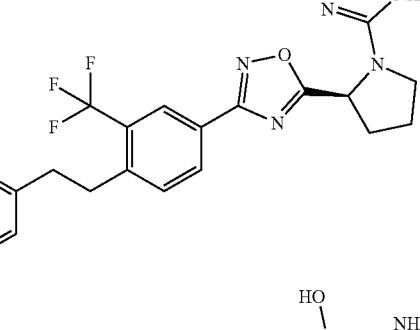 |
| 37 | 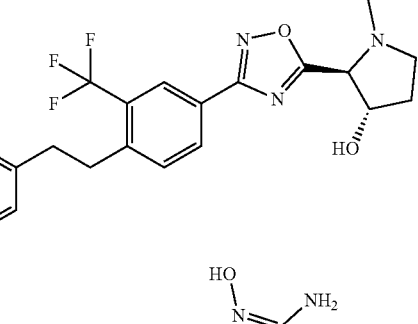 |
| 38 | 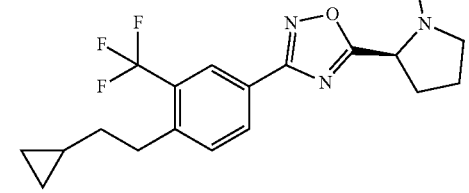 |

TABLE 2-continued
Exemplary Formula I Compounds
| Cpd. # | Structure |
|---|---|
| 39 | 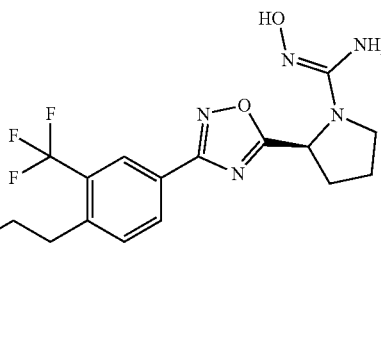 |
| 40 | 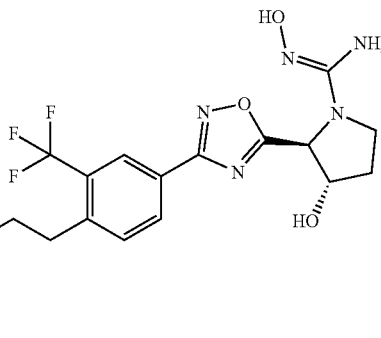 |
| 41 | 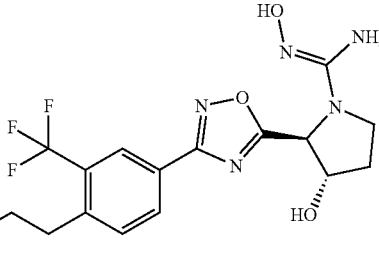 |
| 42 | 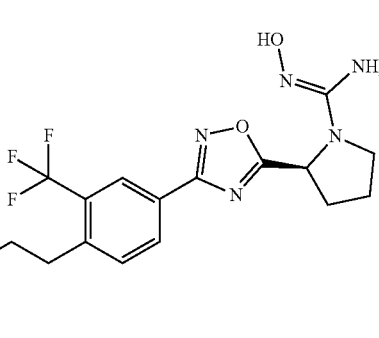 |

TABLE 2-continued

Exemplary Formula I Compounds

| Cpd. # | Structure |
|---|---|
| 43 | 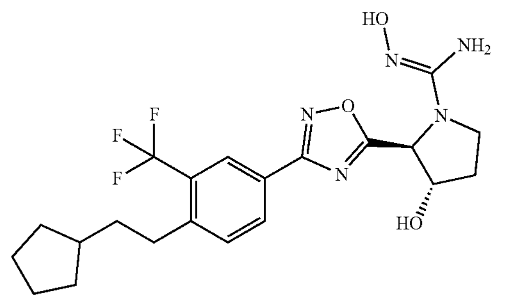 [SMILES: N/C(=N\O)N1CC[C@H](O)[C@H]1c1nc(-c2ccc(CCC3CCCC3)c(C(F)(F)F)c2)no1] |
| 44 | 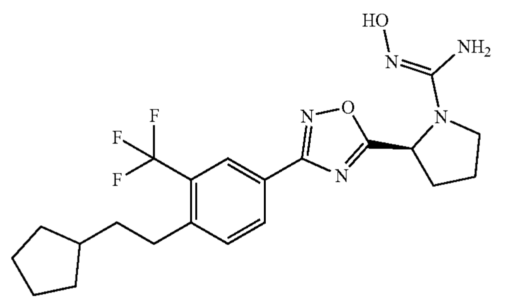 [SMILES: N/C(=N\O)N1CCC[C@H]1c1nc(-c2ccc(CCC3CCCC3)c(C(F)(F)F)c2)no1] |
| 45 | 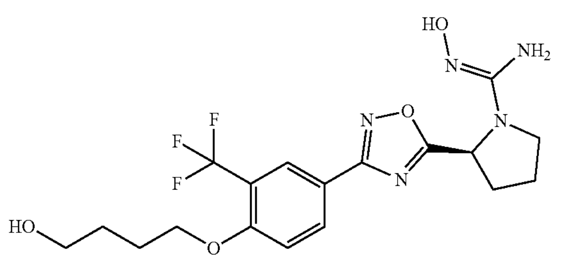 [SMILES: N/C(=N\O)N1CCC[C@H]1c1nc(-c2ccc(OCCCCO)c(C(F)(F)F)c2)no1] |
| 46 | 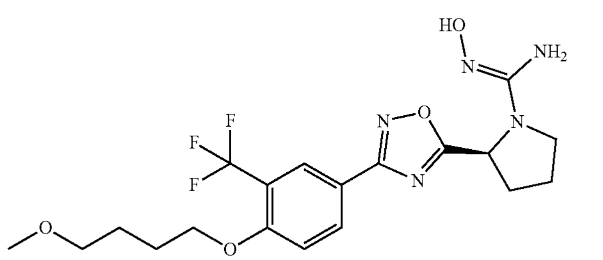 [SMILES: COCCCCOc1ccc(-c2noc([C@@H]3CCCN3/C(N)=N/O)n2)cc1C(F)(F)F] |
| 47 | 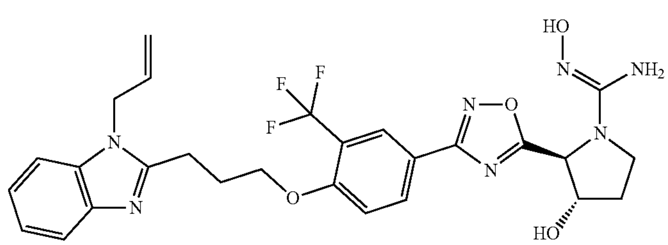 [SMILES: C=CCn1c(CCCOc2ccc(-c3noc([C@@H]4[C@@H](O)CCN4/C(N)=N/O)n3)cc2C(F)(F)F)nc2ccccc21] |

TABLE 2-continued
Exemplary Formula I Compounds
| Cpd. # | Structure |
|---|---|
| 48 | 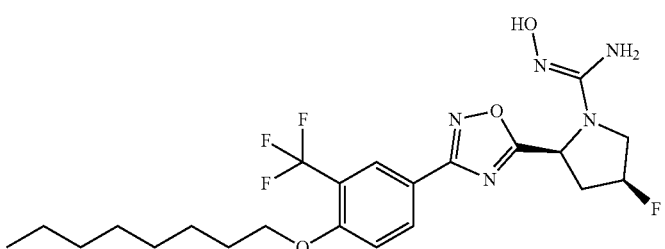 |
| 49 | 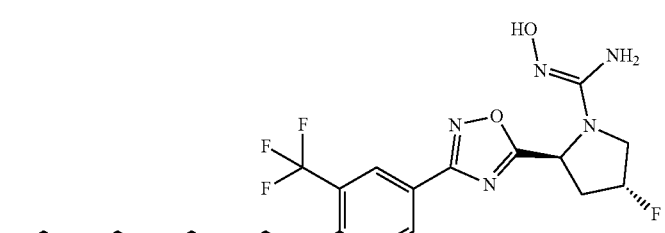 |
| 50 | 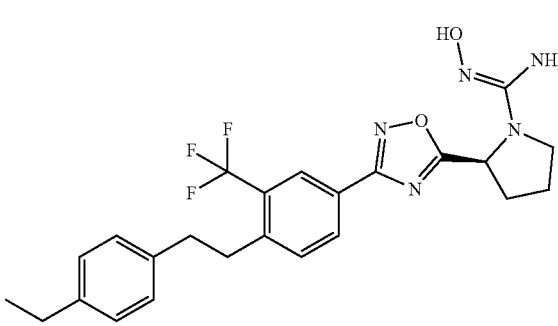 |
| 51 | 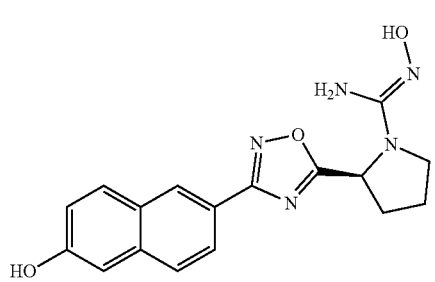 [SMILES: N/C(=N\O)N1CCC[C@H]1c1nc(-c2ccc3cc(O)ccc3c2)no1] |
| 52 | 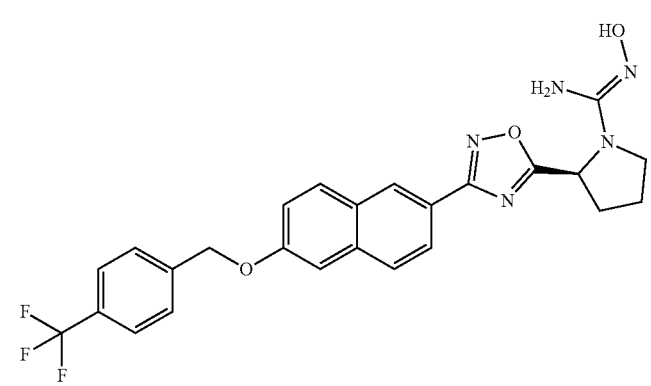 [SMILES: N/C(=N\O)N1CCC[C@H]1c1nc(-c2ccc3cc(OCc4ccc(C(F)(F)F)cc4)ccc3c2)no1] |

TABLE 2-continued
Exemplary Formula I Compounds
| Cpd. # | Structure |
|---|---|
| 53 | 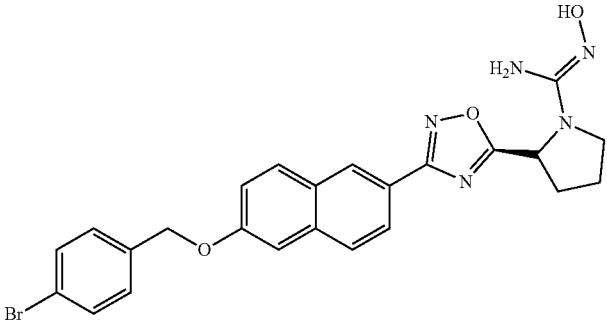 |
| 54 | 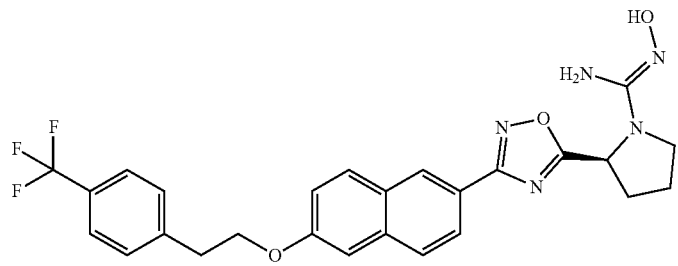 [SMILES: N/C(=N\O)N1CCC[C@H]1c1nc(-c2ccc3cc(OCCc4ccc(C(F)(F)F)cc4)ccc3c2)no1] |
| 55 | 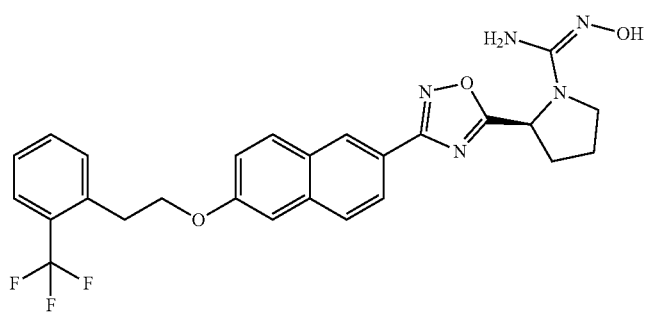 [SMILES: N/C(=N/O)N1CCC[C@H]1c1nc(-c2ccc3cc(OCCc4ccccc4C(F)(F)F)ccc3c2)no1] |
| 56 | 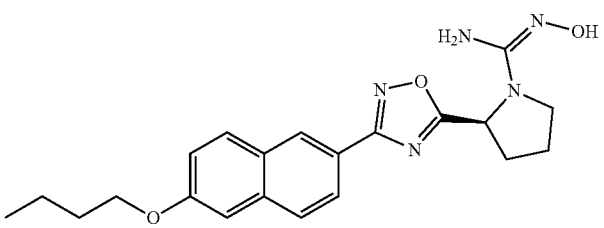 [SMILES: CCCCOc1ccc2cc(-c3noc([C@@H]4CCCN4/C(N)=N\O)n3)ccc2c1] |
| 57 | 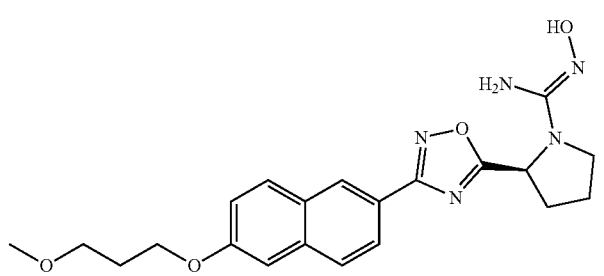 [SMILES: COCCCOc1ccc2cc(-c3noc([C@@H]4CCCN4/C(N)=N/O)n3)ccc2c1] |

TABLE 2-continued
Exemplary Formula I Compounds
| Cpd. # | Structure |
|---|---|
| 58 | 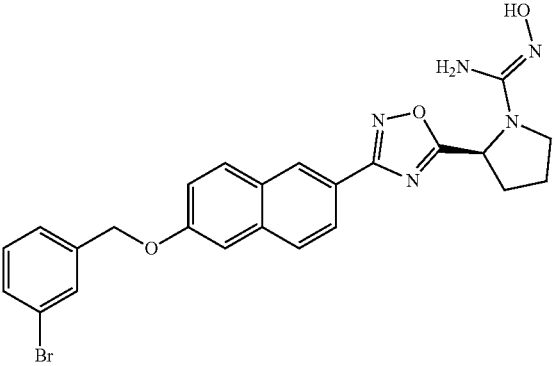 |
| 59 | 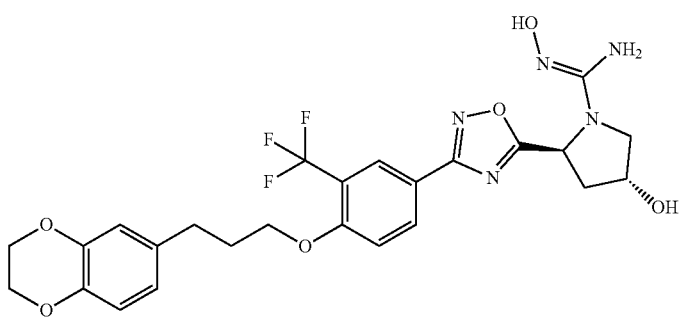 [SMILES: N/C(=N\O)N1C[C@H](O)C[C@H]1c1nc(-c2ccc(OCCCc3ccc4c(c3)OCCO4)c(C(F)(F)F)c2)no1] |
| 60 | 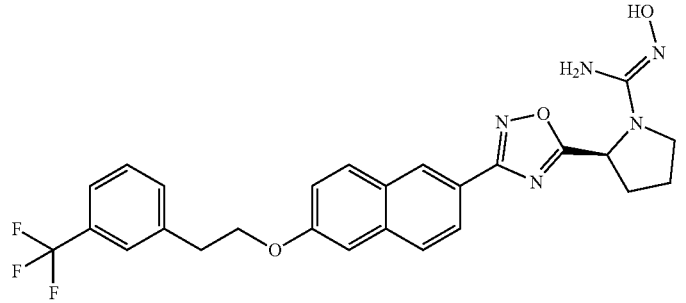 [SMILES: N/C(=N\O)N1CCC[C@H]1c1nc(-c2ccc3cc(OCCc4cccc(C(F)(F)F)c4)ccc3c2)no1] |
| 61 | 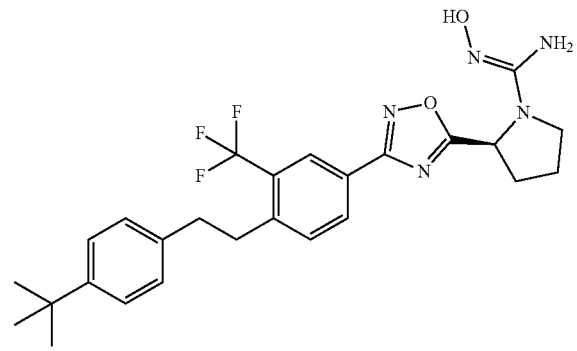 [SMILES: CC(C)(C)c1ccc(CCc2ccc(-c3noc([C@@H]4CCCN4/C(N)=N/O)n3)cc2C(F)(F)F)cc1] |

TABLE 2-continued
Exemplary Formula I Compounds
| Cpd. # | Structure |
|---|---|
| 62 | 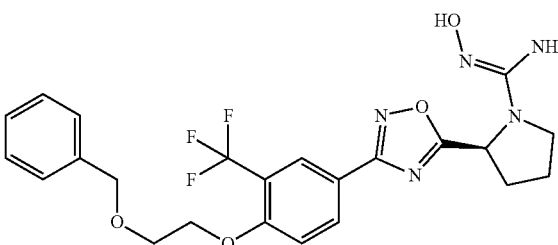 |
| 63 | 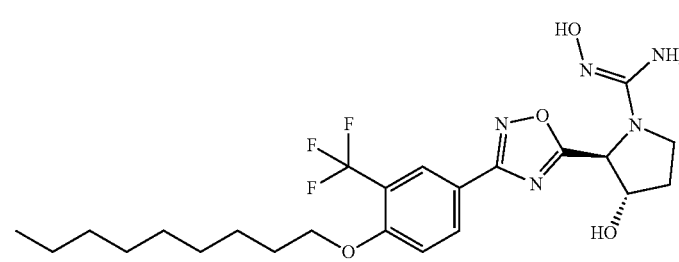 |
| 64 | 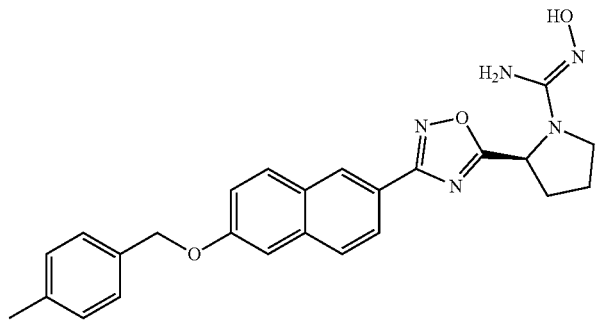 [SMILES: Cc1ccc(COc2ccc3cc(-c4noc([C@@H]5CCCN5/C(N)=N/O)n4)ccc3c2)cc1] |
| 65 | 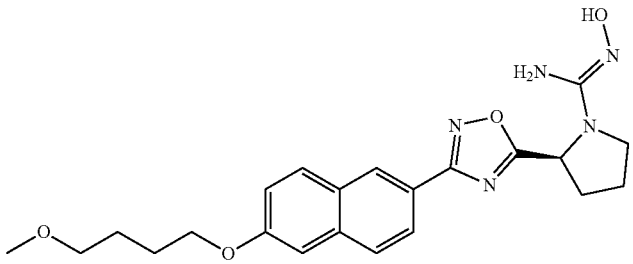 [SMILES: COCCCCOc1ccc2cc(-c3noc([C@@H]4CCCN4/C(N)=N/O)n3)ccc2c1] |
| 66 | 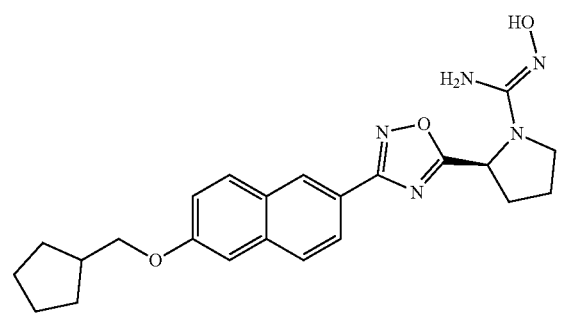 [SMILES: N/C(=N\O)N1CCC[C@H]1c1nc(-c2ccc3cc(OCC4CCCC4)ccc3c2)no1] |

TABLE 2-continued
Exemplary Formula I Compounds
| Cpd. # | Structure |
|---|---|
| 67 | 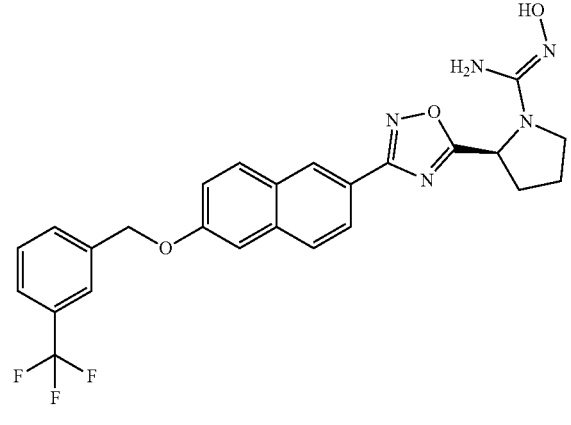 [SMILES: N/C(=N\O)N1CCC[C@H]1c1nc(-c2ccc3cc(OCc4cccc(C(F)(F)F)c4)ccc3c2)no1] |
| 68 | 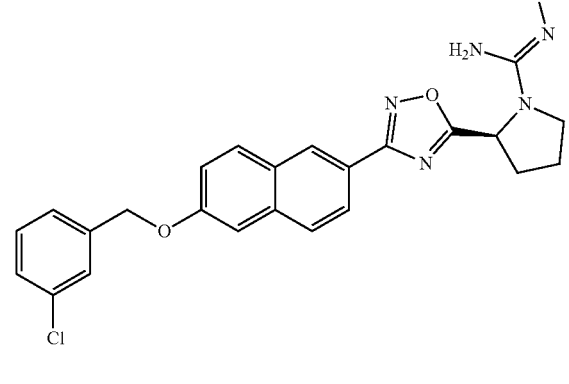 |
| 69 | 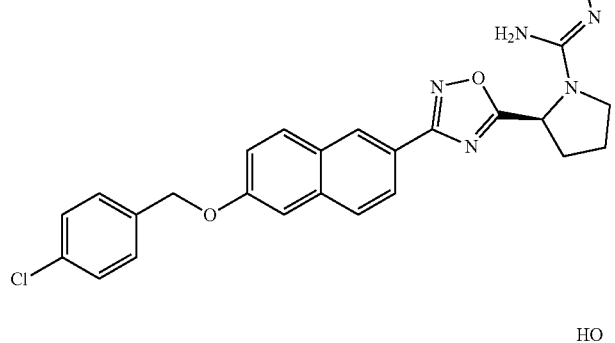 |
| 70 | 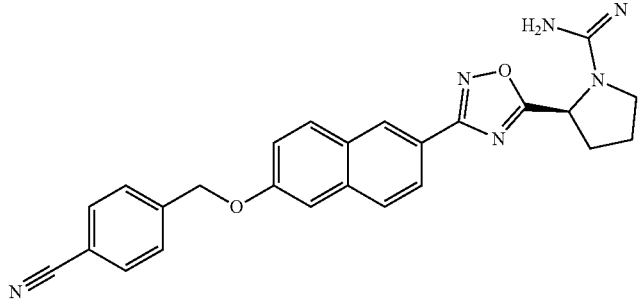 |

TABLE 2-continued
Exemplary Formula I Compounds
| Cpd. # | Structure |
|---|---|
| 71 | 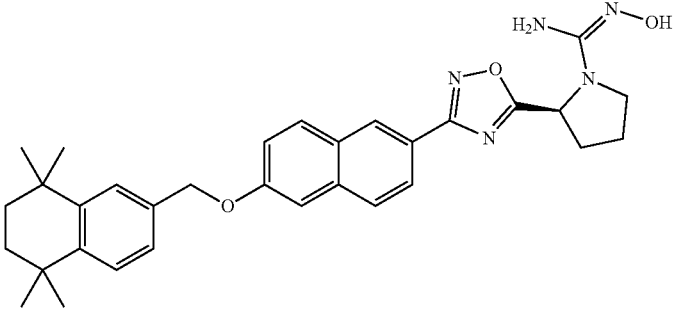 [SMILES: CC1(C)CCC(C)(C)c2cc(COc3ccc4cc(-c5noc([C@@H]6CCCN6/C(N)=N\O)n5)ccc4c3)ccc21] |
| 72 | 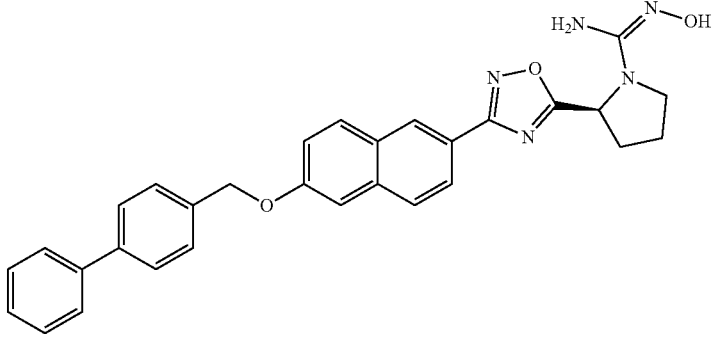 [SMILES: N/C(=N/O)N1CCC[C@H]1c1nc(-c2ccc3cc(OCc4ccc(-c5ccccc5)cc4)ccc3c2)no1] |
| 73 | 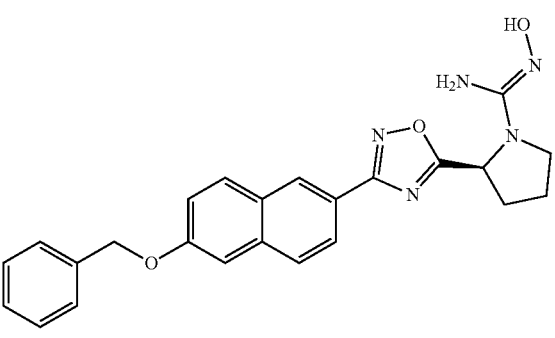 [SMILES: N/C(=N\O)N1CCC[C@H]1c1nc(-c2ccc3cc(OCc4ccccc4)ccc3c2)no1] |
| 74 | 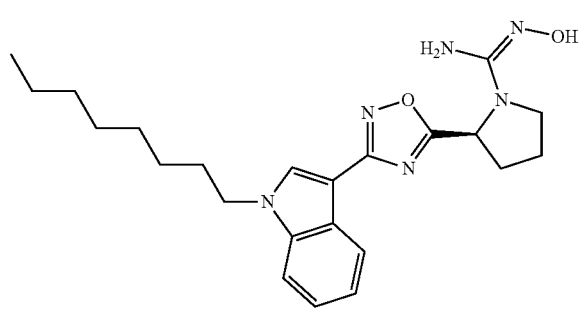 [SMILES: CCCCCCCCn1cc(-c2noc([C@@H]3CCCN3/C(N)=N\O)n2)c2ccccc21] |

TABLE 2-continued
Exemplary Formula I Compounds
| Cpd. # | Structure |
|---|---|
| 75 | 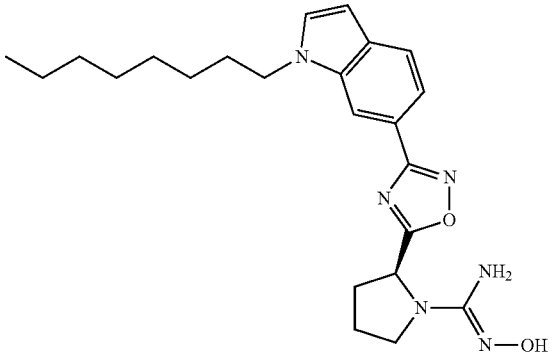 [SMILES: CCCCCCCCn1ccc2ccc(-c3noc([C@@H]4CCCN4/C(N)=N/O)n3)cc21] |
| 76 | 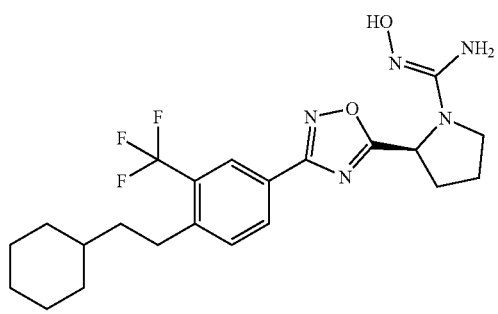 [SMILES: N/C(=N\O)N1CCC[C@H]1c1nc(-c2ccc(CCC3CCCCC3)c(C(F)(F)F)c2)no1] |
| 77 | 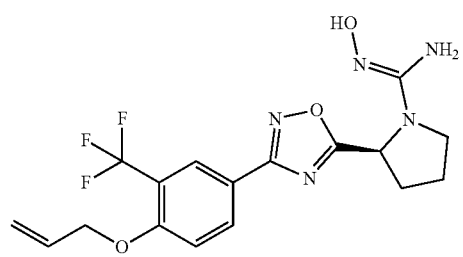 [SMILES: C=CCOc1ccc(-c2noc([C@@H]3CCCN3/C(N)=N/O)n2)cc1C(F)(F)F] |
| 78 | 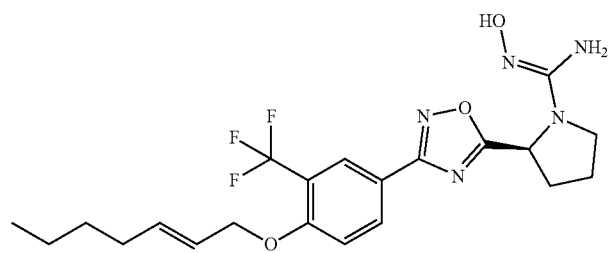 |
| 79 | 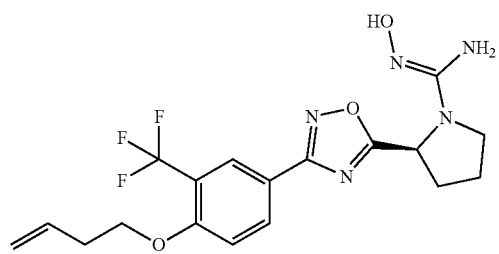 [SMILES: C=CCCOc1ccc(-c2noc([C@@H]3CCCN3/C(N)=N/O)n2)cc1C(F)(F)F] |

95                                                                                              96
TABLE 2-continued
Exemplary Formula I Compounds
| Cpd. # | Structure |
|---|---|
| 80 | 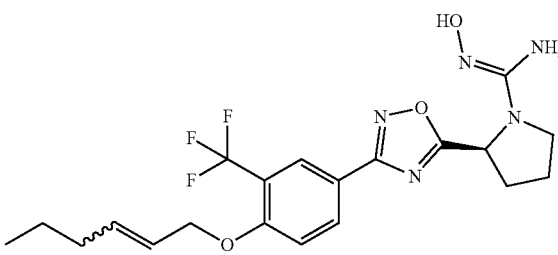 |
| 81 | 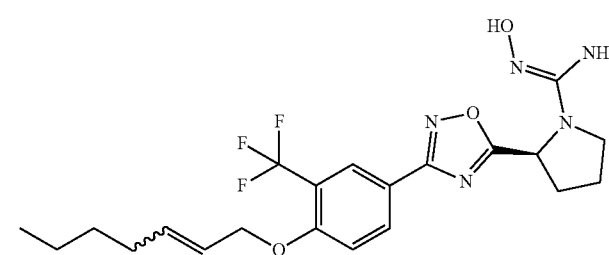 |
| 82 | 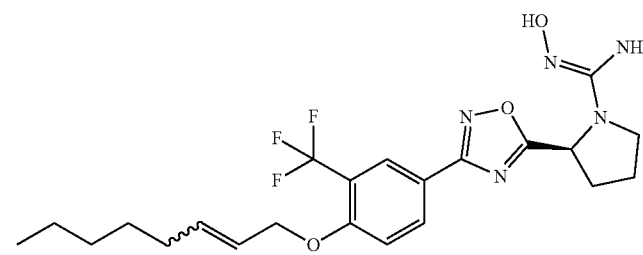 |
| 83 | 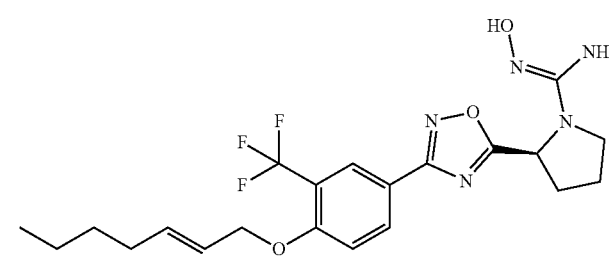 |
| 84 | 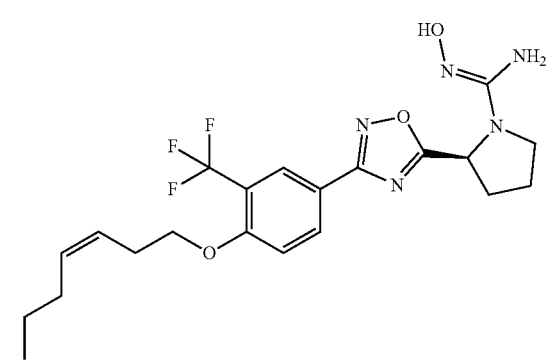 [SMILES: CCC/C=C\CCOc1ccc(-c2noc([C@@H]3CCCN3/C(N)=N/O)n2)cc1C(F)(F)F] |

TABLE 2-continued
Exemplary Formula I Compounds
| Cpd. # | Structure |
|---|---|
| 85 | 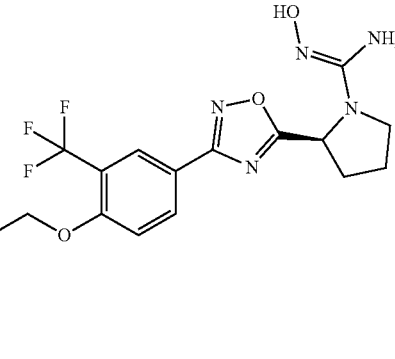 |
| 86 | 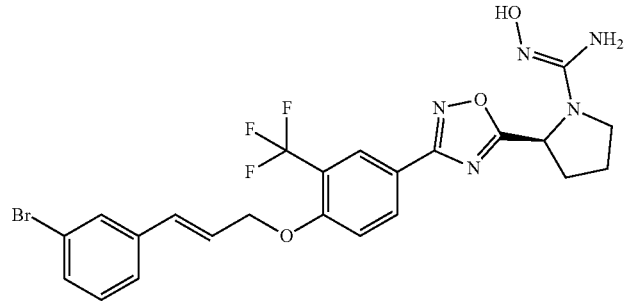 [SMILES: N/C(=N\O)N1CCC[C@H]1c1nc(-c2ccc(OC/C=C/c3cccc(Br)c3)c(C(F)(F)F)c2)no1] |
| 87 | 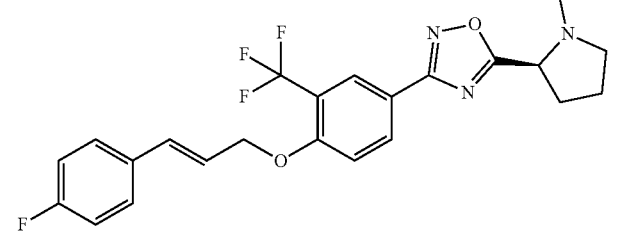 |
| 88 | 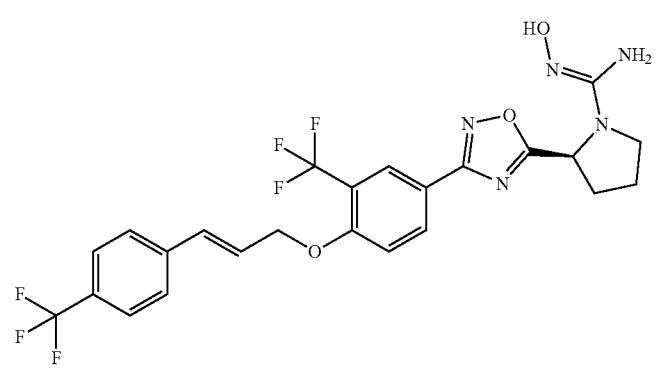 [SMILES: N/C(=N\O)N1CCC[C@H]1c1nc(-c2ccc(OC/C=C/c3ccc(C(F)(F)F)cc3)c(C(F)(F)F)c2)no1] |

TABLE 2-continued

Exemplary Formula I Compounds

| Cpd. # | Structure |
|---|---|
| 89 | 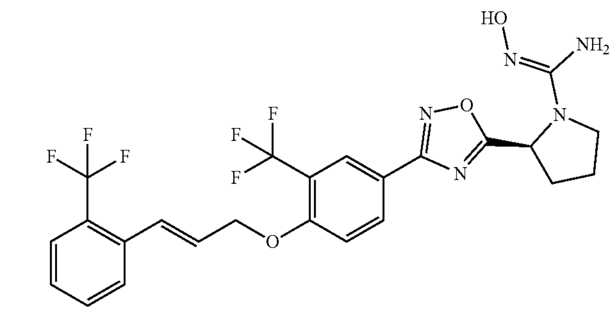 [SMILES: N/C(=N\O)N1CCC[C@H]1c1nc(-c2ccc(OC/C=C/c3ccccc3C(F)(F)F)c(C(F)(F)F)c2)no1] |
| 90 | 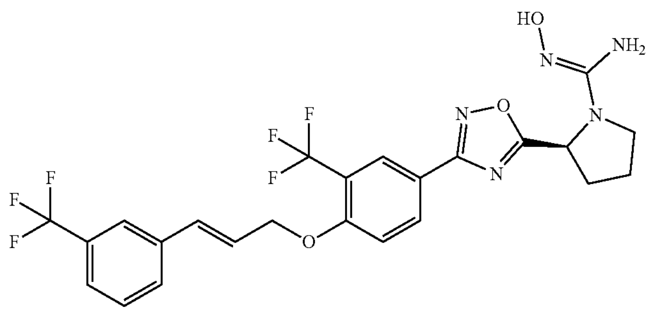 [SMILES: N/C(=N\O)N1CCC[C@H]1c1nc(-c2ccc(OC/C=C/c3cccc(C(F)(F)F)c3)c(C(F)(F)F)c2)no1] |
| 91 | 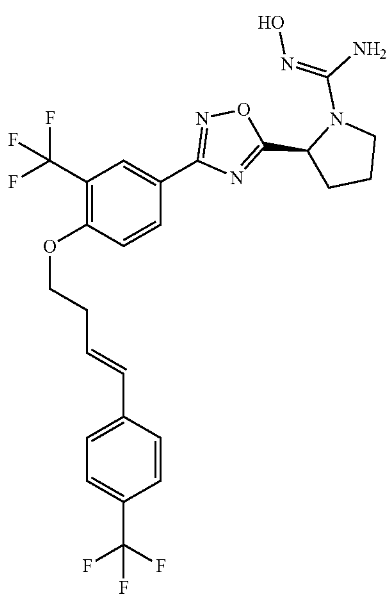 [SMILES: N/C(=N\O)N1CCC[C@H]1c1nc(-c2ccc(OCC/C=C/c3ccc(C(F)(F)F)cc3)c(C(F)(F)F)c2)no1] |
| 92 | 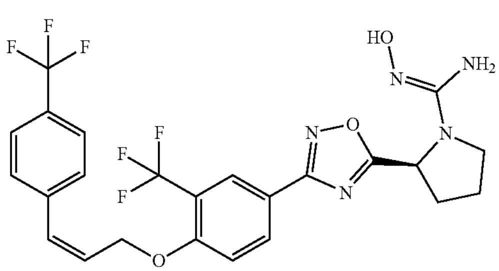 [SMILES: N/C(=N\O)N1CCC[C@H]1c1nc(-c2ccc(OC/C=C\c3ccc(C(F)(F)F)cc3)c(C(F)(F)F)c2)no1] |

101 102
TABLE 2-continued
Exemplary Formula I Compounds
| Cpd. # | Structure |
|---|---|
| 93 | 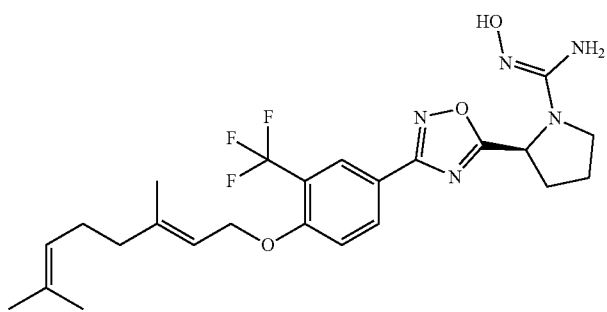 [SMILES: CC(C)=CCC/C(C)=C/COc1ccc(-c2noc([C@@H]3CCCN3/C(N)=N/O)n2)cc1C(F)(F)F] |
| 94 | 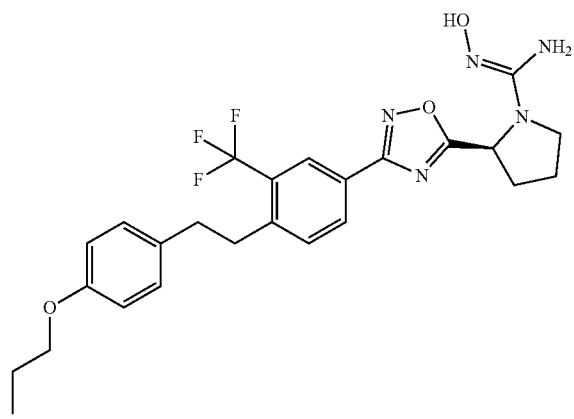 [SMILES: CCCOc1ccc(CCc2ccc(-c3noc([C@@H]4CCCN4/C(N)=N/O)n3)cc2C(F)(F)F)cc1] |
| 95 | 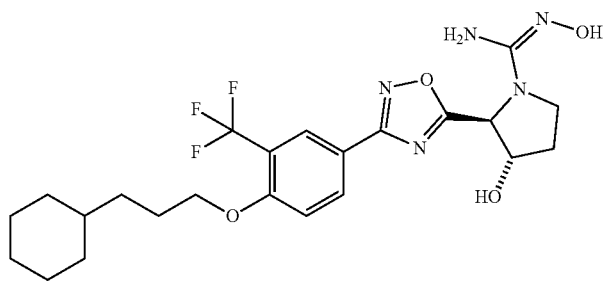 [SMILES: N/C(=N/O)N1CC[C@H](O)[C@H]1c1nc(-c2ccc(OCCCC3CCCCC3)c(C(F)(F)F)c2)no1] |
| 96 | 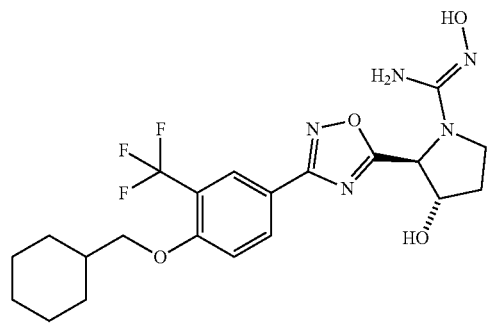 [SMILES: N/C(=N\O)N1CC[C@H](O)[C@H]1c1nc(-c2ccc(OCC3CCCCC3)c(C(F)(F)F)c2)no1] |

TABLE 2-continued

Exemplary Formula I Compounds

| Cpd. # | Structure |
|---|---|
| 97 | 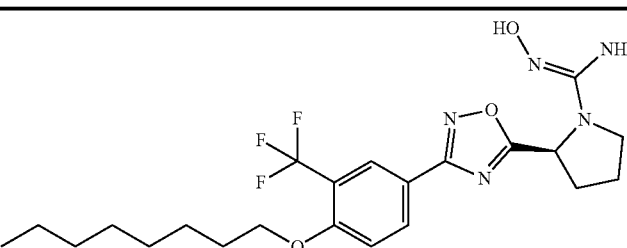 |

In various embodiments, the invention provides a pharmaceutical composition comprising a compound of the invention and a pharmaceutically acceptable excipient. Suitable excipients and dosage forms are discussed above.

The amidoxime compounds of the invention exhibit far greater oral availability than their counterparts without N-hydroxylation on the guanadino moiety. When the inventive compounds are reduced, they reveal the active drugs that are highly potent and selective inhibitors of hSPHK2, having sub-micromolar $K_I$ values. For instance, active compounds can have a $K_I$ for hSPHK2 in the sub-micromolar range, while the $K_I$ for hSPHK1 can be greater than 1 micromolar, or can be greater than 10 micromolar.

Potential uses of Formula I compounds include, but are not limited to, anti-angiogenesis, treating neoplastic disease, treating autoimmune disorders, treating disease characterized by inflammation, treating diseases characterized by fibrosis, and treating vascular injury, such as acute lung injury, sepsis, capillary and vascular leak syndromes, pneumonia, ischemia reperfusion injury, acute kidney injury, as well as enhancing the delivery of therapeutics by improving the integrity of vascular barriers (e.g., Blood Brain Barrier) in diseases where they are disrupted such as, but not limited to cancer and Alzheimer's disease. In various embodiments of the invention, the method of treating any of the foregoing conditions may include administration of an antagonist of any one, or combination thereof, of S1P1, S1P2, S1P3, S1P4, and S1P5.

Formula I compounds also are used to treat autoimmune and inflammatory conditions, i.e., immunomodulate components of the immune system. Hence, in various embodiments of the invention, the SphK inhibitors, once liberated, may affect the cell signaling events associated with, but not limited to, the following interleukins, cytokines, and immunomodulators: a) members of the interleukin-1 (IL-1) family; b) interleukin 2 (IL-2); c) interleukin 4 (IL-4); d) interleukin 5 (IL-5); e) interleukin-6 (IL-6); f) interleukin-12 (IL-12); g) interleukin 13 (IL-13); h) interleukin-23 (IL-23); i) tumor necrosis factor (TNF) alpha; and j) interferon gamma. For example, an inventive compound can be used to treat a disease that is at least in part characterized by the over-expression or undesirable cell-signaling activities mediated by any of the above factors. Thus, in various embodiments, the presently disclosed subject matter provides a method for preventing, treating, managing, and/or ameliorating an autoimmune or inflammatory disorder or one or more symptoms thereof, said method comprising administering to a subject in need thereof a prophylactically and/or therapeutically effective amount of a compound of the presently disclosed subject matter and a prophylactically or therapeutically effective amount of one or more immunomodulatory agents.

Formula I compounds are also useful for the treatment of diseases or disorders that are associated with excessive vascular permeability. Thus, provided herein is a method of treating or preventing these or any other disease associated with an increase in vascular permeability or edema. For example, inhibiting edema formation should be beneficial to overall patient outcome in situations such as inflammation, allergic diseases, cancer, cerebral stroke, myocardial infarction, pulmonary and cardiac insufficiency, renal failure, and retinopathies, to name a few. Furthermore, as edema is a general consequence of tissue hypoxia, it can also be concluded that inhibition of vascular leakage represents a potential approach to the treatment of tissue hypoxia. For example, interruption of blood flow by pathologic conditions (such as thrombus formation) or medical intervention (such as cardioplegia, organ transplantation, and angioplasty) could be treated both acutely and prophylactically using inhibitors of vascular leakage.

Ischemia/reperfusion injury following stroke and myocardial infarction is also characterized by vascular permeability and edema. A deficit in tissue perfusion leads to persistent post-ischemic vasogenic edema, which develops as a result of increased vascular permeability. Tissue perfusion is a measure of oxygenated blood reaching the given tissue due to the patency of an artery and the flow of blood in an artery. Tissue vascularization may be disrupted due to blockage, or alternatively, it may result from the loss of blood flow resulting from blood vessel leakage or hemorrhage upstream of the affected site. The deficit in tissue perfusion during acute myocardial infarction, cerebral stroke, surgical revascularization procedures, and other conditions in which tissue vascularization has been disrupted, is a crucial factor in outcome of the patient's condition. Edema can cause various types of damage including vessel collapse and impaired electrical function, particularly in the heart. Subsequent reperfusion, however, can also cause similar damage in some patients, leading to a treatment paradox. While it is necessary, to unblock an occluded blood vessel or to repair or replace a damaged blood vessel, the ensuing reperfusion can, in some cases, lead to further damage. Likewise, during bypass surgery, it is necessary to stop the heart from beating and to have the patient hooked to a heart pump. Some patients who undergo bypass surgery, for example, may actually experience a worsening of condition ("post-pump syndrome"), which may be the result of ischemia during cessation of cardiac function during surgery. An arterial blockage may cause a reduction in the flow of blood, but even after the blockage is removed and the artery is opened, if tissue reperfusion fails to occur, further tissue damage may result. For example, disruption of a clot may trigger a chain of events leading to loss of tissue perfusion, rather than a gain of perfusion.

Additional diseases and disorders characterized by undesirable vascular permeability include, for example, infectious and non-infectious diseases that may result in a cytokine storm. A cytokine storm can be precipitated by a number of infectious and non-infectious diseases including, for example, graft versus host disease (GVHD), adult respiratory distress syndrome (ARDS), sepsis, avian influenza, smallpox, and systemic inflammatory response syndrome (SIRS).

Accordingly, in various embodiments, the invention can provide a method of inhibiting a sphingosine kinase, comprising contacting the sphingosine kinase with an effective amount or concentration of a compound of formula (I) of the invention, or an effective amount of a pharmaceutical composition of the invention. For example, the sphingosine kinase can be sphingosine kinase type 1 or sphingosine kinase type 2, or both.

In various embodiments the compound of formula (I) liberates a selective inhibitor of one of sphingosine kinases type 1 or type 2 relative to the other of sphingosine kinases type 1 or type 2.

The invention provides, in various embodiments, a method of inhibiting angiogenesis in a tumor, comprising contacting the tumor with an effective amount or concentration of a compound of formula (I).

The invention provides, in various embodiments, a method of treatment of a patient afflicted by a neoplastic disease, comprising administering to the patient an effective dose of a compound of formula (I). For example, the effective dose of the compound of formula (I) can inhibit tumor growth, metastasis, or angiogenesis. More specifically, the compound of formula (I) can inhibit angiogenesis associated with the neoplastic disease, such as by regulation of S1P levels in tissue or serum.

The invention provides, in various embodiments, a method of treatment of a disease in a patient afflicted therewith, wherein the disease involves excess vascular growth, comprising administering to the patient an effective dose of a compound of formula (I). For example, the disease can be macular degeneration or diabetic retinopathy. More specifically, administering to the patient can comprise injecting a pharmaceutical composition comprising an effective dose of a compound of formula (I) into the posterior eye in depot form.

The invention provides, in various embodiments, a method of treatment of an allergic disease in a patient afflicted therewith, comprising administering to the patient an effective dose of a compound of formula (I). For example, the allergic disease can be asthma. The asthma can be due to overproduction of Th2 cytokines.

The invention provides, in various embodiments, a method of treatment of an inflammatory disease of the eye in a patient afflicted therewith, comprising administering to the patient an effective dose of a compound of formula (I). For example, the disease of the eye can be uveitis, scleritis, or vitritis.

The invention provides, in various embodiments, a method of treatment of an inflammatory disease of the kidney in a patient afflicted therewith, comprising administering to the patient an effective dose of a compound of formula (I). More specifically, the inflammatory disease of the kidney can be glomerulonephritis, glomerular injury, nephrotic syndrome, interstitial nephritis, lupus nephritis, Goodpasture's disease, Wegener's granulomatosis, renal vasculitis, IgA nephropathy, diabetic nephropathy, chronic allograft nephropathy, or idiopathic glomerular disease.

The invention provides, in various embodiments, a method of treatment of a fibrotic disease in a patient afflicted therewith, comprising administering to the patient an effective dose of a compound of formula (I). For example, the fibrotic disease can be pulmonary fibrosis, renal fibrosis, cardiac fibrosis, or hepatic fibrosis.

The invention provides, in various embodiments, a method of treatment of a patient afflicted with any of acute lung injury, sepsis, capillary leak syndrome, pneumonia, ischemia reperfusion injury, acute kidney injury, diabetic nephropathy, age-related macular degeneration, diabetic retinopathy, pulmonary fibrosis, or renal fibrosis, comprising administering to the patient an effective dose of a compound of formula (I).

The invention provides, in various embodiments, a method of enhancing delivery of a therapeutic agent to a patient by improving the integrity of a vascular barrier in a disease where the vascular barrier is disrupted, comprising administering to the patient an effective dose of a compound of formula (I). More specifically, the disease can be cancer or Alzheimer's disease. The vascular barrier can be the blood-brain barrier.

The invention provides, in various embodiments, a method of medical treatment of disease in a patient afflicted therewith, wherein the treatment involves the regulation of endothelial cell barrier function as a result of the inhibition of sphingosine kinase enzymatic activity, comprising administering to the patient an effective dose of a compound of Formula (I). For example, the disease can be acute lung injury, sepsis, capillary leak syndrome, pneumonia, ischemia reperfusion injury, acute kidney injury, diabetic nephropathy, age-related macular degeneration, diabetic retinopathy, pulmonary fibrosis, or renal fibrosis. For example, the compound of formula (I) can be a selective inhibitor of sphingosine kinase type 2. The administration of the effective dose of the compound of formula (I) can increase blood levels of sphingosine-1-phosphate.

The invention provides, in various embodiments, a method of treatment of an autoimmune disease in a patient afflicted therewith, comprising administering to the patient an effective dose of a compound of formula (I). For example, the autoimmune disease can be multiple sclerosis, type I diabetes, inflammatory bowel diseases, Crohn's disease, ulcerative colitis, Grave's disease, Addison's disease, dermatomyositis, myasthenia gravis, systemic lupus erythematosus, scleroderma, or psoriasis.

The invention provides, in various embodiments, a method of treatment of atherosclerosis in a patient afflicted therewith, comprising administering to the patient an effective dose of a compound of formula (I).

The invention provides, in various embodiments, a method of treatment of pulmonary arterial hypertension in a patient afflicted therewith, comprising administering to the patient an effective dose of a compound of formula (I).

In any of the methods of treatment and medical uses disclosed and claimed herein, the compound of formula (I) can be any of the embodiments of the compound as disclosed in Table 1, or as covered by any of the generic and subgeneric descriptions of the bioactive inhibitor of a sphingosine kinase.

Materials and Methods

Recombinant baculovirus encoding human sphingosine kinase type 1 (SPHK1) was used to infect Sf9 insect cells and after 2-5 days, cleared lysates were prepared and used without further purification. Human SPHK2, which was partially purified from baculovirus-infected Sf9 cell lysates, was purchased from a commercial source. Sphingosine kinase assays were performed using standard protocols. Product [$^{32}$P]S1P was recovered by binding to cation exchange paper and quantified by scintillation counting. In some cases, [$^{32}$P]S1P was recovered by organic extraction, displayed by thin layer chromatography, recovered and quantified by scintillation counting.

EXAMPLES

Example 1: Synthesis and Characterization of (S)-amino(2-(3-(4-(octyloxy)-3-(trifluoromethyl)phenyl)-1,2,4-oxadiazol-5-yl)pyrrolidin-1-yl)methaniminium chloride (2A)

Scheme 1 below exemplifies synthetic methodology for making compounds of Formulae IA and IB. With the exception of final compound 2A, compound numbering in Scheme 1 pertains only to the depicted compounds.

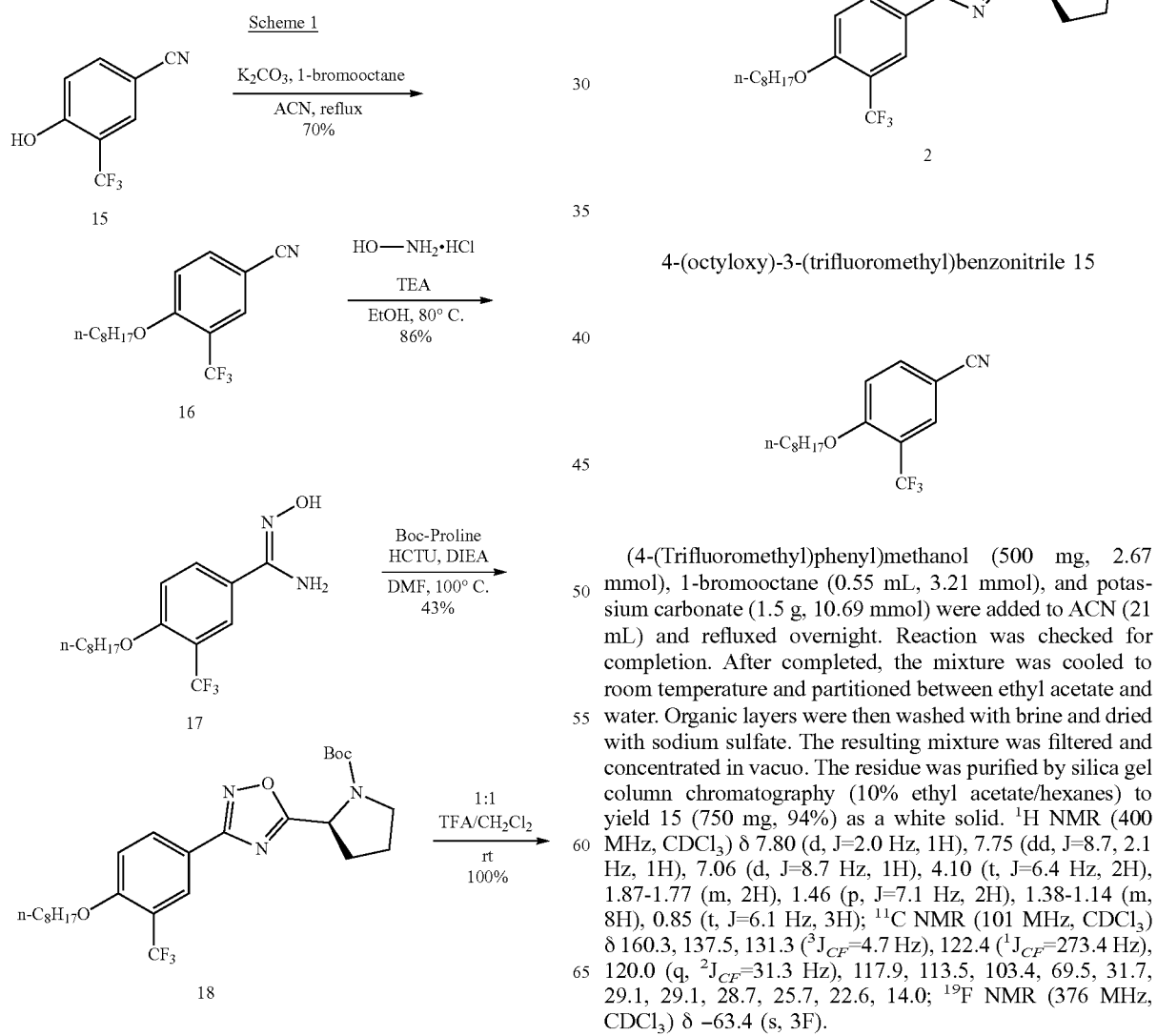

4-(octyloxy)-3-(trifluoromethyl)benzonitrile 15

(4-(Trifluoromethyl)phenyl)methanol (500 mg, 2.67 mmol), 1-bromooctane (0.55 mL, 3.21 mmol), and potassium carbonate (1.5 g, 10.69 mmol) were added to ACN (21 mL) and refluxed overnight. Reaction was checked for completion. After completed, the mixture was cooled to room temperature and partitioned between ethyl acetate and water. Organic layers were then washed with brine and dried with sodium sulfate. The resulting mixture was filtered and concentrated in vacuo. The residue was purified by silica gel column chromatography (10% ethyl acetate/hexanes) to yield 15 (750 mg, 94%) as a white solid. $^1$H NMR (400 MHz, CDCl$_3$) δ 7.80 (d, J=2.0 Hz, 1H), 7.75 (dd, J=8.7, 2.1 Hz, 1H), 7.06 (d, J=8.7 Hz, 1H), 4.10 (t, J=6.4 Hz, 2H), 1.87-1.77 (m, 2H), 1.46 (p, J=7.1 Hz, 2H), 1.38-1.14 (m, 8H), 0.85 (t, J=6.1 Hz, 3H); $^{13}$C NMR (101 MHz, CDCl$_3$) δ 160.3, 137.5, 131.3 ($^3J_{CF}$=4.7 Hz), 122.4 ($^1J_{CF}$=273.4 Hz), 120.0 (q, $^2J_{CF}$=31.3 Hz), 117.9, 113.5, 103.4, 69.5, 31.7, 29.1, 29.1, 28.7, 25.7, 22.6, 14.0; $^{19}$F NMR (376 MHz, CDCl$_3$) δ −63.4 (s, 3F).

(Z)—N'-hydroxy-4-(octyloxy)-3-(trifluoromethyl)benzimidamide 16

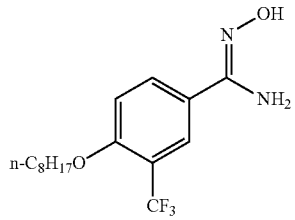

15 (750 mg, 2.5 mmol) was dissolved in ethanol (13 mL). Triethylamine (1.15 mL, 8.27 mmol) and hydroxylamine hydrochloride (348 mg, 5.01 mmol) was added and the reaction mixture was refluxed overnight. The organic solvent was removed under reduced pressure and the residue was purified by silica gel column chromatography (50% ethyl acetate/hexanes) to yield 16 (700 mg, 84%) as white solid. $^1$H NMR (400 MHz, Methanol-$d_4$) δ 7.89 (d, J=2.1 Hz, 1H), 7.82 (dd, J=8.7, 2.2 Hz, 1H), 7.15 (d, J=8.7 Hz, 1H), 4.17 (t, J=6.2 Hz, 2H), 1.86-1.75 (m, 2H), 1.51 (p, J=7.1 Hz, 2H), 1.41-1.23 (m, 8H), 0.91 (t, J=6.6 Hz, 3H); $^{13}$C NMR (101 MHz, Methanol-$d_4$) δ 159.3, 154.1, 132.4, 125.9 (q, $^3J_{CF}$=5.3 Hz), 125.0 (q, $^1J_{CF}$=273.1 Hz), 119.6 (q, $^2J_{CF}$=30.9 Hz), 113.9, 69.9, 32.9, 30.3, 30.3, 30.1, 26.9, 23.7, 14.4; $^{19}$F NMR (376 MHz, Methanol-$d_4$) δ −63.7 (s, 3F); HRMS (ESI+): Calcd for $C_{16}H_{24}F_3N_2O_2$ [M+H]: 333.1789, Found: 333.1778.

(S)-tert-butyl 2-(3-(4-(octyloxy)-3-(trifluoromethyl)phenyl)-1,2,4-oxadiazol-5-yl)pyrrolidine-1-carboxylate 17

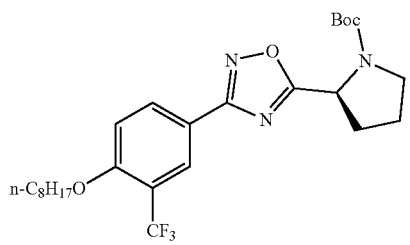

DIEA (0.66 mL, 3.79 mmol) was added to a solution of (S)-1-(tert-butoxycarbonyl)pyrrolidine-2-carboxylic acid (554 mg, 2.53 mmol) and 16 (700 mg, 2.11 mmol) in DMF (11 mL). HCTU (1.3 g, 3.16 mmol) was then added to the resulting mixture at room temperature and stirred at 100° C. overnight. At this time, TLC showed complete conversion of starting material. The solution was partitioned between ethyl acetate and LiBr aqueous solution. The aqueous solution was extracted with ethyl acetate and the combined organic layers were washed with brine, dried over $Na_2SO_4$ and concentrated via vacuum. The residue was purified by silica gel column chromatography (100% $CH_2Cl_2$ then switched to 15% ethyl acetate/hexanes) to yield 17 (690 mg, 64%) as an oil. $^1$H NMR (400 MHz, CDCl$_3$) δ 8.28 (s, 1H), 8.18 (d, J=8.7 Hz, 1H), 7.07 (d, J=8.6 Hz, 1H), 5.26-4.85 (m, 1H), 4.11 (t, J=6.2 Hz, 2H), 3.76-3.64 (m, 1H), 3.62-3.44 (m, 1H), 2.48-2.31 (m, 1H), 2.21-2.10 (m, 2H), 2.07-1.96 (m, 1H), 1.84 (p, J=6.7 Hz, 2H), 1.53-1.43 (m, 5H), 1.39-1.22 (m, 14H), 0.88 (t, J=6.5 Hz, 3H); $^{13}$C NMR (101 MHz, CDCl$_3$) δ 180.9, 167.4, 159.4, 153.6, 132.5, 126.5, 123.6 (q, $^1J_{CF}$=275.9 Hz), 119.8, 118.6, 113.0, 80.6, 69.2, 53.9, 46.5, 32.5, 31.9, 31.6, 29.3, 29.0, 28.3, 25.9, 24.5, 23.8, 22.8, 14.2; $^{19}$F NMR (376 MHz, CDCl$_3$) δ −62.8 (d, J=15.1 Hz, 3F); HRMS (ESI+): Calcd for $C_{26}H_{36}F_3N_3O_4Na$ [M+Na]: 534.2555, Found: 534.2506.

(S)-2-(3-(4-(octyloxy)-3-(trifluoromethyl)phenyl)-1,2,4-oxadiazol-5-yl)pyrrolidin-1-ium 2,2,2-trifluoroacetate 18

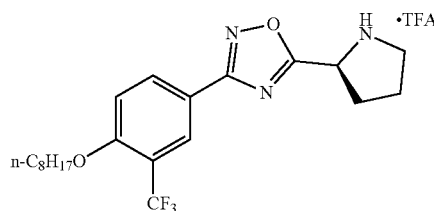

17 (690 mg 1.35 mmol) was dissolved in dichloromethane (3.4 mL). Trifluoroacetic acid (3.4 mL) was added to the reaction mixture and the mixture was stirred 1-2 hours open to air at room temperature. The organic solvent was then removed under reduced pressure. The residue was concentrated via vacuum to yield 18 as a yellow oil. $^1$H NMR (400 MHz, Methanol-$d_4$) δ 8.26 (d, J=7.4 Hz, 2H), 7.32 (d, J=9.4 Hz, 1H), 5.18 (t, J=7.8 Hz, 1H), 4.17 (t, J=6.2 Hz, 2H), 3.67-3.45 (m, 2H), 2.70-2.60 (m, 1H), 2.48-2.34 (m, 1H), 2.33-2.16 (m, 2H), 1.88-1.76 (m, 2H), 1.50 (p, J=7.1 Hz, 2H), 1.41-1.22 (m, 8H), 0.88 (t, J=6.7 Hz, 3H); $^{13}$C NMR (101 MHz, Methanol-$d_4$) δ 176.3, 168.7, 161.0, 134.0, 127.3 (q, $^3J_{CF}$=5.5 Hz), 124.6 (q, $^1J_{CF}$=274.9 Hz), 120.3 (q, $^2J_{CF}$=39.0 Hz), 119.0, 114.9, 70.3, 55.5, 47.3, 32.9, 30.3, 30.2, 30.0, 26.9, 24.5, 23.7, 14.4; $^{19}$F NMR (376 MHz, CDCl$_3$) δ −64.2 (s, 3F); HRMS (ESI+): Calcd for $C_{21}H_{29}F_3N_3O_2$+[M+]: 412.2211, Found: 412.2215.

(S,Z)-tert-butyl (((tert-butoxycarbonyl)amino)(2-(3-(4-(octyloxy)-3-(trifluoromethyl)phenyl)-1,2,4-oxadiazol-5-yl)pyrrolidin-1-yl)methylene)carbamate 20

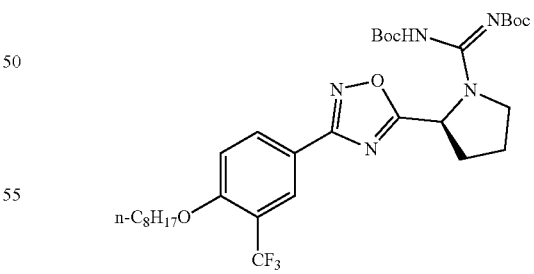

DIEA (0.1 mL, 0.50 mmol) was added to a solution of 19 (34 mg, 0.08 mmol) and (Z)-tert-butyl (((tert-butoxycarbonyl)imino)(1H-pyrazol-1-yl)methyl)carbamate (20 mg, 0.07 mmol) in acetonitrile (0.4 mL). The resulting reaction mixture was then stirred at room temperature for 3 days. The organic solvent was removed under reduced pressure and the residue was purified by silica gel column chromatography (2:1 ethyl acetate:hexane) to yield 20 (24 mg, 45%) as a clear oil. $^1$H NMR (400 MHz, CDCl$_3$) δ 8.28 (d, J=2.0 Hz, 1H), 8.18 (dd, J=8.7, 2.1 Hz, 1H), 7.05 (d, J=8.8 Hz, 1H), 5.60 (dd, J=7.8, 4.5 Hz, 1H), 4.11 (t, J=6.4 Hz, 2H), 3.94-3.75 (m, 2H), 2.50-2.40 (m, 1H), 2.30-2.12 (m, 2H), 2.08-1.99 (m, 1H), 1.89-1.77 (m, 2H), 1.56-1.22 (m, 27H), 0.88 (t, J=6.4 Hz, 3H); $^{13}$C NMR (101 MHz, CDCl$_3$) δ 179.3, 167.4, 162.1, 159.4, 153.8, 150.5, 132.6, 126.9 (q, $^3J_{CF}$=5.0 Hz), 123.4 (q, $^1J_{CF}$=276.7 Hz), 119.5 (q, $^2J_{CF}$=33.3 Hz), 113.0, 110.2, 82.4, 79.7, 69.2, 55.4, 49.6, 31.9, 29.8, 29.3, 29.0, 28.2, 28.1, 25.9, 22.8, 14.2; $^{19}$F NMR (376 MHz, CDCl$_3$) δ -62.8 (s, 3F); HRMS (ESI+): Calcd for C$_{32}$H$_{47}$F$_3$N$_5$O$_6$ [M+H]: 654.3478, Found: 654.3506.

(S)-amino(2-(3-(4-(octyloxy)-3-(trifluoromethyl)phenyl)-1,2,4-oxadiazol-5-yl)pyrrolidin-1-yl)methaniminium chloride (2A)

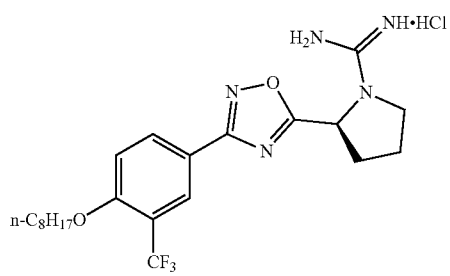

Hydrogen chloride gas is passed through a solution of 20 (9 mg, 0.01 mmol) in methanol (1 mL) for 5 minutes. The organic solvent was then removed under reduced pressure to yield 2 (5 mg, 80%) as white solid. $^1$H NMR (400 MHz, Methanol-d$_4$) δ 8.27 (dd, J=8.6, 2.1 Hz, 2H), 8.24 (d, J=2.0 Hz, 1H), 7.35 (d, J=8.7 Hz, 1H), 5.46 (dd, J=7.9, 1.7 Hz, 1H), 4.20 (t, J=6.2 Hz, 2H), 3.80 (td, J=9.5, 2.5 Hz, 1H), 3.64 (td, J=9.6, 7.4 Hz, 1H), 2.65-2.47 (m, 2H), 2.30-2.21 (m, 1H), 2.19-2.04 (m, 1H), 1.90-1.81 (m, 2H), 1.54 (p, J=6.7 Hz, 2H), 1.46-1.30 (m, 8H), 0.92 (t, J=6.7 Hz, 3H); $^{13}$C NMR (126 MHz, Methanol-d$_4$) δ 179.2, 168.6, 160.9, 157.1, 133.9, 127.1 (q, $^3J_{CF}$=5.5 Hz), 124.8 (q, $^1J_{CF}$=272.8 Hz), 120.3 (q, $^2J_{CF}$=29.9 Hz), 119.3, 114.8, 70.3, 56.5, 32.9, 32.7, 30.3, 30.2, 30.0, 26.9, 24.3, 23.7, 14.4; $^{19}$F NMR (376 MHz, Methanol-d$_4$) δ -64.2 (s, 3F); HRMS (ESI+): Calcd for C$_{22}$H$_{31}$F$_3$N$_5$O$_2$+[M+H]: 454.2429, Found: 454.2435.

Examples 2-14: Synthesis and Characterization of Formula IA and IB Compounds Wherein X is Indolyl Scheme 2 outlines general synthetic methodology for the preparation of Compound Nos 1A-4A, 7A, 8B, 9B, 10B, 11B, 17A, 18A, 74A, 75A. Compound numbering in Scheme 2 is internal to the Scheme, while the subsequent procedures refer where applicable to the final compounds.

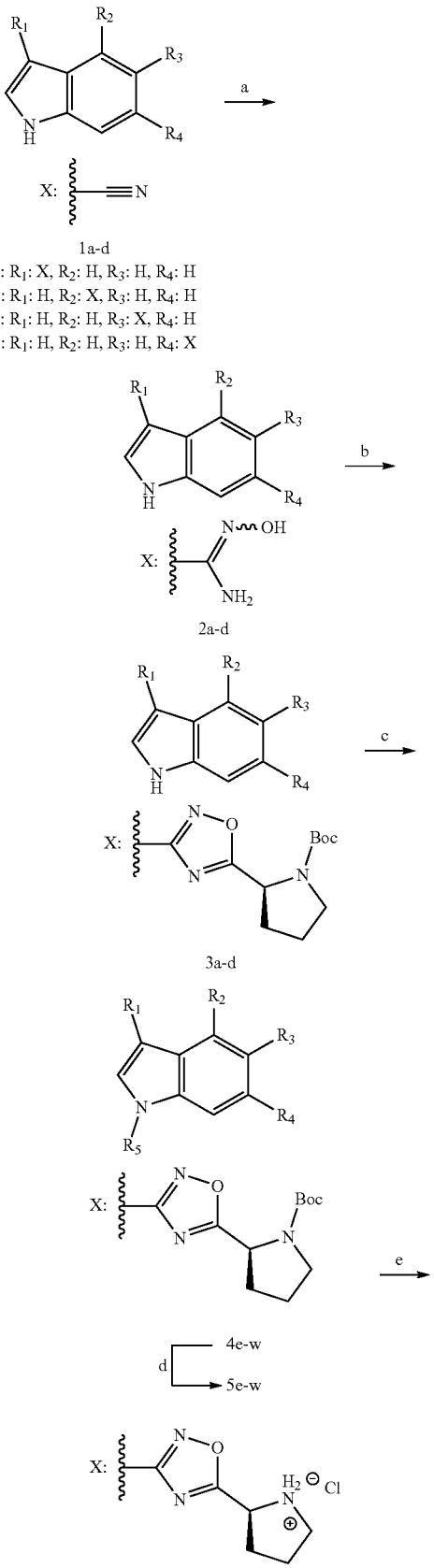

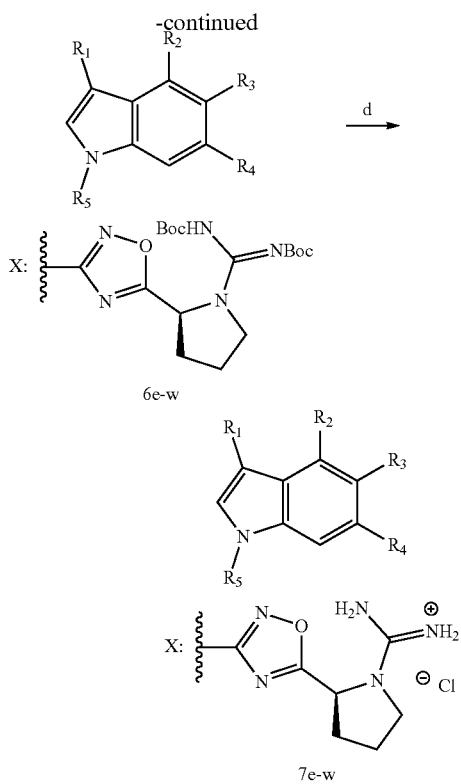

6e-w 7e-w e: $R_1$: X, $R_2$: H, $R_3$: H, $R_4$: H, $R_5$: heptyl
f: $R_1$: X, $R_2$: H, $R_3$: H, $R_4$: H, $R_5$: octyl
g: $R_1$: X, $R_2$: H, $R_3$: H, $R_4$: H, $R_5$: nonyl
h: $R_1$: X, $R_2$: H, $R_3$: H, $R_4$: H, $R_5$: decyl
i: $R_1$: X, $R_2$: H, $R_3$: H, $R_4$: H, $R_5$: undecyl
j: $R_1$: X, $R_2$: H, $R_3$: H, $R_4$: H, $R_5$: dodecyl
k: $R_1$: H, R2: X, $R_3$: H, $R_4$: H, $R_5$: heptyl
l: $R_1$: H, R2: X, $R_3$: H, $R_4$: H, $R_5$: octyl
m: $R_1$: H, R2: X, $R_3$: H, $R_4$: H, $R_5$: nonyl
n: $R_1$: H, R2: X, $R_3$: H, $R_4$: H, $R_5$: decyl
o: $R_1$: H, R2: H, $R_3$: X, $R_4$: H, $R_5$: hexyl
p: $R_1$: H, R2: H, $R_3$: X, $R_4$: H, $R_5$: heptyl
q: $R_1$: H, R2: H, $R_3$: X, $R_4$: H, $R_5$: octyl
r: $R_1$: H, R2: H, $R_3$: X, $R_4$: H, $R_5$: nonyl
s: $R_1$: H, R2: H, $R_3$: X, $R_4$: H, $R_5$: decyl
t: $R_1$: H, R2: H, $R_3$: H, $R_4$: X, $R_5$: heptyl
u: $R_1$: H, R2: H, $R_3$: H, $R_4$: X, $R_5$: octyl
v: $R_1$: H, R2: H, $R_3$: H, $R_4$: X, $R_5$: nonyl
w: $R_1$: H, R2: H, $R_3$: H, $R_4$: X, $R_5$: decyl Scheme 2:
a) $NH_2OH \cdot HCl$, (3 equiv.), TEA (3 equiv.), EtOH, 80° C., 6 h, (91-99%);
b) Boc-L-proline (1.4 equiv.), DIEA (1.4 equiv.), HCTU (1.8 equiv.), DMF, 110° C., 18 h, (5-28%);
c) R-Br (3 equiv.), NaH (1.5 equiv.), DMF, 0° C.-RT, 30 min, (9-97%);
d) HCl/MeOH, (80-100%);
e) DIEA (3 equiv.), N,N-DiBoc-1H-pyrazole-1carboxamidine (1.05 equiv.),$CH_3CN$, 80° C., microwave, 2 h, (41-99%).

General Procedures (Scheme 2)
General Procedure 1: Amidoxime Formation

Cyanoindole 1a-d (1 equiv.) and hydroxylamine hydrochloride (3 equiv.), and TEA (3 equiv.) were added to a round bottom flask containing ethanol. The reaction mixture was heated to 80° C. for 12 hours or until the reaction appeared to have gone to completion via monitoring by TLC. The solution was cooled to room temperature and the solvent was removed under reduced pressure. The resulting solid was loaded onto celite and purified on a silica gel column with 0-10% methanol in ethyl acetate.

General Procedure 2: 1,2,4-Oxadiazole Formation

Amidoxime 2a-d (1 equiv.), Boc-L-Proline (1.4 equiv.), and DIEA (1.4 equiv.) were added to a round bottom flask containing DMF. After adding HCTU (1.8 equiv.) to the reaction, the solution was heated to 120° C. for 12-16 hours. Once the reaction cooled to room temperature, the solution was extracted with ethyl acetate and saturated LiBr solution. The combined organic layers were washed with brine and dried over sodium sulfate. After filtration to remove the sodium sulfate and concentration via reduced pressure, the resulting brown oil was purified on a silica column with hexane and ethyl acetate.

General Procedure 3: N-alkylation of Indole

Indole 3a-d was added to a round bottom flask which was subsequently purged with nitrogen and sealed with a rubber septum. The flask was placed in an ice bath and DMF (1 mL) was added. Sodium hydride (1.5 equiv.) was added to the flask in one addition and the septum was replaced on the vessel. The reaction mixture was stirred for 30 minutes at 0° C. and the ice bath was replenished. Alkyl halide (3 equiv.) was added to the cooled solution drop-wise. The reaction solution was stirred for an additional 30 minutes while the solution warmed to room temperature. The reaction was quenched with the slow addition of D.I. water. The product was extracted with ethyl acetate and saturated LiBr. The combined organic layers were washed with brine and dried over sodium sulfate. After filtration and concentration via reduced pressure, the resulting oil was purified on a silica column with hexane and ethyl acetate.

General Procedure 4: Boc-deprotection

Boc-amine 4e-w or Di-Boc-guanidine 6e-w was dissolved in methanol. HCl gas was bubbled into the solution for 1 minute. The solution was stirred until TLC indicated that all of the Boc-protected amine had been consumed. The solvent was removed under reduced pressure. The resulting white to light yellow solid was washed with diethyl ether to yield pure product.

General Procedure 5: Guanylation of Secondary Amines

Hydrogen chloride salt of 5e-w (1 equiv.) was added to a round bottom flask with acetonitrile and DIEA (3 equiv.). The solution was allowed to stir for 10 minutes before being transferred to a microwave vial containing (Z)-Tert-butyl (((tert-butoxycarbonyl)imino)(1H-pyrazol-1-yl)methyl)carbamate (1.05 equiv). The vessel was capped and placed in the CEM microwave where it was heated to 80° C. for 2 hours. The solvent was removed under reduced pressure and the resulting yellow oil was purified on silica gel with hexanes and ethyl acetate to yield pure product.

Characterization (Scheme 2)

N'-hydroxy-1H-indole-3-carboximidamide (2a)

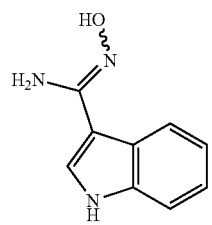 [SMILES: NC(=NO)c1c[nH]c2ccccc12]

2a was prepared using general procedure 1. Purification on a silica gel column with 70-100% ethyl acetate in hexanes produced 2a as a mixture of enantiomers (0.61 g, 99%), a tan solid. $^1$H NMR (400 MHz, CD$_3$OD) δ 8.14-8.10 (m, 0.4H), 7.96 (ddd, J=7.9, 1.3, 0.8 Hz, 1H), 7.92 (s, 0.4H), 7.61 (s, 1H), 7.43-7.40 (m, 0.4H), 7.40-7.36 (m, 1H), 7.19-7.06 (m, 3H). $^{13}$C NMR (101 MHz, CD$_3$OD) δ 173.06, 170.88, 153.79, 138.03, 130.13, 126.08, 123.42, 123.24, 122.06, 121.68, 121.60, 121.16, 112.81, 112.56, 108.63. HRMS (ESI+): Calcd for C$_9$H$_9$N$_3$O [M+H]$^+$: 176.1592, Found: 176.0813.

N'-hydroxy-1H-indole-4-carboximidamide (2b)

2b was prepared using general procedure 1. Purification on a silica gel column with 70-100% ethyl acetate in hexanes produced 2b as a mixture of enantiomers (1.12 g, 91%), a tan solid. $^1$H NMR (500 MHz, CD$_3$OD) δ 7.45 (dd, J=8.1, 1.6 Hz, 1H), 7.28 (dd, J=3.4, 1.8 Hz, 1H), 7.24 (dd, J=7.2, 1.6 Hz, 1H), 7.13 (td, J=7.8, 1.8 Hz, 1H), 6.78 (dd, J=3.0, 1.8 Hz, 1H). $^{13}$C NMR (126 MHz, CD$_3$OD) δ 156.61, 138.10, 127.13, 126.30, 125.70, 121.84, 119.25, 113.79, 102.54. HRMS (ESI+): Calcd for C$_9$H$_9$N$_3$O [M+H]$^+$: 176.1592, Found: 176.0825.

N'-hydroxy-1H-indole-5-carboximidamide (2c)

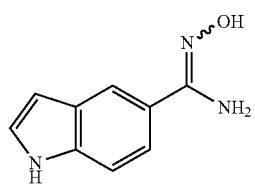 [SMILES: NC(=NO)c1ccc2[nH]ccc2c1]

2c was prepared using general procedure 1. Purification on a silica gel column with 70-100% ethyl acetate in hexanes produced 2c as a mixture of enantiomers (1.78 g, 96%), a tan solid. $^1$H NMR (400 MHz, CD$_3$OD) δ 7.88 (dd, J=1.6, 0.8 Hz, 1H), 7.43-7.37 (m, 2H), 7.25 (d, J=3.2 Hz, 1H), 6.49 (dd, J=3.2, 0.8 Hz, 1H). $^{13}$C NMR (101 MHz, CD$_3$OD) δ 157.16, 137.03, 130.71, 128.86, 127.55, 127.38, 126.62, 121.11, 120.89, 119.19, 118.35, 112.59, 110.45, 102.60, 102.41. HRMS (ESI+): Calcd for C$_9$H$_9$N$_3$O [M+H]$^+$: 176.1592, Found: 176.0812.

N'-hydroxy-1H-indole-6-carboximidamide (2d)

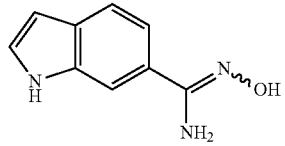

2d was prepared using general procedure 1. Purification on a silica gel column with 70-100% ethyl acetate in hexanes produced 2d as a mixture of enantiomers (1.12 g, 91%), a tan solid. $^1$H NMR (400 MHz, CD$_3$OD) δ 8.03 (dt, J=1.7, 0.9 Hz, 0.1H), 7.72 (dt, J=1.7, 0.8 Hz, 1H), 7.61-7.54 (m, 1H), 7.34 (dd, J=8.3, 1.6 Hz, 1H), 7.27 (d, J=3.2 Hz, 1H), 6.50 (dd, J=3.1, 1.0 Hz, 0.1H), 6.46 (dd, J=3.1, 1.0 Hz, 1H). $^{13}$C NMR (101 MHz, CD$_3$OD) δ 157.16, 137.03, 130.71, 128.86, 127.55, 127.38, 126.62, 121.11, 120.89, 119.19, 118.35, 112.59, 110.50, 110.45, 102.60, 102.46, 102.41. HRMS (ESI+): Calcd for C$_9$H$_9$N$_3$O [M+H]$^+$: 176.1592, Found: 176.0812.

Tert-butyl (S)-2-(3-(1H-indol-3-yl)-1,2,4-oxadiazol-5-yl)pyrrolidine-1-carboxylate (3a)

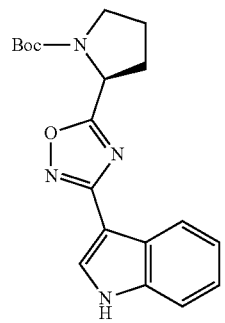 [SMILES: CC(C)(C)OC(=O)N1CCC[C@H]1c1nc(-c2c[nH]c3ccccc23)no1]

3a was prepared using general procedure 2. Purification on a silica gel column with 20-40% ethyl acetate in hexanes produced 3a (100 mg, 5%), a light yellow solid. $^1$H NMR (400 MHz, CDCl$_3$) δ 9.29 (s, 1H), 8.28-8.10 (m, 1H), 7.91 (d, J=2.8 Hz, 1H), 7.45-7.36 (m, 1H), 7.32-7.13 (m, 2H), 5.17 (ddd, J=78.1, 8.5, 3.5 Hz, 1H), 3.76-3.68 (m, 1H), 3.64-3.47 (m, 1H), 2.43-2.30 (m, 1H), 2.24-2.12 (m, 1H), 2.05-1.95 (m, 1H), 1.41 (d, J=82.0 Hz, 8H). $^{13}$C NMR (101 MHz, CDCl$_3$) δ 179.25, 165.41, 154.04, 136.77, 128.73, 127.54, 124.91, 123.31, 122.96, 121.76, 121.56, 121.27, 111.71, 104.43, 80.77, 60.54, 53.95, 46.97, 46.50, 32.46, 31.60, 28.60, 28.29, 24.50, 23.79, 14.30. HRMS (ESI+): Calcd for C$_{19}$H$_{22}$N$_4$O$_3$ [M+Na]$^+$: 377.3927, Found: 377.1582.

Tert-butyl (S)-2-(3-(1H-indol-4-yl)-1,2,4-oxadiazol-5-yl)pyrrolidine-1-carboxylate (3b)

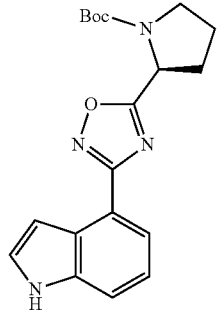 [SMILES: CC(C)(C)OC(=O)N1CCC[C@H]1c1nc(-c2cccc3[nH]ccc23)no1]

3b was prepared using general procedure 2. Purification on a silica gel column with 20-35% ethyl acetate in hexanes produced 3b (0.65 g, 32%), a tan solid. $^1$H NMR (400 MHz, CDCl$_3$) δ 9.31-9.16 (m, 1H), 7.98-7.85 (m, 1H), 7.80-7.72 (m, 1H), 7.56-7.47 (m, 1H), 7.36-7.27 (m, 1H), 7.25-7.16 (m, 1H), 5.31-5.12 (m, 1H), 3.80-3.68 (m, 1H), 3.60-3.47 (m, 1H), 2.44-2.30 (m, 1H), 2.24-2.11 (m, 2H), 2.07-1.94 (m, 1H), 1.46-1.20 (m, 9H). HRMS (ESI+): Calcd for C$_{19}$H$_{22}$N$_4$O$_3$ [M+Na]t 377.3927, Found: 377.1587.

Tert-butyl (S)-2-(3-(1H-indol-5-yl)-1,2,4-oxadiazol-5-yl)pyrrolidine-1-carboxylate (3c)

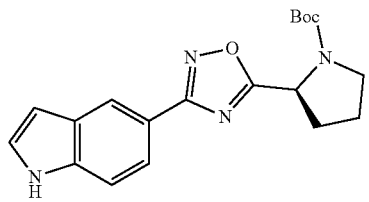 [SMILES: CC(C)(C)OC(=O)N1CCC[C@H]1c1nc(-c2ccc3[nH]ccc3c2)no1]

3c was prepared using general procedure 2. Purification on a silica gel column with 20-40% ethyl acetate in hexanes produced 3c (0.47 g, 16%), a tan solid. $^1$H NMR (400 MHz, CDCl$_3$) δ 8.45-8.28 (m, 1H), 7.94-7.77 (m, 1H), 7.44 (dd, J=31.5, 8.7 Hz, 1H), 7.34-7.23 (m, 1H), 6.66-6.51 (m, 1H), 5.16 (ddd, J=59.4, 8.7, 3.2 Hz, 1H), 3.78-3.64 (m, 1H), 3.62-3.43 (m, 1H), 2.48-2.31 (m, 1H), 2.25-2.10 (m, 2H), 2.05-1.94 (m, 1H), 1.39 (d, J=67.9 Hz, 9H). $^{13}$C NMR (101 MHz, CDCl$_3$) δ 180.08, 179.56, 169.46, 154.53, 153.90, 137.62, 127.97, 125.85, 125.64, 120.89, 120.77, 117.92, 111.77, 111.61, 103.09, 80.55, 77.48, 77.16, 76.84, 53.90, 46.75, 46.44, 38.65, 32.36, 31.52, 28.43, 28.17, 24.33, 23.70. HRMS (ESI+): Calcd for C$_{19}$H$_{22}$N$_4$O$_3$ [M+Na]$^+$: 377.3927, Found: 377.1589.

Tert-butyl (S)-2-(3-(1H-indol-6-yl)-1,2,4-oxadiazol-5-yl)pyrrolidine-1-carboxylate (3d)

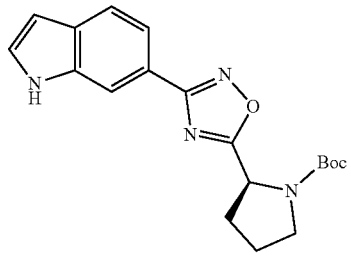 [SMILES: CC(C)(C)OC(=O)N1CCC[C@H]1c1nc(-c2ccc3cc[nH]c3c2)no1]

3d was prepared using general procedure 2. Purification on a silica gel column with 20-50% ethyl acetate in hexanes produced 3d (0.57 g, 28%), a tan solid. $^1$H NMR (500 MHz, CDCl$_3$) δ 8.85 (s, 1H), 8.13 (d, J=50.4 Hz, 1H), 7.88-7.64 (m, 2H), 7.38-7.28 (m, 1H), 6.65-6.54 (m, 1H), 5.17 (ddd, J=75.7, 8.4, 3.3 Hz, 1H), 3.81-3.66 (m, 1H), 3.62-3.46 (m, 1H), 2.48-2.31 (m, 1H), 2.22-2.13 (m, 2H), 2.07-1.93 (m, 1H), 1.40 (d, J=87.4 Hz, 10H). $^{13}$C NMR (126 MHz, CDCl$_3$) δ 180.27, 169.42, 153.99, 135.72, 130.38, 126.81, 121.20, 120.16, 118.92, 111.12, 103.01, 80.84, 54.03, 46.54, 32.47, 28.55, 28.29, 23.81. HRMS (ESI+): Calcd for C$_{19}$H$_{22}$N$_4$O$_3$ [M+H]: 377.3927, Found: 377.1600.

Tert-butyl (S)-2-(3-(1-heptyl-1H-indol-3-yl)-1,2,4-oxadiazol-5-yl)pyrrolidine-1-carboxylate (4e)

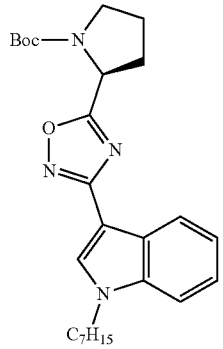

4e was prepared using general procedure 3. Purification on a silica gel column with 0-20% ethyl acetate in hexanes produced 4e (34 mg, 89%), a yellow oil. $^1$H NMR (400 MHz, CDCl$_3$) δ 8.30-8.21 (m, 1H), 7.83 (s, 1H), 7.42-7.36 (m, 1H), 7.35-7.26 (m, 2H), 5.26-5.04 (m, 1H), 4.16 (q, J=6.4, 5.7 Hz, 2H), 3.75 (ddd, J=10.6, 7.4, 5.0 Hz, 1H), 3.57 (dt, J=10.6, 7.0 Hz, 1H), 2.40 (tt, J=10.7, 6.0 Hz, 1H), 2.23-2.11 (m, 2H), 2.01 (ddt, J=9.6, 6.9, 3.6 Hz, 1H), 1.88 (q, J=7.0 Hz, 2H), 1.51-1.18 (m, 17H), 0.93-0.83 (m, 3H). $^{13}$C NMR (101 MHz, CDCl$_3$) δ 179.20, 165.27, 153.81, 136.91, 130.58, 125.63, 122.87, 122.73, 122.13, 121.33, 121.22, 110.01, 102.92, 80.52, 77.48, 77.16, 76.84, 53.93, 47.03, 46.77, 46.47, 32.54, 31.77, 31.63, 30.13, 28.99, 28.55, 28.29, 27.01, 24.50, 23.84, 22.68, 14.17. HRMS (ESI+): Calcd for C$_{26}$H$_{36}$N$_4$O$_3$ [M+K]$^+$: 491.6873, Found: 491.2428.

Tert-butyl (S)-2-(3-(1-octyl-1H-indol-3-yl)-1,2,4-oxadiazol-5-yl)pyrrolidine-1-carboxylate (4f)

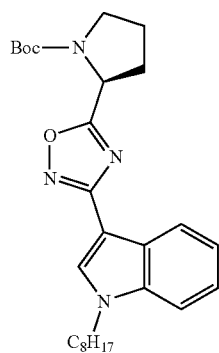

4f was prepared using general procedure 3. Purification on a silica gel column with 0-20% ethyl acetate in hexanes produced 4f (15 mg, 9%), a yellow oil. $^1$H NMR (400 MHz, CDCl$_3$) δ 1H NMR (400 MHz, Chloroform-d) δ 8.29-8.18 (m, 1H), 7.83 (s, 1H), 7.40 (d, J=7.8 Hz, 1H), 7.36-7.23 (m, 3H), 5.27-5.03 (m, 1H), 4.17 (t, J=7.1 Hz, 2H), 3.77-3.65 (m, 1H), 3.62-3.49 (m, 1H), 2.47-2.31 (m, 1H), 2.22-2.11 (m, 2H), 2.03-1.97 (m, 1H), 1.91-1.85 (m, 2H), 1.52-1.16 (m, 18H), 0.93-0.78 (m, 3H). HRMS (ESI+): Calcd for C$_{27}$H$_{38}$N$_4$O$_3$ [M+K]: 505.7139, Found: 505.2567.

Tert-butyl (S)-2-(3-(1-nontyl-1H-indol-3-yl)-1,2,4-oxadiazol-5-yl)pyrrolidine-1-carboxylate (4g)

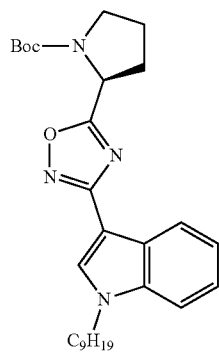

4g was prepared using general procedure 3. Purification on a silica gel column with 0-20% ethyl acetate in hexanes produced 4g (40 mg, 74%), a yellow oil. $^1$H NMR (400 MHz, CDCl$_3$) 8.31-8.20 (m, 1H), 7.83 (s, 1H), 7.44-7.35 (m, 1H), 7.35-7.21 (m, 2H), 5.23-5.03 (m, 1H), 4.16 (t, J=7.1 Hz, 2H), 3.81-3.63 (m, 1H), 3.61-3.50 (m, 1H), 2.45-2.31 (m, 1H), 2.26-2.09 (m, 2H), 2.05-195 (m, 1H), 1.89 (p, J=7.0 Hz, 2H), 1.52-1.19 (m, 19H), 0.87 (t, J=7.0 Hz, 3H). $^{13}$C NMR (101 MHz, MeOD) δ 179.19, 165.27, 153.80, 136.91, 130.57, 125.63, 122.86, 122.72, 122.13, 121.32, 110.00, 102.93, 80.50, 53.93, 47.02, 46.47, 32.53, 31.92, 31.62, 30.12, 29.52, 29.32, 28.54, 28.28, 27.04, 24.49, 23.83, 22.75, 22.74, 14.21. HRMS (ESI+): Calcd for C$_{28}$H$_{40}$N$_4$O$_3$ [M+K]$^+$: 519.7405, Found: 519.2736.

Tert-butyl (S)-2-(3-(1-decyl-1H-indol-3-yl)-1,2,4-oxadiazol-5-yl)pyrrolidine-1-carboxylate (4h)

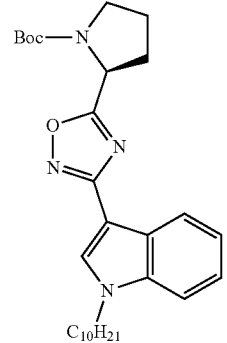

4h was prepared using general procedure 3. Purification on a silica gel column with 0-20% ethyl acetate in hexanes produced 4h (42 mg, 100%), a yellow oil. $^1$H NMR (400 MHz, CDCl$_3$) δ 8.26-8.20 (m, 1H), 7.84 (s, 1H), 7.44-7.35 (m, 1H), 7.35-7.24 (m, 2H), 5.24-5.04 (m, 1H), 4.16 (t, J=7.0 Hz, 2H), 3.75 (m, 1H), 3.61-3.52 (m, 1H), 2.46-2.31 (m, 1H), 2.26-2.12 (m, 2H), 2.07-1.94 (m, 1H), 1.93-1.83 (m, 2H), 1.50-1.20 (m, 22H), 0.87 (t, J=7.0 Hz, 3H). $^{13}$C NMR (101 MHz, CDCl$_3$) δ 179.19, 165.26, 153.80, 136.90, 130.57, 125.62, 122.86, 122.72, 122.12, 121.32, 121.20, 110.00, 102.91, 80.51, 53.92, 47.03, 46.76, 46.46, 32.53, 31.96, 31.62, 30.12, 29.61, 29.56, 29.38, 29.33, 28.54, 28.28, 27.04, 24.49, 23.83, 22.78, 14.23. HRMS (ESI+): Calcd for C$_{29}$H$_{42}$N$_4$O$_3$ [M+K]$^+$: 533.7616, Found: 533.2902.

Tert-butyl (S)-2-(3-(1-undecyl-1H-indol-3-yl)-1,2,4-oxadiazol-5-yl)pyrrolidine-1-carboxylate (4i)

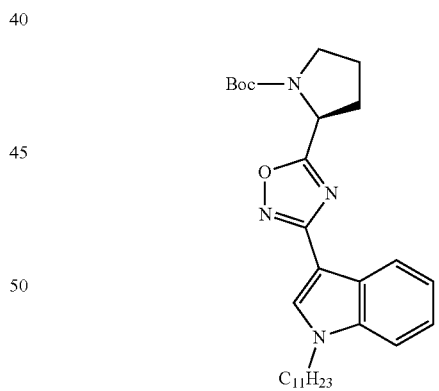

4i was prepared using general procedure 3. Purification on a silica gel column with 0-20% ethyl acetate in hexanes produced 4i (22 mg, 77%), a yellow oil. $^1$H NMR (400 MHz, CDCl$_3$) δ 8.24 (dd, J=6.9, 2.0 Hz, 1H), 7.83 (s, 1H), 7.40 (d, J=7.8 Hz, 1H), 7.28 (d, J=14.4 Hz, 2H), 5.23-5.06 (m, 1H), 4.16 (t, J=7.1 Hz, 2H), 3.75 (dt, J=12.1, 6.0 Hz, 1H), 3.57 (dt, J=10.4, 7.0 Hz, 1H), 2.45-2.29 (m, 1H), 2.24-2.10 (m, 2H), 2.06-1.98 (m, 1H), 1.89 (t, J=7.1 Hz, 2H), 1.53-1.14 (m, 24H), 0.94-0.82 (m, 3H). $^{13}$C NMR (101 MHz, CDCl$_3$) δ 179.21, 165.31, 153.83, 136.95, 130.57, 125.69, 122.88, 122.17, 121.34, 110.00, 103.00, 80.52, 53.96, 47.05, 46.49, 32.56, 32.03, 30.16, 29.69, 29.59, 29.43, 29.36, 28.57, 28.31, 27.08, 23.85, 22.81, 14.25. HRMS (ESI+): Calcd for $C_{30}H_{44}N_4O_3$ [M+Na]$^+$: 531.6851, Found: 531.3354.

Tert-butyl (S)-2-(3-(1-dodecyl-1H-indol-3-yl)-1,2,4-oxadiazol-5-yl)pyrrolidine-1-carboxylate (4j)

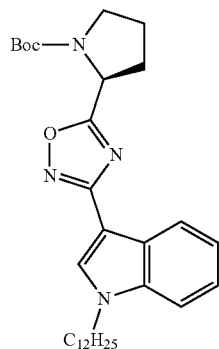

4j was prepared using general procedure 3. Purification on a silica gel column with 0-20% ethyl acetate in hexanes produced 4j (26 mg, 59%), a yellow oil. $^1$H NMR (400 MHz, CDCl$_3$) 1H NMR (400 MHz, Chloroform-d) δ 8.24 (d, J=7.3 Hz, 1H), 7.83 (s, 1H), 7.40 (d, J=7.7 Hz, 1H), 7.26 (s, 2H), 5.29-5.05 (m, 1H), 4.17 (t, J=7.0 Hz, 2H), 3.81-3.67 (m, 1H), 3.61-3.47 (m, 1H), 2.46-2.30 (m, 1H), 2.21-2.12 (m, 1H), 2.05 (s, 1H), 1.88 (d, J=7.1 Hz, 2H), 1.49-1.20 (m, 17H), 0.92-0.77 (m, 3H). $^{13}$C NMR (101 MHz, CDCl$_3$) δ 179.21, 165.30, 145.25, 136.93, 130.60, 125.67, 122.88, 122.17, 121.35, 110.02, 102.96, 80.54, 53.96, 47.07, 46.50, 32.57, 32.05, 30.16, 29.74, 29.60, 29.48, 29.37, 28.31, 27.09, 23.86, 22.83, 14.28. HRMS (ESI+): Calcd for $C_{31}H_{46}N_4O_3$ [M+Na]$^+$: 545.7117, Found: 545.3447.

Tert-butyl (S)-2-(3-(1-heptyl-1H-indol-4-yl)-1,2,4-oxadiazol-5-yl)pyrrolidine-1-carboxylate (4k)

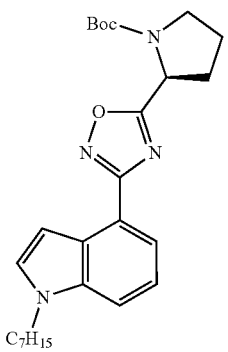

4k was prepared using general procedure 3. Purification on a silica gel column with 0-20% ethyl acetate in hexanes produced 4k (22 mg, 57%), a yellow oil. $^1$H NMR (500 MHz, solvent) δ 7.97-7.91 (m, 1H), 7.50 (d, J=8.2 Hz, 1H), 7.30 (t, J=7.8 Hz, 1H), 7.26-7.22 (m, 1H), 7.20 (d, J=3.1 Hz, 1H), 5.30-5.08 (m, 1H), 4.17 (t, J=7.0 Hz, 2H), 3.77-3.61 (m, 1H), 3.61-3.48 (m, 1H), 2.44-2.35 (m, 1H), 2.24-2.13 (m, 2H), 2.05-1.95 (m, 1H), 1.85 (p, J=8.0, 7.2 Hz, 2H), 1.48-1.20 (m, 19H), 0.86 (t, J=6.9 Hz, 4H). $^{13}$C NMR (126 MHz, CDCl$_3$) δ 179.70, 169.01, 153.81, 136.65, 129.53, 126.32, 121.19, 120.78, 118.50, 112.63, 102.48, 80.57, 54.02, 46.75, 46.50, 32.59, 31.83, 30.50, 29.04, 28.58, 28.33, 27.09, 23.85, 22.70, 14.17. HRMS (ESI+): Calcd for $C_{26}H_{36}N_4O_3$ [M+Na]$^+$: 475.5788, Found: 475.2673.

Tert-butyl (S)-2-(3-(1-octyl-1H-indol-4-yl)-1,2,4-oxadiazol-5-yl)pyrrolidine-1-carboxylate (4l)

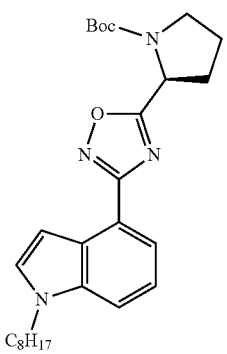

4l was prepared using general procedure 3. Purification on a silica gel column with 0-20% ethyl acetate in hexanes produced 4l (30 mg, 76%), a yellow oil. $^1$H NMR (500 MHz, CDCl$_3$) δ 7.86 (d, J=7.3 Hz, 1H), 7.43 (d, J=8.2 Hz, 1H), 7.23 (t, J=7.8 Hz, 1H), 7.17 (d, J=3.2 Hz, 1H), 7.12 (d, J=3.2 Hz, 1H), 5.22-5.01 (m, 1H), 4.09 (t, J=7.0 Hz, 2H), 3.72-3.58 (m, 1H), 3.54-3.45 (m, 1H), 2.40-2.24 (m, 1H), 2.17-2.06 (m, 2H), 1.99-1.89 (m, 1H), 1.78 (p, J=7.0 Hz, 2H), 1.40 (s, 2H), 1.28-1.12 (m, 19H), 0.79 (t, J=7.1 Hz, 3H). $^{13}$C NMR (126 MHz, CDCl$_3$) δ 179.70, 169.00, 153.81, 136.64, 129.53, 126.32, 121.18, 120.78, 118.50, 112.63, 102.47, 80.56, 54.02, 46.75, 46.50, 32.59, 31.89, 30.49, 29.33, 29.28, 28.57, 28.32, 27.12, 23.85, 22.74, 14.26, 14.19. HRMS (ESI+): Calcd for $C_{27}H_{38}N_4O_3$ [M+Na]$^+$: 489.6054, Found: 489.2820.

Tert-butyl (S)-2-(3-(1-nonyl-1H-indol-4-yl)-1,2,4-oxadiazol-5-yl)pyrrolidine-1-carboxylate (4m)

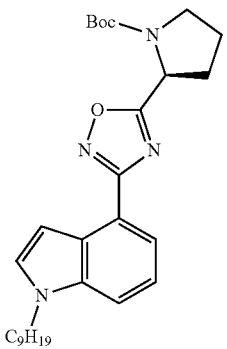

4m was prepared using general procedure 3. Purification on a silica gel column with 0-20% ethyl acetate in hexanes produced 4m (29 mg, 71%), a yellow oil. $^1$H NMR (400 MHz, CDCl$_3$) δ 7.93 (dd, J=7.4, 0.9 Hz, 1H), 7.50 (d, J=8.3 Hz, 1H), 7.30 (t, J=7.9 Hz, 1H), 7.26-7.23 (m, 1H), 7.20 (d, J=3.0 Hz, 1H), 5.31-5.10 (m, 1H), 4.16 (t, J=7.1 Hz, 2H), 3.81-3.68 (m, 1H), 3.62-3.49 (m, 1H), 2.47-2.34 (m, 1H), 2.26-2.13 (m, 2H), 2.06-1.96 (m, 1H), 1.86 (p, J=7.2 Hz, 2H), 1.52-1.19 (m, 19H), 0.87 (t, J=7.0 Hz, 3H). $^{13}$C NMR (101 MHz, CDCl$_3$) δ 179.66, 168.95, 153.76, 136.57, 129.52, 126.25, 121.14, 120.73, 118.42, 112.62, 102.40, 80.51, 53.97, 46.70, 46.46, 32.55, 31.91, 30.45, 29.54, 29.33, 29.31, 28.53, 28.28, 27.07, 23.81, 22.74, 14.20. HRMS (ESI+): Calcd for C$_{28}$H$_{40}$N$_4$O$_3$ [M+Na]t 503.6320, Found: 503.2987.

Tert-butyl (S)-2-(3-(1-decyl-1H-indol-4-yl)-1,2,4-oxadiazol-5-yl)pyrrolidine-1-carboxylate (4n)

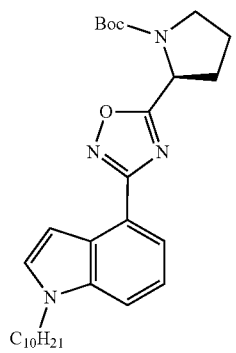

4n was prepared using general procedure 3. Purification on a silica gel column with 0-20% ethyl acetate in hexanes produced 4n (30 mg, 72%), a yellow oil. $^1$H NMR (400 MHz, CDCl$_3$) δ 7.93 (dd, J=7.4, 0.9 Hz, 1H), 7.50 (d, J=8.3 Hz, 1H), 7.30 (t, J=7.9 Hz, 1H), 7.25 (d, J=3.2 Hz, 1H), 7.20 (d, J=3.1 Hz, 1H), 5.30-5.09 (m, 1H), 4.16 (t, J=7.1 Hz, 2H), 3.78-3.62 (m, 1H), 3.60-3.52 (m, 1H), 2.44-2.31 (m, 1H), 2.24-2.11 (m, 2H), 2.05-1.94 (m, 1H), 1.85 (p, J=7.0 Hz, 2H), 1.51-1.21 (m, 21H), 0.87 (t, J=7.0 Hz, 3H). $^{13}$C NMR (101 MHz, CDCl$_3$) δ 179.67, 168.97, 153.78, 136.59, 129.54, 126.26, 121.16, 121.06, 120.75, 118.44, 112.63, 102.42, 80.53, 53.99, 46.73, 46.48, 32.57, 31.97, 30.47, 29.62, 29.60, 29.38, 29.35, 28.55, 28.30, 27.09, 23.83, 22.78, 14.24. HRMS (ESI+): Calcd for C$_{29}$H$_{42}$N$_4$O$_3$ [M+Na]$^-$: 517.6585, Found: 517.3177.

Tert-butyl (S)-2-(3-(1-nonyl-1H-indol-5-yl)-1,2,4-oxadiazol-5-yl)pyrrolidine-1-carboxylate (4r)

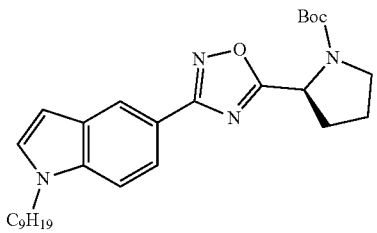

4r was prepared using general procedure 3. Purification on a silica gel column with 0-20% ethyl acetate in hexanes produced 4r (28 mg, 52%), a yellow oil. $^1$H NMR (400 MHz, CDCl$_3$) δ 8.38 (d, J=1.6 Hz, 1H), 7.92 (dd, J=8.6, 1.6 Hz, 1H), 7.40 (d, J=8.6 Hz, 1H), 7.15 (d, J=3.1 Hz, 1H), 6.57 (d, J=3.2 Hz, 1H), 5.26-5.04 (m, 1H), 4.13 (t, J=7.2 Hz, 2H), 3.79-3.66 (m, 1H), 3.57 (dt, J=10.5, 7.0 Hz, 1H), 2.45-2.33 (m, 1H), 2.17 (ddd, J=18.7, 14.1, 6.7 Hz, 2H), 2.01 (ddd, J=12.1, 6.1, 3.4 Hz, 1H), 1.90-1.80 (m, 2H), 1.57-1.12 (m, 20H), 0.97-0.78 (m, 3H). $^{13}$C NMR (101 MHz, CDCl$_3$) δ 169.51, 153.78, 137.61, 129.13, 128.67, 121.33, 120.68, 117.90, 109.91, 102.25, 80.53, 77.48, 77.16, 76.84, 54.02, 46.73, 46.50, 32.55, 31.94, 30.41, 29.56, 29.35, 29.33, 28.56, 28.30, 27.09, 23.85, 22.76, 14.21. HRMS (ESI+): Calcd for C$_{28}$H$_{40}$N$_4$O$_3$ [M+Na]$^+$: 503.6320, Found: 503.2966.

Tert-butyl (S)-2-(3-(1-octyl-1H-indol-6-yl)-1,2,4-oxadiazol-5-yl)pyrrolidine-1-carboxylate (4u)

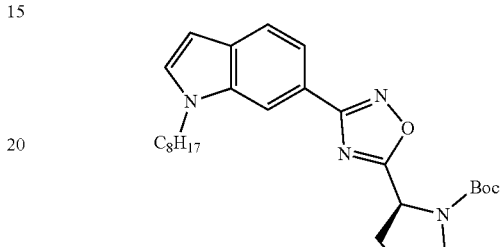

4u was prepared using general procedure 3. Purification on a silica gel column with 0-20% ethyl acetate in hexanes produced 4u (51 mg, 97%), a yellow oil. $^1$H NMR (400 MHz, CDCl$_3$) δ 8.09 (d, J=1.2 Hz, 1H), 7.88-7.77 (m, 1H), 7.69 (d, J=8.4 Hz, 1H), 7.21 (t, J=3.6 Hz, 1H), 6.53 (d, J=3.2 Hz, 1H), 5.24-5.06 (m, 1H), 4.18 (t, J=7.1 Hz, 2H), 3.81-3.69 (m, 1H), 3.58 (dt, J=10.3, 7.0 Hz, 1H), 2.48-2.32 (m, 1H), 2.28-2.13 (m, 2H), 2.07-1.96 (m, 1H), 1.86 (t, J=7.2 Hz, 2H), 1.49-1.19 (m, 17H), 0.91-0.82 (m, 3H). $^{13}$C NMR (101 MHz, solvent) δ 180.26, 169.55, 153.77, 135.86, 130.99, 130.21, 121.40, 119.69, 118.48, 109.24, 101.50, 80.56, 77.48, 77.16, 76.84, 54.02, 46.70, 46.50, 32.55, 31.88, 30.47, 29.33, 29.28, 28.53, 28.28, 27.10, 23.88, 22.72, 14.19. HRMS (ESI+): Calcd for C$_{27}$H$_{38}$N$_4$O$_3$ [M+Na]$^+$: 489.6054, Found: 489.2836.

Tert-butyl (S)-2-(3-(1-decyl-1H-indol-6-yl)-1,2,4-oxadiazol-5-yl)pyrrolidine-1-carboxylate (4w)

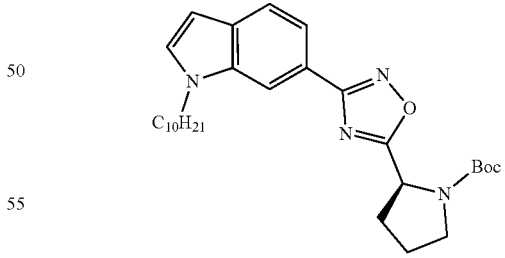

4w was prepared using general procedure 3. Purification on a silica gel column with 0-20% ethyl acetate in hexanes produced 4w (92 mg, 94%), a yellow oil. $^1$H NMR (400 MHz, CDCl$_3$) δ 8.09 (s, 1H), 7.83 (d, J=8.1 Hz, 1H), 7.69 (d, J=8.4 Hz, 1H), 7.21 (d, J=3.1 Hz, 1H), 6.53 (d, J=3.1 Hz, 1H), 5.26-5.07 (m, 1H), 4.18 (t, J=7.1 Hz, 2H), 3.82-3.68 (m, 1H), 3.63-3.50 (m, 1H), 2.48-2.32 (m, 1H), 2.25-2.13 (m, 2H), 2.07-1.97 (m, 1H), 1.85 (p, J=7.1 Hz, 2H), 1.47 (s, 3H), 1.37-1.19 (m, 19H), 0.87 (t, J=7.1 Hz, 3H). $^{13}$C NMR (101 MHz, CDCl$_3$) δ 180.25, 169.52, 153.75, 135.83, 130.98, 130.21, 130.05, 121.38, 121.24, 119.66, 118.58, 118.45, 109.37, 109.22, 101.48, 101.41, 80.53, 54.00, 46.76, 46.68, 46.49, 32.53, 31.96, 31.66, 30.46, 29.61, 29.60, 29.55, 29.37, 29.36, 28.51, 28.27, 27.08, 24.48, 23.86, 22.77, 14.22. HRMS (ESI+): Calcd for C$_{29}$H$_{42}$N$_4$O$_3$ [M+Na]$^+$: 517.6585, Found: 517.3124.

(S)-2-(3-(1-heptyl-1H-indol-3-yl)-1,2,4-oxadiazol-5-yl)pyrrolidin-1-ium chloride (5e)

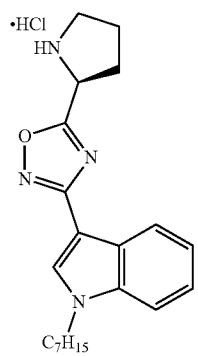

5e was prepared using general procedure 4 and carried on to the next reaction without purification.

(S)-2-(3-(1-octyl-1H-indol-3-yl)-1,2,4-oxadiazol-5-yl)pyrrolidin-1-ium chloride (5f)

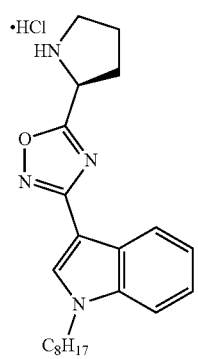

5f was prepared using general procedure 4 and carried on to the next reaction without purification.

(S)-2-(3-(1-nonyl-1H-indol-3-yl)-1,2,4-oxadiazol-5-yl)pyrrolidin-1-ium chloride (5g)

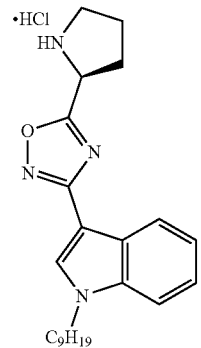

5g was prepared using general procedure 4 and carried on to the next reaction without purification.

(S)-2-(3-(1-decyl-1H-indol-3-yl)-1,2,4-oxadiazol-5-yl)pyrrolidin-1-ium chloride (5h)

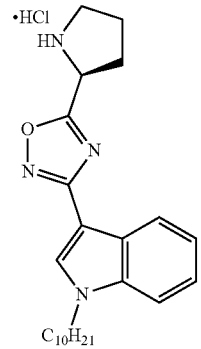

5h was prepared using general procedure 4 and carried on to the next reaction without purification.

(S)-2-(3-(1-undecyl-1H-indol-3-yl)-1,2,4-oxadiazol-5-yl)pyrrolidin-1-ium chloride (5i)

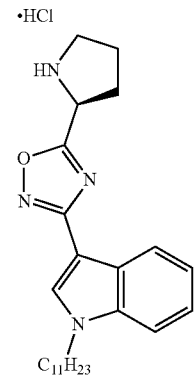

5i was prepared using general procedure 4 and carried on to the next reaction without purification.

(S)-2-(3-(1-dodecyl-1H-indol-3-yl)-1,2,4-oxadiazol-5-yl)pyrrolidin-1-ium chloride (5j)

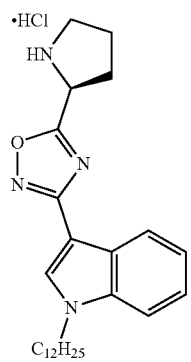

5j was prepared using general procedure 4 and carried on to the next reaction without purification.

(S)-2-(3-(1-heptyl-1H-indol-4-yl)-1,2,4-oxadiazol-5-yl)pyrrolidin-1-ium chloride (5k)

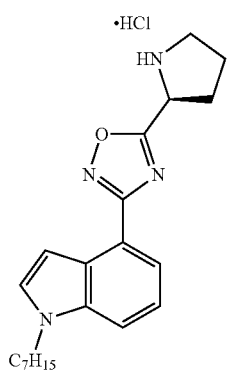

5k was prepared using general procedure 4 and carried on to the next reaction without purification.

(S)-2-(3-(1-octyl-1H-indol-4-yl)-1,2,4-oxadiazol-5-yl)pyrrolidin-1-ium chloride (5l)

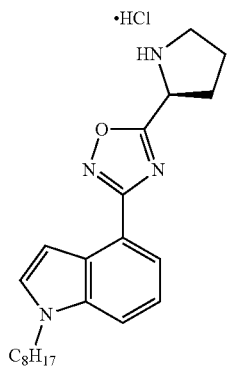

5l was prepared using general procedure 4 and carried on to the next reaction without purification.

(S)-2-(3-(1-nonyl-1H-indol-4-yl)-1,2,4-oxadiazol-5-yl)pyrrolidin-1-ium chloride (5m)

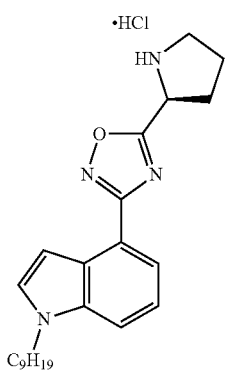

5m was prepared using general procedure 4 and carried on to the next reaction without purification.

(S)-2-(3-(1-decyl-1H-indol-4-yl)-1,2,4-oxadiazol-5-yl)pyrrolidin-1-ium chloride (5n)

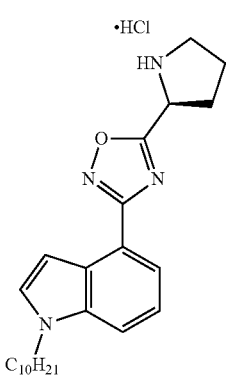

5n was prepared using general procedure 4 and carried on to the next reaction without purification.

(S)-2-(3-(1-nonyl-1H-indol-5-yl)-1,2,4-oxadiazol-5-yl)pyrrolidin-1-ium chloride (5r)

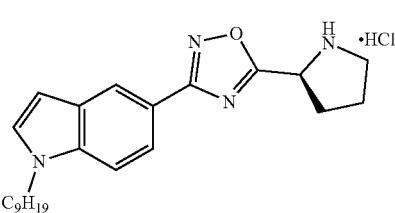

5r was prepared using general procedure 4 and carried on to the next reaction without purification.

(S)-2-(3-(1-octyl-1H-indol-6-yl)-1,2,4-oxadiazol-5-yl)pyrrolidin-1-ium chloride (5u)

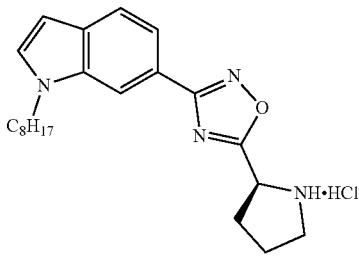

5u was prepared using general procedure 4 and carried on to the next reaction without purification.

(S)-2-(3-(1-decyl-1H-indol-6-yl)-1,2,4-oxadiazol-5-yl)pyrrolidin-1-ium chloride (5w)

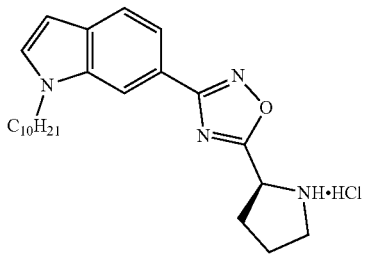

5w was prepared using general procedure 4 and carried on to the next reaction without purification.

Tert-butyl (S,Z)-(((tert-butoxycarbonyl)imino)(2-(3-(1-hexyl-1H-indol-3-yl)-1,2,4-oxadiazol-5-yl)pyrrolidin-1-yl)methyl)carbamate (6e)

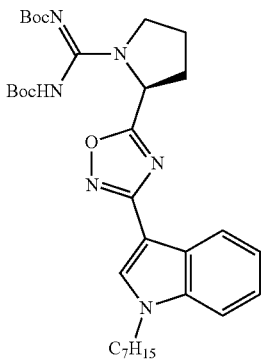

6e was prepared using general procedure 5. Purification on a silica gel column with 10-40% ethyl acetate in hexanes produced 6e (21 mg, 53%), a clear oil. $^1$H NMR (500 MHz, CDCl$_3$) δ 8.20-8.05 (m, 1H), 7.77 (s, 1H), 7.40-7.30 (m, 1H), 7.27-7.12 (m, 2H), 5.52 (s, 1H), 4.09 (t, J=7.2 Hz, 2H), 3.83 (ddd, J=11.5, 7.5, 6.0 Hz, 1H), 3.73 (d, J=9.9 Hz, 1H), 2.38 (dq, J=12.7, 7.7 Hz, 1H), 2.22 (s, 1H), 2.16-2.07 (m, 1H), 2.01-1.92 (m, 1H), 1.81 (t, J=7.3 Hz, 2H), 1.42 (d, J=18.3 Hz, 19H), 1.29-1.04 (m, 9H), 0.79 (t, J=6.9 Hz, 3H). $^{13}$C NMR (126 MHz, CDCl$_3$) δ 177.45, 165.30, 161.89, 153.52, 151.07, 136.94, 130.79, 125.64, 122.85, 122.13, 121.35, 109.98, 102.77, 81.77, 79.82, 76.91, 55.43, 49.54, 47.06, 36.78, 31.77, 31.51, 30.20, 29.01, 28.26, 28.12, 27.03, 22.69, 14.15. HRMS (ESI+): Calcd for C$_{32}$H$_{46}$N$_6$O$_5$ [M+H]$^+$: 595.7528, Found: 595.3608.

Tert-butyl (S,Z)-(((tert-butoxycarbonyl)imino)(2-(3-(1-octyl-1H-indol-3-yl)-1,2,4-oxadiazol-5-yl)pyrrolidin-1-yl)methyl)carbamate (6f)

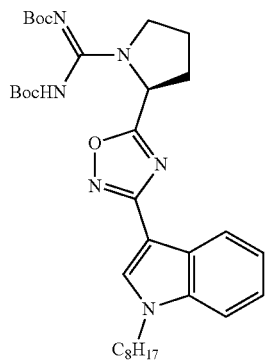

6f was prepared using general procedure 5. Purification on a silica gel column with 10-40% ethyl acetate in hexanes produced 6f (15 mg, 76%), a clear oil. $^1$H NMR (500 MHz, CDCl) δ 8.27-8.18 (m, 1H), 7.83 (s, 1H), 7.42-7.36 (m, 1H), 7.32-7.25 (m, 2H), 5.59 (d, J=6.4 Hz, 1H), 4.16 (t, J=7.2 Hz, 2H), 3.93-3.88 (m, 1H), 3.82 (q, J=6.0, 4.9 Hz, 1H), 2.51-2.41 (m, 1H), 2.29 (s, 1H), 2.17-2.11 (m, 1H), 2.04 (dt, J=12.7, 6.4 Hz, 1H), 1.89 (p, J=7.1 Hz, 2H), 1.49 (d, J=19.9 Hz, 21H), 1.35-1.21 (m, 10H), 0.87 (t, J=7.0 Hz, 3H). $^{13}$C NMR (126 MHz, CDCl$_3$) δ 177.46, 165.36, 161.98, 153.46, 150.70, 137.00, 130.75, 125.71, 122.87, 122.18, 121.37, 109.98, 102.88, 81.69, 79.82, 55.48, 49.57, 47.08, 31.90, 31.52, 30.22, 29.33, 29.24, 28.29, 28.14, 27.71, 27.09, 24.00, 22.73, 14.18. HRMS (ESI+): Calcd for C$_{33}$H$_{48}$N$_6$O$_5$ [M+H]$^+$: 609.7794, Found: 609.3371.

Tert-butyl (S,Z)-(((tert-butoxycarbonyl)imino)(2-(3-(1-nonyl-1H-indol-3-yl)-1,2,4-oxadiazol-5-yl)pyrrodinyl-1-yl)methyl)carbamate (6g)

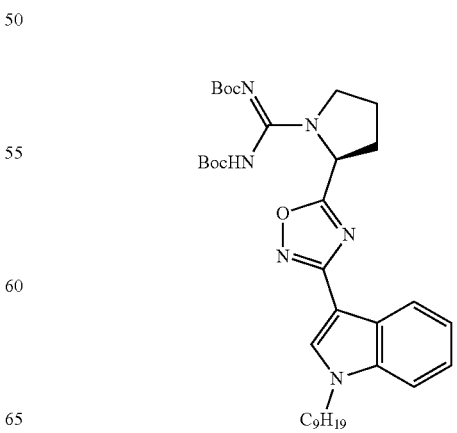

6g was prepared using general procedure 5. Purification on a silica gel column with 10-40% ethyl acetate in hexanes produced 6g (25 mg, 64%), a clear oil. $^1$H NMR (500 MHz, CDCl$_3$) δ 8.31-8.19 (m, 1H), 7.86 (s, 1H), 7.46-7.41 (m, 1H), 7.37-7.28 (m, 2H), 5.61 (s, 1H), 4.18 (t, J=7.2 Hz, 2H), 3.94-3.88 (m, 1H), 3.85-3.79 (m, 1H), 2.51-2.45 (m, 1H), 2.36-2.26 (m, 1H), 2.24-2.15 (m, 1H), 2.08-1.98 (m, 1H), 1.90 (p, J=7.4 Hz, 3H), 1.64-1.43 (m, 18H), 1.40-1.32 (m, 4H) 1.32-1.21 (m, 8H), 0.89 (t, J=6.9 Hz, 3H). $^{13}$C NMR (126 MHz, CDCl$_3$) δ 177.46, 165.30, 162.05, 153.60, 150.56, 136.94, 130.78, 125.64, 122.84, 122.13, 121.35, 109.98, 102.78, 82.24, 79.67, 55.42, 49.53, 47.06, 31.93, 31.53, 31.37, 30.20, 29.52, 29.35, 28.26, 28.12, 27.07, 22.75, 14.21. HRMS (ESI+): Calcd for C$_{34}$H$_{50}$N$_6$O$_5$ [M+H]$^+$: 623.8059, Found: 623.3915.

Tert-butyl (S,Z)-(((tert-butoxycarbonyl)imino)(2-(3-(1-decyl-1H-indol-3-yl)-1,2,4-oxadiazol-5-yl)pyrrolidin-1-yl)methyl)carbamate (6h)

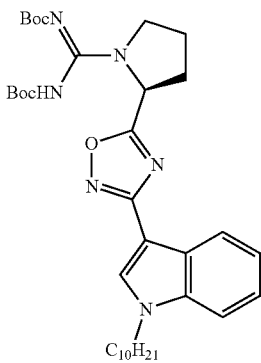

6h was prepared using general procedure 5. Purification on a silica gel column with 10-40% ethyl acetate in hexanes produced 6h (23 mg, 52%), a clear oil. $^1$H NMR (500 MHz, CDCl$_3$) δ 8.17-8.12 (m, 1H), 7.77 (s, 1H), 7.34-7.28 (m, 1H), 7.26-7.20 (m, 2H), 5.52 (s, 1H), 4.09 (t, J=7.2 Hz, 2H), 3.86-3.79 (m, 1H), 3.76-3.68 (m, 1H), 2.39-2.34 (m, 1H), 2.29-2.17 (m, 1H), 2.16-2.06 (m, 1H), 2.01-1.92 (m, 1H), 1.81 (p, J=7.4 Hz, 2H), 1.48-1.32 (m, 22H), 1.27-1.23 (m, 4H), 1.18 (d, J=14.9 Hz, 10H), 0.80 (t, J=7.0 Hz, 3H). $^{13}$C NMR (126 MHz, CDCl$_3$) δ 177.46, 165.30, 162.12, 153.53, 150.94, 136.94, 130.79, 125.64, 122.84, 122.13, 121.35, 109.98, 102.78, 82.17, 79.82, 55.42, 49.53, 47.07, 31.97, 31.53, 31.37, 30.21, 29.64, 29.57, 29.37, 28.27, 28.12, 27.98, 27.07, 22.79, 14.23. HRMS (ESI+): Calcd for C$_{35}$H$_{52}$N$_6$O$_5$ [M+H]$^+$: 637.8325, Found: 637.4073.

Tert-butyl (S,Z)-(((tert-butoxycarbonyl)imino)(2-(3-(1-undecyl-1H-indol-3-yl)-1,2,4-oxadiazol-5-yl)pyrrolidin-1-yl)methyl)carbamate (6i)

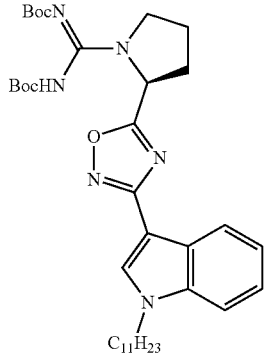

6i was prepared using general procedure 5. Purification on a silica gel column with 10-40% ethyl acetate in hexanes produced 6l (21 mg, 100%), a clear oil. $^1$H NMR (500 MHz, CDCl$_3$) δ 8.26-8.19 (m, 1H), 7.83 (s, 1H), 7.44-7.36 (m, 1H), 7.33-7.26 (m, 2H), 4.16 (t, J=7.2 Hz, 2H), 3.97-3.88 (m, 1H), 3.81 (d, J=10.4 Hz, 1H), 2.51-2.42 (m, 1H), 2.29 (s, 1H), 2.18 (dd, J=13.1, 6.8 Hz, 1H), 2.04 (dp, J=13.0, 6.6 Hz, 1H), 1.89 (t, J=7.2 Hz, 2H), 1.68-1.41 (m, 19H), 1.38-1.12 (m, 18H), 0.87 (t, J=7.0 Hz, 3H). $^{13}$C NMR (126 MHz, CDCl$_3$) δ 177.43, 165.33, 161.84, 153.32, 150.29, 136.96, 130.78, 125.66, 122.86, 122.16, 121.37, 109.99, 102.81, 82.20, 79.73, 55.48, 49.58, 47.09, 32.03, 31.53, 30.23, 29.70, 29.59, 29.41, 28.28, 27.10, 24.05, 22.82, 14.26. HRMS (ESI+): Calcd for C$_{36}$H$_{54}$N$_6$O$_5$ [M+H]$^+$: 651.8591, Found: 651.4249.

Tert-butyl (S,Z)-(((tert-butoxycarbonyl)imino)(2-(3-(1-dodecyl-1H-indol-3-yl)-1,2,4-oxadiazol-5-yl)pyrrolidin-1-yl)methyl)carbamate (6j)

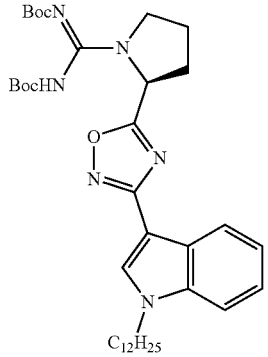

6j was prepared using general procedure 5. Purification on a silica gel column with 10-40% ethyl acetate in hexanes produced 6j (21 mg, 99%), a clear oil. $^1$H NMR (500 MHz, CDCl$_3$) δ 8.26-8.18 (m, 1H), 7.83 (s, 1H), 7.45-7.35 (m, 1H), 7.32-7.26 (m, 2H), 5.58 (s, 1H), 4.16 (t, J=7.2 Hz, 2H), 3.89 (ddd, J=11.6, 7.5, 5.9 Hz, 1H), 3.81 (s, 1H), 2.43 (d, J=7.6 Hz, 1H), 2.18 (dq, J=13.7, 6.8 Hz, 1H), 2.05 (d, J=6.4 Hz, 1H), 1.88 (t, J=7.2 Hz, 2H), 1.59-1.18 (m, 38H), 0.87 (t, J=7.0 Hz, 3H). $^{13}$C NMR (126 MHz, CDCl$_3$) δ 177.46, 165.31, 162.06, 150.60, 148.74, 136.93, 130.78, 125.63, 122.84, 122.13, 121.35, 109.98, 102.78, 82.23, 79.66, 77.73, 77.41, 77.36, 77.16, 76.91, 55.42, 49.53, 47.07, 32.04, 31.52, 30.21, 29.84, 29.73, 29.70, 29.62, 29.58, 29.46, 29.38, 28.27, 28.12, 27.09, 22.82, 14.26. HRMS (ESI+): Calcd for $C_{37}H_{56}N_6O_5$ [M+H]$^+$: 665.8857, Found: 665.4401.

Tert-butyl (S,Z)-(((tert-butoxycarbonyl)amino)(2-(3-(1-heptyl-1H-indol-4-yl)-1,2,4-oxadiazol-5-yl)pyrrolidin-1-yl)methylene)carbamate (6k)

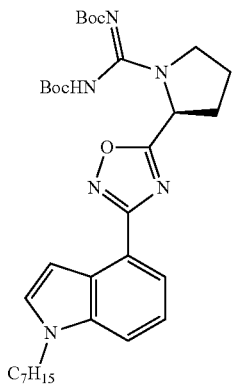

6k was prepared using general procedure 5. Purification on a silica gel column with 10-40% ethyl acetate in hexanes produced 6k (13 mg, 43%), a clear oil. $^1$H NMR (400 MHz, CDCl$_3$) δ 7.93 (dd, J=7.4, 0.9 Hz, 1H), 7.54-7.47 (m, 1H), 7.32-7.27 (m, 1H), 7.23 (t, J=1.6 Hz, 1H), 7.18 (dd, J=3.1, 0.8 Hz, 1H), 5.64 (t, J=6.2 Hz, 1H), 4.17 (t, J=7.1 Hz, 2H), 3.95-3.87 (m, 1H), 3.86-3.76 (m, 1H), 2.52-2.41 (m, 1H), 2.37-2.26 (m, 1H), 2.25-2.13 (m, 2H), 2.10-1.99 (m, 1H), 1.86 (p, J=7.1 Hz, 2H), 1.53-1.39 (m, 17H), 1.35-1.29 (d, J=5.2 Hz, 4H), 1.29-1.20 (m, 6H), 0.86 (t, J=6.9 Hz, 3H). $^{13}$C NMR (126 MHz, CDCl$_3$) δ 177.97, 169.01, 162.19, 153.75, 150.66, 136.64, 129.53, 129.44, 126.30, 121.10, 120.96, 118.32, 112.67, 102.52, 81.88, 79.71, 55.48, 49.55, 46.75, 31.83, 31.56, 30.50, 29.84, 29.04, 28.28, 27.08, 24.07, 22.71, 14.18. HRMS (ESI+): Calcd for $C_{32}H_{46}N_6O_5$ [M+Na]$^+$:617.7346, Found: 617.3426.

Tert-butyl (S,Z)-(((tert-butoxycarbonyl)amino)(2-(3-(1-heptyl-1H-indol-4-yl)-1,2,4-oxadiazol-5-yl)pyrrolidin-1-yl)methylene)carbamate (6l)

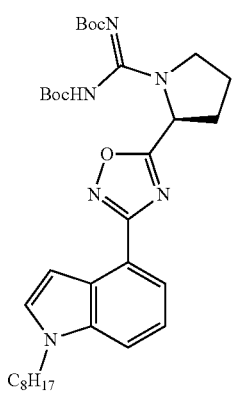

6l was prepared using general procedure 5. Purification on a silica gel column with 10-40% ethyl acetate in hexanes produced 6l (7 mg, 15%), a clear oil. $^1$H NMR (500 MHz, CDCl$_3$) δ 7.93 (dd, J=7.5, 0.9 Hz, 1H), 7.49 (d, J=8.2 Hz, 1H), 7.28 (dd, J=8.2, 7.4 Hz, 1H), 7.24-7.22 (m, 1H), 7.18 (dd, J=3.1, 0.9 Hz, 1H), 5.65 (s, 1H), 4.17 (t, J=7.1 Hz, 2H), 3.94-3.87 (m, 1H), 3.87-3.77 (m, 1H), 2.50-2.42 (m, 1H), 2.35-2.26 (m, 1H), 2.20 (dt, J=13.7, 6.7 Hz, 1H), 2.10-2.01 (m, 1H), 1.85 (p, J=7.5 Hz, 2H), 1.51-1.38 (m, 20H), 1.33-1.29 (m, 4H), 1.28-1.20 (m, 8H), 0.86 (t, J=7.0 Hz, 3H). $^{13}$C NMR (126 MHz, CDCl$_3$) δ 177.97, 169.02, 162.12, 153.64, 150.64, 136.65, 129.50, 126.32, 121.11, 120.96, 118.35, 112.67, 102.53, 82.22, 79.80, 55.49, 49.55, 46.75, 31.90, 31.54, 30.50, 29.84, 29.32, 28.28, 27.13, 24.04, 22.75, 14.20. HRMS (ESI+): Calcd for $C_{33}H_{48}N_6O_5$ [M+H]$^-$: 609.7794, Found: 609.3785.

Tert-butyl (S,Z)-(((tert-butoxycarbonyl)amino)(2-(3-(1-heptyl-1H-indol-4-yl)-1,2,4-oxadiazol-5-yl)pyrrolidin-1-yl)methylene)carbamate (6m)

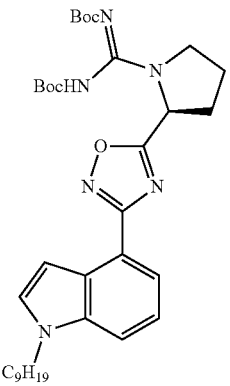

6m was prepared using general procedure 5. Purification on a silica gel column with 10-40% ethyl acetate in hexanes produced 6m (20 mg, 45%), a clear oil. $^1$H NMR (500 MHz, CDCl$_3$) δ 7.93 (d, J=7.3 Hz, 1H), 7.49 (d, J=8.2 Hz, 1H), 7.33-7.26 (m, 2H), 7.24-7.22 (m, 1H), 7.18 (d, J=3.1 Hz, 1H), 5.65 (s, 1H), 4.16 (t, J=7.1 Hz, 2H), 3.95-3.90 (m, 1H), 3.84-3.78 (m, 1H), 2.52-2.46 (m, 1H), 2.22-2.18 (m, 1H), 2.11-2.03 (m, 1H), 1.85 (p, J=7.2 Hz, 2H), 1.56-1.34 (m, 21H), 1.33-1.28 (m, 4H), 1.27-1.18 (m, 10H), 0.86 (t, J=6.9 Hz, 3H). $^{13}$C NMR (126 MHz, CDCl$_3$) δ 177.95, 169.00, 162.07, 153.64, 150.64, 136.64, 129.52, 126.33, 121.10, 120.96, 118.32, 112.67, 102.52, 82.29, 79.76, 55.48, 49.54, 46.75, 31.96, 31.57, 30.49, 29.85, 29.58, 29.38, 29.35, 28.28, 28.14, 27.12, 24.05, 22.77, 14.23. HRMS (ESI+): Calcd for $C_{34}H_{50}N_6O_5$ [M+H]$^+$: 623.8059, Found: 623.3915.

Tert-butyl (S,Z)-(((tert-butoxycarbonyl)amino)(2-(3-(1-heptyl-1H-indol-4-yl)-1,2,4-oxadiazol-5-yl)pyrrolidin-1-yl)methylene)carbamate (6n)

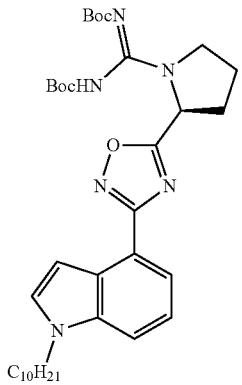

6n was prepared using general procedure 5. Purification on a silica gel column with 10-40% ethyl acetate in hexanes produced 6n (10 mg, 34%), a clear oil. $^1$H NMR (400 MHz, CDCl$_3$) δ 7.93 (dd, J=7.4, 0.9 Hz, 1H), 7.49 (d, J=8.2 Hz, 1H), 7.28 (dd, J=8.2, 7.4 Hz, 1H), 7.24-7.22 (m, 1H), 7.18 (dd, J=3.1, 0.8 Hz, 1H), 5.64 (s, 1H), 4.16 (t, J=7.1 Hz, 2H), 3.96-3.87 (m, 1H), 3.86-3.76 (m, 1H), 2.51-2.41 (m, 1H), 2.30 (s, 1H), 2.24-2.13 (m, 1H), 2.10-2.00 (m, 1H), 1.85 (p, J=7.0 Hz, 2H), 1.53-1.38 (m, 21H), 1.35-1.28 (m, 6H), 1.28-1.19 (m, 12H), 0.86 (t, J=7.1 Hz, 3H). $^{13}$C NMR (126 MHz, CDCl$_3$) δ 177.95, 169.01, 162.08, 153.49, 150.61, 136.64, 129.52, 129.43, 126.32, 121.10, 120.96, 118.32, 112.67, 102.52, 82.28, 79.69, 55.48, 49.54, 46.75, 31.99, 31.56, 30.49, 29.85, 29.63, 29.39, 28.28, 27.12, 24.02, 22.80, 14.24. HRMS (ESI+): Calcd for $C_{35}H_{52}N_6O_5$ [M+H]$^+$: 637.8325, Found: 637.4083.

Tert-butyl (S,Z)-(((tert-butoxycarbonyl)imino)(2-(3-(1-nonyl-1H-indol-5-yl)-1,2,4-oxadiazol-5-yl)pyrrolidin-1-yl)methyl)carbamate (6r)

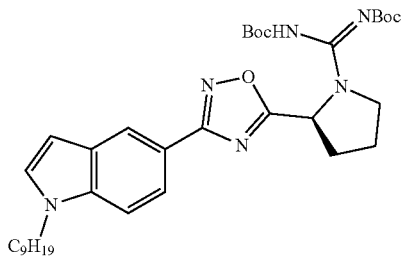

6r was prepared using general procedure 5. Purification on a silica gel column with 10-40% ethyl acetate in hexanes produced 6r (11 mg, 41%), a clear oil. $^1$H NMR (500 MHz, CDCl$_3$) δ 8.37 (d, J=1.5 Hz, 1H), 7.91 (dd, J=8.6, 1.6 Hz, 1H), 7.39 (d, J=8.7 Hz, 1H), 7.14 (t, J=1.6 Hz, 1H), 6.56 (dd, J=3.1, 0.8 Hz, 0H), 5.59 (dd, J=7.9, 4.6 Hz, 1H), 4.13 (t, J=7.2 Hz, 2H), 3.94-3.89 (m, 1H), 3.84-3.78 (m, 1H), 2.50-2.42 (m, 1H), 2.30 (s, 1H), 2.17 (dd, J=8.1, 6.0 Hz, 1H), 2.09-2.01 (m, 1H), 1.86-1.79 (m, 2H), 1.49 (d, J=18.9 Hz, 20H), 1.37-1.17 (m, 14H), 0.86 (t, J=6.9 Hz, 3H). $^{13}$C NMR (126 MHz, CDCl$_3$) δ 178.35, 169.51, 153.46, 137.65, 129.05, 128.61, 121.49, 120.75, 117.69, 109.87, 102.28, 81.06, 77.41, 77.16, 76.91, 55.50, 49.61, 46.75, 31.95, 31.48, 30.43, 29.85, 29.58, 29.36, 28.27, 27.99, 27.11, 24.06, 22.78, 14.23. HRMS (ESI+): Calcd for $C_{34}H_{50}N_6O_5$ [M+Na]$^+$: 645.7878, Found: 645.3714.

Tert-butyl (S,Z)-(((tert-butoxycarbonyl)imino)(2-(3-(1-octyl-1H-indol-6-yl)-1,2,4-oxadiazol-5-yl)pyrrolidin-1-yl)methyl)carbamate (6u)

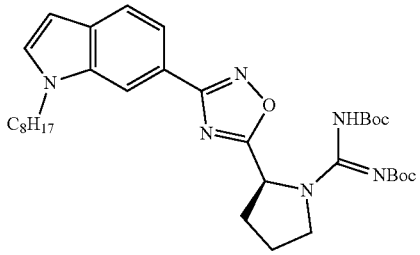

6u was prepared using general procedure 5. Purification on a silica gel column with 10-40% ethyl acetate in hexanes produced 6u (33 mg, 55%), a clear oil. $^1$H NMR (500 MHz, CDCl$_3$) δ 8.08 (s, 1H), 7.81 (dd, J=8.3, 1.4 Hz, 1H), 7.68 (d, J=8.2 Hz, 1H), 7.20 (d, J=3.1 Hz, 1H), 6.52 (d, J=3.0 Hz, 1H), 5.62 (dd, J=7.8, 4.7 Hz, 1H), 4.17 (t, J=7.2 Hz, 2H), 3.92 (dt, J=11.4, 6.9 Hz, 1H), 3.82 (d, J=12.7 Hz, 1H), 2.46 (dd, J=13.1, 7.0 Hz, 1H), 2.34-2.12 (m, 2H), 2.04 (dt, J=12.8, 6.6 Hz, 1H), 1.85 (q, J=7.0 Hz, 2H), 1.68-1.15 (m, 28H), 0.86 (t, J=6.8 Hz, 3H). $^{13}$C NMR (126 MHz, CDCl$_3$) δ 178.57, 169.58, 162.11, 153.72, 150.54, 135.87, 131.02, 130.17, 130.08, 121.32, 121.29, 119.64, 118.65, 109.30, 101.48, 82.30, 79.70, 49.63, 46.70, 31.88, 30.47, 29.33, 29.28, 28.25, 28.11, 27.11, 22.72, 14.18. HRMS (ESI+): Calcd for $C_{33}H_{48}N_6O_5$ [M+H]$^+$: 609.7794, Found: 609.3791.

Tert-butyl (S,Z)-(((tert-butoxycarbonyl)imino)(2-(3-(1-decyl-1H-indol-6-yl)-1,2,4-oxadiazol-5-yl)pyrrolidin-1-yl)methyl)carbamate (6w)

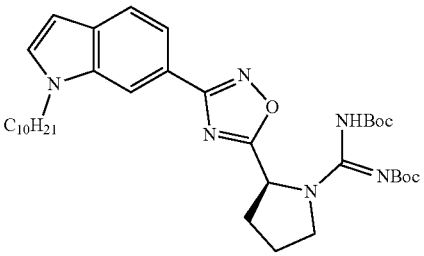

6w was prepared using general procedure 5. Purification on a silica gel column with 10-30% ethyl acetate in hexanes produced 6w (19 mg, 43%), a clear oil. $^1$H NMR (500 MHz, CDCl$_3$) δ 8.01 (d, J=4.9 Hz, 1H), 7.88-7.74 (m, 1H), 7.61 (d, J=8.3 Hz, 1H), 7.15-7.11 (m, 1H), 6.45 (dd, J=3.1, 0.8 Hz, 1H), 5.60-5.53 (m, 1H), 4.12-4.03 (m, 2H), 3.90-3.80 (m, 1H), 3.80-3.70 (m, 1H), 2.45-2.36 (m, 1H), 2.21-2.10 (m, 2H), 2.00-1.93 (m, 1H), 1.78 (h, J=7.7 Hz, 2H), 1.48-1.31 (m, 25H), 1.27-1.12 (m, 17H), 0.80 (t, J=6.9 Hz, 3H). $^{13}$C NMR (151 MHz, CDCl$_3$) δ 178.58, 169.62, 162.15, 153.77, 150.51, 148.72, 135.91, 135.08, 131.05, 130.18, 130.09, 126.56, 121.34, 119.26, 119.01, 118.70, 109.64, 109.32, 105.10, 101.52, 83.56, 82.35, 79.72, 55.55, 49.65, 46.95, 46.74, 32.00, 30.50, 29.86, 29.66, 29.60, 29.41, 28.28, 28.15, 27.16, 27.05, 22.80, 14.24. HRMS (ESI+): Calcd for $C_{35}H_{52}N_6O_5$ [M+Na]$^+$: 659.8143, Found: 659.3884.

Example 2: (S)-amino(2-(3-(1-heptyl-1H-indol-3-yl)-1,2,4-oxadiazol-5-yl)pyrrolidin-1-yl)methaniminium chloride (7e, Compound 1A)

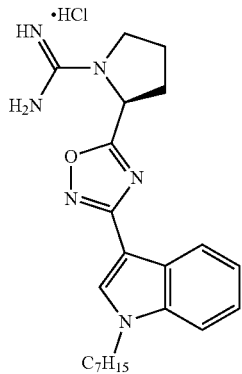

7e was prepared using general procedure 4 and isolated as a light yellow tinted solid (11 mg, 100%). $^1$H NMR (400 MHz, CD$_3$OD) δ 8.10 (ddd, J=7.9, 1.3, 0.8 Hz, 1H), 7.98 (s, 1H), 7.51 (dt, J=8.3, 0.9 Hz, 1H), 7.29 (ddd, J=8.3, 7.1, 1.3 Hz, 1H), 7.22 (ddd, J=8.0, 7.1, 1.0 Hz, 1H), 5.44 (dd, J=7.8, 2.0 Hz, 1H), 4.26 (t, J=7.0 Hz, 2H), 3.82-3.74 (m, 1H), 3.63 (td, J=9.6, 7.2 Hz, 1H), 2.61-2.45 (m, 2H), 2.31-2.21 (m, 1H), 2.14 (ddd, J=12.2, 6.0, 2.8 Hz, 1H), 1.88 (p, J=7.1 Hz, 2H), 1.40-1.18 (m, 9H), 0.92-0.81 (m, 3H). $^{13}$C NMR (400 MHz, CD$_3$OD) δ 177.32, 166.65, 157.08, 138.40, 132.31, 126.65, 123.93, 122.50, 122.21, 111.39, 103.06, 56.44, 49.64, 49.43, 49.21, 49.21, 49.17, 49.07, 49.00, 48.99, 48.79, 48.57, 48.36, 47.66, 32.84, 32.70, 31.17, 29.97, 27.81, 24.36, 23.56, 14.34. HRMS (ESI+): Calcd for $C_{22}H_{30}N_6O$ [M+H]$^+$: 395.5211, Found: 395.2543.

Example 3: (S)-amino(2-(3-(1-octyl-1H-indol-3-yl)-1,2,4-oxadiazol-5-yl)pyrrolidin-1-yl)methaniminium chloride (7f, Compound 74A)

7f was prepared using general procedure 4 and isolated as a light yellow tinted solid (10 mg, 91%). $^1$H NMR (500 MHz, CD$_3$OD) δ 8.12 (dt, J=8.0, 1.0 Hz, 1H), 8.00 (s, 1H), 7.53 (dt, J=8.3, 0.9 Hz, 1H), 7.31 (ddd, J=8.3, 7.1, 1.2 Hz, 1H), 7.26-7.21 (m, 1H), 5.45 (dd, J=7.9, 1.9 Hz, 1H), 4.29 (t, J=7.0 Hz, 2H), 3.84-3.77 (m, 1H), 3.67-3.58 (m, 1H), 2.63-2.48 (m, 2H), 2.29-2.22 (m, 1H), 2.18-2.07 (m, 1H), 1.92-1.85 (m, 2H), 1.38-1.19 (m, 12H), 0.92-0.85 (m, 3H). $^{13}$C NMR (126 MHz, CD$_3$OD) δ 177.33, 166.66, 157.08, 138.41, 132.32, 126.66, 123.94, 122.51, 122.22, 111.41, 103.06, 56.45, 49.51, 49.49, 49.34, 49.32, 49.17, 49.12, 49.02, 49.00, 48.83, 48.66, 48.49, 47.66, 32.87, 32.72, 31.16, 30.26, 30.24, 27.84, 24.36, 23.64, 14.38. HRMS (ESI+): Calcd for $C_{23}H_{32}N_6O$ [M+H]$^+$: 409.5477, Found: 409.2728.

Example 4: (S)-amino(2-(3-(1-nonyl-1H-indol-3-yl)-1,2,4-oxadiazol-5-yl)pyrrolidin-1-yl)methaniminium chloride (7g, Compound 2A)

7g was prepared using general procedure 4 and isolated as a light yellow tinted solid (15 mg, 100%). $^1$H NMR (400 MHz, CD$_3$OD) δ 8.10 (ddd, J=7.9, 1.3, 0.7 Hz, 1H), 7.98 (s, 1H), 7.51 (dt, J=8.3, 0.9 Hz, 1H), 7.32-7.26 (m, 1H), 7.24-7.19 (m, 1H), 5.45-5.41 (m, 1H), 4.27 (t, J=7.0 Hz, 2H), 3.79 (td, J=9.3, 8.9, 2.6 Hz, 1H), 3.63 (td, J=9.6, 7.2 Hz, 1H), 2.61-2.47 (m, 1H), 2.29-2.21 (m, 1H) 2.17-2.08 (m, 1H), 1.92-1.82 (m, 2H), 1.35-1.21 (m, 14H), 0.88-0.84 (m, 3H). $^{13}$C NMR (101 MHz, CD$_3$OD) δ 177.32, 166.65, 157.08, 138.41, 132.31, 126.66, 123.93, 122.51, 122.21, 111.40, 103.06, 56.44, 47.67, 32.95, 32.71, 31.15, 30.52, 30.27, 27.82, 24.36, 23.67, 14.39. HRMS (ESI+): Calcd for $C_{24}H_{34}N_6O$ [M+H]$^+$: 423.5743, Found: 423.2890.

Example 5: (S)-amino(2-(3-(1-decyl-1H-indol-3-yl)-1,2,4-oxadiazol-5-yl)pyrrolidin-1-yl)methaniminium chloride (7h, Compound 7A)

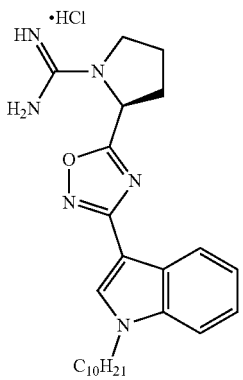

7h was prepared using general procedure 4 and isolated as a light yellow tinted solid (13 mg, 100%). $^1$H NMR (500 MHz, CD$_3$OD) δ 8.14-8.09 (m, 1H), 7.98 (s, 1H), 7.55-7.50 (m, 1H), 7.29 (ddd, J=8.3, 7.0, 1.2 Hz, 1H), 7.22 (ddd, J=8.0, 7.0, 1.0 Hz, 1H), 5.43 (dd, J=7.9, 1.9 Hz, 1H), 4.27 (t, J=7.0 Hz, 2H), 3.81-3.76 (m, 1H), 3.65-3.57 (m, 1H), 2.60-2.47 (m, 2H), 2.28-2.21 (m, 1H), 1.92-1.84 (m, 2H), 1.40-1.17 (m, 14H), 0.87 (t, J=7.0 Hz, 3H). $^{13}$C NMR (126 MHz, CD$_3$OD) δ 205.49, 194.81, 185.23, 166.56, 160.48, 154.81, 152.09, 150.67, 150.37, 139.57, 131.22, 84.60, 75.83, 61.17, 60.87, 59.31, 58.72, 58.52, 58.42, 55.98, 52.52, 51.85, 42.58. HRMS (ESI+): Calcd for C$_{25}$H$_{36}$N$_6$O [M+H]$^+$: 437.6009, Found: 437.3010.

Example 6: (S)-amino(2-(3-(1-undecyl-1H-indol-3-yl)-1,2,4-oxadiazol-5-yl)pyrrolidin-1-yl)methaniminium chloride (7i, Compound 4A)

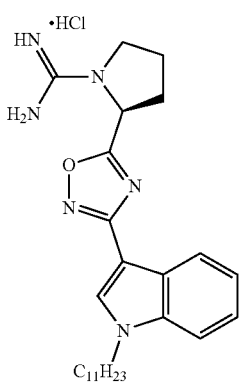

7i was prepared using general procedure 4 and isolated as a light yellow tinted solid (6 mg, 80%). $^1$H NMR (500 MHz, CD$_3$OD) δ 8.10 (d, J=7.8 Hz, 1H), 7.98 (s, 1H), 7.51 (d, J=8.2 Hz, 1H), 7.29 (ddd, J=8.3, 7.0, 1.2 Hz, 1H), 7.22 (t, J=7.5 Hz, 1H), 5.43 (dd, J=7.9, 1.8 Hz, 1H), 4.27 (t, J=7.0 Hz, 2H), 3.79 (td, J=9.2, 2.4 Hz, 1H), 3.66-3.59 (m, 1H), 2.56 (dd, J=12.9, 6.4 Hz, 1H), 2.49 (dd, J=13.0, 6.5 Hz, 1H), 2.24 (q, J=6.8, 6.2 Hz, 1H), 2.11 (d, J=12.9 Hz, 1H), 1.88 (p, J=7.1 Hz, 2H), 1.39-1.20 (m, 18H), 0.88 (t, J=7.0 Hz, 4H). $^{13}$C NMR (126 MHz, CD$_3$OD) δ 177.32, 166.65, 157.06, 138.41, 132.31, 126.65, 123.94, 122.51, 122.22, 111.41, 103.05, 56.46, 47.67, 33.02, 32.73, 31.16, 30.65, 30.60, 30.56, 30.42, 30.27, 27.82, 24.37, 23.71, 14.42. HRMS (ESI+): Calcd for C$_{26}$H$_{38}$N$_6$O [M+H]$^+$: 451.6275, Found: 451.3192.

Example 7: (S)-amino(2-(3-(1-dodecyl-1H-indol-3-yl)-1,2,4-oxadiazol-5-yl)pyrrolidin-1-yl)methaniminium chloride (7j, Compound 3A)

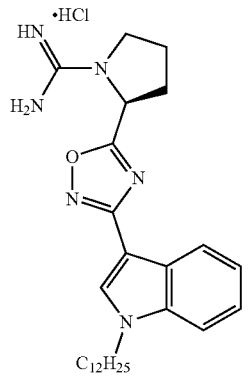

7j was prepared using general procedure 4 and isolated as a light yellow tinted solid (10 mg, 88%). $^1$H NMR (400 MHz, CD$_3$OD) δ 8.10 (ddd, J=7.9, 1.3, 0.8 Hz, 1H), 7.98 (s, 1H), 7.51 (dt, J=8.3, 0.9 Hz, 1H), 7.29 (ddd, J=8.3, 7.1, 1.3 Hz, 1H), 7.22 (ddd, J=8.0, 7.1, 1.0 Hz, 1H), 5.44 (dd, J=7.8, 2.0 Hz, 1H), 4.27 (t, J=7.0 Hz, 2H), 3.85-3.75 (m, 1H), 3.63 (td, J=9.7, 7.3 Hz, 1H), 2.63-2.46 (m, 2H), 2.31-2.20 (m, 1H), 2.21-2.07 (m, 1H), 1.88 (t, J=7.1 Hz, 2H), 1.25 (s, 18H), 0.95-0.83 (m, 3H). $^{13}$C NMR (101 MHz, CD$_3$OD) δ 177.32, 166.66, 157.08, 138.41, 132.30, 126.66, 123.93, 122.51, 122.21, 111.40, 103.07, 56.44, 47.67, 33.04, 32.71, 31.15, 30.70, 30.69, 30.58, 30.55, 30.42, 30.26, 27.82, 24.37, 23.71, 14.42. HRMS (ESI+): Calcd for C$_{27}$H$_{40}$N$_6$O [M+H]$^+$: 465.6540, Found: 465.3352.

Example 8: (S)-amino(2-(3-(1-heptyl-1H-indol-4-yl)-1,2,4-oxadiazol-5-yl)pyrrolidin-1-yl)methaniminium chloride (7k, Compound 8B)

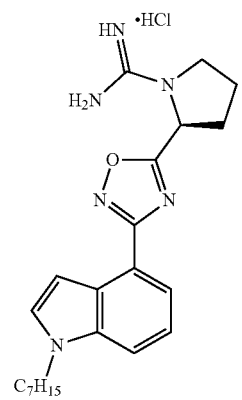

7k was prepared using general procedure 4 and isolated as a light yellow tinted solid (9 mg, 100%). $^1$H NMR (500 MHz, CD$_3$OD) δ 7.86 (dd, J=7.5, 0.9 Hz, 1H), 7.64 (dd, J=8.3, 0.9 Hz, 1H), 7.45-7.38 (m, 2H), 7.29 (dd, J=8.3, 7.4 Hz, 1H), 7.09 (dd, J=3.2, 0.8 Hz, 1H), 5.47 (dd, J=7.7, 2.1 Hz, 1H), 4.25 (t, J=7.0 Hz, 2H), 3.84-3.78 (m, 1H), 3.67-3.61 (m, 1H), 2.64-2.50 (m, 2H), 2.31-2.22 (m, 1H), 2.18-2.09 (m, 1H), 1.86 (p, J=7.1 Hz, 2H), 1.32-1.24 (m, 10H), 0.87 (t, J=7.0 Hz, 3H). $^{13}$C NMR (126 MHz, CD$_3$OD) δ 177.82, 170.29, 157.14, 138.07, 130.99, 130.90, 127.39, 121.83, 121.57, 118.60, 114.25, 56.50, 47.31, 32.88, 32.69, 31.49, 30.00, 28.12, 27.89, 24.37, 23.57, 14.34. HRMS (ESI+): Calcd for C$_{22}$H$_{30}$N$_6$O [M+H]$^+$: 395.5211, Found: 395.2577.

Example 9: (S)-amino(2-(3-(1-octyl-1H-indol-4-yl)-1,2,4-oxadiazol-5-yl)pyrrolidin-1-yl)methaniminium chloride (7l, Compound 9B)

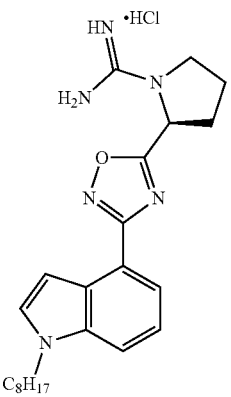

7l was prepared using general procedure 4 and isolated as a light yellow tinted solid (6 mg, 100%). $^1$H NMR (500 MHz, CD$_3$OD) δ 7.86 (dd, J=7.5, 0.9 Hz, 1H), 7.64 (dd, J=8.3, 0.9 Hz, 1H), 7.39 (s, 1H), 7.29 (dd, J=8.2, 7.4 Hz, 1H), 7.09 (dd, J=3.1, 0.8 Hz, 1H), 5.48 (dd, J=7.8, 2.0 Hz, 1H), 4.25 (t, J=7.0 Hz, 2H), 3.83-3.78 (m, 1H), 3.66-3.61 (m, 1H), 2.62-2.50 (m, 2H), 2.29-2.22 (m, 1H), 2.18-2.07 (m, 1H), 1.89-1.85 (p, J=6.9 Hz, 2H), 1.36-1.22 (m, 16H), 0.87 (t, J=6.9 Hz, 3H). $^{13}$C NMR (126 MHz, CD$_3$OD) δ 177.81, 170.29, 157.14, 138.06, 130.99, 130.90, 127.40, 121.82, 121.57, 118.60, 114.25, 103.03, 61.53, 56.50, 47.30, 32.87, 32.69, 31.46, 30.28, 30.26, 27.91, 24.37, 23.64, 20.85, 14.45, 14.37. HRMS (ESI+): Calcd for C$_{23}$H$_{32}$N$_6$O [M+H]$^+$: 409.5477, Found: 409.2731.

Example 10: (S)-amino(2-(3-(1-nonyl-1H-indol-4-yl)-1,2,4-oxadiazol-5-yl)pyrrolidin-1-yl)methaniminium chloride (7m, Compound 10B)

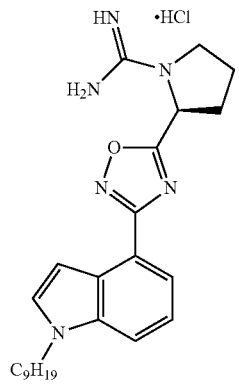

7m was prepared using general procedure 4 and isolated as a light yellow tinted solid (7 mg, 95%). $^1$H NMR (500 MHz, CD$_3$OD) δ 7.90-7.70 (m, 1H), 7.45 (s, 1H), 7.42-7.38 (m, 1H), 7.37-7.32 (m, 1H), 7.12-7.08 (m, 1H), 5.54-5.48 (m, 1H), 4.34-4.18 (m, 2H), 3.86-3.79 (m, 1H), 3.70-3.64 (m, 1H), 2.46-2.46 (m, 2H), 2.29-2.21 (m, 1H), 2.19-2.08 (m, 1H), 1.86 (p, J=6.7 Hz, 1H), 1.42-1.20 (m, 14H), 0.91-0.87 (m, 3H). $^{13}$C NMR (126 MHz, CD$_3$OD) δ 176.64, 168.90, 155.73, 135.89, 134.62, 127.33, 122.51, 122.34, 121.39, 117.49, 112.85, 55.09, 54.90, 31.55, 31.33, 29.87, 29.13, 28.86, 26.40, 22.88, 22.26, 12.97. HRMS (ESI+): Calcd for C$_{24}$H$_{34}$N$_6$O [M+H]$^+$: 423.5743, Found: 424.2938.

Example 11: (S)-amino(2-(3-(1-decyl-1H-indol-4-yl)-1,2,4-oxadiazol-5-yl)pyrrolidin-1-yl)methaniminium chloride (7n, Compound 11B)

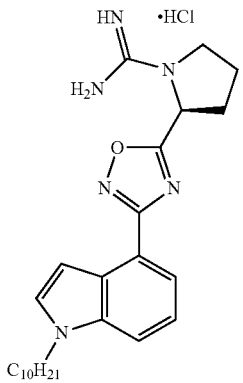

7n was prepared using general procedure 4 and isolated as a light yellow tinted solid (6 mg, 81%). $^1$H NMR (500 MHz, CD$_3$OD) δ 7.88 (d, J=7.3 Hz, 1H), 7.66 (dd, J=8.3, 5.0 Hz, 1H), 7.40 (d, J=3.1 Hz, 1H), 7.35-7.29 (m, 1H), 7.10 (dd, J=6.0, 3.1 Hz, 1H), 5.50 (dd, J=7.8, 2.0 Hz, 1H), 4.27 (t, J=6.7 Hz, 2H), 3.85-3.79 (m, 1H), 3.70-3.63 (m, 1H), 2.65-2.52 (m, 2H), 2.32-2.23 (m, 1H), 2.18-2.08 (m, 1H), 1.87 (p, J=6.9 Hz, 2H), 1.35-1.22 (m, 25H), 0.90-0.87 (m, 3H). $^{13}$C NMR (126 MHz, CD$_3$OD) δ 177.80, 170.28, 157.13, 138.06, 130.99, 130.90, 128.73, 127.47, 123.75, 122.79, 121.82, 121.59, 114.25, 103.04, 56.50, 56.32, 47.31, 33.03, 33.01, 32.70, 31.44, 31.29, 30.71, 30.58, 30.54, 30.39, 30.36, 30.26, 28.13, 27.87, 24.37, 24.29, 23.72, 23.68, 14.41. HRMS (ESI+): Calcd for $C_{25}H_{36}N_6O$ [M+H]$^+$: 437.6009, Found: 437.3033.

Example 12: (S)-amino(2-(3-(1-nonyl-1H-indol-5-yl)-1,2,4-oxadiazol-5-yl)pyrrolidin-1-yl)methaniminium chloride (7r, Compound 17A)

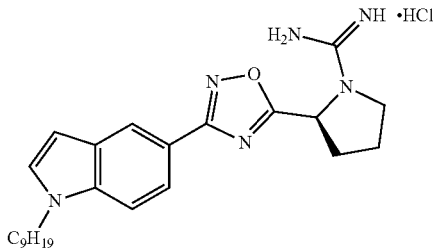

7r was prepared using general procedure 4 and isolated as a light yellow solid (7 mg, 95%). $^1$H NMR (500 MHz, CD$_3$OD) δ 8.29 (d, J=1.6 Hz, 1H), 7.84 (dd, J=8.7, 1.6 Hz, 1H), 7.52 (d, J=8.7 Hz, 1H), 7.32 (d, J=3.2 Hz, 1H), 6.56 (dd, J=3.2, 0.8 Hz, 1H), 5.44 (dd, J=7.9, 1.9 Hz, 1H), 4.22 (td, J=7.0, 4.4 Hz, 2H), 3.87-3.72 (m, 1H), 3.67-3.58 (m, 1H), 2.63-2.51 (m, 1H), 2.25-2.19 (m, 1H), 2.12 (dd, J=8.3, 4.4 Hz, 1H), 1.84 (q, J=7.0 Hz, 2H), 1.34-1.07 (m, 15H), 0.86 (d, J=7.1 Hz, 3H). $^{13}$C NMR (126 MHz, CD$_3$OD) δ 178.35, 170.83, 157.11, 139.15, 130.86, 130.10, 122.26, 121.98, 121.19, 118.15, 111.95, 111.15, 102.92, 56.48, 47.29, 32.97, 32.70, 31.39, 30.57, 30.30, 30.29, 27.88, 24.36, 23.69, 14.40. HRMS (ESI+): Calcd for $C_{24}H_{34}N_6O$ [M+H]$^+$: 423.5743, Found: 423.2858.

Example 13: (S)-amino(2-(3-(1-octyl-1H-indol-6-yl)-1,2,4-oxadiazol-5-yl)pyrrolidin-1-yl)methaniminium chloride (7u, Compound 75A)

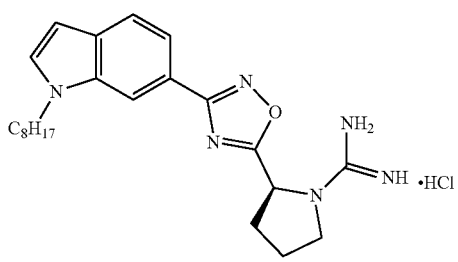

7u was prepared using general procedure 4 and isolated as a light yellow tinted solid (6 mg, 82%). $^1$H NMR (500 MHz, CD$_3$OD) δ 8.15 (ddd, J=21.7, 1.3, 0.7 Hz, 1H), 7.89-7.73 (m, 1H), 7.68 (ddd, J=8.4, 7.1, 0.7 Hz, 1H), 7.53-7.39 (m, 1H), 6.54 (dd, J=3.1, 0.9 Hz, 1H), 5.48 (ddd, J=8.0, 3.7, 2.1 Hz, 1H), 4.27 (td, J=7.0, 3.4 Hz, 2H), 3.82 (td, J=8.2, 7.2, 5.3 Hz, 1H), 3.65-3.56 (m, 1H), 2.65-2.47 (m, 3H), 2.33-2.27 (m, 1H), 2.17-2.08 (m, 1H), 1.86 (d, J=14.0 Hz, 2H), 1.36-1.20 (m, 13H), 0.88 (t, J=7.0 Hz, 5H). $^{13}$C NMR (126 MHz, CD$_3$OD) δ 178.54, 170.93, 157.14, 137.16, 131.99, 128.79, 122.27, 119.98, 119.80, 119.64, 119.06, 110.71, 110.13, 102.38, 56.52, 47.26, 32.87, 32.79, 31.43, 31.38, 30.29, 30.26, 30.21, 27.91, 27.80, 24.40, 23.65, 14.38. HRMS (ESI+): Calcd for $C_{23}H_{32}N_6O$ [M+H]$^+$: 409.5477, Found: 409.2732.

Example 14: (S)-amino(2-(3-(1-decyl-1H-indol-6-yl)-1,2,4-oxadiazol-5-yl)pyrrolidin-1-yl)methaniminium chloride (7w, Compound 18A)

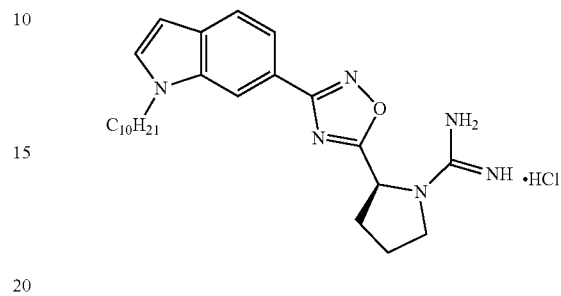

7w was prepared using general procedure 4 and isolated as a light yellow tinted solid (7 mg, 94%). $^1$H NMR (500 MHz, CD$_3$OD) δ 8.20-8.08 (m, 1H), 7.85 (dd, J=8.4, 1.3 Hz, 1H), 7.76-7.66 (m, 1H), 7.50 (s, 1H), 6.55-6.54 (m, 1H), 5.52-5.45 (m, 1H), 4.26 (t, J=7.0 Hz, 2H), 3.82 (td, J=9.2, 8.8, 2.5 Hz, 1H), 3.65 (td, J=9.6, 7.0 Hz, 1H), 2.63-2.51 (m, 2H), 2.31-2.21 (m, 1H), 2.18-2.07 (m, 1H), 1.91-1.82 (m, 2H), 1.38-1.11 (m, 14H), 0.89 (t, J=7.0 Hz, 3H). HRMS (ESI+): Calcd for $C_{25}H_{36}N_6O$ [M+H]$^+$: 437.6009, Found: 437.3017.

Examples 15-58 Synthesis and Characterization of Formulae IA and IB Compounds Wherein X is Phenyl Schemes 3-11 outline general and specific synthetic methodologies for the preparation of Compound Nos. 5A, 6A, 8A-11A, 19A-50A, 60A, and 62A-64A. Compound numbering in Scheme 3 is internal to the Scheme, while the subsequent procedures refer where applicable to the final compounds.

Scheme 3. General synthetic scheme.

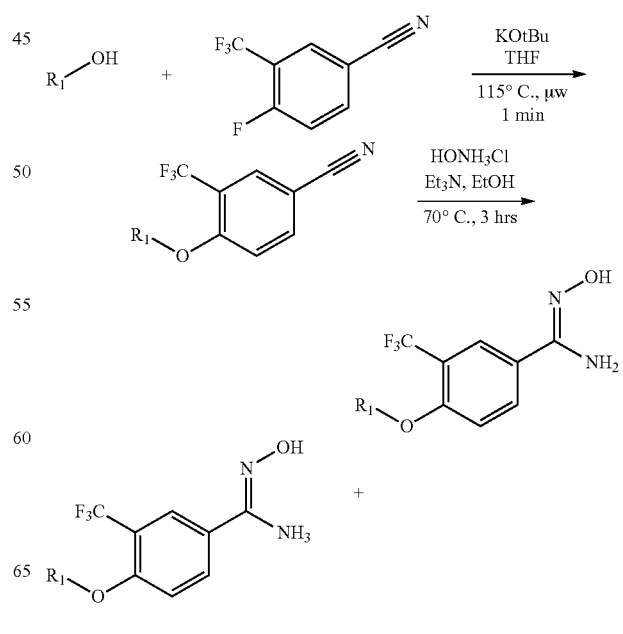

-continued
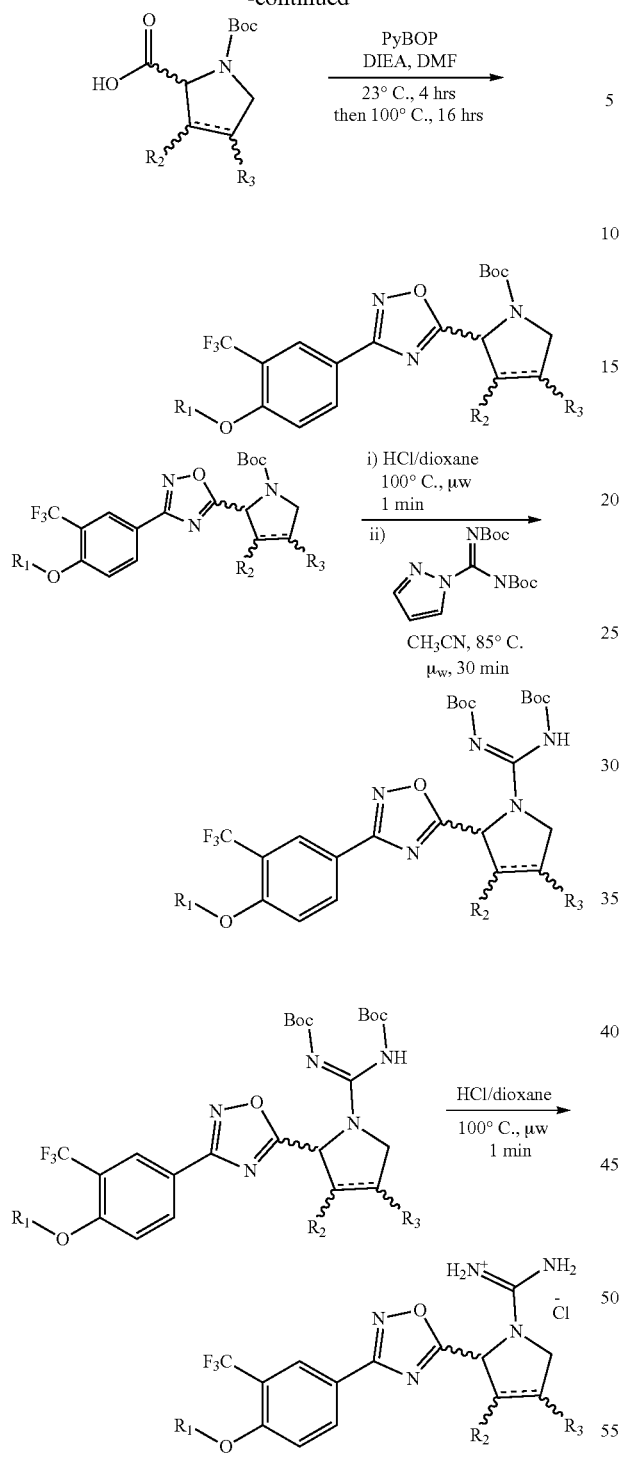
Scheme 4. Synthesis of alcohols from carboxylic acids.
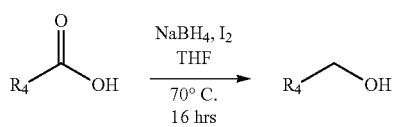
Scheme 5. Synthesis of hydroxyguanidines.
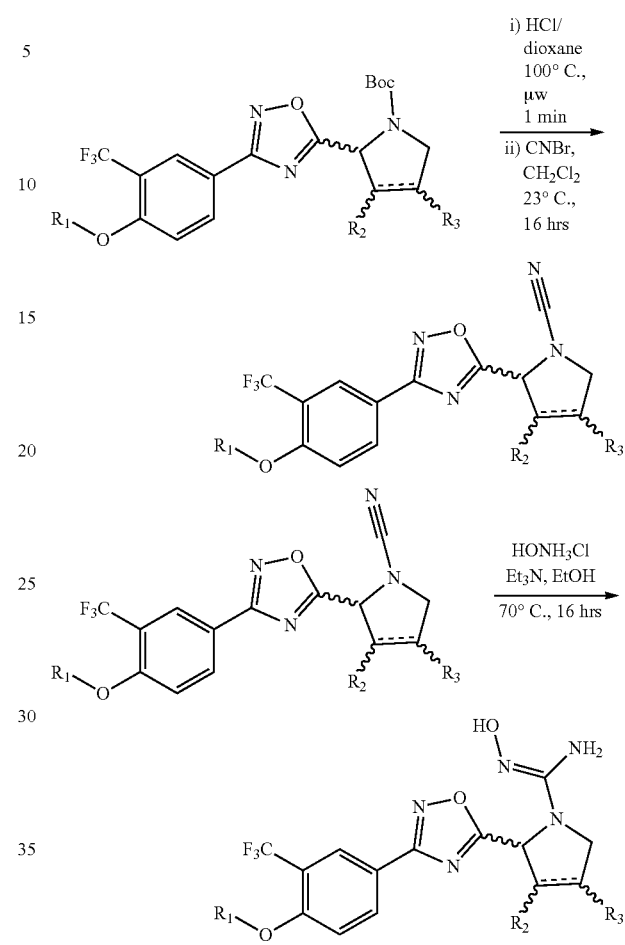
Scheme 6. Tert-butyl ester deprotection and N-Boc protection.
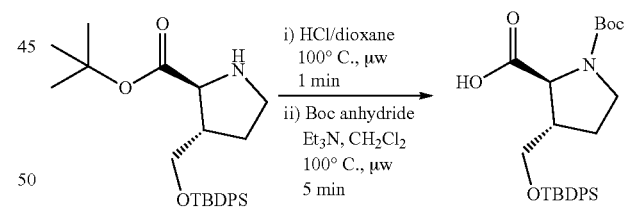
Scheme 7. TBDPS ether deprotection.
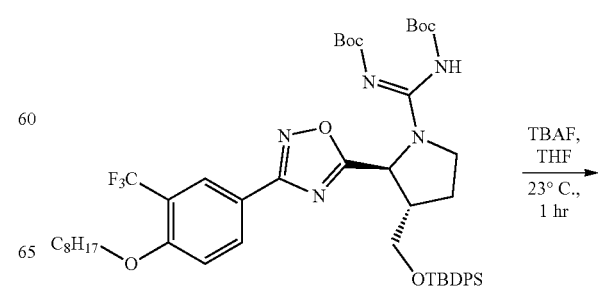

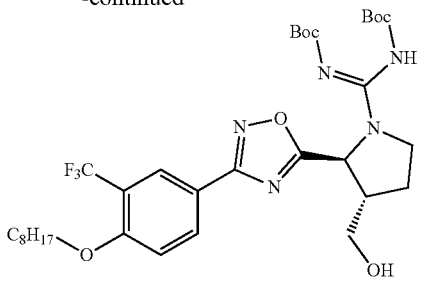

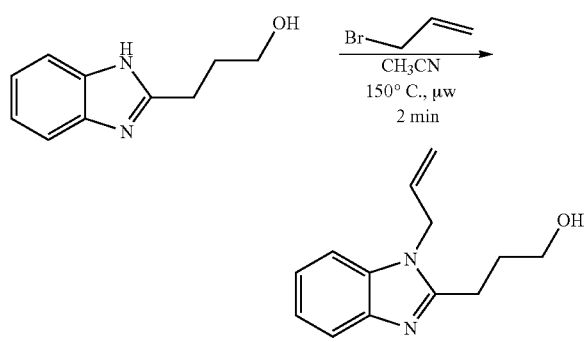

Scheme 8. Allylation of benzimidazole.

General Procedure A. Nucleophilic Aromatic Substitution 4-fluoro-3-(trifluoromethyl)benzonitrile (1 equiv) and the alcohol (1 equiv) were added to a microwave vial and cooled in an ice bath, then 0.5M potassium tert-butoxide in tetrahydrofuran (1.1 equiv) was carefully added and allowed to warm to room temperature. The contents were then heated to 115° C. for 1 minute in the microwave. After cooling, celite was added and the solvent was removed under reduced pressure. The resulting powder was subjected to flash chromatography on silica gel.

General Procedure B. Conversion of Nitrile to Amidoxime

The nitrile (1 equiv) and hydroxylamine hydrochloride (2.2 equiv) were suspended in absolute ethanol. Triethylamine (2.3 equiv) was added and the contents were heated to 70° C. for 3 hours. Multi-gram scale reactions were heated overnight. Upon cooling, the solvent was evaporated under reduced pressure. To the resulting residue, ethyl acetate and saturated $NaHCO_3$ solution were added and stirred until all residue was dissolved. The mixture was transferred to a separatory funnel and the aqueous layer was discarded. The organic layer was washed with brine, dried over $Na_2SO_4$, filtered, and concentrated to provide the product in sufficiently pure form to be used without further purification.

General Procedure C. PyBOP-Mediated Oxadiazole Formation

The carboxylic acid (1.1 equiv) and PyBOP (1.2 equiv) were dissolved in dry N,N-dimethylformamide. N,N-diisopropylethylamine (3 equiv) was added and stirred for 15 minutes at room temperature. The amidoxime (1 equiv) dissolved in minimal N,N-dimethylformamide was added and the mixture was stirred for 4 hours at room temperature, then heated to 100° C. overnight. The mixture was allowed to cool to room temperature, then poured into a separatory funnel and diluted with ethyl acetate. The organics were washed with saturated $NaHCO_3$, followed by brine. The bicarbonate wash was back-extracted with ethyl acetate and all organics were combined, dried over $Na_2SO_4$ and filtered. Celite was added to the flask and the solvent was evaporated under reduced pressure. The resulting powder was subjected to flash chromatography on silica gel.

General Procedure D. Guanidine Formation

The Boc-protected pyrrolidine (1 equiv) was dissolved in 4M HCl in dioxane and heated to 100° C. in the microwave for 1 minute. The solvent was removed and the crude was reconstituted in dry acetonitrile. tert-butyl (Z)-(((tert-butoxycarbonyl)amino)(1H-pyrazol-1-yl)methylene)carbamate (0.9 equiv) and N,N-diisopropylethylamine (3 equiv) were added and the mixture was heated to 85° C. for 30 minutes in the microwave (or alternatively, room temperature for 72 hours). Upon cooling, celite was added and the solvent was evaporated under reduced pressure. The resulting powder was subjected to flash chromatography on silica gel.

General Procedure E. Bis-Boc Guanidine Deprotection

The bis-Boc guanidine was dissolved in 4M HCl in dioxane and heated to 100° C. in the microwave for 1 minute. The solvent was removed to provide the final product, which was optionally purified by reverse-phase HPLC.

General Procedure F. Conversion of Carboxylic Acid to Alcohol

The carboxylic acid (1 equiv) and sodium borohydride (5 equiv) were suspended in dry tetrahydrofuran. The mixture was cooled in an ice bath and a solution of iodine (2 equiv) in THE was added dropwise over 30 minutes. The mixture was warmed to room temperature and when the solution became clear, it was heated to 70° C. for 16 hours. Upon cooling, aqueous 2M sodium hydroxide solution was slowly added and stirred for 1 hour. The mixture was transferred to a seperatory funnel and diluted with ethyl acetate. The aqueous layer was discarded and the organic layer was washed with brine, dried over $Na_2SO_4$, and filtered. Celite was added and the solvent was evaporated under reduced pressure. The resulting powder was subjected to flash chromatography on silica gel.

General Procedure G. Tert-Butyl Ester Deprotection and Boc-Protection

The tert-butyl ester was dissolved in 4M HCl in dioxane and heated in the microwave to 100° C. for 1 minute. The solvent was removed under reduced pressure and the crude was reconstituted in dry dichloromethane. Boc-anhydride (1.5 equiv) and triethylamine (3 equiv) were added and the mixture was heated in the microwave to 100° C. for 5 minutes. Aqueous 1M HCl solution was added to achieve pH=1 and the product was extracted into dichloromethane. Celite was added and the solvent was evaporated under reduced pressure. The resulting powder was subjected to flash chromatography on silica gel.

General Procedure H. Silyl Ether Deprotection

The TBDPS ether was dissolved in excess 1M tetrabutylammonium fluoride in THF and stirred for 1 hour at room temperature and open to air. Celite was added and the solvent was evaporated under reduced pressure. The resulting powder was subjected to flash chromatography on silica gel.

General Procedure I. Allylation of Benzimidazole

The Benzimidazole was Dissolved in Acetonitrile. Allyl Bromide (1.1 Equiv) was added and the mixture was heated in the microwave to 150° C. for 2 minutes. Celite was added and the solvent was removed under reduced pressure. The resulting powder was subjected to flash chromatography on silica gel.

General Procedure J. Alternative Boc deprotection.

The bis-Boc guanidine was dissolved in dichloromethane and trifluoroacetic acid was added. The mixture was stirred at room temperature for 4 hours. The solvent was removed to provide the final product, which was optionally purified by reverse-phase HPLC.

4-(octyloxy)-3-(trifluoromethyl)benzonitrile

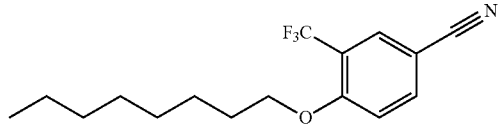 [SMILES: CCCCCCCCOc1ccc(C#N)cc1C(F)(F)F]

Synthesized by General Procedure A. 96% yield, colorless oil; $^1$H NMR (600 MHz, Chloroform-d) δ 7.85 (d, J=2.1 Hz, 1H), 7.77 (dd, J=8.7, 2.1 Hz, 1H), 7.05 (d, J=8.7 Hz, 1H), 4.11 (t, J=6.3 Hz, 2H), 1.88-1.80 (m, 2H), 1.47 (p, J=7.5, 7.1 Hz, 2H), 1.38-1.24 (m, 8H), 0.88 (t, J=6.8 Hz, 3H).

N-hydroxy-4-(octyloxy)-3-(trifluoromethyl)benzimidamide

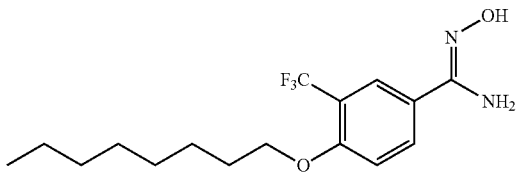 [SMILES: CCCCCCCCOc1ccc(/C(N)=N/O)cc1C(F)(F)F]

Synthesized by General Procedure B. 100% yield, white solid; $^1$H NMR (600 MHz, Chloroform-d) δ 9.25 (s, 1H), 7.82 (d, J=2.3 Hz, 1H), 7.72 (dd, J=8.7, 2.3 Hz, 1H), 6.95 (d, J=8.7 Hz, 1H), 4.98 (s, 2H), 4.03 (t, J=6.4 Hz, 2H), 1.81 (tt, J=12.4, 6.4 Hz, 2H), 1.46 (p, J=7.7, 7.3 Hz, 2H), 1.40-1.23 (m, 8H), 0.89 (t, J=6.8 Hz, 3H).

tert-butyl (S)-4,4-difluoro-2-(3-(4-(octyloxy)-3-(trifluoromethyl)phenyl)-1,2,4-oxadiazol-5-yl)pyrrolidine-1-carboxylate

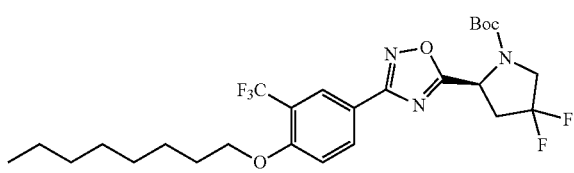 [SMILES: CCCCCCCCOc1ccc(-c2noc([C@@H]3CC(F)(F)CN3C(=O)OC(C)(C)C)n2)cc1C(F)(F)F]

Synthesized by General Procedure C. 84% yield, colorless oil; $^1$H NMR (600 MHz, Chloroform-d) δ 8.28 (s, 1H), 8.18 (d, J=8.6 Hz, 1H), 7.11-7.03 (m, 1H), 5.45-5.20 (m, 1H), 4.11 (t, J=6.4 Hz, 2H), 4.06-3.90 (m, 2H), 0.92-0.84 (m, 3H), 2.97-2.85 (m, 1H), 2.80-2.63 (m, 1H), 1.91-1.79 (m, 2H), 1.55-1.40 (m, 6H), 1.40-1.22 (m, 13H), 0.89 (t, J=7.0 Hz, 3H).

tert-butyl (S)-(((tert-butoxycarbonyl)amino)(4,4-difluoro-2-(3-(4-(octyloxy)-3-(trifluoromethyl)phenyl)-1,2,4-oxadiazol-5-yl)pyrrolidin-1-yl)methylene)carbamate

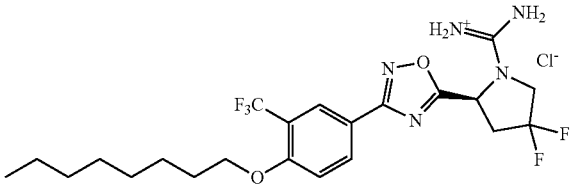 [SMILES: CCCCCCCCOc1ccc(-c2noc([C@@H]3CC(F)(F)CN3C(N)=[NH2+])n2)cc1C(F)(F)F ; [Cl-]]

Synthesized by General Procedure D. 48% yield, yellow oil; $^1$H NMR (600 MHz, Chloroform-d) δ 8.29 (d, J=2.1 Hz, 1H), 8.23-8.16 (m, 1H), 7.07 (d, J=8.7 Hz, 1H), 4.79 (dd, J=8.2, 6.9 Hz, 1H), 4.11 (t, J=6.3 Hz, 2H), 3.56-3.47 (m, 1H), 3.45-3.35 (m, 1H), 2.89-2.68 (m, 2H), 1.88-1.80 (m, 2H), 1.53-1.45 (m, 2H), 1.40-1.23 (m, 9H), 0.89 (t, J=6.9 Hz, 3H).

Example 15: (S)-amino(4,4-difluoro-2-(3-(4-(octyloxy)-3-(trifluoromethyl)phenyl)-1,2,4-oxadiazol-5-yl)pyrrolidin-1-yl)methaniminium chloride (Compound 19A)

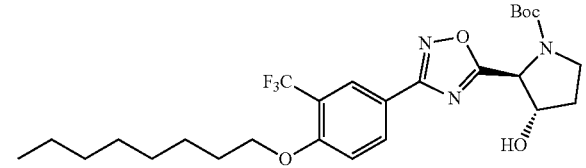 [SMILES: CCCCCCCCOc1ccc(-c2noc([C@@H]3[C@@H](O)CCN3C(=O)OC(C)(C)C)n2)cc1C(F)(F)F]

Synthesized by General Procedure E. 100% yield, white solid; $^1$H NMR (600 MHz, Methanol-d$_4$) δ 8.33-8.27 (m, 2H), 7.36 (dd, J=8.7, 2.5 Hz, 1H), 5.62 (t, J=8.8 Hz, 1H), 4.19 (td, J=6.2, 2.4 Hz, 2H), 4.03 (dq, J=35.0, 13.0 Hz, 2H), 3.28 (dt, J=14.5, 6.0 Hz, 1H), 3.13 (qd, J=14.8, 10.5 Hz, 1H), 1.84 (dtd, J=8.0, 6.3, 3.1 Hz, 2H), 1.57-1.46 (m, 2H), 1.46-1.25 (m, 8H), 0.90 (td, J=7.0, 2.8 Hz, 3H); $^{13}$C NMR (151 MHz, cd$_3$od) δ 174.55, 168.91, 161.13, 134.09, 127.29, 118.76, 114.97, 70.39, 68.12, 53.83, 52.77, 49.28, 49.14, 49.00, 48.86, 48.72, 38.82, 38.64, 38.46, 32.89, 30.31, 30.23, 30.00, 26.89, 23.68, 14.40; MS (ESI+): Calc'd for C$_{22}$H$_{29}$F$_5$N$_5$O$_2$ [M+H]: 490.2, Found: 490.8.

tert-butyl (2S,3S)-3-hydroxy-2-(3-(4-(octyloxy)-3-(trifluoromethyl)phenyl)-1,2,4-oxadiazol-5-yl)pyrrolidine-1-carboxylate Synthesized by General Procedure C. 87% yield, colorless oil; ¹H NMR (600 MHz, Chloroform-d) δ 8.29-8.24 (m, 1H), 8.20-8.12 (m, 1H), 7.09-7.02 (m, 1H), 5.12-4.93 (m, 1H), 4.61-4.54 (m, 1H), 4.10 (q, J=6.6 Hz, 2H), 3.83-3.69 (m, 2H), 2.40-2.28 (m, 1H), 2.09-2.01 (m, 1H), 1.84 (p, J=6.7 Hz, 2H), 1.50-1.44 (m, 5H), 1.40-1.24 (m, 14H), 0.89 (t, J=7.0 Hz, 2H); MS (ESI+): Calcd for $C_{26}H_{37}F_3N_3O_5$ [M+H]: 528.3, Found: 528.4.

tert-butyl (((tert-butoxycarbonyl)amino)((2S,3S)-3-hydroxy-2-(3-(4-(octyloxy)-3-(trifluoromethyl)phenyl)-1,2,4-oxadiazol-5-yl)pyrrolidin-1-yl)methylene)carbamate

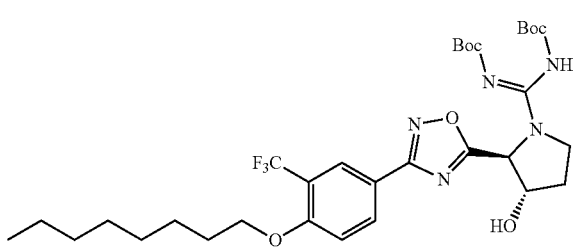 [SMILES: CCCCCCCCOc1ccc(-c2noc([C@@H]3[C@@H](O)CCN3/C(=N/C(=O)OC(C)(C)C)NC(=O)OC(C)(C)C)n2)cc1C(F)(F)F]

Synthesized by General Procedure D. 25% yield, yellow oil; ¹H NMR (600 MHz, Chloroform-d) δ 8.25 (d, J=2.1 Hz, 1H), 8.16 (dd, J=8.7, 2.2 Hz, 1H), 7.05 (d, J=8.7 Hz, 1H), 5.53 (dd, J=2.4, 1.0 Hz, 1H), 4.65 (s, 1H), 4.14-4.06 (m, 2H), 4.07-3.99 (m, 1H), 3.98-3.91 (m, 1H), 3.13 (s, 1H), 2.40-2.32 (m, 1H), 1.88-1.78 (m, 2H), 1.53-1.43 (m, 21H), 1.40-1.23 (m, 6H), 0.88 (t, J=7.0 Hz, 3H).

Example 16: amino((2S,3S)-3-hydroxy-2-(3-(4-(octyloxy)-3-(trifluoromethyl)phenyl)-1,2,4-oxadiazol-5-yl)pyrrolidin-1-yl)methaniminium chloride (Compound 6A)

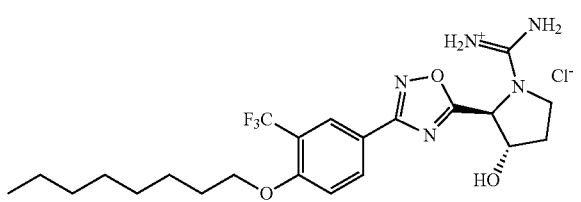 [SMILES: CCCCCCCCOc1ccc(-c2noc([C@@H]3[C@@H](O)CCN3C(N)=[NH2+])n2)cc1C(F)(F)F ; [Cl-]]

Synthesized by General Procedure E. 100% yield, white solid; ¹H NMR (600 MHz, Methanol-d4) δ 8.29-8.18 (m, 2H), 7.32 (d, J=8.7 Hz, 1H), 5.26 (t, J=1.0 Hz, 1H), 4.81-4.77 (m, 1H), 4.17 (t, J=6.2 Hz, 2H), 3.89-3.77 (m, 2H), 2.28-2.14 (m, 2H), 1.87-1.76 (m, 2H), 1.56-1.47 (m, 2H), 1.44-1.25 (m, 8H), 0.90 (d, J=7.0 Hz, 3H); ¹³C NMR (151 MHz, cd₃od) δ 176.97, 168.66, 160.88, 157.57, 133.97, 127.06, 119.22, 114.82, 75.98, 70.31, 64.78, 47.42, 32.88, 32.47, 30.31, 30.23, 30.00, 26.89, 23.68, 14.41; MS (ESI+): Calc'd for $C_{22}H_{31}F_3N_5O_3$ [M+H]: 470.2, Found: 470.2.

(2S,3S)-1-(tert-butoxycarbonyl)-3-(((tert-butyldiphenylsilyl)oxy)methyl)pyrrolidine-2-carboxylic acid

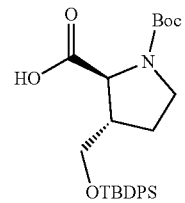

Synthesized by General Procedure H. 64% yield, white solid; ¹H NMR (600 MHz, Chloroform-d) δ 7.70-7.64 (m, 4H), 7.46-7.37 (m, 6H), 4.33-4.21 (m, 1H), 3.73-3.64 (m, 2H), 3.59-3.43 (m, 2H), 2.69-2.54 (m, 1H), 2.08-2.00 (m, 1H), 1.89-1.75 (m, 1H), 1.52-1.40 (m, 9H), 1.13-1.05 (m, 9H).

tert-butyl (2S,3S)-3-(((tert-butyldiphenylsilyl)oxy)methyl)-2-(3-(4-(octyloxy)-3-(trifluoromethyl)phenyl)-1,2,4-oxadiazol-5-yl)pyrrolidine-1-carboxylate

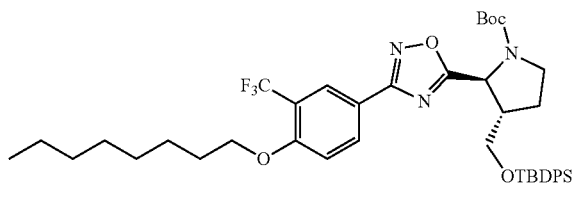

Synthesized by General Procedure C. 66% yield, yellow oil; ¹H NMR (600 MHz, Chloroform-d) δ 8.31-8.27 (m, 1H), 8.21-8.15 (m, 1H), 7.67-7.62 (m, 4H), 7.46-7.35 (m, 6H), 7.10-7.02 (m, 1H), 5.13-5.00 (m, 1H), 4.14-4.08 (m, 2H), 3.76-3.63 (m, 2H), 2.20-2.11 (m, 1H), 1.90-1.80 (m, 4H), 1.54-1.41 (m, 4H), 1.39-1.25 (m, 17H), 1.05 (s, 9H), 0.89 (t, J=6.8 Hz, 3H).

tert-butyl ((E)-((tert-butoxycarbonyl)amino)((2S,3S)-3-(((tert-butyldiphenylsilyl)oxy)methyl)-2-(3-(4-(octyloxy)-3-(trifluoromethyl)phenyl)-1,2,4-oxadiazol-5-yl)pyrrolidin-1-yl)methylene)carbamate

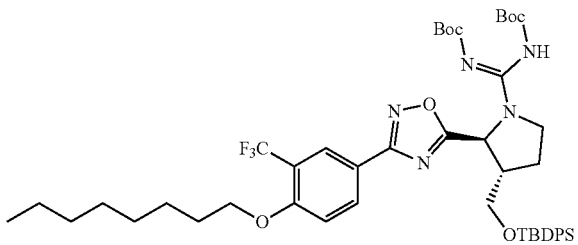

Synthesized by General Procedure D. 20% yield, yellow solid; ¹H NMR (600 MHz, Chloroform-d) δ 8.29 (d, J=2.1 Hz, 1H), 8.19 (dd, J=8.7, 2.2 Hz, 1H), 7.70-7.61 (m, 4H), 7.46-7.30 (m, 6H), 7.05 (d, J=8.7 Hz, 1H), 4.53 (d, J=5.9 Hz, 1H), 4.16-4.06 (m, 2H), 3.84-3.68 (m, 2H), 3.28-3.20 (m, 1H), 3.19-3.12 (m, 1H), 2.79-2.70 (m, 1H), 2.12-2.03 (m, 1H), 1.88-1.80 (m, 2H), 1.77-1.68 (m, 1H), 1.53-1.23 (m, 13H), 1.04 (s, 9H), 0.88 (t, J=7.0 Hz, 3H).

tert-butyl ((E)-((tert-butoxycarbonyl)amino)((2S,3S)-3-(hydroxymethyl)-2-(3-(4-(octyloxy)-3-(trifluoromethyl)phenyl)-1,2,4-oxadiazol-5-yl)pyrrolidin-1-yl)methylene)carbamate

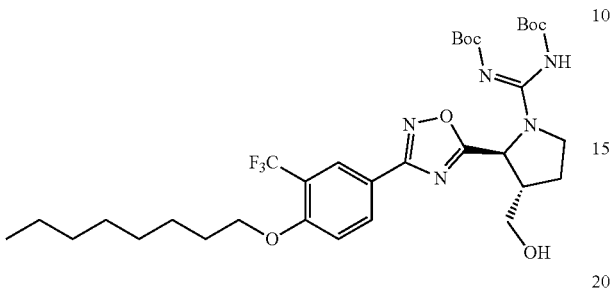

Synthesized by General Procedure H. 90% yield, white solid; $^1$H NMR (600 MHz, Chloroform-d) δ 10.11 (s, 1H), 8.27 (d, J=2.1 Hz, 1H), 8.17 (dd, J=8.7, 2.2 Hz, 1H), 7.05 (d, J=8.7 Hz, 1H), 5.57-5.55 (m, 0H), 4.10 (t, J=6.4 Hz, 2H), 4.09-4.06 (m, 1H), 3.97-3.89 (m, 1H), 3.85-3.70 (m, 3H), 2.75 (s, 1H), 2.30-2.20 (m, 2H), 0.88 (t, J=7.0 Hz, 3H), 5.55-5.52 (m, 0H), 1.97-1.70 (m, 5H), 1.54-1.19 (m, 26H).

Example 17: amino((2S,3S)-3-(hydroxymethyl)-2-(3-(4-(octyloxy)-3-(trifluoromethyl)phenyl)-1,2,4-oxadiazol-5-yl)pyrrolidin-1-yl)methaniminium chloride (Compound 20A)

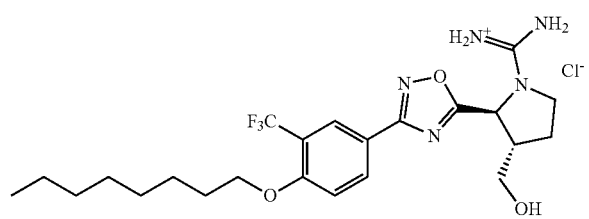 [SMILES: CCCCCCCCOc1ccc(-c2noc([C@@H]3[C@@H](CO)CCN3C(N)=[NH2+])n2)cc1C(F)(F)F ; [Cl-]]

Synthesized by General Procedure E. 100% yield, white solid; $^1$H NMR (600 MHz, Methanol-d$_4$) δ 8.28-8.17 (m, 2H), 7.33 (d, J=8.7 Hz, 1H), 5.43 (d, J=2.5 Hz, 1H), 4.19 (t, J=6.2 Hz, 2H), 3.81-3.69 (m, 3H), 3.16-3.10 (m, 2H), 2.30-2.20 (m, 1H), 2.11-2.03 (m, 1H), 1.88-1.80 (m, 2H), 1.57-1.48 (m, 2H), 1.36-1.27 (m, 8H), 0.91 (t, J=6.9 Hz, 3H); MS (ESI+): Calc'd for $C_{23}H_{33}F_3N_5O_3$ [M+H]: 484.3, Found: 484.8.

tert-butyl (S)-2-(3-(4-(octyloxy)-3-(trifluoromethyl)phenyl)-1,2,4-oxadiazol-5-yl)-2,5-dihydro-1H-pyrrole-1-carboxylate

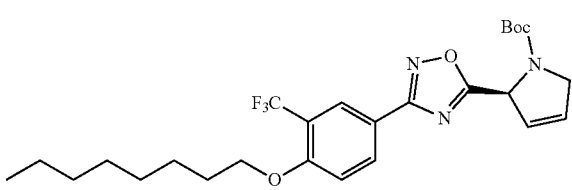 [SMILES: CCCCCCCCOc1ccc(-c2noc([C@@H]3C=CCN3C(=O)OC(C)(C)C)n2)cc1C(F)(F)F]

Synthesized by General Procedure C. 85% yield, yellow oil; $^1$H NMR (600 MHz, Chloroform-d) δ 8.31-8.26 (m, 1H), 8.21-8.15 (m, 1H), 7.09-7.02 (m, 1H), 6.13 (dt, J=6.2, 2.1 Hz, 1H), 5.91-5.77 (m, 2H), 4.48-4.28 (m, 2H), 4.15-4.07 (m, 2H), 1.88-1.79 (m, 2H), 1.53-1.44 (m, 5H), 1.40-1.23 (m, 14H), 0.88 (t, J=7.0 Hz, 3H).

tert-butyl (S)-(((tert-butoxycarbonyl)amino)(2-(3-(4-(octyloxy)-3-(trifluoromethyl)phenyl)-1,2,4-oxadiazol-5-yl)-2,5-dihydro-1H-pyrrol-1-yl)methylene)carbamate

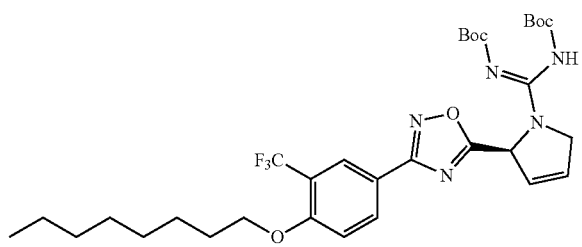 [SMILES: CCCCCCCCOc1ccc(-c2noc([C@@H]3C=CCN3/C(=N/C(=O)OC(C)(C)C)NC(=O)OC(C)(C)C)n2)cc1C(F)(F)F]

Synthesized by General Procedure D. 34% yield, yellow oil; $^1$H NMR (600 MHz, Chloroform-d) δ 10.11 (s, 1H), 8.27 (d, J=2.1 Hz, 1H), 8.17 (dd, J=8.7, 2.2 Hz, 1H), 7.05 (d, J=8.7 Hz, 1H), 6.46-6.40 (m, 1H), 6.19-6.11 (m, 1H), 5.91-5.86 (m, 1H), 4.81-4.74 (m, 1H), 4.47 (d, J=16.4 Hz, 1H), 8.29-8.24 (m, 0H), 1.88-1.80 (m, 2H), 8.24-8.10 (m, 0H), 4.15-4.08 (m, 2H), 1.57-1.23 (m, 28H), 0.88 (t, J=6.9 Hz, 3H).

Example 18: (S)-amino(2-(3-(4-(octyloxy)-3-(trifluoromethyl)phenyl)-1,2,4-oxadiazol-5-yl)-2,5-dihydro-1H-pyrrol-1-yl)methaniminium chloride (Compound 21A)

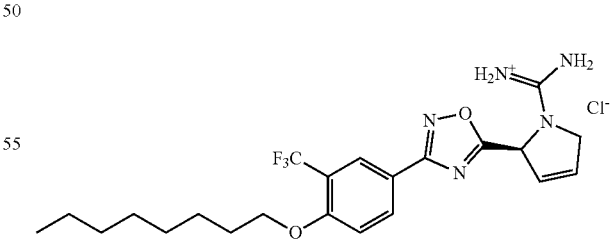

Synthesized by General Procedure E. 95% yield, white solid; $^1$H NMR (600 MHz, Chloroform-d) δ 8.26-8.18 (m, 1H), 8.17-8.07 (m, 1H), 7.12-7.04 (m, 1H), 6.40-6.23 (m, 1H), 6.14-6.00 (m, 1H), 4.15-4.06 (m, 1H), 1.90-1.78 (m, 2H), 1.74-1.56 (m, 4H), 1.54-1.44 (m, 2H), 1.42-1.20 (m, 8H), 0.98-0.81 (m, 3H); MS (ESI+): Calc'd for $C_{22}H_{29}F_3N_5O_2$ [M+H]: 452.2, Found: 452.6.

tert-butyl (2S,4R)-4-hydroxy-2-(3-(4-(octyloxy)-3-(trifluoromethyl)phenyl)-1,2,4-oxadiazol-5-yl)pyrrolidine-1-carboxylate

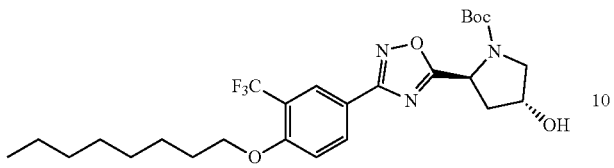

Synthesized by General Procedure C. 73% yield, yellow oil; ¹H NMR (600 MHz, Chloroform-d) δ 8.28 (d, J=2.2 Hz, 1H), 8.18 (dd, J=8.8, 2.1 Hz, 1H), 7.07 (d, J=8.9 Hz, 1H), 5.23 (t, J=8.0 Hz, 1H), 4.69-4.63 (m, 1H), 4.13-4.08 (m, 3H), 3.82 (dd, J=11.8, 4.3 Hz, 1H), 3.70 (d, J=11.9 Hz, 1H), 2.50-2.47 (m, 1H), 2.36-2.30 (m, 1H), 1.88-1.80 (m, 2H), 1.53-1.45 (m, 2H), 1.40-1.23 (m, 17H), 0.89 (t, J=7.0 Hz, 3H).

tert-butyl ((E)-((tert-butoxycarbonyl)amino)((2S,4R)-4-hydroxy-2-(3-(4-(octyloxy)-3-(trifluoromethyl)phenyl)-1,2,4-oxadiazol-5-yl)pyrrolidin-1-yl)methylene)carbamate

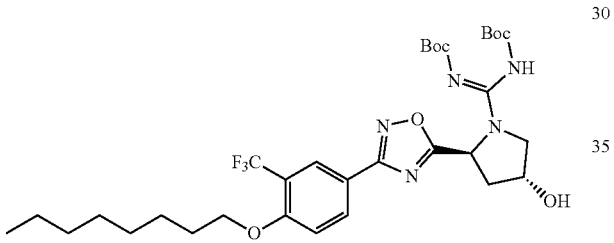

Synthesized by General Procedure D. 21% yield, yellow oil; ¹H NMR (600 MHz, Chloroform-d) δ 8.27 (d, J=2.1 Hz, 1H), 8.24-8.13 (m, 1H), 7.07-7.02 (m, 1H), 5.86 (t, J=8.2 Hz, 1H), 4.66 (d, J=4.2 Hz, 1H), 4.10 (t, J=6.4 Hz, 2H), 4.05 (dd, J=12.5, 3.4 Hz, 1H), 3.80-3.74 (m, 1H), 2.79 (s, 1H), 2.62-2.56 (m, 1H), 2.41-2.33 (m, 1H), 1.88-1.80 (m, 2H), 1.55-1.40 (m, 18H), 1.39-1.23 (m, 10H), 0.88 (t, J=7.0 Hz, 3H).

Example 19: amino((2S,4R)-4-hydroxy-2-(3-(4-(octyloxy)-3-(trifluoromethyl)phenyl)-1,2,4-oxadiazol-5-yl)pyrrolidin-1-yl)methaniminium chloride (Compound 8A)

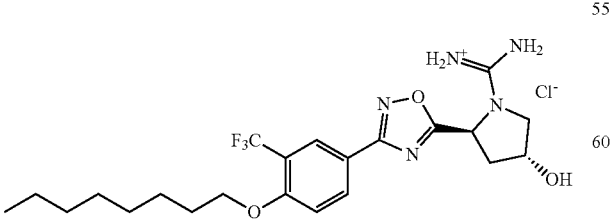

Synthesized by General Procedure E. 100% yield, white solid; ¹H NMR (600 MHz, Methanol-d₄) δ 8.27-8.20 (m, 2H), 7.33 (d, J=8.7 Hz, 1H), 5.60-5.54 (m, 1H), 4.65-4.59 (m, 1H), 4.19 (t, J=6.2 Hz, 2H), 3.91-3.85 (m, 1H), 3.63-3.56 (m, 1H), 2.68-2.61 (m, 1H), 2.56-2.48 (m, 1H), 1.88-1.80 (m, 2H), 1.57-1.48 (m, 2H), 1.44-1.27 (m, 8H), 0.91 (t, J=7.0 Hz, 3H); MS (ESI+): Calc'd for $C_{22}H_{31}F_3N_5O_3$ [M+H]: 470.2, Found: 470.8.

tert-butyl (2S,4S)-4-hydroxy-2-(3-(4-(octyloxy)-3-(trifluoromethyl)phenyl)-1,2,4-oxadiazol-5-yl)pyrrolidine-1-carboxylate

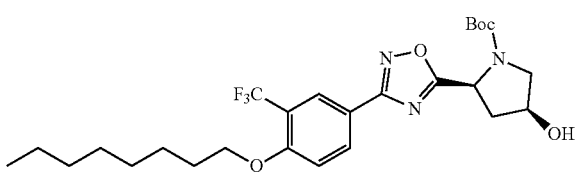 [SMILES: CCCCCCCCOc1ccc(-c2noc([C@@H]3C[C@H](O)CN3C(=O)OC(C)(C)C)n2)cc1C(F)(F)F]

Synthesized by General Procedure C. 46% yield, yellow oil; ¹H NMR (600 MHz, Chloroform-d) δ 8.26-8.21 (m, 1H), 8.13 (dd, J=8.7, 2.1 Hz, 1H), 7.06 (t, J=10.0 Hz, 1H), 5.13 (d, J=9.3 Hz, 1H), 4.53 (t, J=4.7 Hz, 1H), 4.15-4.08 (m, 3H), 3.84 (d, J=12.0 Hz, 1H), 3.77-3.65 (m, 1H), 2.63-2.53 (m, 1H), 2.32 (t, J=14.4 Hz, 1H), 1.88-1.80 (m, 2H), 1.52-1.41 (m, 5H), 1.40-1.25 (m, 14H), 0.89 (t, J=7.0 Hz, 3H).

tert-butyl ((E)-((tert-butoxycarbonyl)amino)-((2S,4S)-4-hydroxy-2-(3-(4-(octyloxy)-3-(trifluoromethyl)phenyl)-1,2,4-oxadiazol-5-yl)pyrrolidin-1-yl)methylene)carbamate

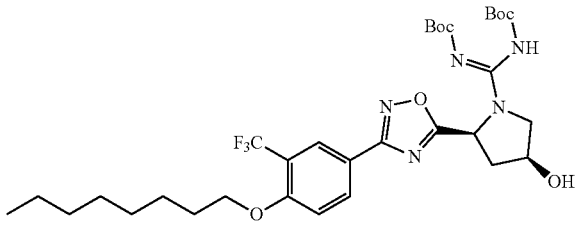 [SMILES: CCCCCCCCOc1ccc(-c2noc([C@@H]3C[C@H](O)CN3/C(=N/C(=O)OC(C)(C)C)NC(=O)OC(C)(C)C)n2)cc1C(F)(F)F]

Synthesized by General Procedure D. 26% yield, yellow oil; ¹H NMR (600 MHz, Chloroform-d) δ 10.06 (s, 1H), 8.22 (d, J=2.1 Hz, 1H), 8.12 (dd, J=8.7, 2.2 Hz, 1H), 7.05 (d, J=8.7 Hz, 1H), 5.61 (d, J=8.8 Hz, 1H), 4.58 (s, 1H), 4.13-4.04 (m, 3H), 3.90 (d, J=12.5 Hz, 1H), 2.64-2.56 (m, 1H), 2.36 (d, J=14.1 Hz, 1H), 1.84 (ddt, J=9.3, 7.9, 6.3 Hz, 2H), 1.57-1.22 (m, 28H), 0.88 (t, J=7.0 Hz, 3H).

Example 20: amino((2S,4S)-4-hydroxy-2-(3-(4-(octyloxy)-3-(trifluoromethyl)phenyl)-1,2,4-oxadiazol-5-yl)pyrrolidin-1-yl)methaniminium chloride (Compound 9A)

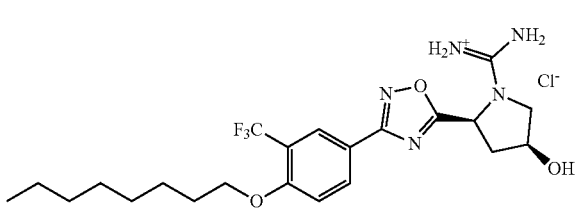 [SMILES: CCCCCCCCOc1ccc(-c2noc([C@@H]3C[C@H](O)CN3C(N)=[NH2+])n2)cc1C(F)(F)F ; [Cl-]]

Synthesized by General Procedure E. 88% yield, white solid; ¹H NMR (600 MHz, Methanol-d4) δ 8.26-8.20 (m, 2H), 7.32 (d, J=8.7 Hz, 1H), 5.40 (dd, J=7.9, 1.8 Hz, 1H), 4.65-4.59 (m, 1H), 4.18 (t, J=6.2 Hz, 2H), 3.77 (td, J=10.7, 4.6 Hz, 1H), 3.70-3.59 (m, 1H), 2.73-2.62 (m, 2H), 1.88-1.80 (m, 2H), 1.57-1.48 (m, 2H), 1.44-1.27 (m, 8H), 0.91 (t, J=7.0 Hz, 3H); MS (ESI+): Calc'd for $C_{22}H_{31}F_3N_5O_3$ [M+H]: 470.2, Found: 470.8.

tert-butyl (2S,3R)-3-hydroxy-2-(3-(4-(octyloxy)-3-(trifluoromethyl)phenyl)-1,2,4-oxadiazol-5-yl)pyrrolidine-1-carboxylate

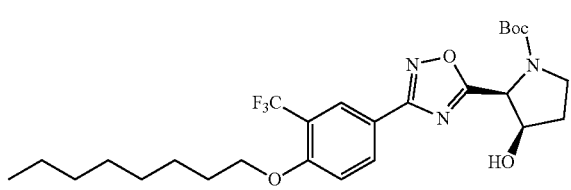 [SMILES: CCCCCCCCOc1ccc(-c2noc([C@@H]3[C@H](O)CCN3C(=O)OC(C)(C)C)n2)cc1C(F)(F)F]

Synthesized by General Procedure C. 15% yield, yellow oil; ¹H NMR (600 MHz, Chloroform-d) δ 8.29 (s, 1H), 8.20 (d, J=8.5 Hz, 1H), 7.10-7.05 (m, 2H), 5.15 (d, J=6.5 Hz, 1H), 4.76-4.71 (m, 1H), 4.11 (t, J=6.2 Hz, 2H), 3.83-3.75 (m, 1H), 3.64-3.56 (m, 1H), 2.30-2.17 (m, 2H), 1.88-1.80 (m, 2H), 1.53-1.44 (m, 5H), 1.40-1.24 (m, 14H), 0.89 (t, J=7.0 Hz, 3H).

tert-butyl (((tert-butoxycarbonyl)amino)((2S,3R)-3-hydroxy-2-(3-(4-(octyloxy)-3-(trifluoromethyl)phenyl)-1,2,4-oxadiazol-5-yl)pyrrolidin-1-yl)methylene)carbamate

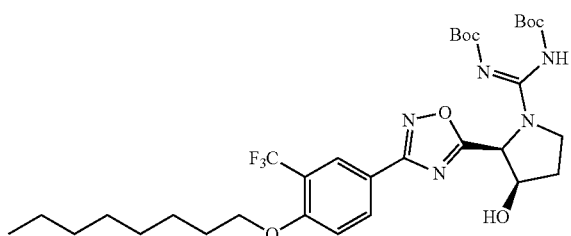

Synthesized by General Procedure D. 29% yield, yellow oil; ¹H NMR (600 MHz, Chloroform-d) δ 8.29-8.25 (m, 1H), 8.21-8.15 (m, 1H), 7.08-7.03 (m, 1H), 5.88 (s, 1H), 4.84-4.81 (m, 1H), 4.22-4.19 (m, 1H), 4.10 (td, J=6.4, 2.0 Hz, 2H), 3.81-3.78 (m, 1H), 2.83 (s, 1H), 2.29-2.24 (m, 2H), 1.88-1.80 (m, 2H), 1.53-1.39 (m, 18H), 1.38-1.24 (m, 10H), 0.88 (t, J=7.0 Hz, 3H).

Example 21: amino((2S,3R)-3-hydroxy-2-(3-(4-(octyloxy)-3-(trifluoromethyl)phenyl)-1,2,4-oxadiazol-5-yl)pyrrolidin-1-yl)methaniminium chloride (Compound 10A)

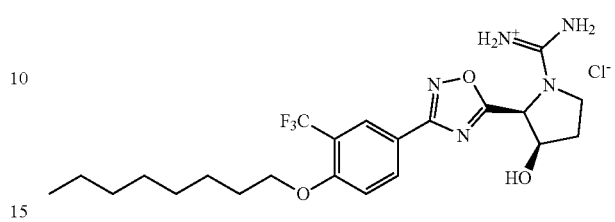

Synthesized by General Procedure E. 88% yield, white solid; ¹H NMR (600 MHz, Methanol-d₄) δ 8.28-8.21 (m, 2H), 7.33 (d, J=8.7 Hz, 1H), 5.45 (d, J=6.8 Hz, 1H), 4.18 (t, J=6.2 Hz, 2H), 3.96-3.88 (m, 1H), 3.72-3.63 (m, 1H), 2.41-2.33 (m, 1H), 2.23-2.14 (m, 1H), 1.88-1.80 (m, 2H), 1.57-1.49 (m, 2H), 1.42-1.27 (m, 8H), 0.91 (t, J=7.0 Hz, 3H); MS (ESI+): Calc'd for $C_{22}H_{31}F_3N_5O_3$ [M+H]: 470.2, Found: 470.8.

3-(4-(trifluoromethyl)phenyl)propan-1-ol

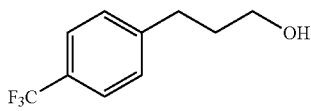

Synthesized by General Procedure F. 100% yield, yellow oil; ¹H NMR (600 MHz, Chloroform-d) δ 7.54 (d, J=8.2 Hz, 2H), 7.31 (d, J=8.2 Hz, 2H), 3.68 (t, J=6.3 Hz, 2H), 2.78 (t, J=7.7 Hz, 2H), 1.92-1.88 (m, 2H), 1.61 (s, 1H).

3-(trifluoromethyl)-4-(3-(4-(trifluoromethyl)phenyl)propoxy)benzonitrile

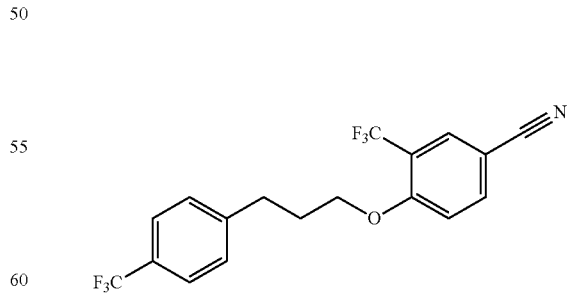

Synthesized by General Procedure A. 81% yield, yellow oil; ¹H NMR (600 MHz, Chloroform-d) δ 7.87 (d, J=2.1 Hz, 1H), 7.77 (dd, J=8.7, 2.1 Hz, 1H), 7.54 (d, J=8.0 Hz, 2H), 7.31 (d, J=7.9 Hz, 2H), 7.02 (d, J=8.7 Hz, 1H), 4.10 (t, J=5.9 Hz, 2H), 2.91 (t, J=7.5 Hz, 2H), 2.23-2.14 (m, 2H).

tert-butyl (2S,3S)-3-hydroxy-2-(3-(3-(trifluoromethyl)-4-(3-(4-(trifluoromethyl)phenyl)propoxy)phenyl)-1,2,4-oxadiazol-5-yl)pyrrolidine-1-carboxylate

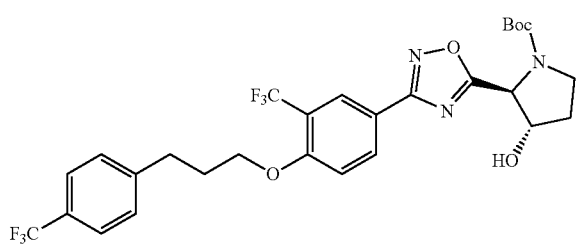 [SMILES: CC(C)(C)OC(=O)N1CC[C@H](O)[C@H]1c1nc(-c2ccc(OCCCc3ccc(C(F)(F)F)cc3)c(C(F)(F)F)c2)no1]

Synthesized by General Procedures B and C. 74% yield, yellow oil; ¹H NMR (600 MHz, Chloroform-d) δ 8.33-8.30 (m, 1H), 8.21-8.16 (m, 1H), 7.54 (d, J=7.7 Hz, 2H), 7.32 (d, J=7.7 Hz, 2H), 7.02 (t, J=10.1 Hz, 1H), 4.96 (s, 1H), 4.58 (d, J=17.5 Hz, 1H), 4.09 (t, J=5.7 Hz, 2H), 3.84-3.72 (m, 2H), 2.93 (t, J=7.5 Hz, 2H), 2.21-2.15 (m, 2H), 2.07-2.04 (m, 2H), 1.48 (s, 3H), 1.32 (s, 6H).

tert-butyl (((tert-butoxycarbonyl)amino)((2S,3S)-3-hydroxy-2-(3-(3-(trifluoromethyl)-4-(3-(4-(trifluoromethyl)phenyl)propoxy)phenyl)-1,2,4-oxadiazol-5-yl)pyrrolidin-1-yl)methylene)carbamate

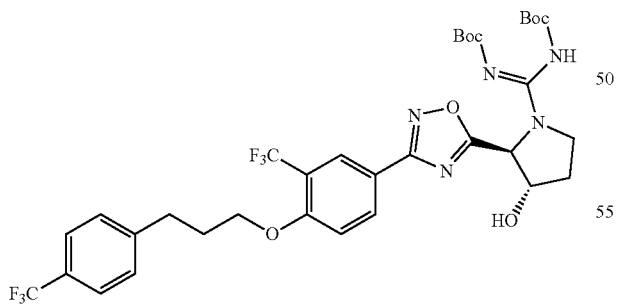

Synthesized by General Procedure D. 22% yield, yellow oil; ¹H NMR (600 MHz, Chloroform-d) δ 8.29 (d, J=2.1 Hz, 1H), 8.17 (dd, J=8.7, 2.2 Hz, 1H), 7.54 (d, J=8.1 Hz, 2H), 7.32 (d, J=8.0 Hz, 2H), 7.01 (d, J=8.8 Hz, 1H), 5.61-5.57 (m, 1H), 4.69 (s, 1H), 4.12-4.04 (m, 3H), 3.18 (s, 1H), 2.93 (t, J=7.5 Hz, 2H), 2.39-2.32 (m, 1H), 2.22-2.12 (m, 3H), 1.47 (s, 18H).

Example 22: amino((2S,3S)-3-hydroxy-2-(3-(3-(trifluoromethyl)-4-(3-(4-(trifluoromethyl)phenyl)propoxy)phenyl)-1,2,4-oxadiazol-5-yl)pyrrolidin-1-yl)methaniminium chloride (Compound 22A)

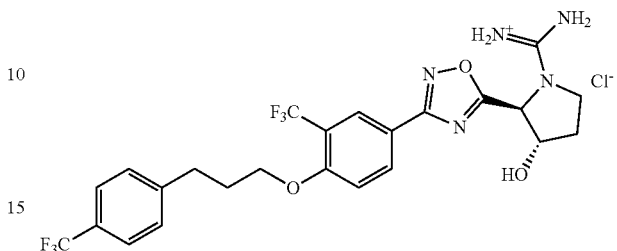

Synthesized by General Procedure E. 100% yield, white solid; ¹H NMR (600 MHz, Methanol-$d_4$) δ 8.28-8.22 (m, 2H), 7.58 (d, J=7.9 Hz, 2H), 7.41 (d, J=8.0 Hz, 2H), 7.36-7.28 (m, 1H), 5.24 (t, J=1.0 Hz, 1H), 4.79 (dt, J=3.7, 1.3 Hz, 1H), 4.29-4.15 (m, 2H), 3.97-3.90 (m, 0H), 3.89-3.78 (m, 2H), 3.66 (s, 1H), 2.94 (t, J=7.6 Hz, 2H), 2.28-2.14 (m, 4H); ¹³C NMR (151 MHz, $cd_3od$) δ 175.58, 167.22, 159.22, 156.16, 145.87, 132.63, 128.76, 124.97, 124.94, 124.92, 118.08, 113.42, 74.57, 67.50, 66.70, 63.38, 47.99, 47.85, 47.71, 47.57, 47.42, 47.28, 47.14, 45.99, 31.18, 31.05, 30.07; MS (ESI+): Calc'd for $C_{24}H_{24}F_6N_5O_3$ [M+H]: 544.2, Found: 544.6.

2-(4-(trifluoromethyl)phenyl)ethan-1-ol

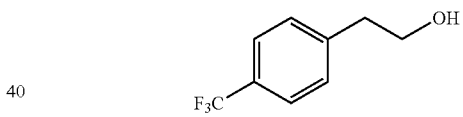

Synthesized by General Procedure F. 69% yield, yellow oil; ¹H NMR (600 MHz, Chloroform-d) δ 7.34 (d, J=7.9 Hz, 1H), 7.16 (d, J=7.9 Hz, 1H), 4.19 (s, 1H), 3.61 (t, J=6.8 Hz, 1H), 2.70 (t, J=6.9 Hz, 1H).

3-(trifluoromethyl)-4-(4-(trifluoromethyl)phenethoxy)benzonitrile

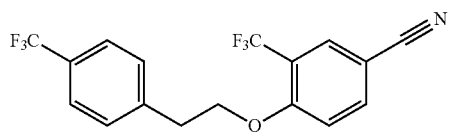 [SMILES: N#Cc1ccc(OCCc2ccc(C(F)(F)F)cc2)c(C(F)(F)F)c1]

Synthesized by General Procedure A. 30% yield, yellow oil; ¹H NMR (600 MHz, Chloroform-d) δ 7.86 (d, J=2.0 Hz, 1H), 7.77 (dd, J=8.7, 2.1 Hz, 1H), 7.58 (d, J=8.0 Hz, 2H), 7.41 (d, J=7.9 Hz, 2H), 7.03 (d, J=8.7 Hz, 1H), 4.32 (t, J=6.3 Hz, 2H), 3.22 (t, J=6.3 Hz, 2H).

161 tert-butyl (2S,3S)-3-hydroxy-2-(3-(3-(trifluoromethyl)-4-(4-(trifluoromethyl)phenethoxy)phenyl)-1,2,4-oxadiazol-5-yl)pyrrolidine-1-carboxylate

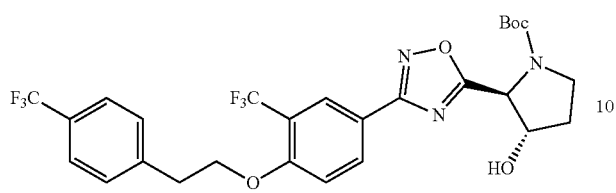

Synthesized by General Procedures B and C. 62% yield, yellow oil; $^1$H NMR (600 MHz, Chloroform-d) δ 8.30-8.24 (m, 1H), 8.20-8.13 (m, 1H), 7.58 (d, J=8.0 Hz, 2H), 7.44 (d, J=7.9 Hz, 2H), 7.06-6.99 (m, 1H), 4.94 (s, 1H), 4.56 (d, J=19.9 Hz, 1H), 4.32 (q, J=6.0 Hz, 2H), 3.82-3.68 (m, 2H), 3.22 (t, J=6.3 Hz, 2H), 2.39-2.28 (m, 1H), 2.08-2.01 (m, 2H), 1.47 (s, 3H), 1.31-1.24 (m, 6H).

tert-butyl (((tert-butoxycarbonyl)amino)((2S,3S)-3-hydroxy-2-(3-(3-(trifluoromethyl)-4-(4-(trifluoromethyl)phenethoxy)phenyl)-1,2,4-oxadiazol-5-yl)pyrrolidin-1-yl)methylene)carbamate

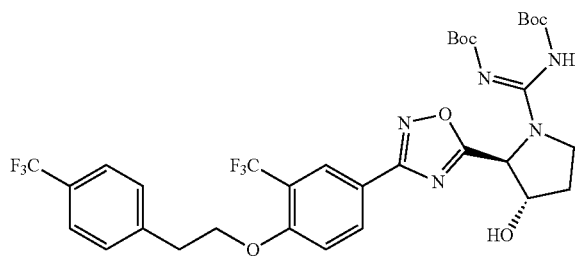 [SMILES: CC(C)(C)OC(=O)/N=C(\NC(=O)OC(C)(C)C)N1CC[C@H](O)[C@H]1c1nc(-c2ccc(OCCc3ccc(C(F)(F)F)cc3)c(C(F)(F)F)c2)no1]

Synthesized by General Procedure D. 20% yield, yellow oil; $^1$H NMR (600 MHz, Chloroform-d) δ 8.27 (d, J=2.1 Hz, 1H), 8.17 (dd, J=8.7, 2.2 Hz, 1H), 7.58 (d, J=8.2 Hz, 2H), 7.44 (d, J=8.2 Hz, 2H), 7.03 (d, J=8.7 Hz, 1H), 5.58 (s, 1H), 4.66 (s, 1H), 4.32 (t, J=6.3 Hz, 2H), 4.09-4.01 (m, 1H), 3.98-3.92 (m, 1H), 3.22 (t, J=6.3 Hz, 2H), 2.85 (s, 1H), 2.40-2.32 (m, 1H), 2.16-2.10 (m, 1H), 1.46 (s, 18H).

Example 23: amino((2S,3S)-3-hydroxy-2-(3-(3-(trifluoromethyl)-4-(4-(trifluoromethyl)phenethoxy)phenyl)-1,2,4-oxadiazol-5-yl)pyrrolidin-1-yl)methaniminium chloride (Compound 23A)

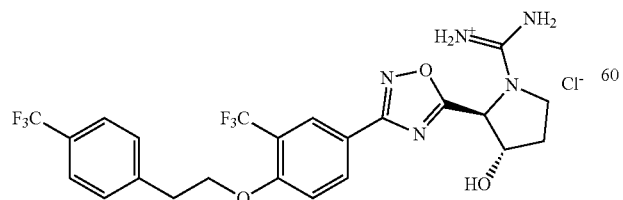

162

Synthesized by General Procedure E. 100% yield, white solid; $^1$H NMR (600 MHz, Methanol-d4) δ 8.26-8.19 (m, 2H), 7.60 (d, J=8.0 Hz, 2H), 7.53 (d, J=8.0 Hz, 2H), 7.35 (d, J=8.8 Hz, 1H), 5.21 (s, 1H), 4.78 (d, J=3.6 Hz, 1H), 4.44 (t, J=6.3 Hz, 2H), 4.23-4.18 (m, 1H), 3.87-3.78 (m, 1H), 3.77-3.62 (m, 2H), 3.24 (t, J=6.2 Hz, 2H), 2.24-2.15 (m, 1H); MS (ESI+): Calc'd for $C_{23}H_{22}F_6N_5O_3$ [M+H]: 530.2, Found: 530.8.

3-(trifluoromethyl)-4-((4-(trifluoromethyl)benzyl)oxy)benzonitrile

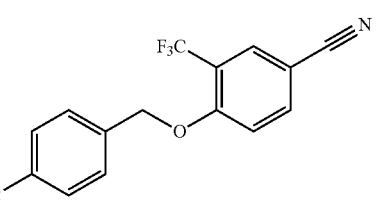

Synthesized by General Procedure A. 89% yield, yellow oil; $^1$H NMR (600 MHz, Chloroform-d) δ 7.91 (d, J=2.1 Hz, 1H), 7.79 (dd, J=8.8, 2.1 Hz, 1H), 7.68 (d, J=8.0 Hz, 2H), 7.55 (d, J=8.0 Hz, 2H), 7.11 (d, J=8.7 Hz, 1H), 5.32 (s, 2H).

tert-butyl (2S,3S)-3-hydroxy-2-(3-(3-(trifluoromethyl)-4-((4-(trifluoromethyl)benzyl)oxy)phenyl)-1,2,4-oxadiazol-5-yl)pyrrolidine-1-carboxylate

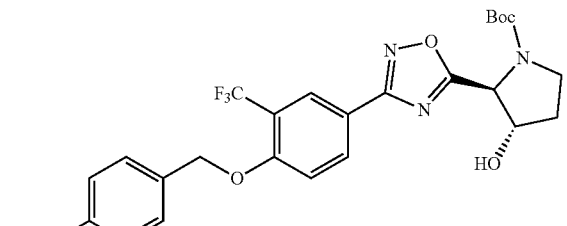

Synthesized by General Procedures B and C. 91% yield, yellow oil; $^1$H NMR (600 MHz, Chloroform-d) δ 8.33 (d, J=9.3 Hz, 1H), 8.19 (t, J=8.8 Hz, 1H), 7.67 (d, J=8.0 Hz, 2H), 7.58 (d, J=8.0 Hz, 2H), 7.14-7.07 (m, 1H), 5.31 (d, J=8.1 Hz, 2H), 5.10 (s, 0H), 4.96 (s, 1H), 4.57 (d, J=16.8 Hz, 1H), 3.83-3.69 (m, 2H), 2.40-2.28 (m, 1H), 2.08-2.01 (m, 2H), 1.47 (s, 3H), 1.31 (s, 6H).

tert-butyl (((tert-butoxycarbonyl)amino)((2S,3S)-3-hydroxy-2-(3-(3-(trifluoromethyl)-4-((4-(trifluoromethyl)benzyl)oxy)phenyl)-1,2,4-oxadiazol-5-yl)pyrrolidin-1-yl)methylene)carbamate

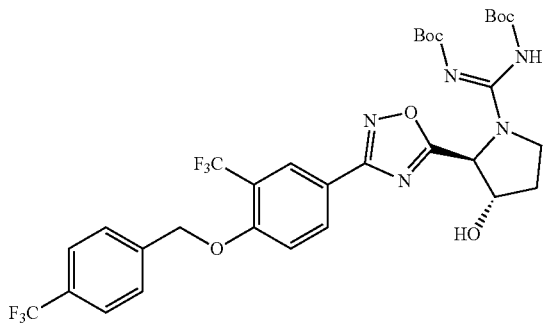 [SMILES: CC(C)(C)OC(=O)/N=C(\NC(=O)OC(C)(C)C)N1CC[C@H](O)[C@H]1c1nc(-c2ccc(OCc3ccc(C(F)(F)F)cc3)c(C(F)(F)F)c2)no1]

Synthesized by General Procedure D. 46% yield, yellow oil; ¹H NMR (600 MHz, Chloroform-d) δ 8.31 (d, J=2.1 Hz, 1H), 8.19 (dd, J=8.7, 2.1 Hz, 1H), 7.67 (d, J=8.2 Hz, 2H), 7.58 (d, J=8.0 Hz, 2H), 7.11 (d, J=8.8 Hz, 1H), 5.69 (d, J=1.7 Hz, 1H), 5.31 (s, 2H), 4.77-4.72 (m, 1H), 4.18-4.08 (m, 1H), 3.97-3.91 (m, 1H), 2.37-2.28 (m, 1H), 2.21-2.15 (m, 1H), 1.47 (s, 18H).

Example 24: amino((2S,3S)-3-hydroxy-2-(3-(3-(trifluoromethyl)-4-((4-(trifluoromethyl)benzyl)oxy)phenyl)-1,2,4-oxadiazol-5-yl)pyrrolidin-1-yl)methaniminium chloride (Compound 24A)

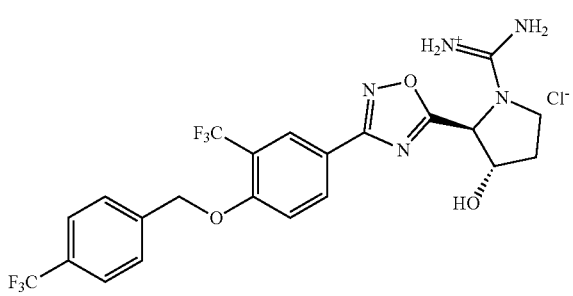 [SMILES: NC(=[NH2+])N1CC[C@H](O)[C@H]1c1nc(-c2ccc(OCc3ccc(C(F)(F)F)cc3)c(C(F)(F)F)c2)no1 ; [Cl-]]

Synthesized by General Procedure E. 94% yield, white solid; ¹H NMR (600 MHz, Methanol-d₄) δ 8.26 (d, J=2.2 Hz, 1H), 7.98 (d, J=2.4 Hz, 1H), 7.73-7.65 (m, 4H), 7.46-7.41 (m, 1H), 6.59 (t, J=2.2 Hz, 1H), 5.42 (s, 2H), 5.27 (t, J=1.0 Hz, 1H), 4.81-4.77 (m, 1H), 3.89-3.79 (m, 2H), 2.28-2.14 (m, 2H); ¹³C NMR (151 MHz, cd₃od) δ 175.66, 167.13, 158.49, 156.17, 140.48, 133.63, 132.66, 127.11, 125.80, 125.13, 125.11, 125.09, 125.06, 118.70, 114.07, 74.58, 69.46, 66.70, 63.38, 46.03, 31.05; MS (ESI+): Calc'd for C₂₂H₃₁F₃N₅O₄ [M+H]: 516.2, Found: 516.4.

4-(4-(trifluoromethyl)phenyl)butan-1-ol

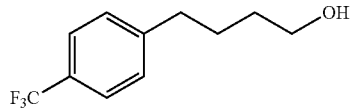 [SMILES: OCCCCc1ccc(C(F)(F)F)cc1]

Synthesized by General Procedure F. 24% yield, yellow oil; ¹H NMR (600 MHz, Chloroform-d) δ 7.53 (d, J=8.0 Hz, 1H), 7.29 (d, J=7.9 Hz, 2H), 3.67 (t, J=6.4 Hz, 2H), 2.71 (t, J=7.7 Hz, 2H), 1.76-1.68 (m, 1H), 1.65-1.57 (m, 2H), 1.44 (s, 1H).

3-(trifluoromethyl)-4-(4-(4-(trifluoromethyl)phenyl)butoxy)benzonitrile

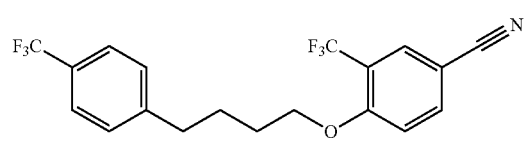 [SMILES: N#Cc1ccc(OCCCCc2ccc(C(F)(F)F)cc2)c(C(F)(F)F)c1]

Synthesized by General Procedure A. 85% yield, yellow oil; ¹H NMR (600 MHz, Chloroform-d) δ 7.86 (d, J=2.2 Hz, 1H), 7.77 (dd, J=8.7, 2.1 Hz, 1H), 7.54 (d, J=7.9 Hz, 2H), 7.30 (d, J=7.9 Hz, 2H), 7.03 (d, J=8.7 Hz, 1H), 4.12 (t, J=5.5 Hz, 2H), 2.76 (t, J=7.0 Hz, 2H), 1.93-1.82 (m, 4H).

tert-butyl (2S,3S)-3-hydroxy-2-(3-(3-(trifluoromethyl)-4-(4-(4-(trifluoromethyl)phenyl)butoxy)phenyl)-1,2,4-oxadiazol-5-yl)pyrrolidine-1-carboxylate

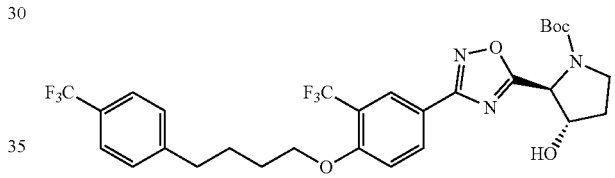

Synthesized by General Procedures B and C. 74% yield, yellow oil; ¹H NMR (600 MHz, Chloroform-d) δ 8.30-8.25 (m, 1H), 8.20-8.14 (m, 1H), 7.54 (d, J=8.0 Hz, 2H), 7.31 (d, J=8.0 Hz, 2H), 7.07-7.00 (m, 1H), 4.95 (d, J=1.9 Hz, 1H), 4.57 (d, J=17.8 Hz, 1H), 4.15-4.10 (m, 2H), 3.83-3.67 (m, 2H), 2.79-2.73 (m, 2H), 2.40-2.28 (m, 1H), 2.09-2.01 (m, 1H), 1.92-1.84 (m, 4H), 1.47 (s, 3H), 1.31 (s, 6H).

tert-butyl (((tert-butoxycarbonyl)amino)((2S,3S)-3-hydroxy-2-(3-(3-(trifluoromethyl)-4-(4-(4-(trifluoromethyl)phenyl)butoxy)phenyl)-1,2,4-oxadiazol-5-yl)pyrrolidin-1-yl)methylene)carbamate

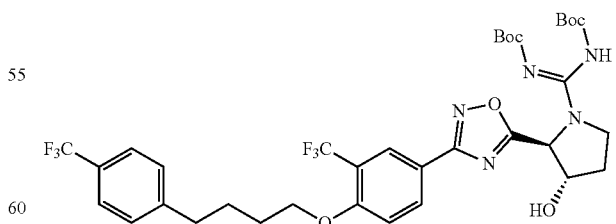

Synthesized by General Procedure D. 21% yield, yellow oil; ¹H NMR (600 MHz, Chloroform-d) δ 8.27 (d, J=2.2 Hz, 1H), 8.17 (dd, J=8.7, 2.2 Hz, 1H), 7.54 (d, J=8.0 Hz, 2H), 7.31 (d, J=8.0 Hz, 2H), 7.04 (d, J=8.8 Hz, 1H), 5.57-5.53 (m, 1H), 4.65 (s, 1H), 4.15-4.10 (m, 2H), 4.07-3.92 (m, 2H), 2.79-2.73 (m, 3H), 2.42-2.33 (m, 1H), 2.16-2.09 (m, 1H), 1.88 (h, J=2.5 Hz, 4H), 1.46 (s, 18H).

Example 25: amino((2S,3S)-3-hydroxy-2-(3-(3-(trifluoromethyl)-4-(4-(4-(trifluoromethyl)phenyl)butoxy)phenyl)-1,2,4-oxadiazol-5-yl)pyrrolidin-1-yl)methaniminium chloride (Compound 25A)

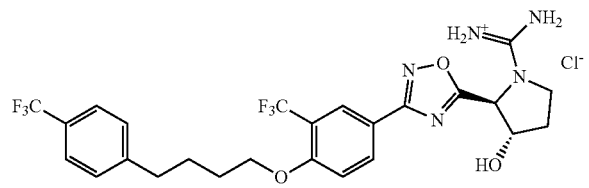 [SMILES: NC(=[NH2+])N1CC[C@H](O)[C@H]1c1nc(-c2ccc(OCCCCc3ccc(C(F)(F)F)cc3)c(C(F)(F)F)c2)no1 ; [Cl-]]

Synthesized by General Procedure E. 87% yield, white solid; $^1$H NMR (600 MHz, Methanol-d$_4$) δ 8.27-8.19 (m, 2H), 7.55 (d, J=8.0 Hz, 2H), 7.40 (d, J=8.0 Hz, 2H), 7.31 (d, J=8.7 Hz, 1H), 5.25 (t, J=1.0 Hz, 1H), 4.79 (dt, J=3.8, 1.2 Hz, 1H), 4.21 (h, J=2.9 Hz, 2H), 3.89-3.79 (m, 2H), 2.82-2.76 (m, 2H), 2.27-2.14 (m, 2H), 1.94-1.84 (m, 4H); $^{13}$C NMR (151 MHz, cd$_3$od) δ 175.56, 167.23, 156.16, 146.75, 132.56, 128.61, 125.66, 124.80, 124.77, 124.75, 124.72, 117.92, 113.45, 74.57, 68.53, 63.37, 45.99, 34.64, 31.05, 28.04, 26.98; MS (ESI+): Calc'd for $C_{25}H_{26}F_6N_5O_3$ [M+H]: 558.2, Found: 558.4.

tert-butyl (S)-2-(3-(3-(trifluoromethyl)-4-(4-(4-(trifluoromethyl)phenyl)butoxy)phenyl)-1,2,4-oxadiazol-5-yl)pyrrolidine-1-carboxylate

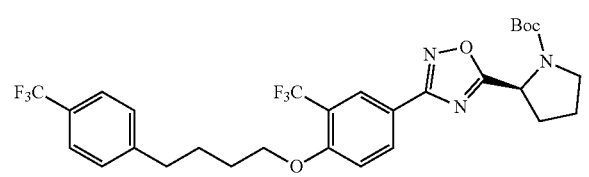 [SMILES: CC(C)(C)OC(=O)N1CCC[C@H]1c1nc(-c2ccc(OCCCCc3ccc(C(F)(F)F)cc3)c(C(F)(F)F)c2)no1]

Synthesized by General Procedures B and C. 69% yield, yellow oil; $^1$H NMR (600 MHz, Chloroform-d) δ 8.30 (d, J=2.6 Hz, 1H), 8.19 (dd, J=8.3, 2.4 Hz, 1H), 7.54 (d, J=8.0 Hz, 3H), 7.31 (d, J=8.0 Hz, 2H), 7.07-7.00 (m, 1H), 5.21-5.03 (m, 1H), 4.15-4.10 (m, 2H), 3.75-3.66 (m, 1H), 3.61-3.45 (m, 1H), 2.79-2.73 (m, 2H), 2.46-2.33 (m, 1H), 2.20-2.09 (m, 2H), 2.06-1.96 (m, 1H), 1.92-1.84 (m, 4H), 1.46 (s, 3H), 1.30 (s, 6H).

tert-butyl (S)-(((tert-butoxycarbonyl)amino)(2-(3-(3-(trifluoromethyl)-4-(4-(4-(trifluoromethyl)phenyl)butoxy)phenyl)-1,2,4-oxadiazol-5-yl)pyrrolidin-1-yl)methylene)carbamate

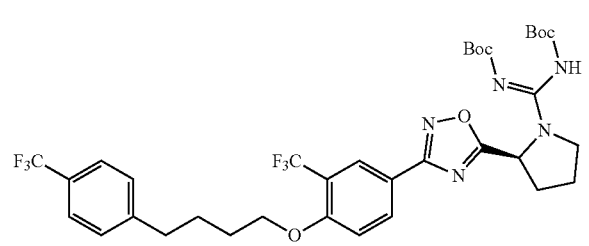 [SMILES: CC(C)(C)OC(=O)/N=C(\NC(=O)OC(C)(C)C)N1CCC[C@H]1c1nc(-c2ccc(OCCCCc3ccc(C(F)(F)F)cc3)c(C(F)(F)F)c2)no1]

Synthesized by General Procedure D. 36% yield, yellow oil; $^1$H NMR (600 MHz, Chloroform-d) δ 8.28 (d, J=2.1 Hz, 1H), 8.17 (dd, J=8.7, 2.2 Hz, 1H), 7.53 (d, J=8.0 Hz, 2H), 7.30 (d, J=8.0 Hz, 2H), 7.03 (d, J=8.7 Hz, 1H), 5.59 (dd, J=7.9, 4.6 Hz, 1H), 4.14-4.09 (m, 2H), 3.93-3.85 (m, 1H), 3.79 (s, 1H), 2.78-2.73 (m, 3H), 2.44 (dd, J=13.6, 7.2 Hz, 1H), 2.21-2.14 (m, 2H), 2.07-1.99 (m, 1H), 1.90-1.86 (m, 4H), 1.44 (d, J=39.8 Hz, 18H).

Example 26: (S)-amino(2-(3-(3-(trifluoromethyl)-4-(4-(4-(trifluoromethyl)phenyl)butoxy)phenyl)-1,2,4-oxadiazol-5-yl)pyrrolidin-1-yl)methaniminium chloride (Compound 26A)

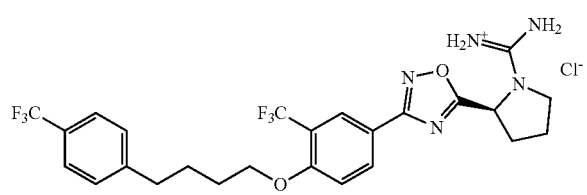 [SMILES: NC(=[NH2+])N1CCC[C@H]1c1nc(-c2ccc(OCCCCc3ccc(C(F)(F)F)cc3)c(C(F)(F)F)c2)no1 ; [Cl-]]

Synthesized by General Procedure E. 76% yield, white solid; $^1$H NMR (600 MHz, Methanol-d$_4$) δ 8.26-8.20 (m, 2H), 7.56 (d, J=8.0 Hz, 2H), 7.41 (d, J=8.0 Hz, 2H), 7.31 (d, J=8.7 Hz, 1H), 5.49-5.44 (m, 1H), 4.25-4.18 (m, 2H), 3.82-3.56 (m, 4H), 2.79 (t, J=6.6 Hz, 2H), 2.63-2.53 (m, 1H), 2.51-2.44 (m, 1H), 2.32-2.20 (m, 1H), 2.15-2.03 (m, 1H), 1.89 (dp, J=4.7, 2.8 Hz, 4H); $^{13}$C NMR (151 MHz, cd$_3$od) δ 177.78, 167.11, 159.30, 155.66, 146.76, 132.52, 128.61, 125.65, 124.78, 124.75, 124.73, 118.03, 113.43, 68.52, 66.70, 55.03, 34.64, 31.29, 28.05, 26.99, 22.89; MS (ESI+): Calc'd for $C_{25}H_{26}F_6N_5O_2$ [M+H]: 542.2, Found: 542.4.

3-(2,3-dihydrobenzo[b][1,4]dioxin-6-yl)propan-1-ol

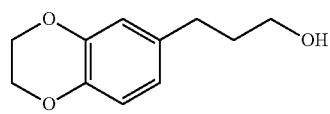 [SMILES: OCCCc1ccc2c(c1)OCCO2]

Synthesized by General Procedure F. 95% yield, yellow oil; $^1$H NMR (600 MHz, Chloroform-d) δ 6.78 (d, J=8.2 Hz, 1H), 6.72-6.64 (m, 2H), 4.29-4.20 (m, 4H), 3.66 (t, J=6.4 Hz, 2H), 2.63-2.57 (m, 2H) 1.89-1.80 (m, 2H).

4-(3-(2,3-dihydrobenzo[b][1,4]dioxin-6-yl)propoxy)-3-(trifluoromethyl)benzonitrile

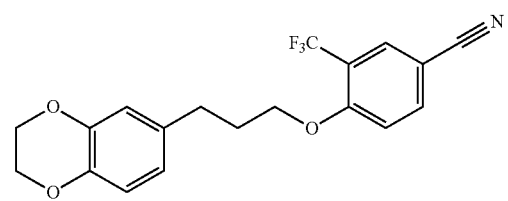 [SMILES: N#Cc1ccc(OCCCc2ccc3c(c2)OCCO3)c(C(F)(F)F)c1]

Synthesized by General Procedure A. 100% yield, yellow oil; $^1$H NMR (600 MHz, Chloroform-d) δ 7.87 (d, J=2.1 Hz, 1H), 7.76 (dd, J=8.7, 2.2 Hz, 1H), 7.00 (d, J=8.7 Hz, 1H), 6.77 (d, J=8.2 Hz, 1H), 6.69 (d, J=2.1 Hz, 1H), 6.64 (dd, J=8.2, 2.1 Hz, 1H), 4.30-4.20 (m, 4H), 4.07 (t, J=6.1 Hz, 2H), 2.73 (t, J=7.4 Hz, 2H), 2.18-2.08 (m, 2H).

tert-butyl (2S,3S)-2-(3-(4-(3-(2,3-dihydrobenzo[b][1,4]dioxin-6-yl)propoxy)-3-(trifluoromethyl)phenyl)-1,2,4-oxadiazol-5-yl)-3-hydroxypyrrolidine-1-carboxylate

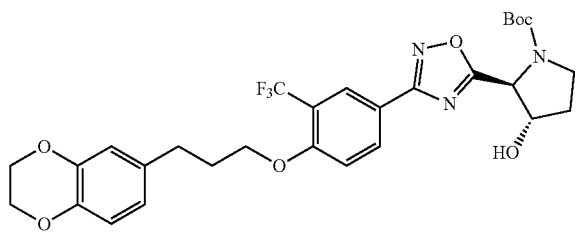 [SMILES: CC(C)(C)OC(=O)N1CC[C@H](O)[C@H]1c1nc(-c2ccc(OCCCc3ccc4c(c3)OCCO4)c(C(F)(F)F)c2)no1]

Synthesized by General Procedures B and C. 57% yield, yellow oil; $^1$H NMR (600 MHz, Chloroform-d) δ 8.31-8.28 (m, 1H), 8.19-8.14 (m, 1H), 7.05-6.98 (m, 1H), 6.78 (d, J=8.2 Hz, 1H), 6.71 (d, J=2.1 Hz, 1H), 6.66 (dd, J=8.2, 2.1 Hz, 1H), 4.95 (s, 1H), 4.58 (d, J=17.4 Hz, 1H), 4.27-4.19 (m, 4H), 4.08 (t, J=6.0 Hz, 3H), 3.83-3.72 (m, 1H), 2.74 (t, J=7.4 Hz, 2H), 2.36-2.33 (m, 1H), 2.16-2.08 (m, 2H), 2.07-2.03 (m, 1H), 1.48 (s, 3H), 1.32 (s, 6H).

tert-butyl ((((tert-butoxycarbonyl)amino)((2S,3S)-2-(3-(4-(3-(2,3-dihydrobenzo[b][1,4]dioxin-6-yl)propoxy)-3-(trifluoromethyl)phenyl)-1,2,4-oxadiazol-5-yl)-3-hydroxypyrrolidin-1-yl)methylene)carbamate

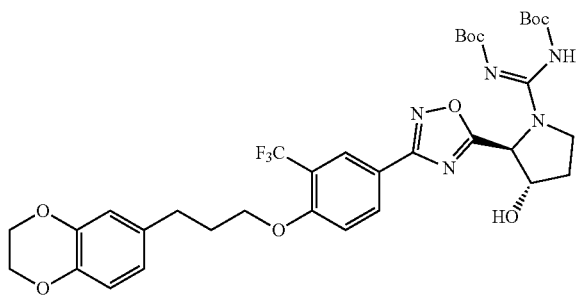 [SMILES: CC(C)(C)OC(=O)/N=C(\NC(=O)OC(C)(C)C)N1CC[C@H](O)[C@H]1c1nc(-c2ccc(OCCCc3ccc4c(c3)OCCO4)c(C(F)(F)F)c2)no1]

Synthesized by General Procedure D. 18% yield, yellow oil; $^1$H NMR (600 MHz, Chloroform-d) δ 8.27 (d, J=2.1 Hz, 1H), 8.16 (dd, J=8.7, 2.1 Hz, 1H), 7.01 (d, J=8.8 Hz, 1H), 6.77 (d, J=8.2 Hz, 1H), 6.71 (d, J=2.1 Hz, 1H), 6.66 (dd, J=8.2, 2.1 Hz, 1H), 5.56 (dd, J=2.3, 1.0 Hz, 1H), 4.67 (s, 1H), 4.27-4.20 (m, 4H), 4.10-4.02 (m, 4H), 3.98-3.92 (m, 1H), 3.03 (s, 1H), 2.74 (t, J=7.4 Hz, 2H), 2.41-2.32 (m, 1H), 2.19-2.07 (m, 3H), 1.46 (s, 18H).

Example 27: (S)-amino(2-(3-(4-(3-(2,3-dihydrobenzo[b][1,4]dioxin-6-yl)propoxy)-3-(trifluoromethyl)phenyl)-1,2,4-oxadiazol-5-yl)pyrrolidin-1-yl)methaniminium chloride (Compound 27)

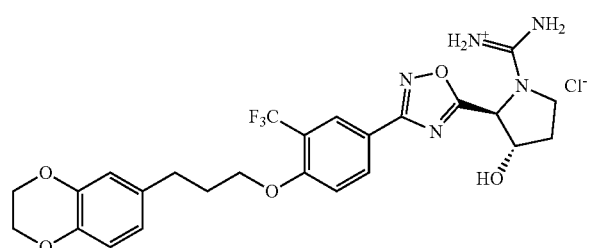

Synthesized by General Procedure E. 98% yield, white solid; 1H NMR (600 MHz, Methanol-d4) δ 8.35-8.04 (m, 2H), 7.36-7.10 (m, 1H), 6.75-6.57 (m, 3H), 4.86 (s, 4H), 4.21-4.15 (m, 3H), 4.15-3.96 (m, 2H), 3.66 (s, 3H), 2.78-2.59 (m, 2H), 2.14-1.93 (m, 2H); MS (ESI+): Calc'd for $C_{25}H_{27}F_3N_5O_5$ [M+H]: 534.2, Found: 534.4.

3-(3,4-dichlorophenyl)propan-1-ol

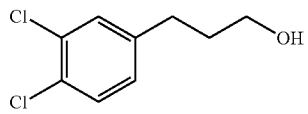 [SMILES: OCCCc1ccc(Cl)c(Cl)c1]

Synthesized by General Procedure F. 100% yield, yellow oil; $^1$H NMR (600 MHz, Chloroform-d) δ 7.34 (d, J=8.2 Hz, 1H), 7.28 (d, J=2.1 Hz, 1H), 7.03 (dd, J=8.2, 2.1 Hz, 1H), 3.69 (t, J=6.4 Hz, 2H), 2.67 (t, J=7.7 Hz, 2H), 1.91-1.84 (m, 2H).

4-(3-(3,4-dichlorophenyl)propoxy)-3-(trifluoromethyl)benzonitrile

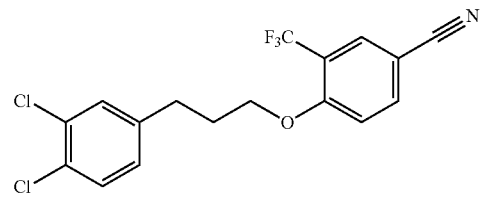 [SMILES: N#Cc1ccc(OCCCc2ccc(Cl)c(Cl)c2)c(C(F)(F)F)c1]

Synthesized by General Procedure A. 47% yield, yellow oil; $^1$H NMR (600 MHz, Chloroform-d) δ 7.88 (d, J=2.1 Hz, 1H), 7.78 (dd, J=8.7, 2.1 Hz, 1H), 7.35 (d, J=8.2 Hz, 1H), 7.28 (d, J=2.0 Hz, 1H), 7.04-6.99 (m, 2H), 4.08 (t, J=5.9 Hz, 2H), 2.81 (t, J=7.5 Hz, 2H), 2.19-2.11 (m, 2H).

tert-butyl (2S,3S)-2-(3-(4-(3-(3,4-dichlorophenyl)propoxy)-3-(trifluoromethyl)phenyl)-1,2,4-oxadiazol-5-yl)-3-hydroxypyrrolidine-1-carboxylate

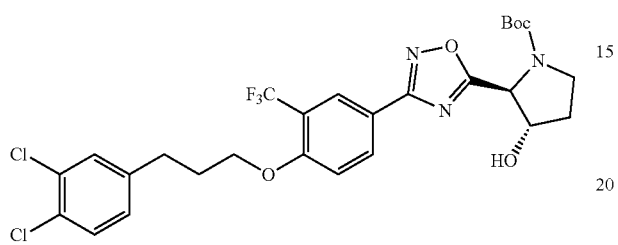

Synthesized by General Procedure B and C. 65% yield, yellow oil; ¹H NMR (600 MHz, Chloroform-d) δ 8.30 (d, J=7.8 Hz, 1H), 8.21-8.16 (m, 1H), 7.34 (d, J=8.2 Hz, 1H), 7.30 (d, J=2.1 Hz, 1H), 7.08-6.98 (m, 2H), 4.96 (s, 1H), 4.58 (d, J=17.9 Hz, 1H), 4.11-4.06 (m, 2H), 3.83-3.71 (m, 2H), 2.82 (t, J=7.5 Hz, 2H), 2.39-2.31 (m, 2H), 2.19-2.10 (m, 2H), 2.09-2.03 (m, 1H), 1.48 (s, 3H), 1.31 (s, 6H).

tert-butyl (((tert-butoxycarbonyl)amino)((2S,3S)-2-(3-(4-(3-(3,4-dichlorophenyl)propoxy)-3-(trifluoromethyl)phenyl)-1,2,4-oxadiazol-5-yl)-3-hydroxypyrrolidin-1-yl)methylene)carbamate

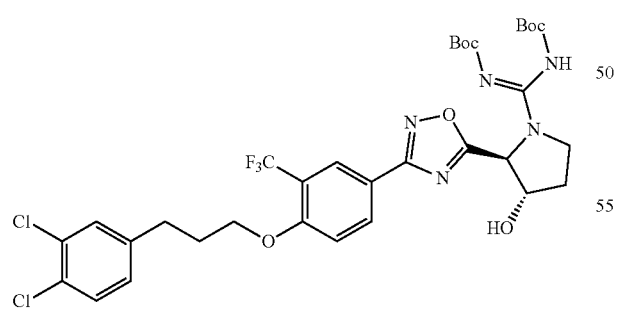

Synthesized by General Procedure D. 10% yield, yellow oil; ¹H NMR (600 MHz, Chloroform-d) δ 8.29 (d, J=2.1 Hz, 1H), 8.17 (dd, J=8.7, 2.2 Hz, 1H), 7.34 (d, J=8.2 Hz, 1H), 7.30 (d, J=2.1 Hz, 1H), 7.06-6.99 (m, 2H), 5.54 (d, J=2.3 Hz, 1H), 4.65 (s, 1H), 4.10-3.99 (m, 3H), 3.99-3.92 (m, 1H), 2.88 (s, 1H), 2.82 (t, J=7.5 Hz, 2H), 2.42-2.33 (m, 1H), 2.19-2.09 (m, 3H), 1.46 (s, 18H).

Example 28: (S)-amino(2-(3-(4-(3-(3,4-dichlorophenyl)propoxy)-3-(trifluoromethyl)phenyl)-1,2,4-oxadiazol-5-yl)pyrrolidin-1-yl)methaniminium chloride (Compound 28)

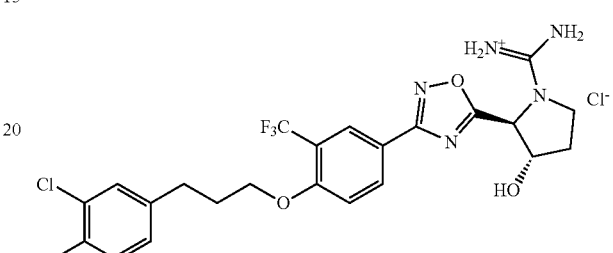

Synthesized by General Procedure E. 100% yield, white solid; ¹H NMR (600 MHz, Methanol-d4) δ 8.28-8.21 (m, 2H), 7.41 (d, J=8.2 Hz, 1H), 7.37 (d, J=2.2 Hz, 1H), 7.33-7.28 (m, 1H), 7.15 (dd, J=8.3, 2.0 Hz, 1H), 5.25 (d, J=1.0 Hz, 1H), 4.79 (dd, J=3.6, 1.3 Hz, 1H), 4.16 (t, J=5.9 Hz, 2H), 3.89-3.78 (m, 2H), 2.84 (t, J=7.6 Hz, 2H), 2.28-2.10 (m, 4H); MS (ESI+): Calc'd for $C_{23}H_{23}Cl_2F_3N_5O_3$ [M+H]: 544.1, Found: 544.4.

tert-butyl (S)-2-(3-(4-(3-(2,3-dihydrobenzo[b][1,4]dioxin-6-yl)propoxy)-3-(trifluoromethyl)phenyl)-1,2,4-oxadiazol-5-yl)pyrrolidine-1-carboxylate

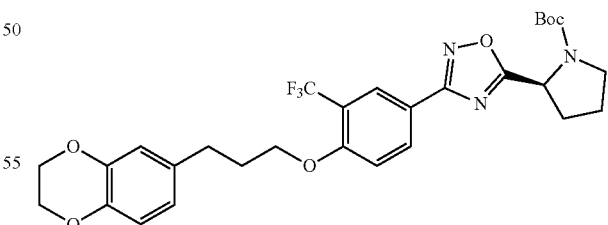

Synthesized by General Procedures B and C. 62% yield, yellow oil; ¹H NMR (600 MHz, Chloroform-d) δ 8.30 (s, 1H), 8.17 (d, J=8.2 Hz, 1H), 7.05-6.98 (m, 1H), 6.77 (d, J=8.2 Hz, 1H), 6.71 (d, J=2.1 Hz, 1H), 6.66 (dd, J=8.2, 2.1 Hz, 1H), 5.06 (dd, J=8.3, 3.7 Hz, 1H), 4.23 (d, J=1.1 Hz, 4H), 4.08 (t, J=5.9 Hz, 2H), 3.76-3.66 (m, 1H), 3.60-3.53 (m, 1H), 2.74 (t, J=7.4 Hz, 2H), 2.46-2.32 (m, 1H), 2.20-2.08 (m, 4H), 2.06-1.97 (m, 1H), 1.46 (s, 3H), 1.30 (s, 6H).

tert-butyl (S)-(((tert-butoxycarbonyl)amino)(2-(3-(4-(3-(2,3-dihydrobenzo[b][1,4]dioxin-6-yl)propoxy)-3-(trifluoromethyl)phenyl)-1,2,4-oxadiazol-5-yl)pyrrolidin-1-yl)methylene)carbamate tert-butyl (2S,4R)-2-(3-(4-(3-(2,3-dihydrobenzo[b][1,4]dioxin-6-yl)propoxy)-3-(trifluoromethyl)phenyl)-1,2,4-oxadiazol-5-yl)-4-hydroxypyrrolidine-1-carboxylate

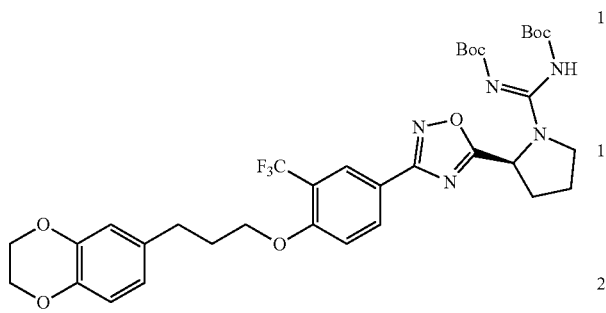

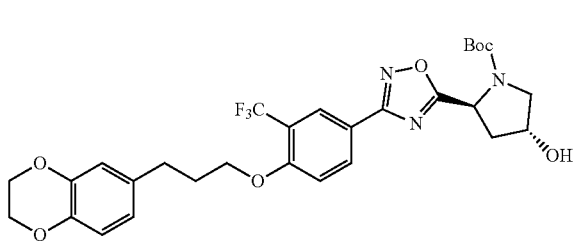 [SMILES: CC(C)(C)OC(=O)N1C[C@H](O)C[C@H]1c1nc(-c2ccc(OCCCc3ccc4c(c3)OCCO4)c(C(F)(F)F)c2)no1]

Synthesized by General Procedure D. 29% yield, yellow oil; $^1$H NMR (600 MHz, Chloroform-d) δ 10.12 (s, 1H), 8.29 (d, J=2.1 Hz, 1H), 8.17 (dd, J=8.7, 2.1 Hz, 1H), 7.01 (d, J=8.8 Hz, 1H), 6.77 (d, J=8.2 Hz, 1H), 6.71 (d, J=2.1 Hz, 1H), 6.66 (dd, J=8.2, 2.1 Hz, 1H), 5.61 (dd, J=7.9, 4.5 Hz, 1H), 4.23 (s, 4H), 4.15-4.05 (m, 2H), 3.94-3.87 (m, 1H), 3.80 (s, 1H), 2.74 (t, J=7.4 Hz, 2H), 2.50-2.42 (m, 1H), 2.24-1.99 (m, 5H), 1.58 (s, 0H), 1.46 (s, 18H).

Synthesized by General Procedures B and C. 44% yield, yellow oil; $^1$H NMR (600 MHz, Chloroform-d) δ 8.30 (d, J=2.2 Hz, 1H), 8.16 (dd, J=8.7, 2.1 Hz, 1H), 7.02 (d, J=9.1 Hz, 1H), 6.77 (d, J=8.2 Hz, 1H), 6.71 (d, J=2.1 Hz, 1H), 6.66 (dd, J=8.2, 2.1 Hz, 1H), 5.35-5.20 (m, 2H), 4.69-4.63 (m, 1H), 4.27-4.20 (m, 4H), 4.08 (t, J=6.0 Hz, 2H), 3.81 (dd, J=11.8, 4.3 Hz, 1H), 3.70 (d, J=11.9 Hz, 1H), 3.59 (d, J=11.5 Hz, 0H), 2.74 (t, J=7.4 Hz, 2H), 2.52-2.45 (m, 1H), 2.36-2.28 (m, 1H), 2.15-2.08 (m, 2H), 1.45 (s, 3H), 1.28 (s, 6H).

Example 29: (S)-amino(2-(3-(4-(3-(2,3-dihydrobenzo[b][1,4]dioxin-6-yl)propoxy)-3-(trifluoromethyl)phenyl)-1,2,4-oxadiazol-5-yl)pyrrolidin-1-yl)methaniminium chloride (Compound 29)

tert-butyl (((tert-butoxycarbonyl)amino)((2S,4R)-2-(3-(4-(3-(2,3-dihydrobenzo[b][1,4]dioxin-6-yl)propoxy)-3-(trifluoromethyl)phenyl)-1,2,4-oxadiazol-5-yl)-4-hydroxypyrrolidin-1-yl)methylene)carbamate

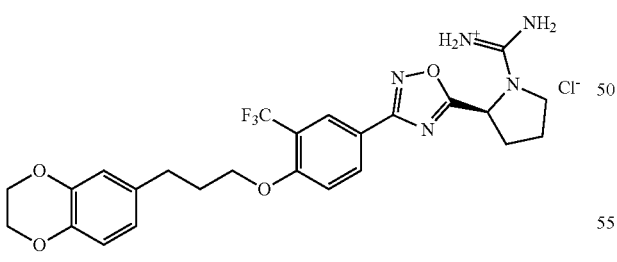

Synthesized by General Procedure E. 95% yield, white solid; $^1$H NMR (600 MHz, Methanol-d4) δ 8.23 (d, J=7.8 Hz, 1H), 7.29-7.24 (m, 1H), 6.71 (d, J=8.2 Hz, 1H), 6.68-6.59 (m, 2H), 5.46 (dd, J=8.1, 1.7 Hz, 1H), 4.22-4.15 (m, 4H), 4.12 (t, J=5.9 Hz, 2H), 3.82-3.71 (m, 1H), 3.68-3.56 (m, 2H), 2.71 (t, J=7.4 Hz, 2H), 2.62-2.53 (m, 1H), 2.52-2.44 (m, 1H), 2.28-2.20 (m, 1H), 2.10-2.04 (m, 3H); MS (ESI+): Calc'd for $C_{25}H_{27}F_3N_5O_4$ [M+H]: 518.2, Found: 518.6.

Synthesized by General Procedure D. 29% yield, yellow oil; $^1$H NMR (600 MHz, Chloroform-d) δ 8.29 (d, J=2.1 Hz, 1H), 8.17 (dd, J=8.7, 2.2 Hz, 1H), 7.65 (d, J=2.2 Hz, 1H), 7.01 (d, J=8.7 Hz, 1H), 6.77 (d, J=8.2 Hz, 1H), 6.71 (d, J=2.1 Hz, 1H), 6.66 (dd, J=8.2, 2.1 Hz, 1H), 5.91 (t, J=8.3 Hz, 1H), 4.65 (d, J=4.0 Hz, 1H), 4.23 (s, 4H), 4.11-4.02 (m, 0H), 3.80 (d, J=12.7 Hz, 1H), 2.74 (t, J=7.4 Hz, 2H), 2.64-2.56 (m, 1H), 2.42-2.36 (m, 1H), 2.15-2.08 (m, 2H), 1.46 (s, 18H).

Example 30: amino((2S,4R)-2-(3-(4-(3-(2,3-dihydrobenzo[b][1,4]dioxin-6-yl)propoxy)-3-(trifluoromethyl)phenyl)-1,2,4-oxadiazol-5-yl)-4-hydroxypyrrolidin-1-yl)methaniminium chloride (Compound 60A)

tert-butyl (S)-(((tert-butoxycarbonyl)amino)(2-(3-(4-(3-(3,4-dichlorophenyl)propoxy)-3-(trifluoromethyl)phenyl)-1,2,4-oxadiazol-5-yl)pyrrolidin-1-yl)methylene)carbamate

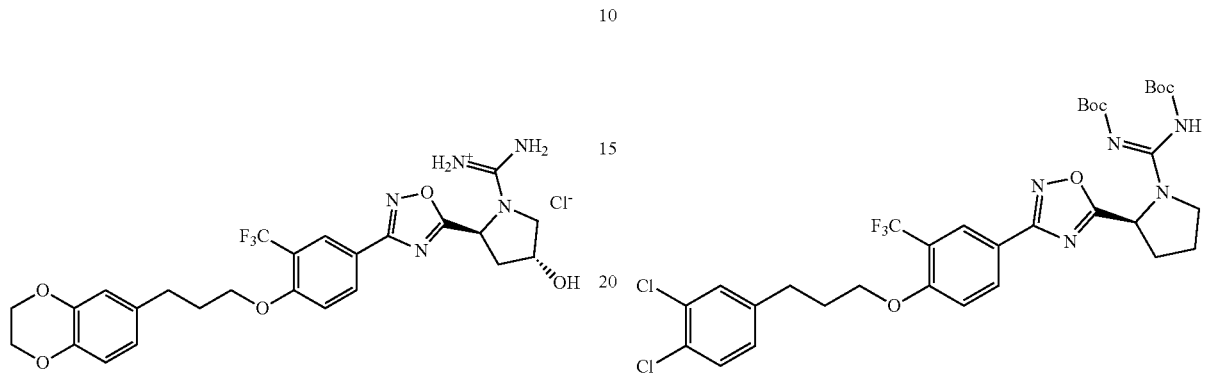

Synthesized by General Procedure E. 98% yield, white solid; $^1$H NMR (600 MHz, Methanol-d4) δ 8.31 (d, J=2.6 Hz, 1H), 8.23 (d, J=7.5 Hz, 2H), 7.30-7.24 (m, 1H), 6.84 (t, J=2.6 Hz, 0H), 6.71 (d, J=8.2 Hz, 1H), 6.68-6.61 (m, 2H), 5.61-5.55 (m, 1H), 4.65-4.59 (m, 1H), 4.19 (s, 4H), 4.13 (t, J=6.0 Hz, 2H), 3.89 (dd, J=10.7, 4.6 Hz, 1H), 3.63-3.56 (m, 1H), 2.75-2.61 (m, 3H), 2.56-2.48 (m, 1H), 2.12-2.04 (m, 2H); MS (ESI+): Calc'd for $C_{25}H_{27}F_3N_5O_5$ [M+H]: 534.2, Found: 534.4.

Synthesized by General Procedure D. 34% yield, yellow oil; $^1$H NMR (600 MHz, Chloroform-d) δ 10.12 (s, 1H), 8.31 (d, J=2.2 Hz, 1H), 8.18 (dd, J=8.7, 2.2 Hz, 1H), 7.34 (d, J=8.2 Hz, 1H), 7.30 (d, J=2.1 Hz, 1H), 7.06-6.99 (m, 2H), 5.61 (dd, J=7.9, 4.6 Hz, 1H), 4.08 (t, J=5.8 Hz, 2H), 3.91 (dt, J=11.5, 7.0 Hz, 1H), 3.80 (s, 1H), 2.82 (t, J=7.5 Hz, 2H), 2.45 (dq, J=15.8, 8.8, 8.2 Hz, 1H), 2.25-2.10 (m, 4H), 2.09-1.99 (m, 1H), 1.46 (s, 18H).

tert-butyl (S)-2-(3-(4-(3-(3,4-dichlorophenyl)propoxy)-3-(trifluoromethyl)phenyl)-1,2,4-oxadiazol-5-yl)pyrrolidine-1-carboxylate

Example 31: (S)-amino(2-(3-(4-(3-(3,4-dichlorophenyl)propoxy)-3-(trifluoromethyl)phenyl)-1,2,4-oxadiazol-5-yl)pyrrolidin-1-yl)methaniminium chloride (Compound 30A)

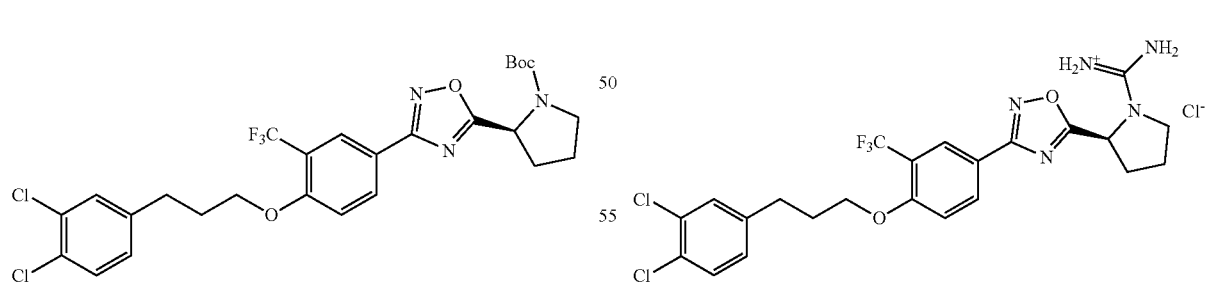

Synthesized by General Procedures B and C. 74% yield, yellow oil; $^1$H NMR (600 MHz, Chloroform-d) δ 8.31 (d, J=2.4 Hz, 1H), 8.21-8.16 (m, 1H), 7.34 (d, J=8.1 Hz, 1H), 7.30 (d, J=2.1 Hz, 1H), 7.06-6.98 (m, 2H), 5.06 (dd, J=8.0, 3.7 Hz, 1H), 4.08 (t, J=6.0 Hz, 2H), 3.76-3.69 (m, 1H), 3.61-3.46 (m, 1H), 2.83 (t, J=7.5 Hz, 2H), 2.46-2.34 (m, 1H), 2.20-2.10 (m, 4H), 2.06-1.98 (m, 1H), 1.47 (s, 3H), 1.30 (s, 6H).

Synthesized by General Procedure E. 80% yield, white solid; $^1$H NMR (600 MHz, Methanol-d4) δ 8.26-8.20 (m, 2H), 7.40 (d, J=8.3 Hz, 1H), 7.37 (d, J=2.5 Hz, 1H), 7.29 (d, J=9.7 Hz, 1H), 7.14 (dd, J=8.5, 2.4 Hz, 1H), 5.42 (dd, J=8.2, 2.2 Hz, 1H), 4.15 (t, J=6.2 Hz, 2H), 3.81-3.53 (m, 3H), 2.83 (t, J=7.8 Hz, 2H), 2.61-2.42 (m, 2H), 2.27-2.17 (m, 1H), 2.16-2.09 (m, 2H); MS (ESI+): Calc'd for $C_{23}H_{23}Cl_2F_3N_5O_2$ [M+H]: 528.1, Found: 528.8.

tert-butyl (2S,4R)-2-(3-(4-(3-(3,4-dichlorophenyl)propoxy)-3-(trifluoromethyl)phenyl)-1,2,4-oxadiazol-5-yl)-4-hydroxypyrrolidine-1-carboxylate

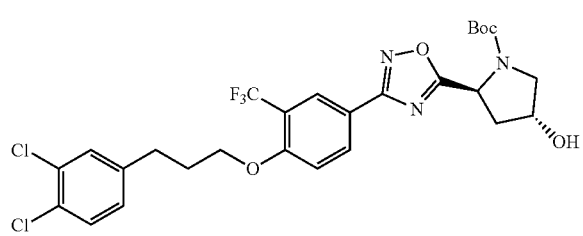 [SMILES: CC(C)(C)OC(=O)N1C[C@H](O)C[C@H]1c1nc(-c2ccc(OCCCc3ccc(Cl)c(Cl)c3)c(C(F)(F)F)c2)no1]

Synthesized by General Procedures B and C. 63% yield, yellow oil; $^1$H NMR (600 MHz, Chloroform-d) δ 8.31 (d, J=2.1 Hz, 1H), 8.18 (dd, J=8.8, 2.1 Hz, 1H), 7.34 (d, J=8.1 Hz, 1H), 7.30 (d, J=2.1 Hz, 1H), 7.08-7.01 (m, 2H), 5.23 (t, J=7.9 Hz, 1H), 4.69-4.64 (m, 1H), 4.08 (t, J=5.9 Hz, 2H), 3.82 (dd, J=11.8, 4.3 Hz, 1H), 3.70 (d, J=12.1 Hz, 1H), 2.83 (t, J=7.5 Hz, 2H), 2.51-2.46 (m, 1H), 2.34-2.31 (m, 1H), 2.19-2.10 (m, 2H), 1.45 (s, 3H), 1.28 (s, 6H).

tert-butyl (((tert-butoxycarbonyl)amino)((2S,4R)-2-(3-(4-(3-(3,4-dichlorophenyl)propoxy)-3-(trifluoromethyl)phenyl)-1,2,4-oxadiazol-5-yl)-4-hydroxypyrrolidin-1-yl)methylene)carbamate

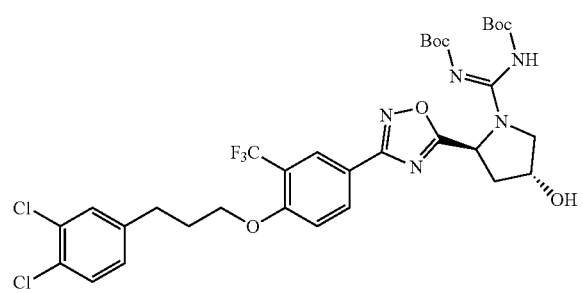 [SMILES: CC(C)(C)OC(=O)/N=C(\NC(=O)OC(C)(C)C)N1C[C@H](O)C[C@H]1c1nc(-c2ccc(OCCCc3ccc(Cl)c(Cl)c3)c(C(F)(F)F)c2)no1]

Synthesized by General Procedure D. 44% yield, yellow oil; $^1$H NMR (600 MHz, Chloroform-d) δ 8.30 (d, J=2.1 Hz, 1H), 8.18 (dd, J=8.7, 2.2 Hz, 1H), 7.34 (d, J=8.2 Hz, 1H), 7.29 (d, J=2.0 Hz, 1H), 7.06-6.99 (m, 2H), 5.84 (t, J=8.3 Hz, 1H), 4.68-4.63 (m, 1H), 4.10-4.03 (m, 3H), 3.76 (d, J=12.0 Hz, 1H), 2.82 (t, J=7.6 Hz, 2H), 2.57 (ddt, J=13.4, 7.7, 2.1 Hz, 1H), 2.41-2.33 (m, 1H), 2.19-2.10 (m, 2H), 2.04 (s, 1H), 1.46 (s, 18H).

Example 32: amino((2S,4R)-2-(3-(4-(3-(3,4-dichlorophenyl)propoxy)-3-(trifluoromethyl)phenyl)-1,2,4-oxadiazol-5-yl)-4-hydroxypyrrolidin-1-yl)methaniminium chloride (Compound 31)

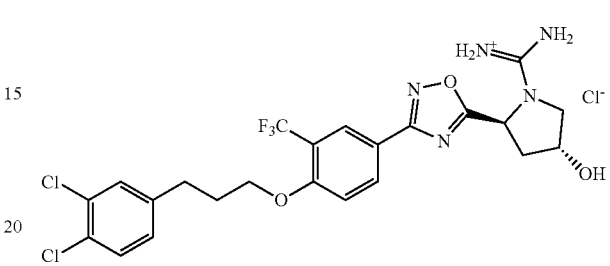

Synthesized by General Procedure E. 100% yield, white solid; $^1$H NMR (600 MHz, Methanol-d4) δ 8.23 (s, 2H), 7.40 (d, J=7.7 Hz, 1H), 7.36 (s, 1H), 7.32-7.27 (m, 1H), 7.14 (d, J=7.8 Hz, 1H), 5.61-5.56 (m, 1H), 4.64-4.61 (m, 1H), 4.17-4.14 (m, 2H), 3.92-3.86 (m, 1H), 3.63-3.55 (m, 1H), 2.86-2.80 (m, 2H), 2.68-2.62 (m, 1H), 2.55-2.51 (m, 1H), 2.15-2.12 (m, 2H); $^{13}$C NMR (151 MHz, cd$_3$od) δ 177.87, 167.17, 159.15, 156.22, 142.03, 132.67, 131.75, 130.23, 130.15, 129.41, 128.19, 125.77, 118.14, 113.56, 68.38, 67.52, 66.74, 55.80, 53.50, 39.70, 30.51, 30.02; MS (ESI+): Calc'd for $C_{23}H_{23}Cl_2F_3N_5O_3$ [+H]: 544.1, Found: 544.4.

tert-butyl (S)-2-(3-(3-(trifluoromethyl)-4-(3-(4-(trifluoromethyl)phenyl)propoxy)phenyl)-1,2,4-oxadiazol-5-yl)pyrrolidine-1-carboxylate

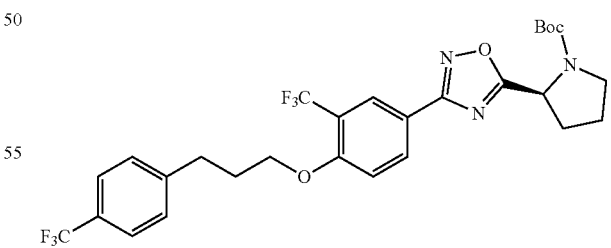

Synthesized by General Procedures B and C. 62% yield, yellow oil; $^1$H NMR (600 MHz, Chloroform-d) δ 8.32 (s, 1H), 8.21-8.15 (m, 1H), 7.54 (d, J=7.9 Hz, 3H), 7.32 (d, J=7.9 Hz, 2H), 7.02 (dd, J=13.8, 8.5 Hz, 1H), 5.23-5.03 (m, 1H), 4.09 (t, J=5.9 Hz, 2H), 3.76-3.66 (m, 1H), 2.93 (t, J=7.6 Hz, 2H), 2.46-2.34 (m, 1H), 2.22-2.09 (m, 4H), 2.06-1.97 (m, 1H), 1.47 (s, 3H), 1.30 (s, 6H).

tert-butyl (S)-(((tert-butoxycarbonyl)amino)(2-(3-(3-(trifluoromethyl)-4-(3-(4-(trifluoromethyl)phenyl)propoxy)phenyl)-1,2,4-oxadiazol-5-yl)pyrrolidin-1-yl)methylene)carbamate tert-butyl (2S,4R)-4-hydroxy-2-(3-(3-(trifluoromethyl)-4-(3-(4-(trifluoromethyl)phenyl)propoxy)phenyl)-1,2,4-oxadiazol-5-yl)pyrrolidine-1-carboxylate

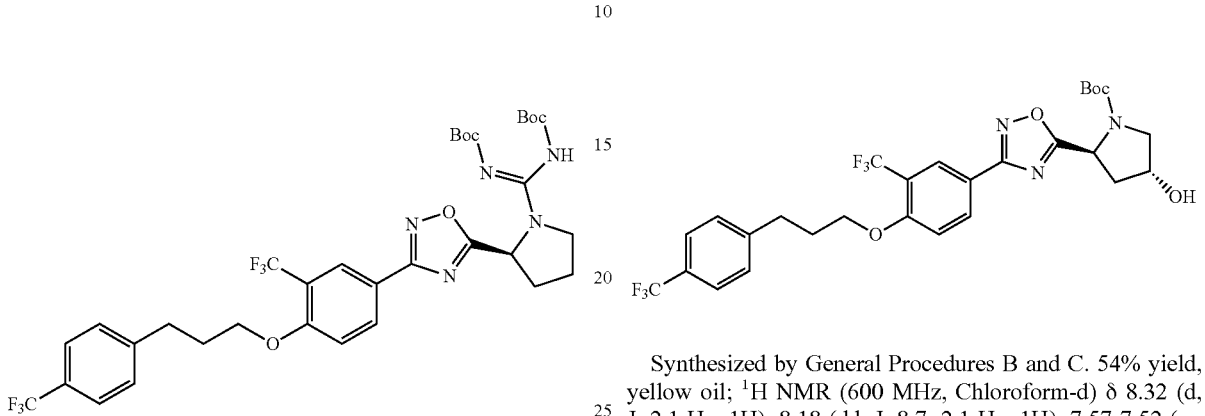

Synthesized by General Procedures B and C. 54% yield, yellow oil; $^1$H NMR (600 MHz, Chloroform-d) δ 8.32 (d, J=2.1 Hz, 1H), 8.18 (dd, J=8.7, 2.1 Hz, 1H), 7.57-7.52 (m, 2H), 7.32 (d, J=7.9 Hz, 2H), 7.03 (d, J=8.9 Hz, 1H), 5.23 (t, J=7.9 Hz, 1H), 4.69-4.63 (m, 1H), 4.09 (t, J=5.9 Hz, 2H), 3.82 (dd, J=11.8, 4.3 Hz, 1H), 3.70 (d, J=11.9 Hz, 1H), 2.93 (t, J=7.5 Hz, 2H), 2.50-2.47 (m, 1H), 2.34-2.28 (m, 1H), 2.22-2.14 (m, 2H), 1.45 (s, 3H), 1.28 (s, 6H).

Synthesized by General Procedure D. 37% yield, yellow oil; $^1$H NMR (600 MHz, Chloroform-d) δ 8.31 (d, J=2.1 Hz, 1H), 8.18 (dd, J=8.7, 2.2 Hz, 1H), 7.54 (d, J=8.1 Hz, 2H), 7.31 (d, J=8.1 Hz, 2H), 7.01 (d, J=8.7 Hz, 1H), 5.61 (dd, J=7.9, 4.6 Hz, 1H), 4.09 (t, J=5.9 Hz, 2H), 3.94-3.87 (m, 1H), 3.80 (s, 1H), 2.93 (t, J=7.5 Hz, 2H), 2.49-2.42 (m, 1H), 2.22-2.14 (m, 4H), 2.08-2.01 (m, 1H), 1.46 (s, 18H).

tert-butyl (((tert-butoxycarbonyl)amino)((2S,4R)-4-hydroxy-2-(3-(3-(trifluoromethyl)-4-(3-(4-(trifluoromethyl)phenyl)propoxy)phenyl)-1,2,4-oxadiazol-5-yl)pyrrolidin-1-yl)methylene)carbamate Example 33: (S)-amino(2-(3-(3-(trifluoromethyl)-4-(3-(4-(trifluoromethyl)phenyl)propoxy)phenyl)-1,2,4-oxadiazol-5-yl)pyrrolidin-1-yl)methaniminium chloride (Compound 32A)

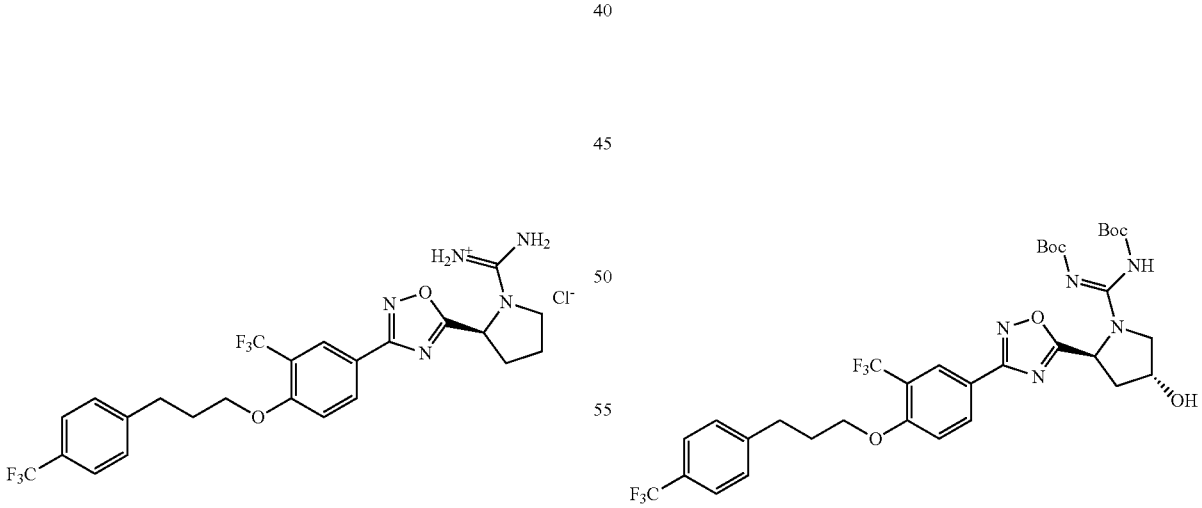

Synthesized by General Procedure E. 100% yield, white solid; $^1$H NMR (600 MHz, Methanol-d4) δ 8.27-8.22 (m, 2H), 7.58 (d, J=8.0 Hz, 2H), 7.41 (d, J=7.9 Hz, 2H), 7.31 (d, J=9.3 Hz, 1H), 5.46 (dd, J=8.0, 1.7 Hz, 1H), 4.18 (t, J=5.9 Hz, 2H), 3.82-3.71 (m, 1H), 3.65-3.57 (m, 1H), 2.94 (t, J=7.6 Hz, 2H), 2.63-2.53 (m, 1H), 2.52-2.44 (m, 1H), 2.32-2.03 (m, 4H); MS (ESI+): Calc'd for $C_{24}H_{24}F_6N_5O_2$ [M+H]: 528.1, Found: 528.6.

Synthesized by General Procedure D. 10% yield, yellow oil; $^1$H NMR (600 MHz, Chloroform-d) δ 8.31 (d, J=2.1 Hz, 0H), 8.18 (dd, J=8.8, 2.2 Hz, 0H), 7.54 (d, J=8.0 Hz, 0H), 7.32 (d, J=8.0 Hz, 0H), 7.02 (d, J=8.7 Hz, 0H), 6.01 (s, 0H), 4.66 (s, 0H), 4.12-4.02 (m, 0H), 3.83 (d, J=12.4 Hz, 0H), 3.53 (s, 0H), 2.93 (t, J=7.5 Hz, 0H), 2.67-2.60 (m, 0H), 2.47-2.38 (m, 1H), 2.22-2.14 (m, 0H), 1.48 (s, 1H).

Example 34: amino((2S,4R)-4-hydroxy-2-(3-(3-(trifluoromethyl)-4-(3-(4-(trifluoromethyl)phenyl)propoxy)phenyl)-1,2,4-oxadiazol-5-yl)pyrrolidin-1-yl)methaniminium chloride (Compound 33A)

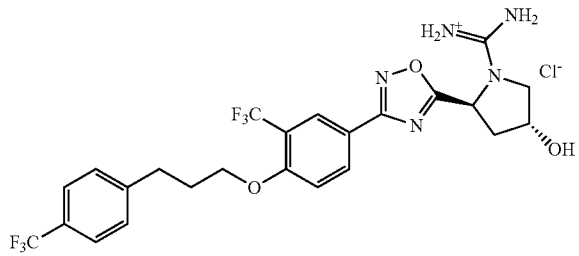 [SMILES: NC(=[NH2+])N1C[C@H](O)C[C@H]1c1nc(-c2ccc(OCCCc3ccc(C(F)(F)F)cc3)c(C(F)(F)F)c2)no1 ; [Cl-]]

Synthesized by General Procedure E. 85% yield, white solid; $^1$H NMR (600 MHz, Methanol-d4) δ 8.27-8.22 (m, 2H), 7.58 (d, J=2.1 Hz, 8H), 7.42 (d, J=8.1 Hz, 9H), 7.30 (d, J=9.6 Hz, 4H), 5.60-5.55 (m, 1H), 4.65-4.59 (m, 1H), 4.18 (t, J=5.9 Hz, 2H), 3.88 (dd, J=10.7, 4.6 Hz, 1H), 3.67-3.56 (m, 1H), 2.94 (t, J=7.6 Hz, 2H), 2.70-2.61 (m, 1H), 2.56-2.48 (m, 1H), 2.23-2.15 (m, 2H); MS (ESI+): Calc'd for $C_{24}H_{24}F_6N_5O_3$ [M+H]: 544.2, Found: 544.6.

3-(1-allyl-1H-benzo[d]imidazol-2-yl)propan-1-ol

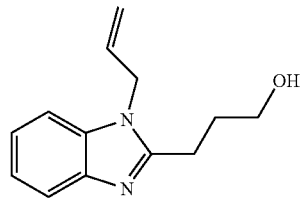 [SMILES: C=CCn1c(CCCO)nc2ccccc21]

Synthesized by General Procedure I. 26% yield, white solid; $^1$H NMR (600 MHz, Chloroform-d) δ 7.75-7.68 (m, 1H), 7.35-7.20 (m, 3H), 5.99-5.90 (m, 1H), 5.25-5.18 (m, 1H), 5.00-4.93 (m, 1H), 4.85-4.72 (m, 2H), 3.81 (t, J=5.5 Hz, 2H), 3.03 (t, J=6.7 Hz, 2H), 2.20-2.12 (m, 2H).

4-(3-(1-allyl-1H-benzo[d]imidazol-2-yl)propoxy)-3-(trifluoromethyl)benzonitrile

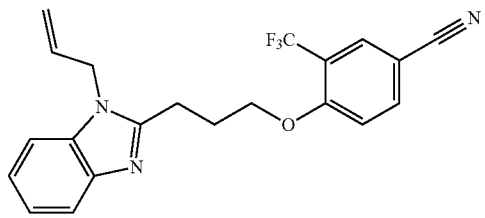 [SMILES: C=CCn1c(CCCOc2ccc(C#N)cc2C(F)(F)F)nc2ccccc21]

Synthesized by General Procedure A. 89% yield, yellow solid; 1H NMR (600 MHz, Chloroform-d) δ 7.88-7.83 (m, 1H), 7.80-7.70 (m, 2H), 7.32-7.20 (m, 3H), 7.09 (d, J=8.7 Hz, 1H), 5.97-5.87 (m, 1H), 5.20-5.14 (m, 1H), 4.96-4.89 (m, 1H), 4.76-4.71 (m, 2H), 4.32 (t, J=5.7 Hz, 2H), 3.08 (t, J=7.3 Hz, 2H), 2.55-2.44 (m, 2H).

tert-butyl (2S,3S)-2-(3-(4-(3-(1-allyl-1H-benzo[d]imidazol-2-yl)propoxy)-3-(trifluoromethyl)phenyl)-1,2,4-oxadiazol-5-yl)-3-hydroxypyrrolidine-1-carboxylate

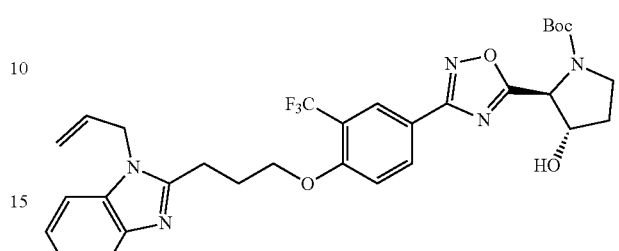

Synthesized by General Procedures B and C. 74% yield, yellow solid; 1H NMR (600 MHz, Chloroform-d) δ 8.28 (s, 1H), 8.18 (t, J=9.7 Hz, 1H), 7.82 (d, J=7.0 Hz, 1H), 7.34 (td, J=8.3, 5.4 Hz, 3H), 7.12-7.03 (m, 1H), 5.95 (ddt, J=15.7, 10.1, 4.9 Hz, 1H), 5.23 (d, J=10.4 Hz, 1H), 5.02-4.93 (m, 2H), 4.82 (dt, J=3.8, 1.8 Hz, 2H), 4.58 (d, J=19.1 Hz, 1H), 4.30 (t, J=6.5 Hz, 2H), 3.81-3.72 (m, 2H), 3.23 (t, J=7.5 Hz, 2H), 2.54 (p, J=6.1 Hz, 2H), 2.41-2.28 (m, 1H), 2.09-2.02 (m, 1H), 1.47 (s, 3H), 1.30 (s, 6H).

tert-butyl (((2S,3S)-2-(3-(4-(3-(1-allyl-1H-benzo[d]imidazol-2-yl)propoxy)-3-(trifluoromethyl)phenyl)-1,2,4-oxadiazol-5-yl)-3-hydroxypyrrolidin-1-yl)((tert-butoxycarbonyl)amino)methylene)carbamate

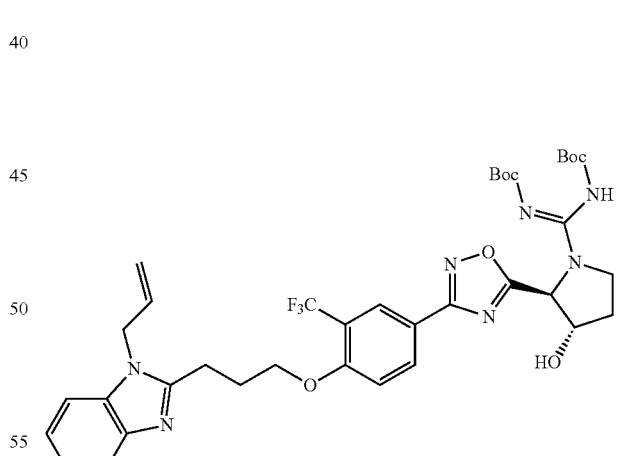

Synthesized by General Procedure D. 58% yield, yellow solid; 1H NMR (600 MHz, Chloroform-d) δ 10.02 (s, 1H), 8.25 (d, J=2.1 Hz, 1H), 8.14 (dd, J=8.7, 2.2 Hz, 1H), 7.77-7.71 (m, 1H), 7.32-7.21 (m, 3H), 7.01 (d, J=8.8 Hz, 1H), 5.97-5.88 (m, 1H), 5.52-5.48 (m, 1H), 5.20-5.15 (m, 1H), 4.97-4.91 (m, 1H), 4.78-4.73 (m, 2H), 4.65 (s, 1H), 4.25 (t, J=5.5 Hz, 2H), 4.04-3.92 (m, 2H), 3.88 (s, 1H), 3.16-3.09 (m, 2H), 2.51-2.43 (m, 2H), 2.43-2.34 (m, 1H), 2.18-2.08 (m, 1H), 1.45 (s, 18H).

Example 35: ((2S,3S)-2-(3-(4-(3-(1-allyl-1H-benzo[d]imidazol-2-yl)propoxy)-3-(trifluoromethyl)phenyl)-1,2,4-oxadiazol-5-yl)-3-hydroxypyrrolidin-1-yl)(amino)methaniminium chloride (Compound 47A)

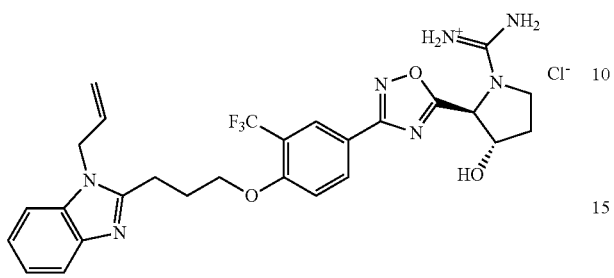

Synthesized by General Procedure E. 100% yield, yellow solid; 1H NMR (600 MHz, Methanol-d4) δ 8.30 (dd, J=8.7, 2.2 Hz, 1H), 8.23 (d, J=2.1 Hz, 1H), 7.88-7.78 (m, 2H), 7.68-7.60 (m, 2H), 7.43 (d, J=8.7 Hz, 1H), 6.14-6.04 (m, 1H), 5.37-5.32 (m, 1H), 5.26-5.16 (m, 4H), 4.81-4.76 (m, 1H), 4.43 (t, J=5.5 Hz, 2H), 3.87-3.78 (m, 2H), 3.52-3.46 (m, 2H), 2.55-2.47 (m, 2H), 2.25-2.15 (m, 2H); MS (ESI+): Calc'd for $C_{27}H_{30}F_3N_7O_3$[M+2H]: 278.6, Found: 279.2.

4-(nonyloxy)-3-(trifluoromethyl)benzonitrile

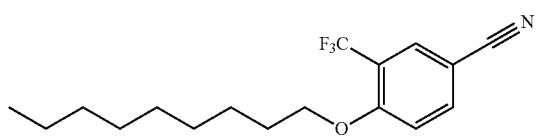 [SMILES: CCCCCCCCCOc1ccc(C#N)cc1C(F)(F)F]

Synthesized by General Procedure A. 100% yield, colorless oil; 1H NMR (600 MHz, Chloroform-d) δ 7.83 (d, J=2.1 Hz, 1H), 7.77 (dd, J=8.7, 2.1 Hz, 1H), 7.06 (d, J=8.7 Hz, 1H), 4.11 (t, J=6.3 Hz, 2H), 1.92-1.79 (m, 2H), 1.50-1.43 (m, 2H), 1.38-1.22 (m, 10H), 0.87 (t, J=7.0 Hz, 3H).

tert-butyl (2S,3S)-3-hydroxy-2-(3-(4-(nonyloxy)-3-(trifluoromethyl)phenyl)-1,2,4-oxadiazol-5-yl)pyrrolidine-1-carboxylate

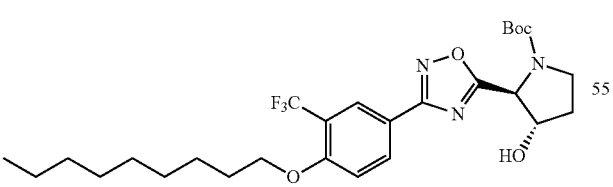

Synthesized by General Procedures B and C. 77% yield, yellow oil; 1H NMR (600 MHz, Chloroform-d) δ 8.29-8.23 (m, 1H), 8.20-8.12 (m, 1H), 7.09-7.01 (m, 1H), 5.12-4.93 (m, 1H), 4.61-4.53 (m, 1H), 4.13-4.06 (m, 2H), 3.82-3.68 (m, 2H), 2.39-2.28 (m, 1H), 2.09-2.01 (m, 1H), 1.88-1.80 (m, 2H), 1.52-1.44 (m, 5H), 1.39-1.22 (m, 16H), 0.88 (t, J=6.9 Hz, 3H).

tert-butyl ((((tert-butoxycarbonyl)imino)((2S,3S)-3-hydroxy-2-(3-(4-(nonyloxy)-3-(trifluoromethyl)phenyl)-1,2,4-oxadiazol-5-yl)pyrrolidin-1-yl)methyl)carbamate

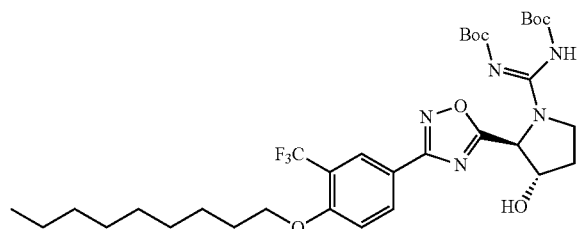

Synthesized by General Procedure D. 60% yield, yellow oil; 1H NMR (600 MHz, Chloroform-d) δ 8.26 (d, J=2.1 Hz, 1H), 8.16 (dd, J=8.7, 2.1 Hz, 1H), 7.05 (d, J=8.7 Hz, 1H), 5.52 (d, J=2.3 Hz, 1H), 4.64 (s, 1H), 4.10 (t, J=6.4 Hz, 2H), 4.06-3.92 (m, 2H), 2.41-2.34 (m, 1H), 2.16-2.09 (m, 1H), 1.88-1.80 (m, 2H), 1.45 (s, 18H), 1.40-1.22 (m, 12H), 0.88 (t, J=6.9 Hz, 3H).

Example 36: amino((2S,3S)-3-hydroxy-2-(3-(4-(nonyloxy)-3-(trifluoromethyl)phenyl)-1,2,4-oxadiazol-5-yl)pyrrolidin-1-yl)methaniminium chloride (Compound 64A)

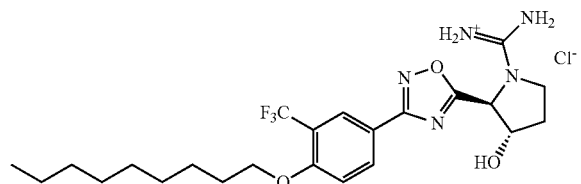

General Procedure E. 100% yield, white solid; 1H NMR (600 MHz, Methanol-d4) δ 8.25-8.18 (m, 2H), 7.31 (d, J=8.7 Hz, 1H), 5.27 (s, 1H), 4.79 (d, J=3.7 Hz, 1H), 4.17 (t, J=6.2 Hz, 2H), 3.90-3.79 (m, 2H), 2.28-2.15 (m, 2H), 1.87-1.79 (m, 2H), 1.51 (ddd, J=15.2, 8.4, 6.2 Hz, 2H), 1.42-1.24 (m, 10H), 0.89 (t, J=6.8 Hz, 3H); 13C NMR (151 MHz, cd3od) δ 176.96, 168.64, 160.86, 157.54, 133.97, 127.38, 127.05, 125.58, 123.77, 121.97, 120.67, 120.52, 120.31, 120.11, 119.19, 114.80, 75.97, 70.29, 64.77, 49.43, 49.29, 49.14, 49.00, 48.86, 48.72, 48.57, 47.43, 32.99, 32.46, 30.59, 30.28, 30.26, 30.00, 26.87, 23.70, 14.43; MS (ESI+): Calc'd for $C_{23}H_{33}F_3N_5O_3$ [M+H]: 484.3, Found: 485.2.

tert-butyl (2S,4R)-4-fluoro-2-(3-(4-(octyloxy)-3-(trifluoromethyl)phenyl)-1,2,4-oxadiazol-5-yl)pyrrolidine-1-carboxylate

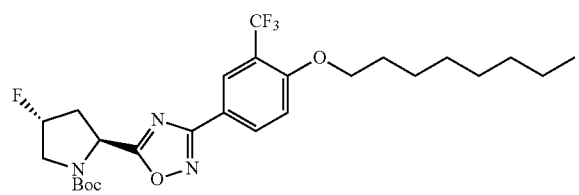 [SMILES: CCCCCCCCOc1ccc(-c2noc([C@@H]3C[C@@H](F)CN3C(=O)OC(C)(C)C)n2)cc1C(F)(F)F]

Synthesized by General Procedures B and C. ¹H NMR (400 MHz, DMSO-d₆) δ 8.26-8.15 (m, 2H), 8.10 (s, 1H), 7.43 (d, J=8.8 Hz, 1H), 5.51-5.41 (m, 1H), 5.35-5.28 (m, 1H), 5.21-5.13 (m, 2H), 4.18 (t, J=6.2 Hz, 2H), 3.88-3.70 (m, 3H), 2.76 (s, 3H), 1.75-1.65 (m, 2H), 1.41-1.31 (m, 3H), 1.30-1.19 (m, 5H), 1.16 (s, 3H), 0.90-0.76 (m, 3H); Calcd for C₂₆H₃₅F₄N₃O₄Na [M+Na]⁺: 552.2456, Found: 552.2469.

tert-butyl ((E)-((tert-butoxycarbonyl)amino)((2S, 4R)-4-fluoro-2-(3-(4-(octyloxy)-3-(trifluoromethyl)phenyl)-1,2,4-oxadiazol-5-yl)pyrrolidin-1-yl)methylene)carbamate

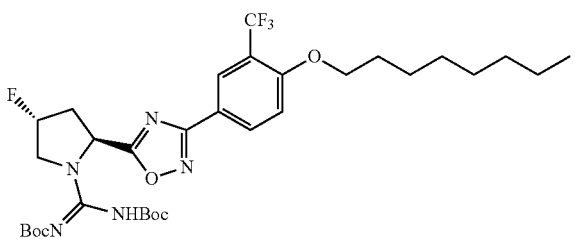

General Procedure D. ¹H NMR (500 MHz, Chloroform-d) δ 10.43 (s, 1H), 8.22 (d, J=2.1 Hz, 1H), 8.11 (dd, J=8.7, 2.2 Hz, 1H), 7.97-7.93 (m, 0.4H), 7.78-7.72 (m, 0.4H), 7.38-7.34 (m, 0.5H), 6.99 (d, J=8.7 Hz, 1H), 6.31-6.28 (m, 0.4H), 5.90-5.70 (m, 1H), 5.38-5.18 (m, 1H), 4.31-3.61 (m, 4H), 2.81-2.69 (m, 1H), 2.48-2.25 (m, 1H), 1.81-1.71 (m, 2H), 1.51-1.11 (m, 30H), 0.88-0.73 (m, 3H).

Example 37: (2S,4R)-4-fluoro-2-(3-(4-(octyloxy)-3-(trifluoromethyl)phenyl)-1,2,4-oxadiazol-5-yl)pyrrolidine-1-carboximidamide 2,2,2-trifluoroacetate) (Compound 49A)

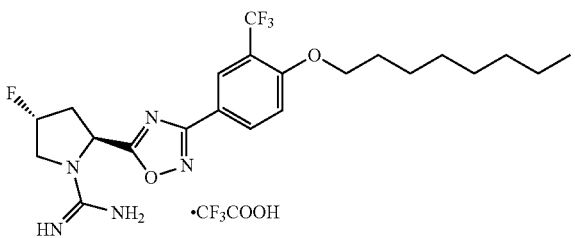 [SMILES: CCCCCCCCOc1ccc(-c2noc([C@@H]3C[C@@H](F)CN3C(=N)N)n2)cc1C(F)(F)F ; "·CF3COOH"]

Synthesized by General Procedure J. ¹H NMR (400 MHz, Methanol-d₄) δ 8.26-8.17 (m, 2H), 7.31 (d, J=8.7 Hz, 1H), 5.66 (t, J=7.9 Hz, 1H), 5.51 (s, 0.4H), 5.41 (s, 0.6H), 4.16 (t, J=6.2 Hz, 2H), 4.03-3.89 (m, 2H), 3.13-2.94 (m, 1H), 2.75-2.57 (m, 1H), 1.87-1.77 (m, 2H), 1.42-1.20 (m, 9H), 0.94-0.79 (m, 3H); ¹³C NMR (101 MHz, cd₃od) δ 177.4, 167.3, 159.5, 156.2, 132.4, 126.5, 125.7, 124.6, 117.7, 113.4, 91.5, 89.8, 68.9, 56.3, 54.6, 53.0, 46.9, 31.5, 28.6, 25.5, 22.8, 22.3, 17.8, 17.2, 15.8, 13.0; Calcd for C₂₂H₃₀F₄N₅O₂ [M+H]⁺: 472.233, Found: 473.0.

tert-butyl (2S,4S)-4-fluoro-2-(3-(4-(octyloxy)-3-(trifluoromethyl)phenyl)-1,2,4-oxadiazol-5-yl)pyrrolidine-1-carboxylate

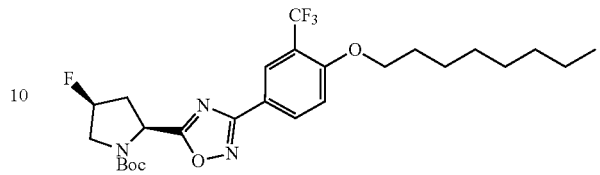

Synthesized by General Procedure B and C. ¹H NMR (400 MHz, Acetone-d₆) δ 8.32-8.18 (m, 2H), 7.40 (dd, J=8.8, 3.9 Hz, 1H), 5.53-5.27 (m, 2H), 4.24-4.18 (m, 2H), 3.91-3.61 (m, 2H), 3.05-2.74 (m, 1H), 2.70-2.44 (m, 1H), 2.08-2.01 (m, 1H), 1.89-1.79 (m, 2H), 1.64-1.21 (m, 18H), 0.92-0.78 (m, 3H)

tert-butyl ((E)-((tert-butoxycarbonyl)amino)((2S, 4S)-4-fluoro-2-(3-(4-(octyloxy)-3-(trifluoromethyl)phenyl)-1,2,4-oxadiazol-5-yl)pyrrolidin-1-yl)methylene)carbamate

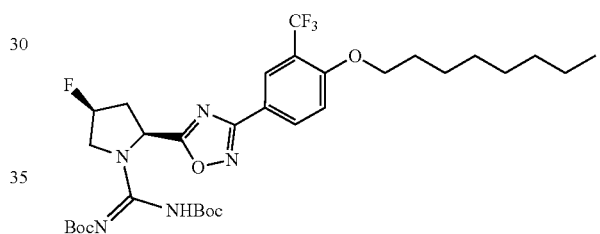

Synthesized by General Procedure D. ¹H NMR (400 MHz, Chloroform-d) δ 9.98 (s, 1H), 8.25 (d, J=2.1 Hz, 1H), 8.16 (dd, J=8.7, 2.2 Hz, 1H), 7.03 (d, J=8.7 Hz, 1H), 5.81-5.41 (m, 1H), 5.40-5.35 (m, 0.5H), 5.28-5.21 (m, 0.5H), 4.19-3.98 (m, 4H), 2.85-2.71 (m, 1H), 2.69-2.51 (m, 1H), 1.91-1.75 (m, 2H), 1.51-1.31 (m, 18H), 1.30-1.21 (m, 9H), 0.94-0.78 (m, 3H).

Example 38: (2S,4S)-4-fluoro-2-(3-(4-(octyloxy)-3-(trifluoromethyl)phenyl)-1,2,4-oxadiazol-5-yl)pyrrolidine-1-carboximidamide 2,2,2-trifluoroacetate (Compound 48A)

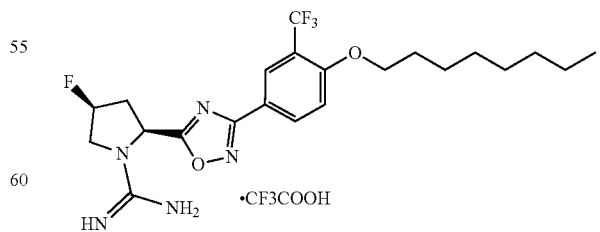

Synthesized by General Procedure J. ¹H NMR (400 MHz, Methanol-d₄) δ 8.25-8.14 (m, 2H), 7.30 (d, J=8.7 Hz, 1H), 5.55 (d, J=8.1 Hz, 1H), 4.15 (t, J=6.2 Hz, 2H), 4.00-3.85 (m, 2H), 2.97-2.72 (m, 2H), 1.86-1.76 (m, 2H), 1.55-1.45 (m, 2H), 1.23-1.41 (m, 8H), 0.93-0.84 (m, 3H); $^{13}$C NMR (101 MHz, cd$_3$od) δ 177.6, 167.3, 159.4, 132.5, 125.7, 125.6, 126.0, 125.5, 121.9, 118.9, 118.6, 117.9, 113.4, 92.3, 90.5, 68.8, 54.4, 54.2, 38.1, 37.9, 31.5, 28.9, 28.8, 28.6, 25.5, 22.3, 13.0. Calcd for C$_{22}$H$_{30}$F$_4$N$_5$O$_2$ [M+H]$^+$: 472.233, Found: 472.2326.

General procedure A. Nucleophilic aromatic substitution. To a roundbottom, the alkyl alcohol (1 equiv) and potassium tert-butoxide (2.5 equiv) were added and dissolved in THF. The solution was then refluxed for 30 minutes. After 30 minutes, the solution was cooled to room temperature. Once cool, 4-fluorobenzonitrile was added to the reaction and the solution was refluxed for 18 h. Once completion was observed, the reaction was cooled to rt. The reaction was the partitioned between dichloromethane and water. The organic layer was subsequently washed with brine, dried with sodium sulfate, filtered, and concentrated under reduced pressure. The resulting residue was purified by silica gel column chromatography to yield the desired product.

General procedure B. Conversion of nitrile to amidoxime. Triethylamine (3.3 equiv) and hydroxylamine hydrochloride (2 equiv) were added to a solution of chosen nitrile intermediate in 95% ethanol (0.2 M solution). The reaction mixture was refluxed for 2-3 h. The organic solvent was removed under reduced pressure and the residue was purified by flash chromatography on silica gel to provide the desired product.

General procedure C. Coupling of amidoxime with amino acids. DIEA (1.8 equiv) was added to a solution of amidoxime (1 equiv) and the appropriate Boc-protected amino acid (1.2 equiv) in DMF (0.2 M solution). HCTU (1.5 equiv) was then added to the resulting mixture at rt and stirred at 80° C. for 18h. At this time, TLC showed complete conversion of starting material. The solution was partitioned between ethyl acetate and water. The organic layer was collected and washed twice with a sat. LiBr. The aqueous solution was then back extracted with ethyl acetate. The organic layers were then combined and washed with sat. NaHCO$_3$ and brine, dried over Na$_2$SO$_4$, and concentrated under reduced pressure. The resulting residue was purified by flash chromatography on silica gel to yield the desired product.

General Procedure D: Deprotection of 1-Boc protecting groups using TFA. To a solution of Boc-protected intermediate in CH$_2$Cl$_2$, a 1N TFA solution in CH$_2$Cl$_2$ was added. The resulting solution was stirred at room temperature until complete consumption of the starting material was observed using TLC. The reaction mixture was concentrated under reduced pressure and triturated with diethyl ether to yield the corresponding free amine TFA salt.

General Procedure E: Guanidylation of amines using the microwave. DIEA (3 equiv) was added to a solution of the corresponding amine hydrochloric acid salt and the reagent (Z)-tert-butyl (((tert-butoxycarbonyl) imino)(1H-pyrazol-1-yl) methyl) carbamate (1.05 equiv) in a reaction tube with acetonitrile (20% vol/wt). The resulting reaction mixture was then placed in the microwave reactor and stirred for 2 hours at 50 degrees Celsius at 200 W. The solvent was then removed under reduced pressure and the resulting colorless residue was purified by flash column chromatography over silica gel to yield the pure product.

General Procedure F: Deprotection of t-Boc protecting groups using HCl gas. Hydrochloric acid gas was bubbled through a solution of the N-Boc protected compound in methanol for 2-5 minutes, or until complete consumption of starting material was observed by TLC. The reaction mixture was concentrated under reduced pressure and triturated with diethyl ether to yield the corresponding free amine hydrochloride salt, which was further purified by trituration with diethyl ether until satisfactory analytical data was obtained.

General procedure G. Williamson ether synthesis with alkyl bromides. To a roundbottom, 1-bromooctane (1.2 equiv), potassium carbonate (4 equiv), and chosen substituted 4-hydroxybenzonitrile were dissolved in ACN. The reaction was then refluxed for 18 h. Once the reaction was complete, the reaction mixture was partitioned between ethyl acetate and water. The organic layer was then washed with brine, dried with sodium sulfate, filtered, and concentrated under reduced pressure. The residue was then purified by silica gel column chromatography to yield the desired product.

General procedure H: Suzuki coupling. Chosen alkene (1.1 equiv) was added to a round bottom flask containing THF. 9-BBN (1.2 equiv) was added as a 0.5 M solution in THF and the solution was stirred overnight at rt. To the above borane solution was added a solution of substituted or non-substituted 4-iodobenzonitrile in DMF. The reaction mixture was degassed for 15 min by bubbling N$_2$ through the solution. Cs$_2$CO$_3$ (2 equiv) and PdCl$_2$ (dppf) (0.03 equiv) were added together. The resulting reaction mixture was then stirred at 80° C. for 18 h, after which it was poured into a saturated solution of LiBr and extracted three times with hexane. The combined organic extracts were washed with brine, dried over Na$_2$SO$_4$ and concentrated under reduced pressure. The resulting brown residue was purified by flash chromatography over silica gel to give the desired product.

4-Octyl-3-(trifluoromethyl) benzonitrile. Synthesized by general procedure H. 47% yield, yellow oil; $^1$H NMR (400 MHz, Chloroform-d) δ 7.89 (d, J=1.2 Hz, 1H), 7.74 (dd, J=8.0, 1.6 Hz, 1H), 7.47 (d, J=8.0 Hz, 1H), 2.82 (t, J=7.6 Hz, 2H), 1.62 (p, J=8.0 Hz, 2H), 1.39 (p, J=6.8 Hz, 2H), 1.35-1.22 (m, 8H), 0.88 (t, J=7.1 Hz, 3H); $^{13}$C NMR (101 MHz, Chloroform-d) δ 147.7 (q, $^4$J$_{CF}$=1.5 Hz), 135.0, 132.1, 129.9 (q, $^3$J$_{CF}$=5.9 Hz), 129.8 (q, $^2$J$_{CF}$=31.2 Hz), 123.5 (q, $^1$J$_{CF}$=276.5 Hz), 117.9, 110.3, 33.0 (q, $^4$J$_{CF}$=1.8 Hz), 31.9, 31.5, 31.5, 29.7, 29.4, 29.3, 22.8, 14.2; $^{19}$F NMR (376 MHz, Chloroform-d) δ −63.5 (s, 3F).

(Z)-Hydroxy-4-octyl-3-(trifluoromethyl) benzimidamide

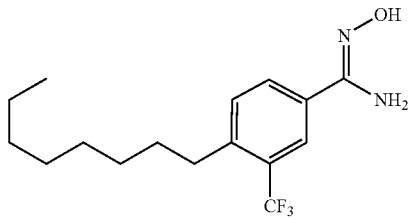 [SMILES: CCCCCCCCc1ccc(/C(N)=N/O)cc1C(F)(F)F]

Synthesized by general procedure B. 84% yield, white solid; $^1$H NMR (400 MHz, Methanol-d$_4$) δ 7.92 (d, J=1.8 Hz, 1H), 7.78 (dd, J=8.1, 1.5 Hz, 1H), 7.44 (d, J=8.1 Hz, 1H), 2.78 (t, J=7.9 Hz, 2H), 1.61 (p, J=8.2 Hz, 2H), 1.45-1.24 (m, 10H), 0.89 (t, J=7.1 Hz, 3H); $^{13}$C NMR (101 MHz, Methanol-d$_4$) δ 154.1, 147.7 (q, $^4$J$_{CF}$=1.4 Hz), 132.5, 132.3, 130.6, 130.0, 129.3 (q, $^2$J$_{CF}$=29.7 Hz), 128.5 (q, $^1$J$_{CF}$=274.5 Hz), 124.7 (q, $^3$J$_{CF}$=5.9 Hz), 33.5, 33.0, 32.9, 30.8, 30.5, 30.3, 23.7, 14.4; $^{19}$F NMR (376 MHz, Methanol-d$_4$) δ −60.5 (s, 3F); HRMS (ESI+): Calcd for C$_{16}$H$_{24}$F$_3$N$_{20}$ [M+H]: 317.1841, Found: 317.1836.

187

(S)-Tert-butyl 2-(3-(4-octyl-3-(trifluoromethyl)phenyl)-1,2,4-oxadiazol-5-yl)pyrrolidine-1-carboxylate

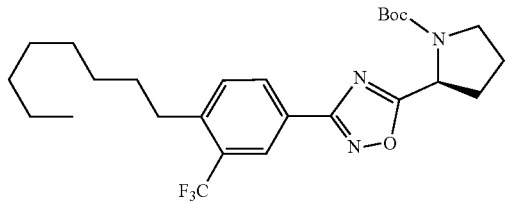 [SMILES: CCCCCCCCc1ccc(C2=NOCC([C@@H]3CCCN3C(=O)OC(C)(C)C)=N2)cc1C(F)(F)F]

Synthesized by general procedure C. 65% yield, yellow oil; $^1$H NMR (400 MHz, Chloroform-d) δ 8.31 (s, 1H), 8.14 (d, J=7.8 Hz, 1H), 7.44 (t, J=9.3 Hz, 1H), 5.27-5.00 (m, 1H), 3.78-3.63 (m, 1H), 3.60-3.47 (m, 1H), 2.81 (t, J=8.2 Hz, 2H), 2.46-2.32 (m, 1H), 2.22-2.08 (m, 2H), 2.08-1.94 (m, 1H), 1.63 (p, J=7.3 Hz, 2H), 1.46 (s, 3H), 1.43-1.23 (m, 18H), 0.87 (t, J=6.8 Hz, 3H); $^{13}$C NMR (101 MHz, Chloroform-d) δ 181.1, 167.6, 153.6, 145.3, 131.8, 130.4, 129.3 (q, $^2J_{CF}$=30.7 Hz), 127.0 (q, $^1J_{CF}$=274.8 Hz), 125.2 (q, $^3J_{CF}$=5.8 Hz), 124.9, 124.6, 122.9, 110.2, 80.6, 53.9, 46.5, 32.9, 32.5, 32.0, 31.7, 31.6, 29.8, 29.5, 29.3, 28.5, 28.3, 24.5, 23.8, 22.8, 14.2; $^{19}$F NMR (376 MHz, Chloroform-d) δ −63.0 (d, J=11.9 Hz, 3F); HRMS (ESI+): Calcd for C$_{26}$H$_{36}$F$_3$N$_3$O$_3$Na [M+Na]: 518.2606, Found: 518.2594.

(S)-2-(3-(4-Octyl-3-(trifluoromethyl)phenyl)-1,2,4-oxadiazol-5-yl)pyrrolidin-1-ium 2,2,2-trifluoroacetate

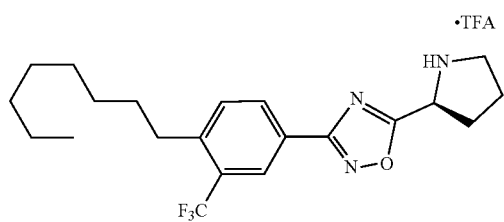 [SMILES: CCCCCCCCc1ccc(C2=NOCC([C@@H]3CCCN3)=N2)cc1C(F)(F)F]

Synthesized by general procedure D. 100% conversion, yellow oil; $^1$H NMR (400 MHz, Chloroform-d) δ 8.24 (s, 1H), 8.07 (d, J=8.1 Hz, 1H), 7.44 (d, J=8.1 Hz, 1H), 5.19 (t, J=7.8 Hz, 1H), 3.76-3.56 (m, 2H), 2.81 (t, J=7.4 Hz, 1H), 2.73-2.64 (m, 1H), 2.51-2.43 (m, 1H), 2.35-2.22 (m, 2H), 1.63 (p, J=7.8 Hz, 2H), 1.46-1.20 (m, 10H), 0.88 (t, J=6.8 Hz, 3H); $^{13}$C NMR (101 MHz, Chloroform-d) δ 174.6, 167.7, 146.2, 131.9, 130.5, 129.4 (q, $^2J_{CF}$=30.7 Hz), 125.3 (q, $^3J_{CF}$=5.7 Hz), 124.2 (q, $^1J_{CF}$=275.1 Hz), 123.3, 77.4, 54.3, 46.5, 32.9, 32.0, 31.6, 30.1, 29.8, 29.5, 29.3, 24.0, 22.8, 14.2; $^{19}$F NMR (376 MHz, Chloroform-d) δ −60.8 (s, 3F); HRMS (ESI+): Calcd for C$_{21}$H$_{29}$F$_3$N$_3$O+[M+]: 396.2262, Found: 396.2271.

188

(S)-Tert-butyl (((tert-butoxycarbonyl)amino)(2-(3-(4-octyl-3-(trifluoromethyl)phenyl)-1,2,4-oxadiazol-5-yl)pyrrolidin-1-yl)methylene)carbamate

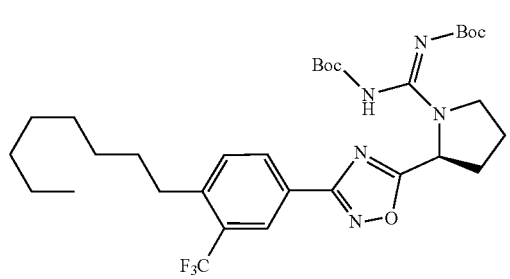 [SMILES: CCCCCCCCc1ccc(C2=NOCC([C@@H]3CCCN3/C(=N\C(=O)OC(C)(C)C)NC(=O)OC(C)(C)C)=N2)cc1C(F)(F)F]

Synthesized by general procedure E. 56% yield, colorless oil; $^1$H NMR (400 MHz, Chloroform-d) δ 10.11 (s, 1H), 8.31 (d, J=1.6 Hz, 1H), 8.14 (dd, J=8.0, 1.6 Hz, 1H), 7.43 (d, J=8.1 Hz, 1H), 5.61 (dd, J=7.8, 4.5 Hz, 1H), 3.94-3.87 (m, 1H), 3.84-3.75 (m, 1H), 2.81 (t, J=7.1 Hz, 2H), 2.50-2.40 (m, 1H), 2.27-2.13 (m, 2H), 2.12-1.98 (m, 1H), 1.63 (p, J=8.8 Hz, 2H), 1.51-1.19 (m, 28H), 0.88 (t, J=7.0 Hz, 3H); $^{13}$C NMR (101 MHz, Chloroform-d) δ 179.5, 167.6, 162.0, 159.4, 153.8, 150.5, 145.3, 131.7, 130.5, 129.2 (q, $^2J_{CF}$=30.5 Hz), 125.4 (q, $^3J_{CF}$=5.8 Hz), 124.7, 124.3 (q, $^1J_{CF}$=275.3 Hz), 82.4, 79.7, 55.4, 49.6, 32.9, 32.0, 31.7, 29.8, 29.5, 29.3, 28.2, 24.1, 22.8, 14.2; $^{19}$F NMR (376 MHz, Chloroform-d) δ −62.9 (s, 3F); HRMS (ESI+): Calcd for C$_{32}$H$_{47}$F$_3$N$_5$O$_5$ [M+H]: 638.3529, Found: 638.3507.

Example 39: (S)-Amino(2-(3-(4-octyl-3-(trifluoromethyl)phenyl)-1,2,4-oxadiazol-5-yl)pyrrolidin-1-yl)methaniminium chloride (Compound 5A)

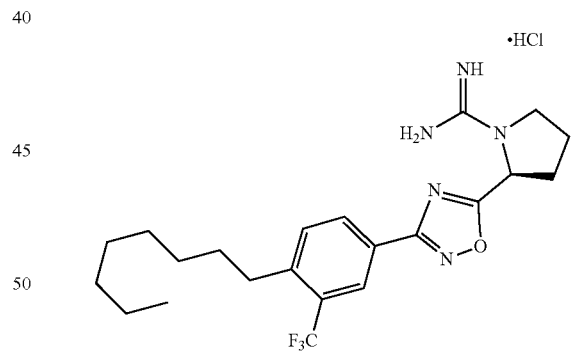

Synthesized by general procedure F. 89% yield, white solid; $^1$H NMR (400 MHz, Methanol-d$_4$) δ 8.30 (s, 1H), 8.23 (d, J=7.9 Hz, 1H), 7.62 (d, J=8.0 Hz, 1H), 5.60 (d, J=7.6 Hz, 1H), 3.86 (t, J=8.5 Hz, 1H), 3.71 (q, J=9.2 Hz, 1H), 2.86 (t, J=8.8 Hz, 2H), 2.70-2.61 (m, 1H), 2.56-2.49 (m, 1H), 2.39-2.24 (m, 1H), 2.22-2.07 (m, 1H), 1.68 (p, J=7.6 Hz, 2H), 1.51-1.25 (m, 10H), 0.93 (t, J=6.5 Hz, 3H); $^{13}$C NMR (101 MHz, Methanol-d$_4$) δ 179.4, 168.5, 157.1, 146.6, 133.3, 131.7, 129.9 (q, $^2J_{CF}$=30.3 Hz), 125.7, 125.7 (q, $^3J_{CF}$=5.9 Hz), 125.6 (q, $^1J_{CF}$=274.7 Hz), 56.4, 49.1, 33.7, 32.9, 32.7, 30.7, 30.4, 30.3, 24.3, 23.6, 14.4; $^{19}$F NMR (376 MHz, Methanol-d$_4$) δ −60.6 (s, 3F); HRMS (ESI+): Calcd for C$_{22}$H$_{31}$F$_3$N$_5$O+[M+]: 438.2481, Found: 438.2484.

3-Fluoro-4-(octyloxy)benzonitrile

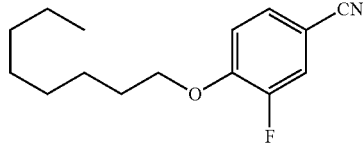 [SMILES: CCCCCCCCOc1ccc(C#N)cc1F]

Synthesized by general procedure G. 99% yield, yellow oil; $^1$H NMR (400 MHz, Chloroform-d) δ 7.39-7.32 (m, 1H), 7.31-7.26 (m, 1H), 6.97 (t, J=8.4 Hz, 1H), 4.04 (t, J=6.6 Hz, 2H), 1.80 (p, J=6.6 Hz, 2H), 1.43 (p, J=7.0 Hz, 2H), 1.37-1.17 (m, 8H), 0.84 (t, J=6.6 Hz, 3H); $^{13}$C NMR (101 MHz, Chloroform-d) δ 151.8 (d, $^1J_{CF}$=251.1 Hz), 151.4 (d, $^2J_{CF}$=10.3 Hz), 129.6 (d, $^3J_{CF}$=3.8 Hz), 119.4 (d, $^2J_{CF}$=21.5 Hz), 118.0 (d, $^3J_{CF}$=2.4 Hz), 114.4 (d, $^3J_{CF}$=2.6 Hz), 103.5 (d, $^2J_{CF}$=8.3 Hz), 69.5, 31.7, 29.2, 29.1, 28.8, 25.8, 22.6, 14.0; $^{19}$F NMR (376 MHz, Chloroform-d) δ -134.5-134.6 (m, 1F).

(Z)-3-Fluoro-N'-hydroxy-4-(octyloxy)benzimidamide

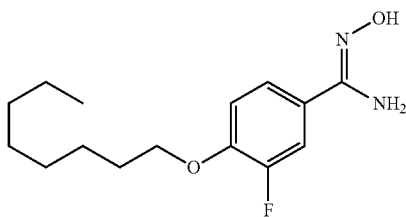 [SMILES: CCCCCCCCOc1ccc(/C(N)=N/O)cc1F]

Synthesized by general procedure B. 44% yield, white solid; $^1$H NMR (400 MHz, Methanol-d$_4$) δ 7.39-7.36 (m, 1H), 7.35 (t, J=2.5 Hz, 1H), 7.03 (t, J=8.7 Hz, 1H), 4.02 (t, J=6.4 Hz, 2H), 1.76 (p, J=7.6 Hz, 2H), 1.45 (p, J=6.4 Hz, 2H), 1.37-1.22 (m, 8H), 0.88 (t, J=7.2 Hz, 3H); $^{13}$C NMR (101 MHz, Methanol-d$_4$) δ 154.2 (d, $^3J_{CF}$=2.2 Hz), 153.4 (d, $^1J_{CF}$=245.7 Hz), 149.7 (d, $^2J_{CF}$=10.9 Hz), 126.8 (d, $^3J_{CF}$=6.8 Hz), 123.4 (d, $^3J_{CF}$=3.6 Hz), 115.3 (d, $^3J_{CF}$=2.2 Hz), 114.8 (d, $^2J_{CF}$=20.6 Hz), 70.3, 33.0, 30.4, 30.4, 30.2, 27.0, 23.7, 14.5; $^{19}$F NMR (376 MHz, Chloroform-d) δ -135.8-135.9 (m, 1F); HRMS (ESI+): Calcd for C$_{15}$H$_{24}$FN$_2$O$_2$[M+H]: 283.1822, Found: 283.1825.

(S)-Tert-butyl 2-(3-(3-fluoro-4-(octyloxy)phenyl)-1,2,4-oxadiazol-5-yl)pyrrolidine-1-carboxylate

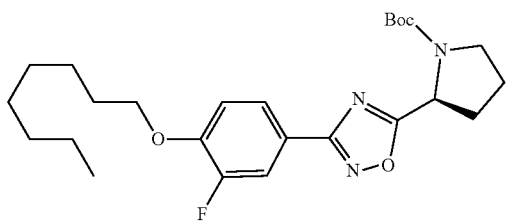 [SMILES: CCCCCCCCOc1ccc(C2=NOCC([C@@H]3CCCN3C(=O)OC(C)(C)C)=N2)cc1F]

Synthesized by general procedure C. 38% yield, yellow oil; $^1$H NMR (400 MHz, Chloroform-d) δ 7.81-7.81 (m, 2H), 7.01 (t, J=8.5 Hz, 1H), 5.27-4.95 (m, 1H), 4.07 (t, J=6.6 Hz, 2H), 3.74-3.63 (m, 1H), 3.59-3.43 (m, 1H), 2.47-2.28 (m, 1H), 2.21-2.06 (m, 2H), 2.05-1.95 (m, 1H), 1.83 (p, J=8.0 Hz, 2H), 1.50-1.41 (m, 5H), 1.40-1.21 (m, 14H), 0.87 (t, J=7.0 Hz, 3H); $^{13}$C NMR (101 MHz, Chloroform-d) δ 180.7, 167.5 (d, $^3J_{CF}$=2.6 Hz), 154.4, 152.5 (d, $^1J_{CF}$=247.9 Hz), 153.6, 149.9 (d, $^2J_{CF}$=10.5 Hz), 124.0 (d, $^3J_{CF}$=3.5 Hz), 119.3 (d, $^2J_{CF}$=7.7 Hz), 115.3 (d, $^2J_{CF}$=20.7 Hz), 114.4, 80.6, 69.5, 53.9, 46.4, 32.5, 31.9, 31.6, 29.8, 29.4, 29.3, 29.2, 28.5, 28.2, 26.0, 24.5, 23.8, 22.8, 14.2; $^{19}$F NMR (376 MHz, Chloroform-d) δ -136.7 (dt, J=11.8, 9.7 Hz, 1F); HRMS (ESI+): Calcd for C$_{25}$H$_{36}$FN$_3$O$_4$Na [M+Na]: 484.2588, Found: 484.2622.

(S)-2-(3-(3-Fluoro-4-(octyloxy)phenyl)-1,2,4-oxadiazol-5-yl)pyrrolidin-1-ium 2,2,2-trifluoroacetate

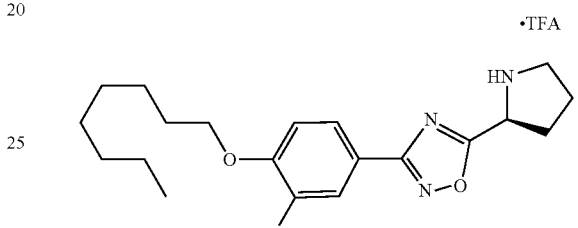

Synthesized by general procedure D. 100% conversion, white solid; $^1$H NMR (400 MHz, Methanol-d$_4$) δ 7.82 (ddd, J=8.6, 2.0, 1.3 Hz, 1H), 7.74 (dd, J=11.8, 2.1 Hz, 1H), 7.19 (t, J=8.5 Hz, 1H), 5.15 (t, J=7.7 Hz, 1H), 4.09 (t, J=6.4 Hz, 2H), 3.65-3.39 (m, 2H), 2.68-2.58 (m, 1H), 2.43-2.34 (m, 1H), 2.30-2.12 (m, 2H), 1.79 (p, J=6.4 Hz, 2H), 1.47 (p, J=7.9 Hz, 2H), 1.41-1.09 (m, 8H), 0.87 (t, J=6.8 Hz, 3H); $^{13}$C NMR (126 MHz, Methanol-d$_4$) δ 176.0, 168.8, 153.7 (d, $^1J_{CF}$=246.7 Hz), 151.6 (d, $^2J_{CF}$=10.6 Hz), 125.4 (d, $^3J_{CF}$=3.6 Hz), 119.6 (d, $^2J_{CF}$=7.4 Hz), 115.9 (d, $^2J_{CF}$=20.9 Hz), 115.8, 70.4, 55.5, 47.3, 32.9, 30.4, 30.3, 30.2, 30.1, 27.0, 24.5, 23.7, 14.4; $^{19}$F NMR (376 MHz, Methanol-d$_4$) δ -135.1 (dd, J=11.4, 8.4 Hz, 1F); HRMS (ESI+): Calcd for C$_{20}$H$_{29}$FN$_3$O$_2$+ [M+]: 362.2244, Found: 362.2254.

(S)-Tert-butyl (((tert-butoxycarbonyl)amino)(2-(3-(3-fluoro-4-(octyloxy)phenyl)-1,2,4-oxadiazol-5-yl)pyrrolidin-1-yl)methylene)carbamate

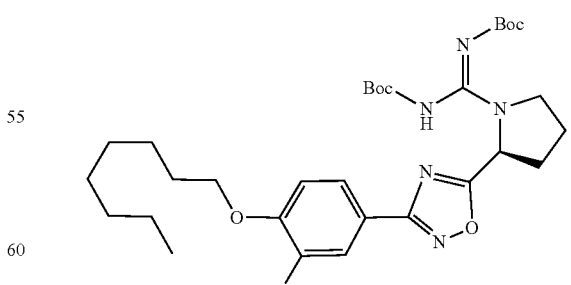

Synthesized by general procedure E. 44% yield, colorless oil; $^1$H NMR (400 MHz, Chloroform-d) δ 10.10 (s, 1H), 7.87-7.65 (m, 2H), 7.01 (d, J=8.5 Hz, 1H), 5.58 (dd, J=7.8, 4.5 Hz, 1H), 4.08 (t, J=6.6 Hz, 2H), 3.92-3.84 (m, 1H), 3.80

(s, 1H), 2.48-2.38 (m, 1H), 2.27-2.13 (m, 2H), 2.09-1.98 (m, 1H), 1.84 (p, J=7.3 Hz, 2H), 1.55-1.22 (m, 28H), 0.88 (t, J=6.7 Hz, 3H); $^{13}$C NMR (126 MHz, Chloroform-d) δ 179.1, 167.5, 162.0, 152.5 (d, $^1J_{CF}$=247.6 Hz), 150.5, 149.9 (d, $^2J_{CF}$=10.5 Hz), 124.1 (d, $^3J_{CF}$=3.0 Hz), 119.4, 115.5 (d, $^2J_{CF}$=20.8 Hz), 114.4, 82.4, 79.7, 69.5, 55.4, 49.8, 31.9, 31.4, 29.8, 29.4, 29.3, 29.2, 28.2, 26.0, 24.1, 22.8, 14.2; $^{19}$F NMR (376 MHz, Chloroform-d) δ −136.7 (s, 1F); HRMS (ESI+): Calcd for $C_{31}H_{47}FN_5O_6$ [M+H]: 604.3512, Found: 604.3534.

Example 40: (S)-Amino(2-(3-(3-fluoro-4-(octyloxy)phenyl)-1,2,4-oxadiazol-5-yl)pyrrolidin-1-yl)methaniminium chloride (Compound 11A)

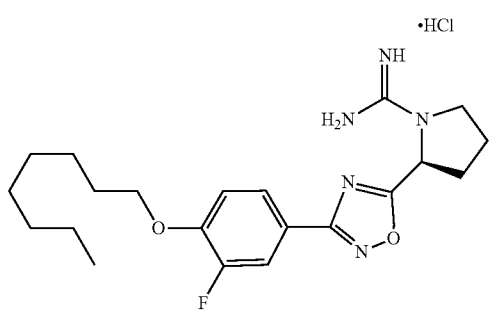 [SMILES: Cl ; CCCCCCCCOc1ccc(C2=NOCC([C@@H]3CCCN3C(=N)N)=N2)cc1F]

Synthesized by general procedure F. 100% conversion, white solid; $^1$H NMR (400 MHz, Methanol-d$_4$) δ 7.81 (d, J=8.2 Hz, 1H), 7.73 (dd, J=11.8, 1.7 Hz, 1H), 7.21 (t, J=8.5 Hz, 1H), 5.43 (d, J=6.4 Hz, 1H), 4.12 (t, J=6.3 Hz, 2H), 3.77 (t, J=8.4 Hz, 1H), 3.61 (q, J=7.4 Hz, 1H), 2.56 (s, 1H), 2.50-2.42 (m, 1H), 2.21 (s, 1H), 2.08 (s, 1H), 1.82 (p, J=6.5 Hz, 2H), 1.50 (p, J=7.0 Hz, 2H), 1.43-1.25 (m, 8H), 0.90 (t, J=7.2 Hz, 3H); $^{13}$C NMR (101 MHz, Methanol-d$_4$) δ 179.0, 168.7, 157.0, 153.6 (d, $^1J_{CF}$=247.1 Hz), 151.4 (d, $^2J_{CF}$=10.6 Hz), 125.3 (d, $^3J_{CF}$=3.6 Hz), 119.9 (d, $^2J_{CF}$=7.4 Hz), 115.8 (d, $^3J_{CF}$=2.1 Hz), 115.7 (d, $^2J_{CF}$=20.9 Hz), 70.4, 56.5, 32.9, 32.7, 30.4, 30.4, 30.2, 27.0, 24.3, 23.7, 14.4; $^{19}$F NMR (376 MHz, Methanol-d$_4$) δ −135.1 (dd, J=11.7, 8.4 Hz, 1F); HRMS (ESI+): Calcd for $C_{21}H_{31}FN_5O_2$+[M+]: 404.2462, Found: 404.2449.

Scheme 9

A)

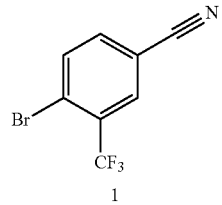

1

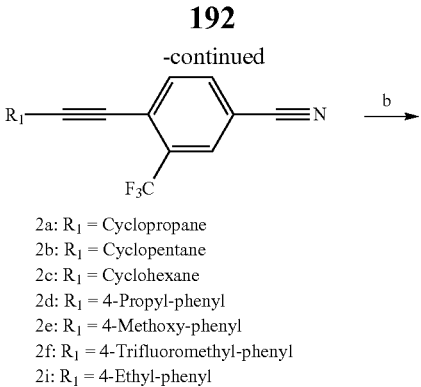

2a: R$_1$ = Cyclopropane
2b: R$_1$ = Cyclopentane
2c: R$_1$ = Cyclohexane
2d: R$_1$ = 4-Propyl-phenyl
2e: R$_1$ = 4-Methoxy-phenyl
2f: R$_1$ = 4-Trifluoromethyl-phenyl
2i: R$_1$ = 4-Ethyl-phenyl

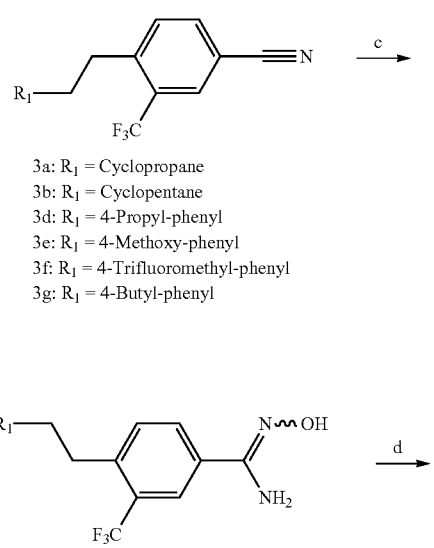

3a: R$_1$ = Cyclopropane
3b: R$_1$ = Cyclopentane
3d: R$_1$ = 4-Propyl-phenyl
3e: R$_1$ = 4-Methoxy-phenyl
3f: R$_1$ = 4-Trifluoromethyl-phenyl
3g: R$_1$ = 4-Butyl-phenyl

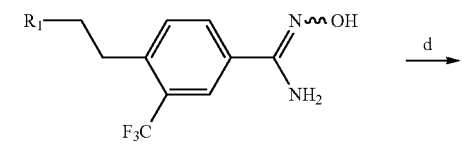

4a: R$_1$ = Cyclopropane
4b: R$_1$ = Cyclopentane
4c: R$_1$ = Cyclohexane
4d: R$_1$ = 4-Propyl-phenyl
4e: R$_1$ = 4-Methoxy-phenyl
4f: R$_1$ = 4-Trifluoromethyl-phenyl
4g: R$_1$ = 4-Butyl-phenyl

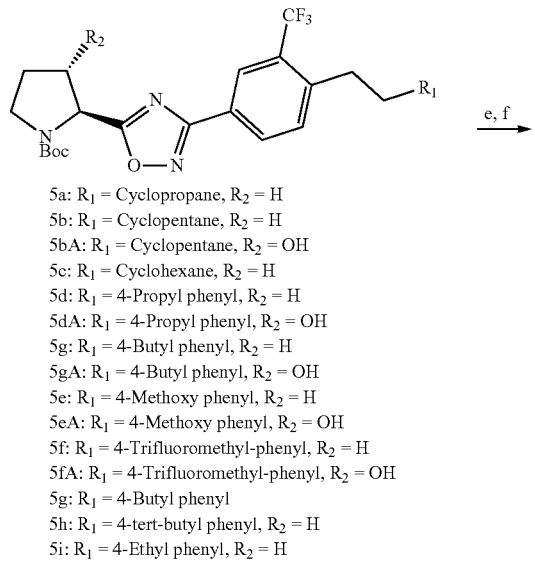

5a: R$_1$ = Cyclopropane, R$_2$ = H
5b: R$_1$ = Cyclopentane, R$_2$ = H
5bA: R$_1$ = Cyclopentane, R$_2$ = OH
5c: R$_1$ = Cyclohexane, R$_2$ = H
5d: R$_1$ = 4-Propyl phenyl, R$_2$ = H
5dA: R$_1$ = 4-Propyl phenyl, R$_2$ = OH
5g: R$_1$ = 4-Butyl phenyl, R$_2$ = H
5gA: R$_1$ = 4-Butyl phenyl, R$_2$ = OH
5e: R$_1$ = 4-Methoxy phenyl, R$_2$ = H
5eA: R$_1$ = 4-Methoxy phenyl, R$_2$ = OH
5f: R$_1$ = 4-Trifluoromethyl-phenyl, R$_2$ = H
5fA: R$_1$ = 4-Trifluoromethyl-phenyl, R$_2$ = OH
5g: R$_1$ = 4-Butyl phenyl
5h: R$_1$ = 4-tert-butyl phenyl, R$_2$ = H
5i: R$_1$ = 4-Ethyl phenyl, R$_2$ = H -continued

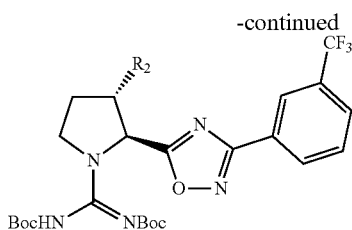

6a: R₁ = Cyclopropane, R₂ = H
6b: R₁ = Cyclopentane, R₂ = H
6bA: R₁ = Cyclopentane, R₂ = OH
6c: R₁ = Cyclohexane, R₂ = H
6d: R₁ = 4-Propyl phenyl, R₂ = H
6dA: R₁ = 4-Propyl phenyl, R₂ = OH
6g: R₁ = 4-Butyl phenyl, R₂ = H
6gA: R₁ = 4-Butyl phenyl, R₂ = OH
6e: R₁ = 4-Methoxy phenyl, R₂ = H
6eA: R₁ = 4-Methoxy phenyl, R₂ = OH
6f: R₁ = 4-Trifluoromethyl-phenyl, R₂ = H
6fA: R₁ = 4-Trifluoromethyl-phenyl, R₂ = OH
6g: R₁ = 4-Butyl phenyl
6h: R₁ = 4-tert-butyl phenyl, R₂ = H
6i: R₁ = 4-Ethyl phenyl, R₂ = H

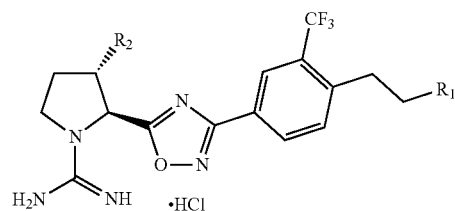

7a: R₁ = Cyclopropane, R₂ = H
7b: R₁ = Cyclopentane, R₂ = H
7bA: R₁ = Cyclopentane, R₂ = OH
7c: R₁ = Cyclohexane, R₂ = H
7d: R₁ = 4-Propyl phenyl, R₂ = H
7dA: R₁ = 4-Propyl phenyl, R₂ = OH
7g: R₁ = 4-Butyl phenyl, R₂ = H
7gA: R₁ = 4-Butyl phenyl, R₂ = OH
7e: R₁ = 4-Methoxy phenyl, R₂ = H
7eA: R₁ = 4-Methoxy phenyl, R₂ = OH
7f: R₁ = 4-Trifluoromethyl-phenyl, R₂ = H
7fA: R₁ = 4-Trifluoromethyl-phenyl, R₂ = OH
7g: R₁ = 4-Butyl phenyl
7h: R₁ = 4-tert-butyl phenyl, R₂ = H
7i: R₁ = 4-Ethyl phenyl, R₂ = H

B)

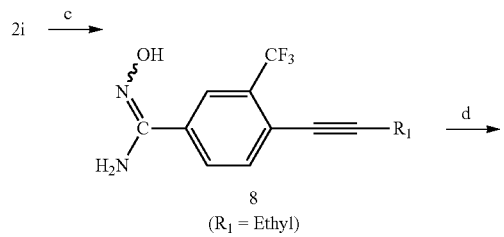

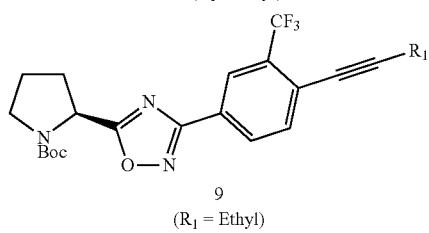

7i (HCl Salt)

C)

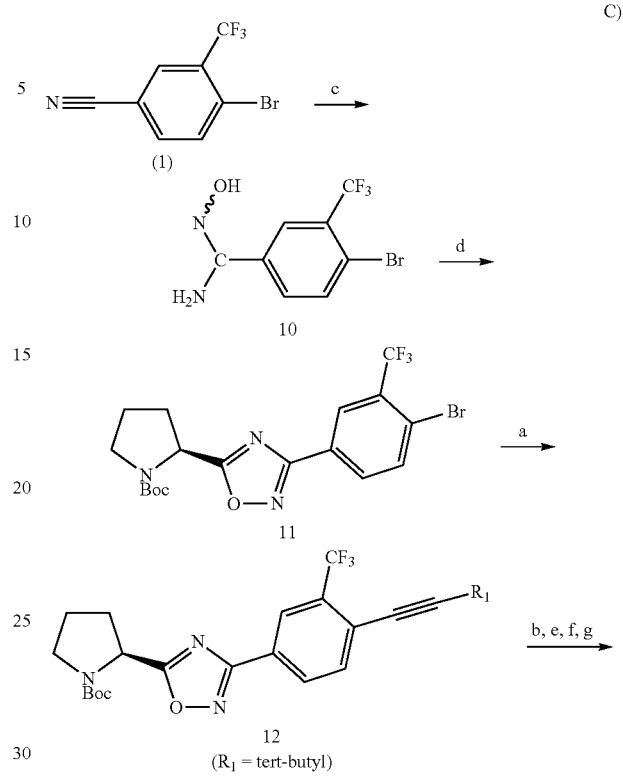

7h (HCl Salt)

Scheme 1: a) R—Br (1.2 equiv.), K₂CO₃ (4 equiv.), CH₃CN, 80° C., 4-12 h, (84-98%); b) [5% Pd-CaCO₃ + Pb(OCOCH₃)₂ + Quinoline] 10 mol % (60-80%); c) NH₂OH•HCl, (3 equiv.), TEA (3 equiv.), EtOH, 80° C., 6 h, (71-90%); d) Boc-L-proline (1.4 equiv.), DIEA (1.4 equiv.), HCTU (1.8 equiv.), DMF, 110° C., 18 h, (50-70%); e) HCl/MeOH, (80-100%); f) DIEA (3 equiv.), N,N-DiBoc-1H-pyrazole-1-carboxamidine (1.05 equiv.), CH₃CN, Microwave irradiation, 55° C., 2-4 h,, (59-70%); g) 4M HCl Dioxane, rt,, 3 h, (67-90%).

Scheme 10

A)

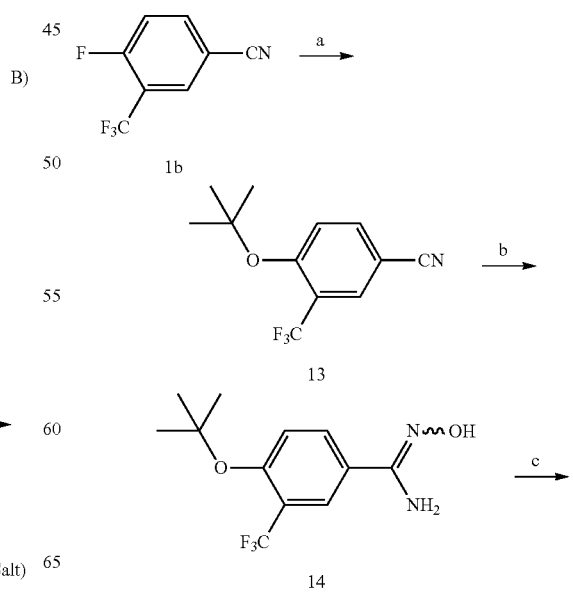

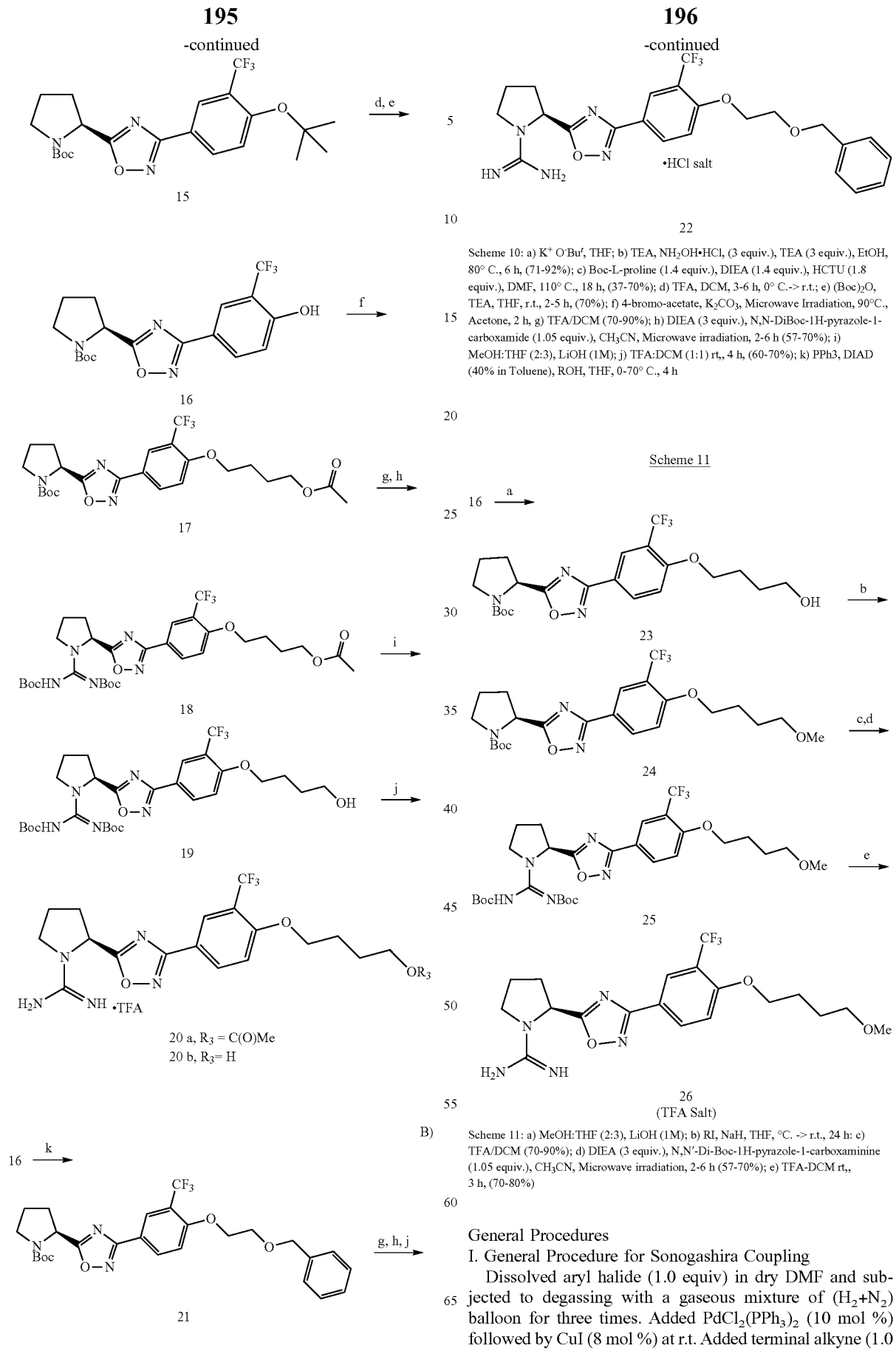

equiv. followed by TEA. The reaction mixture stirred at 50° C. or 90° C. After cooling to room temperature, the resulting solution was subjected to rotary evaporation and partitioned between EtOAc and D.I. water. Aqueous layer was extracted with EtOAc 20 mL (3×). Combined organic layers were given water, brine washes and dried over anhydrous $Na_2SO_4$. After evaporation of the solvent, column chromatography on silica gel afforded the desired product.

II. General Procedure for Chemo Selective Reduction of Alkyne

Dissolved the internal alkyne intermediate in EtOAc (30 mL) at r.t. Added Lindlar's catalyst [(5% Pd-$CaCO_3$+Pb $(OCOCH_3)_2$+Quinoline), 10 mol %]. Subjected to hydrogenation under $H_2$ atmosphere for 30 min to 20 h. Filtered the reaction over Celite bed. Concentrated the filterate and subjected to column chromatography on silica gel afforded the desired saturated product.

III. General Procedure for Synthesis of Amidoxime

Nitrile intermediate (1 equiv.), hydroxylamine hydrochloride (3 equiv.), TEA (3 equiv.) were added to a round bottom flask containing ethanol. The reaction mixture was heated to 80° C. for 6-12 hours and monitored via TLC. Once the starting material was consumed, the solution was cooled to room temperature, concentrated under reduced pressure, loaded onto celite, and purified on a silica column with hexane and ethyl acetate.

IV. General Procedure for Synthesis of 1,2,4-Oxadiazole

Amidoxime intermediate (1 equiv.), Boc-L-proline (1.4 equiv.) or Boc-trans-3-hydroxy-L-proline (1.4 equiv.), and DIEA (1.4 equiv.) were added to a round bottom flask containing DMF. HCTU (1.8 equiv.) was added to the reaction mixture and maintained at 110° C. for 12-16 hours. Cooled the reaction mixture to r.t. and partitioned between ethyl acetate and saturated LiBr solution. The combined organic layers were washed with sat. $NaHCO_3$, brine and dried over sodium sulfate. Combined organic layers were subjected to rotary evaporation and column chromatography to afford the desired Oxadiazole intermediate.

V. General Procedure for Ester Hydrolysis

Dissolved Pyrrolidine acetate in a solution of THF:MeOH (2:3) at r.t. Added 1M LiOH and continued stirring at r.t. for 30 min. Rotary evaporated the reaction mixture and partitioned between Dichloromethane (20 mL) and water (5 mL). Extracted the aqueous layer using Dichloromethane (10 mL, 2×). Combined organic layers were given brine wash and dried over anhydrous $Na_2SO_4$. Rotary evaporated the organic layer and subjected to column chromatography to afford the desired alcohol.

VI. General Procedure for O-Alkylation (1 equiv.), potassium carbonate (2 equiv.), KI (1.5 equiv.) and alkyl halide (1.2 equiv.) were added to a 8 mL microwave reactor containing acetone. The reaction mixture was heated to 80° C. for 4-12 hours until TLC indicated the starting material had been fully consumed. The reaction mixture was extracted with ethyl acetate and D.I. water. The combined organic layers were washed with brine and dried over sodium sulfate. After filtration and concentration via reduced pressure, the resulting brown oil was purified on a silica column with hexane and ethyl acetate.

VII. General Procedure for Boc-Deprotection

N-Boc Pyrrolidine or N', N"-Di-Boc-guanidine 6a-e was dissolved in methanol. HCl gas was bubbled into the solution for 1 minute. The solution was stirred until TLC indicated that all of the Boc-protected amine had been consumed. The solvent was removed under reduced pressure. The resulting white to light yellow solid was washed with diethyl ether to yield pure product as HCl salt.

VIII. General Procedure for Guanylation of Secondary Amines

Pyrrolidine Hydrogen chloride salt (1 equiv.) was added to a 8 mL microwave reaction flash with acetonitrile and DIEA (3 equiv.). The solution was allowed to stir for 10 minutes before the addition of (Z)-Tert-butyl (((tert-butoxycarbonyl)imino)(1H-pyrazol-1-yl)methyl)carbamate (1.05 equiv.). The solution was subjected to microwave irradiation at 55° C. for 2-6 h until TLC indicated that the starting material had been consumed. The reaction mixture is subjected to rotary evaporation and performed column chromatography to afford the N',N'-diboc guanidine intermediate.

IX. General Procedure for O-Alkylation

To a pre-cooled solution of N-Boc Pyrrolidine alcohol in dry THF added (65%) NaH. Stirred for 10 min. and added excess alkyl halide. Maintained at 0° C. for 1 h and allowed to attain r.t. Stirred at r.t. for 18-24 h. Quenched reaction mixture at 0° C. with few drops of methanol and crushed ice. Partitioned reaction mixture between ethyl acetate and water. The Organic layer is subjected to rotatory evaporation and performed column chromatography to afford O-alkylated intermediate.

X. General Procedure for Mitsunobu Reaction

To a pre-cooled solution of 23 in dry THF and $PPh_3$ added DIAD (40% in toluene) and alcohol. The reaction mixture was stirred for 1 h then refluxed for 2 h. Quenched reaction mixture with aqueous $NaHCO_3$, rotary evaporated and partitioned between dichloromethane and DI water. Combined organic layers were subjected to rotatory evaporation and performed column chromatography to afford the desired product.

4-(tert-butoxy)-3-(trifluoromethyl)benzonitrile (20)

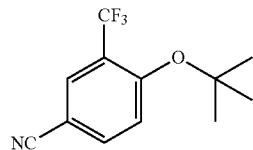 [SMILES: CC(C)(C)Oc1ccc(C#N)cc1C(F)(F)F]

$^1$H NMR (500 MHz, Chloroform-d) δ 7.87 (s, 1H), 7.73 (dd, J=8.8, 2.1 Hz, 1H), 7.27 (d, J=8.7 Hz, 1H), 1.56 (s, 9H).

(Z)-4-(tert-butoxy)-N'-hydroxy-3-(trifluoromethyl) benzimidamide (21)

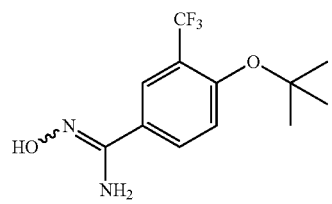 [SMILES: CC(C)(C)Oc1ccc(C(N)=NO)cc1C(F)(F)F]

$^1$H NMR (500 MHz, Chloroform-d) δ 7.85 (d, J=2.3 Hz, 1H), 7.72 (dd, J=8.7, 2.4 Hz, 1H), 7.23 (d, J=8.7 Hz, 1H), 6.72 (s, 1H), 4.84 (s, 2H), 1.52 (s, 9H).

tert-butyl (S)-2-(3-(4-(tert-butoxy)-3-(trifluoromethyl)phenyl)-1,2,4-oxadiazol-5-yl)pyrrolidine-1-carboxylate (22)

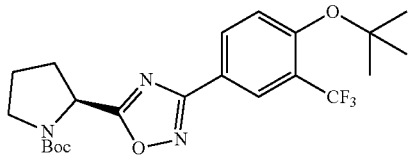 [SMILES: CC(C)(C)OC(=O)N1CCC[C@H]1c1nc(-c2ccc(OC(C)(C)C)c(C(F)(F)F)c2)no1]

¹H NMR (500 MHz, Chloroform-d) δ 8.21 (d, J=2.1 Hz, 1H), 8.05 (dd, J=8.6, 2.2 Hz, 1H), 7.20 (t, J=8.6 Hz, 1H), 5.15-5.05 (m, 0.4H), 5.04-4.95 (m, 0.6H), 3.71-3.55 (m, 1H), 3.53-3.31 (m, 1H), 2.31-2.21 (m, 1H), 2.15-2.05 (m, 2H), 1.99-1.83 (m, 1H), 1.39 (s, 3H), 1.24 (s, 6H).

tert-butyl (S)-2-(3-(4-hydroxy-3-(trifluoromethyl)phenyl)-1,2,4-oxadiazol-5-yl)pyrrolidine-1-carboxylate (23)

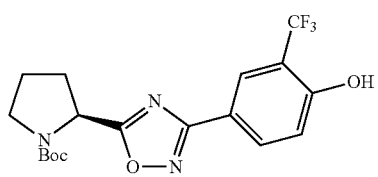 [SMILES: CC(C)(C)OC(=O)N1CCC[C@H]1c1nc(-c2ccc(O)c(C(F)(F)F)c2)no1]

¹H NMR (400 MHz, Methanol-$d_4$) δ 8.16 (d, J=2.1 Hz, 1H), 8.10-8.04 (m, 1H), 7.07 (d, J=8.7 Hz, 1H), 5.16-5.08 (m, 1H), 3.70-3.61 (m, 1H), 3.55-3.48 (m, 1H), 2.53-2.36 (m, 1H), 2.20-2.00 (m, 3H), 1.46 (s, 3H), 1.27 (s, 6H); ¹³C NMR (101 MHz, $cd_3od$) δ 181.0, 167.2, 154.0, 131.9, 125.8, 124.9, 117.2, 117.0, 80.5, 53.8, 46.1, 31.8, 31.0, 27.2, 26.9, 23.9, 23.3.

tert-butyl (S)-2-(3-(4-(4-acetoxybutoxy)-3-(trifluoromethyl)phenyl)-1,2,4-oxadiazol-5-yl)pyrrolidine-1-carboxylate (24)

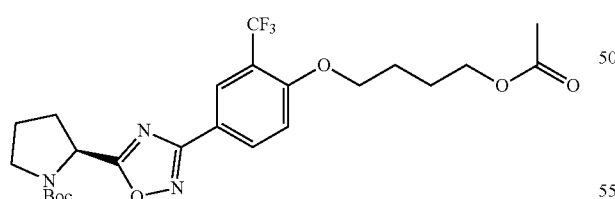

¹H NMR (400 MHz, Chloroform-d) δ 8.27 (s, 1H), 8.17 (d, J=8.7 Hz, 1H), 7.05 (d, J=8.8 Hz, 1H), 5.21-5.05 (m, 0.4H), 5.08-5.01 (m, 0.6H), 4.16-4.10 (m, 4H), 3.76-3.61 (m, 1H), 3.60-3.41 (m, 1H), 2.45-2.25 (m, 1H), 2.24-1.78 (m, 10H), 1.44 (s, 3H), 1.27 (s, 6H); ¹³C NMR (101 MHz, $cdcl_3$) δ 180.8, 180.3, 171.1, 167.2, 158.9, 153.4, 137.9, 132.4, 126.5, 124.5, 118.7, 112.8, 103.3, 80.4, 68.2, 63.8, 53.7, 46.6, 46.3, 32.3, 31.4, 28.1, 25.6, 25.0, 23.7, 20.9; Calcd for $C_{24}H_{31}F_3N_3O_6$ [M+H]⁺: 514.2172, Found: 514.2159.

(S,E)-4-(4-(5-(1-(N,N'-bis(tert-butoxycarbonyl)carbamimidoyl)pyrrolidin-2-yl)-1,2,4-oxadiazol-3-yl)-2-(trifluoromethyl)phenoxy)butyl acetate (25)

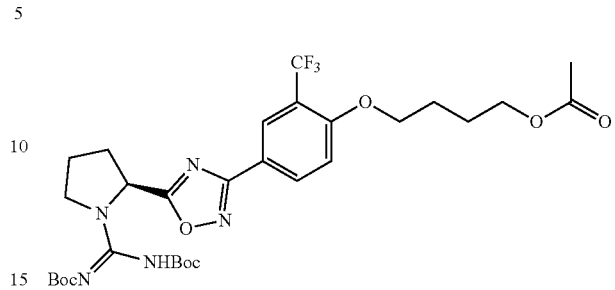

¹H NMR (400 MHz, Chloroform-d) δ 10.08 (s, 1H), 8.26 (s, 1H), 8.16 (d, J=10.8 Hz, 1H), 7.58 (s, 1H), 7.03 (d, J=8.8 Hz, 1H), 5.58 (d, J=4.5 Hz, 1H), 4.12 (t, J=6.3 Hz, 3H), 3.86 (s, 1H), 3.77 (d, J=5.9 Hz, 1H), 2.49-2.36 (m, 1H), 2.21-2.18 (m, 2H), 2.08-1.95 (s, 4H), 1.96-1.80 (m, 4H), 1.46 (s, 18H); ¹³C NMR (101 MHz, $cdcl_3$) δ 179.2, 171.1, 167.1, 158.9, 132.5, 126.8, 126.7, 124.5, 118.7, 112.7, 105.0, 68.2, 63.8, 55.2, 49.4, 29.7, 28.0, 28.0, 25.6, 25.1, 20.9; Calcd for $C_{30}H_{41}F_3N_5O_8$ [M+H]⁺: 658.2959, Found: 658.2971.

4-bromo-N'-hydroxy-3-(trifluoromethyl)benzimidamide (14)

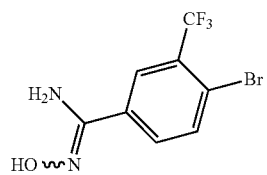 [SMILES: NC(=NO)c1ccc(Br)c(C(F)(F)F)c1]

¹H NMR (400 MHz, Methanol-$d_4$) δ 8.07-8.02 (m, 1H), 7.84-7.79 (m, 1H), 7.78-7.73 (m, 1H); Calcd for $C_8H_7F_3BrN_2O$ [M+H]⁺: 282.9688, Found: 282.9696.

tert-butyl (S)-2-(3-(4-bromo-3-(trifluoromethyl)phenyl)-1,2,4-oxadiazol-5-yl)pyrrolidine-1-carboxylate (15)

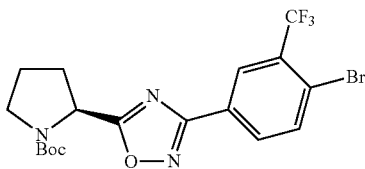 [SMILES: CC(C)(C)OC(=O)N1CCC[C@H]1c1nc(-c2ccc(Br)c(C(F)(F)F)c2)no1]

¹H NMR (400 MHz, Methanol-$d_4$) δ 8.37 (d, J=2.0 Hz, H), 8.16 (t, J=7.0 Hz, 1H), 7.99 (t, J=7.5 Hz, 1H), 5.21-5.12 (m, 1H), 3.71-3.61 (m, 1H), 3.56-3.48 (m, 1H), 2.55-2.39 (m, 1H), 2.23-1.99 (m, 3H), 1.42 (s, 4H), 1.27 (s, 5H); ¹³C NMR (101 MHz, $cdcl_3$) δ 181.5, 166.8, 154.3, 153.4, 135.7, 131.4, 127.0, 126.7, 126.3, 126.3, 126.3, 123.9, 123.2, 123.2, 122.9, 121.2, 80.6 53.8, 46.6, 46.4, 32.4, 31.5, 28.3 28.1, 24.4, 23.7.

4-(cyclopropylethynyl)-3-(trifluoromethyl)benzonitrile (2a)

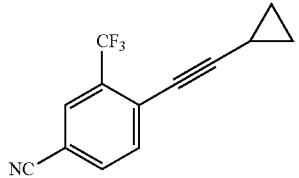 [SMILES: N#Cc1ccc(C#CC2CC2)c(C(F)(F)F)c1]

$^1$H NMR (500 MHz, Chloroform-d) δ 7.82-7.78 (m, 1H), 7.64 (dd, J=8.1, 1.7 Hz, 1H), 7.54-7.49 (m, 1H), 1.48-1.40 (m, 1H), f0.95-0.87 (m, 2H), 0.86-0.78 (m, 2H); $^{13}$C NMR (126 MHz, CDCl$_3$) δ 135.6, 135.2, 133.9, 133.8, 132.4, 132.1, 131.9, 131.6, 129.0, 128.9, 128.9, 128.9, 126.8, 126.8, 126.8, 126.8, 125.1, 122.9, 120.8, 118.6, 116.8, 110.0, 105.4, 79.5, 76.6, 70.5, 60.3, 8.6, 8.1, −0.6

4-(cyclopentylethynyl)-3-(trifluoromethyl)benzonitrile (2b)

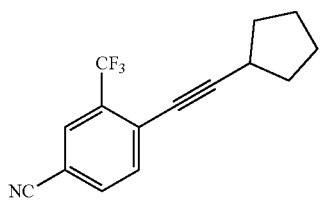 [SMILES: N#Cc1ccc(C#CC2CCCC2)c(C(F)(F)F)c1]

$^1$H NMR (400 MHz, Chloroform-d) δ 7.87-7.84 (m, 1H), 7.69 (dd, J=8.1, 1.7 Hz, 1H), 7.57 (d, J=8.1 Hz, 1H), 2.93-2.81 (m, 1H), 2.04-1.89 (m, 2H), 1.82-1.66 (m, 4H), 1.67-1.51 (m, 2H); $^{13}$C NMR (101 MHz, cdcl$_3$) δ 136.2, 134.5, 134.5, 134.4, 134.4, 133.1, 132.8, 132.4, 132.1, 129.5, 129.4, 129.4, 129.3, 127.5, 127.5, 127.5, 127.5, 126.5, 123.8, 121.1, 118.3, 117.3, 110.7, 106.8, 106.8, 106.8, 77.3, 77.2, 77.0, 76.7, 75.5, 33.5, 33.5, 33.3, 33.2, 33.2, 30.9, 29.7, 25.1, 25.0, 25.0; HRMS (ESI+): Calcd for C$_{15}$H$_{12}$F$_3$N [M+Na]: 286.2475

4-(cyclohex-1-en-1-ylethynyl)-3-(trifluoromethyl)benzonitrile (2c)

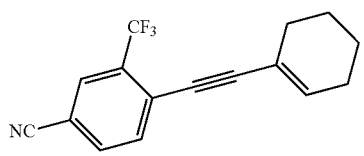 [SMILES: N#Cc1ccc(C#CC2=CCCCC2)c(C(F)(F)F)c1]

$^1$H NMR (400 MHz, Chloroform-d) δ 7.87-7.85 (m, 1H), 7.72-7.67 (m, 1H), 7.60-7.56 (m, 1H), 6.34-6.28 (m, 1H), 2.30-1.99 (m, 4H), 1.76-1.50 (m, 4H); $^{13}$C NMR (101 MHz, cdcl$_3$) δ 139.0, 138.0, 134.5, 134.1, 132.6, 132.3, 132.0, 131.7, 131.3, 129.6, 129.5, 129.5, 129.5, 129.4, 127.3, 126.5, 123.8, 122.6, 121.1, 120.5, 120.2, 119.9, 118.4, 118.4, 117.8, 117.3, 110.8, 110.3, 102.3, 102.2, 83.3, 82.7, 82.0, 28.7, 26.0, 22.0, 21.2.

4-((4-propylphenyl)ethynyl)-3-(trifluoromethyl)benzonitrile (2d)

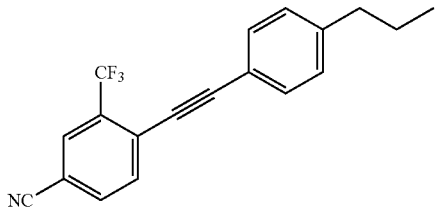 [SMILES: CCCc1ccc(C#Cc2ccc(C#N)cc2C(F)(F)F)cc1]

$^1$H NMR (500 MHz, Methanol-d$_4$) δ 8.18-8.15 (m, 1H), 8.01 (dd, J=8.1, 1.2 Hz, 1H), 7.89 (d, J=8.1 Hz, 1H), 7.51-7.46 (m, 2H), 7.31-7.26 (m, 2H), 2.69-2.64 (m, 2H), 1.71-1.61 (m, 2H), 0.98 (t, J=7.4 Hz, 3H); $^{13}$C NMR (101 MHz, cd$_3$od) δ 187.5, 145.0, 135.2, 134.3, 131.4, 128.5, 127.7, 37.6, 24.0, 12.6.

4-((4-methoxyphenyl)ethynyl)-3-(trifluoromethyl)benzonitrile (2e)

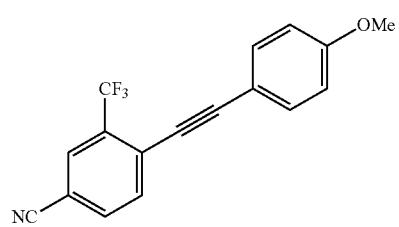 [SMILES: COc1ccc(C#Cc2ccc(C#N)cc2C(F)(F)F)cc1]

$^1$H NMR (400 MHz, Chloroform-d) δ 7.93 (dt, J=1.4, 0.7 Hz, 1H), 7.77-7.73 (m, 1H), 7.70 (dt, J=8.1, 0.7 Hz, 1H), 7.50 (d, J=2.1 Hz, 1H), 7.49 (d, J=2.1 Hz, 1H), 6.92 (d, J=2.2 Hz, 1H), 6.90 (d, J=2.1 Hz, 1H), 3.84 (s, 3H); $^{13}$C NMR (101 MHz, cdcl$_3$) δ 160.8, 134.6, 134.0, 133.6, 132.3, 129.6, 129.6, 129.5, 126.9, 123.9, 121.2, 117.4, 114.3, 113.7, 110.9, 100.6, 83.4, 55.4.

3-(trifluoromethyl)-4-((4-(trifluoromethyl)phenyl)ethynyl)benzonitrile (2f)

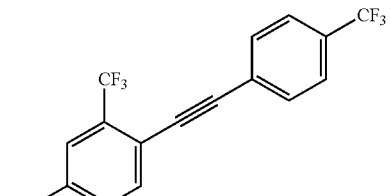

$^1$H NMR (500 MHz, Chloroform-d) δ 8.02 (dt, J=1.4, 0.7 Hz, 1H), 7.88-7.80 (m, 2H), 7.72-7.66 (m, 4H).

4-(2-cyclopropylethyl)-3-(trifluoromethyl)benzonitrile (3a)

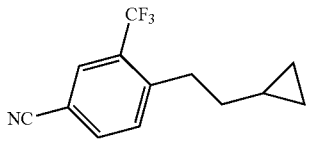 [SMILES: N#Cc1ccc(CCC2CC2)c(C(F)(F)F)c1]

¹H NMR (400 MHz, Chloroform-d) δ 7.90 (s, 1H), 7.76-7.71 (m, 1H), 7.47 (d, J=8.1 Hz, 1H), 2.99-2.92 (m, 0.6H), 2.91-2.79 (m, 1.4H), 1.69-1.57 (m, 1H), 1.57-1.49 (m, 1H), 1.43-1.32 (m, 3H), 0.95-0.87 (m, 2H), 0.50-0.45 (m, 1H), 0.10-s 0.03 (m, 1H); ¹³C NMR (101 MHz, cdcl₃) δ 191.4, 147.5, 134.8, 134.7, 132.2, 132.0, 129.9, 129.8, 129.8, 129.8, 129.8, 124.7, 122.0, 117.7, 110.2, 110.2, 58.9, 36.5, 33.1, 33.0, 32.8, 32.8, 32.8, 31.7, 31.0, 22.3, 13.9, 10.8, 4.6.

4-(2-cyclopentylethyl)-3-(trifluoromethyl)benzonitrile (3b)

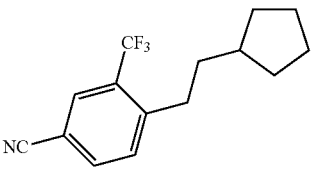 [SMILES: N#Cc1ccc(CCC2CCCC2)c(C(F)(F)F)c1]

¹H NMR (400 MHz, Chloroform-d) δ 7.90 (dt, J=1.8, 0.6 Hz, 1H), 7.77-7.70 (m, 1H), 7.47 (dq, J=8.1, 0.6 Hz, 1H), 2.88-2.78 (m, 2H), 1.91-1.76 (m, 3H), 1.69-1.50 (m, 6H), 1.20-1.08 (m, 2H); ¹³C NMR (101 MHz, cdcl₃) δ 147.7, 134.8, 134.7, 132.0, 130.1, 129.9, 129.8, 129.7, 129.5, 129.2, 124.7, 122.0, 117.7, 110.1, 40.2, 40.1, 38.4, 38.0, 36.3, 36.2, 36.1, 35.0, 32.9, 32.7, 32.6, 32.5, 32.4, 32.3, 32.2, 29.1, 25.2, 25.1.

4-(4-methoxyphenethyl)-3-(trifluoromethyl)benzonitrile (3d)

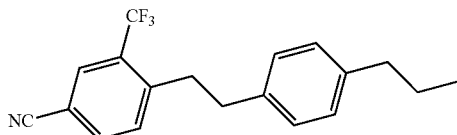

¹H NMR (400 MHz, Chloroform-d) δ 7.92 (dt, J=1.4, 0.6 Hz, 1H), 7.70 (dd, =8.0, 1.7 Hz, 1H), 7.36 (dt, J=8.0, 0.7 Hz, 1H), 7.14-7.04 (m, 4H), 3.14-3.05 (m, 2H), 2.92-2.84 (m, 2H), 2.60-2.48 (m, 2H), 1.69-1.52 (m, 3H), 0.93 (t, J=7.4 Hz, 3H); ¹³C NMR (101 MHz, cdcl₃) δ 146.1, 140.9, 137.4, 134.8, 132.4, 129.9, 129.9, 128.7, 128.2, 117.6, 110.5, 37.6, 37.0, 35.2, 35.1, 24.6, 13.8.

4-(4-methoxyphenethyl)-3-(trifluoromethyl)benzonitrile (3e)

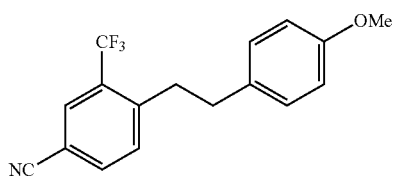 [SMILES: COc1ccc(CCc2ccc(C#N)cc2C(F)(F)F)cc1]

¹H NMR (400 MHz, Chloroform-d) δ 7.96-7.90 (m, 1H), 7.71 (dd, J=8.0, 1.8 Hz, 1H), 7.36 (dd, J=8.1, 0.8 Hz, 1H), 7.13-7.05 (m, 2H), 6.87-6.79 (m, 2H), 3.80 (s, 3H), 3.15-3.07 (m, 2H), 2.91-2.82 (m, 2H); ¹³C NMR (101 MHz, cdcl₃) δ 158.2, 157.6, 146.1, 146.0, 146.0, 134.8, 134.8, 134.7, 132.6, 132.4, 132.2, 130.5, 130.0, 130.0, 129.9, 129.9, 129.8, 129.7, 129.4, 129.2, 127.5, 124.7, 122.0, 119.3, 117.6, 114.0, 113.9, 113.7, 110.6, 55.3, 55.2, 36.5, 36.5, 35.3, 35.3, 35.3, 35.3, 34.9, 31.2.

3-(trifluoromethyl)-4-(4-(trifluoromethyl)phenethyl)benzonitrile (3f)

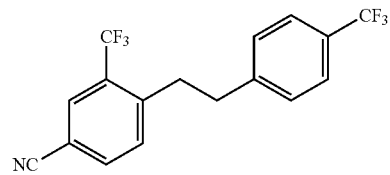 [SMILES: N#Cc1ccc(CCc2ccc(C(F)(F)F)cc2)c(C(F)(F)F)c1]

¹H NMR (400 MHz, Chloroform-d) δ 7.95-7.93 (m, 1H), 7.75-7.72 (m, 1H), 7.57-7.51 (m, 2H), 7.38-7.36 (m, 1H), 7.31-7.25 (m, 2H), 3.14 (dd, J=9.7, 6.6 Hz, 2H), 2.96 (dd, J=10 Hz, 6.3 Hz, 2H).

4-(4-butylphenethyl)-3-(trifluoromethyl)benzonitrile (3g)

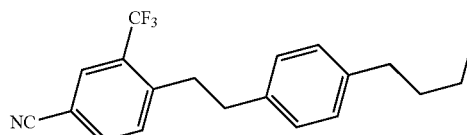

1H NMR (400 MHz, Chloroform-d) δ 7.92 (d, J=1.7 Hz, 1H), 7.70 (dd, J=8.0, 1.7 Hz, 1H), 7.38-7.32 (m, 1H), 7.13-7.02 (m, 4H), 3.11 (dd, J=9.7, 6.7 Hz, 2H), 2.91-2.81 (m, 2H), 2.63-2.51 (m, 2H), 1.63-1.50 (m, 2H), 1.40-1.27 (m, 2H), 0.91 (t, J=7.4 Hz, 3H); ¹³C NMR (101 MHz, cdcl₃) δ 146.2, 146.2, 146.1, 143.2, 141.1, 137.4, 136.2, 135.9, 134.9, 132.4, 130.3, 130.0, 130.0, 129.9, 129.8, 129.8, 129.7, 129.4, 129.2, 128.7, 128.5, 128.3, 127.6, 124.9, 124.1, 122.1, 119.4, 117.6, 110.6, 60.4, 37.1, 35.4, 35.3, 35.2, 35.2, 35.2, 35.1, 33.7, 33.4, 29.8, 29.4, 22.4, 14.2, 14.0, 13.9

4-(2-cyclopropylethyl)-N'-hydroxy-3-(trifluoromethyl)benzimidamide (4a)

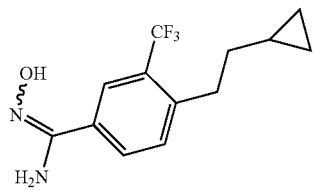 [SMILES: NC(=NO)c1ccc(CCC2CC2)c(C(F)(F)F)c1]

$^1$H NMR (400 MHz, Chloroform-d) δ 9.83 (s, 1H), 7.88 (d, J=1.6 Hz, 1H), 7.70 (dt, J=8.0, 2.3 Hz, 1H), 7.34 (d, J=8.1 Hz, 1H), 5.01 (s, 2H), 2.93-2.71 (m, 2H), 1.71-1.45 (m, 2H), 1.41-1.28 (m, 1H), 1.02-0.79 (m, 2H), 0.57-0.38 (m, 1H), 0.11-0.03 (m, 1H); $^{13}$C NMR (101 MHz, cdcl$_3$) δ 151.9, 151.9, 143.7, 143.7, 143.7, 143.7, 143.3, 143.3, 143.3, 143.3, 131.6, 131.4, 131.3, 130.1, 130.0, 129.1, 129.1, 129.0, 129.0, 129.0, 128.9, 128.9, 128.9, 128.8, 128.8, 128.5, 128.5, 128.4, 128.2, 128.2, 125.7, 125.7, 123.6, 123.6, 123.6, 123.5, 123.5, 123.5, 123.5, 122.9, 120.2, 36.7, 32.7, 32.6, 32.6, 32.6, 32.5, 32.5, 32.5, 32.4, 31.8, 31.2, 29.7, 22.5, 22.4, 14.0, 13.9, 10.9, 10.8, 4.5, 4.4; Calcd for C13H16F3N2O [M+H]$^+$: 273.1209, Found: 273.121.

4-(2-cyclopentylethyl)-N'-hydroxy-3-(trifluoromethyl)benzimidamide (4b)

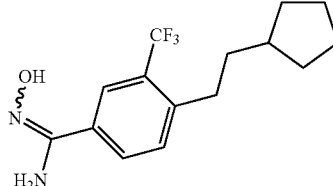

$^1$H NMR (400 MHz, Methanol-d$_4$) δ 7.92 (d, J=1.9 Hz, 1H), 7.77 (dd, J=8.1, 2.0 Hz, 1H), 7.41 (d, J=8.1 Hz, 1H), 2.84-2.74 (m, 2H), 1.92-1.71 (m, 3H), 1.70-1.45 (m, 6H), 1.16-1.12 (m, 2H); $^{13}$C NMR (101 MHz, cd$_3$od) δ 152.6, 143.1, 143.0, 140.6, 140.1, 137.9, 131.7, 131.3, 131.2, 131.1, 130.8, 129.2, 129.2, 129.2, 129.1, 129.1, 128.7, 128.6, 128.3, 128.0, 127.7, 127.4, 127.0, 125.9, 123.4, 123.3, 123.2, 123.0, 120.5, 43.9, 40.1, 40.0, 38.2, 32.5, 32.3, 32.2, 31.5, 31.5, 24.7

(E)-4-(cyclohex-1-en-1-ylethynyl)-N'-hydroxy-3-(trifluoromethyl)benzimidamide (4c)

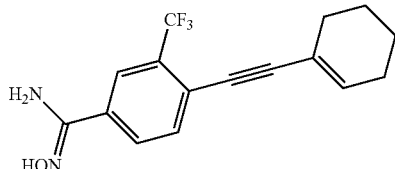

$^1$H NMR (400 MHz, Methanol-d$_4$) δ 7.97 (dq, J=1.9, 0.6 Hz, 1H), 7.81 (ddq, =8.1, 1.8, 0.6 Hz, 1H), 7.57 (dp, J=8.1, 0.7 Hz, 1H), 6.24 (tt, J=3.8, 1.7 Hz, 1H), 2.25-2.14 (m, 4H), 1.75-1.60 (m, 4H).

N'-hydroxy-4-(4-methoxyphenethyl)-3-(trifluoromethyl)benzimidamide (4e)

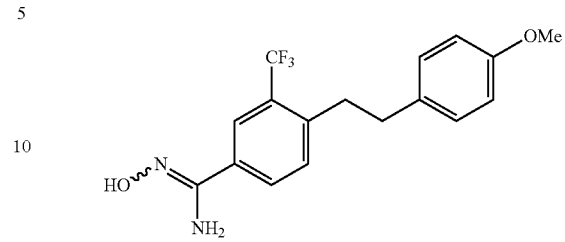

$^1$H NMR (400 MHz, Methanol-d$_4$) δ 7.93 (d, J=1.9 Hz, 1H), 7.74 (dd, J=8.4, 2.0 Hz, 1H), 7.37 (d, J=7.7 Hz, 1H), 7.07 (dd, J=5.9, 3.3 Hz, 2H), 6.86-6.77 (m, 2H), 3.07-2.96 (m, 2H), 2.82 (dd, J=9.9, 5.8 Hz, 2H); $^{13}$C NMR (101 MHz, cd$_3$od) δ 158.2, 152.6, 141.7, 132.9, 131.5, 131.1, 129.0, 129.0, 128.6, 128.1, 127.8, 125.9, 123.4, 123.3, 123.3, 123.2, 123.2, 113.4, 54.2, 47.8, 47.8, 47.6, 47.6, 47.4, 47.3, 47.1, 47.1, 46.9, 46.9, 36.6, 34.7, 34.7, 34.7.

N'-hydroxy-3-(trifluoromethyl)-4-(4-(trifluoromethyl)phenethyl)benzimidamide (4f)

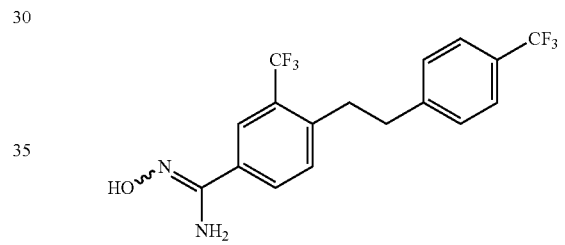

$^1$H NMR (500 MHz, Methanol-d$_4$) δ 7.99 (d, J=1.9 Hz, 1H), 7.86-7.78 (m, 1H), 7.63-7.56 (m, 2H), 7.47 (d, J=8.0 Hz, 1H), 7.45-7.35 (m, 2H), 3.20-3.11 (m, 2H), 3.03 (dd, J=9.9, 6.2 Hz, 2H).

4-(4-butylphenethyl)-N'-hydroxy-3-(trifluoromethyl)benzimidamide (4g)

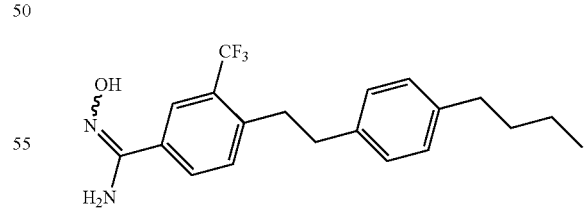

$^1$H NMR (400 MHz, Methanol-d$_4$) δ 8.00-7.98 (m, 0.4H), 7.98-7.96 (m, 0.4H), 7.93-7.91 (m, 0.6H), 7.77-7.73 (m, 0.6H), 7.46 (d, J=8.1 Hz, 0.5H), 7.42-7.38 (m, 0.6H), 3.12-3.01 (m, 2H), 2.89-2.80 (m, 2H), 2.59-2.53 (m, 2H), 1.61-1.51 (m, 2H), 1.39-1.26 (m, 2H), 0.92 (t, J=7.3 Hz, 3H); $^{13}$C NMR (101 MHz, cd$_3$od) δ 147.4, 140.5, 138.1, 131.5, 129.1, 128.1, 127.9, 125.1, 37.1, 36.9, 34.8, 33.6, 21.9, 12.8.

4-((4-ethylphenyl)ethynyl)-N'-hydroxy-3-(trifluoromethyl)benzimidamide (8)

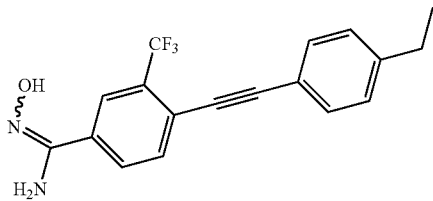 [SMILES: CCc1ccc(C#Cc2ccc(C(N)=NO)cc2C(F)(F)F)cc1]

¹³C NMR (101 MHz, cd₃od) δ 187.5, 154.5, 151.9, 145.7, 133.5, 132.8, 131.2, 131.0, 130.7, 128.8, 127.8, 124.9, 123.3, 123.2, 123.1, 122.2, 122.2, 119.5, 119.5, 96.0, 96.0, 83.9, 83.9, 28.4, 14.4 tert-butyl (S)-2-(3-(4-((4-ethylphenyl)ethynyl)-3-(trifluoromethyl)phenyl)-1,2,4-oxadiazol-5-yl)pyrrolidine-1-carboxylate (9)

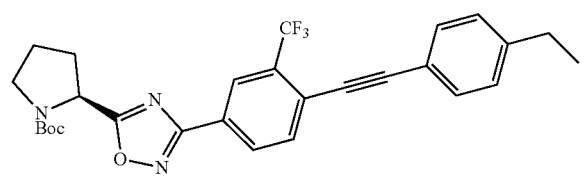 [SMILES: CCc1ccc(C#Cc2ccc(-c3noc([C@@H]4CCCN4C(=O)OC(C)(C)C)n3)cc2C(F)(F)F)cc1]

¹H NMR (400 MHz, Chloroform-d) δ 8.38 (d, J=1.7 Hz, 1H), 8.19 (dd, J=8.0, 1.9 Hz, 1H), 7.72 (t, J=8.2 Hz, 1H), 7.49-7.40 (m, 2H), 7.20-7.15 (m, 2H), 5.21-5.15 (m, 0.4H), 5.08-5.01 (m, 0.6H), 3.75-3.61 (m, 1H), 3.61-3.41 (m, 1H), 2.64 (q, J=7.6 Hz, 2H), 2.45-2.26 (m, 1H), 2.21-2.06 (m, 2H), 2.05-1.92 (m, 1H), 1.44 (s, 3H), 1.25 (s, 6H), 1.21 (t, J=7.6 Hz, 3H); ¹³C NMR (101 MHz, cdcl₃) δ 181.5, 181.3, 180.8, 180.8, 167.0, 166.7, 154.3, 153.4, 14 5.8, 145.8, 145.6, 135.7, 135.5, 134.1, 134.0, 133.8, 132.5, 132.2, 132.1, 131.9, 131.8, 131.7, 131.6, 131.4, 131.2, 130.0, 129.7, 128.3, 128.0, 128.0, 127.4, 127.3, 126.7, 126.3, 126.0, 125.1, 124.9, 124.9, 124.7, 124.6, 124.3, 121.8, 119.4, 119.1, 97.8, 97.6, 97.1, 84.7, 84.6, 84.5, 80.5, 80.4, 53.8, 53.7, 46.6, 46.3, 38.0, 32.4, 31.4, 28.9, 28.3, 28.1, 24.4, 23.7, 15.3; Calcd for C₃₆H₄₇F₃N₅O₅ [M+H]⁺: 686.3524, Found 686.3522.

tert-butyl (S)-2-(3-(4-((4-(tert-butyl)phenyl)ethynyl)-3-(trifluoromethyl)phenyl)-1,2,4-oxadiazol-5-yl)pyrrolidine-1-carboxylate (12)

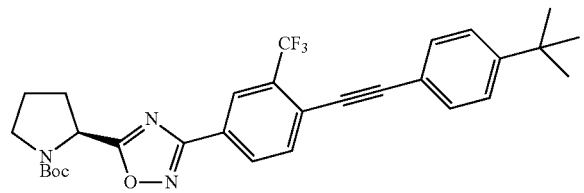 [SMILES: CC(C)(C)OC(=O)N1CCC[C@H]1c1nc(-c2ccc(C#Cc3ccc(C(C)(C)C)cc3)c(C(F)(F)F)c2)no1]

¹H NMR (400 MHz, Chloroform-d) δ 8.39-8.36 (m, 1H), 8.20 (d, J=8.1 Hz, 1H), 7.74 (t, J=8.4 Hz, 1H), 7.52-7.47 (m, 2H), 7.42-7.35 (m, 2H), 5.21-5.15 (m, 0.4H), 5.11-5.03 (m, 0.6H), 3.76-3.62 (m, 1H), 3.61-3.43 (m, 2H), 2.47-2.28 (m, 2H), 2.02 (dq, J=11.0, 7.2, 5.7 Hz, 1H), 1.45 (s, 4H), 1.35-1.24 (m, 17H).

tert-butyl (S)-2-(3-(4-(2-cyclopropylethyl)-3-(trifluoromethyl)phenyl)-1,2,4-oxadiazol-5-yl)pyrrolidine-1-carboxylate (5a)

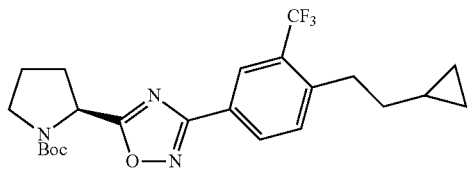 [SMILES: CC(C)(C)OC(=O)N1CCC[C@H]1c1nc(-c2ccc(CCC3CC3)c(C(F)(F)F)c2)no1]

¹H NMR (400 MHz, Chloroform-d) δ 8.30 (s, 1H), 8.15-8.06 (m, 1H), 7.46-7.38 (m, 1H), 5.25-5.13 (m, 0.3H), 5.09-4.99 (m, 0.7H), 3.74-3.61 (m, 1H), 3.59-3.41 (m, 1H), 2.92 (t, J=8.1 Hz, 0.5H), 2.79 (t, J=8.1 Hz, 1.5H), 2.48-2.28 (m, 1H), 2.21-2.05 (m, 2H), 2.04-1.99 (m, 1H), 1.65-1.58 (m, 1H), 1.56-1.18 (m, 12H), 0.93-0.84 (m, 2H), 0.47-0.40 (m, 1H), 0.07-0.01 (m, 1H); ¹³C NMR (101 MHz, cdcl₃) δ 171.1, 167.7, 166.7, 156.9, 153.9, 152.2, 150.8, 149.9, 147.6, 142.5, 134.9, 134.8, 131.9, 129.8, 122.2, 120.4, 119.6, 116.0, 115.8, 115.0, 114.9, 114.1, 113.8, 110.0, 105.9, 104.8, 69.7, 62.6, 60.4, 56.8, 56.4, 56.3, 56.1, 56.0, 56.0, 55.9, 51.9, 34.8, 30.8, 30.6, 29.9, 29.6, 21.4, 21.0, 19.0, 18.9, 18.8, 14.1, 14.1, 13.8; HRMS (ESI+): Calcd for C₂₃H₂₈F₃N₃O₃Na [M+Na]⁺: 474.1975, Found: 474.1986.

tert-butyl (S)-2-(3-(4-(2-cyclopentylethyl)-3-(trifluoromethyl)phenyl)-1,2,4-oxadiazol-5-yl)pyrrolidine-1-carboxylate (5b)

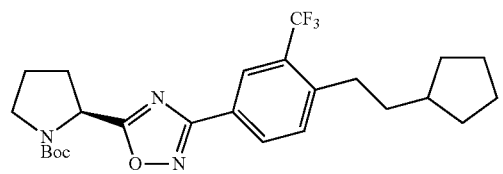 [SMILES: CC(C)(C)OC(=O)N1CCC[C@H]1c1nc(-c2ccc(CCC3CCCC3)c(C(F)(F)F)c2)no1]

¹H NMR (400 MHz, Chloroform-d) δ 8.30 (s, 1H), 8.12 (d, J=8.0 Hz, 1H), 7.41 (dd, J=16.9, 6.4 Hz, 1H), 5.05 (dd, J=8.1, 3.6 Hz, 1H), 3.75-3.57 (m, 1H), 3.56-3.38 (m, 1H), 2.88-2.75 (m, 2H), 2.47-2.27 (m, 1H), 2.21-2.08 (m, 2H), 2.07-1.92 (m, 1H), 1.93-1.72 (m, 3H), 1.68-1.49 (m, 4H), 1.44 (s, 3H), 1.28 (s, 6H), 1.19-1.09 (m, 1H); ¹³C NMR (101 MHz, cdcl₃) δ 181.0, 167.4, 153.5, 131.7, 130.3, 124.4, 110.0, 80.5, 53.8, 46.3, 40.2, 38.2, 33.0, 32.5, 32.4, 32.1, 31.5, 28.3, 28.1, 25.2, 25.2, 23.7.

tert-butyl (2S,3S)-2-(3-(4-(2-cyclopentylethyl)-3-(trifluoromethyl)phenyl)-1,2,4-oxadiazol-5-yl)-3-hydroxypyrrolidine-1-carboxylate (5bA)

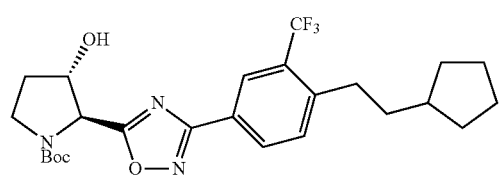 [SMILES: CC(C)(C)OC(=O)N1CC[C@H](O)[C@H]1c1nc(-c2ccc(CCC3CCCC3)c(C(F)(F)F)c2)no1]

¹H NMR (400 MHz, Chloroform-d) δ 8.30 (s, 1H), 8.13 (d, J=8.4 Hz, 1H), 7.44 (s, 1H), 4.97 (s, 1H), 4.59 (s, 1H), 3.85-3.65 (m, 2H), 2.83 (t, J=8.3 Hz, 2H), 2.41-2.12 (m, 1H), 2.10-1.99 (m, 1H), 1.95-1.75 (m, 3H), 1.71-1.38 (m, 9H), 1.31 (s, 6H), 1.22-1.07 (m, 2H); ¹³C NMR (101 MHz, cdcl₃) δ 191.4, 178.6, 167.6, 153.6, 151.1, 131.9, 131.7, 130.3, 125.1, 124.2, 80.9, 77.1, 76.1, 75.1, 62.5, 62.2, 44.7, 44.3 44.0, 40.2, 38.2, 33.8, 33.0, 32.5, 32.2, 32.1, 29.7, 28.3, 28.1, 25.5, 25.2.

tert-butyl (S)-2-(3-(4-(2-(cyclohex-1-en-1-yl)ethyl)-3-(trifluoromethyl)phenyl)-1,2,4-oxadiazol-5-yl) pyrrolidine-1-carboxylate (5c)

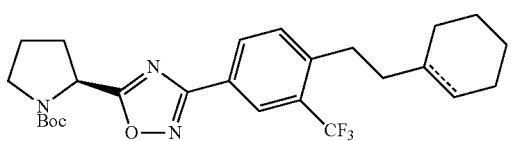

¹H NMR (400 MHz, Chloroform-d) δ 8.36-8.27 (m, 1H), 8.19-8.09 (m, 1H), 7.41-7.29 (m, 1H), 5.44-5.38 (m, 0.4H), 5.21-5.13 (m, 0.6H), 5.08-5.01 (m, 1H), 3.78-3.42 (m, 3H), 2.97-2.72 (m, 2H), 2.44-2.28 (m, 1H), 2.27-1.92 (m, 6H), 1.86-1.40 (m, 9H), 1.37-1.04 (m, 8H), 0.94-0.82 (m, 1H); ¹³C NMR (101 MHz, cdcl₃) δ 191.3, 181.0, 180.5, 167.4, 154.3, 153.5, 145.6, 144.8, 141.5, 136.5, 131.8, 131.7, 131.4, 130.4, 130.3, 130.2, 130.0, 125.5, 125.1, 124.6, 124.5, 123.1, 122.8, 122.0, 117.8, 80.5, 53.8, 46.6, 46.3, 41.4, 39.8, 39.5, 37.9, 37.2, 37.2, 35.4, 33.2, 32.8, 32.6, 32.4, 31.4, 30.3, 29.9, 29.7, 28.8, 28.5, 28.3, 28.3, 28.1, 27.7, 26.8, 26.6, 26.3, 26.0, 25.9, 25.8, 25.5, 25.2, 24.3, 23.7, 22.9, 22.4.

tert-butyl (S)-2-(3-(4-(4-propylphenethyl)-3-(trifluoromethyl)phenyl)-1,2,4-oxadiazol-5-yl)pyrrolidine-1-carboxylate (5d)

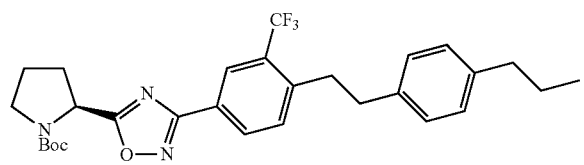 [SMILES: CCCc1ccc(CCc2ccc(-c3noc([C@@H]4CCCN4C(=O)OC(C)(C)C)n3)cc2C(F)(F)F)cc1]

¹H NMR (400 MHz, Chloroform-d) δ 8.36 (d, J=1.6 Hz, 1H), 8.14 (d, J=7.7 Hz, 1H), 7.39 (dd, J=17.8, 8.1 Hz, 1H), 3.61 (d, J=82.5 Hz, 3H), 3.12 (t, J=8.2 Hz, 2H), 2.97-2.87 (m, 2H), 2.61-2.53 (m, 2H), 2.41 (s, 2H), 2.16 (s, 2H), 2.08-1.96 (m, 1H), 1.70-1.58 (m, 2H), 1.51-1.40 (m, 3H), 1.31 (s, 6H), 0.95 (t, J=7.3 Hz, 3H); ¹³C NMR (101 MHz, cdcl₃) δ 191.4, 181.0, 167.4, 153.5, 143.9, 143.9, 140.6, 138.1, 132.0, 132.0, 130.3, 130.3, 128.3, 125.2, 5d80.5, 53.8, 46.6, 46.4, 37.6, 37.4, 35.1, 32.4, 28.4, 28.1, 24.6, 23.7, 13.8.

tert-butyl (S)-2-(3-(4-(4-butylphenethyl)-3-(trifluoromethyl)phenyl)-1,2,4-oxadiazol-5-yl)pyrrolidine-1-carboxylate (5g)

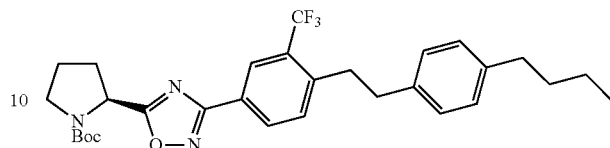

¹H NMR (400 MHz, Chloroform-d) δ 8.34 (s, 1H), 8.13 (d, J=7.5 Hz, 1H), 7.38 (dd, J=18.8, 8.0 Hz, 1H), 7.11 (d, J=3.0 Hz, 4H), 5.23-5.15 (m, 0.4H), 5.09-5.03 (m, 0.6H), 3.80-3.65 (m, 1H), 3.63-3.44 (m, 1H), 3.10 (t, J=8.2 Hz, 2H), 2.88 (dd, J=10.4, 6.2 Hz, 2H), 2.58 (t, J=7.7 Hz, 2H), 2.48-2.31 (m, 1H), 2.21-2.05 (m, 2H), 2.09-1.95 (m, 1H), 1.63-1.53 (m, 2H), 1.45 (s, 3H), 1.32-1.21 (m, 6H), 0.91 (t, J=7.3 Hz, 3H); ¹³C NMR (101 MHz, cdcl₃) δ 181.0, 167.4, 143.9, 143.6, 140.8, 138.0, 132.0, 131.9, 130.3, 128.5, 128.3, 124.9, 80.5, 53.8, 46.6, 46.4, 37.4, 35.2, 35.1, 35.1, 33.7, 32.4, 31.5, 28.4, 28.1, 24.4, 23.7, 22.3, 22.3, 13.9; Calcd for C₃₀H₃₆F₃N₃O₃Na [M+Na]⁺: 566.2601, Found: 566.2602.

tert-butyl (2S,3S)-2-(3-(4-(4-butylphenethyl)-3-(trifluoromethyl)phenyl)-1,2,4-oxadiazol-5-yl)-3-hydroxypyrrolidine-1-carboxylate (5gA)

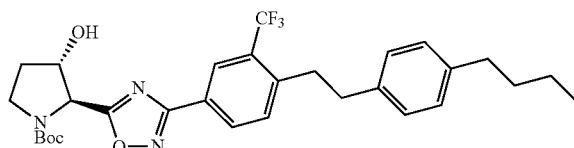

¹H NMR (400 MHz, Chloroform-d) δ 8.35-8.28 (m, 1H), 8.15-8.05 (m, 1H), 7.85-7.75 (m, 1H), 7.44-7.29 (m, 1H), 7.11 (d, J=2.4 Hz, 4H), 5.14-5.11 (m, 0.4H), 4.99-4.95 (m, 0.6H), 4.63-4.53 (m, 1H), 3.83-3.67 (m, 2H), 3.18-3.05 (m, 2H), 2.91-2.81 (m, 2H), 2.62-2.52 (m, 2H), 2.39-2.21 (m, 2H), 2.10-2.01 (m, 2H), 1.64-1.51 (m, 2H), 1.47 (s, 3H), 1.40-1.21 (m, 6H), 0.91 (t, J=7.3 Hz, 3H); ¹³C NMR (101 MHz, cdcl₃) δ 178.7, 167.5, 144.1, 140.9, 138.0, 132.0, 131.9, 130.3, 128.5, 128.3, 126.8, 125.2, 124.6, 81.1, 76.0, 75.0, 62.5, 62.3, 44.9, 44.4, 37.4, 35.2, 35.1, 33.7, 32.5, 32.2, 28.4, 28.1, 22.3, 13.9; Calcd for C₃₀H₃₀F₃N₃O₄Na [M+Na]⁺: 582.255, Found: 582.2511.

tert-butyl (2S,3S)-3-hydroxy-2-(3-(4-(4-propylphenethyl)-3-(trifluoromethyl)phenyl)-1,2,4-oxadiazol-5-yl)pyrrolidine-1-carboxylate (5dA)

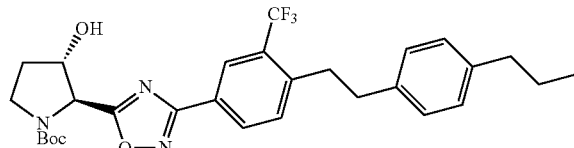

¹H NMR (400 MHz, Chloroform-d) δ 8.35 (s, 1H), 8.13 (d, J=8.4 Hz, 1H), 7.45-7.35 (m, 1H), 7.13 (s, 4H), 5.15-5.08 (m, 0.4H), 4.98 (s, 0.6H), 4.65-4.55 (m, 1H), 3.91-3.61 (m, 2H), 3.18-3.09 (m, 2H), 2.95-2.82 (m, 2H), 2.62-2.48 (m, 2H), 2.45-2.25 (m, 1H), 2.09-2.01 (m, 1H), 1.74-1.55 (m, 2H), 1.48 (s, 3H), 1.32 (s, 6H), 0.95 (t, J=7.3 Hz, 3H); ¹³C NMR (101 MHz, cdcl₃) δ 191.4, 181.1, 167.4, 153.5, 143.9, 140.6, 138.1, 132.0, 130.3, 128.6, 128.3, 125.6, 125.2, 124.9, 80.5, 53.8, 46.6, 46.4, 37.6, 37.4, 35.1, 32.4, 31.5, 28.4, 28.1, 24.6, 24.4, 23.7, 13.8; Calcd for C₂₉H₃₄F₃N₃ONa [M+Na]⁺: 568.2394, Found: 568.2376.

tert-butyl (S)-2-(3-(4-(4-(tert-butyl)phenethyl)-3-(trifluoromethyl)phenyl)-1,2,4-oxadiazol-5-yl)pyrrolidine-1-carboxylate (5h)

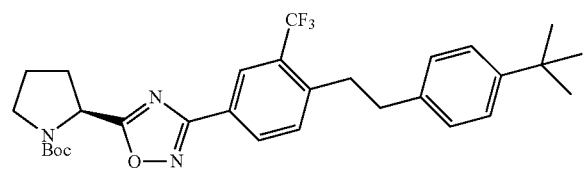 [SMILES: CC(C)(C)OC(=O)N1CCC[C@H]1c1nc(-c2ccc(CCc3ccc(C(C)(C)C)cc3)c(C(F)(F)F)c2)no1]

¹H NMR (400 MHz, Chloroform-d) δ 8.36 (s, 1H), 8.16 (d, J=7.7 Hz, 1H), 7.51-7.38 (m, 1H), 7.35 (m, 2H), 7.24-7.13 (m, 2H), 5.25-5.18 (m, 0.4H), 5.11-5.04 (m, 0.6H), 3.79-3.61 (m, 1H), 3.60-3.42 (m, 1H), 3.20-3.07 (m, 2H), 2.95-2.85 (m, 2H), 2.49-2.31 (m, 1H), 2.21-1.91 (m, 2H), 1.47 (s, 3H), 1.33 (m, 9H), 1.30 (s, 6H); ¹³C NMR (126 MHz, CDCl₃) δ 181.1, 167.4, 153.5, 149.2, 144.0, 137.9, 132.0, 130.4, 129.0, 128.1, 126.9, 125.8, 125.4, 125.2, 80.5, 77.3, 77.2, 77.0, 76.7, 53.8, 46.6, 46.4, 37.3, 35.0, 34.4, 32.4, 31.4, 31.2, 31.2, 29.7, 28.4, 28.2, 27.6, 24.4, 23.7, Calcd for C₃₀H₃₆F₃N₃O₃Na [M+Na]⁺: 569.2691, Found: 569.2712.

tert-butyl (S)-2-(3-(4-(4-methoxyphenethyl)-3-(trifluoromethyl)phenyl)-1,2,4-oxadiazol-5-yl)pyrrolidine-1-carboxylate (5e)

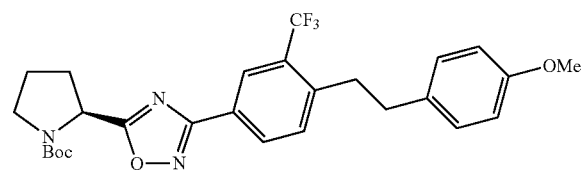 [SMILES: COc1ccc(CCc2ccc(-c3noc([C@@H]4CCCN4C(=O)OC(C)(C)C)n3)cc2C(F)(F)F)cc1]

¹H NMR (500 MHz, Chloroform-d) δ 8.38 (d, J=2.3 Hz, 1H), 8.19-8.11 (m, 1H), 7.39 (dd, J=25.4, 7.8 Hz, 1H), 7.19-7.10 (m, 2H), 6.91-6.83 (m, 2H), 5.23 (dd, J=8.4, 2.7 Hz, 0.4H), 5.10 (dd, J=8.2, 3.8 Hz, 0.6H), 3.79-3.67 (m, 1H), 3.60 (dt, J=10.0, 7.0 Hz, 1H), 3.12 (dt, J=10.1, 5.6 Hz, 2H), 2.95-2.85 (m, 2H), 2.24-2.11 (m, 2H), 2.10-1.99 (m, 1H), 1.49 (s, 3H), 1.33 (s, 6H); ¹³C NMR (101 MHz, cdcl₃) δ 181.0, 180.6, 177.7, 172.2, 171.9, 167.3, 165.6, 162.4, 158.1, 154.4, 154.2, 153.7, 153.4, 143.8, 143.5, 132.9, 132.0, 131.9, 130.3, 129.3, 129.1, 125.6, 125.2, 125.1, 124.9, 122.8, 113.9, 113.8, 80.4, 56.4, 56.3, 55.2, 53.8, 46.7, 46.6, 46.3, 38.5, 36.9, 36.8, 35.2, 35.2, 32.4, 31.4, 31.3, 30.3, 29.5, 28.5, 28.4, 28.3, 28.2, 28.1, 24.3, 24.1, 23.7, 23.6; Calcd for C₂₇H₃₀F₃N₃O₄Na [M+Na]⁺: 542.2141, Found: 542.2141.

tert-butyl (2S,3S)-3-hydroxy-2-(3-(4-(4-methoxyphenethyl)-3-(trifluoromethyl)phenyl)-1,2,4-oxadiazol-5-yl)pyrrolidine-1-carboxylate (5eA)

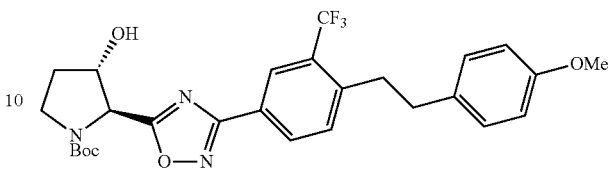

¹H NMR (400 MHz, Chloroform-d) δ 8.32 (d, J=14.4 Hz, 1H), 8.10 (dd, J=17.9, 8.1 Hz, 1H), 7.42-7.29 (m, 1H), 7.17-7.07 (m, 2H), 6.89-6.81 (m, 2H), 5.14 (s, 0H), 4.98 (d, J=2.0 Hz, 0H), 4.63-4.51 (m, 1H), 3.79 (s, 4H), 3.10 (dd, J=10.2, 6.0 Hz, 2H), 2.87 (t, J=8.3 Hz, 2H), 2.34 (tt, J=8.9, 4.9 Hz, 1H), 2.13-2.01 (m, 1H), 1.48 (s, 3H), 1.38-1.21 (m, 5H); ¹³C NMR (101 MHz, cdcl₃) δ 178.7, 178.2, 167.5, 158.1, 154.7, 153.8, 144.0, 143.8, 132.9, 132.1, 131.9, 131.8, 130.5, 130.3, 129.5, 129.4, 129.2, 128.3, 125.5, 125.2, 125.2, 124.8, 124.6, 122.8, 113.9, 113.7, 81.0, 80.9, 76.0, 75.0, 62.5, 62.3, 60.5, 55.3, 55.1, 44.9, 44.4, 36.8, 36.6, 35.2, 32.5, 32.2, 29.7, 28.4, 28.1, 24.7, 23.4, 14.1.

tert-butyl (S)-2-(3-(3-(trifluoromethyl)-4-(4-(trifluoromethyl)phenethyl) phenyl)-1,2,4-oxadiazol-5-yl)pyrrolidine-1-carboxylate (5f)

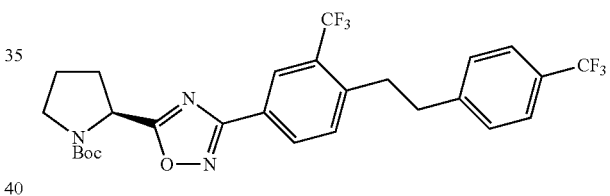

¹H NMR (400 MHz, Chloroform-d) δ 8.37 (d, J=1.7 Hz, 1H), 8.16 (d, J=7.7 Hz, 1H), 7.56 (d, J=8.0 Hz, 2H), 7.36 (dd, J=31.3, 8.0 Hz, 3H), 5.28-5.03 (m, 1H), 3.84-3.46 (m, 2H), 3.15 (t, J=8.2 Hz, 2H), 3.00 (dd, J=10.1, 6.2 Hz, 2H), 2.54-2.32 (m, 1H), 2.27-1.93 (m, 3H), 1.47 (s, 3H), 1.31 (s, 6H); ¹³C NMR (101 MHz, cdcl₃) δ 181.2, 167.3, 153.4, 144.9, 143.0, 131.9, 130.5, 128.8, 128.5, 125.5, 125.5, 125.4, 125.4, 80.5, 77.2, 53.8, 46.6, 46.3, 37.4, 34.6, 32.4, 31.5, 28.3, 28.1, 24.4, 23.7.

tert-butyl (2S,3S)-3-hydroxy-2-(3-(3-(trifluoromethyl)-4-(4-(trifluoromethyl)phenethyl)phenyl)-1,2,4-oxadiazol-5-yl)pyrrolidine-1-carboxylate (5hA)

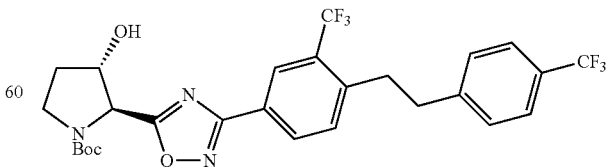

¹H NMR (400 MHz, Chloroform-d) δ 8.35 (d, J=9.8 Hz, 1H), 8.14 (t, J=9.5 Hz, 1H), 7.56 (d, J=8.0 Hz, 2H), 7.36 (dd, J=32.7, 7.9 Hz, 3H), 5.13 (s, 0.3H), 4.98 (s, 0.7H), 4.65-4.55

(m, 1H), 3.86-3.68 (m, 2H), 3.15 (t, J=8.4 Hz, 2H), 2.98 (dd, J=15.2, 7.9 Hz, 2H), 2.45-2.21 (m, 2H), 2.15-2.03 (m, 1H), 1.48 (s, 3H), 1.32 (s, 6H);

$^{13}$C NMR (101 MHz, cdcl$_3$) δ 178.9, 178.3, 167.3, 155.4, 151.2, 144.8, 131.9, 130.4, 128.7, 125.4, 125.4, 125.0, 80.9, 75.9, 65.8, 62.5, 62.3, 44.9, 44.4, 37.4, 34.6, 32.5, 32.2, 28.3, 28.1, 21.0, 15.2, 14.1.

tert-butyl (S)-2-(3-(4-(4-ethylphenethyl)-3-(trifluoromethyl)phenyl)-1,2,4-oxadiazol-5-yl)pyrrolidine-1-carboxylate (5i)

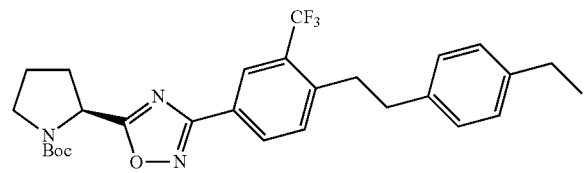 [SMILES: CCc1ccc(CCc2ccc(-c3noc([C@@H]4CCCN4C(=O)OC(C)(C)C)n3)cc2C(F)(F)F)cc1]

$^1$H NMR (400 MHz, Chloroform-d) δ 8.35 (s, 1H), 8.13 (s, 1H), 7.45-7.31 (m, 1H), 7.13 (s, 4H), 5.23-5.16 (m, 0.4H), 5.11-5.03 (m, 0.6H), 3.79-3.62 (m, 1H), 3.62-3.42 (m, 1H), 3.11 (t, J=8.2 Hz, 2H), 2.94-2.83 (m, 2H), 2.62 (q, J=7.6 Hz, 2H), 2.45-2.31 (m, 1H), 2.18-2.08 (m, 2H), 2.05-1.95 (m, 1H), 1.46 (s, 3H), 1.30 (m, 6H), 1.23 (t, J=7.6 Hz, 3H); $^{13}$C NMR (101 MHz, cdcl$_3$) δ 181.0, 180.6, 167.4, 154.3, 153.5, 143.9, 143.6, 142.2, 138.1, 135.7, 132.0, 1318, 131.6, 131.4, 130.3, 130.1, 129.4, 129.1, 128.3, 128.0, 127.9, 125.5, 125.2, 125.1, 125.1, 124.9, 122.8, 80.5, 53.8, 53.7, 46.6, 46.3, 38.1, 37.4, 35.1, 35.1, 32.4, 31.5, 29.7, 28.4, 28.3, 28.1, 24.4, 23.7, 15.6; Calcd for C$_{28}$H$_{32}$F$_3$N$_3$O$_3$Na [M+Na]$^+$: 538.2288, Found: 538.2309.

tert-butyl (S,E)-(((tert-butoxycarbonyl)amino)(2-(3-(4-(2-cyclopropylethyl)-3-(trifluoromethyl)phenyl)-1,2,4-oxadiazol-5-yl)pyrrolidin-1-yl)methylene)carbamate (6a)

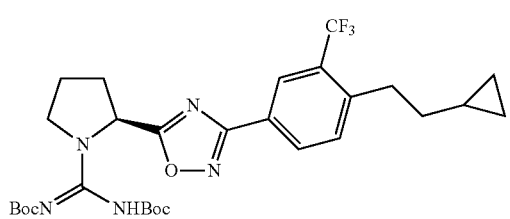

$^1$H NMR (400 MHz, Chloroform-d) δ 10.09 (s, 1H), 8.31 (d, J=1.7 Hz, 1H), 8.14 (dt, J=8.2, 2.5 Hz, 1H), 7.44 (d, J=8.1 Hz, 1H), 5.61 (dd, J=7.8, 4.5 Hz, 1H), 3.96-3.69 (m, 2H), 2.95-2.89 (m, 0.7H), 2.85-2.75 (m, 1.3H), 2.51-2.40 (m, 1H), 2.25-2.19 (m, 1H), 2.08-1.95 (m, 1H), 1.69-1.55 (m, 2H), 1.55-1.30 (m, 18H), 0.48-0.42 (m, 1H), 0.075-0.035 (m, 1H); $^{13}$C NMR (101 MHz, cdcl$_3$) δ 179.4, 167.4, 145.1, 144.7, 131.8, 131.5, 130.4, 130.3, 129.5, 129.2, 128.9, 128.6, 128.3, 125.5, 125.3, 125.2, 125.1, 124.5, 122.8, 120.1, 55.3, 49.4, 36.7, 32.9, 32.7, 32.7, 31.8, 31.2, 29.7, 28.1, 28.0, 24.0, 22.4, 13.9, 10.9, 4.6.

tert-butyl (S,E)-(((tert-butoxycarbonyl)amino)(2-(3-(4-(2-cyclopentylethyl)-3-(trifluoromethyl)phenyl)-1,2,4-oxadiazol-5-yl)pyrrolidin-1-yl)methylene)carbamate (6b)

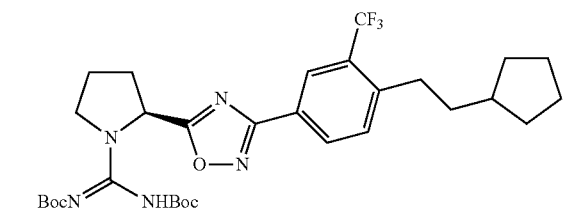

$^1$H NMR (400 MHz, Chloroform-d) δ 8.31 (d, J=1.7 Hz, 1H), 8.14 (dd, J=8.0, 1.8 Hz, 1H), 7.44 (d, J=8.1 Hz, 1H), 5.61 (dd, J=7.8, 4.5 Hz, 1H), 3.95-3.75 (m, 2H), 2.87-2.79 (m, 2H), 1.92-1.76 (m, 3H), 1.70-1.37 (m, 22H), 1.16 (dd, J=13.1, 6.0 Hz, 9H), 0.87 (dt, J=9.7, 6.3 Hz, 2H).

Tert-butyl ((E)-((tert-butoxycarbonyl)amino)((2S,3S)-2-(3-(4-(2-cyclopentylethyl)-3-(trifluoromethyl)phenyl)-1,2,4-oxadiazol-5-yl)-3-hydroxypyrrolidin-1-yl)methylene)carbamate (6bA)

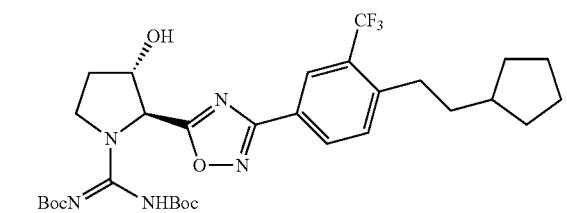

$^1$H NMR (400 MHz, Chloroform-d) δ 10.03 (s, 1H), 8.30 (d, J=1.7 Hz, 1H), 8.13 (dd, J=7.9, 1.8 Hz, 1H), 7.44 (d, J=8.1 Hz, 1H), 5.54-5.49 (m, 1H), 4.63 (s, 1H), 4.10-3.88 (m, 2H), 2.88-2.79 (m, 2H), 2.66-2.41 (m, 1H), 2.40-2.32 (m, 1H), 2.15-2.05 (m, 1H), 1.92-1.75 (m, 2H), 1.69-1.36 (m, 20H), 1.34-1.09 (m, 6H); $^{13}$C NMR (101 MHz, cdcl$_3$) δ 191.3, 177.1, 167.5, 158.4, 150.8, 145.5, 131.7, 130.4, 129.2, 128.9, 125.5, 125.3, 125.2, 124.3, 122.8, 63.3, 46.9, 40.2, 38.1, 32.6, 32.1, 29.7, 28.1, 28.0, 25.2, 25.2, 22.7.

tert-butyl (S,E)-(((tert-butoxycarbonyl)amino)(2-(3-(4-(2-(cyclohex-1-en-1-yl)ethyl)-3-(trifluoromethyl)phenyl)-1,2,4-oxadiazol-5-yl)pyrrolidin-1-yl)methylene)carbamate (6c)

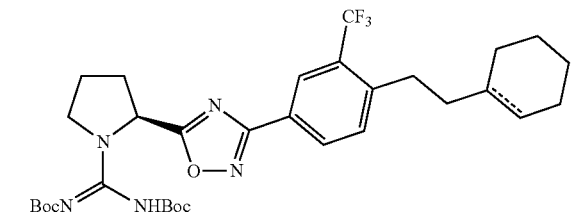

¹H NMR (400 MHz, Chloroform-d) δ 10.07 (s, 1H), 8.43-8.03 (m, 2H), 7.41 (d, J=7.5 Hz, 1H), 5.64 (s, 1H), 3.88 (s, 2H), 2.81 (s, 1H), 2.47 (s, 1H), 2.13 (d, J=57.4 Hz, 3H), 1.90-0.59 (m, 25H).

tert-butyl ((E)-((tert-butoxycarbonyl)amino)((2S, 3S)-2-(3-(4-(4-butylphenethyl)-3-(trifluoromethyl) phenyl)-1,2,4-oxadiazol-5-yl)-3-hydroxypyrrolidin-1-yl)methylene)carbamate (6gA)

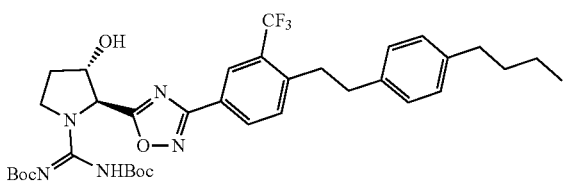

¹H NMR (400 MHz, Chloroform-d) δ 9.99 (s, 1H), 8.33 (d, J=1.7 Hz, 1H), 8.12 (dd, J=8.0, 1.8 Hz, 1H), 7.39 (d, J=8.1 Hz, 1H), 7.12 (s, 4H), 5.53 (d, J=2.3 Hz, 1H), 4.68-4.61 (m, 1H), 4.08-3.90 (m, 2H), 3.14-3.06 (m, 2H), 2.94-2.84 (m, 2H), 2.63-2.55 (m, 2H), 2.41-2.25 (m, 1H), 2.24-2.07 (m, 1H), 1.65-1.53 (m, 3H), 1.54-1.16 (m, 20sH), 0.98-0.81 (m, 3H); ¹³C NMR (101 MHz, cdcl₃) δ 177.2, 167.4, 153.9, 144.0, 140.8, 138.0, 131.9, 130.4, 129.4, 129.1, 128.5, 128.3, 125.4, 125.3, 124.7, 77.2, 74.8, 63.3, 46.9, 45.8, 37.3, 35.2, 35.1, 35.0, 33.7, 32.0, 29.7, 28.1, 22.3, 14.1, 13.9, 8.6; Calcd for $C_{36}H_{47}F_3N_5O_6$ [M+H]⁺: 704.3533, Found: 704.3527.

tert-butyl (S,E)-(((tert-butoxycarbonyl)amino)(2-(3-(4-(4-propylphenethyl)-3-(trifluoromethyl)phenyl)-1,2,4-oxadiazol-5-yl)pyrrolidin-1-yl)methylene)carbamate (6d)

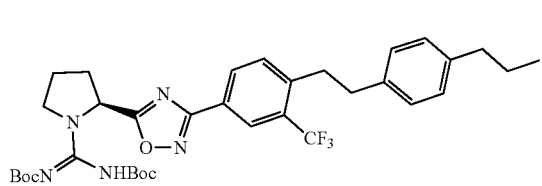

¹H NMR (400 MHz, Chloroform-d) δ 10.4-9.8 (brs, 1H), 8.35 (d, J=1.7 Hz, 1H), 8.13 (dd, J=8.0, 1.8 Hz, 1H), 7.38 (d, J=8.1 Hz, 1H), 7.12 (s, 4H), 5.62 (dd, J=7.8, 4.5 Hz, 1H), 4.02-3.70 (m, 2H), 3.12 (dd, J=10.1, 6.4 Hz, 2H), 3.00-2.80 (m, 2H), 2.65-2.43 (m, 3H), 2.27-2.15 (m, 2H), 2.11-1.94 (m, 1H), 1.69-1.57 (m, 2H), 1.51-1.31 (m, 18H), 0.94 (t, J=7.3 Hz, 3H); ¹³C NMR (101 MHz, cdcl₃) δ 179.4, 167.4, 153.7, 143.8, 140.6, 138.1, 131.9, 130.4, 128.6, 128.3, 125.4, 125.3, 124.9, 82.3, 79.6, 77.2, 55.3, 49.5, 37.6, 37.4, 35.1, 35.1, 28.1, 24.6, 24.0, 13.8; Calcd for $C_{36}H_{47}F_3N_5O_5$ [M+H]⁺: 686.3524, Found: 686.3522.

Tert-butyl((E)-((tert-butoxycarbonyl)amino)((2S, 3S)-3-hydroxy-2-(3-(4-(4-propylphenethyl)-3-(trifluoromethyl)phenyl)-1,2,4-oxadiazol-5-yl)pyrrolidin-1-yl)methylene)carbamate (6dA)

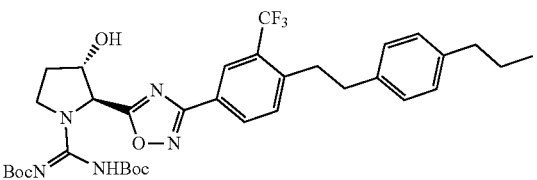

¹H NMR (400 MHz, Chloroform-d) δ 8.34 (d, J=1.6 Hz, 1H), 8.12 (dd, J=7.9, 1.6 Hz, 1H), 7.39 (d, J=8.1 Hz, 1H), 7.12 (s, 4H), 5.56 (s, 1H), 4.61 (s, 1H), 4.10-3.92 (m, 2H), 3.16-3.08 (m, 2H), 2.95-2.85 (m, 2H), 2.85-2.61 (brs, 1H), 2.57 (dd, J=8.3, 7.0 Hz, 2H), 2.45-2.34 (m, 1H), 2.21-2.05 (m, 1H), 1.71-1.58 (m, 2H), 1.47 (s, 18H), 0.94 (t, J=7.3 Hz, 3H); NMR (101 MHz, cdcl₃) δ 179.4, 167.4, 153.7, 143.8, 140.6, 138.1, 131.9, 131.6, 130.4, 129.6, 129.3, 129.0, 128.7, 128.6, 128.3, 125.6, 125.4, 125.4, 125.3, 125.3, 124.9, 122.8, 120.1, 82.3, 79.6, 55.3, 49.5, 37.6, 37.4, 35.1, 35.1, 35.1, 35.0, 31.2, 29.7, 28.1, 28.0, 27.8, 24.6, 24.0, 13.8; Calcd for $C_{36}H_{47}F_3N_5O_6$ [M+H]⁺: 702.3473, Found: 704.3482.

Tert-butyl(S,E)-(((tert-butoxycarbonyl)amino)(2-(3-(4-(4-butylphenethyl)-3-(trifluoromethyl)phenyl)-1,2,4-oxadiazol-5-yl)pyrrolidin-1-yl)methylene)carbamate (6g)

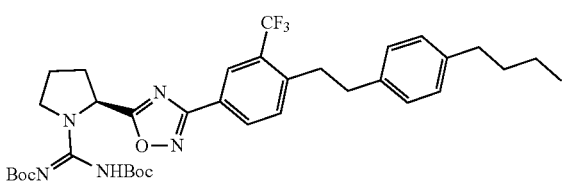

¹H NMR (400 MHz, Chloroform-d) δ 8.34-8.32 (m, 1H), 8.14-8.08 (m, 1H), 7.36 (d, J=8.1 Hz, 1H), 7.10 (s, 4H), 5.65-5.55 (m, 1H), 3.95-3.85 (m, 1H), 3.85-3.73 (m, 2H), 3.15-3.05 (m, 2H), 2.91-2.83 (m, 2H), 2.61-2.54 (m, 1H), 2.49-2.39 (m, 1H), 2.25-2.10 (m, 2H), 2.08-1.97 (m, 1H), 1.61-1.31 (s, 23H), 0.96-0.80 (m, 3H); ¹³C NMR (101 MHz, cdcl₃) δ 179.4, 167.3, 158.3, 153.6, 143.8, 140.8, 138.0, 131.9, 131.8, 130.4, 129.6, 129.3, 129.0, 128.7, 128.5, 128.3, 125.6, 125.4, 125.3, 125.3, 125.2, 124.9, 122.8, 81.3, 55.3, 49.4, 37.3, 35.2, 35.1, 35.0, 33.7, 31.9, 31.4, 29.7, 29.3, 28.3, 28.2, 28.1, 28.0, 28.0, 27.9, 24.0, 22.6, 22.3, 14.1, 13.9; Calcd for $C_{36}H_{47}F_3N_5O_5$ [M+H]⁺: 686.3524, Found: 686.3522.

217

Tert-butyl (S,E)-(((tert-butoxycarbonyl)amino)(2-(3-(4-(4-methoxyphenethyl)-3-(trifluoromethyl)phenyl)-1,2,4-oxadiazol-5-yl)pyrrolidin-1-yl)methylene)carbamate (6e)

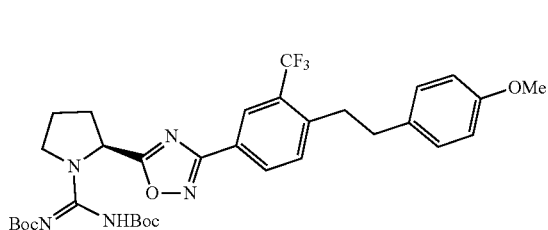

¹H NMR (400 MHz, Chloroform-d) δ 10.10 (s, 2H), 8.35 (d, J=1.7 Hz, 1H), 8.13 (dd, J=8.0, 1.8 Hz, 1H), 7.36 (d, J=8.1 Hz, 1H), 7.15-7.07 (m, 2H), 6.88-6.81 (m, 2H), 5.62 (dd, J=7.8, 4.5 Hz, 1H), 3.91 (dt, J=11.5, 7.1 Hz, 1H), 3.80 (d, J=0.5 Hz, 4H), 3.10 (dd, J=9.9, 6.5 Hz, 2H), 2.92-2.81 (m, 2H), 2.45 (dt, J=13.2, 7.7 Hz, 1H), 2.21 (q, J=6.6 Hz, 2H), 2.12-1.95 (m, 1H), 1.58-1.30 (m, 18H); ¹³C NMR (101 MHz, cd₃od) δ 175.5, 163.4, 158.0, 154.1, 149.8, 146.4, 139.8, 129.0, 128.0, 126.4, 125.7, 125.4, 125.4, 125.1, 124.8, 124.4, 121.6, 121.5, 121.4, 121.4, 121.3, 121.0, 118.9, 110.0, 110.0, 109.8, 78.4, 75.6, 51.3, 45.5, 32.9, 32.7, 31.3, 24.1, 20.7, 20.1.

Tert-butyl ((E)-((tert-butoxycarbonyl)amino)((2S, 3S)-3-hydroxy-2-(3-(4-(4-methoxyphenethyl)-3-(trifluoromethyl)phenyl)-1,2,4-oxadiazol-5-yl)pyrrolidin-1-yl)methylene)carbamate (6eA)

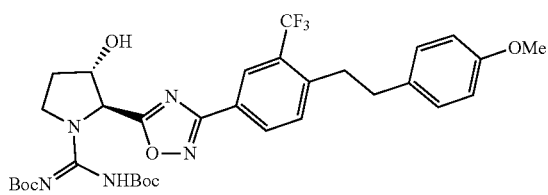

¹H NMR (400 MHz, Chloroform-d) δ 10.25-9.89 (brs, 1H), 8.31 (d, J=1.5 Hz, 1H), 8.10 (dd, J=8.0, 1.5 Hz, 1H), 7.34 (d, J=8.1 Hz, 1H), 7.14-7.05 (m, 2H), 6.86-6.79 (m, 2H), 5.52 (d, J=1.7 Hz, 1H), 4.62 (s, 1H), 4.07-3.89 (m, 2H), 3.78 (s, 3H), 3.44-3.03 (m, 3H), 2.85 (dd, J=9.7, 6.5 Hz, 2H), 2.43-1.31 (m, 1H), 2.17-2.07 (m, 1H), 1.44 (s, 18H); ¹³C NMR (101 MHz, cdcl₃) δ 177.4, 167.3, 153.8, 144.8, 144.8, 143.0, 135.6, 131.9, 131.6, 131.5, 130.5, 129.7, 129.4, 129.2, 129.1, 128.9, 128.8, 128.8, 128.7, 128.6, 128.3, 128.2, 128.2, 127.2, 125.6, 125.5, 125.5, 125.5, 125.4, 125.4, 125.0, 122.9, 122.7, 120.2, 120.0, 77.3, 77.2, 77.0, 76.7, 74.8, 63.3, 46.9, 37.4, 34.6, 32.0, 29.7, 28.0, 28.0.

218 tert-butyl (S,E)-(((tert-butoxycarbonyl)amino)(2-(3-(3-(trifluoromethyl)-4-(4-(trifluoromethyl)phenethyl)phenyl)-1,2,4-oxadiazol-5-yl)pyrrolidin-1-yl)methylene)carbamate (6f)

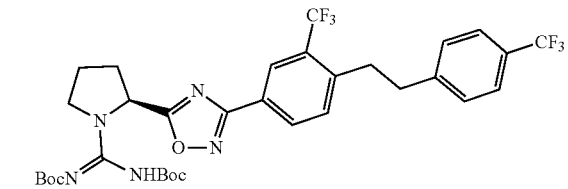

¹³C NMR (101 MHz, cdcl₃) δ 179.5, 167.2, 153.7, 144.8, 142.8, 131.8, 130.5, 129.4, 129.1, 128.8, 125.6, 125.5, 125.5, 125.5, 125.4, 125.4, 125.3, 82.3, 79.6, 77.2, 55.3 49.5, 37.4, 34.6 31.3, 28.1, 28.0 24.1.

tert-butyl ((E)-((tert-butoxycarbonyl)amino)((2S, 3S)-3-hydroxy-2-(3-(3-(trifluoromethyl)-4-(4-(trifluoromethyl)phenethyl)phenyl)-1,2,4-oxadiazol-5-yl)pyrrolidin-1-yl)methylene)carbamate (6fA)

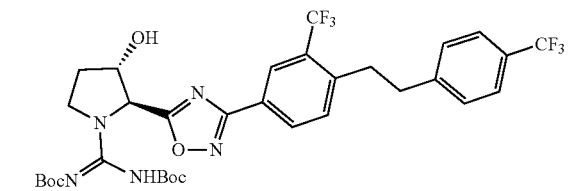

¹H NMR (400 MHz, Chloroform-d) δ 9.95 (s, 2H), 8.34 (d, J=1.7 Hz, 1H), 8.14 (dd, J=8.0, 1.8 Hz, 1H), 7.56 (d, J=8.0 Hz, 2H), 7.36 (d, J=8.1 Hz, 1H), 7.31 (d, J=8.0 Hz, 2H), 5.54 (d, J=2.3 Hz, 1H), 4.64 (dt, J=5.1, 2.9 Hz, 1H), 4.06-3.91 (m, 2H), 3.14 (dd, J=10.0, 6.3 Hz, 2H), 2.99 (dd, J=10.1, 6.2 Hz, 2H), 2.45-2.32 (m, 1H), 2.19-2.06 (m, 1H); ¹³C NMR (101 MHz, cdcl₃) δ 177.4, 167.3, 153.8, 144.8, 144.8, 143.0, 131.9, 130.5, 129.7, 129.4, 129.1, 128.8, 128.7, 128.6, ff125.6, 125.5, 125.5, 125.5, 125.4, 125.4, 125.0, 77.2, 74.8, 63.3, 46.9, 37.4, 34.6, 32.0, 28.0.

Tert-butyl (S,Z)-(((tert-butoxycarbonyl)amino)(2-(3-(4-(4-(tert-butyl)phenethyl)-3-(trifluoromethyl)phenyl)-1,2,4-oxadiazol-5-yl)pyrrolidin-1-yl)methylene)carbamate (6h)

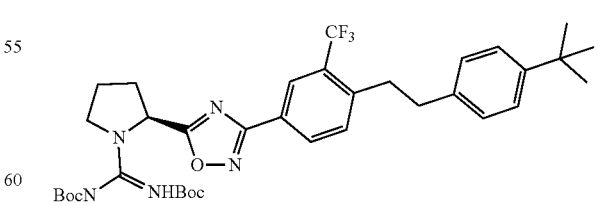

¹H NMR (400 MHz, Chloroform-d) δ 8.33 (d, J=1.7 Hz, 1H), 8.13 (dd, J=8.0, 1.8 Hz, 1H), 7.41 (d, J=8.1 Hz, 1H), 7.36-7.30 (m, 2H), 7.17-7.13 (m, 2H), 5.64 (dd, J=7.8, 4.9 Hz, 1H), 3.98-3.87 (m, 2H), 3.86-3.76 (m, 1H), 3.16-3.05 (m, 2H), 2.94-2.83 (m, 2H), 2.50-2.45 (m, 2H), 2.25-2.20

(m, 2H), 2.12-1.99 (m, 2H), 1.44 (s, 18H), 1.31 (s, 9H); $^{13}$C NMR (101 MHz, cdcl$_3$) δ 179.90, 166.72, 161.96, 135.57, 131.46, 131.12, 131.12, 130.80, 130.80, 130.62, 130.61, 129.36, 126.90, 126.84, 126.78, 126.34, 123.89, 123.06, 121.17, 77.32, 77.20, 77.00, 76.68, 55.31, 49.49, 31.22, 29.68, 28.06, 27.97, 27.49, 27.49; Calcd for C$_{36}$H$_{46}$F$_3$N$_5$O$_5$Na [M+Na]$^+$: 709.3418, Found: 709.3374.

Tert-butyl (S,Z)-(((tert-butoxycarbonyl)amino)(2-(3-(4-(4-hydroxybutoxy)-3-(trifluoromethyl)phenyl)-1,2,4-oxadiazol-5-yl)pyrrolidin-1-yl)methylene)carbamate (19)

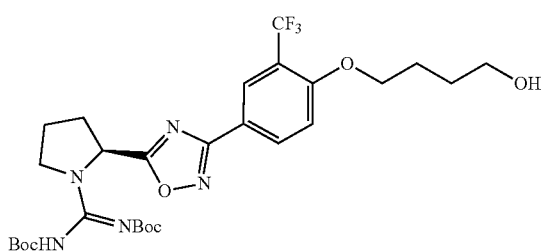

$^1$H NMR (400 MHz, Chloroform-d) δ 10.07 (s, 1H), 8.26 (s, 1H), 8.16 (d, J=2.1 Hz, 1H), 7.04 (d, J=8.8 Hz, 1H), 5.61-5.52 (m, 1H), 4.15 (d, J=6.1 Hz, 2H), 3.91-3.71 (m, 4H), 2.51-2.38 (m, 1H), 2.31-2.11 (m, 2H), 2.03-1.91 (m, 2H), 1.81-1.71 (m, 2H), 1.43 (s, 18H); Calcd for C$_{23}$H$_{33}$F$_3$N$_5$O$_5$ [M*+]$^-$: 514.2272, Found: 514.2259.

Example 41: (S)-2-(3-(4-(2-cyclopropylethyl)-3-(trifluoromethyl)phenyl)-1,2,4-oxadiazol-5-yl)pyrrolidine-1-carboximidamide hydrochloride (7a, compound 38A)

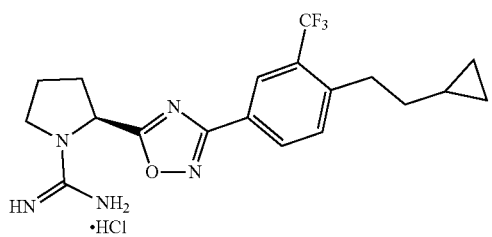 [SMILES: N=C(N)N1CCC[C@H]1c1nc(-c2ccc(CCC3CC3)c(C(F)(F)F)c2)no1 ; Cl]

$^1$H NMR (500 MHz, Methanol-d$_4$) δ 8.21 (d, J=1.8 Hz, 1H), 8.18-8.13 (m, 1H), 7.59-7.53 (m, 1H), 5.41 (dd, J=8.0, 1.8 Hz, 1H), 3.77-3.68 (m, 1H), 3.56 (td, J=9.7, 7.2 Hz, 1H), 2.95-2.86 (m, 0.5H), 2.82-2.74 (m, 1.5H), 2.59-2.36 (m, 2H), 2.56-2.38 (m, 1H), 2.21-2.08 (m, 1H), 2.07-1.95 (m, 1H), 1.65-1.55 (m, 1.5H), 1.52-1.45 (m, 0.5H), 1.39-1.27 (m, 3H), 0.91-0.81 (m, 2H), 0.43-0.38 (m, 0.5H), 0.02-0.01 (m, 0.5H); $^{13}$C NMR (101 MHz, cd$_3$od) δ 178.0, 167.2, 155.7, 145.4, 145.1, 132.3, 132.1, 130.3, 130.2, 124.3, 124.3, 124.3, 55.1, 36.5, 32.4, 32.3, 32.3, 31.5, 31.3, 31.0, 22.9, 22.0, 12.8, 10.3, 3.6; Calcd for C$_{21}$H$_{27}$F$_3$N$_5$O [M+H]$^+$: 422.2162, Found: 422.2163.

Example 42: (S)-2-(3-(4-(2-cyclopentylethyl)-3-(trifluoromethyl)phenyl)-1,2,4-oxadiazol-5-yl)pyrrolidine-1-carboximidamide hydrochloride (7b, compound 44A)

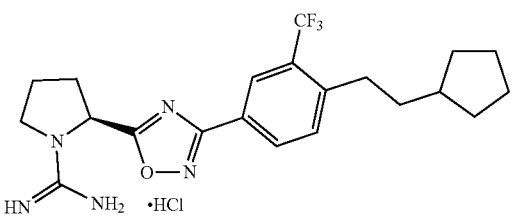 [SMILES: N=C(N)N1CCC[C@H]1c1nc(-c2ccc(CCC3CCCC3)c(C(F)(F)F)c2)no1 ; Cl]

$^1$H NMR (400 MHz, Methanol-d$_4$) δ 8.26 (d, J=1.6 Hz, 1H), 8.19 (dd, J=8.0, 1.7 Hz, 1H), 7.60 (d, J=8.1 Hz, 1H), 7.39 (s, 1H), 5.49-5.39 (m, 1H), 3.83-3.72 (m, 1H), 3.70-3.57 (m, 2H), 2.91-2.80 (m, 2H), 2.63-2.43 (m, 3H), 2.21 (s, 2H), 2.08 (s, 2H), 1.95-1.76 (m, 4H), 1.71-1.49 (m, 6H), 1.37-1.11 (m, 4H); $^{13}$C NMR (101 MHz, cd$_3$od) δ 178.0, 167.2, 147.1, 134.3, 132.1, 124.3, 95.6, 48.2, 48.0, 47.8, 47.6, 47.4, 47.1, 46.9, 40.2, 32.1, 31.7, 31.3, 24.7, 22.9, 19.4, 13.0, 7.8; Calcd for C$_{21}$H$_{26}$F$_3$N$_5$O [M+H]$^+$: 422.2162, Found: 422.

Example 43: (2S,3S)-2-(3-(4-(2-cyclopentylethyl)-3-(trifluoromethyl)phenyl)-1,2,4-oxadiazol-5-yl)-3-hydroxypyrrolidine-1-carboximidamide hydrochloride (7bA, compound 43A)

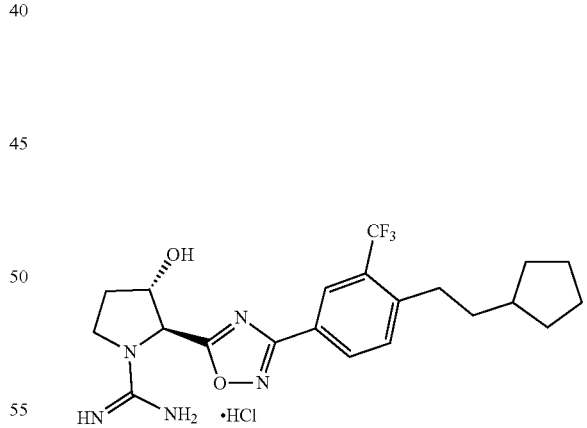

$^1$H NMR (500 MHz, Methanol-d$_4$) δ 8.29 (d, J=1.7 Hz, 1H), 8.23 (dd, J=8.1, 1.7 Hz, 1H), 7.64 (d, J=8.1 Hz, 1H), 5.26 (s, 1H), 3.89-3.81 (m, 2H), 3.23 (q, J=7.3 Hz, 2H), 2.92-2.85 (m, 2H), 2.30-2.15 (m, 2H), 1.99-1.82 (m, 3H), 1.74-1.53 (m, 4H), 1.33 (t, J=7.3 Hz, 1H), 1.28-1.15 (m, 1H), 1.20 (s, 1H); $^{13}$C NMR (126 MHz, MeOD) δ 175.8, 167.4, 145.7, 132.2, 130.3, 128.7, 128.5, 125.3, 124.4, 124.4, 124.3, 124.2, 123.2, 74.6, 63.4, 56.1, 46.6, 46.0, 40.2, 38.1, 32.2, 31.1, 24.7, 7.8; Calcd for C$_{21}$H$_{27}$F$_3$N$_5$O$_2$ [M+H]$^+$: 438.2117, Found: 438.0.

Example 44: (S)-amino(2-(3-(4-(2-cyclohexylethyl)-3-(trifluoromethyl)phenyl)-1,2,4-oxadiazol-5-yl)pyrrolidin-1-yl)methaniminium 2,2,2-trifluoroacetate (7c, compound 76A)

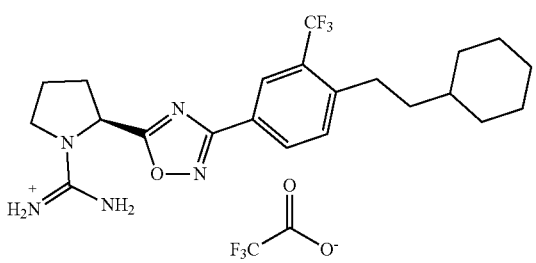 [SMILES: N=C(N)N1CCC[C@H]1c1nc(-c2ccc(CCC3CCCCC3)c(C(F)(F)F)c2)no1 ; O=C([O-])C(F)(F)F]

$^1$H NMR (400 MHz, Methanol-$d_4$) δ 9.26 (s, 2H), 6.44 (s, 1H), 4.77 (s, 1H), 4.70-4.56 (m, 1H), 4.20 (d, J=8.3 Hz, 3H), 3.84 (s, 1H), 3.52 (d, J=26.7 Hz, 2H), 3.15 (d, J=54.8 Hz, 3H), 2.51-2.71 (m, 6H), 2.29 (s, 6H), 2.11-1.72 (m, 3H); $^{13}$C NMR (101 MHz, cd$_3$od) δ 176.8, 164.8, 156.6, 153.2, 129.6, 128.0, 123.2, 122.2, 120.7, 115.7, 110.0, 49.2, 49.0, 48.7, 48.5, 48.3, 48.1, 47.9, 34.7, 32.3, 26.9, 22.8, 18.4, 9.5; Calcd for C$_{22}$H$_{26}$F$_3$N$_5$O [M+H]$^+$: 436.2324, Found: 436.2357.

Example 45: (S)-2-(3-(4-(4-ethylphenethyl)-3-(trifluoromethyl)phenyl)-1,2,4-oxadiazol-5-yl)pyrrolidine-1-carboximidamide hydrochloride (7i, compound 50A)

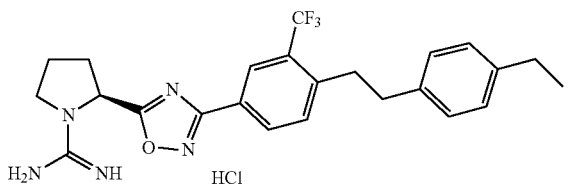 [SMILES: CCc1ccc(CCc2ccc(-c3noc([C@@H]4CCCN4C(=N)N)n3)cc2C(F)(F)F)cc1 ; Cl]

$^1$H NMR (400 MHz, Methanol-$d_4$) δ 8.30 (d, J=1.7 Hz, 1H), 8.20-8.14 (m, 1H), 7.56 (d, J=8.1 Hz, 1H), 7.43 (s, 1H), 7.11 (s, 4H), 5.47 (dd, J=7.9, 1.8 Hz, 1H), 3.83-3.74 (m, 1H), 3.62-3.57 (m, 1H), 3.15-3.07 (m, 2H), 2.93-2.85 (m, 2H), 2.64-2.52 (m, 3H), 2.51-2.44 (m, 1H), 2.29-2.17 (m, 1H), 2.15-2.01 (m, 1H), 1.20 (t, J=7.6 Hz, 3H); $^{13}$C NMR (101 MHz, cd$_3$od) δ 178.1, 167.2, 155.7, 144.2, 142.0, 137.9, 132.4, 130.2, 128.9, 128.6, 128.0, 127.5, 125.6, 124.5, 124.4, 124.4, 124.3, 124.3, 124.3, 122.9, 55.1, 48.2, 48.1, 48.0, 47.9, 47.8, 47.7, 47.6, 47.6, 47.6, 47.4, 47.4, 47.2, 47.2, 46.9, 36.9, 34.8, 34.8, 31.3, 28.1, 22.9, 14.9; Calcd for C$_{24}$H$_{26}$F$_3$N$_5$O [M+H]$^+$: 458.2168, Found: 458.

Example 46: (S)-2-(3-(4-(4-propylphenethyl)-3-(trifluoromethyl)phenyl)-1,2,4-oxadiazol-5-yl)pyrrolidine-1-carboximidamide hydrochloride (7d, compound 35A)

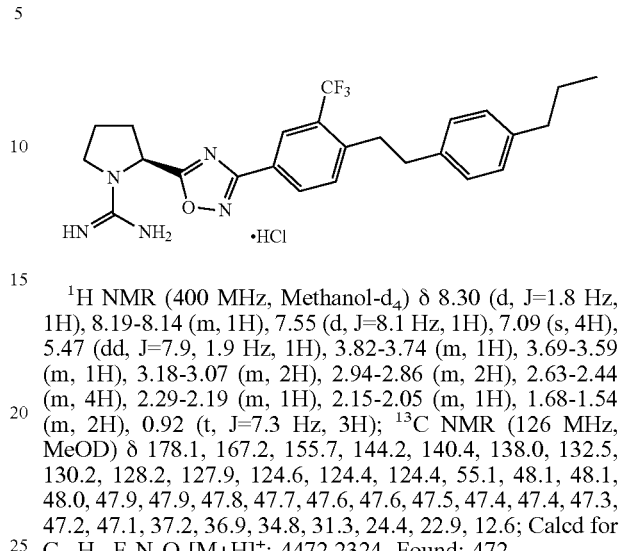

$^1$H NMR (400 MHz, Methanol-$d_4$) δ 8.30 (d, J=1.8 Hz, 1H), 8.19-8.14 (m, 1H), 7.55 (d, J=8.1 Hz, 1H), 7.09 (s, 4H), 5.47 (dd, J=7.9, 1.9 Hz, 1H), 3.82-3.74 (m, 1H), 3.69-3.59 (m, 1H), 3.18-3.07 (m, 2H), 2.94-2.86 (m, 2H), 2.63-2.44 (m, 4H), 2.29-2.19 (m, 1H), 2.15-2.05 (m, 1H), 1.68-1.54 (m, 2H), 0.92 (t, J=7.3 Hz, 3H); $^{13}$C NMR (126 MHz, MeOD) δ 178.1, 167.2, 155.7, 144.2, 140.4, 138.0, 132.5, 130.2, 128.2, 127.9, 124.6, 124.4, 124.4, 55.1, 48.1, 48.1, 48.0, 47.9, 47.9, 47.8, 47.7, 47.6, 47.6, 47.5, 47.4, 47.4, 47.3, 47.2, 47.1, 37.2, 36.9, 34.8, 31.3, 24.4, 22.9, 12.6; Calcd for C$_{25}$H$_{29}$F$_3$N$_5$O [M+H]$^+$: 4472.2324, Found: 472.

Example 47: (2S,3S)-3-hydroxy-2-(3-(4-(4-propylphenethyl)-3-(trifluoromethyl)phenyl)-1,2,4-oxadiazol-5-yl)pyrrolidine-1-carboximidamide hydrochloride (7dA, compound 34A)

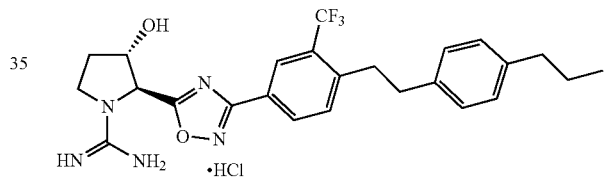

$^1$H NMR (500 MHz, Methanol-$d_4$) δ 8.24-8.17 (m, 1H), 8.07 (td, J=6.1, 5.7, 2.9 Hz, 1H), 7.46 (dd, J=8.1, 3.8 Hz, 1H), 5.46 (d, J=4.4 Hz, 0.4H), 5.15 (s, 0.4H), 4.71-4.69 (m, 1H), 3.80-3.68 (m, 1H), 3.64-3.54 (m, 1H), 3.11-2.95 (m, 2H), 2.85-2.78 (m, 2H), 2.50-2.39 (m, 2H), 2.19-2.03 (m, 2H), 1.58-1.41 (m, 8H), 1.28-1.07 (m, 4H), 0.83 (t, J=7.3 Hz, 3H); $^{13}$C NMR (101 MHz, cd$_3$od) δ 187.5, 175.8, 167.3, 156.2, 147.2, 144.3, 140.3, 137.9, 132.5, 130.2, 129.0, 128.7, 128.2, 127.9, 125.6, 124.5, 122.9, 74.6, 63.4, 46.0, 37.2, 34.7, 31.1, 24.3, 12.6; Calcd for C$_{25}$H$_{29}$F$_3$N$_5$O$_2$ [M+H]$^+$: 488.2269, Found: 488.2268.

Example 48: (S)-2-(3-(4-(4-butylphenethyl)-3-(trifluoromethyl)phenyl)-1,2,4-oxadiazol-5-yl)pyrrolidine-1-carboximidamide hydrochloride (7g, compound 36A)

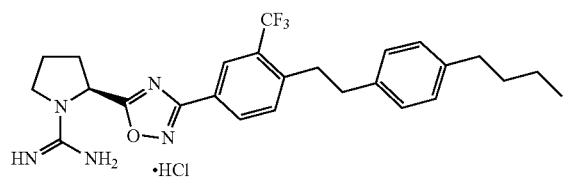 [SMILES: CCCCc1ccc(CCc2ccc(-c3noc([C@@H]4CCCN4C(=N)N)n3)cc2C(F)(F)F)cc1 ; Cl]

¹H NMR (500 MHz, Methanol-d₄) δ 8.20 (s, 1H), 8.08 (d, J=7.4 Hz, 1H), 7.46 (d, J=7.7 Hz, 1H), 5.39 (s, 1H), 3.45-3.55 (m, 2H), 3.08-2.98 (m, 2H), 2.80 (dd, J=9.7, 6.4 Hz, 2H), 2.48 (t, J=7.7 Hz, 3H), 2.14 (s, 1H), 1.99 (s, 1H), 1.31-1.17 (m, 4H), 0.84 (t, J=7.3 Hz, 4H). ¹³C NMR (101 MHz, cd₃od) δ 178.1, 167.2, 155.7, 154.7, 154.1, 154.0, 151.7, 151.2, 144.2, 140.5, 137.9, 132.5, 130.2, 128.1, 128.1, 128.0, 124.6, 85.9, 84.5, 55.2, 48.2, 48.0, 47.8, 47.6, 47.4, 47.2, 47.0, 36.9, 34.8, 31.4, 26.8, 26.7, 26.7, 23.0, 21.9, 12.9; Calcd for C₂₆H₃₁F₃N₅O [M+H]⁺: 486.2481, Found: 486.0.

Example 49: (2S,3S)-2-(3-(4-(4-butylphenethyl)-3-(trifluoromethyl)phenyl)-1,2,4-oxadiazol-5-yl)-3-hydroxypyrrolidine-1-carboximidamide hydrochloride (7gA, compound 37A)

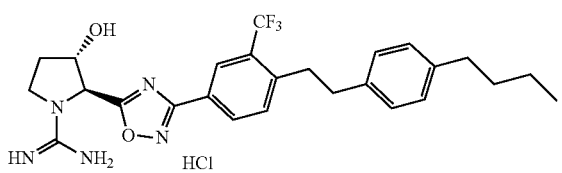 [SMILES: CCCCc1ccc(CCc2ccc(-c3noc([C@@H]4[C@@H](O)CCN4C(=N)N)n3)cc2C(F)(F)F)cc1 ; Cl]

¹H NMR (500 MHz, Methanol-d₄) δ 8.20 (s, 1H), 8.08 (d, J=7.2 Hz, 1H), 7.44-7.35 (m, 1H), 7.00 (s, 4H), 5.15 (s, 1H), 4.73-4.68 (m, 1H), 3.83-3.67 (m, 2H), 3.01-2.97 (m, 2H), 2.85-2.75 (m, 2H), 2.51-2.46 (m, 2H), 2.21-2.01 (m, 2H), 1.55-1.38 (m, 4H), 1.31-1.15 (m, 6H), 0.84 (t, J=7.3 Hz, 4H); ¹³C NMR (101 MHz, cd₃od) δ 187.6, 175.8, 167.3, 156.2, 147.5, 144.3, 140.5, 137.8, 132.5, 130.2, 129.7, 129.4, 129.0, 128.1, 127.9, 125.6, 124.4, 124.4, 122.9, 74.6, 63.4, 36.9, 34.8, 33.6, 31.1, 21.9, 12.8; Calcd for C₂₆H₃₀F₃N₅O₂ [M+H]⁺: 502.2430, Found: 502.

Example 50: (2S,3S)-3-hydroxy-2-(3-(4-(4-methoxyphenethyl)-3-(trifluoromethyl)phenyl)-1,2,4-oxadiazol-5-yl)pyrrolidine-1-carboximidamide hydrochloride (7eA, compound 41A)

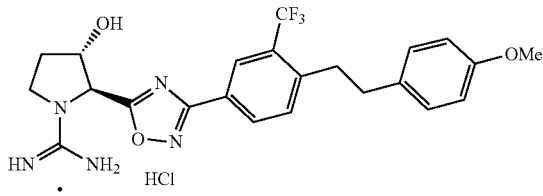 [SMILES: COc1ccc(CCc2ccc(-c3noc([C@@H]4[C@@H](O)CCN4C(=N)N)n3)cc2C(F)(F)F)cc1 ; Cl]

¹H NMR (400 MHz, Chloroform-d) δ 10.10 (s, 1H), 8.35 (d, J=1.7 Hz, 1H), 8.13 (dd, J=8.0, 1.8 Hz, 1H), 7.36 (d, J=8.1 Hz, 1H), 7.18-7.06 (m, 2H), 6.90-6.80 (m, 2H), 5.62 (dd, J=7.8, 4.5 Hz, 1H), 3.80 (d, J=0.5 Hz, 5H), 3.10 (dd, J=9.9, 6.5 Hz, 2H), 2.94-2.80 (m, 2H), 2.45 (dt, J=13.2, 7.7 Hz, 1H), 2.21 (q, J=6.6 Hz, 2H), 2.12-1.94 (m, 1H), 1.74-1.30 (m, 17H); ¹³C NMR (101 MHz, cd₃od) δ 175.8, 167.3, 158.3, 156.2, 144.3, 132.7, 132.5, 130.2, 129.0, 124.4, 113.5, 74.6, 63.4, 54.2, 48.2, 48.1, 48.0, 47.8, 47.6, 47.5, 47.4, 47.2, 47.0, 46.9, 46.0, 36.4, 34.9, 34.9, 31.1, 26.7; Calcd for C₂₃H₂₅F₃N₅O₃ [M+H]⁺: 476.1909, Found: 476.0.

Example 51: (S)-2-(3-(4-(4-methoxyphenethyl)-3-(trifluoromethyl)phenyl)-1,2,4-oxadiazol-5-yl)pyrrolidine-1-carboximidamide hydrochloride (7e, compound 42A)

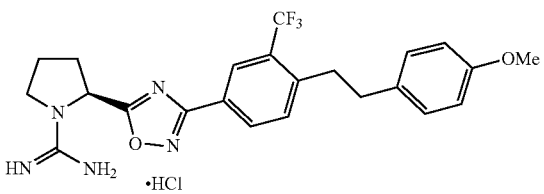 [SMILES: COc1ccc(CCc2ccc(-c3noc([C@@H]4CCCN4C(=N)N)n3)cc2C(F)(F)F)cc1 ; Cl]

¹H NMR (400 MHz, Methanol-d₄) δ 8.22 (d, J=1.6 Hz, 1H), 8.13-8.07 (m, 1H), 7.47 (d, J=8.0 Hz, 1H), 7.07-7.01 (m, 2H), 6.80-6.72 (m, 2H), 5.44 (d, J=7.5 Hz, 1H), 3.73-3.67 (m, 1H), 3.63-3.51 (m, 1H), 3.07-2.97 (m, 2H), 2.83-2.74 (m, 2H), 2.58-2.39 (m, 2H), 2.24-2.12 (m, 1H), 2.02 (d, J=8.1 Hz, 1H); ¹³C NMR (101 MHz, cd₃od) δ 178.0, 167.2, 158.2, 155.7, 144.1, 144.1, 132.7, 132.4, 130.2, 129.0, 128.9, 128.6, 125.6, 124.5, 124.4, 124.4, 124.3, 124.2, 122.9, 113.5, 55.1, 54.3, 54.3, 48.3, 48.1, 47.8, 47.7, 47.6, 47.4, 47.2, 47.0, 36.4, 34.9, 34.8, 31.3, 22.9; Calcd for C₂₃H₂₅F₃N₅O₂ [M+H]⁺: 460.1960, Found: 460.0.

Example 52: (S)-2-(3-(3-(trifluoromethyl)-4-(4-(trifluoromethyl)phenethyl)phenyl)-1,2,4-oxadiazol-5-yl)pyrrolidine-1-carboximidamide hydrochloride (7f, compound 39A)

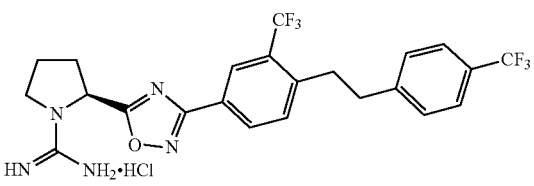

¹H NMR (500 MHz, Methanol-d₄) δ 8.34 (d, J=1.8 Hz, 1H), 8.23 (dd, J=8.0, 1.8 Hz, 1H), 7.62 (dd, J=12.2, 8.0 Hz, 3H), 7.43 (d, J=7.9 Hz, 2H), 5.51 (dd, J=8.0, 1.8 Hz, 1H), 3.85-3.77 (m, 1H), 3.65 (td, J=9.7, 7.3 Hz, 1H), 3.20 (dd, J=9.8, 6.4 Hz, 2H), 3.10-3.02 (m, 2H), 2.66-2.46 (m, 2H), 2.31-2.21 (m, 1H), 2.15-2.05 (m, 1H); ¹³C NMR (101 MHz, cd₃od) δ 178.1, 143.5, 132.4, 130.3, 128.8, 128.7, 128.4, 128.1, 125.0, 125.0, 124.9, 124.8, 124.5, 124.4, 124.3, 122.9, 55.1, 36.8, 34.1, 31.3, 22.9.

Example 54: (2S,3S)-3-hydroxy-2-(3-(3-(trifluoromethyl)-4-(4-(trifluoromethyl)phenethyl)phenyl)-1,2,4-oxadiazol-5-yl)pyrrolidine-1-carboximidamide hydrochloride (7fA, compound 40A)

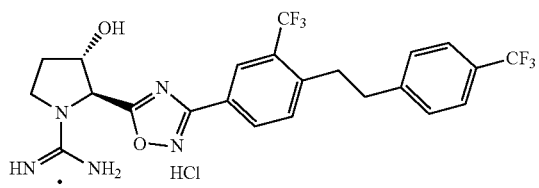 [SMILES: N=C(N)N1CC[C@H](O)[C@H]1c1nc(-c2ccc(CCc3ccc(C(F)(F)F)cc3)c(C(F)(F)F)c2)no1 ; Cl]

¹H NMR (500 MHz, Methanol-d₄) δ 8.22 (dd, J=6.1, 1.6 Hz, 1H), 8.14-8.06 (m, 1H), 7.56-7.42 (m, 3H), 7.32-7.28 (m, 2H), 5.45 (d, J=4.4 Hz, 1H), 4.10 (d, J=10.2 Hz, 1H), 4.00 (q, J=7.1 Hz, 2H), 3.50 (s, 1H), 3.13-3.05 (m, 2H), 2.95 (t, J=7.9 Hz, 2H), 2.12 (d, J=6.0 Hz, 1H), 1.91 (s, 1H); HRMS (ESI+): Calcd for $C_{23}H_{26}F_6N_6O_2NH_4$ [M+NH₄]⁺: 532.2016, Found: 532.1976.

Example 55: (S)-2-(3-(4-(4-(tert-butyl)phenethyl)-3-(trifluoromethyl)phenyl)-1,2,4-oxadiazol-5-yl)pyrrolidine-1-carboximidamide hydrochloride (7h, compound 62A)

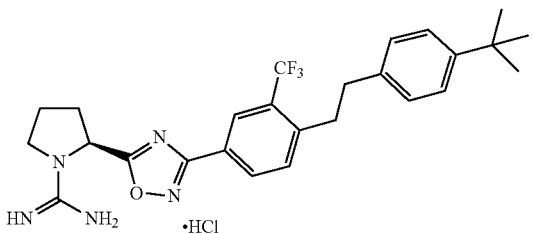 [SMILES: CC(C)(C)c1ccc(CCc2ccc(-c3noc([C@@H]4CCCN4C(=N)N)n3)cc2C(F)(F)F)cc1 ; Cl]

¹H NMR (400 MHz, Methanol-d₄) δ 8.30 (d, J=1.8 Hz, 1H), 8.27-8.15 (m, 1H), 7.59 (t, J=8.6 Hz, 1H), 7.37-7.26 (m, 2H), 7.18-7.07 (m, 2H), 5.46 (dd, J=7.9, 1.9 Hz, 1H), 3.84-3.73 (m, 1H), 3.68-3.50 (m, 1H), 3.17-3.03 (m, 2H), 2.94-2.82 (m, 2H), 2.65-2.42 (m, 2H), 2.33-2.18 (m, 1H), 2.17-2.00 (m, 1H), 1.30 (s, 9H); ¹³C NMR (101 MHz, cd₃od) δ 178.1, 167.2, 155.7, 148.8, 144.3, 137.7, 132.4, 130.2, 127.7, 125.0, 124.6, 124.5, 124.4, 124.4, 124.3, 55.1, 48.2, 48.0, 47.9, 47.8, 47.8, 47.6, 47.5, 47.4, 47.1, 47.1, 46.9, 46.7, 36.8, 36.8, 34.8, 34.7, 33.8, 31.3, 31.3, 30.4, 30.4, 22.9; Calcd for $C_{26}H_{30}F_3N_5O$ [M+H]⁺: 486.2481, Found: 486.0.

tert-butyl (S)-2-(3-(4-(4-hydroxybutoxy)-3-(trifluoromethyl)phenyl)-1,2,4-oxadiazol-5-yl)pyrrolidine-1-carboxylate (23)

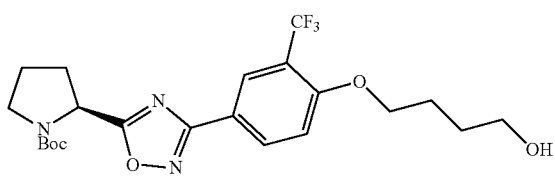 [SMILES: CC(C)(C)OC(=O)N1CCC[C@H]1c1nc(-c2ccc(OCCCCO)c(C(F)(F)F)c2)no1]

¹H NMR (500 MHz, Chloroform-d) δ 8.29 (d, J=2.8 Hz, 1H), 8.20 (d, J=8.2 Hz, 1H), 7.13-7.05 (m, 1H), 5.21-5.18 (m, 0.4H), 5.09-5.03 (m, 0.6H), 4.21-4.11 (m, 2H), 3.80-3.63 (m, 3H), 3.62-3.45 (m, 1H), 2.51-2.31 (m, 1H), 2.21-2.08 (m, 2H), 2.05-1.91 (m, 3H), 1.90-1.71 (m, 3H), 1.52-1.41 (m, 3H), 1.31-1.21 (m, 6H).

Example 56: (S)-2-(3-(4-(4-hydroxybutoxy)-3-(trifluoromethyl)phenyl)-1,2,4-oxadiazol-5-yl)pyrrolidine-1-carboximidamide hydrochloride (20b, compound 45A)

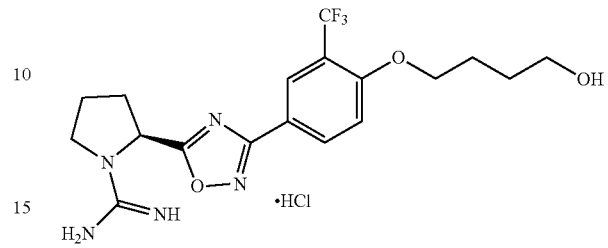

¹H NMR (500 MHz, Methanol-d₄) δ 8.21-8.11 (m, 2H), 7.34-7.24 (m, 1H), 5.41-5.31 (m, 1H), 4.19-4.10 (m, 2H), 3.68-3.41 (m, 7H), 2.55-2.35 (m, 2H), 2.21-2.05 (m, 1H), 2.04-1.87 (m, 1H), 1.86-1.74 (m, 2H), 1.73-1.59 (m, 2H); ¹³C NMR (126 MHz) δ 177.8, 167.2, 159.4, 155.7, 132.6, 125.7, 118.0, 113.5, 72.2, 71.0, 68.8, 66.7, 61.1, 55.1, 47.9, 47.8, 47.6, 47.4, 47.3, 47.3, 47.2, 31.3, 28.6, 25.3, 22.9; Calcd for $C_{18}H_{23}F_3N_5O_3$ [M+H]⁺: 414.1748, Found: 414.175.

tert-butyl (S)-2-(3-(4-(tert-butoxy)-3-(trifluoromethyl)phenyl)-1,2,4-oxadiazol-5-yl)pyrrolidine-1-carboxylate (15)

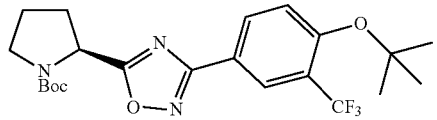 [SMILES: CC(C)(C)OC(=O)N1CCC[C@H]1c1nc(-c2ccc(OC(C)(C)C)c(C(F)(F)F)c2)no1]

¹H NMR (400 MHz, Chloroform-d) δ 8.27 (d, J=2.2 Hz, 1H), 8.12 (dd, J=8.7, 2.2 Hz, 1H), 7.32-7.22 (m, 2H), 5.19 (d, J=8.1 Hz, 0H), 5.06 (dd, J=8.4, 3.5 Hz, 1H), 3.70 (d, J=6.8 Hz, 1H), 3.62-3.42 (m, 1H), 2.48-2.28 (m, 1H), 2.22-1.94 (m, 4H), 1.51 (d, J=8.2 Hz, 9H), 1.46 (s, 3H), 1.30 (s, 5H).

Tert-butyl (S)-2-(3-(4-hydroxy-3-(trifluoromethyl)phenyl)-1,2,4-oxadiazol-5-yl)pyrrolidine-1-carboxylate (16)

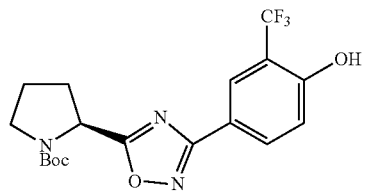 [SMILES: CC(C)(C)OC(=O)N1CCC[C@H]1c1nc(-c2ccc(O)c(C(F)(F)F)c2)no1]

¹H NMR (400 MHz, Methanol-d₄) δ 8.14 (s, 1H), 8.09-7.99 (m, 1H), 7.09-6.99 (m, 1H), 5.15-5.01 (m, 1H), 3.69-3.59 (m, 1H), 3.51-3.41 (m, 1H), 2.53-2.34 (m, 1H), 2.19-1.92 (m, 3H), 1.44 (s, 3H), 1.25 (s, 6H); ¹³C NMR (101 MHz, cd₃od) δ 181.0, 180.6, 167.2, 158.6, 154.7, 154.0, 131.9, 125.7, 124.9, 122.2, 117.1, 80.5, 53.8, 46.5, 46.1, 31.8, 31.0, 27.0, 23.9, 23.3.

Tert-butyl (S)-2-(3-(4-(4-hydroxybutoxy)-3-(trifluoromethyl)phenyl)-1,2,4-oxadiazol-5-yl)pyrrolidine-1-carboxylate (23)

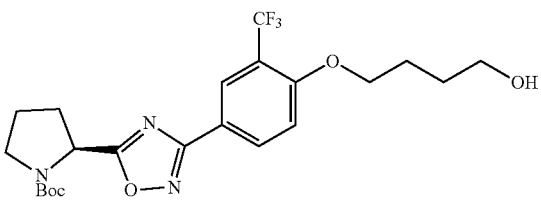 [SMILES: CC(C)(C)OC(=O)N1CCC[C@H]1c1nc(-c2ccc(OCCCCO)c(C(F)(F)F)c2)no1]

¹H NMR (400 MHz, Chloroform-d) 68.28-8.24 (m, 1H), 8.20-8.16 (m, 1H), 7.10-7.01 (m, 1H), 5.23-4.92 (m, 1H), 4.16 (t, J=6.0 Hz, 1H), 3.72 (q, J=6.3 Hz, 3H), 3.64-3.39 (m, 1H), 2.41-2.25 (m, 1H), 2.20-2.06 (m, 2H), 2.05-1.88 (m, 3H), 1.81-1.61 (m, 4H), 1.45 (s, 3H), 1.29 (s, 5H); ¹³C NMR (101 MHz, cdcl₃) δ 180.8, 180.4, 167.2, 159.0, 153.2, 132.4, 126.5, 118.5, 112.9, 80.5, 68.8, 62.0, 53.7, 46.6, 46.3, 32.3, 31.4, 28.9, 28.3, 28.1, 25.4, 24.3, 23.6.

(S)-(2-(3-(4-(4-acetoxybutoxy)-3-(trifluoromethyl)phenyl)-1,2,4-oxadiazol-5-yl)pyrrolidin-1-yl)(amino)methaniminium 2,2,2-trifluoroacetate (20a)

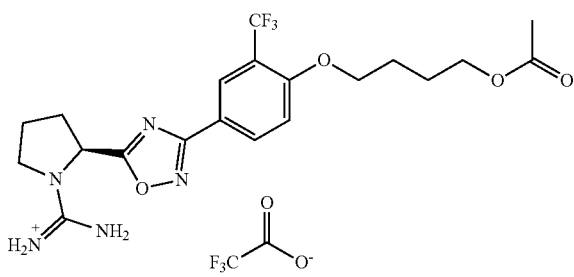 [SMILES: CC(=O)OCCCCOc1ccc(-c2noc([C@@H]3CCCN3C(=N)N)n2)cc1C(F)(F)F ; O=C([O-])C(F)(F)F]

¹H NMR (400 MHz, Methanol-d₄) δ 8.28-8.21 (m, 2H), 7.34 (d, J=8.7 Hz, 1H), 5.44 (dd, J=7.9, 1.9 Hz, 1H), 4.22 (t, J=5.8 Hz, 2H), 4.15 (t, J=6.2 Hz, 2H), 3.77 (td, J=9.3, 2.6 Hz, 1H), 3.61 (td, J=9.7, 7.2 Hz, 1H), 2.64-2.43 (m, 2H), 2.22 (s, 1H), 2.02 (s, 4H), 1.98-1.80 (m, 4H); ¹³C NMR (101 MHz, cdcl₃) δ 184.5, 171.7, 161.7, 143.0, 141.2, 138.2, 137.6, 132.5, 111.6, 98.2, 77.3, 68.2, 63.9, 59.2, 54.4, 49.5, 49.5, 49.3, 49.1, 48.9, 48.6, 48.4, 48.2, 45.1, 40.6, 25.4, 24.9, 20.7; Calcd for C₂₃H₃₀F₃N₃O₅Na [M+H]⁺: 456.1853, Found: 455.

Tert-butyl (S)-2-(3-(4-(4-methoxybutoxy)-3-(trifluoromethyl)phenyl)-1,2,4-oxadiazol-5-yl)pyrrolidine-1-carboxylate (24)

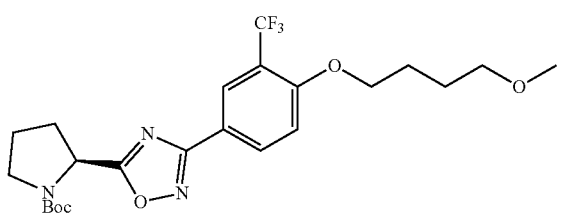 [SMILES: COCCCCOc1ccc(-c2noc([C@@H]3CCCN3C(=O)OC(C)(C)C)n2)cc1C(F)(F)F]

¹H NMR (400 MHz, Chloroform-d) δ 8.26 (s, 1H), 8.17 (d, J=8.6 Hz, 1H), 7.10-6.99 (m, 1H), 5.19-5.14 (m, 0.4H), 5.07-5.01 (m, 0.6H), 4.13 (t, J=6.1 Hz, 2H), 3.79-3.61 (m, 1H), 3.59-4.41 (m, 5H), 2.51-2.29 (m, 1H), 2.18-2.05 (m, 2H), 2.04-1.82 (m, 3H), 1.79-1.71 (m, 2H), 1.44 (s, 3H), 1.28 (s, 6H); ¹¹C NMR (101 MHz, cdcl₃) δ 167.2, 132.4, 112.9, 80.5, 72.1, 68.8, 58.5, 53.8, 53.4, 46.3, 32.4, 28.3, 28.1, 25.9, 25.8, 23.7; Calcd for C₂₃H₃₀F₃N₃O₅Na [M+Na]⁺: 509.2061, Found: 509.2039.

Tert-butyl (S)-2-(4-(4-(2-(benzyloxy)ethoxy)-3-(trifluoromethyl)phenyl)oxazol-2-yl)pyrrolidine-1-carboxylate (21)

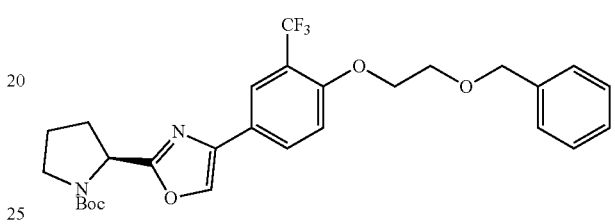

¹H NMR (500 MHz, Chloroform-d) δ 8.33 (d, J=2.2 Hz, 1H), 8.21 (dd, J=8.3, 2.5 Hz, 1H), 7.41-7.35 (m, 4H), 7.34-7.30 (m, 1H), 7.16-7.08 (m, 1H), 5.25-5.15 (m, 0.4H), 5.11-5.05 (m, 0.6H), 4.68 (s, 2H), 4.35-4.29 (m, 2H), 3.95-3.89 (m, 2H), 3.79-3.65 (m, 1H), 3.63-3.46 (m, 1H), 2.48-2.32 (m, 1H), 2.25-2.15 (m, 2H), 2.09-1.99 (m, 1H), 1.48 (s, 3H), 1.32 (s, 6H); ¹³C NMR (101 MHz, cdcl₃) δ 180.5, 167.4, 153.8, 153.8, 137.7, 132.0, 128.4, 128.4, 127.8, 127.8, 127.8, 117.3, 110.0, 80.8, 73.2, 71.5, 69.9, 61.4, 53.8, 49.5, 49.3, 49.0, 48.8, 48.6, 46.3, 32.2, 28.2, 28.0, 24.2, 23.6, 21.8; Calcd for C₂₇H₃₀F₃N₃O₅Na [M+Na]⁺: 556.2061 Found: 556.2082.

tert-butyl (S,E)-((2-(3-(4-(2-(benzyloxy)ethoxy)-3-(trifluoromethyl)phenyl)-1,2,4-oxadiazol-5-yl)pyrrolidin-1-yl)((tert-butoxycarbonyl)amino)methylene)carbamate

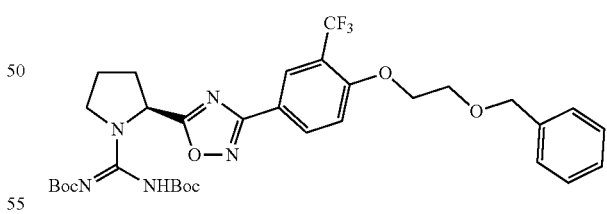

¹H NMR (400 MHz, Chloroform-d) δ 8.33 (d, J=1.8 Hz, 1H), 8.13 (dd, J=8.0, 1.8 Hz, 1H), 7.41 (d, J=8.1 Hz, 1H), 7.35-7.30 (m, 2H), 7.17-7.13 (m, 2H), 5.64 (dd, J=7.8, 4.9 Hz, 1H), 3.97-3.87 (m, 1H), 3.87-3.76 (m, 1H), 3.15-3.07 (m, 2H), 2.92-2.83 (m, 2H), 2.53-2.39 (m, 1H), 2.31-2.15 (m, 2H), 2.11-1.97 (m, 1H), 1.44 (s, 18H), 1.31 (s, 9H); ¹³C NMR (101 MHz, cdcl₃) δ 179.2, 167.4, 153.6, 149.1, 143.9, 137.9, 132.0, 131.9, 130.4, 129.3, 129.0, 128.9, 128.7, 128.1, 127.6, 125.6, 125.5, 125.4, 125.3, 125.2, 125.20, 124.8, 122.8, 81.3, 55.4, 49.7, 37.3, 35.0, 34.4, 31.4, 31.2, 29.7, 28.0, 27.9, 27.6, 24.1;

tert-butyl (S,Z)-(((tert-butoxycarbonyl)amino)(2-(3-(4-(4-methoxybutoxy)-3-(trifluoromethyl)phenyl)-1,2,4-oxadiazol-5-yl)pyrrolidin-1-yl)methylene)carbamate (25)

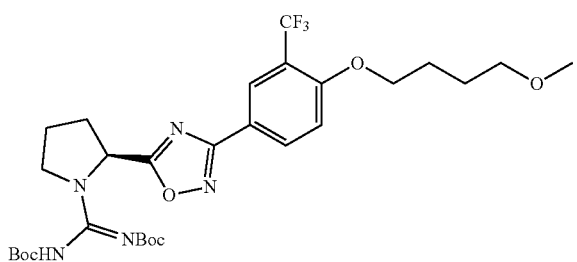

$^1$H NMR (400 MHz, Chloroform-d) δ 8.29-8.26 (m, 1H), 8.21-8.14 (m, 1H), 7.11-6.95 (m, 1H), 5.65-5.55 (m, 1H), 4.21-4.10 (m, 3H), 3.95-3.75 (m, 2H), 3.46 (t, 2H), 3.31 (s, 2H), 2.51-2.38 (m, 1H), 2.25-2.10 (m, 2H), 2.09-1.91 (m, 1H), 1.90-1.87 (m, 2H), 1.82-1.72 (m, 2H), 1.48-1.35 (m, 13H), 1.32-1.15 (m, 9H).

Example 57: (S)-2-(3-(4-(4-methoxybutoxy)-3-(trifluoromethyl)phenyl)-1,2,4-oxadiazol-5-yl)pyrrolidine-1-carboximidamide 2,2,2-trifluoroacetate (26, compound 46A)

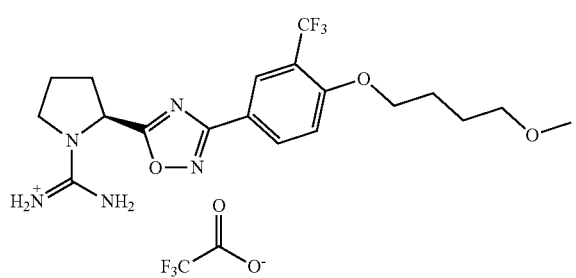 [SMILES: COCCCCOc1ccc(-c2noc([C@@H]3CCCN3C(=N)N)n2)cc1C(F)(F)F ; O=C([O-])C(F)(F)F]

$^1$H NMR (500 MHz, Methanol-$d_4$) δ 8.24-7.85 (m, 1H), 7.26-7.21 (m, 1H), 5.35 (dd, J=8.0, 1.9 Hz, 1H), 4.11 (t, J=6.1 Hz, 1H), 3.24 (s, 2H), 3.22-3.20 (m, 3H), 2.51-2.31 (m, 2H), 2.21-2.11 (m, 1H), 2.05-1.91 (m, 1H), 1.81-1.75 (m, 2H), 1.71-1.62 (m, 2H), 1.51-1.32 (m, 1H), 1.18 (s, 3H);

Example 58: (S)-2-(4-(4-(2-(benzyloxy)ethoxy)-3-(trifluoromethyl)phenyl)oxazol-2-yl)pyrrolidine-1-carboximidamide hydrochloride (22, compound 63A)

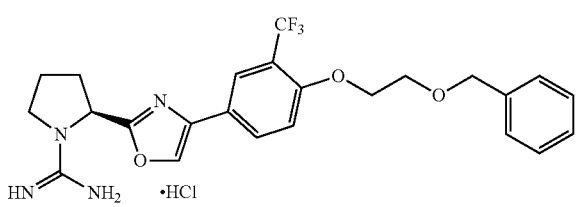 [SMILES: N=C(N)N1CCC[C@H]1c1nc(-c2ccc(OCCOCc3ccccc3)c(C(F)(F)F)c2)co1 ; Cl]

was synthesized using general procedure and isolated as a white solid (12 mg, 80%). $^1$H NMR (400 MHz, Methanol-$d_4$) δ 8.26-8.21 (m, 2H), 7.44-7.21 (m, 6H), 5.48-5.40 (dd, J=7.6, 1.8 Hz, 1H), 4.63 (s, 2H), 4.40-4.33 (m, 2H), 3.93-3.85 (m, 2H), 3.83-3.69 (m, 1H), 3.67-3.56 (m, 1H), 2.58-2.41 (m, 2H), 2.25-2.03 (m, 2H); $^{13}$C NMR (101 MHz, Methanol-$d_4$) δ 177.81, 167.09, 159.26, 155.65, 138.10, 132.48, 127.93, 127.27, 125.68, 125.63, 121.91, 119.16, 118.85, 118.31, 113.80, 72.84, 68.80, 68.02, 55.06, 48.21, 48.00, 48.00, 47.79, 47.57, 47.36, 47.33, 47.15, 46.94, 31.32, 22.91; Calcd for $C_{23}H_{25}F_3N_5O_3$ [M+H]$^+$: 478.1961, Found: 478.1989.

Examples 59-83 Synthesis and Characterization of Formulae IA and IB Compounds

Schemes 12 and 13 below outline general and specific synthetic methodologies for the preparation of Compound Nos. 12A, 14A-16A, 52A, 53A, 57A-59A, 61A, and 65A-75A. Compound numbering in Schemes 12 and 13 are internal to the Schemes, while the subsequent procedures refer where applicable to the final compounds.

Scheme 12

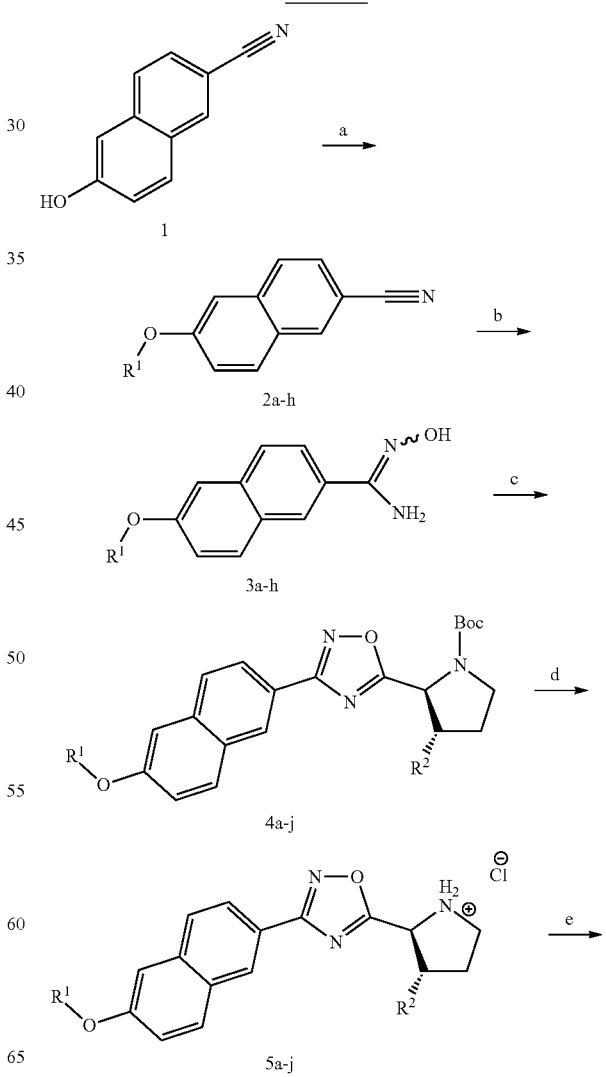

-continued

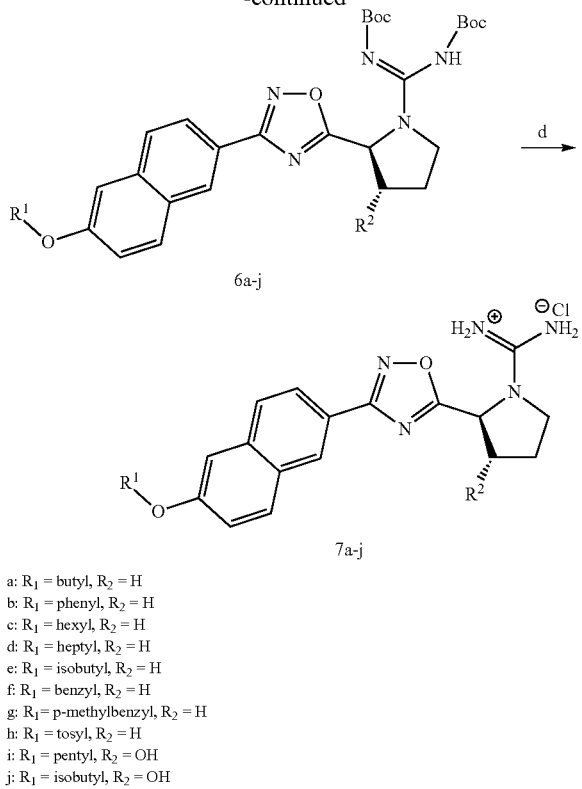

6a-j 7a-j a: R₁ = butyl, R₂ = H
b: R₁ = phenyl, R₂ = H
c: R₁ = hexyl, R₂ = H
d: R₁ = heptyl, R₂ = H
e: R₁ = isobutyl, R₂ = H
f: R₁ = benzyl, R₂ = H
g: R₁ = p-methylbenzyl, R₂ = H
h: R₁ = tosyl, R₂ = H
i: R₁ = pentyl, R₂ = OH
j: R₁ = isobutyl, R₂ = OH Scheme 12: a) R—Br or TosCl (1.2 equiv.), K₂CO₃ (4 equiv.), CH₃CN, 80° C., 4-12 h, (84-100%); b) NH₂OH·HCl, (3 equiv.), TEA (3 equiv.), EtOH, 80° C., 6 h, (67-98%); c) Boc-L-proline (1.4 equiv.), DIEA (1.4 equiv.), HCTU (1.8 equiv.), DMF, 110° C., 18 h, (13-90%); d) HCl/MeOH, (42-100%); e) DIEA (3 equiv.), N,N-DiBoc-1H-pyrazole-1carboxamidine (1.05 equiv.), CH₃CN, rt, 3 days, (27-84%).

General Procedures

General Procedure 1—Williamson Ether Synthesis

6-Hydroxy-2-napthalnitrile 1 (1 equiv.), potassium carbonate (4 equiv.) and alkyl halide (1.2 equiv.) were added to a round bottom flask containing acetonitrile. The reaction mixture was heated to 80° C. for 4-12 hours until TLC indicated the starting material had been fully consumed. The reaction mixture was extracted with ethyl acetate and D.I. water. The combined organic layers were washed with brine and dried over sodium sulfate. After filtration and concentration via reduced pressure, the resulting brown oil was purified on a silica column with hexane and ethyl acetate.

General Procedure 2—Amidoxime Formation

Nitrile 2a-d (1 equiv.), hydroxylamine hydrochloride (3 equiv.), TEA (3 equiv.) were added to a round bottom flask containing ethanol. The reaction mixture was heated to 80° C. for 6-12 hours and monitored via TLC. Once the starting material was consumed, the solution was cooled to room temperature, concentrated under reduced pressure, loaded onto celite, and purified on a silica column with hexane and ethyl acetate.

General Procedure 3-1,2,4-Oxadiazole Formation with HCTU

Amidoxime (3a-d) (1 equiv.), Boc-L-proline (1.4 equiv.) or Boc-trans-3-hydroxy-L-proline (1.4 equiv.), and DIEA (1.4 equiv.) were added to a round bottom flask containing DMF. HCTU (1.8 equiv.) was added to the reaction solution, the flask was connected to a reflux condenser and heated to 120° C. for 12-16 hours. Once the reaction cooled to room temperature, the solution was extracted with ethyl acetate and saturated LiBr solution. The combined organic layers were washed with brine and dried over sodium sulfate. After filtration to remove the sodium sulfate and concentration via reduced pressure, the resulting brown oil was purified on a silica column with hexane and ethyl acetate.

General Procedure 4—Boc-Deprotection

Boc-amine 4a-e or Di-Boc-guanidine 6a-e was dissolved in methanol. HCl gas was bubbled into the solution for 1 minute. The solution was stirred until TLC indicated that all of the Boc-protected amine had been consumed. The solvent was removed under reduced pressure. The resulting white to light yellow solid was washed with diethyl ether to yield pure product.

General Procedure 5—Guanylation of Secondary Amines

Hydrogen chloride salt 5a-e (1 equiv.) was added to a round bottom flask with acetonitrile and DIEA (3 equiv.). The solution was allowed to stir for 10 minutes before the addition of (Z)-Tert-butyl (((tert-butoxycarbonyl)imino) (1H-pyrazol-1-yl)methyl)carbamate (1.05 equiv.). The solution was stirred at room temperature under nitrogen until TLC indicated that the starting material had been consumed.

General Procedure 6—Amidoxime Formation in Microwave

Nitrile 1 (1 equiv.), hydroxylamine hydrochloride (2 equiv.), TEA (3 equiv.) were added to a 20 mL microwave vial containing ethanol. The reaction mixture was heated to 150° C. for 2 minutes in the microwave. The reaction mixture was concentrated under reduced pressure, loaded onto celite, and purified on a silica column with 80-100% ethyl acetate and hexane.

General Procedure 7-1,2,4-Oxadiazole Formation with PyBOP

Amidoxime (8) (1 equiv.), Boc-L-proline (1.1 equiv.), and DIEA (3 equiv.) were added to a round bottom flask containing DMF. PyBOP (1.2 equiv.) was added to the flask and the solution was heated to 110° C. overnight. Once the reaction cooled to room temperature, the solution was extracted with ethyl acetate and saturated Na₂CO₃ solution. The combined organic layers were washed with brine and dried over sodium sulfate. After filtration to remove the sodium sulfate and concentration via reduced pressure, the resulting brown oil was purified on a silica column with 20-35% ethyl acetate in hexane.

General Procedure 8—Boc-Deprotection in Microwave

Boc-amine 9 or Di-Boc-guanidine 11, 6k-bb was dissolved in a 4N HCl in dioxane solution (3 equiv.). The solution was heated to 100° C. for 1 minute in the microwave. The solvent was removed under reduced pressure. The resulting white to light yellow solid was washed with diethyl ether to yield pure product.

General Procedure 9—Guanylation of Secondary Amines in Microwave

Hydrogen chloride salt 10 (1 equiv.) was added to microwave vial with acetonitrile and DIEA (3 equiv.). The solution was allowed to stir for 30 seconds before the addition of (Z)-Tert-butyl (((tert-butoxycarbonyl)imino)(1H-pyrazol-1-yl)methyl)carbamate (0.8 equiv.) The solution was heated to 85° C. in the microwave for 30 minutes. The solvent was removed by reduced pressure and the resulting residue was purified on a silica column with hexane and ethyl acetate.

General Procedure 10—Williamson Ether Synthesis in Microwave

Di-Boc-guanidine 11 (1 equiv.), potassium carbonate (2 equiv.) alkyl halide (1.2 equiv.) and sodium iodide (0.1 equiv.) were added to a microwave vial containing ethanol. The reaction mixture was heated to 100° C. for 15. The solvent was removed under reduced pressure and the resulting residue was extracted with ethyl acetate and D.I. water. The combined organic layers were washed with brine and dried over sodium sulfate. After filtration and concentration via reduced pressure, the resulting residue was purified on a silica column with hexane and ethyl acetate.

Synthesis and Characterization 6-(butyloxy)-2-naphthonitrile (2a)

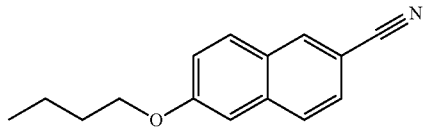 [SMILES: CCCCOc1ccc2cc(C#N)ccc2c1]

2a was synthesized using general procedure 1. Purification on a silica gel column with 0-20% ethyl acetate in hexanes produced 2a (498 mg, 93%), a white solid. $^1$H NMR (500 MHz, CDCl$_3$) δ 8.05 (d, J=1.7 Hz, 1H), 7.71 (dd, J=8.7, 2.6 Hz, 2H), 7.50 (dd, J=8.5, 1.7 Hz, 1H), 7.21 (dd, J=9.0, 2.5 Hz, 1H), 7.09 (d, J=2.5 Hz, 1H), 4.06 (t, J=6.5 Hz, 2H), 1.87-1.78 (m, 2H), 1.53 (h, J=7.5 Hz, 2H), 1.00 (t, J=7.4 Hz, 3H). $^{13}$C NMR (126 MHz, CDCl$_3$) δ 159.55, 136.43, 133.66, 129.84, 127.72, 127.55, 126.90, 120.92, 119.64, 106.51, 106.45, 67.97, 31.13, 19.28, 13.87. HRMS (ESI+): Calcd for C$_{15}$H$_{15}$NO [M+H]$^+$: 226.2936, Found: 226.1230.

6-(pentyloxy)-2-naphthonitrile (2b)

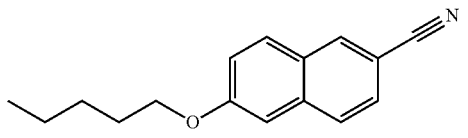 [SMILES: CCCCCOc1ccc2cc(C#N)ccc2c1]

2b was synthesized using general procedure 1. Purification on a silica gel column with 0-20% ethyl acetate in hexanes produced 2b (416 mg, 98%), a white solid. $^1$H NMR (400 MHz, CDCl$_3$) δ 8.10 (s, 1H), 7.75 (dd, J=8.7, 3.3 Hz, 2H), 7.53 (dd, J=8.5, 1.6 Hz, 1H), 7.26-7.22 (m, 1H), 7.12 (d, J=2.3 Hz, 1H), 4.09 (t, J=6.6 Hz, 2H), 1.90-1.82 (m, 2H), 1.54-1.37 (m, 4H), 0.96 (t, J=7.2 Hz, 3H). $^{13}$C NMR (101 MHz, CDCl$_3$) δ 159.69, 136.58, 133.83, 129.99, 127.84, 127.73, 127.08, 121.05, 119.74, 106.69, 106.66, 77.48, 77.16, 76.84, 68.42, 28.91, 28.32, 22.56, 14.13. HRMS (ESI+): Calcd for C$_{16}$H$_{17}$NO [M+H]$^+$: 240.3032, Found: 240.1381.

6-(hexyloxy)-2-naphthonitrile (2c)

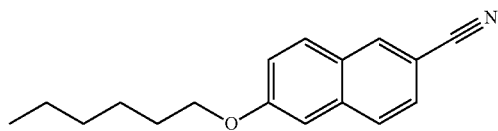 [SMILES: CCCCCCOc1ccc2cc(C#N)ccc2c1]

2c was synthesized using general procedure 1. Purification on a silica gel column with 0-20% ethyl acetate in hexanes produced 2c (517 mg, 86%), a white solid. $^1$H NMR (500 MHz, CDCl$_3$) δ 8.06 (d, J=1.6 Hz, 1H), 7.72 (d, J=8.7 Hz, 2H), 7.51 (dd, J=8.4, 1.7 Hz, 1H), 7.22 (dd, J=9.0, 2.5 Hz, 1H), 7.10 (d, J=2.4 Hz, 1H), 4.06 (t, J=6.6 Hz, 2H), 1.84 (p, J=6.7 Hz, 2H), 1.50 (p, J=7.1 Hz, 2H), 1.41-1.31 (m, 4H), 0.99-0.88 (m, 3H). $^{13}$C NMR (126 MHz, CDCl$_3$) δ 159.58, 136.46, 133.69, 129.87, 127.74, 127.59, 126.93, 120.95, 119.66, 106.54, 106.49, 77.41, 77.16, 76.91, 68.31, 31.60, 29.09, 25.77, 22.64, 14.09. HRMS (ESI+): Calcd for C$_{17}$H$_{19}$NO [M+H]$^-$: 254.3468, Found: 254.1536.

6-(heptyloxy)-2-naphthonitrile (2d)

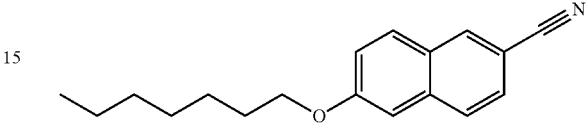

2d was synthesized using general procedure 1. Purification on a silica gel column with 0-20% ethyl acetate in hexanes produced 2d (147 mg, 85%), a white solid. $^1$H NMR (400 MHz, CDCl$_3$) δ 8.10 (s, 1H), 7.75 (dd, J=8.8, 2.2 Hz, 2H), 7.53 (dd, J=8.5, 1.6 Hz, 1H), 7.29-7.19 (m, 1H), 7.12 (d, J=2.4 Hz, 1H), 4.08 (t, J=6.6 Hz, 2H), 1.92-1.80 (m, 2H), 1.50 (ddd, J=15.5, 8.9, 6.8 Hz, 2H), 1.36 (m, 6H), 0.96-0.85 (m, 3H). $^{13}$C NMR (101 MHz, CDCl$_3$) δ 159.68, 136.57, 133.81, 129.97, 127.82, 127.71, 127.06, 121.04, 119.72, 106.68, 106.64, 68.42, 31.88, 29.21, 29.15, 26.13, 22.72, 14.19. HRMS (ESI+): Calcd for C$_{18}$H$_{21}$NO [M+H]$^+$: 268.3734, Found: 268.1681.

6-isobutoxy-2-naphthonitrile (2e)

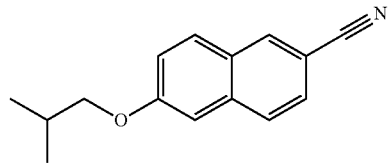 [SMILES: CC(C)COc1ccc2cc(C#N)ccc2c1]

2e was synthesized using general procedure 1. Purification on a silica gel column with 0-20% ethyl acetate in hexanes produced 2e (223 mg, 84%), a white solid. $^1$H NMR (400 MHz, CDCl$_3$) δ 8.09-8.05 (m, 1H), 7.73 (d, J=8.7 Hz, 2H), 7.51 (dd, J=8.5, 1.6 Hz, 1H), 7.27-7.20 (m, 1H), 7.11 (d, J=2.4 Hz, 1H), 3.85 (d, J=6.5 Hz, 2H), 2.16 (dt, J=13.3, 6.7 Hz, 1H), 1.08 (d, J=6.7 Hz, 6H). $^{13}$C NMR (101 MHz, CDCl$_3$) δ 159.71, 136.51, 133.73, 129.89, 127.76, 127.65, 126.98, 120.99, 119.69, 106.66, 106.56, 77.48, 77.16, 76.84, 74.67, 28.28, 19.32. HRMS (ESI+): Calcd for C$_{15}$H$_{15}$NO [M+H]$^+$: 226.2936, Found: 226.1234.

6-(benzyloxy)-2-naphthonitrile (2f)

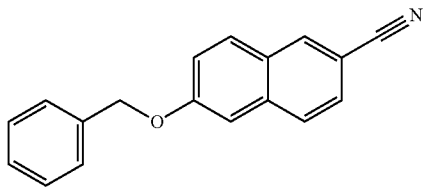 [SMILES: N#Cc1ccc2cc(OCc3ccccc3)ccc2c1]

2f was synthesized using general procedure 1. Purification on a silica gel column with 0-20% ethyl acetate in hexanes produced 2f (153 mg, 100%), a white solid. $^1$H NMR (400 MHz, CDCl$_3$) δ 8.08 (s, 1H), 7.75 (dd, J=8.7, 5.3 Hz, 2H), 7.55-7.48 (m, 3H), 7.44 (t, J=7.3 Hz, 2H), 7.42-7.37 (m, 1H), 7.33 (dd, J=9.0, 2.4 Hz, 1H), 7.23 (d, J=2.1 Hz, 1H), 5.20 (s, 2H). $^{13}$C NMR (101 MHz, CDCl$_3$) δ 159.09, 136.31, 136.18, 133.69, 130.05, 128.73, 128.30, 127.85, 127.78, 127.58, 127.01, 120.91, 119.57, 107.24, 106.80, 70.22. HRMS (ESI+): Calcd for C$_{18}$H$_{13}$NO [M+H]$^+$: 260.3099, Found: 260.1060.

6-((4-methylbenzyl)oxy)-2-naphthonitrile (2g)

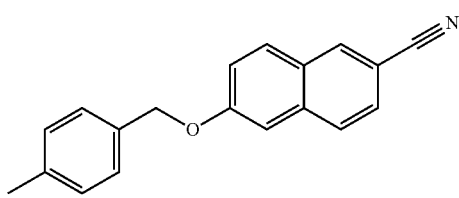 [SMILES: Cc1ccc(COc2ccc3cc(C#N)ccc3c2)cc1]

2g was synthesized using general procedure 1. Purification on a silica gel column with 0-20% ethyl acetate in hexanes produced 2g (237 mg, 98%), a white solid. $^1$H NMR (400 MHz, CDCl$_3$) δ 8.08 (s, 1H), 7.74 (dd, J=8.7, 4.9 Hz, 2H), 7.52 (dd, J=8.5, 1.6 Hz, 1H), 7.37 (d, J=8.0 Hz, 2H), 7.30 (dd, J=9.0, 2.5 Hz, 1H), 7.23 (dd, J=8.4, 2.3 Hz, 3H), 5.15 (s, 2H), 2.38 (s, 3H). $^{13}$C NMR (101 MHz, CDCl$_3$) δ 159.24, 138.19, 136.39, 133.76, 133.17, 130.06, 129.46, 127.90, 127.82, 127.78, 127.05, 121.04, 119.63, 107.26, 106.82, 70.25, 21.28. HRMS (ESI+): Calcd for C$_{19}$H$_{15}$NO [M+H]$^-$: 274.3364, Found: 274.1237.

6-cyanonaphthalen-2-yl 4-methylbenzenesulfonate (2h)

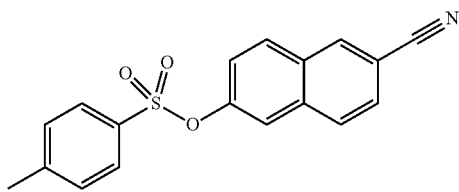 [SMILES: Cc1ccc(S(=O)(=O)Oc2ccc3cc(C#N)ccc3c2)cc1]

2h was synthesized using general procedure 1. Purification on a silica gel column with 0-20% ethyl acetate in hexanes produced 2h (242 mg, 95%), a white solid. $^1$H NMR (400 MHz, CDCl$_3$) δ 8.16 (s, 1H), 7.80 (d, J=8.6 Hz, 2H), 7.71 (d, J=8.0 Hz, 2H), 7.58 (d, J=8.4 Hz, 1H), 7.53 (s, 1H), 7.29 (d, J=7.9 Hz, 2H), 7.20 (d, J=8.6 Hz, 1H), 2.42 (s, 3H). $^{13}$C NMR (101 MHz, CDCl$_3$) δ 149.40, 145.91, 134.99, 133.88, 132.20, 130.69, 130.52, 130.02, 129.22, 128.51, 127.41, 123.18, 120.20, 118.80, 110.02, 21.79. HRMS (ESI+): Calcd for C$_{18}$H$_{13}$NO$_3$S [M+Cl]$^-$: 358.8187, Found: 358.0309.

N'-hydroxy-6-(butyloxy)-2-naphthimidamide (3a)

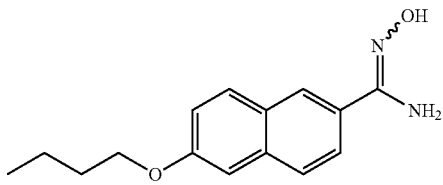 [SMILES: CCCCOc1ccc2cc(C(N)=NO)ccc2c1]

3a was synthesized using general procedure 2. Purification on a silica gel column with 50-100% ethyl acetate in hexanes produced 3a as a mixture of enantiomers (192 mg, 67%), a white solid. $^1$H NMR (400 MHz, CD$_3$OD) δ 8.04-8.01 (m, 1H), 7.87-7.65 (m, 3H), 7.25-7.10 (m, 2H), 4.13-4.04 (m, 2H), 1.86-1.73 (m, 2H), 1.59-1.48 (m, 2H), 0.99 (td, J=7.4, 1.2 Hz, 3H). $^{13}$C NMR (101 MHz, CD$_3$OD) δ 171.14, 158.79, 157.92, 154.22, 136.69, 135.46, 130.11, 129.44, 128.29, 128.21, 127.86, 127.72, 127.62, 126.60, 126.48, 124.99, 124.12, 123.64, 119.49, 119.10, 106.01, 105.96, 67.46, 67.38, 31.03, 30.99, 18.93, 18.92, 12.76. HRMS (ESI+): Calcd for C$_{15}$H$_{18}$N$_2$O$_2$ [M+H]$^+$: 259.3236, Found: 259.1417.

N'-hydroxy-6-(pentyloxy)-2-naphthimidamide (3b)

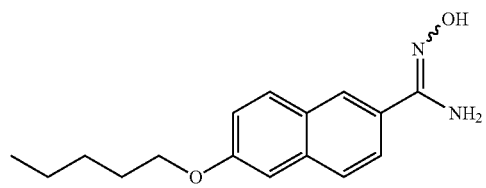 [SMILES: CCCCCOc1ccc2cc(C(N)=NO)ccc2c1]

3b was synthesized using general procedure 2. Purification on a silica gel column with 50-100% ethyl acetate in hexanes produced 3b as a mixture of enantiomers (360 mg, 99%), a white solid. $^1$H NMR (400 MHz, MeOD) δ 8.05 (d, J=1.4 Hz, 1H), 7.81-7.68 (m, 3H), 7.22 (d, J=2.5 Hz, 1H), 7.15 (dd, J=8.9, 2.5 Hz, 1H), 4.10 (t, J=6.5 Hz, 2H), 1.85 (dd, J=8.2, 6.6 Hz, 2H), 1.56-1.38 (m, 4H), 0.97 (t, J=7.2 Hz, 3H). $^{13}$C NMR (101 MHz, MeOD) δ 159.35, 155.65, 136.90, 130.89, 129.74, 129.09, 127.92, 126.42, 125.09, 120.55, 107.46, 69.12, 49.64, 49.43, 49.21, 49.00, 48.79, 48.57, 48.36, 30.08, 29.46, 23.55, 14.38. HRMS (ESI+): Calcd for C$_{16}$H$_{20}$N$_2$O$_2$ [M+H]$^+$: 273.3501, Found: 273.1610.

6-(hexyloxy)-N'-hydroxy-2-naphthimidamide (3c)

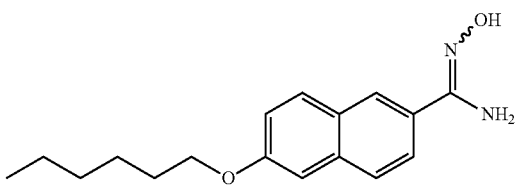 [SMILES: CCCCCCOc1ccc2cc(C(N)=NO)ccc2c1]

3c was synthesized using general procedure 2. Purification on a silica gel column with 50-100% ethyl acetate in hexanes produced 3c as a mixture of enantiomers (225 mg, 77%), a white solid. ¹H NMR (400 MHz, CDCl₃) δ 8.35 (d, J=1.6 Hz, 0H), 8.05 (d, J=1.4 Hz, 1H), 7.91-7.65 (m, 4H), 7.28-7.10 (m, 2H), 4.10 (dt, J=7.7, 6.5 Hz, 2H), 1.87-1.80 (m, 2H), 1.59-1.48 (m, 2H), 1.41-1.36 (m, 4H), 0.97-0.91 (m, 3H). ¹³C NMR (101 MHz, MeOD) δ 158.79, 157.91, 136.69, 135.46, 130.12, 129.44, 128.29, 128.22, 127.86, 127.72, 127.64, 126.60, 126.47, 124.98, 124.12, 123.64, 119.49, 119.10, 106.02, 105.97, 67.77, 67.69, 48.19, 47.98, 47.77, 47.55, 47.34, 47.13, 46.91, 31.35, 31.34, 28.90, 28.86, 25.48, 22.24, 12.92. HRMS (ESI+): Calcd for C₁₇H₂₂N₂O₂ [M+H]⁺: 287.3767, Found: 287.1728.

6-(heptyloxy)-N'-hydroxy-2-naphthimidamide (3d)

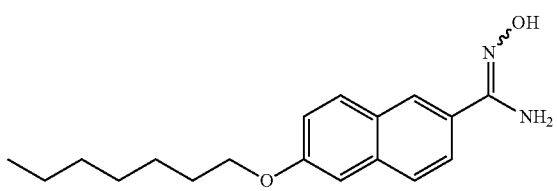 [SMILES: CCCCCCCOc1ccc2cc(C(N)=NO)ccc2c1]

3d was synthesized using general procedure 2. Purification on a silica gel column with 50-100% ethyl acetate in hexanes produced 3d as a mixture of enantiomers (60 mg, 71%), a white solid. ¹H NMR (400 MHz, CDCl₃) δ 8.26 (s, 1H), 7.83-7.73 (m, 3H), 7.20 (dd, J=8.9, 2.5 Hz, 1H), 7.14 (d, J=2.4 Hz, 1H), 4.09 (t, J=6.6 Hz, 2H), 1.90-1.82 (m, 2H), 1.54-1.46 (m, 2H), 1.43-1.28 (m, 7H), 1.26 (s, 1H), 0.93-0.86 (m, 4H). ¹³C NMR (101 MHz, CDCl₃) δ 169.58, 159.01, 136.79, 130.63, 128.14, 128.01, 127.29, 124.41, 120.30, 106.54, 68.35, 31.94, 29.33, 29.22, 26.21, 22.77, 14.23. HRMS (ESI+): Calcd for C₁₈H₂₄N₂O₂ [M+H]⁺: 301.4033, Found: 301.1920.

N'-hydroxy-6-isobutoxy-2-naphthimidamide (3e)

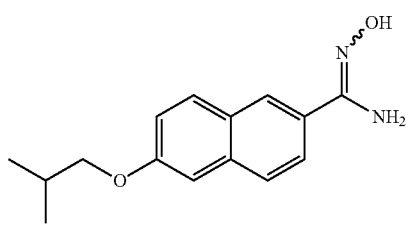 [SMILES: CC(C)COc1ccc2cc(C(N)=NO)ccc2c1]

3e was synthesized using general procedure 2. Purification on a silica gel column with 50-100% ethyl acetate in hexanes produced 3e as a mixture of enantiomers (221 mg, 91%), a white solid. ¹H NMR (400 MHz, CDCl₃) δ 8.30-8.23 (m, 1H), 7.99 (s, 0H), 7.86-7.67 (m, 3H), 7.20 (ddd, J=12.1, 8.9, 2.5 Hz, 1H), 7.13 (dd, J=8.7, 2.5 Hz, 1H), 3.85 (dd, J=6.5, 5.2 Hz, 2H), 2.16 (td, J=6.7, 3.0 Hz, 1H), 1.08 (dd, J=6.7, 1.6 Hz, 6H). ¹³C NMR (101 MHz, CDCl₃) δ 169.67, 159.10, 158.29, 153.21, 136.80, 135.66, 130.62, 129.97, 128.41, 128.15, 127.32, 127.28, 125.17, 124.41, 123.81, 120.32, 119.95, 106.65, 106.56, 74.70, 74.66, 29.85, 28.42, 19.47. HRMS (ESI+): Calcd for C₁₅H₁₈N₂O₂[M+H]⁺: 259.3236, Found: 259.1465.

6-(benzyloxy)-N'-hydroxy-2-naphthimidamide (3f)

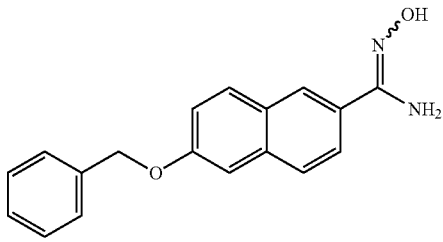 [SMILES: NC(=NO)c1ccc2cc(OCc3ccccc3)ccc2c1]

3e was synthesized using general procedure 2. Purification on a silica gel column with 50-100% ethyl acetate in hexanes produced 3f as a mixture of enantiomers (122 mg, 90%), a white solid. ¹H NMR (400 MHz, DMSO) δ 8.06 (s, 1H), 7.80-7.75 (m, 1H), 7.74-7.67 (m, 2H), 7.47-7.44 (m, 2H), 7.38-7.33 (m, 3H), 7.31-7.26 (m, 1H), 7.19 (dd, J=9.0, 2.5 Hz, 1H), 5.79 (s, 2H), 5.17 (d, J=7.8 Hz, 2H). ¹³C NMR (101 MHz, DMSO) δ 156.75, 150.86, 136.91, 134.47, 129.87, 128.52, 127.98, 127.90, 126.43, 124.23, 123.91, 119.15, 107.32, 69.42.

N'-hydroxy-6-((4-methylbenzyl)oxy)-2-naphthimidamide (3g)

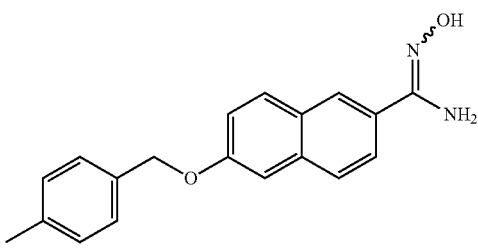 [SMILES: Cc1ccc(COc2ccc3cc(C(N)=NO)ccc3c2)cc1]

3g was synthesized using general procedure 2. Purification on a silica gel column with 50-100% ethyl acetate in hexanes produced 3g as a mixture of enantiomers (175 mg, 98%), a white solid. ¹H NMR (400 MHz, CD₃OD) δ 8.06 (d, J=1.7 Hz, 1H), 7.88 (dd, J=8.6, 1.6 Hz, 1H), 7.84-7.79 (m, 1H), 7.76-7.69 (m, 1H), 7.41-7.29 (m, 3H), 7.28-7.14 (m, 3H), 5.16 (d, J=8.1 Hz, 2H), 2.35 (s, 3H).

6-(N'-hydroxycarbamimidoyl)naphthalen-2-yl 4-methylbenzenesulfonate (3h)

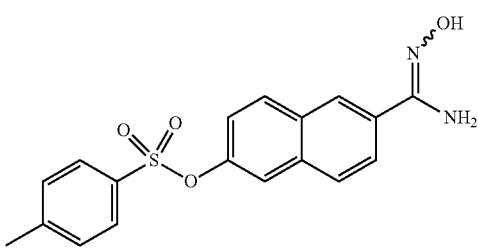 [SMILES: Cc1ccc(S(=O)(=O)Oc2ccc3cc(C(N)=NO)ccc3c2)cc1]

3h was synthesized using general procedure 2. Purification on a silica gel column with 50-100% ethyl acetate in hexanes produced 3h as a mixture of enantiomers (122 mg, 92%), a white solid. $^1$H NMR (400 MHz, CDCl$_3$) δ 8.06-8.02 (m, 1H), 7.81-7.76 (m, 3H), 7.73 (dd, J=8.4, 1.9 Hz, 2H), 7.48 (d, J=2.4 Hz, 1H), 7.33-7.28 (m, 2H), 7.14 (dd, J=8.9, 2.4 Hz, 1H), 4.97 (s, 2H), 2.45 (s, 3H). $^{13}$C NMR (101 MHz, CDCl$_3$) δ 152.48, 148.08, 145.65, 134.28, 132.52, 131.57, 130.54, 130.41, 129.97, 128.70, 128.55, 125.09, 124.45, 122.13, 120.01, 21.88. HRMS (ESI+): Calcd for C$_{18}$H$_{16}$N$_2$O$_4$S [M+H]$^+$: 357.4036, Found: 357.0922.

Tert-butyl (S)-2-(3-(6-(butyloxy)naphthalen-2-yl)-1,2,4-oxadiazol-5-yl)pyrrolidine-1-carboxylate (4a)

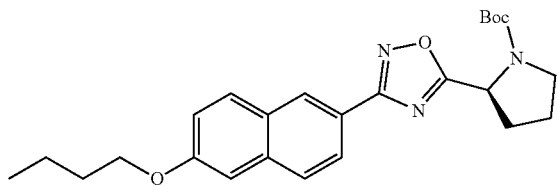 [SMILES: CCCCOc1ccc2cc(-c3noc([C@@H]4CCCN4C(=O)OC(C)(C)C)n3)ccc2c1]

4a was synthesized using general procedure 3. Purification on a silica gel column with 15-30% ethyl acetate in hexanes produced 4a (63 mg, 39%), a yellow oil. $^1$H NMR (400 MHz, CDCl$_3$) δ 8.51 (d, J=1.9 Hz, 1H), 8.08 (d, J=8.5 Hz, 1H), 7.86-7.74 (m, 2H), 7.24-7.11 (m, 2H), 5.28-5.06 (m, 1H), 4.10 (t, J=6.4 Hz, 2H), 3.82-3.66 (m, 1H), 3.63-3.47 (m, 1H), 2.49-2.34 (m, 1H), 2.29-2.12 (m, 2H), 2.09-1.95 (m, 1H), 1.84 (p, J=6.4 Hz, 2H), 1.60-1.50 (m, 2H), 1.50-1.23 (m, 8H), 1.01 (t, J=7.4 Hz, 3H). $^{13}$C NMR (101 MHz, CDCl$_3$) δ 180.66, 168.68, 158.66, 153.72, 136.32, 130.41, 128.49, 127.88, 127.55, 124.46, 121.81, 120.06, 106.75, 80.60, 67.97, 54.02, 46.52, 32.58, 31.38, 28.55, 28.31, 23.87, 19.44, 13.99. HRMS (ESI+): Calcd for C$_{25}$H$_{31}$N$_3$O$_4$ [M+Na]$^+$: 460.5211, Found: 460.2208.

Tert-butyl (S)-2-(3-(6-(pentyloxy)naphthalen-2-yl)-1,2,4-oxadiazol-5-yl)pyrrolidine-1-carboxylate (4b)

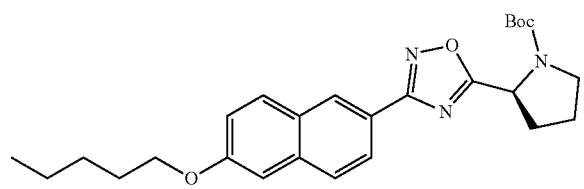 [SMILES: CCCCCOc1ccc2cc(-c3noc([C@@H]4CCCN4C(=O)OC(C)(C)C)n3)ccc2c1]

4b was synthesized using general procedure 3. Purification on a silica gel column with 15-30% ethyl acetate in hexanes produced 4b (65 mg, 49%), a yellow oil. $^1$H NMR (400 MHz, CDCl$_3$) δ 8.51 (s, 1H), 8.08 (d, J=8.5 Hz, 1H), 7.81 (dd, J=15.8, 8.8 Hz, 2H), 7.22-7.13 (m, 2H), 5.26-5.07 (m, 1H), 4.08 (t, J=6.6 Hz, 2H), 3.79-3.66 (m, 1H), 3.62-3.47 (m, 1H), 2.47-2.32 (m, 1H), 2.22-2.13 (m, 2H), 2.07-1.97 (m, 1H), 1.86 (p, J=6.6 Hz, 2H), 1.76 (s, 0H), 1.54-1.24 (m, 13H), 0.95 (t, J=7.2 Hz, 3H). $^{13}$C NMR (101 MHz, CDCl$_3$) δ 180.49, 168.50, 158.48, 153.56, 136.15, 130.23, 128.32, 127.71, 127.38, 127.24, 124.42, 124.28, 121.62, 119.89, 106.57, 80.43, 77.32, 77.01, 76.69, 68.10, 53.85, 46.62, 46.35, 32.40, 31.50, 28.85, 28.37, 28.22, 28.13, 24.36, 23.70, 22.43, 13.99. HRMS (ESI+): Calcd for C$_{26}$H$_{33}$N$_3$O$_4$ [M+H]$^+$: 452.5659, Found: 452.2535.

Tert-butyl (S)-2-(3-(6-(hexyloxy)naphthalen-2-yl)-1,2,4-oxadiazol-5-yl)pyrrolidine-1-carboxylate (4c)

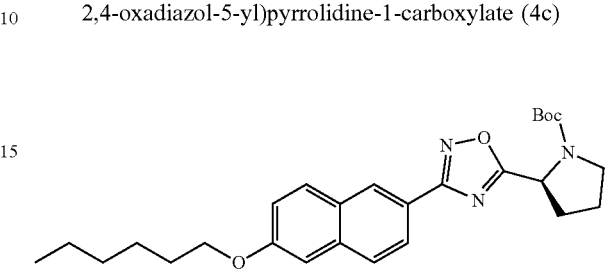

4c was synthesized using general procedure 3. Purification on a silica gel column with 15-30% ethyl acetate in hexanes produced 4c (67 mg, 37%), a yellow oil. $^1$H NMR (500 MHz, CDCl$_3$) δ 8.58-8.49 (m, 1H), 8.08 (dd, J=8.2, 1.8 Hz, 1H), 7.87-7.72 (m, 2H), 7.25-7.10 (m, 2H), 5.17 (ddd, J=73.1, 8.3, 3.3 Hz, 1H), 4.09 (t, J=6.6 Hz, 2H), 3.78-3.70 (m, 1H), 3.65-3.48 (m, 1H), 2.50-2.33 (m, 1H), 2.21-2.16 (m, 2H), 2.03-2.01 (m, 1H), 1.85 (p, J=6.8 Hz, 2H), 1.58-1.16 (m, 17H), 0.96-0.88 (m, 3H). $^{13}$C NMR (126 MHz, CDCl$_3$) δ 180.65, 168.67, 158.64, 153.72, 136.30, 130.41, 128.47, 127.87, 127.55, 127.40, 124.59, 124.44, 121.76, 120.07, 119.93, 106.69, 80.60, 68.27, 54.01, 46.51, 32.58, 31.73, 29.29, 28.54, 28.30, 25.91, 23.87, 22.76, 14.19. HRMS (ESI+): Calcd for C$_{27}$H$_{35}$N$_3$O$_4$ [M+Na]$^+$: 488.5743, Found: 488.2527.

Tert-butyl (S)-2-(3-(6-(heptyloxy)naphthalen-2-yl)-1,2,4-oxadiazol-5-yl)pyrrolidine-1-carboxylate (4d)

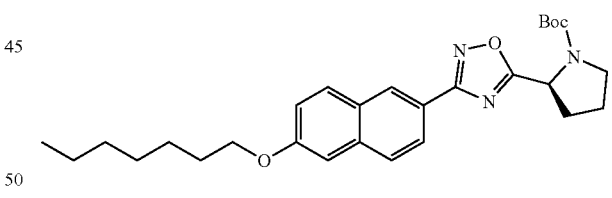

4d was synthesized using general procedure 3. Purification on a silica gel column with 15-30% ethyl acetate in hexanes produced 4d (30 mg, 63%), a yellow oil. $^1$H NMR (400 MHz, CDCl$_3$) δ 8.51 (s, 1H), 8.08 (d, J=8.5 Hz, 1H), 7.81 (dd, J=15.8, 8.8 Hz, 1H), 7.23-7.10 (m, 1H), 5.28-5.04 (m, 1H), 4.09 (t, J=6.6 Hz, 2H), 3.78-3.65 (m, 1H), 3.63-3.44 (m, 1H), 2.49-2.28 (m, 1H), 2.23-2.14 (m, 2H), 2.07-1.96 (m, 1H), 1.86 (dt, J=14.5, 6.6 Hz, 2H), 1.71-1.24 (m, 12H), 0.94-0.84 (m, 3H). $^{13}$C NMR (101 MHz, CDCl$_3$) δ 180.67, 168.69, 158.67, 153.75, 136.33, 130.43, 128.50, 127.90, 127.56, 124.47, 121.80, 120.08, 106.76, 80.64, 68.31, 54.03, 46.54, 32.60, 31.94, 29.35, 29.22, 28.56, 28.32, 26.21, 23.89, 22.77, 14.23. HRMS (ESI+): Calcd for C$_{28}$H$_{37}$N$_3$O$_4$ [M+Na]$^+$: 502.6008, Found: 502.2706.

Tert-butyl (S)-2-(3-(6-isobutoxynaphthalen-2-yl)-1,2,4-oxadiazol-5-yl)pyrrolidine-1-carboxylate (4e)

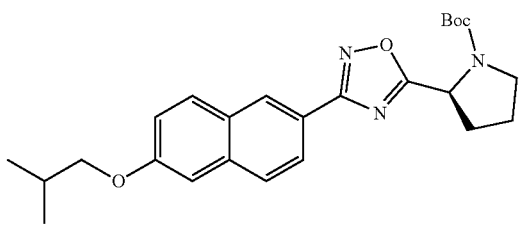 [SMILES: CC(C)COc1ccc2cc(-c3noc([C@@H]4CCCN4C(=O)OC(C)(C)C)n3)ccc2c1]

4e was synthesized using general procedure 3. Purification on a silica gel column with 15-30% ethyl acetate in hexanes produced 4e (176 mg, 87%), a yellow oil. $^1$H NMR (400 MHz, CDCl$_3$) δ 8.51 (s, 1H), 8.08 (d, J=8.5 Hz, 1H), 7.81 (dd, J=17.0, 8.8 Hz, 2H), 7.23-7.09 (m, 2H), 5.09 (dd, J=8.1, 3.6 Hz, 1H), 3.86 (d, J=6.5 Hz, 2H), 3.80-3.66 (m, 1H), 3.58 (d, J=10.5 Hz, 1H), 2.42 (s, 1H), 2.23-2.11 (m, 3H), 2.02 (d, J=4.9 Hz, 1H), 1.47 (d, J=6.3 Hz, 3H), 1.31 (s, 6H), 1.08 (d, J=6.7 Hz, 6H). $^{13}$C NMR (101 MHz, CDCl$_3$) δ 180.49, 168.51, 158.59, 136.16, 130.22, 128.32, 127.72, 127.37, 124.29, 121.62, 119.91, 106.61, 80.44, 74.49, 53.85, 46.35, 32.41, 28.38, 28.23, 28.14, 23.70, 19.27. HRMS (ESI+): Calcd for C$_{25}$H$_{31}$N$_3$O$_4$ [M+H]$^+$: 438.5393, Found: 438.2412.

Tert-butyl (S)-2-(3-(6-(benzyloxy)naphthalen-2-yl)-1,2,4-oxadiazol-5-yl)pyrrolidine-1-carboxylate (4f)

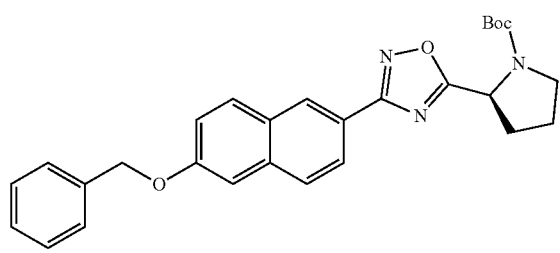 [SMILES: CC(C)(C)OC(=O)N1CCC[C@H]1c1nc(-c2ccc3cc(OCc4ccccc4)ccc3c2)no1]

4f was synthesized using general procedure 3. Purification on a silica gel column with 15-30% ethyl acetate in hexanes produced 4f (59 mg, 39%), a yellow oil. $^1$H NMR (400 MHz, CDCl$_3$) δ 8.54 (d, J=1.6 Hz, 1H), 8.10 (dd, J=8.6, 1.8 Hz, 1H), 7.87 (d, J=8.7 Hz, 1H), 7.80 (t, J=8.5 Hz, 1H), 7.53-7.47 (m, 1H), 7.46-7.39 (m, 2H), 7.37-7.33 (m, 1H), 7.29 (dd, J=8.7, 2.6 Hz, 1H), 5.31-5.08 (m, 2H), 5.21 (s, 2H), 3.83-3.66 (m, 1H), 3.62-3.48 (m, 1H), 2.46-2.33 (m, 1H), 2.26-2.11 (m, 2H), 2.09-1.95 (m, 1H), 1.48 (s, 3H), 1.31 (s, 6H). $^{13}$C NMR (101 MHz, CDCl$_3$) δ 180.70, 168.63, 158.23, 153.71, 136.71, 136.18, 130.57, 128.79, 128.71, 128.26, 127.88, 127.69, 124.55, 122.08, 120.07, 107.39, 80.60, 70.26, 54.02, 46.52, 32.57, 28.54, 28.30, 23.87. HRMS (ESI+): Calcd for C$_{28}$H$_{29}$N$_3$O$_4$ [M+Na]$^+$: 494.5373, Found: 494.2094.

Tert-butyl (S)-2-(3-(6-((4-methylbenzyl)oxy)naphthalen-2-yl)-1,2,4-oxadiazol-5-yl)pyrrolidine-1-carboxylate (4g)

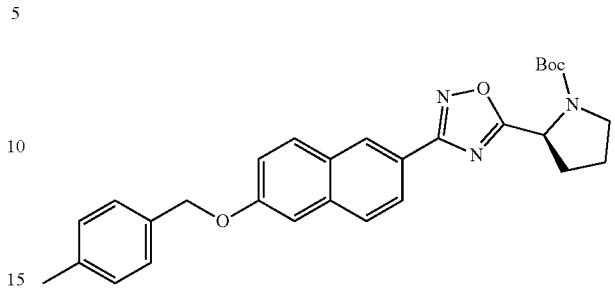

4g was synthesized using general procedure 3. Purification on a silica gel column with 15-30% ethyl acetate in hexanes produced 4g (30 mg, 13%), a yellow oil. $^1$H NMR (500 MHz, CDCl$_3$) δ 8.50 (d, J=4.6 Hz, 1H), 8.11-8.02 (m, 1H), 7.85-7.73 (m, 2H), 7.36 (d, J=7.7 Hz, 2H), 7.27-7.18 (m, 5H), 5.24-5.04 (m, 1H), 5.14 (s, 2H), 3.78-3.67 (m, 1H), 3.63-3.45 (m, 1H), 2.47-2.38 (m, 1H), 2.37 (s, 3H), 2.24-2.12 (m, 2H), 2.06-1.96 (m, 1H), 1.46 (s, 3H), 1.29 (s, 6H). $^{13}$C NMR (126 MHz, CDCl$_3$) δ 180.69, 168.65, 158.32, 153.77, 138.11, 136.21, 133.65, 130.54, 129.49, 128.67, 127.87, 127.68, 127.53, 124.51, 122.00, 120.16, 107.33, 80.66, 70.22, 54.03, 46.54, 32.59, 28.55, 28.31, 23.89, 21.37. HRMS (ESI+): Calcd for C$_{29}$H$_{31}$N$_3$O$_4$ [M+H]$^+$: 508.5639, Found: 508.2244.

Tert-butyl (S)-2-(3-(6-(tosyloxy)naphthalen-2-yl)-1,2,4-oxadiazol-5-yl)pyrrolidine-1-carboxylate (4h)

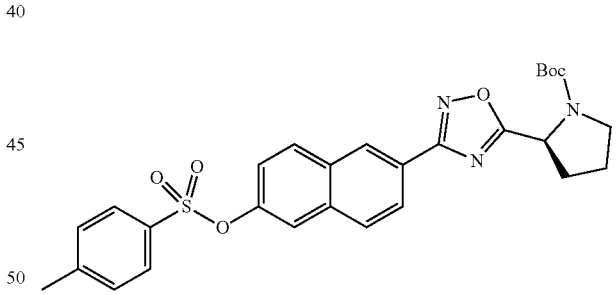

4h was synthesized using general procedure 3. Purification on a silica gel column with 15-30% ethyl acetate in hexanes produced 4h (15 mg, 13%), a yellow oil. $^1$H NMR (400 MHz, CDCl$_3$) δ 8.56 (d, J=6.4 Hz, 1H), 8.14 (t, J=8.5 Hz, 1H), 7.90-7.77 (m, 2H), 7.74 (d, J=8.0 Hz, 2H), 7.55-7.48 (m, 1H), 7.35-7.29 (m, 2H), 7.19-7.11 (m, 1H), 5.26-5.07 (m, 1H), 3.79-3.63 (m, 1H), 3.62-3.48 (m, 1H), 2.48-2.34 (m, 1H), 2.45 (s, 3H), 2.24-2.12 (m, 2H), 2.07-1.98 (m, 1H), 1.47 (s, 3H), 1.29 (s, 6H). $^{13}$C NMR (101 MHz, CDCl$_3$) δ 181.06, 168.20, 153.70, 148.49, 145.71, 134.90, 132.42, 131.61, 130.85, 129.98, 128.85, 128.66, 127.81, 125.10, 124.95, 124.75, 122.29, 122.15, 120.15, 80.69, 53.98, 46.52, 36.75, 32.57, 28.54, 28.53, 28.28, 24.81, 23.87, 21.88. HRMS (ESI+): Calcd for C$_{28}$H$_{29}$N$_3$O$_6$S [M+Na]$^+$: 558.6011, Found: 558.1710.

Tert-butyl (2S,3S)-3-hydroxy-2-(3-(6-(pentyloxy)naphthalen-2-yl)-1,2,4-oxadiazol-5-yl)pyrrolidine-1-carboxylate (4i)

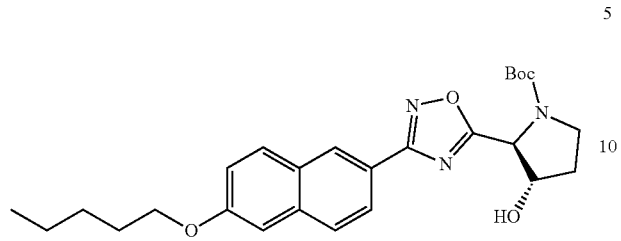

4i was synthesized using general procedure 3. Purification on a silica gel column with 15-30% ethyl acetate in hexanes produced 4l (232 mg, 90%), a yellow oil. $^1$H NMR (400 MHz, CDCl$_3$) δ 8.51-8.43 (m, 1H), 8.10-7.98 (m, 1H), 7.84-7.68 (m, 2H), 7.22-7.06 (m, 2H), 5.20-4.97 (m, 1H), 4.65-4.58 (m, 1H), 4.07 (t, J=6.5 Hz, 2H), 3.85-3.71 (m, 2H), 2.41-2.29 (m, 1H), 2.09-2.05 (m, 1H), 1.85 (p, J=6.8 Hz, 2H), 1.51-1.24 (m, 11H), 0.95 (t, J=7.1 Hz, 3H). $^{13}$C NMR (101 MHz, CDCl$_3$) δ 178.14, 168.64, 158.55, 153.74, 136.20, 130.25, 128.28, 127.80, 127.43, 124.22, 121.33, 119.95, 106.58, 80.80, 77.29, 76.97, 76.66, 76.10, 68.12, 62.34, 44.28, 32.15, 28.85, 28.36, 28.21, 28.12, 22.43, 13.99. HRMS (ESI+): Calcd for C$_{26}$H$_{33}$N$_3$O$_5$ [M+Na]$^+$: 490.5471, Found: 490.2309.

Tert-butyl (2S,3S)-3-hydroxy-2-(3-(6-isobutoxynaphthalen-2-yl)-1,2,4-oxadiazol-5-yl)pyrrolidine-1-carboxylate (4j)

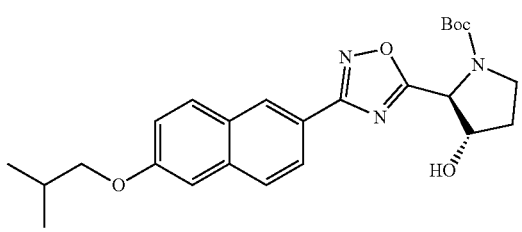 [SMILES: CC(C)COc1ccc2cc(-c3noc([C@@H]4[C@@H](O)CCN4C(=O)OC(C)(C)C)n3)ccc2c1]

4j was synthesized using general procedure 3. Purification on a silica gel column with 40-70% ethyl acetate in hexanes produced 4j (52 mg, 49%), a yellow oil. $^1$H NMR (400 MHz, CDCl$_3$) δ 8.46 (d, J=22.8 Hz, 1H), 8.07-7.97 (m, 1H), 7.83-7.72 (m, 2H), 7.23-7.06 (m, 2H), 5.23-4.96 (m, 1H), 4.62 (d, J=6.9 Hz, 1H), 3.90-3.70 (m, 4H), 2.41-2.33 (m, 1H), 2.23-2.01 (m, 2H), 1.56-1.21 (m, 12H), 1.07 (d, J=6.7 Hz, 6H). $^{13}$C NMR (101 MHz, CDCl$_3$) δ 178.23, 168.64, 158.67, 153.88, 136.23, 130.26, 128.28, 127.83, 127.46, 124.20, 121.28, 120.00, 106.58, 80.92, 77.34, 77.02, 76.70, 76.03, 74.48, 62.36, 44.36, 32.13, 28.38, 28.24, 28.14, 19.30. HRMS (ESI+): Calcd for C$_{25}$H$_{31}$N$_3$O$_5$ [M+Na]$^+$: 476.5205, Found: 476.2168.

(S)-2-(3-(6-butoxynaphthalen-2-yl)-1,2,4-oxadiazol-5-yl)pyrrolidin-1-ium chloride (5a)

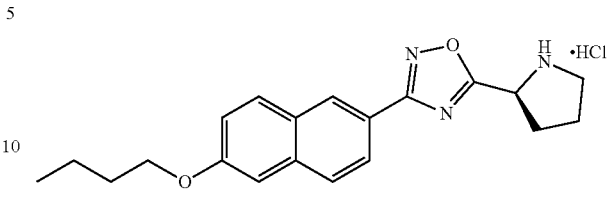

5a was synthesized using general procedure 4 and carried forward without purification.

(S)-2-(3-(6-(pentyloxy)naphthalen-2-yl)-1,2,4-oxadiazol-5-yl)pyrrolidin-1-ium chloride (5b)

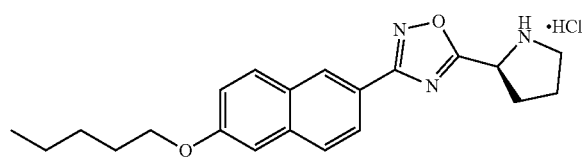 [SMILES: CCCCCOc1ccc2cc(-c3noc([C@@H]4CCCN4)n3)ccc2c1 ; Cl]

5b was synthesized using general procedure 4 and carried forward without purification.

(S)-2-(3-(6-(hexyloxy)naphthalen-2-yl)-1,2,4-oxadiazol-5-yl)pyrrolidin-1-ium chloride (5c)

5c was synthesized using general procedure 4 and carried forward without purification.

(S)-2-(3-(6-(heptyloxy)naphthalen-2-yl)-1,2,4-oxadiazol-5-yl)pyrrolidin-1-ium chloride (5d)

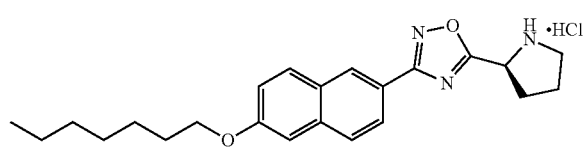 [SMILES: CCCCCCCOc1ccc2cc(-c3noc([C@@H]4CCCN4)n3)ccc2c1 ; Cl]

5d was synthesized using general procedure 4 and carried forward without purification.

(S)-2-(3-(6-isobutoxynaphthalen-2-yl)-1,2,4-oxadiazol-5-yl)pyrrolidin-1-ium chloride (5e)

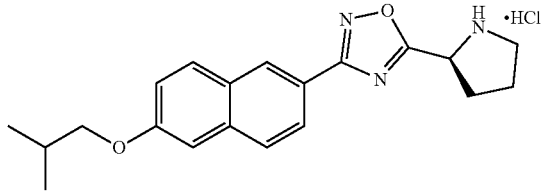 [SMILES: CC(C)COc1ccc2cc(-c3noc([C@@H]4CCCN4)n3)ccc2c1 ; Cl]

5e was synthesized using general procedure 4 and carried forward without purification.

(S)-2-(3-(6-(benzyloxy)naphthalen-2-yl)-1,2,4-oxadiazol-5-yl)pyrrolidin-1-ium chloride (5f)

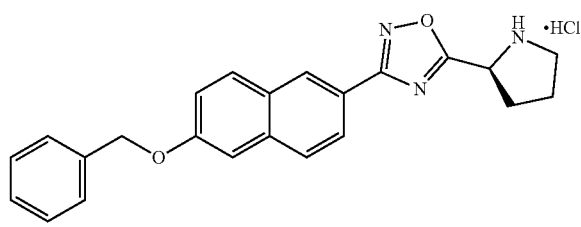 [SMILES: c1ccc(COc2ccc3cc(-c4noc([C@@H]5CCCN5)n4)ccc3c2)cc1 ; Cl]

5f was synthesized using general procedure 4 and carried forward without purification.

(S)-2-(3-(6-((4-methylbenzyl)oxy)naphthalen-2-yl)-1,2,4-oxadiazol-5-yl)pyrrolidin-1-ium chloride (5g)

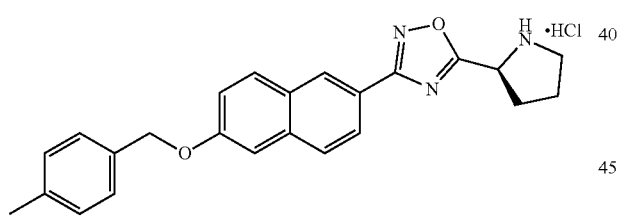

5g was synthesized using general procedure 4 and carried forward without purification.

(S)-2-(3-(6-(tosyloxy)naphthalen-2-yl)-1,2,4-oxadiazol-5-yl)pyrrolidin-1-ium chloride (5h)

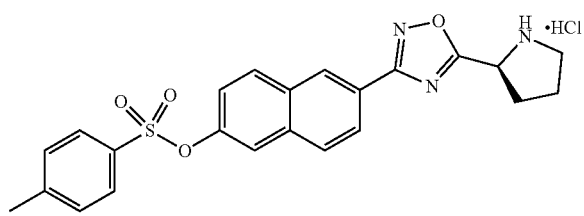 [SMILES: Cc1ccc(S(=O)(=O)Oc2ccc3cc(-c4noc([C@@H]5CCCN5)n4)ccc3c2)cc1 ; Cl]

5h was synthesized using general procedure 4 and carried forward without purification.

(2S,3S)-3-hydroxy-2-(3-(6-(pentyloxy)naphthalen-2-yl)-1,2,4-oxadiazol-5-yl)pyrrolidin-1-ium chloride (5i)

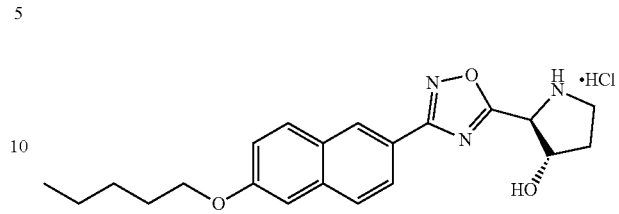

5i was synthesized using general procedure 4 and carried forward without purification.

(2S,3S)-3-hydroxy-2-(3-(6-isobutoxynaphthalen-2-yl)-1,2,4-oxadiazol-5-yl)pyrrolidin-1-ium chloride (5j)

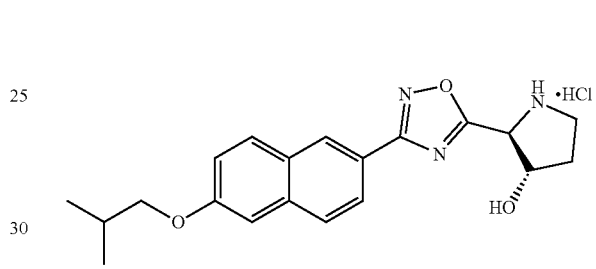

5j was synthesized using general procedure 4 and carried forward without purification.

Tert-butyl (S,Z)-(((tert-butoxycarbonyl)amino)(2-(3-(6-(butyloxy)naphthalen-2-yl)-1,2,4-oxadiazol-5-yl)pyrrolidin-1-yl)methylene)carbamate (6a)

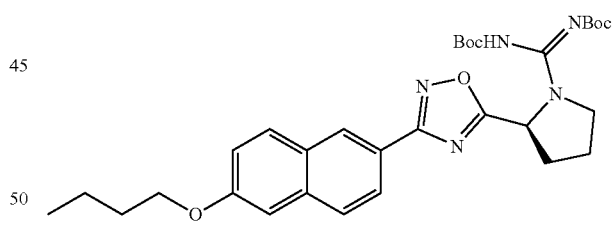

6a was synthesized using general procedure 5. Purification on a silica gel column with 10-30% ethyl acetate in hexanes produced 6a (25 mg, 67%), a clear oil. $^1$H NMR (400 MHz, CDCl$_3$) δ 8.51 (d, J=1.6 Hz, 1H), 8.07 (dd, J=8.6, 1.7 Hz, 1H), 7.80 (dd, J=16.6, 8.8 Hz, 2H), 7.22-7.12 (m, 2H), 5.63 (dd, J=7.9, 4.6 Hz, 1H), 4.11 (t, J=6.5 Hz, 2H), 3.95-3.89 (m, 1H), 3.87-3.76 (m, 1H), 2.52-2.41 (m, 1H), 2.33-2.17 (m, 2H), 2.12-2.00 (m, 1H), 1.85 (p, J=6.7 Hz, 2H), 1.57-1.39 (m, 18H), 1.01 (t, J=7.4 Hz, 3H). $^{13}$C NMR (101 MHz, CDCl$_3$) δ 168.69, 158.66, 153.77, 150.53, 136.34, 130.43, 128.49, 128.03, 127.48, 124.57, 120.03, 106.77, 82.36, 79.72, 67.99, 49.61, 31.41, 28.28, 19.47, 14.02. HRMS (ESI+): Calcd for $C_{31}H_{41}N_5O_6[M+H]^+$: 560.6951, Found: 580.3122.

Tert-butyl (S,Z)-(((tert-butoxycarbonyl)amino)(2-(3-(6-(pentyloxy)naphthalen-2-yl)-1,2,4-oxadiazol-5-yl)pyrrolidin-1-yl)methylene)carbamate (6b)

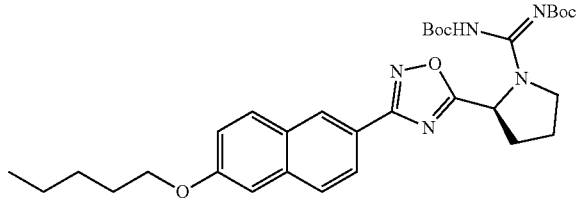

6b was synthesized using general procedure 5. Purification on a silica gel column with 10-30% ethyl acetate in hexanes produced 6b (23 mg, 63%), a clear oil. $^1$H NMR (400 MHz, CDCl$_3$) δ 8.51 (d, J=1.6 Hz, 1H), 8.07 (dd, J=8.6, 1.7 Hz, 1H), 7.80 (dd, J=17.4, 8.8 Hz, 2H), 7.21-7.13 (m, 2H), 5.63 (dd, J=7.9, 4.5 Hz, 1H), 4.09 (t, J=6.6 Hz, 2H), 3.95-3.88 (m, 1H), 3.87-3.77 (m, 1H), 2.53-2.41 (m, 1H), 2.32-2.15 (m, 2H), 2.11-2.02 (m, 1H), 1.90-1.82 (m, 2H), 1.79-1.68 (m, 1H), 1.60-1.36 (m, 24H), 0.95 (t, J=7.1 Hz, 3H). $^{13}$C NMR (101 MHz, CDCl$_3$) δ 178.98, 168.66, 158.63, 154.08, 150.58, 136.32, 130.41, 128.47, 128.02, 127.47, 124.54, 121.74, 120.01, 106.75, 82.28, 79.76, 68.27, 55.52, 49.60, 36.78, 29.03, 28.40, 28.26, 28.12, 24.82, 23.49, 22.61, 14.17. HRMS (ESI+): Calcd for C$_{32}$H$_{43}$N$_5$O$_6$ [M+H]$^+$: 594.7217, Found: 594.3323.

Tert-butyl (S,Z)-(((tert-butoxycarbonyl)amino)(2-(3-(6-(hexyloxy)naphthalen-2-yl)-1,2,4-oxadiazol-5-yl)pyrrolidin-1-yl)methylene)carbamate (6c)

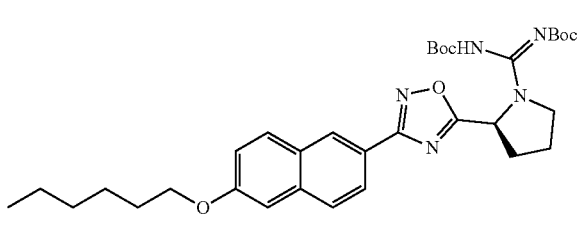

6c was synthesized using general procedure 5. Purification on a silica gel column with 15-30% ethyl acetate in hexanes produced 6c (25 mg, 66%), a clear oil. $^1$H NMR (500 MHz, CDCl$_3$) δ 8.51 (d, J=1.6 Hz, 1H), 8.07 (dd, J=8.5, 1.7 Hz, 1H), 7.80 (dd, J=20.7, 8.8 Hz, 2H), 7.19 (dd, J=8.9, 2.5 Hz, 1H), 7.15 (d, J=2.4 Hz, 1H), 5.64 (d, J=6.3 Hz, 1H), 4.09 (t, J=6.6 Hz, 2H), 3.93 (dd, J=11.5, 6.4 Hz, 1H), 3.83 (s, 1H), 2.51-2.41 (m, 1H), 2.34-2.16 (m, 2H), 2.06 (dd, J=12.9, 6.2 Hz, 1H), 1.91-1.79 (m, 2H), 1.64-1.29 (m, 27H), 0.98-0.88 (m, 3H). $^{13}$C NMR (126 MHz, CDCl$_3$) δ 178.93, 168.67, 158.64, 136.31, 130.42, 128.03, 127.48, 124.54, 120.02, 106.72, 68.29, 55.54, 49.64, 31.74, 29.31, 28.27, 25.93, 22.78, 14.21. HRMS (ESI+): Calcd for C$_{33}$H$_{45}$N$_5$O$_6$ [M+H]$^+$: 608.7482, Found: 608.3447.

Tert-butyl (S,Z)-(((tert-butoxycarbonyl)amino)(2-(3-(6-(heptyloxy)naphthalen-2-yl)-1,2,4-oxadiazol-5-yl)pyrrolidin-1-yl)methylene)carbamate (6d)

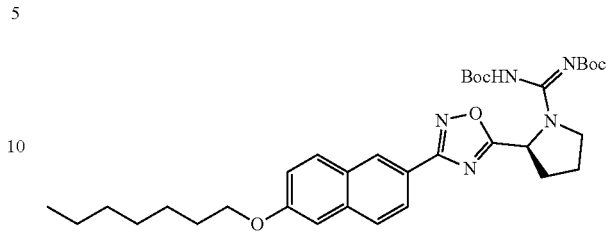

6d was synthesized using general procedure 5. Purification on a silica gel column with 15-30% ethyl acetate in hexanes produced 6d (14 mg, 59%), a clear oil. $^1$H NMR (400 MHz, CDCl$_3$) δ 8.49 (d, J=1.6 Hz, 1H), 8.05 (dd, J=8.6, 1.7 Hz, 1H), 7.78 (dd, J=17.1, 8.8 Hz, 2H), 7.21-7.11 (m, 2H), 5.61 (dd, J=7.9, 4.5 Hz, 1H), 4.08 (t, J=6.5 Hz, 2H), 3.97-3.88 (m, 1H), 3.85-3.75 (m, 1H), 2.51-2.39 (m, 1H), 2.31-2.15 (m, 2H), 2.05 (dd, J=12.8, 6.3 Hz, 1H), 1.84 (p, J=6.7 Hz, 2H), 1.67-1.17 (m, 26H), 0.92-0.83 (m, 3H). $^{13}$C NMR (126 MHz, CDCl$_3$) δ 178.85, 168.54, 162.00, 158.51, 150.38, 136.19, 130.29, 128.33, 127.89, 127.35, 124.40, 121.58, 119.89, 106.59, 82.27, 79.59, 77.60, 77.28, 77.02, 76.77, 68.15, 55.37, 49.49, 36.63, 31.80, 29.71, 29.20, 29.08, 28.12, 26.07, 22.63, 14.11. HRMS (ESI+): Calcd for C$_{34}$H$_{47}$N$_5$O$_6$ [M+H]$^+$: 622.7748, Found: 622.3606.

Tert-butyl (S,Z)-(((tert-butoxycarbonyl)amino)(2-(3-(6-isobutoxynaphthalen-2-yl)-1,2,4-oxadiazol-5-yl)pyrrolidin-1-yl)methylene)carbamate (6e)

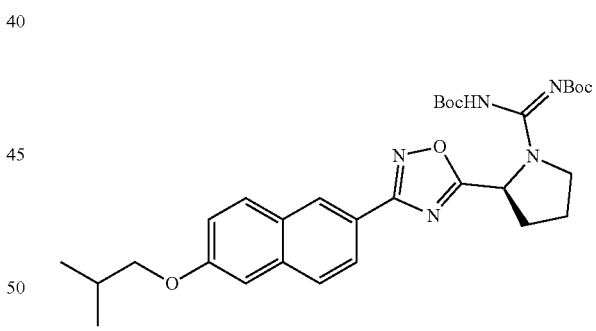

6e was synthesized using general procedure 5. Purification on a silica gel column with 15-30% ethyl acetate in hexanes produced 6e (34 mg, 65%), a clear oil. $^1$H NMR (500 MHz, CDCl$_3$) δ d) δ 8.51 (d, J=1.7 Hz, 1H), 8.07 (dd, J=8.5, 1.7 Hz, 1H), 7.80 (dd, J=22.6, 8.8 Hz, 2H), 7.20 (dd, J=9.0, 2.5 Hz, 1H), 7.14 (d, J=2.5 Hz, 1H), 5.63 (dd, J=8.0, 4.6 Hz, 1H), 3.97-3.88 (m, 1H), 3.95-3.82 (m, 3H), 2.50-2.42 (m, 1H), 2.29-2.14 (m, 3H), 2.12-1.97 (m, 1H), 1.55-1.38 (m, 20H), 1.08 (d, J=6.7 Hz, 6H). $^{13}$C NMR (126 MHz, CDCl$_3$) δ 178.97, 168.67, 162.11, 158.73, 153.76, 150.52, 136.32, 130.40, 128.45, 128.01, 127.46, 124.53, 121.71, 120.03, 106.75, 82.36, 79.72, 74.64, 55.51, 49.61, 28.40, 28.25, 19.46. HRMS (ESI+): Calcd for C$_{31}$H$_{41}$N$_5$O$_6$ [M+H]$^+$: 580.6951, Found: 580.3123.

Tert-butyl (S,E)-((2-(3-(6-(benzyloxy)naphthalen-2-yl)-1,2,4-oxadiazol-5-yl)pyrrolidin-1-yl)((tert-butoxycarbonyl)amino)methylene)carbamate (6f)

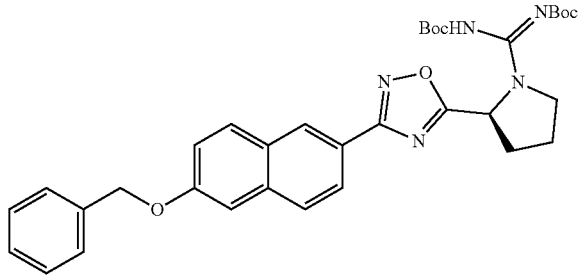

6e was synthesized using general procedure 5. Purification on a silica gel column with 15-30% ethyl acetate in hexanes produced 6e (12 mg, 40%), a clear oil. $^1$H NMR (400 MHz, CDCl$_3$) δ 8.53 (d, J=1.6 Hz, 1H), 8.09 (dd, J=8.6, 1.7 Hz, 1H), 7.85 (d, J=8.8 Hz, 1H), 7.79 (d, J=8.6 Hz, 1H), 7.53-7.48 (m, 2H), 7.45-7.40 (m, 2H), 7.39-7.33 (m, 1H), 7.30-7.25 (m, 2H), 5.64 (dd, J=7.9, 4.5 Hz, 1H), 5.21 (s, 2H), 3.97-3.88 (m, 1H), 3.86-3.75 (m, 1H), 2.55-2.40 (m, 1H), 2.31-2.16 (m, 2H), 2.10-2.00 (m, 1H), 1.57-1.33 (m, 18H). $^{13}$C NMR (101 MHz, CDCl$_3$) δ 179.02, 168.64, 158.24, 153.74, 150.73, 136.74, 136.20, 130.58, 128.82, 128.71, 128.29, 128.02, 127.72, 127.60, 124.65, 122.06, 120.03, 107.40, 82.44, 79.65, 77.36, 55.53, 49.61, 32.07, 29.85, 28.27, 22.84, 14.26. HRMS (ESI+): Calcd for C$_{34}$H$_{39}$N$_5$O$_6$ [M+H]$^+$: 614.7113, Found: 614.2990.

Tert-butyl (S,E)-(((tert-butoxycarbonyl)amino)(2-(3-(6-((4-methylbenzyl)oxy)naphthalen-2-yl)-1,2,4-oxadiazol-5-yl)pyrrolidin-1-yl)methylene)carbamate (6g)

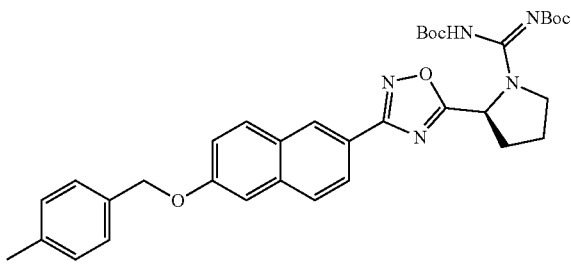

6g was synthesized using general procedure 5. Purification on a silica gel column with 15-30% ethyl acetate in hexanes produced 6g (4 mg, 27%), a clear oil. $^1$H NMR (400 MHz, CDCl$_3$) δ 8.50 (s, 1H), 8.06 (dd, J=8.6, 1.7 Hz, 1H), 7.83 (d, J=8.5 Hz, 1H), 7.77 (d, J=8.7 Hz, 1H), 7.36 (d, J=8.0 Hz, 2H), 7.24-7.18 (m, 4H), 5.62 (dd, J=7.8, 4.6 Hz, 1H), 5.15 (s, 2H), 3.95-3.86 (m, 1H), 3.85-3.77 (m, 1H), 2.50-2.38 (m, 1H), 2.36 (s, 3H), 2.33-2.14 (m, 2H), 2.10-1.99 (m, 1H), 1.49-1.38 (m, 18H). HRMS (ESI+): Calcd for C$_{35}$H$_{41}$N$_5$O$_6$ [M+H]$^+$: 628.3154, Found: 628.7379.

(S,E)-6-(5-(1-(N,N'-bis(tert-butoxycarbonyl)carbamimidoyl)pyrrolidin-2-yl)-1,2,4-oxadiazol-3-yl)naphthalen-2-yl 4-methylbenzenesulfonate (6h)

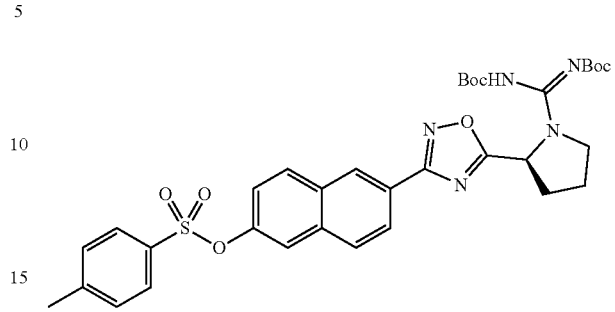

6h was synthesized using general procedure 5. Purification on a silica gel column with 15-30% ethyl acetate in hexanes produced 6h (7 mg, 61%), a clear oil. $^1$H NMR (500 MHz, CDCl$_3$) δ 8.57 (d, J=1.6 Hz, 1H), 8.14 (dd, J=8.6, 1.6 Hz, 1H), 7.85 (d, J=9.0 Hz, 1H), 7.82 (d, J=8.7 Hz, 1H), 7.78-7.70 (m, 2H), 7.52 (d, J=2.3 Hz, 1H), 7.34-7.27 (m, 2H), 7.16 (dd, J=8.9, 2.4 Hz, 1H), 5.64 (dd, J=7.9, 4.6 Hz, 1H), 3.97-3.89 (m, 1H), 3.86-3.77 (m, 1H), 2.54-2.46 (m, 1H), 2.45 (s, 3H), 2.33-2.14 (m, 2H), 2.10-2.01 (m, 1H), 1.46 (s, 18H). $^{13}$C NMR (126 MHz, CDCl$_3$) δ 179.44, 168.24, 162.14, 153.86, 150.35, 148.51, 145.69, 134.92, 132.53, 131.63, 130.85, 129.99, 128.75, 128.70, 127.96, 125.09, 124.82, 122.25, 120.15, 82.48, 79.87, 55.53, 49.64, 31.39, 29.84, 28.25, 24.18, 21.88. HRMS (ESI+): Calcd for C$_{34}$H$_{39}$N$_5$O$_8$S [M+H]$^+$: 678.7751, Found: 678.2600.

Tert-butyl ((E)-((tert-butoxycarbonyl)amino)((2S,3S)-3-hydroxy-2-(3-(6-(pentyloxy)naphthalen-2-yl)-1,2,4-oxadiazol-5-yl)pyrrolidin-1-yl)methylene)carbamate (6i)

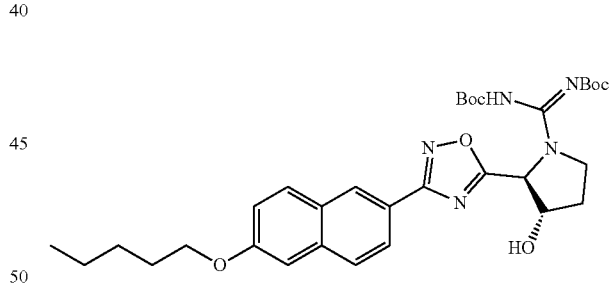

6i was synthesized using general procedure 5. Purification on a silica gel column with 20-40% ethyl acetate in hexanes produced 6i (34 mg, 66%), a clear oil. $^1$H NMR (400 MHz, CDCl$_3$) δ 8.45 (d, J=1.6 Hz, 1H), 8.02 (dd, J=8.6, 1.7 Hz, 1H), 7.78-7.70 (m, 2H), 7.20-7.08 (m, 2H), 5.62-5.56 (m, 1H), 4.69 (s, 1H), 4.05 (t, J=6.5 Hz, 2H), 4.02-3.93 (m, 2H), 2.40-2.33 (m, 1H), 2.22-2.08 (m, 1H), 1.89-1.78 (m, 2H), 1.45 (d, J=14.5 Hz, 21H), 0.95 (t, J=7.1 Hz, 3H). $^{13}$C NMR (126 MHz, CDCl$_3$) δ 176.57, 168.65, 158.57, 136.24, 130.31, 128.30, 127.97, 127.39, 124.34, 121.35, 119.93, 106.60, 82.53, 79.86, 77.58, 77.27, 77.01, 76.76, 74.93, 68.14, 63.41, 46.92, 31.93, 29.70, 28.89, 28.42, 28.26, 28.10, 28.04, 22.70, 22.48, 14.12, 14.03. HRMS (ESI+): Calcd for C$_{32}$H$_{43}$N$_5$O$_7$ [M+H]$^+$: 610.7211, Found: 610.3248.

Tert-butyl ((Z)-((tert-butoxycarbonyl)amino)((2S, 3S)-3-hydroxy-2-(3-(6-isobutoxynaphthalen-2-yl)-1,2,4-oxadiazol-5-yl)pyrrolidin-1-yl)methylene)carbamate (6j)

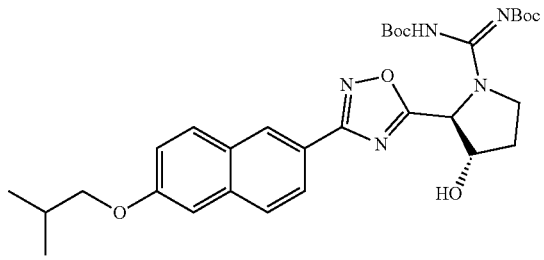

6j was synthesized using general procedure 5. Purification on a silica gel column with 20-40% ethyl acetate in hexanes produced 6j (32 mg, 70%), a clear oil. $^1$H NMR (500 MHz, CDCl$_3$) δ 8.48 (s, 1H), 8.04 (dd, J=8.6, 1.4 Hz, 1H), 7.78 (dd, J=17.2, 8.8 Hz, 2H), 7.21-7.17 (m, 1H), 7.13 (s, 1H), 5.57 (s, 1H), 4.69 (s, 1H), 4.05-3.96 (m, 2H), 3.84 (d, J=6.5 Hz, 2H), 2.38 (dq, J=12.9, 8.4, 6.5 Hz, 1H), 2.14 (ddd, J=13.2, 8.1, 5.3 Hz, 2H), 1.47 (d, J=17.8 Hz, 22H), 1.07 (d, J=6.7 Hz, 7H). $^{13}$C NMR (126 MHz, CDCl$_3$) δ 176.79, 168.76, 158.79, 153.93, 136.38, 130.43, 128.42, 128.12, 127.51, 124.47, 121.44, 120.07, 106.75, 77.73, 77.41, 77.16, 76.91, 74.97, 74.64, 63.57, 47.12, 32.07, 29.84, 29.80, 29.51, 28.40, 28.24, 22.84, 19.45, 14.26. HRMS (ESI+): Calcd for C$_{31}$H$_{41}$N$_5$O$_7$ [M+H]$^+$: 596.6945, Found: 596.3020.

Example 59: (S)-amino(2-(3-(6-(butyloxy)naphthalen-2-yl)-1,2,4-oxadiazol-5-yl)pyrrolidin-1-yl)methaniminium chloride (7a, compound 56A)

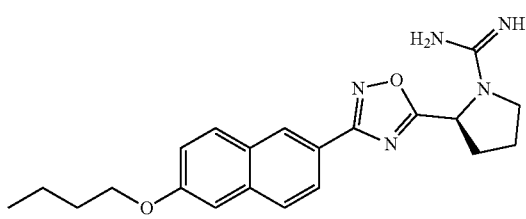

7a was synthesized using general procedure 4 and isolated as a light yellow tinted (6 mg, 42%). $^1$H NMR (400 MHz, CD$_3$OD) δ 8.50 (d, J=1.6 Hz, 1H), 8.03 (dd, J=8.6, 1.7 Hz, 1H), 7.88 (d, J=8.8 Hz, 2H), 7.30 (d, J=2.4 Hz, 1H), 7.21 (dd, J=9.0, 2.4 Hz, 1H), 5.46 (dd, J=7.7, 1.9 Hz, 1H), 4.14 (t, J=6.4 Hz, 2H), 3.85-3.77 (m, 1H), 3.68-3.61 (m, 1H), 2.64-2.47 (m, 2H), 2.29-2.19 (m, 1H), 2.18-2.07 (m, 1H), 1.88-1.80 (m, 2H), 1.63-1.51 (m, 2H), 1.02 (t, J=7.4 Hz, 3H). $^{13}$C NMR (101 MHz, CD$_3$OD) δ 177.39, 168.45, 155.67, 150.38, 129.82, 127.35, 125.45, 123.51, 120.94, 119.72, 118.77, 117.17, 106.28, 104.79, 67.51, 55.07, 30.98, 22.91, 18.91, 12.73. HRMS (ESI+): Calcd for C$_{21}$H$_{25}$N$_5$O$_2$ [M+H]$^+$: 380.4636, Found: 380.2069.

Example 60: (S)-amino(2-(3-(6-(pentyloxy)naphthalen-2-yl)-1,2,4-oxadiazol-5-yl)pyrrolidin-1-yl)methaniminium chloride (7b, compound 12A)

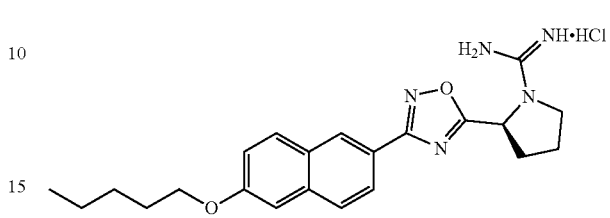

7b was synthesized using general procedure 4 and isolated as a light yellow tinted (5 mg, 95%). $^1$H NMR (400 MHz, MeOD) δ 8.50 (d, J=1.6 Hz, 1H), 8.03 (dd, J=8.5, 1.7 Hz, 1H), 7.88 (d, J=8.7 Hz, 2H), 7.30 (d, J=2.4 Hz, 1H), 7.22 (dd, J=9.0, 2.4 Hz, 1H), 5.47 (dd, J=7.8, 2.0 Hz, 1H), 4.13 (t, J=6.4 Hz, 2H), 3.85-3.77 (m, 1H), 3.69-3.60 (m, 2H), 2.64-2.48 (m, 2H), 2.31-2.21 (m, 1H), 2.19-2.05 (m, 1H), 1.87 (dq, J=8.1, 6.5 Hz, 2H), 1.57-1.26 (m, 6H), 0.98 (t, J=7.2 Hz, 3H). $^{13}$C NMR (126 MHz, MeOD) δ 178.88, 169.89, 160.22, 157.10, 137.94, 131.29, 129.73, 128.80, 124.97, 122.40, 121.18, 107.69, 69.23, 56.51, 49.46, 32.74, 30.05, 29.45, 24.35, 23.56, 14.39. HRMS (ESI+): Calcd for C$_{22}$H$_{27}$N$_5$O$_2$ [M+H]$^+$: 394.4900, Found: 394.2237.

Example 61: (S)-amino(2-(3-(6-(hexyloxy)naphthalen-2-yl)-1,2,4-oxadiazol-5-yl)pyrrolidin-1-yl)methaniminium chloride (7c, compound 16A)

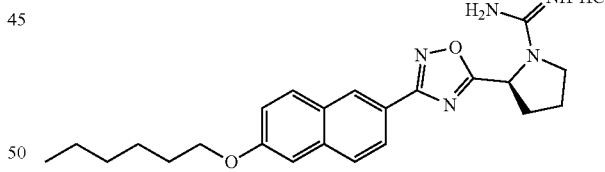

7c was synthesized using general procedure 4 and isolated as a light yellow tinted solid (14 mg, 96%). $^1$H NMR (400 MHz, MeOD) δ 8.51-8.46 (m, 1H), 8.00 (dd, J=8.5, 1.6 Hz, 1H), 7.85 (d, J=8.7 Hz, 2H), 7.29-7.25 (m, 1H), 7.19 (dd, J=9.0, 2.4 Hz, 1H), 5.44 (dd, J=7.8, 2.0 Hz, 1H), 4.11 (t, J=6.4 Hz, 2H), 3.81-3.73 (m, 1H), 3.66-3.55 (m, 1H), 2.61-2.46 (m, 2H), 2.26-2.19 (m, 1H), 2.14-2.06 (m, 1H), 1.88-1.80 (m, 2H), 1.56-1.47 (m, 2H), 1.37 (dtd, J=8.2, 4.4, 3.0 Hz, 4H), 0.97-0.83 (m, 3H). $^{13}$C NMR (101 MHz, MeOD) δ 178.84, 169.91, 160.23, 157.12, 137.95, 131.28, 129.74, 128.80, 124.97, 122.40, 121.17, 107.74, 69.27, 56.51, 49.46, 49.43, 49.21, 49.00, 48.79, 48.57, 48.36, 32.79, 32.74, 30.31, 26.92, 24.35, 23.69, 14.37. HRMS (ESI+): Calcd for C$_{23}$H$_{29}$N$_5$O$_2$ [M+H]$^+$: 408.5166, Found: 408.2408.

Example 62: (S)-amino(2-(3-(6-(heptyloxy)naphthalen-2-yl)-1,2,4-oxadiazol-5-yl)pyrrolidin-1-yl)methaniminium chloride (7d, compound 13A)

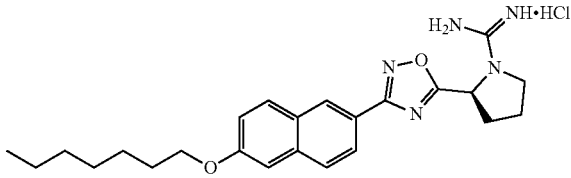

7d was synthesized using general procedure 4 and isolated as a light yellow tinted solid (8 mg, 78%). $^1$H NMR (500 MHz, MeOD) δ 8.51-8.47 (m, 1H), 8.02 (dd, J=8.5, 1.5 Hz, 1H), 7.87 (d, J=8.7 Hz, 2H), 7.44 (s, 1H), 7.29 (d, J=2.1 Hz, 1H), 7.21 (dd, J=8.9, 2.3 Hz, 1H), 5.47 (d, J=7.2 Hz, 1H), 4.12 (t, J=6.4 Hz, 2H), 3.80 (d, J=7.6 Hz, 1H), 3.65 (t, J=8.4 Hz, 1H), 2.54 (dt, J=31.0, 6.3 Hz, 2H), 2.30-2.20 (m, 1H), 2.12 (d, J=7.2 Hz, 1H), 1.87-1.79 (m, 2H), 1.56-1.48 (m, 2H), 1.45-1.28 (m, 7H), 0.95-0.88 (m, 3H). $^{13}$C NMR (126 MHz, MeOD) δ 178.87, 169.88, 160.20, 157.10, 137.93, 131.29, 129.72, 128.80, 124.97, 122.39, 121.16, 107.70, 69.24, 56.52, 32.99, 32.75, 30.34, 30.23, 27.20, 24.35, 23.68, 14.41. HRMS (ESI+): Calcd for $C_{24}H_{31}N_5O_2$ [M+H]$^+$: 422.5432, Found: 422.2564.

Example 63: (S)-amino(2-(3-(6-isobutoxynaphthalen-2-yl)-1,2,4-oxadiazol-5-yl)pyrrolidin-1-yl)methaniminium chloride (7e, compound 14A)

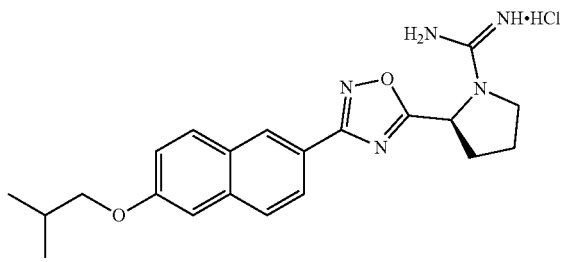

7e was synthesized using general procedure 4 and isolated as a light yellow tinted solid (17 mg, 99%). $^1$H NMR (500 MHz, MeOD δ 8.50 (s, 1H), 8.02 (dd, J=8.5, 1.3 Hz, 1H), 7.87 (d, J=8.7 Hz, 2H), 7.44 (s, 2H), 7.29 (d, J=2.1 Hz, 1H), 7.22 (dd, J=8.9, 2.2 Hz, 1H), 5.47 (d, J=7.0 Hz, 1H), 3.90 (d, J=6.4 Hz, 2H), 3.80 (dd, J=17.0, 8.8 Hz, 1H), 3.64 (q, J=9.1 Hz, 1H), 2.63-2.54 (m, 1H), 2.54-2.47 (m, 1H), 2.24 (s, 1H), 2.14 (dq, J=13.0, 6.5 Hz, 2H), 1.09 (d, J=6.7 Hz, 6H). $^{13}$C NMR (126 MHz, MeOD) δ 178.87, 169.88, 160.27, 157.10, 137.92, 131.29, 129.72, 128.80, 124.96, 122.39, 121.13, 107.74, 75.61, 56.54, 49.51, 49.34, 49.17, 49.00, 48.83, 48.66, 48.49, 32.77, 29.51, 24.37, 19.57. HRMS (ESI+): Calcd for $C_{21}H_{25}N_5O_2$ [M+H]$^+$: 380.4634, Found: 380.2109.

Example 64: (S)-amino(2-(3-(6-(benzyloxy)naphthalen-2-yl)-1,2,4-oxadiazol-5-yl)pyrrolidin-1-yl)methaniminium chloride (7f, compound 73A)

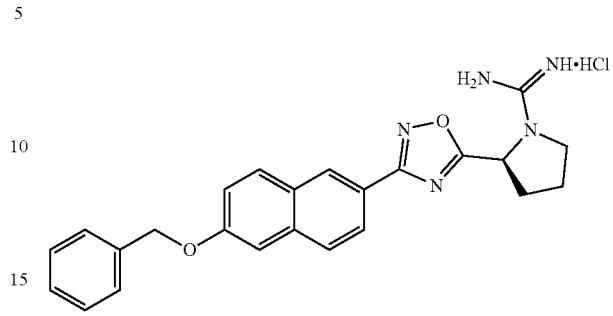

7f was synthesized using general procedure 4 and isolated as a light yellow tinted solid (7 mg, 95%). $^1$H NMR (500 MHz, CD$_3$OD) δ 8.52 (d, J=1.6 Hz, 1H), 8.03 (dd, J=8.6, 1.7 Hz, 1H), 7.89 (dd, J=14.2, 8.8 Hz, 2H), 7.53-7.49 (m, 2H), 7.43-7.37 (m, 3H), 7.36-7.28 (m, 2H), 5.49-5.45 (m, 1H), 5.24 (s, 2H), 3.84-3.79 (m, 1H), 3.68-3.60 (m, 1H), 2.64-2.54 (m, 1H), 2.53-2.47 (m, 1H), 2.28-2.20 (m, 1H), 2.16-2.06 (m, 1H). $^{13}$C NMR (126 MHz, CD$_3$OD) δ 178.88, 169.84, 159.78, 157.08, 138.29, 137.79, 131.42, 129.89, 129.57, 129.04, 128.88, 128.80, 128.71, 125.04, 122.62, 121.19, 108.46, 71.17, 56.53, 32.76, 24.36. HRMS (ESI+): Calcd for $C_{24}H_{23}N_5O_2$ [M+H]$^+$: 414.4797, Found: 414.1926.

Example 65: (S)-amino(2-(3-(6-((4-methylbenzyl)oxy)naphthalen-2-yl)-1,2,4-oxadiazol-5-yl)pyrrolidin-1-yl)methaniminium chloride (7g, compound 64A)

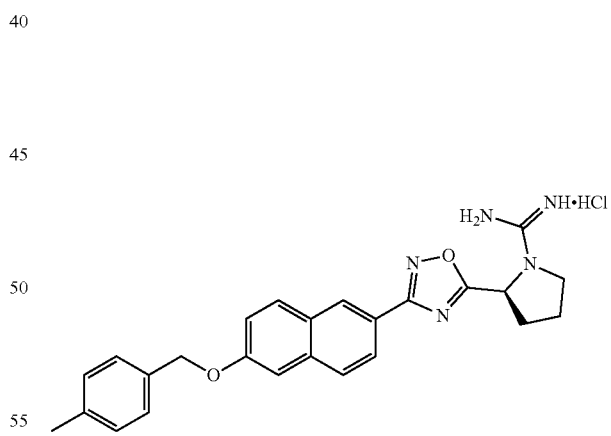

7g was synthesized using general procedure 4 and isolated as a light yellow tinted solid (3 mg, 100%). $^1$H NMR (400 MHz, CD$_3$OD) δ 8.50 (d, J=15.9 Hz, 1H), 8.06-7.96 (m, 1H), 7.88 (dd, J=21.9, 8.7 Hz, 1H), 7.76 (d, J=8.9 Hz, 1H), 7.40 (d, J=20.1 Hz, 4H), 7.31-7.20 (m, 1H), 7.16 (d, J=8.2 Hz, 1H), 5.49 (d, J=1.3 Hz, 1H), 5.46 (d, J=6.9 Hz, 1H), 5.19 (s, 1H), 3.85-3.75 (m, 1H), 3.68-3.58 (m, 1H), 2.65-2.46 (m, 2H), 2.35 (s, 3H), 2.29-2.19 (m, 1H), 2.18-2.06 (m, 1H). HRMS (ESI+): Calcd for $C_{25}H_{25}N_5O_2$ [M+H]$^+$: 428.5062, Found: 428.2083.

(S)-amino(2-(3-(6-(tosyloxy)naphthalen-2-yl)-1,2,4-oxadiazol-5-yl)pyrrolidin-1-yl)methaniminium chloride (7h, compound)

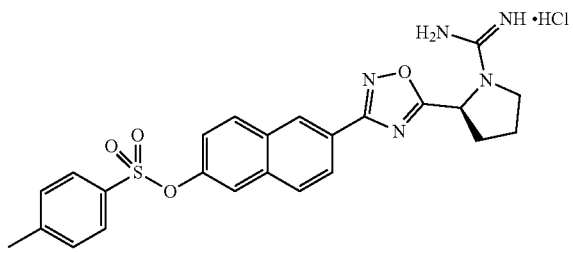

7h was synthesized using general procedure 4 and isolated as a light yellow tinted solid (7 mg, 100%). $^1$H NMR (400 MHz, CD$_3$OD) δ 8.59 (dd, J=1.6, 0.8 Hz, 1H), 8.11 (dd, J=8.6, 1.7 Hz, 1H), 7.99-7.89 (m, 2H), 7.75-7.70 (m, 2H), 7.56 (d, J=2.4 Hz, 1H), 7.43-7.37 (m, 2H), 7.20 (dd, J=8.9, 2.4 Hz, 1H), 5.46 (dd, J=7.9, 2.0 Hz, 1H), 3.78 (td, J=9.2, 2.6 Hz, 1H), 3.66-3.58 (m, 1H), 2.62-2.54 (m, 1H), 2.52-2.45 (m, 1H), 2.43 (s, 3H), 2.27-2.17 (m, 1H), 2.15-2.03 (m, 1H). HRMS (ESI+): Calcd for C$_{24}$H$_{23}$N$_5$O$_4$S [M+H]$^+$: 478.5435, Found: 478.1561.

Example 66: Amino((2S,3S)-3-hydroxy-2-(3-(6-(pentyloxy)naphthalen-2-yl)-1,2,4-oxadiazol-5-yl)pyrrolidin-1-yl)methaniminium chloride (7i, compound 14B)

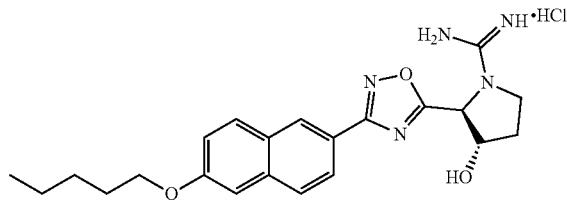 [SMILES: Cl ; CCCCCOc1ccc2cc(-c3noc([C@@H]4[C@@H](O)CCN4C(=N)N)n3)ccc2c1]

7i was synthesized using general procedure 4 and isolated as a light yellow tinted solid (73 mg, 100%). $^1$H NMR (500 MHz, CD$_3$OD) δ 8.51-8.50 (m, 1H), 8.03 (dd, J=8.5, 1.6 Hz, 1H), 7.88 (d, J=8.7 Hz, 2H), 7.50 (s, 1H), 7.30 (d, J=2.3 Hz, 1H), 7.22 (dd, J=9.0, 2.4 Hz, 1H), 5.25 (s, 1H), 4.82 (d, J=3.5 Hz, 1H), 4.13 (t, J=6.5 Hz, 2H), 3.88-3.80 (m, 2H), 2.29-2.16 (m, 2H), 1.88-1.84 (m, 2H), 1.57-1.49 (m, 2H), 1.47-1.42 (m, 2H), 0.98 (t, J=7.2 Hz, 3H). $^{13}$C NMR (126 MHz, CD$_3$OD) δ 176.68, 170.03, 160.26, 157.61, 137.98, 131.30, 129.73, 128.85, 128.82, 124.96, 122.30, 121.20, 107.72, 76.01, 69.24, 64.87, 49.51, 49.49, 49.45, 49.34, 49.28, 49.17, 49.11, 49.00, 48.94, 48.83, 48.66, 48.49, 47.41, 32.52, 30.04, 29.45, 23.55, 14.38. HRMS (ESI+): Calcd for C$_{22}$H$_{27}$N$_5$O$_3$ [M+H]$^+$: 410.4894, Found: 410.2204.

Example 67: Amino((2S,3S)-3-hydroxy-2-(3-(6-isobutoxynaphthalen-2-yl)-1,2,4-oxadiazol-5-yl)pyrrolidin-1-yl)methaniminium chloride (7j, compound 15A)

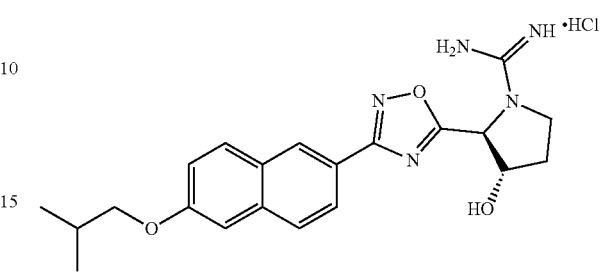

7j was synthesized using general procedure 4 and isolated as a light yellow tinted solid (9 mg, 62%). $^1$H NMR (500 MHz, MeOD) δ 8.50 (s, 1H), 8.04-7.98 (m, 1H), 7.88 (d, J=7.9 Hz, 2H), 7.51 (s, 1H), 7.29 (d, J=1.9 Hz, 1H), 7.22 (dd, J=8.9, 2.1 Hz, 1H), 5.25 (s, 1H), 4.81 (d, J=2.9 Hz, 1H), 3.93-3.74 (m, 4H), 2.29-2.10 (m, 3H), 1.09 (d, J=6.7 Hz, 6H). $^{13}$C NMR (126 MHz, MeOD) δ 176.66, 170.01, 160.30, 157.59, 137.95, 131.31, 129.72, 128.84, 128.83, 124.94, 122.28, 121.14, 107.76, 76.01, 75.62, 64.85, 49.51, 49.34, 49.17, 49.00, 48.83, 48.66, 48.49, 47.43, 32.52, 29.50, 19.56. HRMS (ESI+): Calcd for C$_{21}$H$_{25}$N$_5$O$_3$ [M+H]: 396.4628, Found: 396.2020.

Scheme 13

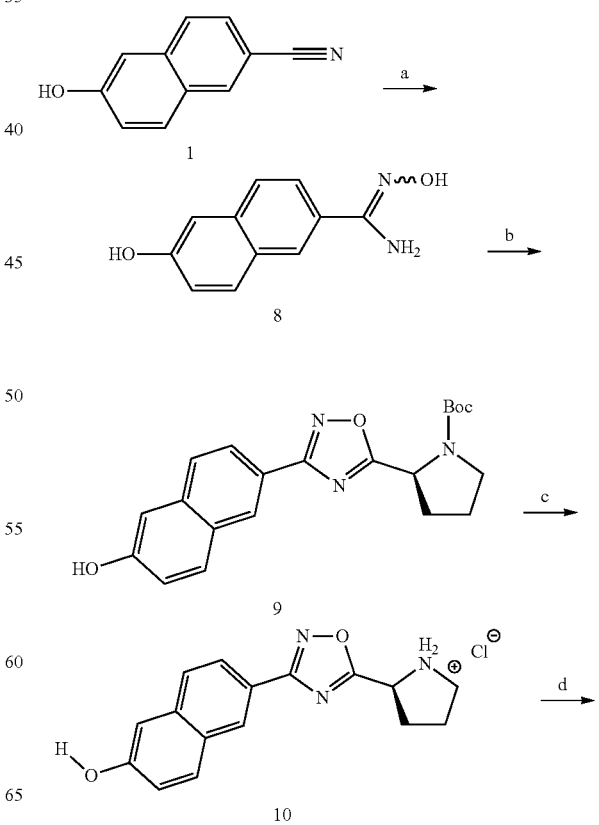

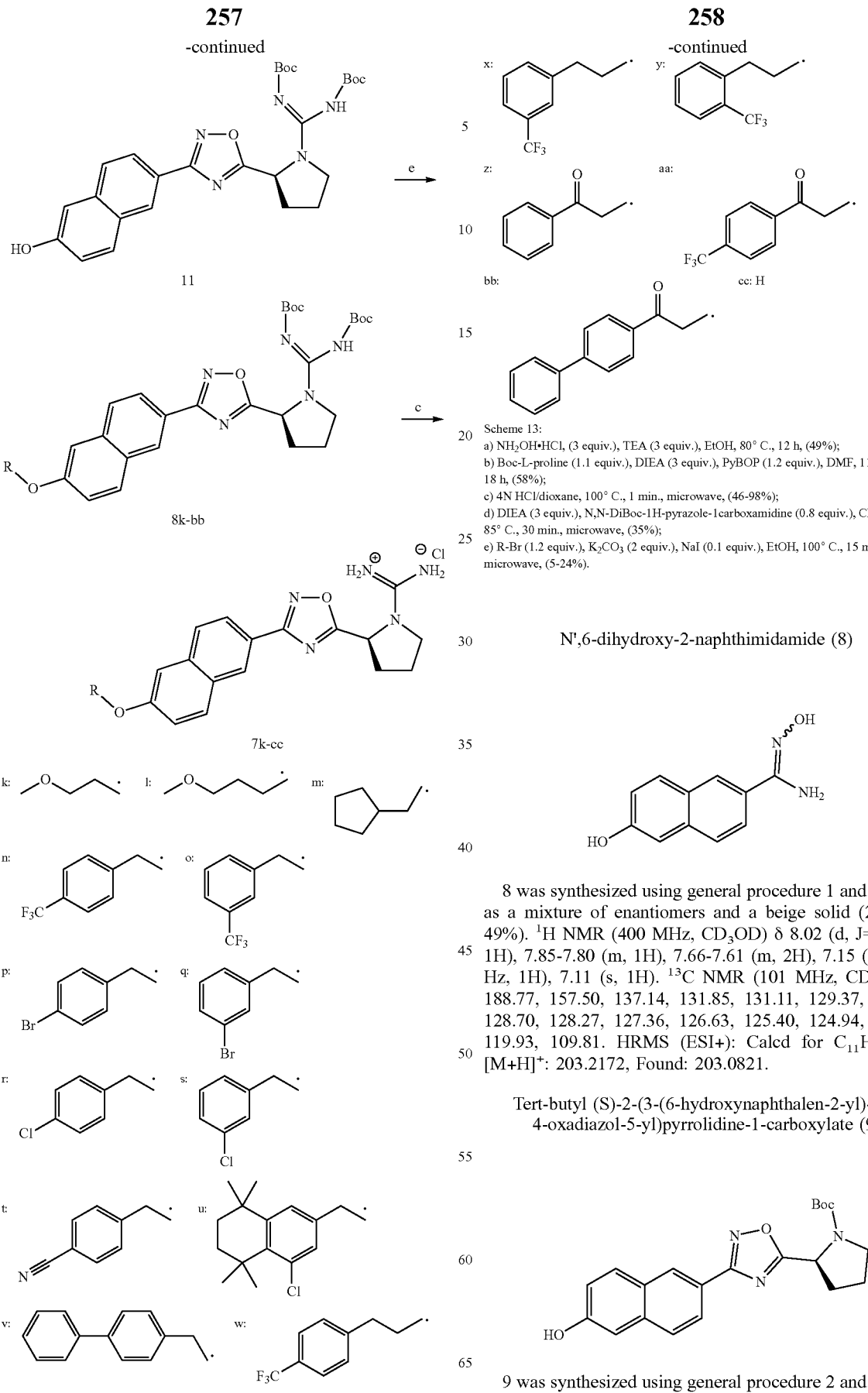

Scheme 13:
a) NH$_2$OH•HCl, (3 equiv.), TEA (3 equiv.), EtOH, 80° C., 12 h, (49%);
b) Boc-L-proline (1.1 equiv.), DIEA (3 equiv.), PyBOP (1.2 equiv.), DMF, 110° C., 18 h, (58%);
c) 4N HCl/dioxane, 100° C., 1 min., microwave, (46-98%);
d) DIEA (3 equiv.), N,N-DiBoc-1H-pyrazole-1carboxamidine (0.8 equiv.), CH$_3$CN, 85° C., 30 min., microwave, (35%);
e) R-Br (1.2 equiv.), K$_2$CO$_3$ (2 equiv.), NaI (0.1 equiv.), EtOH, 100° C., 15 min., microwave, (5-24%).

N',6-dihydroxy-2-naphthimidamide (8)

8 was synthesized using general procedure 1 and isolated as a mixture of enantiomers and a beige solid (293 mg, 49%). $^1$H NMR (400 MHz, CD$_3$OD) δ 8.02 (d, J=1.4 Hz, 1H), 7.85-7.80 (m, 1H), 7.66-7.61 (m, 2H), 7.15 (d, J=1.7 Hz, 1H), 7.11 (s, 1H). $^{13}$C NMR (101 MHz, CD$_3$OD) δ 188.77, 157.50, 137.14, 131.85, 131.11, 129.37, 129.14, 128.70, 128.27, 127.36, 126.63, 125.40, 124.94, 120.30, 119.93, 109.81. HRMS (ESI+): Calcd for C$_{11}$H$_{10}$N$_2$O$_2$ [M+H]$^+$: 203.2172, Found: 203.0821.

Tert-butyl (S)-2-(3-(6-hydroxynaphthalen-2-yl)-1,2,4-oxadiazol-5-yl)pyrrolidine-1-carboxylate (9)

9 was synthesized using general procedure 2 and isolated as a light yellow solid (218 mg, 58%). $^1$H NMR (1:1 rotamer ratio, 400 MHz, CDCl₃) δ ¹H NMR (400 MHz, Chloroform-d) δ 8.50 (s, 1H), 8.06 (d, J=8.6 Hz, 1H), 7.93 (s, 1H), 7.82 (d, J=8.8 Hz, 1H), 7.78-7.71 (m, 1H), 7.70 (s, 1H), 7.50 (d, J=8.7 Hz, 1H), 7.43 (d, J=8.7 Hz, 1H), 7.20 (s, 1H), 7.16 (d, J=8.9 Hz, 1H), 7.00 (d, J=7.3 Hz, 1H), 6.91 (s, 1H), 5.30-5.07 (m, 1H), 3.76 (d, J=7.9 Hz, 1H), 3.69-3.50 (m, 1H), 2.43 (d, J=12.3 Hz, 1H), 2.26-2.09 (m, 2H), 2.07-1.97 (m, 1H), 1.43 (d, J=86.6 Hz, 9H). ¹³C NMR (101 MHz, CDCl₃) δ 180.55, 179.23, 168.53, 156.15, 156.04, 155.13, 154.20, 136.45, 136.08, 130.82, 130.55, 128.20, 128.05, 127.51, 127.28, 126.52, 124.34, 123.76, 121.36, 120.43, 119.20, 118.80, 109.78, 109.35, 81.64, 81.25, 54.28, 54.07, 47.15, 46.58, 32.49, 31.89, 28.63, 28.34, 24.41, 23.85. HRMS (ESI+): Calcd for $C_{21}H_{23}N_3O_4$ [M+Na]⁺: 404.4148, Found: 404.1569.

(S)-2-(3-(6-hydroxynaphthalen-2-yl)-1,2,4-oxadiazol-5-yl)pyrrolidin-1-ium chloride (10)

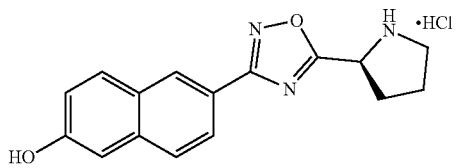 [SMILES: Oc1ccc2cc(-c3noc([C@@H]4CCCN4)n3)ccc2c1 ; Cl]

10 was synthesized using genera procedure 3 and isolated as a light yellow solid (160 mg, 96%). ¹H NMR (400 MHz, CD₃OD) δ 8.55-8.52 (m, 1H), 8.02 (dd, J=8.6, 1.7 Hz, 1H), 7.88-7.83 (m, 1H), 7.78 (dt, J=8.7, 0.7 Hz, 1H), 7.17 (d, J=8.2 Hz, 1H), 5.21 (t, J=7.8 Hz, 1H), 3.68-3.51 (m, 2H), 2.70 (dd, J=13.4, 5.7 Hz, 1H), 2.53-2.42 (m, 1H), 2.35-2.24 (m, 2H). ¹³C NMR (101 MHz, CD₃OD) δ 175.79, 170.13, 158.68, 138.23, 131.58, 129.18, 129.11, 128.29, 124.77, 121.38, 120.62, 110.17, 55.66, 49.64, 49.50, 49.43, 49.28, 49.21, 49.00, 48.79, 48.57, 48.36, 47.42, 30.23, 24.53. HRMS (ESI+): Calcd for $C_{16}H_{15}N_3O_2$ [M+H]⁺: 282.3171, Found: 282.1243.

Tert-butyl (S,Z)-(((tert-butoxycarbonyl)amino)(2-(3-(6-hydroxynaphthalen-2-yl)-1,2,4-oxadiazol-5-yl)pyrrolidin-1-yl)methylene)carbamate (11)

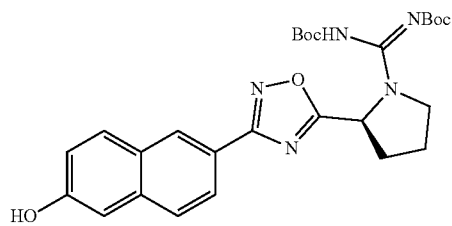

11 was synthesized using general procedure 4 and isolated as a light yellow solid (90 mg, 35%). ¹H NMR (400 MHz, CDCl₃) δ 7.79 (s, 1H), 7.65 (d, J=8.0 Hz, 2H), 7.39 (t, J=9.8 Hz, 2H), 7.02 (d, J=2.4 Hz, 1H), 6.88 (d, J=2.3 Hz, 1H), 5.65 (dd, J=8.0, 4.5 Hz, 1H), 3.97-3.86 (m, 1H), 3.86-3.76 (m, 1H), 2.54-2.44 (m, 1H), 2.31-2.2.25 (m, 1H), 2.17-1.99 (m, 2H), 1.48 (d, J=4.7 Hz, 20H). ¹³C NMR (101 MHz, CDCl₃) δ 177.92, 168.64, 156.35, 154.15, 136.18, 130.38, 127.94, 127.57, 127.44, 126.56, 123.69, 120.14, 119.02, 109.54, 81.69, 77.48, 77.36, 77.16, 76.84, 55.69, 49.85, 31.50, 29.81, 28.22, 24.27. HRMS (ESI+): Calcd for $C_{27}H_{33}N_5O_6$ [M+H]⁺: 524.5888, Found: 524.2532.

Tert-butyl (S,E)-(((tert-butoxycarbonyl)amino)(2-(3-(6-(3-methoxypropoxy)naphthalen-2-yl)-1,2,4-oxadiazol-5-yl)pyrrolidin-1-yl)methylene)carbamate (6k)

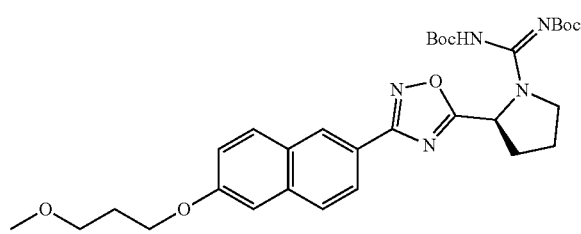

6k was synthesized using general procedure 5 and isolated as a clear residue (3 mg, 9%).

Tert-butyl (S,Z)-(((tert-butoxycarbonyl)amino)(2-(3-(6-(4-methoxybutoxy)naphthalen-2-yl)-1,2,4-oxadiazol-5-yl)pyrrolidin-1-yl)methylene)carbamate (6l)

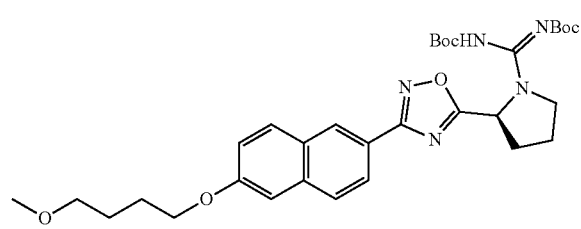

6l was synthesized using general procedure 5 and isolated as a clear residue (5 mg, 14%). ¹H NMR (400 MHz, CDCl₃) δ 8.51 (d, J=1.7 Hz, 1H), 8.07 (dd, J=8.6, 1.7 Hz, 1H), 7.80 (dd, J=16.7, 8.8 Hz, 2H), 7.21-7.11 (m, 2H), 5.63 (dd, J=7.9, 4.5 Hz, 1H), 4.13 (t, J=6.3 Hz, 2H), 3.97-3.89 (m, 1H), 3.87-3.78 (m, 1H), 3.48 (t, J=6.3 Hz, 2H), 3.37 (s, 3H), 2.52-2.41 (m, 1H), 2.29-2.17 (m, 2H), 2.11-2.00 (m, 1H), 1.97-1.88 (m, 2H), 1.86-1.75 (m, 2H), 1.52-1.38 (m, 18H). HRMS (ESI+): Calcd for $C_{32}H_{43}N_5O_7$ [M+H]⁺: 610.7211, Found: 610.3275.

Tert-butyl (S,Z)-(((tert-butoxycarbonyl)amino)(2-(3-(6-(cyclopentylmethoxy)naphthalen-2-yl)-1,2,4-oxadiazol-5-yl)pyrrolidin-1-yl)methylene)carbamate (6m)

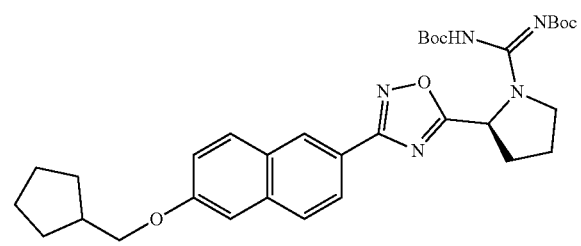

6m was synthesized using general procedure 5 and isolated as a clear residue (2 mg, 6%).

Tert-butyl (S,Z)-(((tert-butoxycarbonyl)amino)(2-(3-(6-((4-(trifluoromethyl)benzyl)oxy)naphthalen-2-yl)-1,2,4-oxadiazol-5-yl)pyrrolidin-1-yl)methylene)carbamate (6n)

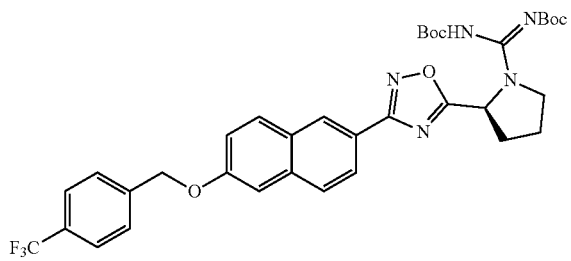

6n was synthesized using general procedure 5 and isolated as a clear residue (8 mg, 20%). $^1$H NMR (400 MHz, CDCl$_3$) δ 8.52 (d, J=1.6 Hz, 1H), 8.08 (dd, J=8.6, 1.7 Hz, 1H), 7.86 (d, J=9.0 Hz, 1H), 7.77 (d, J=8.7 Hz, 1H), 7.66 (d, J=8.2 Hz, 2H), 7.60 (d, J=8.2 Hz, 2H), 7.27 (dd, J=9.0, 2.5 Hz, 1H), 7.21 (d, J=2.6 Hz, 1H), 5.64 (dd, J=7.9, 4.6 Hz, 1H), 5.25 (s, 2H), 3.95-3.89 (m, 1H), 3.87-3.78 (m, 1H), 2.51-2.43 (m, 1H), 2.31-2.14 (m, 2H), 2.05-1.97 (m, 2H), 1.45 (s, 18H). HRMS (ESI+): Calcd for C$_{35}$H$_{38}$F$_3$N$_5$O$_6$ [M+H]$^+$: 682.7093, Found: 682.2889.

Tert-butyl (S,Z)-(((tert-butoxycarbonyl)amino)(2-(3-(6-((3-(trifluoromethyl)benzyl)oxy)naphthalen-2-yl)-1,2,4-oxadiazol-5-yl)pyrrolidin-1-yl)methylene)carbamate (6o)

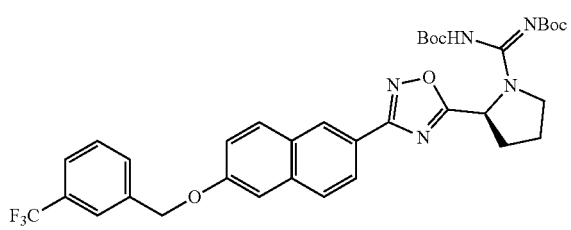

6o was synthesized using general procedure 5 and isolated as a clear residue (4 mg, 10%). HRMS (ESI+): Calcd for C$_{35}$H$_{38}$F$_3$N$_5$O$_6$ [M+H]$^+$: 682.7093, Found: 682.2889.

Tert-butyl (S,Z)-((2-(3-(6-((4-bromobenzyl)oxy)naphthalen-2-yl)-1,2,4-oxadiazol-5-yl)pyrrolidin-1-yl)((tert-butoxycarbonyl)amino)methylene)carbamate (6p)

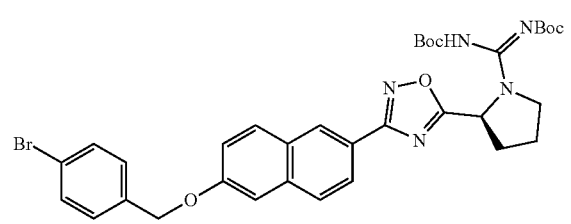

6p was synthesized using general procedure 5 and isolated as a clear residue (3 mg, 8%). $^1$H NMR (400 MHz, CDCl$_3$) δ 8.57-8.49 (m, 1H), 8.36-8.17 (m, 2H), 8.07 (dd, J=8.6, 1.7 Hz, 1H), 7.88-7.78 (m, 2H), 7.56-7.46 (m, 3H), 7.42-7.35 (m, 2H), 5.29 (d, J=5.6 Hz, 1H), 5.16 (s, 1H), 4.66 (s, 1H), 4.21-4.11 (m, 1H), 4.08-4.00 (m, 1H), 2.70-2.58 (m, 1H), 2.55-2.41 (m, 1H), 2.30-2.19 (m, 2H), 1.57-1.45 (m, 17H). HRMS (ESI+): Calcd for C$_{24}$H$_{38}$BrN$_5$O$_6$ [M+H]$^+$: 693.6074, Found: 693.2114.

Tert-butyl (S,Z)-((2-(3-(6-((3-bromobenzyl)oxy)naphthalen-2-yl)-1,2,4-oxadiazol-5-yl)pyrrolidin-1-yl)((tert-butoxycarbonyl)amino)methylene)carbamate (6q)

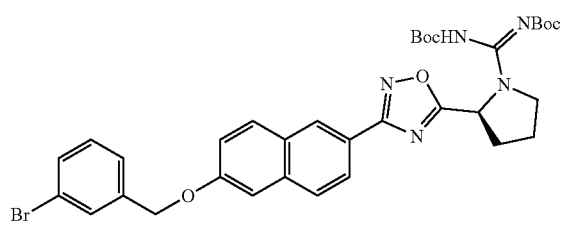

6q was synthesized using general procedure 5 and isolated as a clear residue (2 mg, 5%). HRMS (ESI+): Calcd for C$_{34}$H$_{38}$BrN$_5$O$_6$ [M+K]$^+$: 731.6977, Found: 730.1707.

Tert-butyl (S,Z)-(((tert-butoxycarbonyl)amino)(2-(3-(6-((4-chlorobenzyl)oxy)naphthalen-2-yl)-1,2,4-oxadiazol-5-yl)pyrrolidin-1-yl)methylene)carbamate (6r)

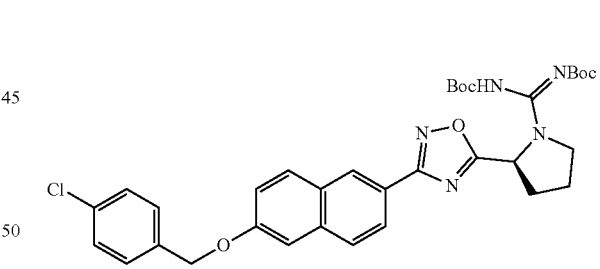

6r was synthesized using general procedure 5 and isolated as a clear residue (4 mg, 10%). $^1$H NMR (500 MHz, CDCl$_3$)$^1$H NMR (500 MHz, CDCl$_3$) δ 8.53 (d, J=1.6 Hz, 1H), 8.09 (dd, J=8.5, 1.7 Hz, 1H), 7.82 (dd, J=34.8, 8.8 Hz, 2H), 7.45-7.36 (m, 4H), 7.26 (dd, J=8.9, 2.5 Hz, 1H), 7.22 (d, J=2.5 Hz, 1H), 5.63 (dd, J=7.9, 4.7 Hz, 1H), 5.17 (s, 2H), 3.95-3.87 (m, 1H), 3.85-3.77 (m, 1H), 2.53-2.40 (m, 1H), 2.30-2.19 (m, 2H), 2.08-2.02 (m, 1H), 1.52-1.42 (m, 24H). $^{13}$C NMR (126 MHz, CDCl$_3$) δ 179.08, 168.59, 157.96, 153.63, 148.81, 136.12, 135.25, 134.11, 130.68, 129.00, 128.78, 128.02, 127.61, 124.73, 122.19, 119.89, 114.87, 107.43, 83.55, 77.73, 69.49, 55.52, 49.62, 31.60, 31.22, 28.26, 28.13, 24.13, 21.18, 14.34. HRMS (ESI+): Calcd for C$_{34}$H$_{38}$ClN$_5$O$_6$ [M+H]$^+$: 649.1564, Found: 649.16.

263

Tert-butyl (S,Z)-(((tert-butoxycarbonyl)amino)(2-(3-(6-((3-chlorobenzyl)oxy)naphthalen-2-yl)-1,2,4-oxadiazol-5-yl)pyrrolidin-1-yl)methylene)carbamate (6s)

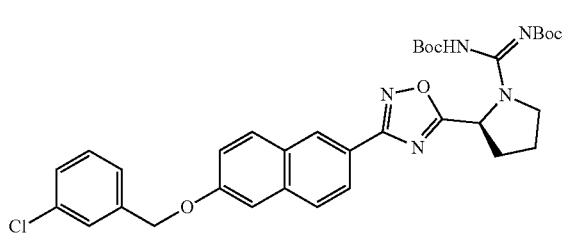

6s was synthesized using general procedure 5 and isolated as a clear residue (7 mg, 19%). $^1$H NMR (500 MHz, CDCl$_3$) δ 8.53 (d, J=1.5 Hz, 1H), 8.09 (dd, J=8.6, 1.7 Hz, 1H), 7.82 (dd, J=34.9, 8.8 Hz, 2H), 7.50 (s, 1H), 7.38-7.29 (m, 3H), 7.29-7.26 (m, 1H), 7.21 (d, J=2.5 Hz, 1H), 5.63 (dd, J=7.9, 4.6 Hz, 1H), 5.17 (s, 2H), 3.95-3.88 (m, 1H), 3.85-3.77 (m, 1H), 2.53-2.39 (m, 1H), 2.36-2.17 (m, 2H), 2.11-2.01 (m, 1H), 1.58-1.38 (m, 22H). $^{13}$C NMR (126 MHz, CDCl$_3$) δ 178.92, 171.10, 168.44, 157.75, 153.54, 150.39, 138.66, 135.96, 134.61, 130.55, 129.94, 128.66, 128.25, 127.87, 127.49, 127.47, 125.42, 124.58, 122.07, 119.71, 107.27, 82.21, 79.33, 69.24, 60.37, 55.37, 49.46, 28.30, 28.11, 28.07, 27.98, 21.03, 14.19. HRMS (ESI+): Calcd for C$_{34}$H$_{38}$ClN$_5$O$_6$ [M+H]$^+$: 649.1564, Found: 649.17.

Tert-butyl (S,Z)-(((tert-butoxycarbonyl)amino)(2-(3-(6-((4-cyanobenzyl)oxy)naphthalen-2-yl)-1,2,4-oxadiazol-5-yl)pyrrolidin-1-yl)methylene)carbamate (6t)

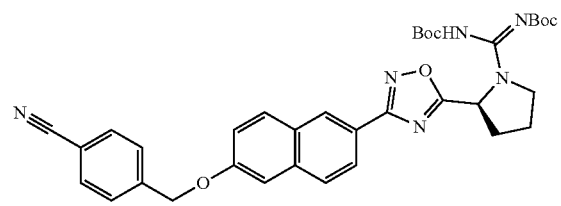

6t was synthesized using general procedure 5 and isolated as a clear residue (4 mg, 11%). $^1$H NMR (500 MHz, CDCl$_3$) δ 8.54 (d, J=1.6 Hz, 1H), 8.09 (dd, J=8.7, 1.7 Hz, 1H), 7.88-7.77 (m, 2H), 7.72 (dd, J=8.2, 1.6 Hz, 2H), 7.66-7.57 (m, 3H), 7.48 (dd, J=7.9, 0.8 Hz, 1H), 7.20 (d, J=2.5 Hz, 1H), 5.39 (d, J=7.0 Hz, 1H), 5.27 (s, 2H), 4.06-3.99 (m, 1H), 3.98-3.89 (m, 1H), 2.62-2.50 (m, 1H), 2.42-2.32 (m, 1H), 2.28-2.20 (m, 1H), 2.17-2.09 (m, 1H), 1.59-1.40 (m, 21H).

264

Tert-butyl (S,Z)-(((tert-butoxycarbonyl)amino)(2-(3-(6-((5,5,8,8-tetramethyl-5,6,7,8-tetrahydronaphthalen-2-yl)methoxy)naphthalen-2-yl)-1,2,4-oxadiazol-5-yl)pyrrolidin-1-yl)methylene)carbamate (6u)

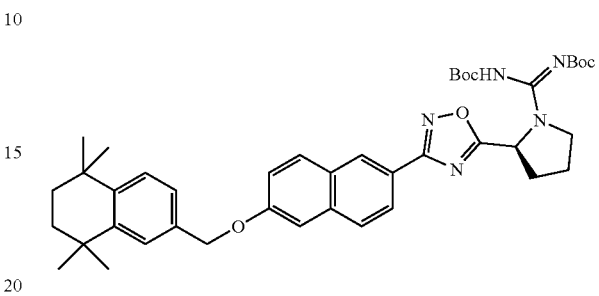

6u was synthesized using general procedure 5 and isolated as a clear residue (10 mg, 24%). $^1$H NMR (400 MHz, CDCl$_3$) δ 8.54-8.50 (m, 1H), 8.06 (dd, J=8.6, 1.7 Hz, 1H), 7.83 (d, J=8.8 Hz, 1H), 7.73 (d, J=8.6 Hz, 1H), 7.29 (d, J=1.9 Hz, 1H), 7.16 (d, J=1.5 Hz, 2H), 7.14-7.11 (m, 1H), 7.06 (dd, J=8.0, 1.9 Hz, 1H), 5.13-5.06 (m, 1H), 4.63 (d, J=4.5 Hz, 2H), 4.04 (dd, J=8.6, 5.9 Hz, 1H), 3.19 (d, J=7.2 Hz, 1H), 2.37-2.27 (m, 1H), 2.19-2.08 (m, 2H), 1.93-1.87 (m, 1H), 1.59 (d, J=1.4 Hz, 2H), 1.52 (s, 2H), 1.27 (s, 3H), 1.26 (s, 3H), 1.25-1.20 (m, 24H), 1.17 (s, 3H), 1.14 (s, 3H). HRMS (ESI+): Calcd for C$_{42}$H$_{53}$N$_5$O$_6$ [M+H]$^+$: 742.9081, Found: 724.4136.

Tert-butyl (S,Z)-((2-(3-(6-([1,1'-biphenyl]-4-ylmethoxy)naphthalen-2-yl)-1,2,4-oxadiazol-5-yl)pyrrolidin-1-yl)((tert-butoxycarbonyl)amino)methylene)carbamate (6v)

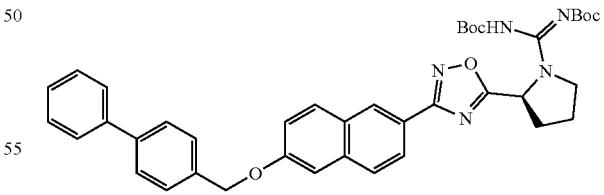

6v was synthesized using general procedure 5 and isolated as a clear residue (3 mg, 8%). $^1$H NMR (400 MHz, CDCl$_3$) δ 8.54-8.43 (m, 1H), 8.36-8.29 (m, 1H), 8.18 (dd, J=8.9, 1.6 Hz, 1H), 8.06 (dd, J=8.6, 1.7 Hz, 1H), 7.90-7.79 (m, 1H), 7.71-7.52 (m, 5H), 7.48-7.35 (m, 3H), 5.39 (s, 1H), 5.36-5.32 (m, 1H), 5.26 (s, 1H), 4.28-4.19 (m, 1H), 4.17-1.09 (m, 1H), 2.77-2.65 (m, 1H), 2.57-2.45 (m, 1H), 2.37-2.20 (m, 2H), 1.70-1.40 (m, 16H). HRMS (ESI+): Calcd for C$_{40}$H$_{43}$N$_5$O$_6$ [M+H]$^+$: 690.8073, Found: 690.3307.

Tert-butyl (S,Z)-(((tert-butoxycarbonyl)amino)(2-(3-(6-(4-(trifluoromethyl)phenethoxy)naphthalen-2-yl)-1,2,4-oxadiazol-5-yl)pyrrolidin-1-yl)methylene)carbamate (6w)

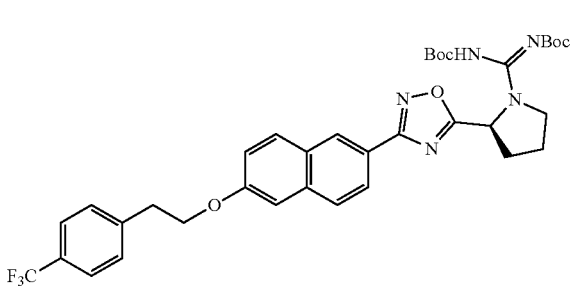

6w was synthesized using general procedure 5 and isolated as a clear residue (4 mg, 10%). ¹H NMR (400 MHz, CDCl₃) δ 8.50 (d, J=15.6 Hz, 1H), 8.27 (d, J=9.0 Hz, 1H), 8.17-8.11 (m, 1H), 8.07-7.98 (m, 1H), 7.89-7.70 (m, 2H), 7.62-7.53 (m, 2H), 7.52-7.46 (m, 1H), 7.46-7.41 (m, 1H), 5.26 (s, 1H), 4.36 (dt, J=29.7, 6.6 Hz, 2H), 4.25-4.18 (m, 1H), 4.17-4.09 (m, 1H), 3.29-3.17 (m, 2H), 2.75-2.64 (m, 1H), 2.58-2.54 (m, 1H), 2.37-2.17 (m, 2H), 1.69-1.39 (m, 21H). ¹⁹F NMR (376 MHz, CDCl₃) δ −62.47.

Tert-butyl (S,Z)-(((tert-butoxycarbonyl)amino)(2-(3-(6-(3-(trifluoromethyl)phenethoxy)naphthalen-2-yl)-1,2,4-oxadiazol-5-yl)pyrrolidin-1-yl)methylene)(6x)

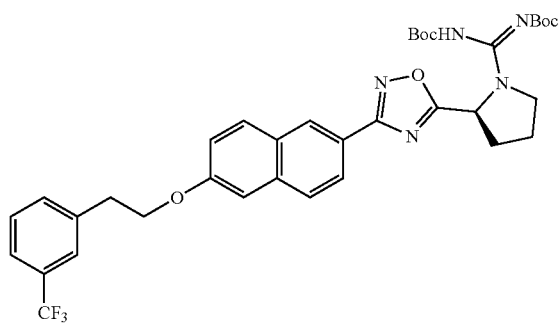

6x was synthesized using general procedure 5 and isolated as a clear residue (3 mg, 8%). ¹H NMR (400 MHz, CDCl₃) δ 8.55-8.44 (m, 1H), 8.29 (d, J=8.9 Hz, 1H), 8.17-8.01 (m, 1H), 7.90-7.74 (m, 2H), 7.68 (s, 1H), 7.60 (s, 1H), 7.55-7.49 (m, 2H), 7.49-7.42 (m, 2H), 5.38-5.28 (s, 1H), 4.45-4.33 (m, 2H), 4.33-4.18 (m, 1H), 4.12-3.93 (m, 1H), 3.29-3.21 (m, 2H), 2.82-2.72 (m, 1H), 2.64-2.50 (m, 1H), 2.38-2.23 (m, 2H), 1.78-1.38 (m, 27H). ¹⁹F NMR (376 MHz, CDCl₃) δ −62.60, −62.63, −62.67.

Tert-butyl (S,Z)-(((tert-butoxycarbonyl)amino)(2-(3-(6-(2-(trifluoromethyl)phenethoxy)naphthalen-2-yl)-1,2,4-oxadiazol-5-yl)pyrrolidin-1-yl)methylene)carbamate (6y)

6y was synthesized using general procedure 5 and isolated as a clear residue (2 mg, 5%). ¹H NMR (400 MHz, CDCl₃) δ 8.50 (d, J=14.8 Hz, 1H), 8.28 (d, J=9.0 Hz, 1H), 8.15 (dd, J=8.9, 1.7 Hz, 1H), 8.03 (dd, J=8.6, 1.7 Hz, 1H), 7.85-7.73 (m, 2H), 7.65 (dd, J=12.8, 7.7 Hz, 2H), 7.51-7.48 (m, 1H), 7.35 (dd, J=8.4, 5.2 Hz, 1H), 7.20-7.12 (m, 1H), 5.54-5.37 (m, 1H), 4.36 (dt, J=33.2, 6.8 Hz, 2H), 4.19-4.12 (m, 2H), 3.41-3.29 (m, 2H), 2.71-2.61 (m, 1H), 2.54-2.41 (m, 1H), 2.34-2.19 (ms, 2H), 1.72-1.36 (m, 24H). ¹⁹F NMR (376 MHz, CDCl₃) δ −59.38, −59.42, −59.44, −59.47, −59.48, −59.64, −59.71, −60.28.

Tert-butyl (S,Z)-(((tert-butoxycarbonyl)amino)(2-(3-(6-(2-oxo-2-phenylethoxy)naphthalen-2-yl)-1,2,4-oxadiazol-5-yl)pyrrolidin-1-yl)methylene)carbamate 6p (6z)

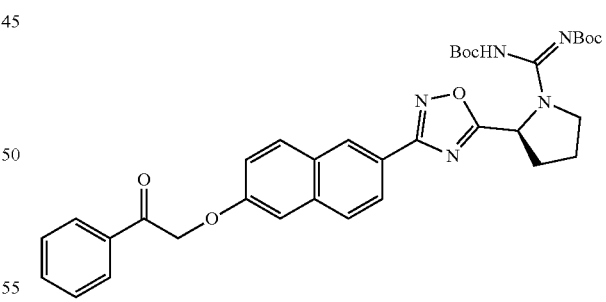

6z was synthesized using general procedure 5 and isolated as a clear residue (3 mg, 8%). 1H NMR (400 MHz, Chloroform-d) δ 8.51 (d, J=1.6 Hz, 1H), 8.09-8.00 (m, 3H), 7.85 (d, J=9.0 Hz, 1H), 7.76 (d, J=8.7 Hz, 1H), 7.65-7.61 (m, 1H), 7.56-7.48 (m, 2H), 7.30 (dd, J=9.0, 2.5 Hz, 1H), 7.13 (d, J=2.6 Hz, 1H), 5.61 (dd, J=7.8, 4.5 Hz, 1H), 5.41 (s, 2H), 3.96-3.85 (m, 1H), 3.86-3.73 (m, 1H), 2.51-2.37 (m, 1H), 2.27-2.16 (m, 2H), 2.02-1.97 (m, 2H), 1.68-1.33 (m, 32H). HRMS (ESI+): Calcd for C₃₅H₃₉N₅O₇ [M+H]⁺: 642.7214, Found: 642.2962.

Tert-butyl (S,Z)-(((tert-butoxycarbonyl)amino)(2-(3-(6-(2-oxo-2-(4-(trifluoromethyl)phenyl)ethoxy)naphthalen-2-yl)-1,2,4-oxadiazol-5-yl)pyrrolidin-1-yl)methylene)carbamate (6aa)

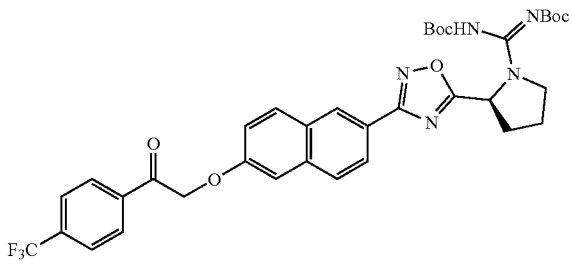

6aa was synthesized using general procedure 5 and isolated as a clear residue (4 mg, 10%). $^1$H NMR (400 MHz, CDCl$_3$) δ 8.52 (d, J=1.6 Hz, 1H), 8.15 (dt, J=8.0, 0.9 Hz, 2H), 8.08 (dd, J=8.6, 1.7 Hz, 1H), 7.86 (d, J=9.0 Hz, 1H), 7.81-7.74 (m, 3H), 7.28 (dd, J=9.0, 2.6 Hz, 1H), 7.13 (d, J=2.6 Hz, 1H), 5.61 (dd, J=7.9, 4.6 Hz, 1H), 5.38 (s, 2H), 3.93-3.88 (m, 1H), 3.84-3.73 (m, 1H), 2.49-2.39 (m, 1H), 2.28-2.17 (m, 2H), 2.02-1.96 (m, 2H), 1.57-1.33 (m, 33H). HRMS (ESI+): Calcd for C$_{36}$H$_{38}$F$_3$N$_5$O$_7$ [M+H]$^+$710.7194, Found: 710.2802.

Tert-butyl (S,Z)-((2-(3-(6-(2-([1,1'-biphenyl]-4-yl)-2-oxoethoxy)naphthalen-2-yl)-1,2,4-oxadiazol-5-yl)pyrrolidin-1-yl)((tert-butoxycarbonyl)amino)methylene)carbamate (6bb)

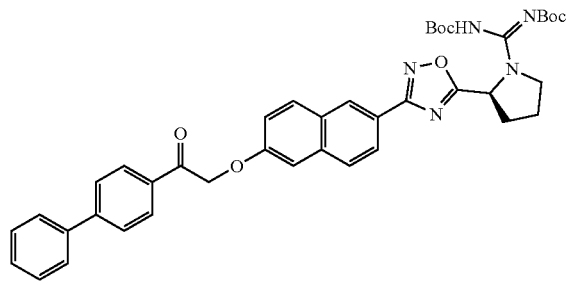

6bb was synthesized using general procedure 5 and isolated as a clear residue (6 mg, 15%). $^1$H NMR (400 MHz, CDCl$_3$) δ 8.51 (d, J=1.6 Hz, 1H), 8.14-8.10 (m, 1H), 8.07 (dd, J=8.6, 1.7 Hz, 1H), 7.86 (d, J=9.0 Hz, 1H), 7.79-7.71 (m, 2H), 7.65-7.60 (m, 2H), 7.51-7.45 (m, 2H), 7.42 (d, J=7.2 Hz, 1H), 7.32 (dd, J=9.0, 2.6 Hz, 1H), 7.16 (d, J=2.6 Hz, 1H), 5.74-5.64 (m, 1H), 5.43 (s, 2H), 3.98-3.88 (m, 1H), 3.88-3.79 (m, 1H), 2.51-2.39 (m, 1H), 2.32-2.16 (m, 2H), 2.10-2.00 (m, 1H), 1.67-1.32 (m, 21H). HRMS (ESI+): Calcd for C$_{41}$H$_{43}$N$_5$O$_7$ [M+H]$^+$: 718.8174, Found: 718.3275.

Example 68: (S)-amino(2-(3-(6-(3-methoxypropoxy)naphthalen-2-yl)-1,2,4-oxadiazol-5-yl)pyrrolidin-1-yl)methaniminium chloride (7k, compound 57A)

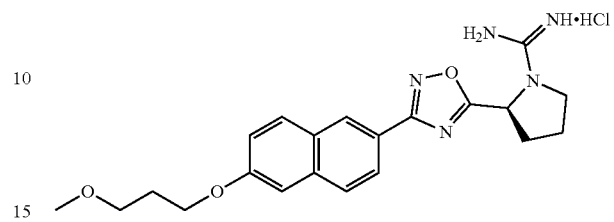

7k was synthesized using general procedure 3 and isolated as a white solid (1 mg, 47%). MS (ESI+): Calcd for C$_{21}$H$_{25}$N$_5$O$_3$ [M+H]$^+$: 395.4628, Found: 396.72.

Example 69: (S)-amino(2-(3-(6-(4-methoxybutoxy)naphthalen-2-yl)-1,2,4-oxadiazol-5-yl)pyrrolidin-1-yl)methaniminium chloride (7l, compound 65A)

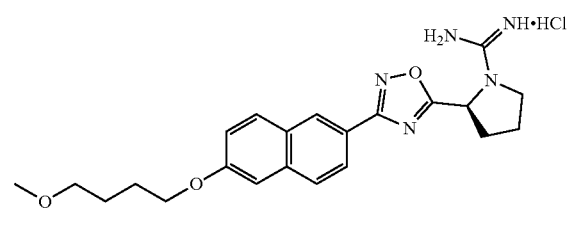

7l was synthesized using general procedure 3 and isolated as a white solid (2 mg, 91%). $^1$H NMR (400 MHz, CD$_3$OD) δ 8.53-8.48 (m, 1H), 8.07-7.99 (m, 1H), 7.88 (d, J=8.7 Hz, 1H), 7.47 (s, 1H), 7.33-7.29 (m, 1H), 7.24-7.16 (m, 1H), 5.46 (dd, J=7.7, 2.1 Hz, 1H), 4.16 (t, J=6.3 Hz, 2H), 3.85-3.77 (m, 1H), 3.77-3.70 (m, 1H), 3.52-3.45 (m, 2H), 3.36 (s, 3H), 2.61-2.45 (m, 2H), 2.29-2.22 (m, 1H), 2.17-2.09 (m, 1H), 1.96-1.89 (m, 1H), 1.83-1.76 (m, 1H). MS (ESI+): Calcd for C$_{22}$H$_{27}$N$_5$O$_3$ [M+H]$^+$: 410.4894, Found: 410.46.

Example 70: (S)-amino(2-(3-(6-(cyclopentylmethoxy)naphthalen-2-yl)-1,2,4-oxadiazol-5-yl)pyrrolidin-1-yl)methaniminium chloride (7m, compound 66A)

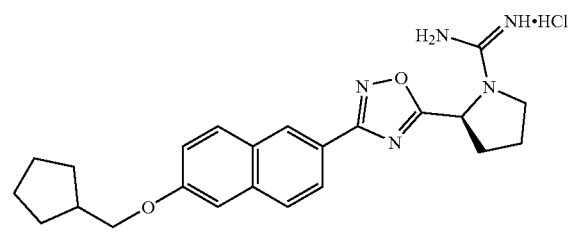

7m was synthesized using general procedure 3 and isolated as a white solid (1 mg, 69%). MS (ESI+): Calcd for C$_{23}$H$_{27}$N$_5$O$_2$ [M+H]$^+$: 406.5007, Found: 406.24.

Example 71: (S)-amino(2-(3-(6-((4-(trifluoromethyl)benzyl)oxy)naphthalen-2-yl)-1,2,4-oxadiazol-5-yl)pyrrolidin-1-yl)methaniminium chloride (7n, compound 52A)

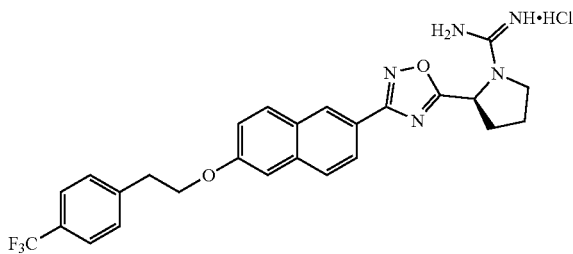

7n was synthesized using general procedure 3 and isolated as a white solid (2 mg, 66%). $^1$H NMR (400 MHz, CD$_3$OD) δ 8.54 (s, 1H), 8.05 (dd, J=8.6, 1.8 Hz, 1H), 7.92 (dd, J=16.1, 8.8 Hz, 2H), 7.72 (s, 2H), 7.48 (s, 1H), 7.43 (d, J=2.5 Hz, 1H), 7.35 (dd, J=9.0, 2.5 Hz, 1H), 5.47 (dd, J=7.8, 2.0 Hz, 1H), 5.36 (s, 2H), 3.84-3.77 (m, 1H), 3.67-3.62 (m, 1H), 2.61-2.52 (m, 2H), 2.29-2.22 (m, 1H), 2.14 (t, J=9.6 Hz, 1H), 2.03 (d, J=7.8 Hz, 1H). MS (ESI+): Calcd for C$_{25}$H$_{22}$F$_3$N$_5$O$_2$ [M+H]$^+$: 482.4776, Found: 482.43.

Example 72: (S)-amino(2-(3-(6-((3-(trifluoromethyl)benzyl)oxy)naphthalen-2-yl)-1,2,4-oxadiazol-5-yl)pyrrolidin-1-yl)methaniminium chloride (7o, compound 67A)

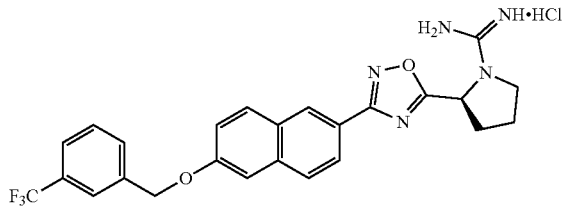

7o was synthesized using general procedure 3 and isolated as a white solid (2 mg, 66%). $^1$H NMR (400 MHz, CD$_k$OD) δ 8.46-8.43 (m, 1H), 7.98-7.91 (m, 2H), 7.86-7.78 (m, 2H), 7.76 (d, J=8.7 Hz, 1H), 7.70 (s, 1H), 7.64 (d, J=7.7 Hz, 1H), 7.45 (s, 1H), 7.17-7.13 (m, 1H), 5.21 (t, J=8.4 Hz, 1H), 4.64 (d, J=13.1 Hz, 2H), 3.79-3.68 (m, 2H), 2.87-2.77 (m, 1H), 2.49-2.32 (m, 2H), 2.30-2.19 (m, 1H). MS (ESI+): Calcd for C$_{25}$H$_{22}$F$_3$N$_5$O$_2$ [M+H]$^+$: 482.4776, Found: 482.43.

Example 73: (S)-amino(2-(3-(6-((4-bromobenzyl)oxy)naphthalen-2-yl)-1,2,4-oxadiazol-5-yl)pyrrolidin-1-yl)methaniminium chloride (7p, compound 53A)

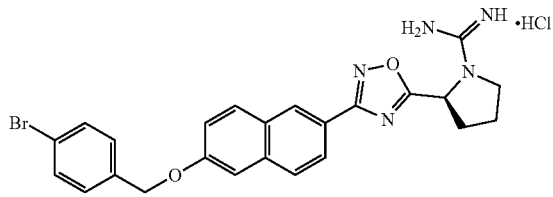

7p was synthesized using general procedure 3 and isolated as a white solid (2 mg, 87%). MS (ESI+): Calcd for C$_{24}$H$_{22}$BrN$_5$O$_2$ [M+H]$^+$: 493.3757, Found: 493.19.

Example 74: (S)-amino(2-(3-(6-((3-bromobenzyl)oxy)naphthalen-2-yl)-1,2,4-oxadiazol-5-yl)pyrrolidin-1-yl)methaniminium chloride (7q, compound 58A)

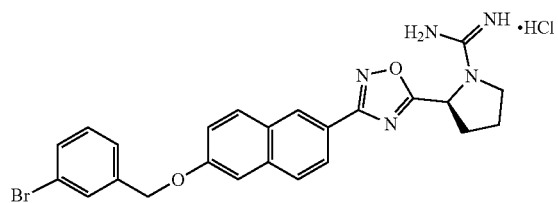 [SMILES: N=C(N)N1CCC[C@H]1c1nc(-c2ccc3cc(OCc4cccc(Br)c4)ccc3c2)no1 ; Cl]

7q was synthesized using general procedure 3 and isolated as a white solid (1 mg, 66%). MS (ESI+): Calcd for C$_{24}$H$_{22}$BrN$_5$O$_2$ [M+H]$^+$: 493.3757, Found: 493.18.

Example 75: (S)-amino(2-(3-(6-((4-chlorobenzyl)oxy)naphthalen-2-yl)-1,2,4-oxadiazol-5-yl)pyrrolidin-1-yl)methaniminium chloride (7r, compound 69A)

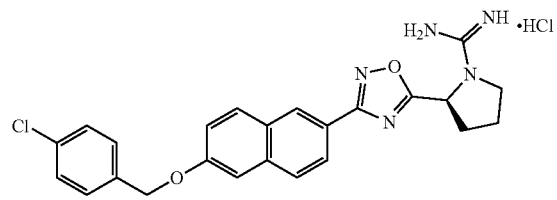 [SMILES: N=C(N)N1CCC[C@H]1c1nc(-c2ccc3cc(OCc4ccc(Cl)cc4)ccc3c2)no1 ; Cl]

7r was synthesized using general procedure 3 and isolated as a white solid (2 mg, 67%). $^1$H NMR (400 MHz, CD$_3$OD) δ 8.53-8.44 (m, 1H), 7.98 (dd, J=8.6, 1.7 Hz, 1H), 7.94-7.85 (m, 1H), 7.79 (d, J=8.6 Hz, 1H), 7.61-7.52 (m, 2H), 7.52-7.41 (m, 2H), 7.24-7.14 (m, 2H), 5.24 (t, J=8.5 Hz, 1H), 4.60 (d, J=13.0 Hz, 2H), 3.76-3.73 (m, 1H), 3.60-3.56 (m, 1H), 2.90-2.80 (m, 1H), 2.54-2.45 (m, 1H), 2.45-2.35 (m, 1H), 2.33-2.21 (m, 1H). MS (ESI+): Calcd for C$_{24}$H$_{22}$ClN$_5$O$_2$ [M+H]$^+$: 448.9247, Found: 448.92.

Example 76: (S)-amino(2-(3-(6-((3-chlorobenzyl)oxy)naphthalen-2-yl)-1,2,4-oxadiazol-5-yl)pyrrolidin-1-yl)methaniminium chloride (7s, compound 68A)

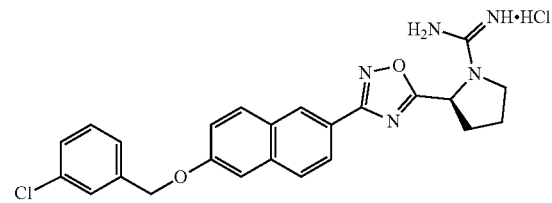

7s was synthesized using general procedure 3 and isolated as a white solid (2 mg, 89%). $^1$H NMR (400 MHz, CD$_3$OD)

δ 8.51-8.46 (m, 1H), 7.98 (dd, J=8.6, 1.7 Hz, 1H), 7.90-7.85 (m, 1H), 7.79 (d, J=8.7 Hz, 1H), 7.68 (q, J=1.4 Hz, 1H), 7.52-7.46 (m, 1H), 7.46-7.41 (m, 2H), 7.21-7.15 (m, 2H), 5.27 (t, J=8.4 Hz, 1H), 4.61 (d, J=13.0 Hz, 1H), 3.84-3.76 (m, 1H), 3.62-3.55 (m, 1H), 291-2.78 (m, 1H), 2.57-2.38 (m, 2H), 2.33-2.23 (m, 1H). MS (ESI+): Calcd for $C_{24}H_{22}ClN_5O_2$ [M+H]$^+$: 448.9247, Found: 448.92.

Example 77: (S)-amino(2-(3-(6-((4-cyanobenzyl)oxy)naphthalen-2-yl)-1,2,4-oxadiazol-5-yl)pyrrolidin-1-yl)methaniminium chloride (7t, compound 70A)

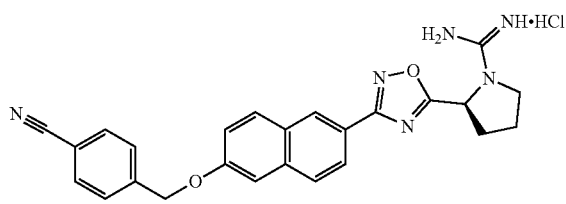

7t was synthesized using general procedure 3 and isolated as a white solid (2 mg, 67%). HRMS (ESI+): Calcd for $C_{32}H_{37}N_6O_2$ [M+H]$^+$: 439.4891, Found: 439.36.

Example 78: (S)-amino(2-(3-(6-((5,5,8,8-tetramethyl-5,6,7,8-tetrahydronaphthalen-2-yl)methoxy)naphthalen-2-yl)-1,2,4-oxadiazol-5-yl)pyrrolidin-1-yl)methaniminium chloride (7u, compound 71A)

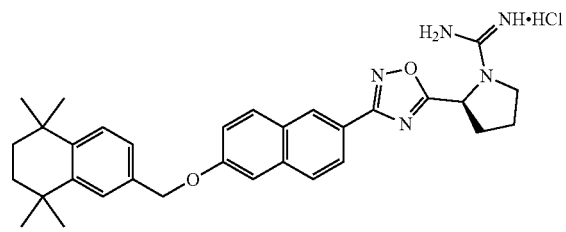

7u was synthesized using general procedure 3 and isolated as a white solid (3 mg, 93%). $^1$H NMR (400 MHz, CD$_3$OD) δ 8.44 (d, J=1.6 Hz, 1H), 7.93 (d, J=9.4 Hz, 1H), 7.84 (d, J=9.5 Hz, 1H), 7.76 (d, J=8.7 Hz, 1H), 7.47 (d, J=1.5 Hz, 1H), 7.31 (d, J=8.1 Hz, 1H), 7.25 (dd, J=8.1, 1.9 Hz, 1H), 7.20-7.16 (m, 2H), 5.21 (t, J=8.2 Hz, 1H), 4.60 (s, 2H), 3.92-3.82 (m, 2H), 2.86-2.77 (m, 1H), 2.44-2.26 (s, 3H), 1.58 (d, J=9.1 Hz, 4H), 1.31-1.28 (m, 3H), 1.23 (s, 3H), 1.11 (s, 3H), 1.04 (s, 3H). MS (ESI+): Calcd for $C_{32}H_{37}N_5O_2$ [M+H]$^+$: 524.6764, Found: 524.68.

Example 79: (S)-(2-(3-(6-([1,1'-biphenyl]-4-ylmethoxy)naphthalen-2-yl)-1,2,4-oxadiazol-5-yl)pyrrolidin-1-yl)(amino)methaniminium chloride (7v, compound 72A)

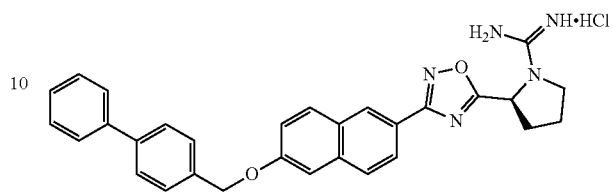

7v was synthesized using general procedure 3 and isolated as a white solid (2 mg, 87%). $^1$H NMR (400 MHz, CD$_3$OD) δ 8.60-8.52 (m, 2H), 8.35-8.31 (m, 1H), 8.20 (dd, J=9.0, 1.7 Hz, 1H), 8.04 (d, J=1.7 Hz, 1H), 8.02-7.97 (m, 1H), 7.90 (d, J=9.3 Hz, 1H), 7.68-7.59 (m, 4H), 7.47-7.42 (m, 2H), 7.36-7.31 (m, 2H), 5.47 (d, J=7.9 Hz, 1H), 5.44 (s, 1H), 5.31 (s, 1H), 3.77-3.73 (m, 2H), 2.60-2.51 (m, 2H), 2.29-2.23 (m, 1H), 2.16-2.10 (m, 1H). MS (ESI+): Calcd for $C_{30}H_{27}N_5O_2$ [M+H]$^+$: 490.5756, Found: 490.36.

Example 80: (S)-amino(2-(3-(6-(4-(trifluoromethyl)phenethoxy)naphthalen-2-yl)-1,2,4-oxadiazol-5-yl)pyrrolidin-1-yl)methaniminium chloride (7w, compound 54A)

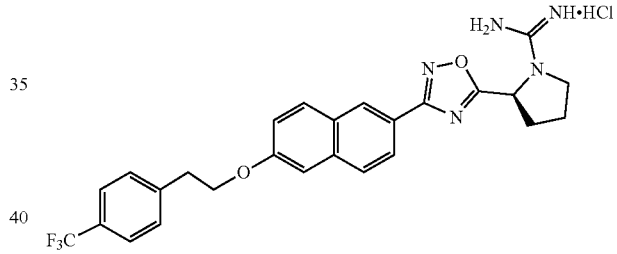

7w was synthesized using general procedure 3 and isolated as a white solid (3 mg, 98%). $^{19}$F NMR (376 MHz, CD$_3$OC) δ −63.94. MS (ESI+): Calcd for $C_{26}H_{24}F_3N_5O_2$ [M+H]$^+$: 496.5042, Found: 496.27.

Example 81: (S)-amino(2-(3-(6-(3-(trifluoromethyl)phenethoxy)naphthalen-2-yl)-1,2,4-oxadiazol-5-yl)pyrrolidin-1-yl)methaniminium chloride (7x, compound 60A)

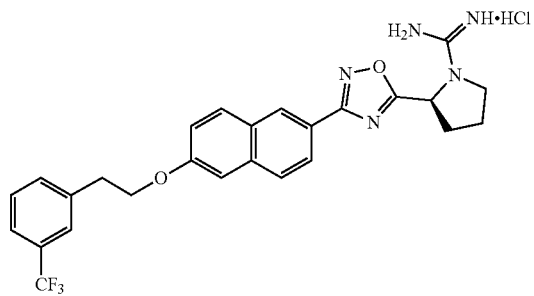

7x was synthesized using general procedure 3 and isolated as a white solid (2 mg, 87%) HRMS (ESI+): Calcd for $C_{26}H_{24}F_3N_5O_2$ [M+H]$^+$: 496.5042, Found: 496.27.

Example 82: (S)-amino(2-(3-(6-(2-(trifluoromethyl)phenethoxy)naphthalen-2-yl)-1,2,4-oxadiazol-5-yl)pyrrolidin-1-yl)methaniminium chloride (7y, compound 55A)

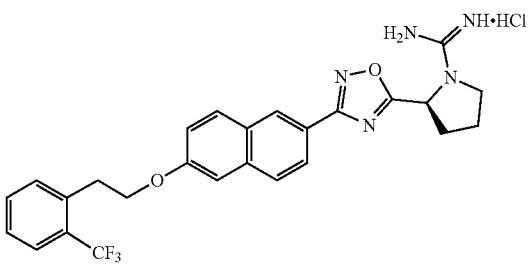

7y was synthesized using general procedure 3 and isolated as a white solid (1 mg, 65%). HRMS (ESI+): Calcd for $C_{26}H_{24}F_3N_5O_2$ [M+H]$^+$: 496.5042, Found: 496.27.

(S)-amino(2-(3-(6-(2-oxo-2-phenylethoxy)naphthalen-2-yl)-1,2,4-oxadiazol-5-yl)pyrrolidin-1-yl)methaniminium chloride (7z)

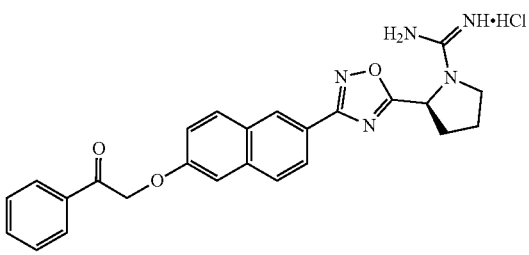

7z was synthesized using general procedure 3 and isolated as a white solid (2 mg, 90%). $^1$H NMR (400 MHz, CD$_3$OD) δ 8.54 (d, J=1.6 Hz, 1H), 8.11 (dd, J=8.5, 1.3 Hz, 1H), 8.04 (dd, J=8.6, 1.7 Hz, 1H), 7.94 (d, J=8.9 Hz, 1H), 7.88 (d, J=8.7 Hz, 1H), 7.72-7.67 (m, 1H), 7.58 (dd, J=8.3, 7.1 Hz, 2H), 7.47 (s, 1H), 7.38-7.34 (m, 1H), 5.64 (s, 2H), 5.46 (dd, J=7.8, 2.1 Hz, 1H), 3.84-3.77 (m, 1H), 3.76-3.72 (m, 1H), 2.59-2.49 (m, 2H), 2.28-2.22 (m, 1H), 2.16-2.10 (m, 1H). MS (ESI+): Calcd for $C_{25}H_{23}N_5O_3$ [M+H]$^+$: 442.4898, Found: 442.44.

(S)-amino(2-(3-(6-(2-oxo-2-(4-(trifluoromethyl)phenyl)ethoxy)naphthalen-2-yl)-1,2,4-oxadiazol-5-yl)pyrrolidin-1-yl)methaniminium chloride (7aa)

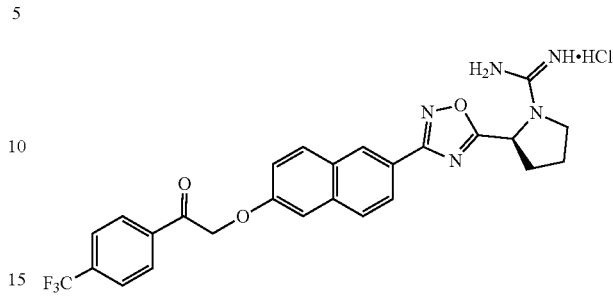

7aa was synthesized using general procedure 3 and isolated as a white solid (2 mg, 65%). $^1$H NMR (400 MHz, CD$_3$OD) δ 8.54 (d, J=1.8 Hz, 1H), 8.28 (d, J=8.1 Hz, 2H), 8.05 (dd, J=8.6, 1.7 Hz, 1H), 7.94 (d, J=8.5 Hz, 1H), 7.90-7.83 (m, 2H), 7.50-7.44 (m, 3H), 7.39-7.35 (m, 1H), 5.67 (s, 2H), 5.47-5.44 (m, 1H), 2.58-2.45 (m, 2H), 2.16-2.11 (m, 1H), 2.06-2.01 (m, 1H). MS (ESI+): Calcd for $C_{26}H_{22}F_3N_5O_3$ [M+H]$^+$: 510.4877, Found: 510.44.

(S)-(2-(3-(6-(2-([1,1'-biphenyl]-4-yl)-2-oxoethoxy)naphthalen-2-yl)-1,2,4-oxadiazol-5-yl)pyrrolidin-1-yl)(amino)methaniminium chloride (7bb)

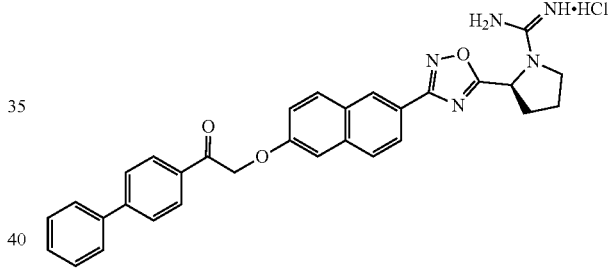

7bb was synthesized using general procedure 3 and isolated as a white solid (6 mg, 66%). $^1$H NMR (400 MHz, CD$_3$OD) δ 8.54 (d, J=1.7 Hz, 1H), 8.23-8.17 (m, 1H), 8.05 (dd, J=8.6, 1.7 Hz, 1H), 7.92 (dd, J=23.2, 9.2 Hz, 2H), 7.87-7.80 (m, 1H), 7.75-7.69 (m, 1H), 7.52-7.34 (m, 5H), 5.67 (s, 1H), 5.46 (dd, J=7.8, 2.0 Hz, 1H), 3.83-3.77 (m, 1H), 3.76-3.72 (m, 1H), 2.65-2.48 (m, 2H), 2.28-2.20 (m, 1H), 2.15-2.07 (m, 1H). MS (ESI+): Calcd for $C_{31}H_{27}F_3N_5O_3$ [M+H]$^+$: 518.5857, Found: 518.48.

Example 83: (S)-amino(2-(3-(6-hydroxynaphthalen-2-yl)-1,2,4-oxadiazol-5-yl)pyrrolidin-1-yl)methaniminium chloride (7cc, compound 51)

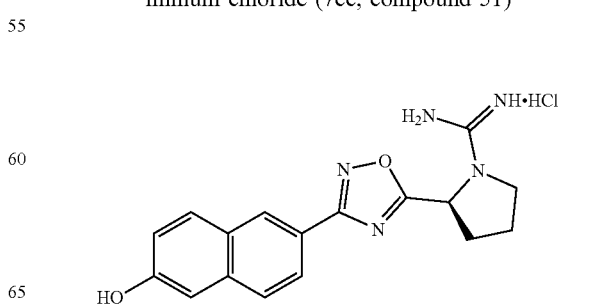

7cc was synthesized using general procedure 3 and isolated as a white solid (7 mg, 93%). $^1$H NMR (400 MHz, Methanol-$d_4$) δ 8.47 (d, J=1.6 Hz, 1H), 7.98 (dd, J=8.6, 1.7 Hz, 1H), 7.84 (d, J=8.5 Hz, 1H), 7.76 (d, J=8.6 Hz, 1H), 7.16 (d, J=8.5 Hz, 2H), 5.47 (d, J=7.1 Hz, 1H), 3.85-3.76 (m, 1H), 3.66 (s, 1H), 2.64-2.54 (m, 2H), 2.30-2.20 (m, 1H), 2.18-2.04 (m, 1H). HRMS (ESI+): Calcd for $C_{17}H_{17}N_5O_2$ [M+H]$^+$: 324.3571, Found: 324.49.

Examples 84-93 Synthesis and Characterization of Formulae IA and IB Compounds

Schemes 14(A) through 14(D) below outline general and specific synthetic methodologies for the preparation of Compound Nos. 77A-96A. Compound numbering in the Schemes are internal to the Schemes, while the subsequent procedures refer where applicable to the final compounds.

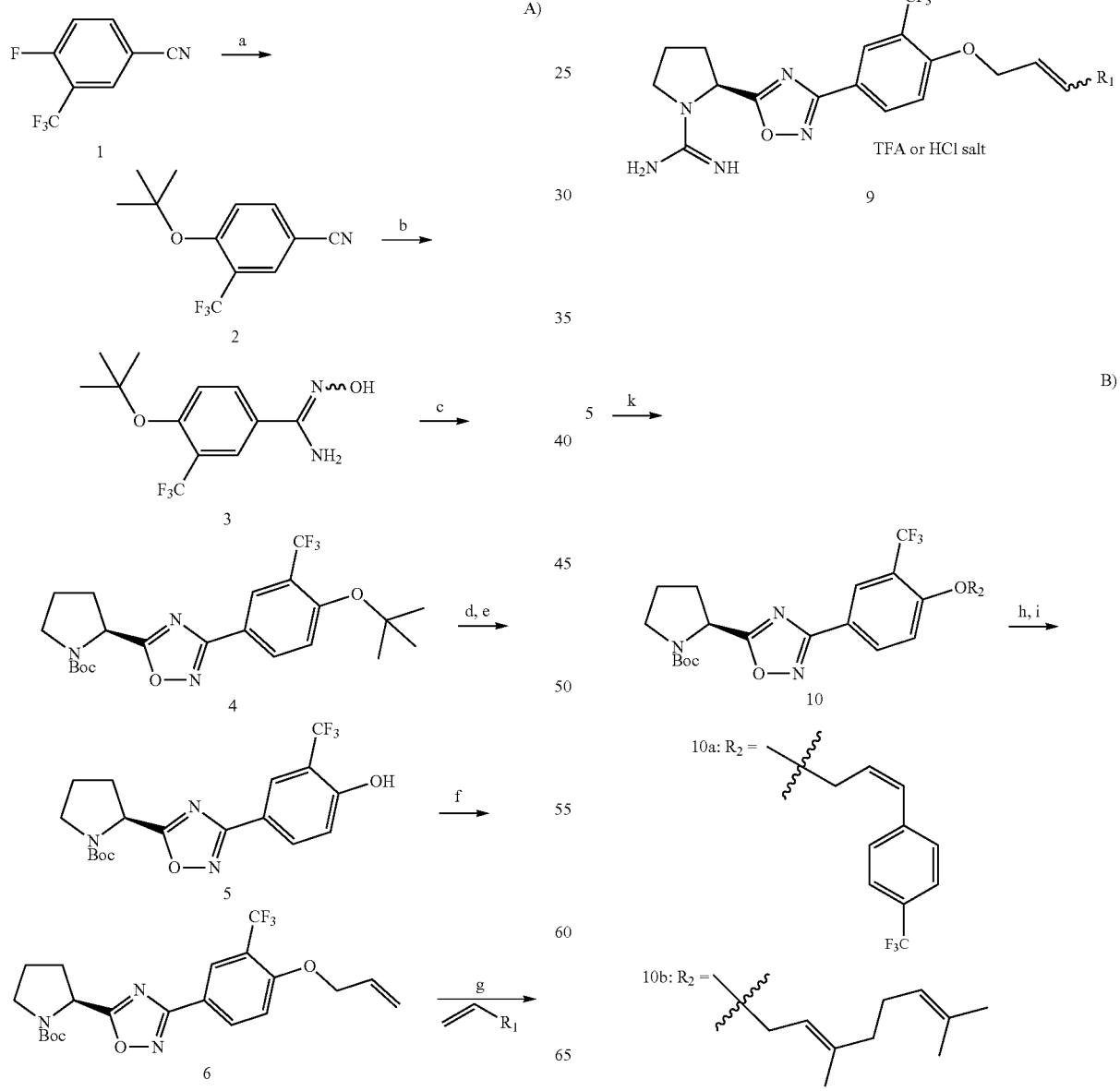

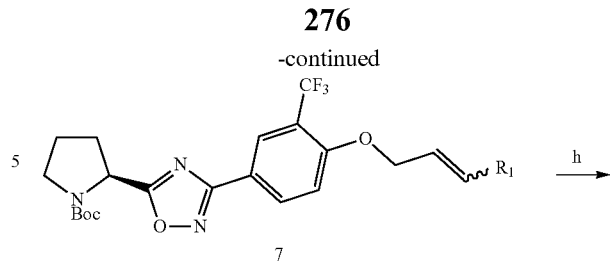

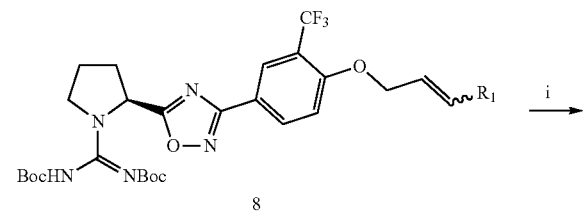

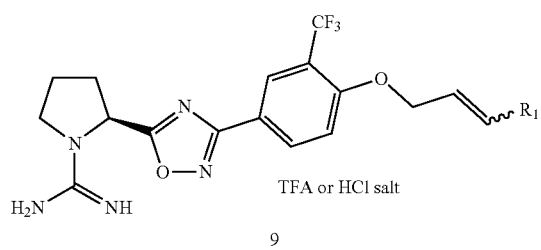

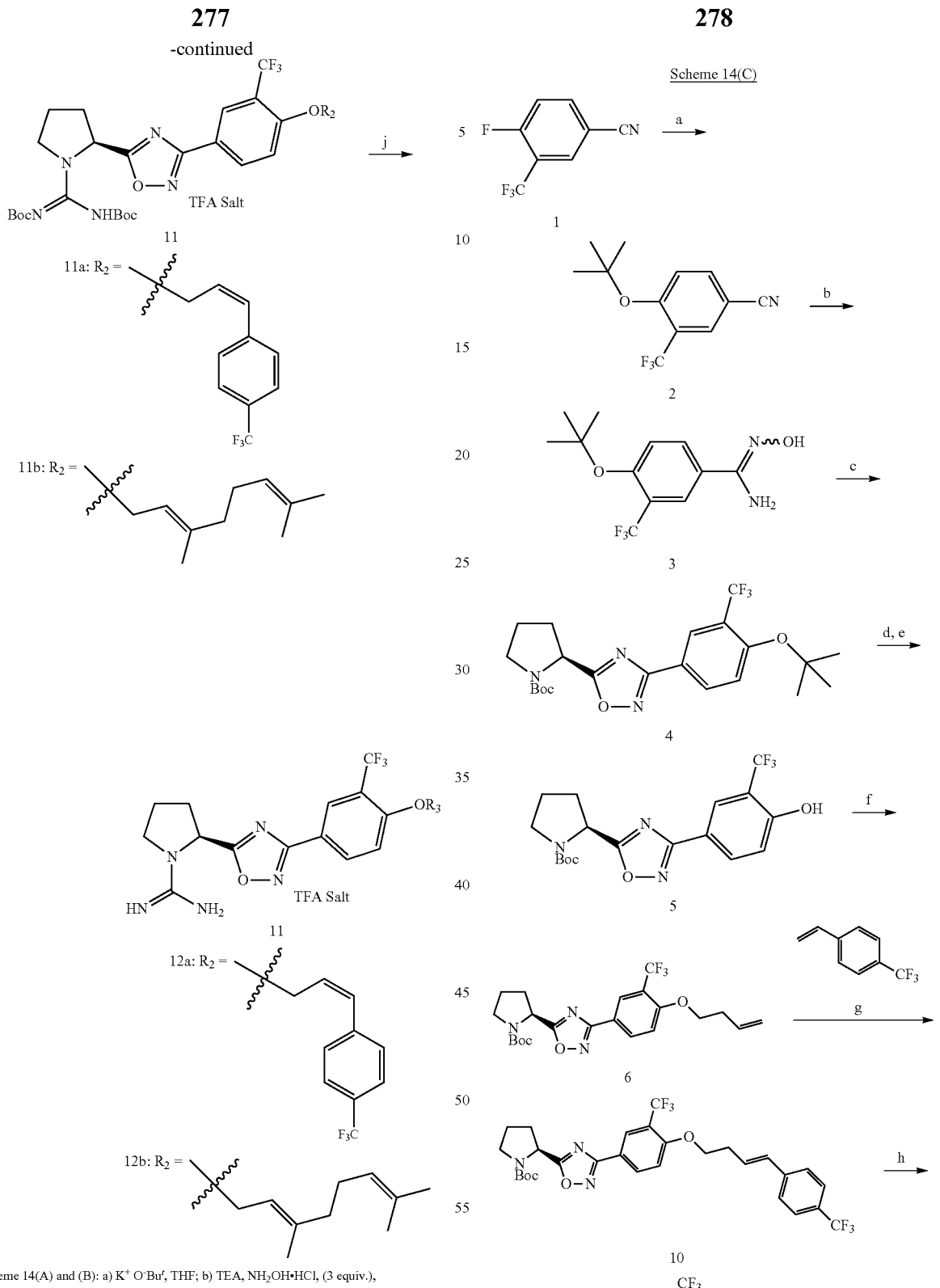

Scheme 14(A) and (B): a) K⁺ O⁻Buᵗ, THF; b) TEA, NH₂OH•HCl, (3 equiv.), TEA (3 equiv.), EtOH, 80° C., 6 h, (71-92%); c) Boc-L-proline (1.4 equiv.), DIEA (1.4 equiv.), HCTU (1.8 equiv.), DMF, 110° C., 18 h, (37-70%); d) TFA, DCM, 3-6 h, 0° C -> r.t.; e) (Boc)₂O, TEA, THF, r.t., 2-5 h, (70%); f) Allyl bromide, K₂CO₃, Microwave Irradiation, 90° C., Acetone, 2 h, g) Grubb's II Catalyst, DCM (50-70%); h) TFA/DCM (70-90%); i) DIEA (3 equiv.), N,N-DiBoc-1H-pyrazole-1-carboxamidine (1.05 equiv.), CH₃CN, Microwave irradiation, 2-6 h (57-70%); j) TFA:DCM (1:1) rt,, 4h, (60-70%) PPh₃, DIAD, ROH, THF, 2-4 h, (60-80%)

-continued

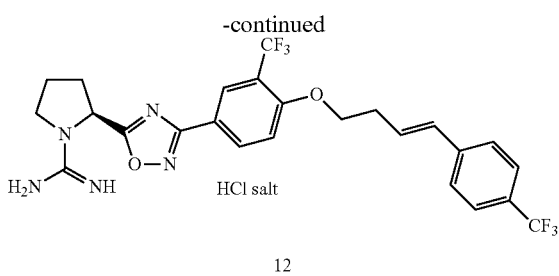

12 HCl salt

Scheme 14(C): a) K⁺ O⁻Buᵗ, THF; b) TEA, NH₂OH•HCl, (3 equiv.), TEA (3 equiv.), EtOH, 80° C., 6 h, (71-92%); c) Boc-L-proline (1.4 equiv.), DIEA (1.4 equiv.), HCTU (1.8 equiv.), DMF, 110° C., 18 h, (37-70%); d) TFA, DCM, 3-6 h, 0° C.->r.t.; e) (Boc)₂O, TEA, THF, r.t., 2-5 h, (70%); f) Ally bromide, K₂CO₃, Microwave Irradiation, 90° C., Acetone, 2 h, g) Grubbs's II Catalyst, DCM (50-70%); h) TFA/DCM (70-90%); i) DIEA (3 equiv.), N,N-DiBoc-1H-pyrazole-1-carboxamidine (1.05 equiv.), CH₃CN, Microwave irradiation, 2-6 h (57-70%); j) TFA:DCM (1:1) rt,, 4 h, (60-70%).

Scheme 14(D)

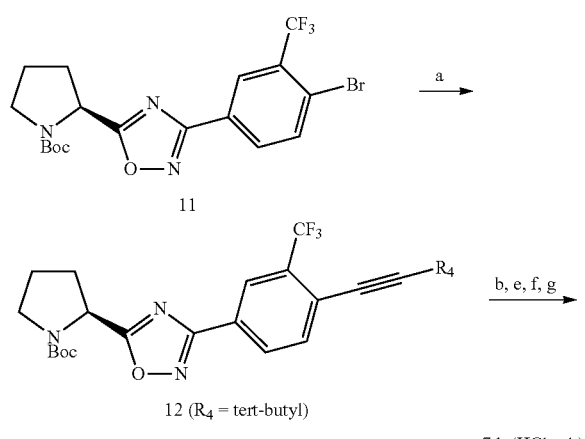

12 (R₄ = tert-butyl)

7 h (HCl salt)

Scheme 1: a) Alkyne (1.1 equiv.), PdCl(PPh₃)₂ (10 mol %), CuI (6 mol %), DMF, TEA, 80° C., 4 h b) [5% Pd-CaCO₃ + Pb(OCOCH₃)₂ + Quinoline] 10 mol % (60-80%) e) HCl/MeOH, (80-100%); f) DIEA (3 equiv.), N,N-DiBoc-1H-pyrazole-1-carboxamidine (1.05 equiv.), CH₃CN, Microwave irradiation, 55° C., 2-4 h,, (59-70%); g) 4M HCl Dioxane, rt,, 3 h, (67-90%).

General Procedures

I. General Procedure for Nucleophilic Aromatic Substitution

To a solution of (1) in THF was added potassium tertiary butoxide (1M in THF) under cooling. The resultant solution was maintained at 75° C. for 7-10 h. Cooled the reaction mixture to rt and partitioned between ethylacetate and water. Extracted the aqueous layer twice with ethylacetate. Combined organic layers were given water, brine washes. Dried over anhydrous Na₂SO₄ and purified on a silica column with hexane and ethyl acetate.

II. General Procedure for Synthesis of Amidoxime

Nitrile intermediate (1 equiv.), hydroxylamine hydrochloride (3 equiv.), TEA (3 equiv.) were added to a round bottom flask containing ethanol. The reaction mixture was heated to 80° C. for 6-12 hours and monitored via TLC. Once the starting material was consumed, the solution was cooled to room temperature, concentrated under reduced pressure, loaded onto celite, and purified on a silica column with hexane and ethyl acetate.

III. General Procedure for Synthesis of 1,2,4-Oxadiazole

Amidoxime intermediate (1 equiv.), Boc-L-proline (1.4 equiv.) or Boc-trans-3-hydroxy-L-proline (1.4 equiv.), and DIEA (1.4 equiv.) were added to a round bottom flask containing DMF. HCTU (1.8 equiv.) was added to the reaction mixture and maintained at 110° C. for 12-16 hours. Cooled the reaction mixture to r.t. and partitioned between ethyl acetate and saturated LiBr solution. The combined organic layers were washed with sat. NaHCO₃, brine and dried over sodium sulfate. Combined organic layers were subjected to rotary evaporation and column chromatography to afford the desired Oxadiazole intermediate.

IV. General Procedure for O-Alkylation (1 equiv.), potassium carbonate (2 equiv.), KI (1.5 equiv.) and alkyl halide (1.2 equiv.) were added to a 8 mL microwave reactor containing acetone. The reaction mixture was heated to 80° C. for 4-12 hours until TLC indicated the starting material had been fully consumed. The reaction mixture was extracted with ethyl acetate and D.I. water. The combined organic layers were washed with brine and dried over sodium sulfate. After filtration and concentration via reduced pressure, the resulting brown oil was purified on a silica column with hexane and ethyl acetate.

V. General Procedure for Boc-Deprotection

N-Boc Pyrrolidine or N', N''-Di-Boc-guanidine 6a-e was dissolved in methanol. HCl gas was bubbled into the solution for 1 minute. The solution was stirred until TLC indicated that all of the Boc-protected amine had been consumed. The solvent was removed under reduced pressure. The resulting white to light yellow solid was washed with diethyl ether to yield pure product as HCl salt.

VI. General Procedure for Guanylation of Secondary Amines

Pyrrolidine Hydrogen chloride salt (1 equiv.) was added to a 8 mL microwave reaction flash with acetonitrile and DIEA (3 equiv.). The solution was allowed to stir for 10 minutes before the addition of (Z)-Tert-butyl (((tert-butoxy-carbonyl)imino)(1H-pyrazol-1-yl)methyl)carbamate (1.05 equiv.). The solution was subjected to microwave irradiation at 55° C. for 2-6 h until TLC indicated that the starting material had been consumed. The reaction mixture is subjected to rotary evaporation and performed column chromatography to afford the N',N'-diboc guanidine intermediate.

VII. General Procedure for Mitsunobu Reaction

To a pre-cooled solution of 23 in dry THF and PPh₃ added DIAD (40% in toluene) and alcohol. The reaction mixture was stirred for 1 h then refluxed for 2 h. Quenched reaction mixture with aqueous NaHCO₃, rotary evaporated and partitioned between dichloromethane and DI water. Combined organic layers were subjected to rotatory evaporation and performed column chromatography to afford the desired product.

VIII. General Procedure for Cross Metathesis Using Microwave Synthesizer

Dissolved the O-Allyl intermediate (6) in dry DCM. Added terminal alkene (excess) followed by Grubbs's II generation catalyst (10 mol %) at rt in a microwave reaction capsule. Subjected to microwave irradiation 70° C., 300 power, 2-4 h. Rotary evaporated the crude, performed column chromatography to afford the desired product.

IX. General Procedure for Cross Metathesis Using Bench Top

Dissolved the O-Allyl intermediate (6) in dry DCM. Added terminal alkene (excess) followed by Grubbs's II generation catalyst (4×4 mol %). Subjected to vigorous reflux for 2-3 days Rotary evaporated the crude, performed column chromatography to afford the desired product.

4-(tert-butoxy)-3-(trifluoromethyl)benzonitrile (2)

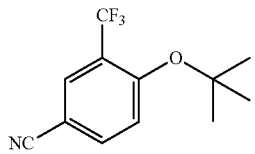 [SMILES: CC(C)(C)Oc1ccc(C#N)cc1C(F)(F)F]

¹H NMR (500 MHz, Chloroform-d) δ 7.87 (s, 1H), 7.73 (dd, J=8.8, 2.1 Hz, 1H), 7.27 (d, J=8.7 Hz, 1H), 1.56 (s, 9H).

(Z)-4-(tert-butoxy)-N'-hydroxy-3-(trifluoromethyl)benzimidamide (3)

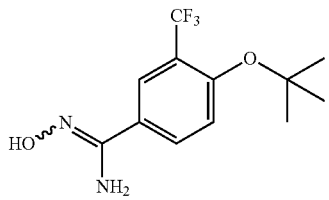

¹H NMR (500 MHz, Chloroform-d) δ 7.85 (d, J=2.3 Hz, 1H), 7.72 (dd, J=8.7, 2.4 Hz, 1H), 7.23 (d, J=8.7 Hz, 1H), 6.72 (s, 1H), 4.84 (s, 2H), 1.52 (s, 9H).

tert-butyl (S)-2-(3-(4-(tert-butoxy)-3-(trifluoromethyl)phenyl)-1,2,4-oxadiazol-5-yl)pyrrolidine-1-carboxylate (4)

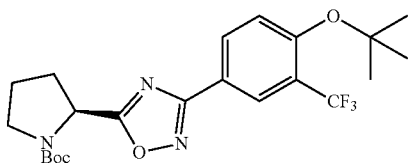 [SMILES: CC(C)(C)OC(=O)N1CCC[C@H]1c1nc(-c2ccc(OC(C)(C)C)c(C(F)(F)F)c2)no1]

¹H NMR (500 MHz, Chloroform-d) δ 8.21 (d, J=2.1 Hz, 1H), 8.05 (dd, J=8.6, 2.2 Hz, 1H), 7.20 (t, J=8.6 Hz, 1H), 5.15-5.05 (m, 0.4H), 5.04-4.95 (m, 0.6H), 3.71-3.55 (m, 1H), 3.53-3.31 (m, 1H), 2.31-2.21 (m, 1H), 2.15-2.05 (m, 2H), 1.99-1.83 (m, 1H), 1.39 (s, 3H), 1.24 (s, 6H).

tert-butyl (S)-2-(3-(4-hydroxy-3-(trifluoromethyl)phenyl)-1,2,4-oxadiazol-5-yl)pyrrolidine-1-carboxylate (5)

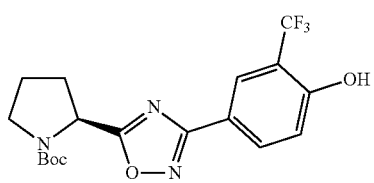 [SMILES: CC(C)(C)OC(=O)N1CCC[C@H]1c1nc(-c2ccc(O)c(C(F)(F)F)c2)no1]

¹H NMR (400 MHz, Methanol-d₄) δ 8.16 (d, J=2.1 Hz, 1H), 8.10-8.04 (m, 1H), 7.07 (d, J=8.7 Hz, 1H), 5.16-5.08 (m, 1H), 3.70-3.61 (m, 1H), 3.55-3.48 (m, 1H), 2.53-2.36 (m, 1H), 2.20-2.00 (m, 3H), 1.46 (s, 3H), 1.27 (s, 6H); ¹³C NMR (101 MHz, Methanol-d₄) δ 181.0, 167.2, 154.0, 131.9, 125.8, 124.9, 117.2, 117.0, 80.5, 53.8, 46.1, 31.8, 31.0, 27.2, 26.9, 23.9, 23.3.

tert-butyl (S)-2-(3-(4-(allyloxy)-3-(trifluoromethyl)phenyl)-1,2,4-oxadiazol-5-yl)pyrrolidine-1-carboxylate

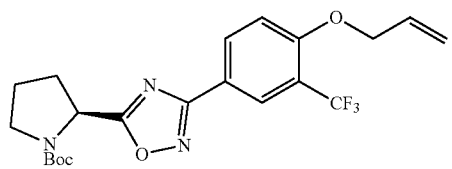 [SMILES: C=CCOc1ccc(-c2noc([C@@H]3CCCN3C(=O)OC(C)(C)C)n2)cc1C(F)(F)F]

¹H NMR (400 MHz, Chloroform-d) δ 8.29 (d, J=2.1 Hz, 1H), 8.17 (d, J=8.7 Hz, 1H), 7.05 (t, J=8.5 Hz, 1H), 6.03 (ddt, J=17.3, 10.7, 4.8 Hz, 1H), 5.57-5.39 (m, 1H), 5.32 (d, J=10.6 Hz, 1H), 5.04 (dd, J=8.3, 3.6 Hz, 1H), 4.69 (d, J=4.7 Hz, 2H), 3.70 (s, 1H), 3.64-3.40 (m, 1H), 2.49-2.26 (m, 1H), 2.19-1.91 (m, 3H), 1.45 (s, 3H), 1.28 (s, 5H); ¹³C NMR (126 MHz, CDCl₃) δ 180.9, 180.4, 167.2, 158.6, 154.3, 153.5, 132.4, 131.7, 126.7, 124.3, 122.1, 119.2, 119.0, 113.4, 80.5, 69.3, 53.8, 46.4, 32.4, 31.5, 28.1, 24.4, 23.7.

tert-butyl (S)-2-(3-(4-(but-3-en-1-yloxy)-3-(trifluoromethyl)phenyl)-1,2,4-oxadiazol-5-yl)pyrrolidine-1-carboxylate

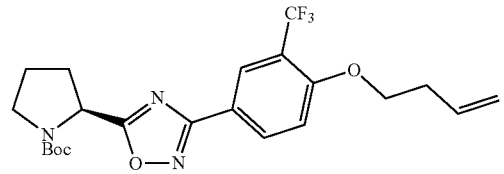 [SMILES: C=CCCOc1ccc(-c2noc([C@@H]3CCCN3C(=O)OC(C)(C)C)n2)cc1C(F)(F)F]

¹H NMR (400 MHz, Chloroform-d) δ 8.27 (d, J=2.2 Hz, 1H), 8.17 (dd, J=8.6, 2.4 Hz, 1H), 7.04 (t, J=9.0 Hz, 1H), 5.95-5.83 (m, 1H), 5.22-5.01 (m, 3H), 4.13 (t, J=6.4 Hz, 2H), 3.76-3.41 (m, 2H), 2.58 (qt, J=6.7, 1.3 Hz, 2H), 2.47-2.26 (m, 1H), 2.21-2.01 (m, 2H), 2.06-1.90 (m, 2H), 1.44 (s, 3H), 1.22 (s, 6H); ¹³C NMR (101 MHz, cdcl₃) δ 180.8, 167.2, 158.9, 153.5, 133.6, 132.4, 126.5, 126.5, 118.7, 117.5, 112.9, 112.8, 80.4, 68.3, 53.7, 46.6, 46.3, 33.3, 32.4, 31.4, 28.3, 28.1, 24.3, 23.7.

tert-butyl (S)-2-(3-(4-(hex-2-en-1-yloxy)-3-(trifluoromethyl)phenyl)-1,2,4-oxadiazol-5-yl)pyrrolidine-1-carboxylate

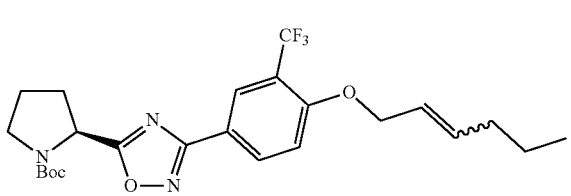 [SMILES: CCCC=CCOc1ccc(-c2noc([C@@H]3CCCN3C(=O)OC(C)(C)C)n2)cc1C(F)(F)F]

¹H NMR (400 MHz, Chloroform-d) δ 8.27 (d, J=2.1 Hz, 1H), 8.15 (dd, J=8.8, 2.3 Hz, 1H), 7.05 (t, J=8.7 Hz, 1H), 5.85 (dt, J=15.4, 6.8 Hz, 1H), 5.72-5.58 (m, 1H), 5.04 (dd, J=8.1, 3.6 Hz, 1H), 4.63 (d, J=5.7 Hz, 2H), 3.74-3.61 (m, 1H), 3.60-3.41 (m, 1H), 2.36 (s, 1H), 2.19-1.91 (m, 6H), 1.50-1.35 (m, 5H), 0.89 (q, J=7.7 Hz, 3H).

tert-butyl (S)-2-(3-(4-(hept-2-en-1-yloxy)-3-(trifluoromethyl)phenyl)-1,2,4-oxadiazol-5-yl)pyrrolidine-1-carboxylate

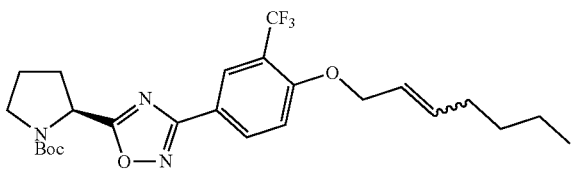 [SMILES: CCCCC=CCOc1ccc(-c2noc([C@@H]3CCCN3C(=O)OC(C)(C)C)n2)cc1C(F)(F)F]

¹H NMR (400 MHz, Chloroform-d) δ 8.27 (d, J=2.1 Hz, 1H), 8.16 (dd, J=8.8, 2.3 Hz, 1H), 7.05 (t, J=8.6 Hz, 1H), 5.86 (dt, J=14.2, 6.8 Hz, 1H), 5.72-5.58 (m, 1H), 5.04 (dd, J=7.9, 3.6 Hz, 1H), 4.71-4.52 (m, 2H), 3.75-3.65 (m, 1H), 3.54-3.48 (m, 1H), 2.21-1.92 (m, 5H), 1.49-1.17 (m, 12H), 0.95-0.82 (m, 3H); ¹³C NMR (101 MHz, Methanol-$d_4$) δ 187.5, 163.3, 132.1, 132.1, 128.4, 119.5, 119.5, 109.6, 109.6, 73.4, 73.0, 72.7, 65.7, 65.7, 51.3, 45.5, 45.5, 28.0, 27.1, 27.1, 25.7, 25.7, 24.1, 24.1, 18.2, 18.2, 9.9.

tert-butyl (S)-2-(3-(4-(oct-2-en-1-yloxy)-3-(trifluoromethyl)phenyl)-1,2,4-oxadiazol-5-yl)pyrrolidine-1-carboxylate

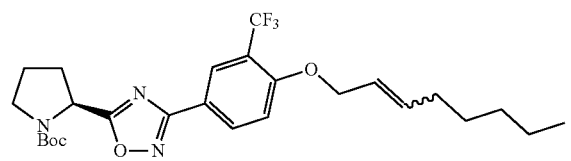 [SMILES: CCCCCC=CCOc1ccc(-c2noc([C@@H]3CCCN3C(=O)OC(C)(C)C)n2)cc1C(F)(F)F]

¹H NMR (500 MHz, Chloroform-d) δ 8.22 (d, J=2.2 Hz, 1H), 8.11 (qd, J=5.8, 3.7, 3.3 Hz, 1H), 7.00 (dd, J=11.0, 8.2 Hz, 1H), 5.81 (dt, J=15.7, 6.8 Hz, 1H), 5.64-5.53 (m, 1H), 5.14-5.05 (m, 0H), 4.99 (dd, J=8.3, 3.7 Hz, 1H), 4.58 (d, J=5.4 Hz, 2H), 3.71-3.38 (m, 2H), 2.33 (dtd, J=18.9, 10.3, 8.3, 5.3 Hz, 1H), 2.14-1.86 (m, 5H), 1.40-1.07 (m, 13H), 0.92-0.71 (m, 3H).

tert-butyl (S,E)-2-(3-(4-(hept-2-en-1-yloxy)-3-(trifluoromethyl)phenyl)-1,2,4-oxadiazol-5-yl)pyrrolidine-1-carboxylate

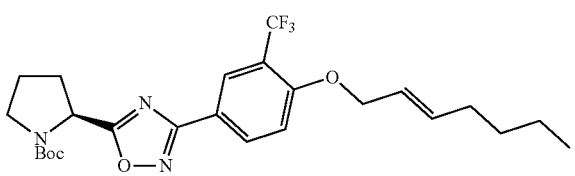 [SMILES: CCCC/C=C/COc1ccc(-c2noc([C@@H]3CCCN3C(=O)OC(C)(C)C)n2)cc1C(F)(F)F]

¹H NMR (400 MHz, Chloroform-d) δ 8.27 (s, 1H), 8.16 (s, 1H), 7.06 (d, J=8.7 Hz, 1H), 5.85 (d, J=7.1 Hz, 1H), 5.64 (d, J=15.5 Hz, 1H), 5.16 (s, 0H), 5.02 (s, 1H), 4.62 (s, 2H), 3.69 (s, 1H), 3.56 (s, 1H), 2.39 (s, 1H), 2.21-1.92 (m, 5H), 1.44 (s, 3H), 1.41-1.22 (m, 9H), 0.89 (s, 3H).

tert-butyl (S,E)-2-(3-(4-(oct-2-en-1-yloxy)-3-(trifluoromethyl)phenyl)-1,2,4-oxadiazol-5-yl)pyrrolidine-1-carboxylate

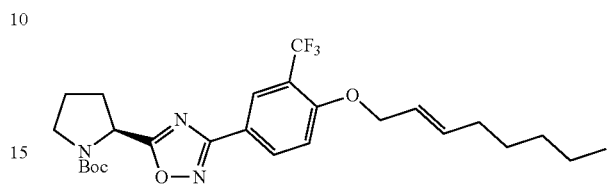

¹H NMR (400 MHz, Chloroform-d) δ 8.27 (d, J=2.1 Hz, 1H), 8.15 (dd, J=8.7, 2.3 Hz, 1H), 7.05 (t, J=8.8 Hz, 1H), 5.85 (dtt, J=15.0, 6.8, 1.4 Hz, 1H), 5.64 (dtt, J=15.4, 5.7, 1.4 Hz, 1H), 4.63 (d, J=5.4 Hz, 2H), 3.74-3.59 (m, 1H), 3.59-3.42 (m, 1H), 2.47-2.28 (m, 1H), 2.22-1.94 (m, 6H), 1.49-1.14 (m, 16H), 0.90-0.79 (m, 3H); ¹³C NMR (101 MHz, cdcl₃) δ 180.8, 167.2, 158.8, 153.5, 136.1, 132.2, 123.4, 113.6, 113.4, 80.4, 69.6, 53.7, 46.6, 46.3, 32.4, 32.2, 31.4, 31.3, 28.5, 28.3, 28.1, 24.3, 23.7, 22.4, 14.0.

tert-butyl (S,Z)-2-(3-(4-(hept-3-en-1-yloxy)-3-(trifluoromethyl)phenyl)-1,2,4-oxadiazol-5-yl)pyrrolidine-1-carboxylate

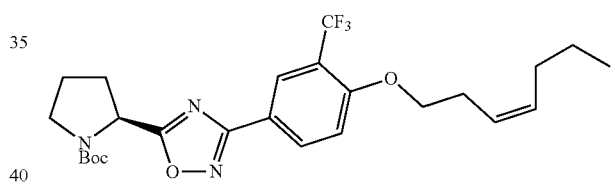

¹H NMR (400 MHz, Chloroform-d) δ 8.27 (d, J=2.1 Hz, 1H), 8.17 (dd, J=8.7, 2.3 Hz, 1H), 7.04 (t, J=8.7 Hz, 1H), 5.60-5.40 (m, 2H), 4.09 (t, J=6.8 Hz, 2H), 3.68 (dd, J=12.2, 6.6 Hz, 1H), 3.52 (ddd, J=28.5, 15.2, 8.0 Hz, 1H), 2.59 (q, J=6.9 Hz, 2H), 2.38 (td, J=11.1, 10.3, 5.3 Hz, 1H), 2.19-1.90 (m, 6H), 1.49-1.20 (m, 12H), 0.90 (t, J=7.4 Hz, 3H); ¹³C NMR (101 MHz, cdcl₃) δ 180.8, 167.2, 132.9, 132.3, 126.6, 124.0, 112.9, 112.8, 80.4, 68.7, 53.7 46.6, 46.3, 32.4, 31.4, 29.3, 28.3, 28.1, 27.1, 24.3, 23.7, 22.7, 13.7.

tert-butyl (S,Z)-2-(3-(4-(oct-3-en-1-yloxy)-3-(trifluoromethyl)phenyl)-1,2,4-oxadiazol-5-yl)pyrrolidine-1-carboxylate

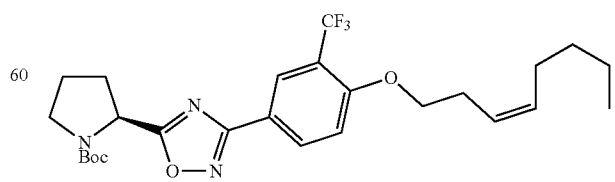

¹H NMR (400 MHz, Chloroform-d) δ 8.27 (s, 1H), 8.17 (d, J=8.7 Hz, 1H), 7.04 (t, J=8.5 Hz, 1H), 5.60-5.40 (m, 2H), 5.17 (d, J=7.9 Hz, 1H), 5.04 (dd, J=8.1, 3.7 Hz, 1H), 4.09 (t, J=6.8 Hz, 2H), 3.77-3.62 (m, 1H), 3.62-3.40 (m, 1H), 2.59 (q, J=6.9 Hz, 2H), 2.48-2.29 (m, 1H), 2.26-1.91 (m, 6H), 1.45 (s, 3H), 1.40-1.18 (m, 10H), 0.94-0.79 (m, 3H); $^{13}$C NMR (101 MHz, cdcl$_3$) δ 180.8, 167.2, 159.0, 153.5, 133.1, 132.3, 126.7, 126.6, 126.5, 123.8, 118.6, 112.9, 112.8, 80.4, 68.7, 53.7, 46.6, 46.3, 32.4, 31.7, 31.4, 28.3, 28.1, 27.1, 27.0, 24.3, 23.7, 22.3, 13.9.

tert-butyl (S,E)-2-(3-(4-((3-(4-fluorophenyl)allyl)oxy)-3-(trifluoromethyl)phenyl)-1,2,4-oxadiazol-5-yl)pyrrolidine-1-carboxylate

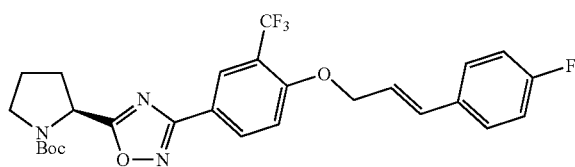 [SMILES: CC(C)(C)OC(=O)N1CCC[C@H]1c1nc(-c2ccc(OC/C=C/c3ccc(F)cc3)c(C(F)(F)F)c2)no1]

$^1$H NMR (400 MHz, Chloroform-d) δ 8.30 (s, 1H), 8.19 (d, J=8.8 Hz, 1H), 7.40-7.32 (m, 2H), 7.15-7.07 (m, 1H), 7.04-6.95 (m, 2H), 6.74 (d, J=16.1 Hz, 1H), 6.33-6.22 (m, 1H), 5.17 (d, J=8.1 Hz, 1H), 5.04 (dd, J=8.3, 3.6 Hz, 1H), 4.85 (d, J=5.4 Hz, 2H), 3.69 (s, 1H), 3.61-3.38 (m, 2H), 2.39 (s, 1H), 2.22-1.89 (m, 3H), 1.45 (s, 3H), 1.28 (s, 6H); $^{13}$C NMR (101 MHz, cdcl$_3$) δ 191.4, 180.9, 167.2, 132.4, 132.1, 128.2, 128.1, 126.7, 122.6, 119.1, 115.7, 115.4, 113.4, 113.3, 80.5, 69.3, 53.7, 46.6, 46.3, 32.4, 31.4, 28.3, 28.1, 24.3, 23.7.

tert-butyl (S,E)-2-(3-(4-((3-(3-bromophenyl)allyl)oxy)-3-(trifluoromethyl)phenyl)-1,2,4-oxadiazol-5-yl)pyrrolidine-1-carboxylate

$^1$H NMR (400 MHz, DMSO-d$_6$) δ 8.34 (s, 1H), 8.23 (d, J=8.7 Hz, 1H), 7.58 (t, J=1.8 Hz, 1H), 7.42 (ddd, J=7.9, 2.0, 1.0 Hz, 1H), 7.37-7.33 (m, 1H), 7.23 (t, J=7.8 Hz, 1H), 7.14 (t, J=8.9 Hz, 1H), 6.75 (d, J=16.0 Hz, 1H), 6.41 (dt, J=16.0, 5.2 Hz, 1H), 5.08 (dd, J=8.1, 3.6 Hz, 1H), 4.90 (d, J=5.1 Hz, 2H), 3.77-3.42 (m, 2H); $^{13}$C NMR (101 MHz, cdcl$_3$) δ 167.2, 138.3, 132.4, 131.6, 130.1, 129.5, 126.8, 125.3, 124.5, 122.8, 113.4, 110.0, 80.5, 69.0, 53.8, 46.3, 32.4, 29.7, 28.4, 28.1, 23.7.

((3-(3-(trifluoromethyl)phenyl)allyl)oxy)phenyl)-1,2,4-oxadiazol-5-yl)pyrrolidine-1-carboxylate

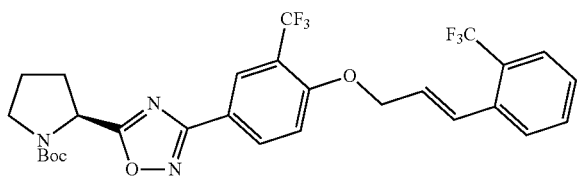 [SMILES: CC(C)(C)OC(=O)N1CCC[C@H]1c1nc(-c2ccc(OC/C=C/c3ccccc3C(F)(F)F)c(C(F)(F)F)c2)no1]

$^1$H NMR (400 MHz, Chloroform-d) δ 8.31 (d, J=2.1 Hz, 1H), 8.19 (dd, J=8.7, 2.3 Hz, 1H), 7.63 (dd, J=8.2, 1.3 Hz, 2H), 7.50 (td, J=7.7, 1.4 Hz, 1H), 7.35 (t, J=7.8 Hz, 1H), 7.20 (dq, J=15.9, 2.1 Hz, 1H), 7.11 (t, J=8.8 Hz, 1H), 6.33 (dt, J=15.8, 5.1 Hz, 1H), 5.22-4.98 (m, 1H), 3.76-3.63 (m, 1H), 3.58-3.31 (m, 1H), 2.48-2.21 (m, 1H), 2.21-2.05 (m, 2H), 2.04-1.93 (m, 1H), 1.45 (s, 3H), 1.39-1.13 (m, 6H); $^{13}$C NMR (101 MHz, cdcl$_3$) δ 180.8, 167.2, 158.8, 158.8, 153.5, 136.1, 132.2, 132.2, 126.6, 126.6, 123.4, 118.6, 113.6, 113.4, 113.4, 110.0, 80.5, 80.5, 69.6, 69.6, 53.7, 53.7, 46.6, 46.3, 46.3, 32.4, 31.9, 31.4, 31.0, 28.3, 28.1, 24.3, 23.7, 22.1, 13.8.

tert-butyl (S,E)-2-(3-(3-(trifluoromethyl)-4-((3-(3-(trifluoromethyl)phenyl)allyl)oxy)phenyl)-1,2,4-oxadiazol-5-yl)pyrrolidine-1-carboxylate

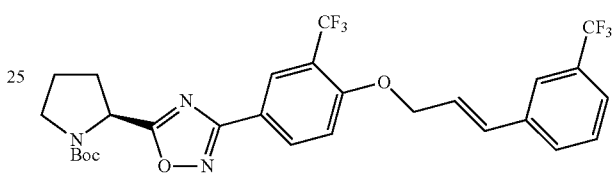

$^1$H NMR (400 MHz, Chloroform-d) δ 8.33 (d, J=2.1 Hz, 1H), 8.24-8.18 (m, 1H), 7.65 (s, 1H), 7.59 (d, J=7.6 Hz, 1H), 7.52 (d, J=8.0 Hz, 1H), 7.46 (t, J=7.7 Hz, 1H), 7.14 (d, J=8.6 Hz, 1H), 6.87-6.79 (m, 1H), 6.46 (dt, J=16.0, 5.1 Hz, 1H), 5.06 (dd, J=8.2, 3.6 Hz, 1H), 4.89 (d, J=5.1 Hz, 2H), 3.77-3.44 (m, 2H), 2.51-2.28 (m, 1H), 2.21-2.15 (m, 2H), 2.08-1.91 (m, 1H), 1.67-1.20 (m, 9H); $^{13}$C NMR (101 MHz, cdcl$_3$) δ 167.1, 136.9, 132.4, 131.5, 129.8, 129.7, 129.1, 124.9, 124.6, 123.3, 123.2, 113.4, 80.5, 68.9, 53.8, 46.6, 46.3, 32.4, 29.7, 28.3, 28.1, 24.4, 23.7; tert-butyl (S,E)-2-(3-(3-(trifluoromethyl)-4-((3-(4-(trifluoromethyl)phenyl)allyl)oxy)phenyl)1,2,4-oxadiazol-5-yl)pyrrolidine-1-carboxylate

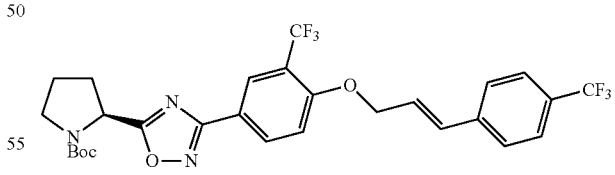

$^1$H NMR (500 MHz, Chloroform-d) δ 8.29-8.22 (m, 1H), 8.19-8.10 (m, 1H), 7.52 (d, J=8.2 Hz, 1H), 7.44 (d, J=8.1 Hz, 1H), 7.05 (dd, J=12.8, 8.6 Hz, 1H), 6.77 (d, J=16.1 Hz, 1H), 6.42 (dt, J=16.1, 5.1 Hz, 1H), 5.13 (d, J=7.8 Hz, 0H), 4.99 (dd, J=8.1, 3.7 Hz, 1H), 4.83 (dt, J=6.0, 2.8 Hz, 1H), 3.64 (dd, J=14.6, 8.8 Hz, 1H), 3.55-3.36 (m, 1H), 2.43-2.21 (m, 1H), 2.16-2.01 (m, 2H), 1.94 (s, 1H), 1.39 (s, 3H), 1.21 (s, 6H); $^{13}$C NMR (126 MHz, CDCl$_3$) δ 153.4, 146.4, 137.7, 127.6, 121.9, 120.7, 120.7, 120.5, 108.4, 100.0, 72.7, 72.4, 72.3, 72.2, 72.1, 72.0, 72.0, 71.8, 71.8, 71.7, 48.9, 23.2, 23.2.

287 tert-butyl (S,Z)-2-(3-(3-(trifluoromethyl)-4-((3-(4-trifluoromethyl)phenyl)allyl)oxy)phenyl)-1,2,4-oxadiazol-5-yl)pyrrolidine-1-carboxylate

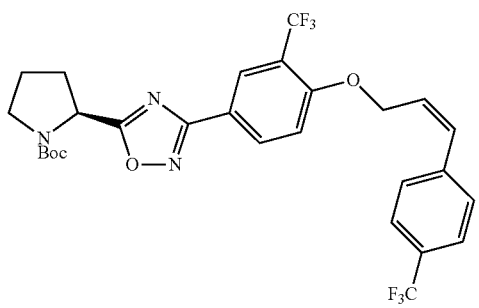 [SMILES: CC(C)(C)OC(=O)N1CCC[C@H]1c1nc(-c2ccc(OC/C=C\c3ccc(C(F)(F)F)cc3)c(C(F)(F)F)c2)no1]

$^1$H NMR (500 MHz, Chloroform-d) δ 8.24 (d, J=2.4 Hz, 1H), 8.08 (dd, J=8.6, 2.4 Hz, 1H), 7.58 (d, J=8.1 Hz, 2H), 7.31 (d, J=8.0 Hz, 2H), 6.87 (t, J=9.3 Hz, 1H), 6.74 (d, J=11.9 Hz, 1H), 6.04 (dt, J=11.7, 6.4 Hz, 1H), 4.99 (dd, J=8.1, 3.8 Hz, 1H), 4.91 (p, J=6.3 Hz, 1H), 4.87-4.81 (m, 2H), 3.70-3.56 (m, 1H), 3.50 (dt, J=10.3, 7.1 Hz, 1H), 2.42-2.23 (m, 1H), 2.15-2.01 (m, 2H), 2.00-1.90 (m, 1H), 1.39 (s, 3H), 1.29-1.13 (m, 6H).

tert-butyl (S,E)-2-(3-(3-(trifluoromethyl)-4-((4-(4-(trifluoromethyl)phenyl)but-3-en-1-yl)oxy)phenyl)-1,2,4-oxadiazol-5-yl)pyrrolidine-1-carboxylate

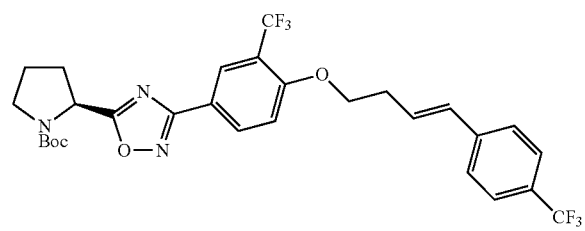 [SMILES: CC(C)(C)OC(=O)N1CCC[C@H]1c1nc(-c2ccc(OCC/C=C/c3ccc(C(F)(F)F)cc3)c(C(F)(F)F)c2)no1]

$^1$H NMR (400 MHz, Chloroform-d) δ 8.30 (d, J=2.2 Hz, 1H), 8.23-8.17 (m, 1H), 7.55 (d, J=8.2 Hz, 2H), 7.44 (d, J=8.1 Hz, 2H), 7.08 (t, J=9.1 Hz, 1H), 6.58 (d, J=15.9 Hz, 1H), 6.43 (dt, J=15.9, 6.9 Hz, 1H), 5.23-5.14 (m, 1H), 5.06 (dd, J=8.2, 3.7 Hz, 1H), 4.24 (t, J=6.1 Hz, 2H), 3.77-3.44 (m, 2H), 2.78 (q, J=6.4 Hz, 2H), 2.41 (ddd, J=19.3, 14.3, 9.7 Hz, 1H), 2.15 (dtd, J=19.0, 10.2, 8.4, 5.2 Hz, 2H), 2.06-1.92 (m, 1H), 1.46 (s, 3H), 1.29 (s, 6H); $^{13}$C NMR (101 MHz, cdcl$_3$) δ 180.9, 167.2, 167.2, 158.8, 153.5, 140.7, 132.4, 131.6, 128.2, 126.8, 126.2, 125.5, 125.4, 125.4, 122.8, 118.9, 118.9, 112.9, 80.5, 77.2, 77.0, 68.2, 53.8, 46.6, 46.3, 32.6, 32.4, 31.5, 28.3, 28.1, 24.4, 23.7.

288 tert-butyl (S,E)-2-(3-(4-((3,7-dimethylocta-2,6-dien-1-yl)oxy)-3-(trifluoromethyl)phenyl)-1,2,4-oxadiazol-5-yl)pyrrolidine-1-carboxylate

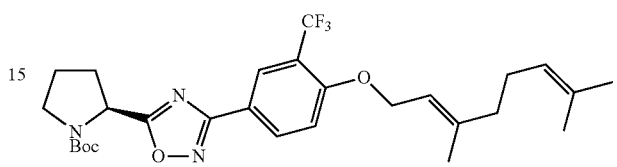

$^1$H NMR (400 MHz, Chloroform-d) δ 8.28 (d, J=2.1 Hz, 1H), 8.17 (dd, J=8.7, 2.2 Hz, 1H), 7.06 (t, J=8.0 Hz, 1H), 5.49-5.38 (m, 1H), 5.12-5.02 (m, 2H), 4.71 (d, J=6.3 Hz, 2H), 4.15 (dq, J=6.9, 0.7 Hz, 1H), 3.78-3.61 (m, 1H), 3.60-3.43 (m, 1H), 2.49-2.28 (m, 2H), 2.25-1.91 (m, 9H), 1.74 (d, J=1.3 Hz, 3H), 1.69-1.62 (m, 3H), 1.46 (s, 3H), 1.29 (s, 6H); $^{13}$C NMR (101 MHz, cdcl$_3$) δ 191.3, 180.8, 180.3, 167.3, 159.0, 153.5, 150.9, 150.8, 142.1, 142.0, 139.7, 132.2, 131.9, 131.7, 131.2, 126.6, 124.6, 123.9, 123.5, 123.3, 121.8, 118.7, 118.5, 113.5, 80.5, 66.0, 59.4, 53.8, 46.6, 46.3, 39.5, 39.4, 32.4, 31.4, 28.4, 28.1, 26.4, 26.1, 25.7, 25.6, 24.4, 23.7, 22.4, 22.0, 21.7, 17.7, 17.4, 16.7, 16.3, 16.2; Calcd for C$_{28}$H$_{36}$F$_3$N$_3$O$_4$Na [M+Na]: 560.2611, Found: 560.2640.

tert-butyl (S,E)-((2-(3-(4-(allyloxy)-3-(trifluoromethyl)phenyl)-1,2,4-oxadiazol-5-yl)pyrrolidin-1-yl)((tert-butoxycarbonyl)amino)methylene)carbamate

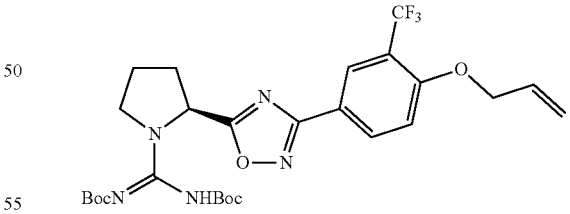

$^1$H NMR (500 MHz, Chloroform-d) δ 8.31 (d, J=2.1 Hz, 1H), 8.20 (dd, J=8.7, 2.2 Hz, 1H), 7.08 (d, J=8.7 Hz, 1H), 6.11-5.98 (m, 1H), 5.62 (dd, J=7.8, 4.6 Hz, 1H), 5.50 (dq, J=17.3, 1.7 Hz, 1H), 5.35 (dq, J=10.7, 1.5 Hz, 1H), 4.72 (dt, J=4.9, 1.7 Hz, 2H), 3.92 (dt, J=11.6, 6.8 Hz, 1H), s 3.82 (ddd, J=11.4, 7.3, 5.7 Hz, 1H), 2.51-2.40 (m, 1H), 2.28-2.15 (m, 2H), 2.10-2.00 (m, 1H), 1.47 (s, 18H); $^{13}$C NMR (126 MHz, CDCl$_3$) δ 179.2, 167.2, 167.2, 158.5, 153.6, 132.4, 131.7, 126.9, 126.8, 119.0, 117.9, 113.3, 81.0, 77.2, 69.3, 55.3, 49.5, 31.4, 28.1, 28.0, 24.0.

tert-butyl (S,Z)-((2-(3-(4-(but-3-en-1-yloxy)-3-(trifluoromethyl)phenyl)-1,2,4-oxadiazol-5-yl)pyrrolidin-1-yl)((tert-butoxycarbonyl)amino)methylene)carbamate

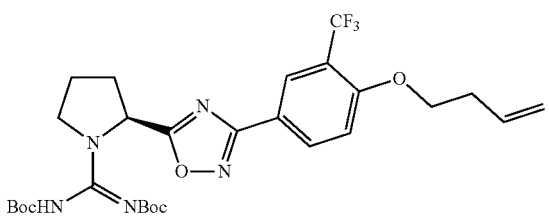

$^1$H NMR (400 MHz, Chloroform-d) δ 8.26 (d, J=2.1 Hz, 1H), 8.16 (dd, J=8.7, 2.2 Hz, 1H), 7.03 (d, J=8.7 Hz, 1H), 5.90 (ddt, J=17.1, 10.2, 6.8 Hz, 1H), 5.61 (dd, J=7.9, 4.5 Hz, 1H), 5.20-5.06 (m, 2H), 4.14 (t, J=6.5 Hz, 2H), 3.89 (dt, J=13.0, 6.8 Hz, 1H), 3.78 (dt, J=10.6, 5.9 Hz, 1H), 2.51-2.38 (m, 2H), 2.44 (dq, J=16.0, 8.9, 7.9 Hz, 1H), 2.11-1.99 (m, 2H), 2.09-1.95 (m, 2H), 1.45 (s, 18H); $^{13}$C NMR (101 MHz, cdcl$_3$) δ 179.1, 167.2, 158.9, 153.5, 133.6, 132.5, 126.8, 126.7, 119.6, 119.3, 118.7, 117.6, 112.8, 81.1, 68.3, 55.3, 49.6, 33.3, 31.4, 29.7, 28.1, 28.0, 24.0.

tert-butyl ((1E)-((tert-butoxycarbonyl)amino)((S)-2-(3-(4-(hex-2-en-1-yloxy)-3-(trifluoromethyl)phenyl)-1,2,4-oxadiazol-5-yl)pyrrolidin-1-yl)methylene)carbamate

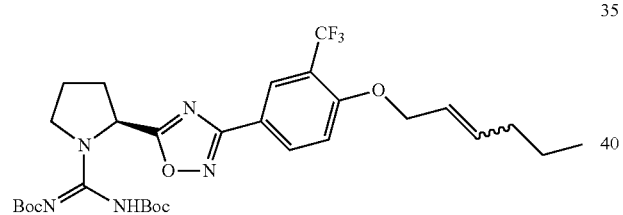

$^1$H NMR (400 MHz, Chloroform-d) δ 10.09 (s, 2H), 8.27 (d, J=2.1 Hz, 1H), 8.15 (dd, J=8.7, 2.2 Hz, 1H), 7.05 (d, J=8.7 Hz, 1H), 5.85 (dtt, J=15.0, 6.7, 1.4 Hz, 1H), 5.71-5.51 (m, 2H), 4.63 (dd, J=5.6, 1.3 Hz, 2H), 3.97-3.67 (m, 2H), 2.43 (dq, J=13.4, 7.8 Hz, 1H), 2.30-1.91 (m, 5H), 1.57-1.33 (m, 17H), 1.33-1.12 (m, 6H), 0.98-0.74 (m, 6H).

tert-butyl ((1E)-((tert-butoxycarbonyl)amino)((S)-2-(3-(4-(hept-2-en-1-yloxy)-3-(trifluoromethyl)phenyl)-1,2,4-oxadiazol-5-yl)pyrrolidin-1-yl)methylene)carbamate

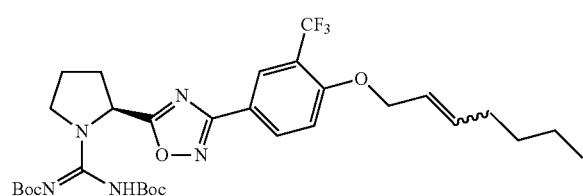

$^1$H NMR (500 MHz, Chloroform-d) δ 10.05 (s, 1H), 8.22 (d, J=2.1 Hz, 1H), 8.10 (dd, J=8.7, 2.2 Hz, 1H), 7.00 (d, J=8.8 Hz, 1H), 5.85-5.78 (m, 1H), 5.67-5.49 (m, 2H), 4.59-4.53 (m, 2H), 3.88-3.65 (m, 2H), 2.46-2.30 (m, 1H), 2.23-1.90 (m, 5H), 1.74-0.98 (m, 22H), 0.83 (t, J=7.2 Hz, 3H); $^{13}$C NMR (126 MHz, CDCl$_3$) δ 179.2, 167.2, 158.8, 158.8, 136.1, 132.3, 126.8, 123.4, 118.7, 118.7, 113.5, 113.5, 100.0, 77.2, 69.6, 55.3, 49.5, 32.0, 31.0, 29.7, 28.1, 22.1, 13.9.

tert-butyl ((1E)-((tert-butoxycarbonyl)amino)((S)-2-(3-(4-(oct-2-en-1-yloxy)-3-(trifluoromethyl)phenyl)-1,2,4-oxadiazol-5-yl)pyrrolidin-1-yl)methylene)carbamate

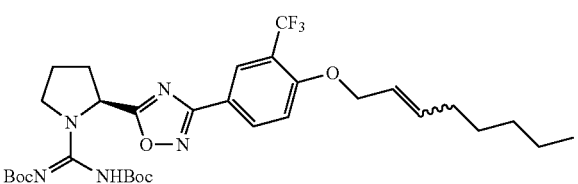

$^1$H NMR (500 MHz, Chloroform-d) δ 8.50-7.88 (m, 1H), 7.19 (s, 2H), 6.03-5.25 (m, 2H), 4.79-4.19 (m, 1H), 4.01-3.58 (m, 1H), 2.38 (dd, J=13.4, 7.1 Hz, 1H), 2.26-1.82 (m, 3H), 1.54-0.52 (m, 24H); $^{13}$C NMR (101 MHz, cdcl$_3$) δ 167.2, 167.2, 158.8, 136.1, 132.3, 132.3, 126.7, 123.4, 113.5, 113.5, 77.2, 69.6, 69.6, 49.5, 49.5, 32.2, 32.2, 31.3, 31.3, 29.7, 29.7, 28.5, 28.1, 28.0, 22.4, 14.0; $^{13}$C NMR (101 MHz, cdcl$_3$) δ 176.9, 167.2, 166.6, 158.8, 158.4, 136.1, 132.3, 126.7, 123.4, 113.5, 93.9, 69.6, 49.5, 42.3, 32.2, 28.0, 22.4, 14.0.

tert-butyl ((E)-((tert-butoxycarbonyl)amino)((S)-2-(3-(4-(((E)-hept-2-en-1-yl)oxy)-3-(trifluoromethyl)phenyl)-1,2,4-oxadiazol-5-yl)pyrrolidin-1-yl)methylene)carbamate

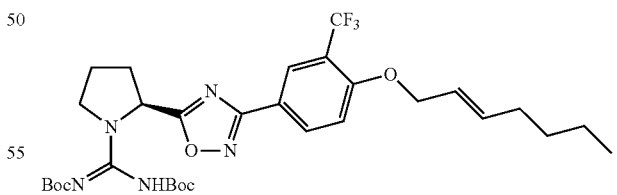

$^1$H NMR (500 MHz, Chloroform-d) δ 10.02 (s, 1H), 8.22 (d, J=2.1 Hz, 1H), 8.11 (dd, J=8.7, 2.2 Hz, 1H), 7.00 (d, J=8.7 Hz, 1H), 5.81 (dtt, J=15.2, 6.8, 1.4 Hz, 1H), 5.65-5.47 (m, 2H), 4.58 (dd, J=5.6, 1.4 Hz, 2H), 3.88-3.64 (m, 2H), 2.39 (dt, J=13.6, 7.3 Hz, 1H), 2.20-1.90 (m, 6H), 1.51-1.08 (m, 20H), 0.83 (t, J=7.2 Hz, 5H); $^{13}$C NMR (101 MHz, Methanol-d$_4$) δ 187.5, 163.3, 147.0, 132.1, 132.1, 128.4, 128.4, 127.9, 119.5, 119.5, 115.9, 115.5, 114.8, 109.6, 109.6, 73.4, 73.0, 72.7, 65.7, 65.7, 45.5, 45.5, 27.1, 25.7, 24.1, 18.2.

tert-butyl ((E)-((tert-butoxycarbonyl)amino)((S)-2-(3-(4-(((E)-oct-2-en-1-yl)oxy)-3-(trifluoromethyl)phenyl)-1,2,4-oxadiazol-5-yl)pyrrolidin-1-yl)methylene)carbamate

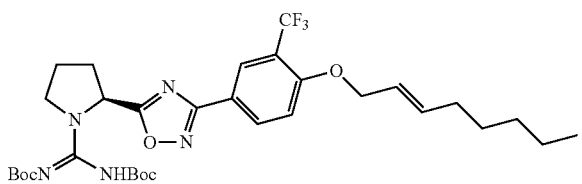

¹H NMR (400 MHz, Chloroform-d) δ 10.09 (s, 2H), 8.27 (d, J=2.1 Hz, 1H), 8.15 (dd, J=8.7, 2.2 Hz, 1H), 7.05 (d, J=8.8 Hz, 1H), 5.86 (dtt, J=15.0, 6.8, 1.4 Hz, 1H), 5.73-5.54 (m, 2H), 4.63 (dd, J=5.7, 1.3 Hz, 2H), 4.01-3.57 (m, 3H), 2.29-1.95 (m, 5H), 1.73-1.10 (m, 26H), 1.03-0.71 (m, 4H); ¹³C NMR (101 MHz, cdcl₃) δ 153.3, 136.1, 135.9, 132.3, 126.8, 123.4, 113.5, 77.4, 77.1, 76.7, 76.4, 69.6, 57.5, 55.2, 49.4, 32.2, 32.2, 31.3, 28.1, 22.4, 14.0.

tert-butyl ((E)-((tert-butoxycarbonyl)amino)((S)-2-(3-(4-(((Z)-oct-3-en-1-yl)oxy)-3-(trifluoromethyl)phenyl)-1,2,4-oxadiazol-5-yl)pyrrolidin-1-yl)methylene)carbamate

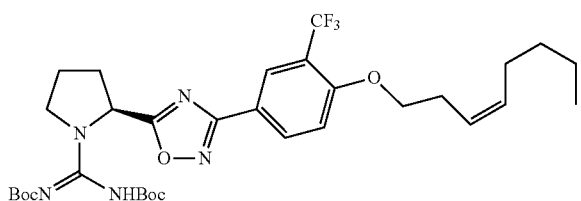

¹H NMR (400 MHz, Chloroform-d) δ 10.08 (s, 2H), 8.28-8.25 (m, 1H), 8.20-8.15 (m, 1H), 7.08-7.01 (m, 1H), 7.06 (d, J=8.8 Hz, 1H), 5.62-5.41 (m, 3H), 4.10 (t, J=6.8 Hz, 2H), 3.93-3.84 (m, 1H), 3.84-3.72 (m, 1H), 2.60 (qd, J=6.9, 1.3 Hz, 2H), 2.48-2.38 (m, 1H), 2.20-2.12 (m, 2H), 2.18-1.81 (m, 3H), 1.45 (s, 18H), 1.37-1.29 (m, 4H), 0.93-0.86 (m, 3H); ¹³C NMR (126 MHz, CDCl₃) δ 179.1, 167.2, 159.0, 133.1, 132.4, 126.8, 126.8, 124.2, 123.9, 122.1, 119.6, 119.3, 118.7, 118.6, 112.9, 77.2, 68.7, 55.3, 49.5, 31.7, 28.1, 27.1, 27.0, 22.3, 14.0.

tert-butyl ((E)-((S)-2-(3-(4-(((E)-3-(3-bromophenyl)allyl)oxy)-3-(trifluoromethyl)phenyl)-1,2,4-oxadiazol-5-yl)pyrrolidin-1-yl)((tert-butoxycarbonyl)amino)methylene)carbamate

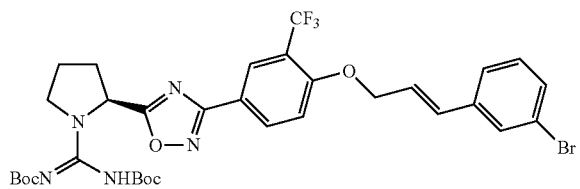

¹H NMR (400 MHz, Chloroform-d) δ 8.32 (d, J=2.1 Hz, 1H), 8.21 (dd, J=8.6, 2.2 Hz, 1H), 7.56 (t, J=1.8 Hz, 1H), 7.39 (dt, J=8.0, 1.4 Hz, 1H), 7.35-7.30 (m, 1H), 7.20 (t, J=7.8 Hz, 1H), 7.11 (d, J=8.7 Hz, 1H), 6.78-6.68 (m, 1H), 6.70 (s, 1H), 6.39 (dt, J=16.0, 1H), 5.60 (dd, J=7.9, 4.4 Hz, 1H), 4.87 (dd, J=5.2, 1.7 Hz, 2H), 3.90 (dt, J=13.2, 6.8 Hz, 1H), 3.81 (s, 1H), 2.45 (dd, J=13.0, 7.1 Hz, 2H), 2.23-1.95 (m, 4H), 1.48 (s, 18H); ¹³C NMR (126 MHz, CDCl₃) δ 179.3, 167.1, 158.4, 147.6, 146.7, 138.3, 132.5, 131.6, 130.9, 130.1, 129.5, 125.3, 124.5, 122.8, 113.3, 113.3, 77.6, 77.2, 69.0, 49.5, 29.7, 28.1, 28.0.

tert-butyl ((E)-((tert-butoxycarbonyl)amino)((S)-2-(3-(4-(((E)-3-(4-fluorophenyl)allyl)oxy)-3-(trifluoromethyl)phenyl)-1,2,4-oxadiazol-5-yl)pyrrolidin-1-yl)methylene)carbamate

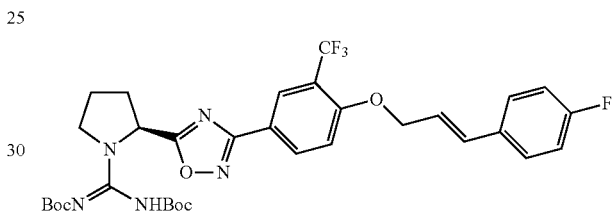

1H NMR (400 MHz, Chloroform-d) δ 10.51-9.51 (brs, 2H), 8.31 (d, J=2.1 Hz, 1H), 8.20 (dd, J=8.7, 2.2 Hz, 1H), 7.42-7.34 (m, 2H), 7.12 (d, J=8.8 Hz, 1H), 7.06-6.97 (m, 2H), 6.79-6.72 (m, 1H), 6.30 (dt, J=16.0, 5.4 Hz, 1H), 5.63 (dd, J=7.7, 4.4 Hz, 1H), 4.86 (dd, J=5.5, 1.6 Hz, 2H), 3.96-3.74 (m, 2H), 2.46 (s, 1H), 2.28-2.13 (m, 2H), 2.04 (dt, J=12.6, 6.7 Hz, 1H), 1.48 (d, =20.4 Hz, 18H); ¹³C NMR (101 MHz, cdcl₃) δ 191.5, 179.2, 179.2, 167.1, 163.8, 158.5, 132.5, 132.3, 132.3, 132.2, 128.2, 128.2, 126.9, 126.9, 122.6, 122.6, 121.8, 119.6, 119.1, 115.7, 115.4, 113.4, 77.2, 69.3, 55.3, 49.5, 36.6, 31.2, 28.1, 28.0, 24.7, 23.3.

tert-butyl ((E)-((tert-butoxycarbonyl)amino)((S)-2-(3-(3-(trifluoromethyl)-4-(((E)-3-(2-(trifluoromethyl)phenyl)allyl)oxy)phenyl)-1,2,4-oxadiazol-5-yl)pyrrolidin-1-yl)methylene)carbamate

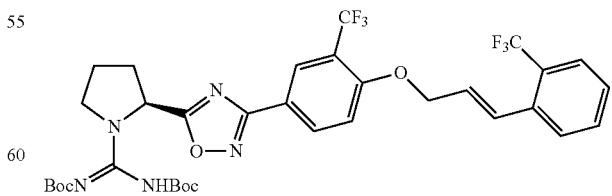

¹³C NMR (101 MHz, cdcl₃) δ 191.5, 167.1, 167.1, 158.5, 151.2, 135.3, 132.4, 131.9, 129.1, 127.7, 127.5, 127.2, 126.9, 125.8, 125.8, 124.5, 113.4, 77.2, 68.9, 49.5, 29.7, 28.1, 28.0.

tert-butyl ((E)-((tert-butoxycarbonyl)amino)((S)-2-(3-(3-(trifluoromethyl)-4-(((E)-3-(3-(trifluoromethyl)phenyl)allyl)oxy)phenyl)-1,2,4-oxadiazol-5-yl)pyrrolidin-1-yl)methylene)carbamate

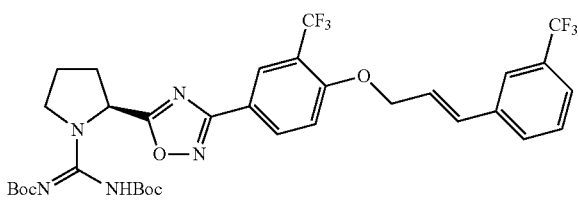

¹³C NMR (101 MHz, cdcl₃) δ 191.5, 179.3, 167.1, 158.3, 136.9, 132.5, 132.1, 131.6, 130.9, 129.8, 129.1, 127.0, 126.9, 124.9, 124.6, 123.3, 123.2, 123.2, 119.6, 119.3, 113.3, 77.2, 68.9, 55.3, 49.5, 29.7, 28.1, 28.0.

tert-butyl ((E)-((tert-butoxycarbonyl)amino)((S)-2-(3-(3-(trifluoromethyl)-4-(((E)-3-(4-(trifluoromethyl)phenyl)allyl)oxy)phenyl)-1,2,4-oxadiazol-5-yl)pyrrolidin-1-yl)methylene)carbamate

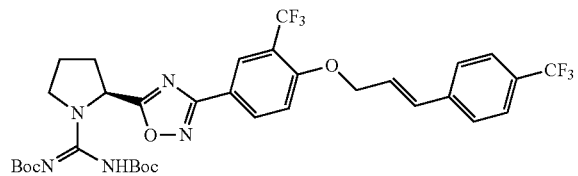

¹H NMR (500 MHz, Chloroform-d) δ 10.09 (s, 1H), 8.26 (d, J=2.1 Hz, 1H), 8.15 (dd, J=8.7, 2.1 Hz, 1H), 7.52 (d, J=8.2 Hz, 2H), 7.44 (d, J=8.2 Hz, 2H), 7.05 (d, J=8.7 Hz, 1H), 6.80-6.73 (m, 1H), 6.42 (dt, J=16.1, 5.1 Hz, 1H), 5.54 (dd, J=7.9, 4.5 Hz, 1H), 4.83 (dd, J=5.1, 1.7 Hz, 2H), 3.91-3.65 (m, 2H), 2.45-2.33 (m, 1H), 2.23-2.05 (m, 2H), 1.98 (s, 3H), 1.39 (s, 19H), 1.24-1.13 (m, 4H); ¹³C NMR (101 MHz, cdcl₃) δ 167.1, 158.3, 132.5, 131.5, 126.9, 126.9, 126.8, 125.6, 125.6, 119.8, 113.3, 110.0, 77.2, 68.8, 49.5, 31.9, 29.7, 28.1, 28.0, 22.7, 14.1.

tert-butyl ((E)-((tert-butoxycarbonyl)amino)((S)-2-(3-(3-(trifluoromethyl)-4-(((Z)-3-(4-(trifluoromethyl)phenyl)allyl)oxy)phenyl)-1,2,4-oxadiazol-5-yl)pyrrolidin-1-yl)methylene)carbamate

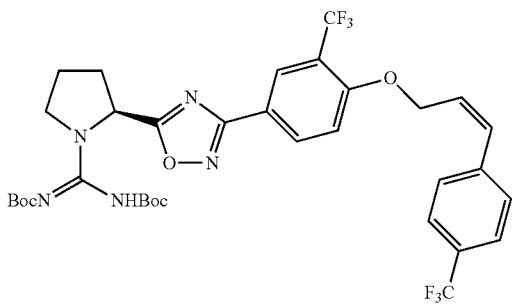

¹H NMR (400 MHz, Chloroform-d) δ 10.10 (s, 2H), 8.30 (d, J=2.1 Hz, 1H), 8.14 (dd, J=8.7, 2.2 Hz, 1H), 7.69-7.61 (m, 2H), 7.42-7.34 (m, 2H), 6.94 (d, J=8.7 Hz, 1H), 6.80 (d, J=11.8 Hz, 1H), 6.10 (dt, J=11.8, 6.4 Hz, 1H), 5.61 (dd, J=7.8, 4.5 Hz, 1H), 4.91 (dd, J=6.4, 1.7 Hz, 2H), 3.90 (dt, J=11.4, 7.0 Hz, 1H), 3.85-3.75 (m, 1H), 2.55-2.39 (m, 1H), 2.20 (s, 2H), 2.11-1.96 (m, 1H), 1.61-1.36 (m, 15H), 1.27 (s, 3H).

tert-butyl ((E)-((tert-butoxycarbonyl)amino)((S)-2-(4-(3-(trifluoromethyl)-4-(((E)-4-(4-(trifluoromethyl)phenyl)but-3-en-1-yl)oxy)phenyl)oxazol-2-yl)pyrrolidin-1-yl)methylene)carbamate

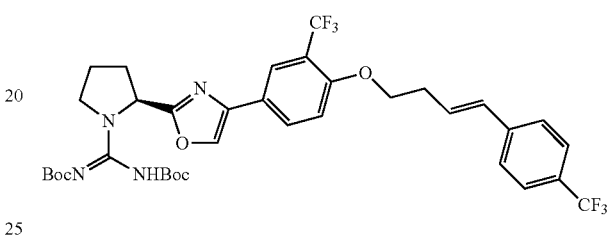

¹H NMR (400 MHz, Chloroform-d) δ 8.28 (d, J=2.1 Hz, 1H), 8.18 (dd, J=8.7, 2.2 Hz, 1H), 7.53 (d, J=8.2 Hz, 2H), 7.43 (d, J=8.1 Hz, 2H), 7.06 (d, J=8.7 Hz, 1H), 6.58 (s, 0H), 6.54 (s, 1H), 6.42 (dt, J=15.9, 6.9 Hz, 1H), 5.58 (dd, J=7.8, 4.6 Hz, 1H), 4.23 (t, J=6.2 Hz, 2H), 3.88 (dt, J=11.5, 7.0 Hz, 1H), 3.83-3.70 (m, 1H), 2.77 (qd, J=6.3, 1.3 Hz, 2H), 2.42 (ddd, J=15.7, 10.4, 6.8 Hz, 2H), 2.24-2.12 (m, 2H), 2.07-1.96 (m, 2H); ¹³C NMR (101 MHz, cdcl₃) δ 179.2, 167.1, 158.8, 140.7, 140.7, 132.5, 131.6, 129.2, 128.9, 128.2, 126.8, 126.8, 126.7, 126.2, 125.6, 125.5, 125.5, 125.4, 125.4, 124.6, 121.8, 119.6, 119.3, 118.9, 112.8, 77.2, 68.2, 55.3, 49.5, 32.6, 29.7, 28.1, 28.1, 28.0, 24.0, 14.1.

tert-butyl ((E)-((tert-butoxycarbonyl)amino)((S)-2-(3-(4-(((E)-3,7-dimethylocta-2,6-dien-1-yl)oxy)-3-(trifluoromethyl)phenyl)-1,2,4-oxadiazol-5-yl)pyrrolidin-1-yl)methylene)carbamate compound 77

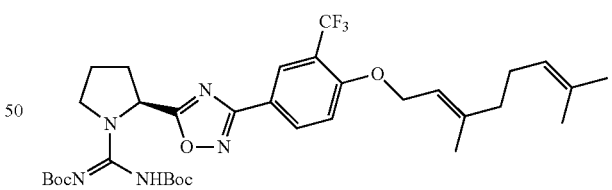

¹H NMR (400 MHz, Chloroform-d) δ 10.10 (s, 2H), 8.28 (d, J=2.1 Hz, 1H), 8.18 (dd, J=8.7, 2.3 Hz, 1H), 7.06 (d, J=8.8 Hz, 1H), 5.60 (dd, J=7.8, 4.5 Hz, 1H), 5.52-5.43 (m, 1H), 4.71 (d, J=6.4 Hz, 1), 3.98-3.74 (m, 2H), 2.52-2.39 (m, 2H), 2.28-1.99 (m, 6H), 1.71 (s, 3H), 1.72-1.31 (m, 24H); ¹³C NMR (101 MHz, cdcl₃) δ 181.5, 181.0, 166.8, 158.4, 154.3, 153.4, 150.6, 149.3, 148.8, 135.9, 135.7, 135.5, 135.3, 131.4, 130.4, 128.8, 128.7, 126.7, 126.3, 125.5, 125.1, 123.9, 123.2, 121.2, 80.6, 77.3, 77.2, 77.0, 76.7, 70.9, 70.8, 63.7, 63.3, 53.8, 53.8, 46.6, 46.4, 38.6, 37.6, 34.4, 34.3, 32.4, 32.1, 32.0, 31.5, 31.4, 31.4, 29.7, 28.3, 28.1, 26.4, 26.2, 24.4, 23.7, 22.0; Calcd for C₃₄H₄₈ClF₃N₅O₆ [M+H]⁺: 714.324, Found: 714.3307.

(S)-2-(3-(4-(allyloxy)-3-(trifluoromethyl)phenyl)-1,2,4-oxadiazol-5-yl)pyrrolidine-1-carboximidamide hydrochloride

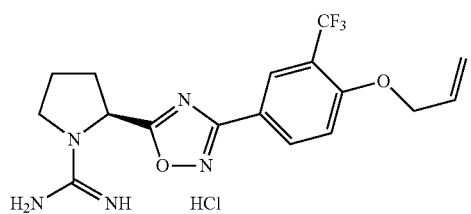 [SMILES: C=CCOc1ccc(-c2noc([C@@H]3CCCN3C(=N)N)n2)cc1C(F)(F)F ; Cl]

¹H NMR (500 MHz, Methanol-d₄) δ 8.14 (d, J=8.4 Hz, 2H), 7.24 (d, J=8.5 Hz, 1H), 5.98 (ddt, J=17.3, 10.7, 4.9 Hz, 1H), 5.41-5.31 (m, 2H), 5.22 (q, J=1.5 Hz, 1H), 4.67 (dt, J=4.9, 1.7 Hz, 2H), 3.68 (td, J=9.2, 2.6 Hz, 1H), 3.52 (td, J=9.6, 7.2 Hz, 1H), 2.53-2.30 (m, 2H), 2.15-2.01 (m, 1H), 1.81-1.99 (m, 1H); ¹³C NMR (126 MHz, MeOD) δ 177.8, 167.1, 158.8, 155.7, 132.5, 132.5, 132.0, 125.7, 124.3, 122.2, 119.2, 118.3, 116.6, 113.9, 69.2, 55.0, 48.1, 47.9, 47.9, 47.8, 47.7, 47.6, 47.6, 47.4, 47.3, 47.1, 31.3, 22.9; Found [M+H]⁺ 345.0.

Example 84: (S)-2-(3-(4-(but-3-en-1-yloxy)-3-(trifluoromethyl)phenyl)-1,2,4-oxadiazol-5-yl)pyrrolidine-1-carboximidamide hydrochloride (compound 79A)

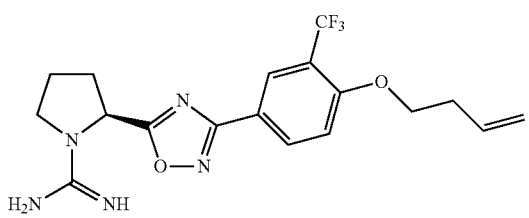 [SMILES: C=CCCOc1ccc(-c2noc([C@@H]3CCCN3C(=N)N)n2)cc1C(F)(F)F]

¹H NMR (400 MHz, Methanol-d₄) δ 8.30-8.15 (m, 2H), 7.33 (d, J=8.3 Hz, 1H), 6.01-5.85 (m, 1H), 5.48-5.37 (m, 1H), 5.23-5.17 (m, 1H), 5.12-5.06 (m, 1H), 4.21 (t, J=6.2 Hz, 2H), 3.77 (t, J=8.6 Hz, 1H), 3.69-3.52 (m, 1H), 2.63-2.42 (m, 4H), 2.31-2.01 (m, 2H); ¹³C NMR (101 MHz, Methanol-d₄) δ 177.8, 167.1, 159.2, 155.6, 133.9, 132.5, 125.6, 124.6, 121.9, 119.0, 118.1, 113.5, 68.4, 55.1, 48.2, 48.2, 48.0, 47.8, 47.6, 47.4, 47.2, 47.0, 33.0, 31.4; Found [M+H]⁺ 360.0.

Example 85: (S)-amino(2-(3-(4-(hex-2-en-1-yloxy)-3-(trifluoromethyl)phenyl)-1,2,4-oxadiazol-5-yl)pyrrolidin-1-yl)methaniminium 2,2,2-trifluoroacetate (Compound 80A)

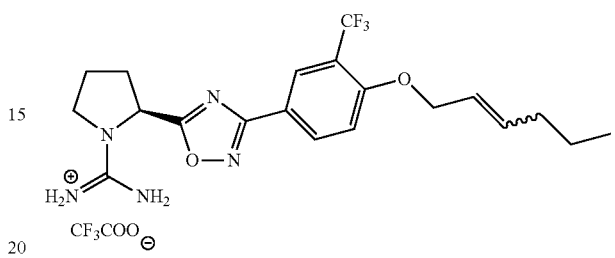

¹H NMR (400 MHz, Methanol-d₄) δ 8.26-8.18 (m, 1.6H), 8.16-8.13 (m, 0.4H), 8.09-8.01 (m, 0.4H), 7.35-7.28 (m, 1H), 7.09-7.02 (d, J=8.5 Hz, 0.4H), 6.00-5.84 (m, 1H), 5.80-5.52 (m, 1H), 5.48-5.32 (m, 1H), 4.72-4.65 (m, 1H), 3.76 (td, J=9.2, 2.6 Hz, 1H), 3.70-3.51 (m, 1H), 2.68-2.37 (m, 2H), 2.30-2.00 (m, 1H), 1.42 (h, J=7.3 Hz, 1H), 0.90 (q, J=7.5 Hz, 3H); ¹³C NMR (101 MHz, Methanol-d₄) δ 190.0, 188.1, 175.9, 167.6, 159.9, 139.5, 136.3, 132.0, 110.0, 99.9, 99.3, 69.2, 63.9, 55.0, 45.6, 31.3, 22.9, 12.8. Found [M+H]⁺ 424.1955.

Example 86: (S)-amino(2-(3-(4-(hept-2-en-1-yloxy)-3-(trifluoromethyl)phenyl)-1,2,4-oxadiazol-5-yl)pyrrolidin-1-yl)methaniminium 2,2,2-trifluoroacetate (Compound 81A)

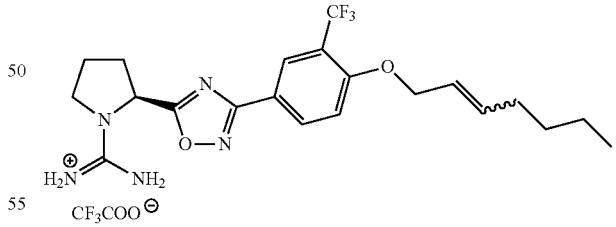

¹H NMR (400 MHz, Methanol-d₄) δ 8.25-8.19 (m, 1.5H), 8.15-8.13 (m, 0.5H), 8.05-8.08 (m, 0.5H), 7.38-7.21 (d, J=8.5 Hz, 1H), 7.07-7.03 (m, J=8.6, 0.7 Hz, 1H), 5.97-5.84 (m, 1H), 5.74-5.62 (m, 1H), 5.41-5.38 (m, J=7.9, 4.1, 1.9 Hz, 2H), 4.71-4.63 (m, J=1H), 3.81-3.73 (td, J=9.2, 2.6 Hz, 2H), 3.59 (q, J=9.2 Hz, 2H), 2.60-2.40 (m, 2H), 2.21-2.08 (m, 2H), 2.16-2.00 (m, 3H), 1.44-1.24 (m, 4H), 0.94-0.84 (m, 3H); ¹³C NMR (101 MHz, Methanol-d₄) δ 190.0, 175.9, 159.9, 157.8, 139.5, 136.3, 132.0, 110.0, 99.9, 80.9, 69.2, 63.9, 55.0, 45.6, 41.8, 31.3, 22.9.

Example 87: (S)-amino(2-(3-(4-(oct-2-en-1-yloxy)-3-(trifluoromethyl)phenyl)-1,2,4-oxadiazol-5-yl)pyrrolidin-1-yl)methaniminium 2,2,2-trifluoroacetate (Compound 82A)

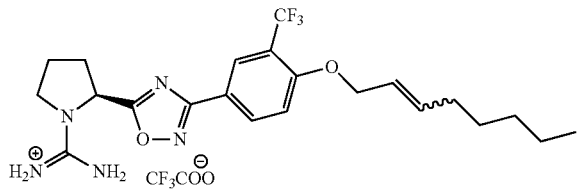

¹H NMR (400 MHz, Methanol-d₄) δ 8.31-8.12 (m, 2H), 7.38-7.27 (m, 1H), 5.97-5.84 (m, 1H), 5.76-5.59 (m, 1H), 5.42 (dd, J=7.9, 2.0 Hz, 1H), 4.69 (dq, J=5.8, 1.2 Hz, 2H), 2.64-2.42 (m, 2H), 2.30-1.94 (m, 4H), 1.61-1.14 (m, 11H), 0.97-0.81 (m, 4H); ¹³C NMR (126 MHz, MeOD) δ 177.8, 167.2, 159.0, 155.7, 135.8, 135.4, 132.3, 125.7, 124.3, 123.6, 123.1, 118.1, 114.2, 69.3, 55.0, 48.1, 47.9, 47.8, 47.6, 47.4, 47.2, 47.1, 31.0, 29.4, 28.4, 26.7, 22.9, 22.1, 12.9. ESI found [M+H]⁺ 452.2285.

Example 88: (S,E)-amino(2-(3-(4-(hept-2-en-1-yloxy)-3-(trifluoromethyl)phenyl)-1,2,4-oxadiazol-5-yl)pyrrolidin-1-yl)methaniminium 2,2,2-trifluoroacetate (Compound 78A)

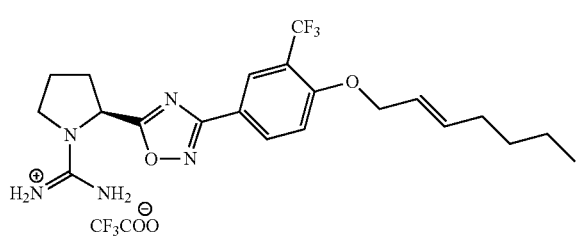

¹H NMR (400 MHz, Chloroform-d) δ 8.31-8.23 (m, 2H), 7.48-7.28 (m, 1H), 6.03-5.81 (m, 1H), 5.76-5.41 (m, 1H), 5.48 (dd, J=7.9, 2.0 Hz, 1H), 4.75 (dd, J=5.8, 1.3 Hz, 2H), 3.82 (td, J=9.1, 2.7 Hz, 1H), 3.66 (td, J=9.6, 7.3 Hz, 1H), 2.68-2.47 (m, 2H), 2.34-2.22 (m, 1H), 2.16 (q, J=7.0 Hz, 3H), 1.50-1.30 (m, 4H), 1.00-0.90 (m, 3H); ¹³C NMR (101 MHz, Methanol-d₄) δ 187.5, 177.8, 167.1, 147.2, 135.7, 132.5, 128.2, 123.6, 114.1, 69.3, 55.0, 48.2, 47.8, 47.6, 47.3, 47.1, 46.9, 30.9, 22.9, 21.7, 12.8; ESI found [M+H]⁺ 438.0.

Example 89: (S,E)-amino(2-(3-(4-(oct-2-en-1-yloxy)-3-(trifluoromethyl)phenyl)-1,2,4-oxadiazol-5-yl)pyrrolidin-1-yl)methaniminium 2,2,2-trifluoroacetate (Compound 83A)

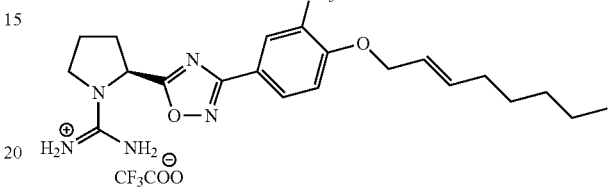

¹H NMR (400 MHz, Methanol-d₄) δ 8.23-8.19 (m, 2H), 7.32 (d, J=8.6 Hz, 1H), 5.96-5.85 (m, 1H), 5.66 (dtt, J=15.5, 5.8, 1.4 Hz, 1H), 5.42 (dd, J=7.9, 2.0 Hz, 1H), 4.69 (dd, J=5.8, 1.2 Hz, 2H), 3.80-3.71 (m, 1H), 3.59 (td, J=9.7, 7.2 Hz, 1H), 2.63-2.38 (m, 3H), 2.29-1.97 (m, 5H), 1.50-1.17 (m, 7H), 0.97-0.74 (m, 3H); ¹³C NMR (101 MHz, Methanol-d₄) δ 187.5, 177.8, 167.1, 159.0, 155.7, 147.3, 135.8, 132.3, 132.3, 128.2, 125.7, 124.6, 123.6, 123.6, 121.9, 119.3, 118.1, 114.1, 69.2, 55.0, 48.2, 48.0, 47.8, 47.6, 47.5, 47.3, 47.2, 47.1, 46.9, 31.8, 31.3, 28.3, 22.9, 22.1; ESI found [M+H]⁺ 452.2285

Example 90: (S,Z)-amino(2-(3-(4-(hept-3-en-1-yloxy)-3-(trifluoromethyl)phenyl)-1,2,4-oxadiazol-5-yl)pyrrolidin-1-yl)methaniminium 2,2,2-trifluoroacetate (Compound 84)

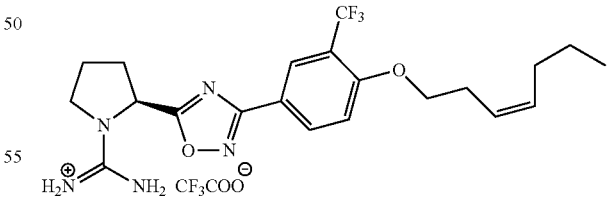

¹H NMR (500 MHz, Methanol-d₄) δ 8.33-8.09 (m, 2H), 7.33 (d, J=8.7 Hz, 1H), 5.72-5.18 (m, 3H), 4.18 (t, J=6.5 Hz, 2H), 3.84-3.73 (m, 1H), 3.61 (td, 9.7, 7.2 Hz, 1H), 2.63-2.41 (m, 4H), 2.22 (dtd, J=10.9, 4.9, 4.4, 2.4 Hz, 1H), 2.13-2.02 (m, 2H), 1.39 (p, J=7.4 Hz, 2H), 0.92 (t, J=7.4 Hz, 3H); ¹³C NMR (126 MHz, MeOD) δ 177.8, 167.1, 159.3, 155.7, 132.5, 132.0, 125.7, 124.4, 118.1, 113.5, 113.5, 68.7, 55.0, 48.1, 47.9, 47.8, 47.6, 47.5, 47.4, 47.4, 47.2, 47.1, 31.3, 26.7, 22.9; ESI found [M+H]⁺ 438.2104.

Example 91: (S,Z)-amino(2-(3-(4-(oct-3-en-1-yloxy)-3-(trifluoromethyl)phenyl)-1,2,4-oxadiazol-5-yl)pyrrolidin-1-yl)methaniminium 2,2,2-trifluoroacetate (Compound 85A)

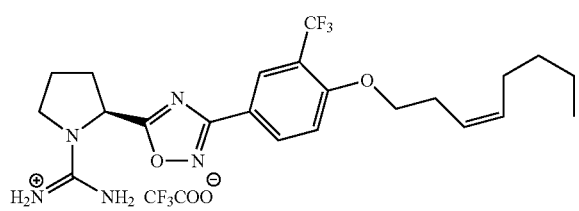

$^1$H NMR (400 MHz, Methanol-d$_4$) δ 8.52-8.07 (m, 2H), 7.49-7.28 (m, 1H), 5.77-5.30 (m, 2H), 4.38-4.15 (m, 2H), 3.81-3.01 (m, 2H), 2.85-1.87 (m, 8H), 1.62-0.70 (m, 7H); $^{13}$C NMR (101 MHz, Methanol-d$_4$) δ 187.5, 177.8, 167.1, 159.3, 155.7, 132.5, 132.5, 132.2, 132.2, 125.7, 124.2, 124.2, 121.9, 118.8, 118.1, 68.7, 68.7, 55.0, 55.0, 48.2, 48.0, 48.0, 47.8, 47.6, 47.4, 47.1, 46.9, 31.5, 31.5, 31.3, 31.3, 26.7, 26.6, 22.9, 22.9, 21.9, 21.9, 12.9; ESI found [M+H]$^+$ 452.2260.

Example 92: (S,E)-2-(3-(4-((3-(3-bromophenyl)allyl)oxy)-3-(trifluoromethyl)phenyl)-1,2,4-oxadiazol-5-yl)pyrrolidine-1-carboximidamide hydrochloride (Compound 86A)

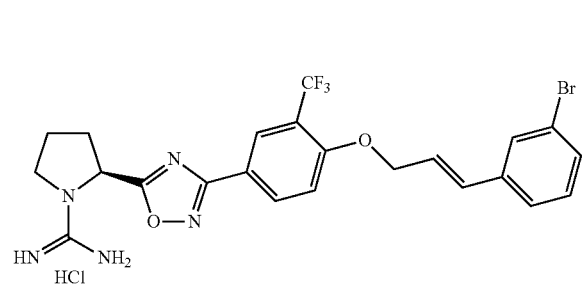 [SMILES: N=C(N)N1CCC[C@H]1c1nc(-c2ccc(OC/C=C/c3cccc(Br)c3)c(C(F)(F)F)c2)no1 ; Cl]

$^1$H NMR (400 MHz, Methanol-d$_4$) δ 8.40-8.13 (m, 1H), 7.59 (t, J=1.9 Hz, 0H), 7.48-7.31 (m, 1H), 7.32-7.13 (m, 0H), 6.88-6.70 (m, 0H), 6.49 (dt, J=16.0, 5.4 Hz, 0H), 5.42 (dd, J=7.8, 2.0 Hz, 0H), 4.86 (s, 10H), 3.76 (td, J=9.2, 2.6 Hz, 1H), 3.59 (td, J=9.7, 7.3 Hz, 1H), 2.65-2.42 (m, 1H), 2.32-2.14 (m, 0H), 2.06 (ddd, J=11.8, 9.4, 5.2 Hz, 1H); $^{13}$C NMR (101 MHz, Methanol-d$_4$) δ 177.8, 167.1, 158.8, 155.6, 138.7, 132.5, 131.2, 130.0, 129.0, 125.8, 124.9, 122.3, 118.4, 114.0, 68.9, 55.0, 48.2, 48.0, 47.8, 47.7, 47.6, 47.3, 47.1, 46.9, 31.3, 22.9.

Example 93: (S,E)-2-(3-(4-((3-(4-fluorophenyl)allyl)oxy)-3-(trifluoromethyl)phenyl)-1,2,4-oxadiazol-5-yl)pyrrolidine-1-carboximidamide hydrochloride (Compound 87A)

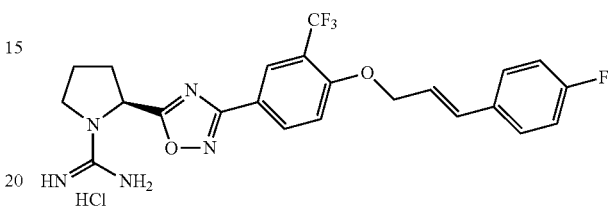

$^1$H NMR (400 MHz, Methanol-d$_4$) δ 8.22 (d, J=6.6 Hz, 2H), 7.54-7.28 (m, 3H), 7.04 (q, J=8.3 Hz, 2H), 6.79 (d, J=15.5 Hz, 1H), 6.39 (d, J=15.0 Hz, 1H), 5.42 (s, 1H), 3.86-3.52 (m, 3H), 2.50 (d, J=37.7 Hz, 2H), 2.18-2.13 (m, 2H), 1.50 (d, J=7.0 Hz, 2H); $^{13}$C NMR (101 MHz, Methanol-d4) δ 147.4, 140.4, 138.1, 131.7, 131.5, 130.6, 129.1, 128.1, 128.1, 127.9, 125.1, 123.3, 100.7, 61.0, 48.2, 48.0, 47.8, 47.5, 47.3, 47.1, 46.9. ESI found [M+H]$^+$ 476.1715.

Example 94: (S,E)-2-(3-(3-(trifluoromethyl)-4-((3-(2-(trifluoromethyl)phenyl)allyl)oxy)phenyl)-1,2,4-oxadiazol-5-yl)pyrrolidine-1-carboximidamide hydrochloride (Compound 89A)

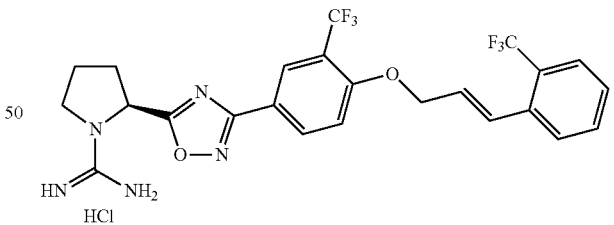

$^1$H NMR (400 MHz, Methanol-d$_4$) δ 8.28-8.24 (m, 2H), 7.76 (d, J=7.9 Hz, 1H), 7.65 (d, J=7.8 Hz, 1H), 7.59 (t, J=7.6 Hz, 1H), 7.47-7.36 (m, 2H), 7.20 (dd, J=16.1, 2.8 Hz, 1H), 6.48 (dt, J=15.8, 4.5 Hz, 1H), 5.47-5.40 (m, 1H), 4.98 (dd, J=4.6, 2.0 Hz, 2H), 3.80-3.56 (m, 2H), 2.62-2.43 (m, 2H), 2.26-2.20 (m, 1H), 2.13-2.01 (m, 1H); $^{13}$C NMR (101 MHz, Methanol-d$_4$) δ 187.6, 177.8, 167.1, 158.4, 155.7, 135.4, 132.4, 132.0, 127.5, 127.4, 127.2, 125.8, 125.8, 125.7, 125.3, 125.3, 118.5, 114.0, 68.3, 55.1, 48.2, 48.0, 47.8, 47.6, 47.4, 47.1, 46.9, 31.3, 26.7, 22.9; ESI found [M+H]$^+$ 526.1653.

Example 95: (S,E)-amino(2-(3-(3-(trifluoromethyl)-4-((3-(3-(trifluoromethyl)phenyl)allyl)oxy)phenyl)-1,2,4-oxadiazol-5-yl)pyrrolidin-1-yl)methaniminium 2,2,2-trifluoroacetate (Compound 90A)

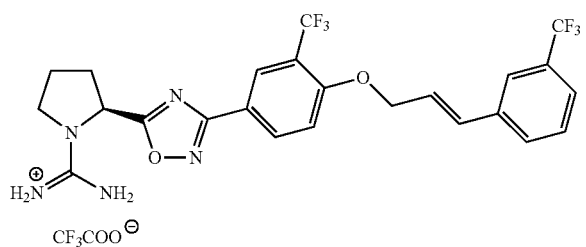

¹H NMR (400 MHz, Methanol-d₄) δ 8.30-8.22 (m, 1H), 7.70 (d, J=8.4 Hz, 2H), 7.59-7.49 (m, 2H), 7.48-7.33 (m, 2H), 6.89 (d, J=16.1 Hz, 1H), 6.59 (dt, J=16.1, 5.3 Hz, 1H), 5.43 (dd, J=7.9, 1.9 Hz, 1H), 4.96 (dd, J=5.3, 1.6 Hz, 2H), 3.82-3.50 (m, 4H), 2.60-2.39 (m, 2H), 2.23 (dd, J=12.9, 6.9 Hz, 1H), 2.14-2.01 (m, 1H); ¹³C NMR (101 MHz, Methanol-d4) δ 177.8, 167.1, 158.8, 155.7, 137.4, 132.5, 131.1, 129.6, 129.1, 127.9, 125.8, 125.3, 124.0, 122.7, 119.3, 118.5, 114.0, 68.9, 55.0, 48.2, 48.0, 47.8, 47.6, 47.4, 47.2, 46.9, 31.3, 22.9. ESI found [M+H]⁺ 526.0.

Example 96: (S,E)-amino(2-(3-(3-(trifluoromethyl)-4-((3-(4-(trifluoromethyl)phenyl)allyl)oxy)phenyl)-1,2,4-oxadiazol-5-yl)pyrrolidin-1-yl)methaniminium 2,2,2-trifluoroacetate (Compound 88A)

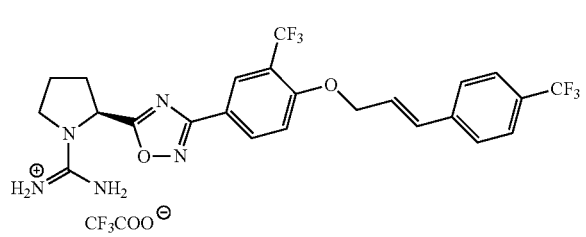

¹H NMR (400 MHz, Methanol-d₄) δ 8.26 (d, J=11.0 Hz, 2H), 7.62 (s, 3H), 7.41 (d, J=8.5 Hz, 1H), 6.92-6.85 (m, 1H), 6.64 (t, J=5.2 Hz, 0.5H), 6.60 (t, J=5.3 Hz, 0.5H), 5.42 (d, J=9.7 Hz, 1H), 4.96 (d, J=6.6 Hz, 2H), 3.76 (t, J=9.1 Hz, 1H), 3.66-3.53 (m, 1H), 2.62-2.40 (m, 2H), 2.28-2.15 (m, 1H), 2.15-2.00 (m, 1H); ¹³C NMR (101 MHz, Methanol-d₄) δ 174.9, 167.2, 158.9, 140.2, 132.6, 131.1, 126.6, 126.6, 125.2, 118.1, 114.1, 68.8, 54.1, 48.2, 48.0, 47.8, 47.6, 47.3, 47.3, 47.1, 46.9, 46.0, 28.8, 23.1; ESI found [M+H]⁺ 526.1672.

Example 97: (S,Z)-amino(2-(3-(3-(trifluoromethyl)-4-((3-(4-(trifluoromethyl)phenyl)allyl)oxy)phenyl)-1,2,4-oxadiazol-5-yl)pyrrolidin-1-yl)methaniminium 2,2,2-trifluoroacetate (Compound 92A)

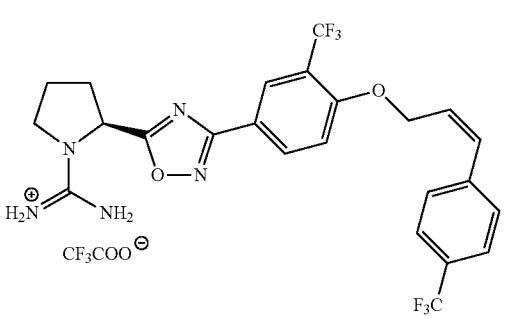

¹H NMR (400 MHz, Methanol-d₄) δ 8.30-8.17 (m, 2H), 7.77-7.66 (m, 2H), 7.58-7.45 (m, 2H), 7.25 (d, J=8.7 Hz, 1H), 6.86 (d, J=11.8 Hz, 1H), 6.12 (dt, J=11.8, 6.3 Hz, 1H), 5.44 (dd, J=7.9, 1.9 Hz, 1H), 5.01 (dd, J=6.3, 1.7 Hz, 2H), 3.77 (ddd, J=11.3, 8.7, 2.6 Hz, 1H), 3.61 (td, J=9.6, 7.2 Hz, 1H), 2.65-2.40 (m, 2H), 2.33-2.00 (m, 2H).

Example 98: (S,E)-2-(3-(3-(trifluoromethyl)-4-((4-(4-(trifluoromethyl)phenyl)but-3-en-1-yl)oxy)phenyl)-1,2,4-oxadiazol-5-yl)pyrrolidine-1-carboximidamide hydrochloride (Compound 91A)

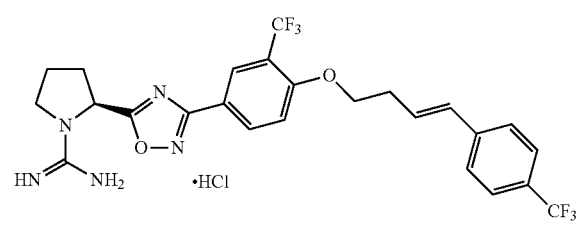 [SMILES: N=C(N)N1CCC[C@H]1c1nc(-c2ccc(OCC/C=C/c3ccc(C(F)(F)F)cc3)c(C(F)(F)F)c2)no1 ; Cl]

¹H NMR (400 MHz, Methanol-d₄) δ 8.30-8.14 (m, 2H), 7.55 (q, J=8.3 Hz, 4H), 7.37 (d, J=8.4 Hz, 1H), 6.64 (d, J=15.9 Hz, 1H), 6.57-6.46 (m, 1H), 5.49-5.37 (m, 1H), 4.33 (t, J=6.0 Hz, 2H), 3.84-3.49 (m, 2H), 2.77 (q, J=6.1 Hz, 2H), 2.54-2.48 (m, 2H), 2.31-1.95 (m, 2H); ¹³C NMR (101 MHz, cd₃od) δ 177.8, 167.1, 159.1, 155.6, 141.3, 132.6, 131.1, 131.1, 128.6, 128.6, 126.1, 125.0, 118.2, 113.6, 72.2, 71.0, 68.2, 68.2, 60.8, 55.1, 48.2, 48.0, 47.8, 47.7, 47.6, 47.4, 47.2, 47.0, 32.2, 32.2, 31.4, 26.7, 23.0, 18.0; Calc for $C_{25}H_{23}F_6N_5O_2$ [M+H]⁺: 539.1756, Found: 540.0.

Example 99: (S,E)-(2-(3-(4-((3,7-dimethylocta-2,6-dien-1-yl)oxy)-3-(trifluoromethyl)phenyl)-1,2,4-oxadiazol-5-yl)pyrrolidin-1-yl)(13-iodanylidene)methanamine hydrochloride (Compound 93A)

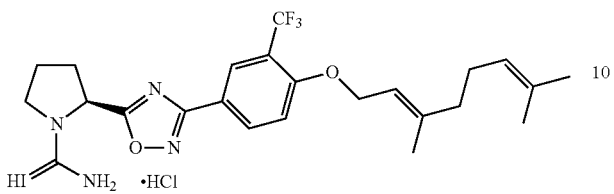

¹H NMR (400 MHz, Methanol-d₄) δ 8.25-8.17 (m, 1H), 8.15-8.12 (m, 1H), 8.09-8.03 (m, 1H), 7.31 (d, J=8.7 Hz, 0.4H), 7.07 (d, J=8.6 Hz, 0.6H), 5.51-5.45 (m, 0.4H), 5.44-5.38 (m, 0.6H), 4.81-4.75 (m, 1H), 3.82-3.66 (m, 1H), 3.63-3.54 (m, 1H), 3.27-3.14 (m, 1H), 2.61-2.39 (m, 2H), 2.29-1.99 (m, 3H), 1.79-1.75 (m, 1H), 1.67-1.59 (m, 1H), 1.57-1.44 (m, 3H), 1.39-1.26 (m, 2H).

Example 100: tert-butyl (S)-2-(3-(4-((4-propoxyphenyl)ethynyl)-3-(trifluoromethyl)phenyl)-1,2,4-oxadiazol-5-yl)pyrrolidine-1-carboxylate

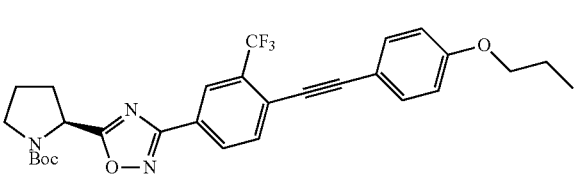 [SMILES: CCCOc1ccc(C#Cc2ccc(-c3noc([C@@H]4CCCN4C(=O)OC(C)(C)C)n3)cc2C(F)(F)F)cc1]

¹H NMR (400 MHz, Chloroform-d) δ 8.37 (d, J=1.6 Hz, 1H), 8.18 (d, J=8.2 Hz, 1H), 7.71 (t, J=8.2 Hz, 1H), 7.53-7.40 (m, 2H), 6.93-6.82 (m, 2H), 5.21-5.01 (m, 1H), 3.93 (t, J=6.6 Hz, 2H), 3.71 (q, J=5.9 Hz, 1H), 3.41-3.59 (m, 1H), 2.49-2.27 (m, 1H), 2.21-1.95 (m, 3H), 1.76-1.87 (m, 2H), 1.45 (s, 3H), 1.26 (s, 7H), 1.03 (t, J=7.4 Hz, 3H); ¹³C NMR (101 MHz, cdcl₃) δ 167.1, 160.0, 133.9, 133.8, 133.4, 129.9, 124.9, 114.6, 114.1, 84.0, 80.6, 69.6, 53.8, 46.6, 46.3, 32.4, 31.4, 29.7, 28.3, 28.1, 24.4, 23.7, 22.5, 10.5.

Example 101: tert-butyl (S)-2-(3-(4-(4-propoxyphenethyl)-3-(trifluoromethyl)phenyl)-1,2,4-oxadiazol-5-yl)pyrrolidine-1-carboxylate

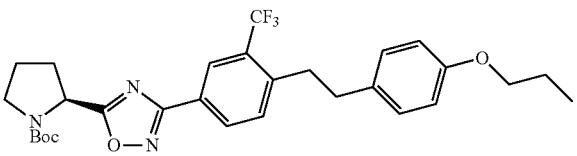

¹H NMR (500 MHz, Chloroform-d) δ 8.35 (s, 1H), 8.13 (t, J=8.3 Hz, 1H), 7.41-7.32 (m, 1H), 7.15-7.07 (m, 2H), 6.87-6.81 (m, 2H), 5.25-5.04 (m, 1H), 3.91 (t, J=6.6 Hz, 2H), 3.79-3.65 (m, 1H), 3.64-3.45 (m, 1H), 3.10 (t, J=8.3 Hz, 2H), 2.87 (t, J=8.3 Hz, 2H), 2.48-2.31 (m, 1H), 2.24-2.09 (m, 2H), 2.05-1.95 (m, 1H), 1.81 (q, J=6.9 Hz, 2H), 1.47 (s, 3H), 1.31 (s, 6H), 1.04 (t, J=7.4 Hz, 3H); ¹³C NMR (101 MHz, cdcl₃) δ 181.0, 167.4, 157.6, 143.8, 132.8, 132.0, 131.9, 130.3, 129.3, 125.2, 114.5, 80.5, 77.2, 69.5, 53.8, 46.6, 46.3, 36.9, 35.3, 32.4, 31.5, 31.2, 29.7, 28.3, 28.1, 24.4, 23.7, 22.6, 14.1, 10.5.

Example 102: tert-butyl (S,Z)-(((tert-butoxycarbonyl)amino)(2-(3-(4-(4-propoxyphenethyl)-3-(trifluoromethyl)phenyl)-1,2,4-oxadiazol-5-yl)pyrrolidin-1-yl)methylene)carbamate

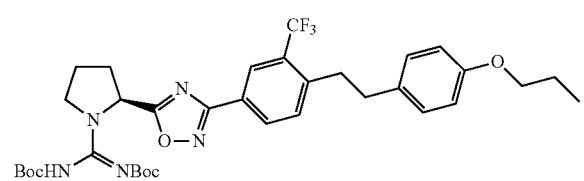

¹H NMR (500 MHz, Chloroform-d) δ 8.34 (d, J=1.7 Hz, 1H), 8.13 (dd, J=8.1, 1.7 Hz, 1H), 7.36 (d, J=8.0 Hz, 1H), 7.14-7.07 (m, 2H), 6.88-6.78 (m, 2H), 5.71 (s, 1H), 3.91 (t, J=6.6 Hz, 4H), 3.10 (dd, J=9.8, 6.6 Hz, 2H), 2.92-2.83 (m, 2H), 2.49 (s, 1H), 2.23 (s, 2H), 2.02-2.15 (m, 1H), f1.85-1.75 (m, 2H) i, 1.46 (s, 18H), 1.04 (t, J=7.4 Hz, 3H)

Example 103: (S)-2-(3-(4-(4-propoxyphenethyl)-3-(trifluoromethyl)phenyl)-1,2,4-oxadiazol-5-yl)pyrrolidine-1-carboximidamide hydrochloride (Compound 94A)

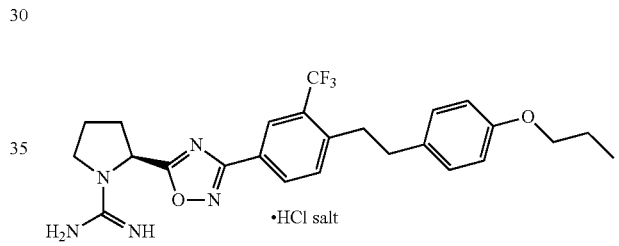

¹H NMR (400 MHz, Methanol-d₄) δ 8.29 (d, J=1.6 Hz, 1H), 8.17 (dd, J=8.0, 1.7 Hz, 1H), 7.54 (d, J=8.0 Hz, 1H), 7.41 (s, 1H), 7.09 (d, J=8.5 Hz, 2H), 6.82 (d, J=8.5 Hz, 2H), 5.46 (d, J=7.3 Hz, 1H), 3.89 (t, J=6.5 Hz, 2H), 3.78 (t, J=8.8 Hz, 1H), 3.62 (q, J=9.0 Hz, 1H), 3.15-3.05 (m, 2H), 2.91-2.82 (m, 2H), 2.63-2.43 (m, 2H), 2.31-2.05 (m, 2H), 1.81-1.71 (m, 2H), 1.03 (t, J=7.4 Hz, 3H); ¹³C NMR (101 MHz, cd₃od) δ 178.1, 167.2, 157.7, 155.7, 144.2, 132.6, 130.2, 129.0, 128.6, 125.6, 124.4, 124.4, 124.3, 122.9, 114.1, 69.1, 55.1, 48.2, 48.0, 47.8, 47.6, 47.4, 47.1, 46.9, 36.5, 34.9, 31.3, 22.9, 22.3, 9.4.

Example 104: tert-butyl (S,E)-2-(4-(3-(trifluoromethyl)-4-((4-(4-(trifluoromethyl)phenyl)but-3-en-1-yl)oxy)phenyl)oxazol-2-yl)pyrrolidine-1-carboxylate

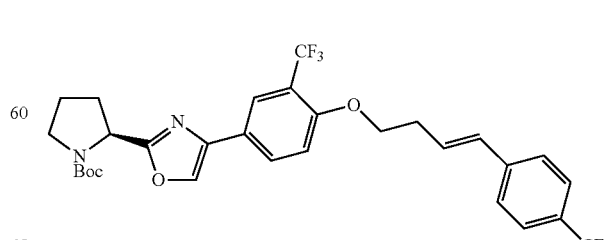

¹H NMR (400 MHz, Chloroform-d) δ 8.30 (d, J=2.2 Hz, 1H), 8.23-8.17 (m, 1H), 7.55 (d, J=8.2 Hz, 2H), 7.44 (d, J=8.1 Hz, 2H), 7.08 (t, J=9.1 Hz, 1H), 6.58 (d, J=15.9 Hz, 1H), 6.43 (dt, J=15.9, 6.9 Hz, 1H), 5.23-5.14 (m, 1H), 5.06 (dd, J=8.2, 3.7 Hz, 1H), 4.24 (t, J=6.1 Hz, 2H), 3.77-3.44 (m, 3H), 2.78 (q, J=6.4 Hz, 2H), 2.31-2.45 (m, 1H), 2.04-2.21 (m, 2H), 2.06-1.92 (m, 1H), 1.46 (s, 3H), 1.29 (s, 6H); ¹³C NMR (101 MHz, cdcl₃) δ 199.7, 180.9, 174.5, 167.2, 167.2, 158.8, 153.5, 140.7, 132.4, 131.6, 128.2, 126.8, 126.2, 125.5, 125.4, 125.4, 122.8, 118.9, 118.9, 112.9, 80.5, 77.2, 77.0, 68.2, 53.8, 46.6, 46.3, 32.6, 32.4, 31.5, 28.3, 28.1, 24.4, 23.7.

Example 105: tert-butyl ((E)-((tert-butoxycarbonyl)amino)((S)-2-(4-(3-(trifluoromethyl)-4-(((E)-4-(4-(trifluoromethyl)phenyl)but-3-en-1-yl)oxy)phenyl)oxazol-2-yl)pyrrolidin-1-yl)methylene)carbamate (10)

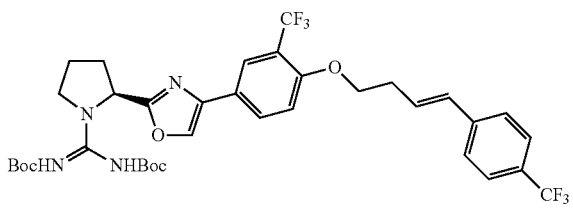

¹H NMR (400 MHz, Chloroform-d) δ 8.28 (d, J=2.1 Hz, 1H), 8.18 (dd, J=8.7, 2.2 Hz, 1H), 7.53 (d, J=8.2 Hz, 2H), 7.43 (d, J=8.1 Hz, 2H), 7.06 (d, J=8.7 Hz, 1H), 6.58 (s, 0H), 6.54 (s, 1H), 6.42 (dt, J=15.9, 6.9 Hz, 1H), 5.58 (dd, J=7.8, 4.6 Hz, 1H), 4.23 (t, J=6.2 Hz, 2H), 3.88 (dt, J=11.5, 7.0 Hz, 1H), 3.83-3.70 (m, 1H), 2.77 (qd, J=6.3, 1.3 Hz, 2H), 2.42 (ddd, J=15.7, 10.4, 6.8 Hz, 2H), 2.24-2.12 (m, 2H), 2.07-1.96 (m, 2H); ¹³C NMR (101 MHz, cdcl₃) δ 179.2, 167.1, 158.8, 140.7, 140.7, 132.5, 131.6, 129.2, 128.9, 128.2, 126.8, 126.8, 126.7, 126.2, 125.6, 125.5, 125.5, 125.4, 125.4, 124.6, 121.8, 119.6, 119.3, 118.9, 112.8, 77.2, 68.2, 55.3, 49.5, 32.6, 29.7, 28.1, 28.1, 28.0, 24.0, 14.1.

Example 106: 4-(3-cyclohexylpropoxy)-3-(trifluoromethyl)benzonitrile

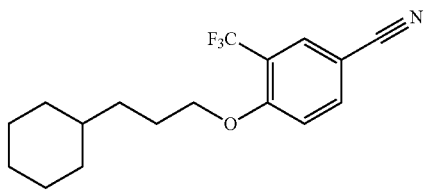 [SMILES: N#Cc1ccc(OCCCC2CCCCC2)c(C(F)(F)F)c1]

Synthesized by General Procedure A. 89% yield, white solid; ¹H NMR (600 MHz, Chloroform-d) δ 7.85 (d, J=2.1 Hz, 1H), 7.77 (dd, J=8.7, 2.1 Hz, 1H), 7.05 (d, J=8.7 Hz, 1H), 4.09 (t, J=6.4 Hz, 2H), 1.89-1.81 (m, 2H), 1.76-1.61 (m, 5H), 1.39-1.09 (m, 6H), 0.99-0.83 (m, 2H).

Example 107: tert-butyl (2S,3S)-2-(3-(4-(3-cyclohexylpropoxy)-3-(trifluoromethyl)phenyl)-1,2,4-oxadiazol-5-yl)-3-hydroxypyrrolidine-1-carboxylate

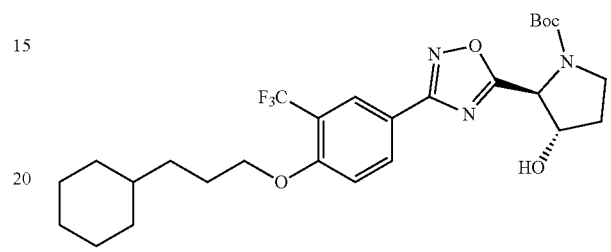

Synthesized by General Procedures B and C. 79% yield, white solid; ¹H NMR (600 MHz, Chloroform-d) δ 8.29-8.24 (m, 1H), 8.20-8.13 (m, 1H), 7.09-7.01 (m, 1H), 5.13-4.93 (m, 1H), 4.60-4.54 (m, 1H), 4.15-4.05 (m, 2H), 3.82-3.67 (m, 2H), 2.48 (s, 0H), 2.40-2.28 (m, 1H), 2.08-2.01 (m, 1H), 1.89-1.81 (m, 2H), 1.77-1.59 (m, 6H), 1.47 (s, 3H), 1.40-1.33 (m, 2H), 1.32-1.10 (m, 10H), 0.97-0.85 (m, 2H).

Example 108: tert-butyl ((E)-((tert-butoxycarbonyl)imino)((2S,3S)-2-(3-(4-(3-cyclohexylpropoxy)-3-(trifluoromethyl)phenyl)-1,2,4-oxadiazol-5-yl)-3-hydroxypyrrolidin-1-yl)methyl)carbamate

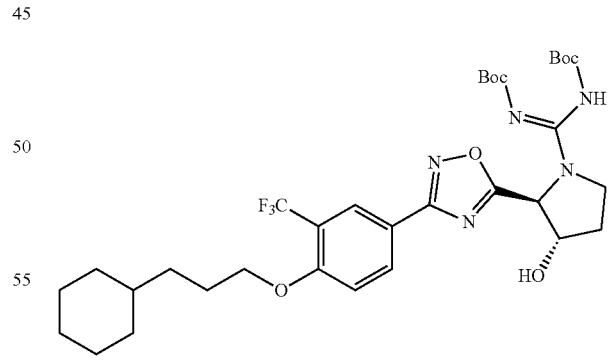

Synthesized by General Procedure D. 31% yield, white solid; ¹H NMR (600 MHz, Chloroform-d) δ 8.26 (d, J=2.1 Hz, 1H), 8.16 (dd, J=8.7, 2.2 Hz, 1H), 7.05 (d, J=8.7 Hz, 1H), 5.61 (s, 1H), 4.73-4.68 (m, 1H), 4.13-4.05 (m, 3H), 3.98-3.91 (m, 1H), 2.39-2.30 (m, 1H), 2.19-2.11 (m, 1H), 1.89-1.81 (m, 2H), 1.77-1.66 (m, 4H), 1.68-1.62 (m, 1H), 1.47 (s, 18H), 1.40-1.33 (m, 2H), 1.31-1.12 (m, 5H), 0.97-0.87 (m, 2H).

Example 109: amino((2S,3S)-2-(3-(4-(3-cyclohexylpropoxy)-3-(trifluoromethyl)phenyl)-1,2,4-oxadiazol-5-yl)-3-hydroxypyrrolidin-1-yl)methaniminium chloride (Compound 95A)

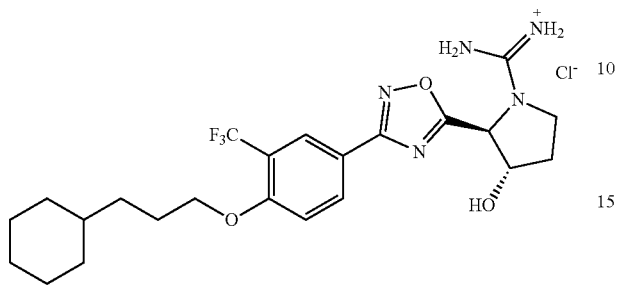

Synthesized by General Procedure E. 84% yield, white solid; ¹H NMR (600 MHz, Methanol-d₄) δ 8.28-8.19 (m, 2H), 7.32 (d, J=8.7 Hz, 1H), 5.25 (t, J=1.0 Hz, 1H), 4.81-4.76 (m, 1H), 4.16 (t, J=6.2 Hz, 2H), 3.89-3.78 (m, 2H), 2.28-2.14 (m, 2H), 1.84 (ddt, J=10.1, 8.2, 6.1 Hz, 2H), 1.80-1.62 (m, 6H), 1.44-1.25 (m, 6H), 0.99-0.90 (m, 2H); ¹³C NMR (151 MHz, cd₃od) δ 176.97, 168.69, 160.92, 157.58, 133.97, 127.12, 127.08, 125.61, 123.80, 120.38, 120.17, 119.23, 114.85, 75.99, 70.67, 64.80, 47.42, 38.58, 34.66, 34.46, 32.48, 27.75, 27.42, 27.40; HRMS (ESI+): Calc'd for $C_{23}H_{31}F_3N_5O_3$ [M+H]: 482.2379, Found: 482.2369.

Example 110: 4-(cyclohexylmethoxy)-3-(trifluoromethyl)benzonitrile

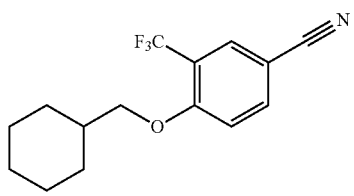 [SMILES: N#Cc1ccc(OCC2CCCCC2)c(C(F)(F)F)c1]

Synthesized by General Procedure A. 90% yield, white solid; ¹H NMR (600 MHz, Chloroform-d) δ 7.85 (d, J=2.1 Hz, 1H), 7.77 (dd, J=8.7, 2.1 Hz, 1H), 7.04 (d, J=8.7 Hz, 1H), 3.90 (d, J=5.7 Hz, 2H), 1.91-1.67 (m, 6H), 1.36-1.05 (m, 5H).

Example 111: tert-butyl (2S,3S)-2-(3-(4-(cyclohexylmethoxy)-3-(trifluoromethyl)phenyl)-1,2,4-oxadiazol-5-yl)-3-hydroxypyrrolidine-1-carboxylate

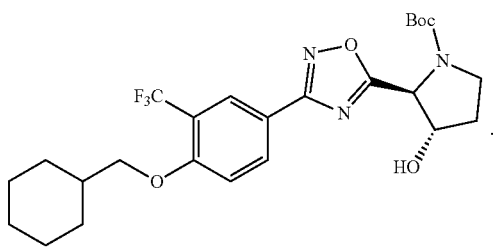 [SMILES: CC(C)(C)OC(=O)N1CC[C@H](O)[C@H]1c1nc(-c2ccc(OCC3CCCCC3)c(C(F)(F)F)c2)no1]

Synthesized by General Procedures B and C. 80% yield, white solid; ¹H NMR (600 MHz, Chloroform-d) δ 8.29-8.23 (m, 1H), 8.19-8.12 (m, 1H), 7.08-7.00 (m, 1H), 5.12-4.93 (m, 1H), 4.61-4.54 (m, 1H), 3.92-3.87 (m, 2H), 3.83-3.67 (m, 2H), 2.41-2.27 (m, 2H), 2.09-2.01 (m, 1H), 1.90-1.81 (m, 3H), 1.82-1.68 (m, 3H), 1.47 (s, 3H), 1.37-1.16 (m, 9H), 1.16-1.06 (m, 2H).

Example 112: tert-butyl ((E)-((tert-butoxycarbonyl)imino)((2S,3S)-2-(3-(4-(cyclohexylmethoxy)-3-(trifluoromethyl)phenyl)-1,2,4-oxadiazol-5-yl)-3-hydroxypyrrolidin-1-yl)methyl)carbamate

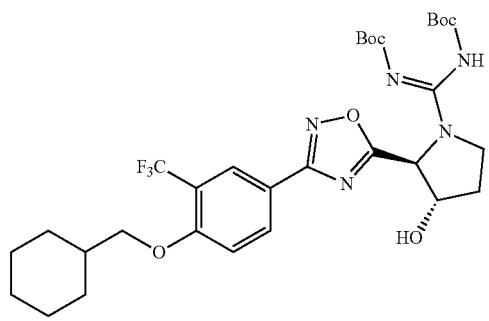 [SMILES: CC(C)(C)OC(=O)/N=C(\NC(=O)OC(C)(C)C)N1CC[C@H](O)[C@H]1c1nc(-c2ccc(OCC3CCCCC3)c(C(F)(F)F)c2)no1]

Synthesized by General Procedure D. 38% yield, white solid; ¹H NMR (600 MHz, Chloroform-d) δ 8.25 (d, J=2.1 Hz, 1H), 8.16 (dd, J=8.7, 2.2 Hz, 1H), 7.04 (d, J=8.8 Hz, 1H), 5.63-5.59 (m, 1H), 4.73-4.68 (m, 1H), 4.13-4.05 (m, 1H), 3.97-3.88 (m, 3H), 2.39-2.30 (m, 1H), 2.20-2.11 (m, 1H), 1.91-1.83 (m, 3H), 1.82-1.74 (m, 2H), 1.75-1.68 (m, 1H), 1.47 (s, 18H), 1.37-1.23 (m, 3H), 1.25-1.17 (m, 1H), 1.16-1.07 (m, 2H).

Example 112: amino((2S,3S)-2-(3-(4-(cyclohexylmethoxy)-3-(trifluoromethyl)phenyl)-1,2,4-oxadiazol-5-yl)-3-hydroxypyrrolidin-1-yl)methaniminium chloride (Compound 96A)

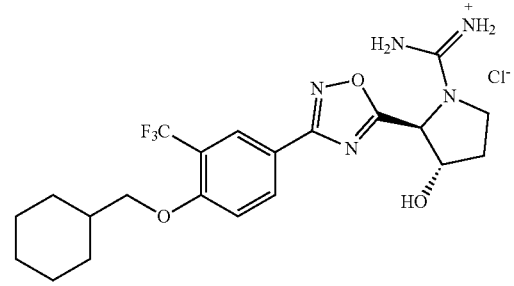 [SMILES: N=C(N)N1CC[C@H](O)[C@H]1c1nc(-c2ccc(OCC3CCCCC3)c(C(F)(F)F)c2)no1 ; [Cl-]]

Synthesized by General Procedure E. 92% yield, white solid; ¹H NMR (600 MHz, Methanol-d₄) δ 8.27-8.19 (m, 2H), 7.31 (d, J=8.7 Hz, 1H), 5.25 (t, J=1.0 Hz, 1H), 4.81-4.77 (m, 1H), 3.98 (d, J=5.9 Hz, 2H), 3.89-3.79 (m, 2H), 2.28-2.14 (m, 2H), 1.92-1.69 (m, 6H), 1.41-1.12 (m, 6H); ¹³C NMR (151 MHz, cd₃od) δ 176.97, 168.68, 160.98, 157.58, 134.00, 127.15, 127.10, 127.06, 127.03, 125.64, 123.83, 120.03, 119.17, 114.73, 75.99, 75.53, 68.12, 64.79, 47.42, 38.93, 32.48, 30.57, 27.51, 26.91; HRMS (ESI+): Calc'd for $C_{21}H_{27}F_3N_5O_3$ [M+H]: 454.2066, Found: 454.2060.

Synthesis of N-hydroxlated Compounds of Formula I

Scheme 15. General Synthetic Scheme.

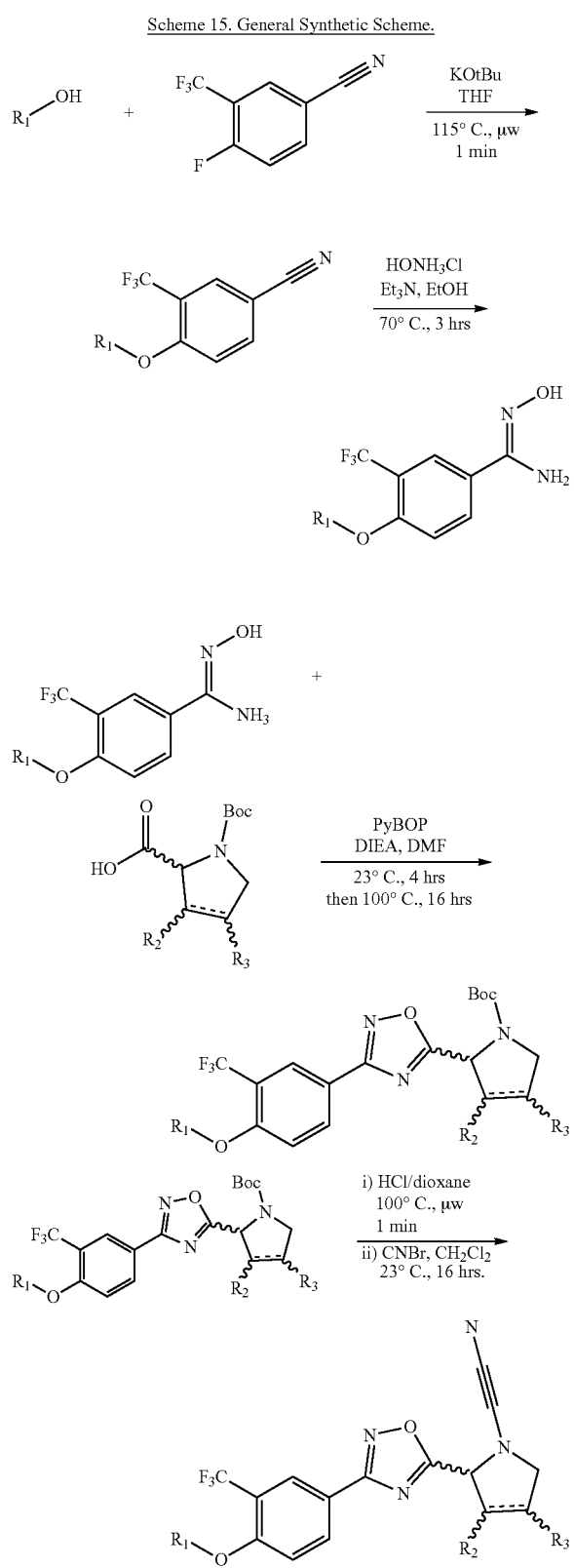

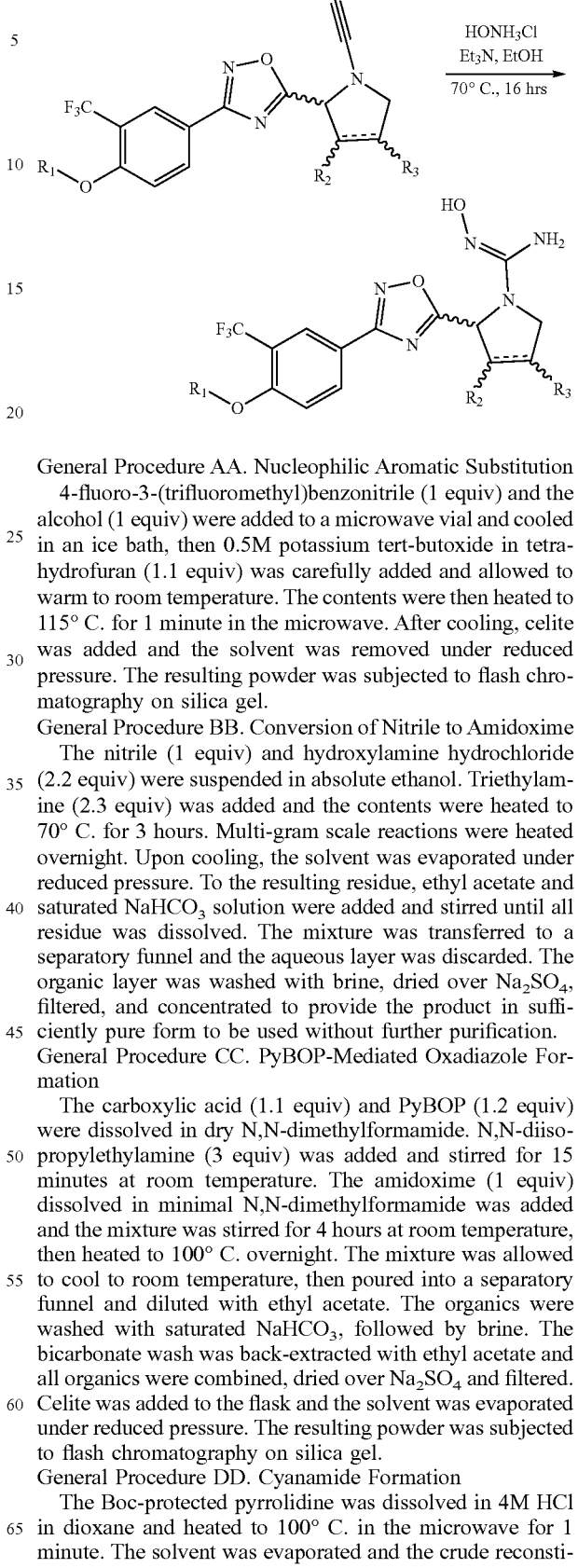

General Procedure AA. Nucleophilic Aromatic Substitution 4-fluoro-3-(trifluoromethyl)benzonitrile (1 equiv) and the alcohol (1 equiv) were added to a microwave vial and cooled in an ice bath, then 0.5M potassium tert-butoxide in tetrahydrofuran (1.1 equiv) was carefully added and allowed to warm to room temperature. The contents were then heated to 115° C. for 1 minute in the microwave. After cooling, celite was added and the solvent was removed under reduced pressure. The resulting powder was subjected to flash chromatography on silica gel.

General Procedure BB. Conversion of Nitrile to Amidoxime

The nitrile (1 equiv) and hydroxylamine hydrochloride (2.2 equiv) were suspended in absolute ethanol. Triethylamine (2.3 equiv) was added and the contents were heated to 70° C. for 3 hours. Multi-gram scale reactions were heated overnight. Upon cooling, the solvent was evaporated under reduced pressure. To the resulting residue, ethyl acetate and saturated $NaHCO_3$ solution were added and stirred until all residue was dissolved. The mixture was transferred to a separatory funnel and the aqueous layer was discarded. The organic layer was washed with brine, dried over $Na_2SO_4$, filtered, and concentrated to provide the product in sufficiently pure form to be used without further purification.

General Procedure CC. PyBOP-Mediated Oxadiazole Formation

The carboxylic acid (1.1 equiv) and PyBOP (1.2 equiv) were dissolved in dry N,N-dimethylformamide. N,N-diisopropylethylamine (3 equiv) was added and stirred for 15 minutes at room temperature. The amidoxime (1 equiv) dissolved in minimal N,N-dimethylformamide was added and the mixture was stirred for 4 hours at room temperature, then heated to 100° C. overnight. The mixture was allowed to cool to room temperature, then poured into a separatory funnel and diluted with ethyl acetate. The organics were washed with saturated $NaHCO_3$, followed by brine. The bicarbonate wash was back-extracted with ethyl acetate and all organics were combined, dried over $Na_2SO_4$ and filtered. Celite was added to the flask and the solvent was evaporated under reduced pressure. The resulting powder was subjected to flash chromatography on silica gel.

General Procedure DD. Cyanamide Formation

The Boc-protected pyrrolidine was dissolved in 4M HCl in dioxane and heated to 100° C. in the microwave for 1 minute. The solvent was evaporated and the crude reconstituted in dry dichloromethane. 3M Cyanogen bromide in dichloromethane (0.95 equiv) was added, followed by triethylamine (3 equiv) and the mixture was stirred at room temperature overnight. Saturated NaHCO₃ was carefully added, and the mixture was transferred to a seperatory funnel and diluted with ethyl acetate. The organic layer was washed with brine, dried over Na₂SO₄, and filtered. Celite was added and the solvent was evaporated under reduced pressure. The resulting powder was subjected to flash chromatography on silica gel.

General Procedure EE. Hydroxyguanidine Formation

The cyanamide (1 equiv) and hydroxylamine hydrochloride (2.2 equiv) were suspended in absolute ethanol. Triethylamine (2.3 equiv) was added and the mixture was stirred at 70° C. for 16 hours. Celite was added and the solvent was evaporated under reduced pressure. The resulting powder was subjected to flash chromatography on a Biotage KP—NH column.

4-(octyloxy)-3-(trifluoromethyl)benzonitrile

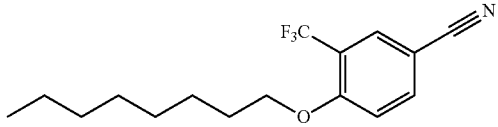 [SMILES: CCCCCCCCOc1ccc(C#N)cc1C(F)(F)F]

Synthesized by General Procedure AA. 96% yield, colorless oil; ¹H NMR (600 MHz, Chloroform-d) δ 7.85 (d, J=2.1 Hz, 1H), 7.77 (dd, J=8.7, 2.1 Hz, 1H), 7.05 (d, J=8.7 Hz, 1H), 4.11 (t, J=6.3 Hz, 2H), 1.88-1.80 (m, 2H), 1.47 (p, J=7.5, 7.1 Hz, 2H), 1.38-1.24 (m, 8H), 0.88 (t, J=6.8 Hz, 3H).

N-hydroxy-4-(octyloxy)-3-(trifluoromethyl)benzimidamide

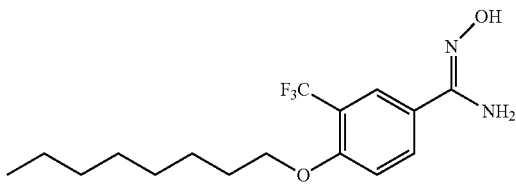 [SMILES: CCCCCCCCOc1ccc(/C(N)=N/O)cc1C(F)(F)F]

Synthesized by General Procedure BB. 100% yield, white solid; ¹H NMR (600 MHz, Chloroform-d) δ 9.25 (s, 1H), 7.82 (d, J=2.3 Hz, 1H), 7.72 (dd, J=8.7, 2.3 Hz, 1H), 6.95 (d, J=8.7 Hz, 1H), 4.98 (s, 2H), 4.03 (t, J=6.4 Hz, 2H), 1.81 (tt, J=12.4, 6.4 Hz, 2H), 1.46 (p, J=7.7, 7.3 Hz, 2H), 1.40-1.23 (m, 8H), 0.89 (t, J=6.8 Hz, 3H).

tert-butyl (2S,3S)-3-hydroxy-2-(3-(4-(octyloxy)-3-(trifluoromethyl)phenyl)-1,2,4-oxadiazol-5-yl)pyrrolidine-1-carboxylate

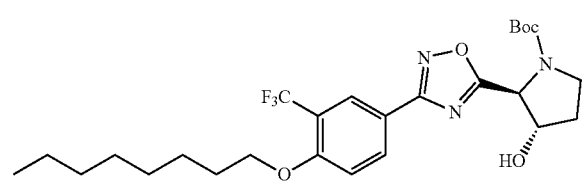 [SMILES: CCCCCCCCOc1ccc(-c2noc([C@@H]3[C@@H](O)CCN3C(=O)OC(C)(C)C)n2)cc1C(F)(F)F]

Synthesized by General Procedure CC. 87% yield, colorless oil; ¹H NMR (600 MHz, Chloroform-d) δ 8.29-8.24 (m, 1H), 8.20-8.12 (m, 1H), 7.09-7.02 (m, 1H), 5.12-4.93 (m, 1H), 4.61-4.54 (m, 1H), 4.10 (q, J=6.6 Hz, 2H), 3.83-3.69 (m, 2H), 2.40-2.28 (m, 1H), 2.09-2.01 (m, 1H), 1.84 (p, J=6.7 Hz, 2H), 1.50-1.44 (m, 5H), 1.40-1.24 (m, 14H), 0.89 (t, J=7.0 Hz, 2H); MS (ESI+): Calcd for C₂₆H₃₇F₃N₃O₅ [M+H]: 528.3, Found: 528.4.

(2S,3S)-3-hydroxy-2-(3-(4-(octyloxy)-3-(trifluoromethyl)phenyl)-1,2,4-oxadiazol-5-yl)pyrrolidine-1-carbonitrile

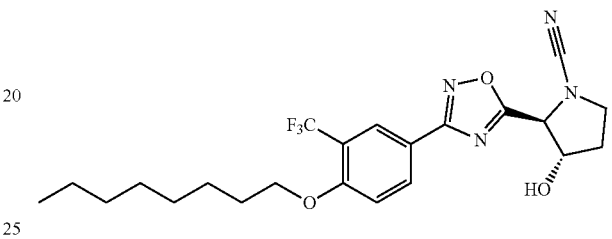

Synthesized by General Procedure DD. 31% yield, colorless oil; ¹H NMR (600 MHz, Chloroform-d) δ 8.27 (d, J=2.2 Hz, 1H), 8.18 (dd, J=8.7, 2.2 Hz, 1H), 7.07 (d, J=8.8 Hz, 1H), 4.94-4.91 (m, 1H), 4.76-4.72 (m, 1H), 4.12 (t, 6.4 Hz, 2H), 3.91-3.82 (m, 2H), 2.42-2.31 (m, 2H), 2.18-2.10 (m, 1H), 1.89-1.81 (m, 2H), 1.53-1.45 (m, 2H), 1.40-1.24 (m, 8H), 0.92-0.86 (m, 3H).

Example 113: (2S,3S)—N,3-dihydroxy-2-(3-(4-(octyloxy)-3-(trifluoromethyl)phenyl)-1,2,4-oxadiazol-5-yl)pyrrolidine-1-carboximidamide (Compound 6)

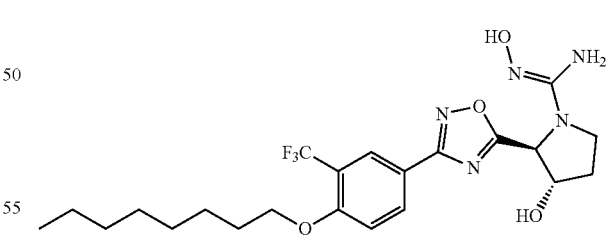

Synthesized by General Procedure EE. 44% yield, white solid; ¹H NMR (600 MHz, Chloroform-d) δ 8.30-8.24 (m, 1H), 8.16 (ddd, J=8.6, 4.0, 2.4 Hz, 1H), 7.09-7.02 (m, 1H), 4.78-4.66 (m, 1H), 4.51-4.48 (m, 1H), 4.14-4.06 (m, 2H), 3.39-3.25 (m, 1H), 2.96 (s, 2H), 2.27-2.17 (m, 1H), 1.96 (ddt, J=16.0, 7.6, 3.5 Hz, 1H), 1.83 (dtt, J=12.4, 6.3, 3.0 Hz, 2H), 1.48 (p, J=7.2 Hz, 2H), 1.40-1.24 (m, 10H), 0.89 (td, J=7.1, 1.3 Hz, 3H); MS (ESI+): Calc'd for C₂₂H₃₁F₃N₅O₄ [M+H]: 486.2, Found: 486.4.

tert-butyl (S)-2-(3-(4-(octyloxy)-3-(trifluoromethyl)phenyl)-1,2,4-oxadiazol-5-yl)pyrrolidine-1-carboxylate

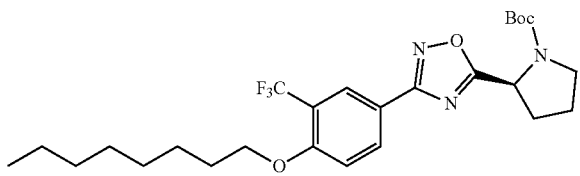 [SMILES: CCCCCCCCOc1ccc(-c2noc([C@@H]3CCCN3C(=O)OC(C)(C)C)n2)cc1C(F)(F)F]

Synthesized by General Procedures CC. 76% yield, yellow oil; $^1$H NMR (400 MHz, CDCl$_3$) δ 8.28 (s, 1H), 8.185 (d, J=8.7 Hz, 1H), 7.07 (d, J=8.6 Hz, 1H), 5.26-4.85 (m, 1H), 4.11 (t, J=6.2 Hz, 2H), 3.76-3.64 (m, 1H), 3.62-3.44 (m, 1H), 2.48-2.31 (m, 1H), 2.21-2.10 (m, 2H), 2.07-1.96 (m, 1H), 1.84 (p, J=6.7 Hz, 2H), 1.53-1.43 (m, 5H), 1.39-1.22 (m, 14H), 0.88 (t, J=6.5 Hz, 3H);

$^1$H NMR (101 MHz, CDCl$_3$) δ 180.9, 167.4, 159.4, 153.6, 132.5, 126.5, 123.6 (q, 1J$_{CF}$=275.9 Hz), 119.8, 118.6, 113.0, 80.6, 69.2, 10 53.9, 46.5, 32.5, 31.9, 31.6, 29.3, 29.0, 28.3, 25.9, 24.5, 23.8, 22.8, 14.2. $^{19}$F NMR (376 MHz, CDCl$_3$) δ −62.8 (d, J=15.1 Hz, 3F); HRMS (ESI+): Calcd for C$_{26}$H$_{36}$F$_3$N$_3$O$_4$Na[M+Na]: 534.2555, Found: 534.2506.

(S)-2-(3-(4-(octyloxy)-3-(trifluoromethyl)phenyl)-1,2,4-oxadiazol-5-yl)pyrrolidine-1-carbonitrile

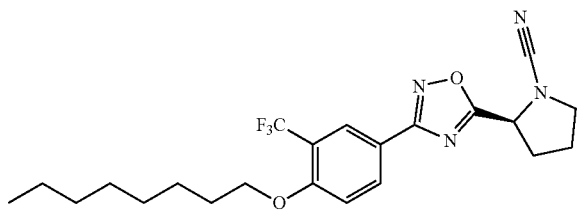 [SMILES: CCCCCCCCOc1ccc(-c2noc([C@@H]3CCCN3C#N)n2)cc1C(F)(F)F]

Synthesized by General Procedure DD. 68% yield, colorless oil; $^1$H NMR (600 MHz, Chloroform-d) δ 8.28 (d, J=2.1 Hz, 1H), 8.20 (dd, J=8.7, 2.2 Hz, 1H), 7.07 (d, J=8.7 Hz, 1H), 5.02 (dd, J=8.1, 3.9 Hz, 1H), 4.12 (t, J=6.4 Hz, 2H), 3.82-3.75 (m, 1H), 3.65-3.57 (m, 1H), 2.50-2.41 (m, 1H), 2.39-2.31 (m, 1H), 2.27-2.09 (m, 2H), 1.89-1.81 (m, 2H), 1.53-1.45 (m, 2H), 1.42-1.22 (m, 9H), 0.89 (d, J=7.0 Hz, 3H).

Example 114: (S)—N-hydroxy-2-(3-(4-(octyloxy)-3-(trifluoromethyl)phenyl)-1,2,4-oxadiazol-5-yl)pyrrolidine-1-carboximidamide (Compound 97)

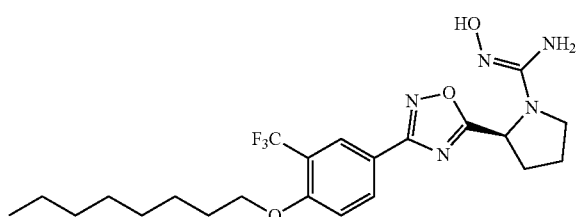

Synthesized by General Procedure EE. 37% yield, white solid; $^1$H NMR (600 MHz, Chloroform-d) δ 8.26 (d, J=2.1 Hz, 1H), 8.17 (dd, J=8.7, 2.2 Hz, 1H), 7.05 (d, J=8.7 Hz, 1H), 5.29 (d, J=8.1 Hz, 1H), 4.74 (s, 2H), 4.10 (t, J=6.4 Hz, 2H), 3.68-3.62 (m, 1H), 3.51 (q, J=8.1 Hz, 1H), 2.43-2.33 (m, 1H), 2.32-2.21 (m, 2H), 2.19-2.10 (m, 1H), 1.88-1.80 (m, 2H), 1.53-1.44 (m, 2H), 1.40-1.22 (m, 10H), 0.88 (t, J=7.0 Hz, 4H); MS (ESI+): Calc'd for C$_{22}$H$_{31}$F$_3$N$_5$O$_3$ [M+H]: 470.2, Found: 470.4.

Inhibition of Sphingosine Kinase Type 2

Four C57Bl/6 mice were dosed by oral gavage with 20 mg/kg of Compound 6 (Example 113). Blood was drawn immediately, at 2h, 6, and 24 h after administration, whole prepared for analysis, and the amount of sphingosine 1-phosphate (S1P) was quantified by LC-MS-MS, as shown in FIG. 1A. The results show a rise in S1P, which rise is indicative of inhibition of sphingosine kinase type 2 (SphK2).

Figure 1B:
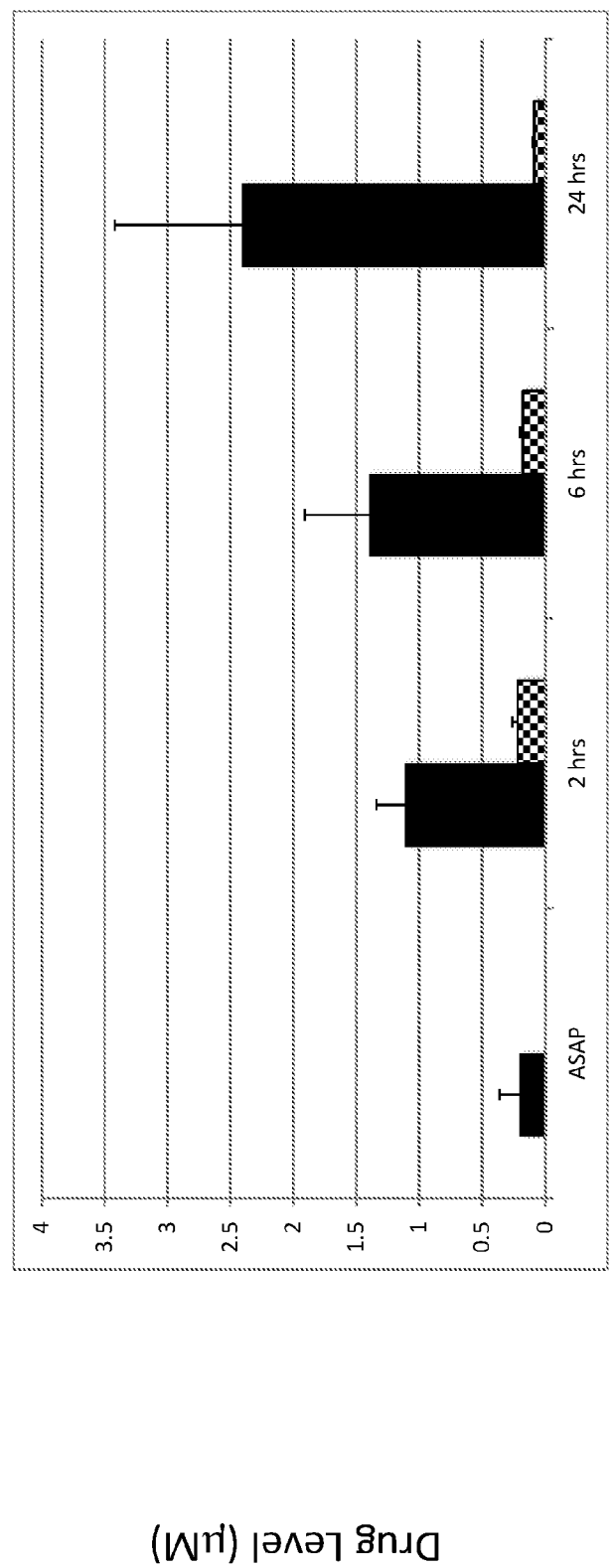

The amount of Compound 6 (red) and its reduced form Compound 6A (the active drug, blue) were detected by LC-MS-MS in the same blood samples. FIG. 1B shows that pro-drug Compound 6 gave rise to Compound 6A over the period of measurement.

Where descriptions of various embodiments use the term "comprising," those skilled in the art would understand that in some specific instances, an embodiment can be alternatively described using language "consisting essentially of" or "consisting of."

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

We claim:

1. A method of treating a disease in a patient suffering therefrom, wherein the disease is selected from a neoplastic disease, a disease involving excess vascular growth, an allergic disease, an inflammatory disease of the eye, an inflammatory disease of the kidney, a fibrotic disease, an autoimmune disease, acute lung injury, sepsis, capillary leak syndrome, pneumonia, ischemia reperfusion injury, acute kidney injury, age-related macular degeneration, diabetic retinopathy, atherosclerosis, and pulmonary arterial hypertension, the method comprising administering to the patient an effective amount of a compound according to formula (I)

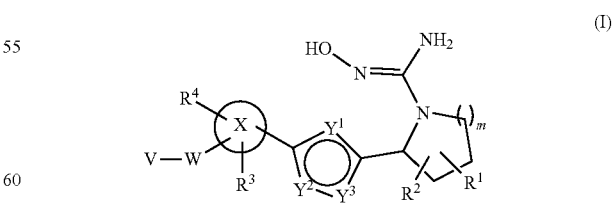

wherein
X is phenyl;
R$^1$ and R$^2$ are independently selected from the group consisting of H, OH, —(C$_1$-C$_6$)alkyl-OH, halo, NH$_2$, NOH, NHOH, and CN;

or R¹ and R², if bound to adjacent carbon atoms, in combination with the existing carbon-carbon bond represent a double bond between the adjacent carbon atoms;

R³ and R⁴ are independently selected from the group consisting of H, $(C_1-C_6)$alkyl, $(C_3-C_8)$cycloalkyl, $(C_1-C_6)$haloalkyl, CN, and halo;

wherein one of R³ and R⁴ is —CF₃;

m=1;

W is CH₂ or O;

V is selected from the group consisting of $(C_1-C_{10})$alkyl, $(C_2-C_{12})$alkenyl, —$(C_1-C_{10})$alkyl-$(C_6-C_{10})$aryl, —$(C_2-C_{12})$alkenyl-$(C_6-C_{10})$aryl, —$(C_1-C_{10})$alkyl-$(C_6-C_{10})$aryl-$(C_1-C_{10})$alkyl, —$(C_1-C_{10})$alkyl-$(C_3-C_8)$cycloalkyl, —$(C_1-C_{10})$alkyl-heterocyclyl containing from 1 to 3 ring heteroatoms selected from N, O, and S;

wherein any aryl is optionally fused to $(C_6-C_{10})$aryl, $(C_3-C_8)$cycloalkyl, or heterocyclyl containing from 1 to 3 ring heteroatoms selected from N, O, and S wherein any alkyl, alkenyl, cycloalkyl, heterocyclyl, or aryl is optionally substituted by 1-4 substituents independently selected from the group consisting of F, Cl, Br, $(C_1-C_6)$alkyl, —O—$(C_1-C_6)$alkyl, $(C_2-C_6)$alkenyl, $(C_1-C_6)$haloalkyl, $(C_6-C_{10})$aryl, and CN;

Y¹ is N;

Y² is N and Y³ is O, or Y² is O and Y³ is N;

or a pharmaceutically acceptable salt thereof.

2. The method according to claim 1, wherein R¹ and R² are independently selected from the group consisting of H, OH, CH₂OH, F, and Cl.

3. The method according to claim 1, where the compound is according to formula (II):

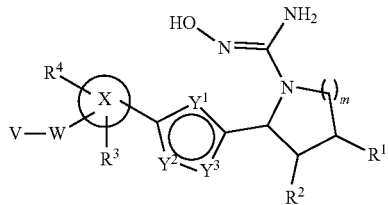

(II)

wherein:

R¹ and R² are H, or when m=1, one of R¹ and R² can be OH;

R³ and R⁴ are each independently H, $(C_1-C_4)$alkyl, cyclopropyl, $(C_1-C_2)$fluoroalkyl, cyano, or halo; wherein one of R³ and R⁴ is —CF₃;

m is 1;

X is phenyl, naphthyl, or indolyl;

W is O or CH₂;

V is $(C_5-C_{10})$alkyl;

or a pharmaceutically acceptable salt thereof.

4. The method according to claim 3, wherein R¹ and R² are both hydrogen.

5. The method according to claim 3 wherein R² is OH.

6. The method according to claim 1 wherein R³ is trifluoromethyl.

7. The method according to claim 1 wherein R⁴ is hydrogen.

8. The method according to claim 1, wherein the compound or a pharmaceutically acceptable sale thereof is one selected from the following table:

6

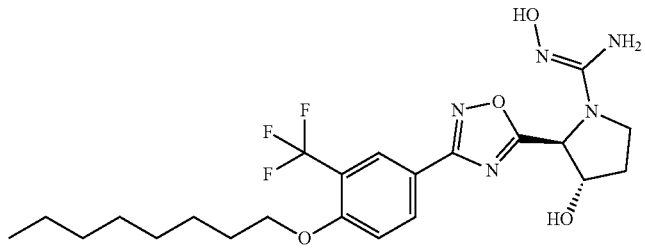 [SMILES: CCCCCCCCOc1ccc(-c2noc([C@@H]3[C@@H](O)CCN3/C(N)=N/O)n2)cc1C(F)(F)F]

8

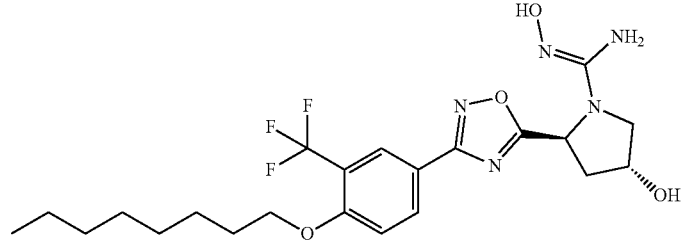 [SMILES: CCCCCCCCOc1ccc(-c2noc([C@@H]3C[C@@H](O)CN3/C(N)=N/O)n2)cc1C(F)(F)F]

9

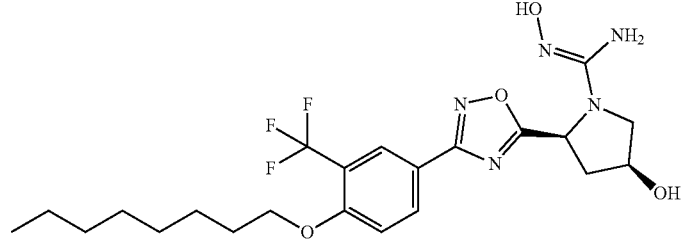 [SMILES: CCCCCCCCOc1ccc(-c2noc([C@@H]3C[C@H](O)CN3/C(N)=N/O)n2)cc1C(F)(F)F]

18 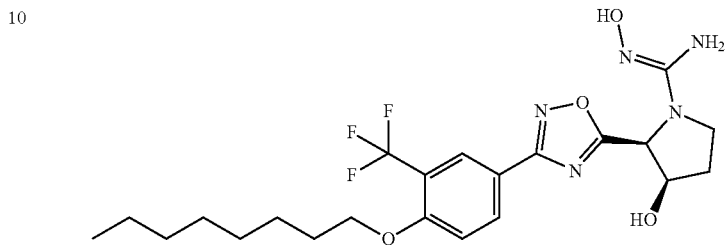
19 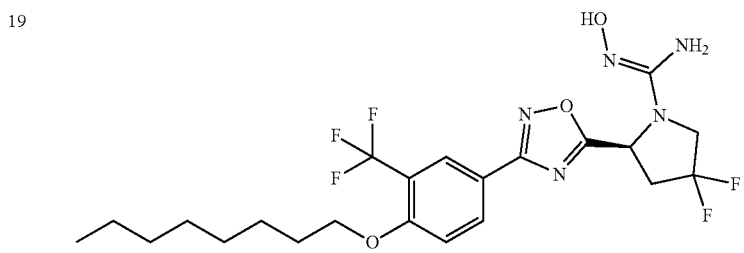
20 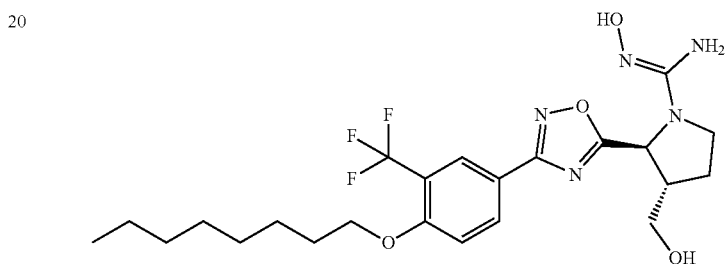
21 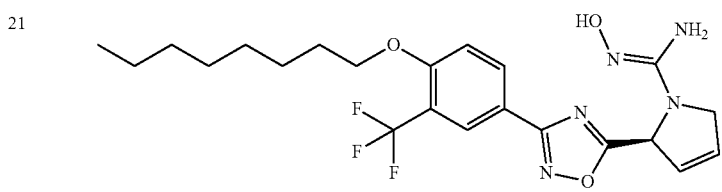
22 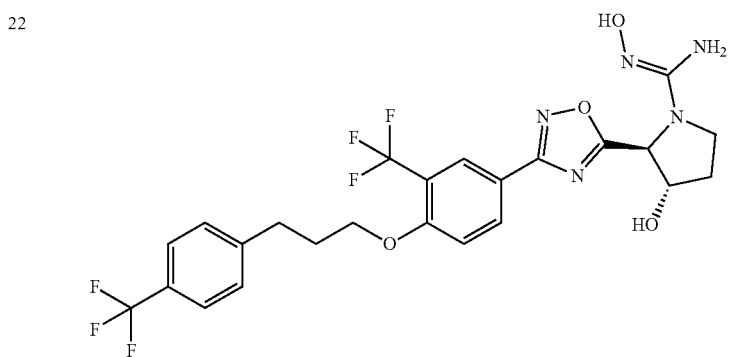
23 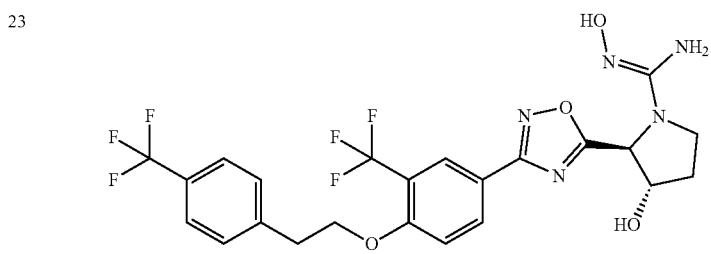

24
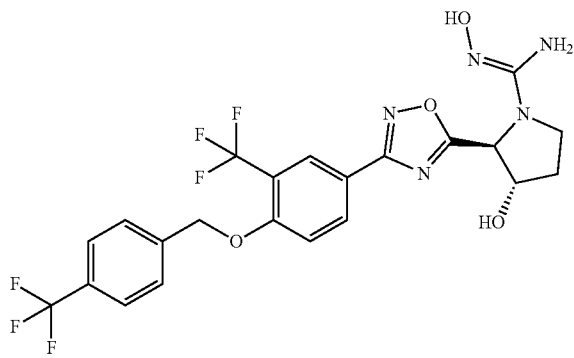 [SMILES: N/C(=N\O)N1CC[C@H](O)[C@H]1c1nc(-c2ccc(OCc3ccc(C(F)(F)F)cc3)c(C(F)(F)F)c2)no1]
25
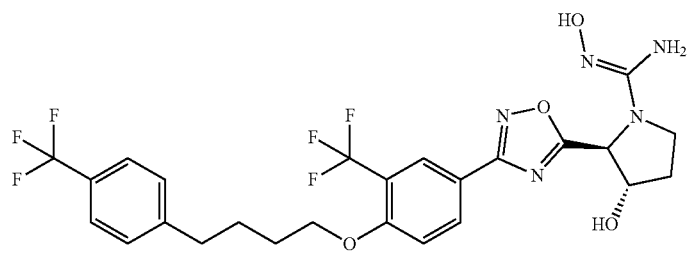 [SMILES: N/C(=N\O)N1CC[C@H](O)[C@H]1c1nc(-c2ccc(OCCCCc3ccc(C(F)(F)F)cc3)c(C(F)(F)F)c2)no1]
26
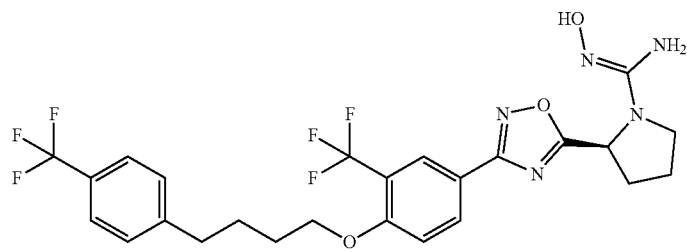 [SMILES: N/C(=N\O)N1CCC[C@H]1c1nc(-c2ccc(OCCCCc3ccc(C(F)(F)F)cc3)c(C(F)(F)F)c2)no1]
27
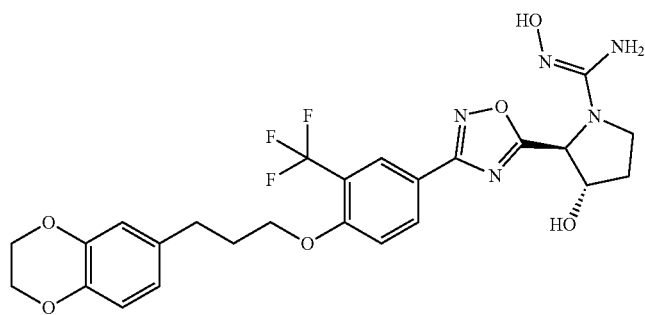 [SMILES: N/C(=N\O)N1CC[C@H](O)[C@H]1c1nc(-c2ccc(OCCCc3ccc4c(c3)OCCO4)c(C(F)(F)F)c2)no1]
28
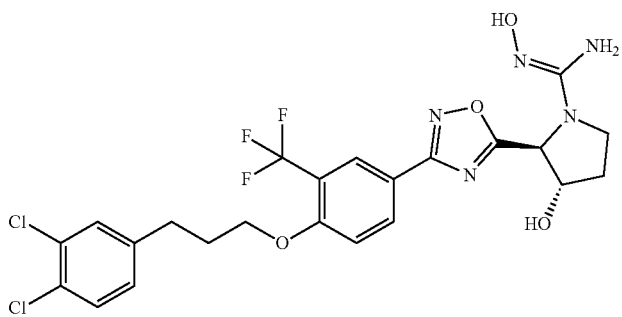 [SMILES: N/C(=N\O)N1CC[C@H](O)[C@H]1c1nc(-c2ccc(OCCCc3ccc(Cl)c(Cl)c3)c(C(F)(F)F)c2)no1]

29
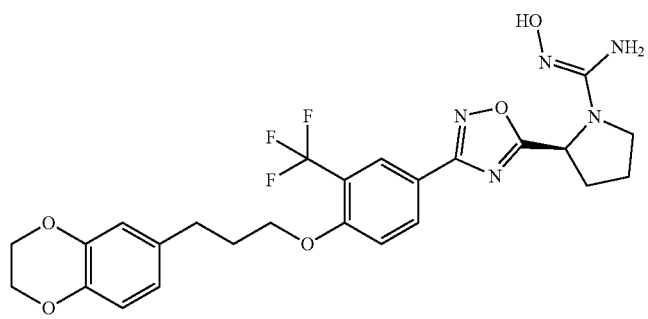 [SMILES: N/C(=N\O)N1CCC[C@H]1c1nc(-c2ccc(OCCCc3ccc4c(c3)OCCO4)c(C(F)(F)F)c2)no1]
30
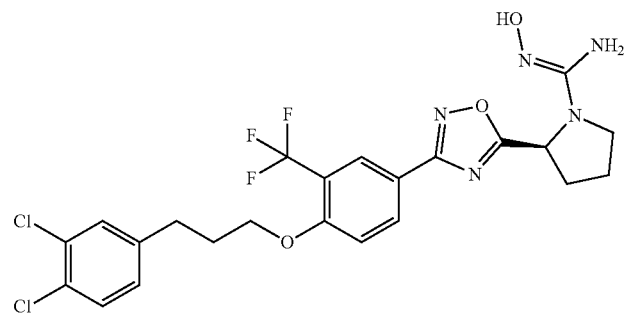 [SMILES: N/C(=N\O)N1CCC[C@H]1c1nc(-c2ccc(OCCCc3ccc(Cl)c(Cl)c3)c(C(F)(F)F)c2)no1]
31
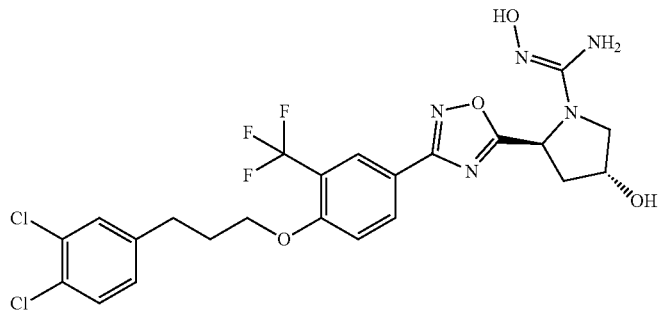 [SMILES: N/C(=N\O)N1C[C@H](O)C[C@H]1c1nc(-c2ccc(OCCCc3ccc(Cl)c(Cl)c3)c(C(F)(F)F)c2)no1]
32
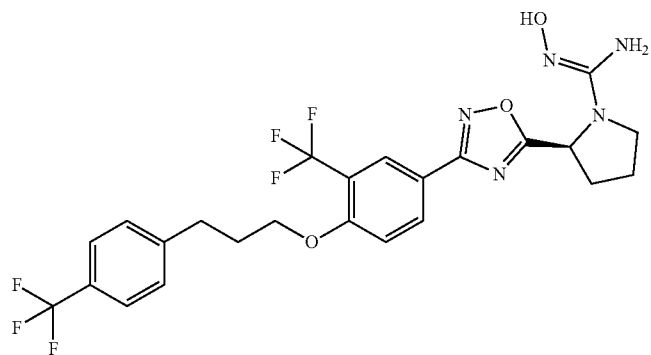 [SMILES: N/C(=N\O)N1CCC[C@H]1c1nc(-c2ccc(OCCCc3ccc(C(F)(F)F)cc3)c(C(F)(F)F)c2)no1]

33 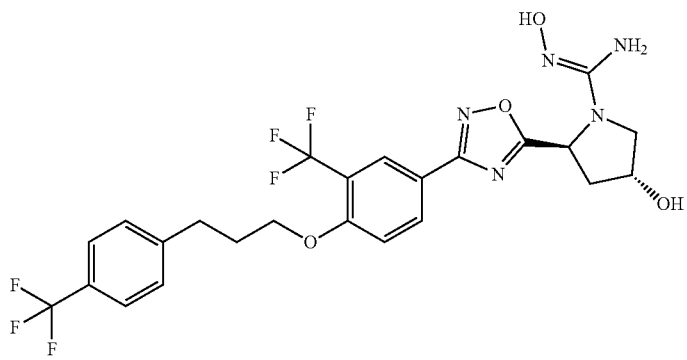 [SMILES: N/C(=N\O)N1C[C@H](O)C[C@H]1c1nc(-c2ccc(OCCCc3ccc(C(F)(F)F)cc3)c(C(F)(F)F)c2)no1]
34 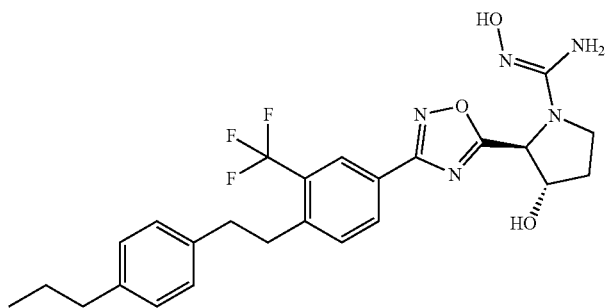 [SMILES: CCCc1ccc(CCc2ccc(-c3noc([C@@H]4[C@@H](O)CCN4/C(N)=N/O)n3)cc2C(F)(F)F)cc1]
35 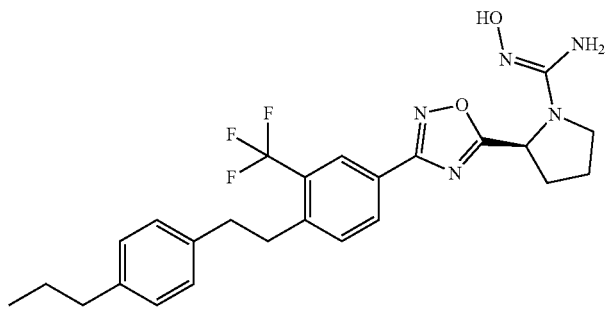 [SMILES: CCCc1ccc(CCc2ccc(-c3noc([C@@H]4CCCN4/C(N)=N/O)n3)cc2C(F)(F)F)cc1]
36 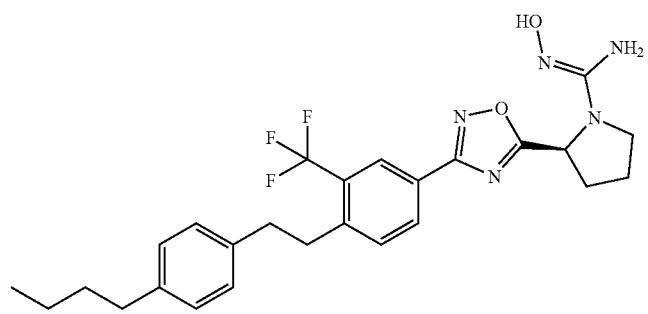 [SMILES: CCCCc1ccc(CCc2ccc(-c3noc([C@@H]4CCCN4/C(N)=N/O)n3)cc2C(F)(F)F)cc1]
37 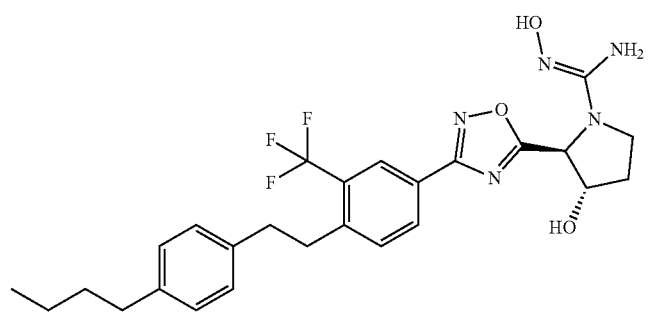 [SMILES: CCCCc1ccc(CCc2ccc(-c3noc([C@@H]4[C@@H](O)CCN4/C(N)=N/O)n3)cc2C(F)(F)F)cc1]

-continued
38 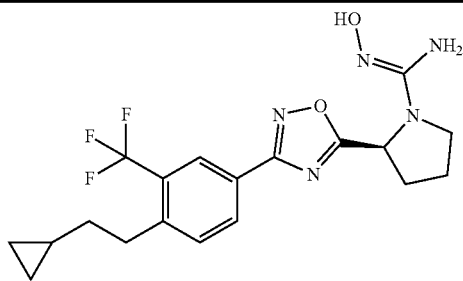
39 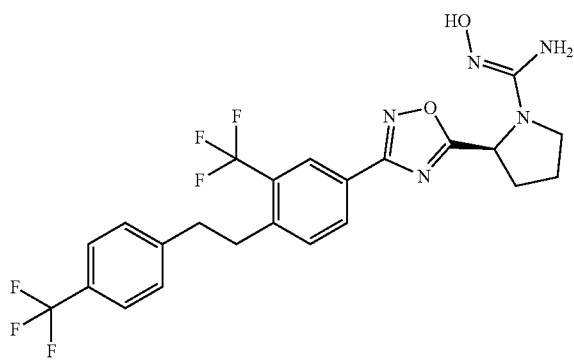 [SMILES: N/C(=N\O)N1CCC[C@H]1c1nc(-c2ccc(CCc3ccc(C(F)(F)F)cc3)c(C(F)(F)F)c2)no1]
40 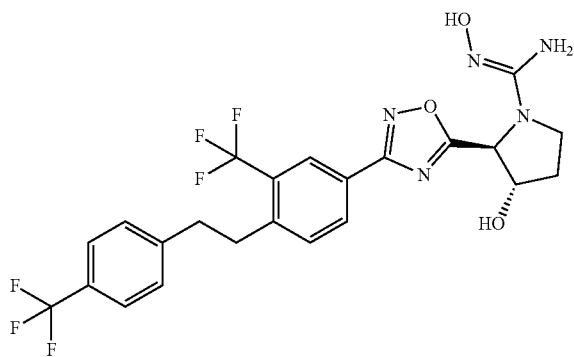
41 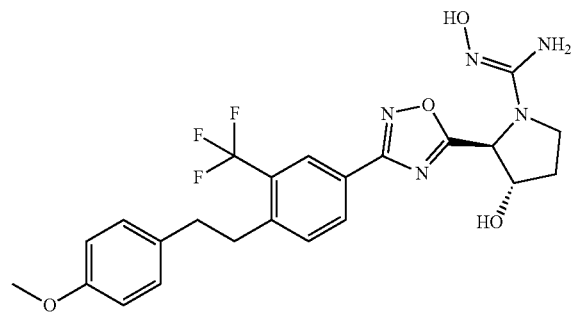 [SMILES: COc1ccc(CCc2ccc(-c3noc([C@@H]4[C@@H](O)CCN4/C(N)=N/O)n3)cc2C(F)(F)F)cc1]
42 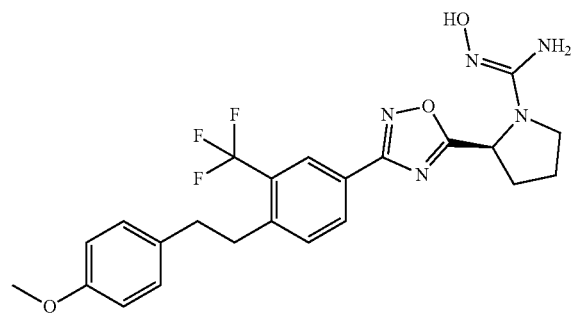 [SMILES: COc1ccc(CCc2ccc(-c3noc([C@@H]4CCCN4/C(N)=N/O)n3)cc2C(F)(F)F)cc1]

43
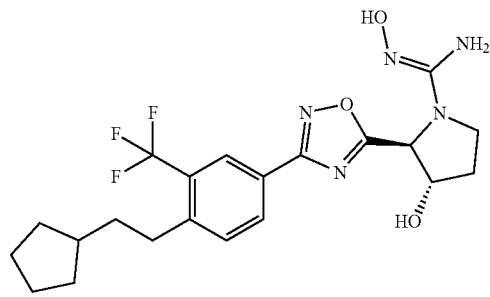 [SMILES: N/C(=N\O)N1CC[C@H](O)[C@H]1c1nc(-c2ccc(CCC3CCCC3)c(C(F)(F)F)c2)no1]
44
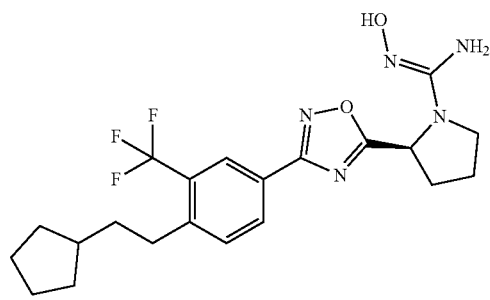 [SMILES: N/C(=N\O)N1CCC[C@H]1c1nc(-c2ccc(CCC3CCCC3)c(C(F)(F)F)c2)no1]
45
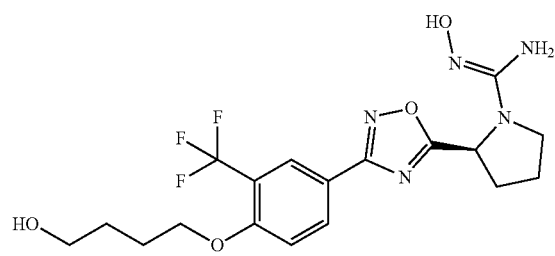 [SMILES: N/C(=N\O)N1CCC[C@H]1c1nc(-c2ccc(OCCCCO)c(C(F)(F)F)c2)no1]
46
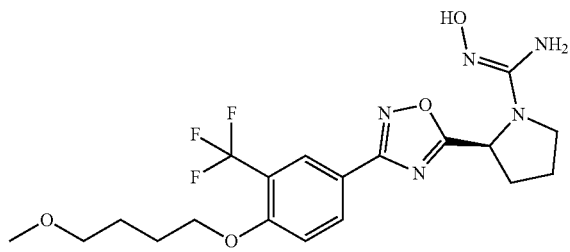 [SMILES: COCCCCOc1ccc(-c2noc([C@@H]3CCCN3/C(N)=N/O)n2)cc1C(F)(F)F]
47
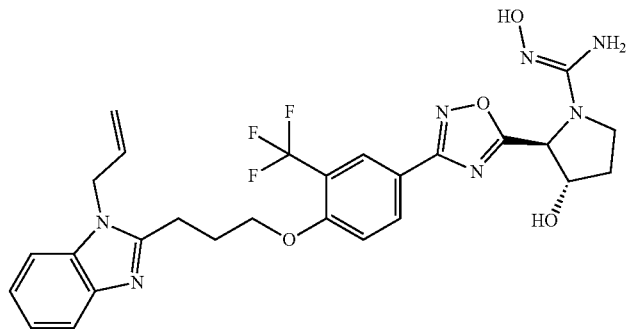 [SMILES: C=CCn1c(CCCOc2ccc(-c3noc([C@@H]4[C@@H](O)CCN4/C(N)=N/O)n3)cc2C(F)(F)F)nc2ccccc21]

| | |
|---|---|
| 48 | 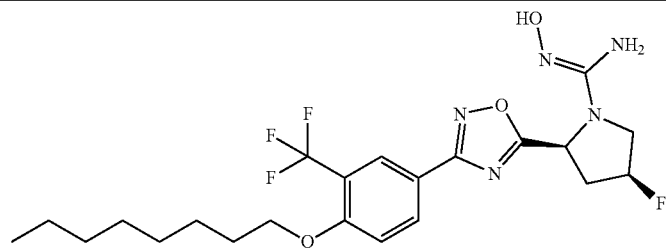 |
| 49 | 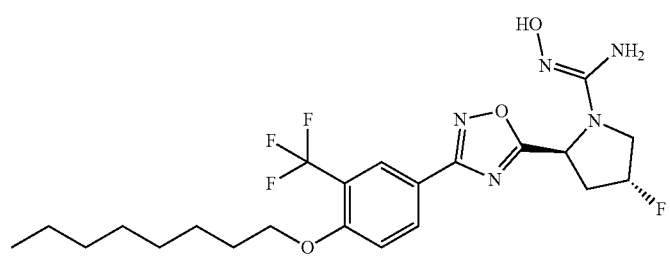 [SMILES: CCCCCCCCOc1ccc(-c2noc([C@@H]3C[C@@H](F)CN3/C(N)=N/O)n2)cc1C(F)(F)F] |
| 50 | 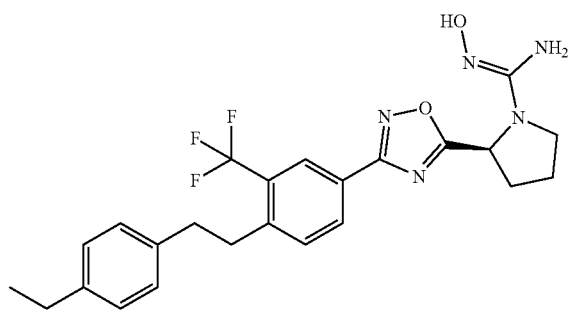 [SMILES: CCc1ccc(CCc2ccc(-c3noc([C@@H]4CCCN4/C(N)=N/O)n3)cc2C(F)(F)F)cc1] |
| 59 | 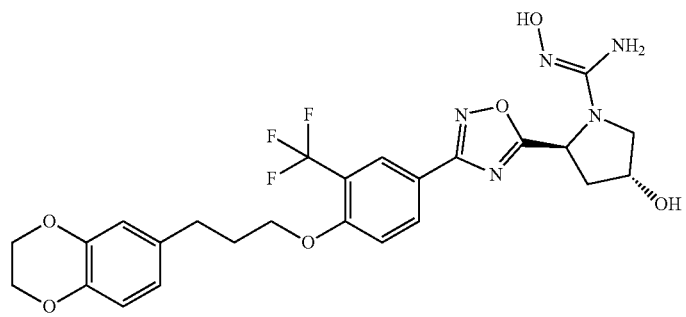 [SMILES: N/C(=N\O)N1C[C@H](O)C[C@H]1c1nc(-c2ccc(OCCCc3ccc4c(c3)OCCO4)c(C(F)(F)F)c2)no1] |
| 61 | 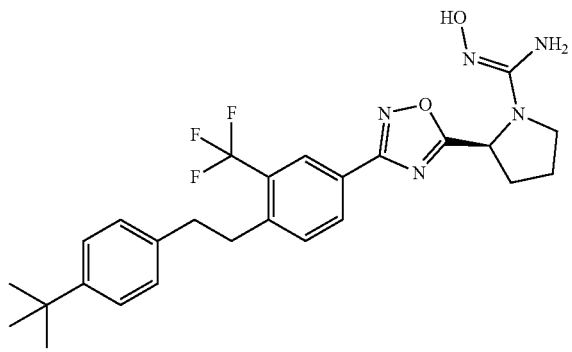 [SMILES: CC(C)(C)c1ccc(CCc2ccc(-c3noc([C@@H]4CCCN4/C(N)=N/O)n3)cc2C(F)(F)F)cc1] |

-continued
62
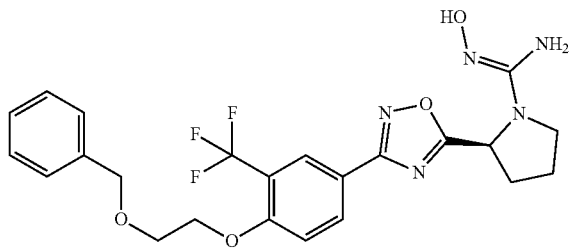 [SMILES: N/C(=N\O)N1CCC[C@H]1c1nc(-c2ccc(OCCOCc3ccccc3)c(C(F)(F)F)c2)no1]
63
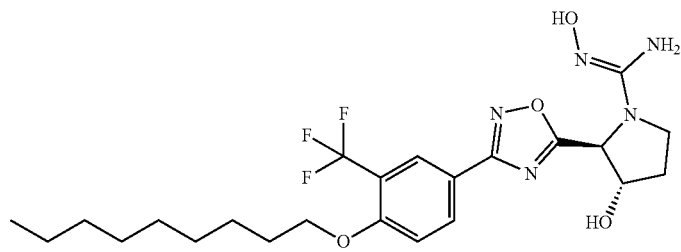 [SMILES: CCCCCCCCCOc1ccc(-c2noc([C@@H]3[C@@H](O)CCN3/C(N)=N/O)n2)cc1C(F)(F)F]
76
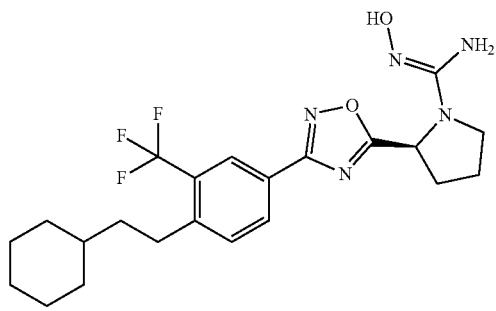 [SMILES: N/C(=N\O)N1CCC[C@H]1c1nc(-c2ccc(CCC3CCCCC3)c(C(F)(F)F)c2)no1]
77
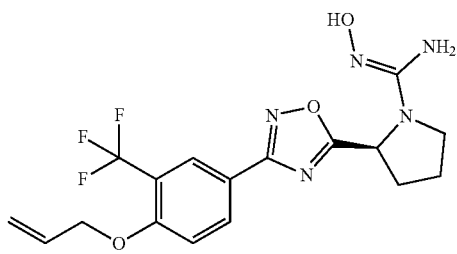 [SMILES: C=CCOc1ccc(-c2noc([C@@H]3CCCN3/C(N)=N/O)n2)cc1C(F)(F)F]
78
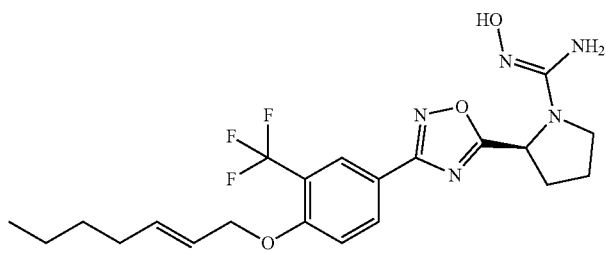
79
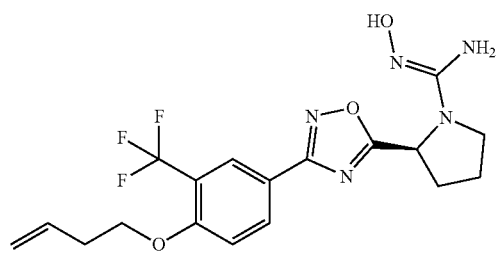 [SMILES: C=CCCOc1ccc(-c2noc([C@@H]3CCCN3/C(N)=N/O)n2)cc1C(F)(F)F]

| | |
|---|---|
| 80 | 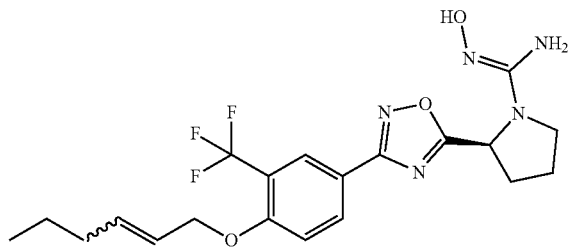 [SMILES: CCCC=CCOc1ccc(-c2noc([C@@H]3CCCN3/C(N)=N/O)n2)cc1C(F)(F)F] |
| 81 | 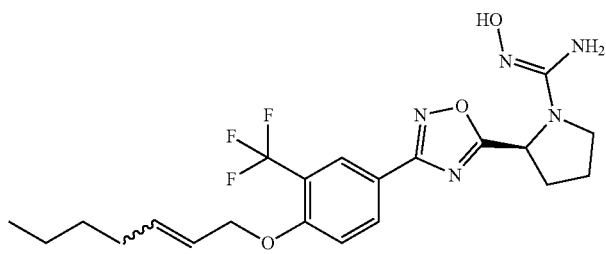 [SMILES: CCCCC=CCOc1ccc(-c2noc([C@@H]3CCCN3/C(N)=N/O)n2)cc1C(F)(F)F] |
| 82 | 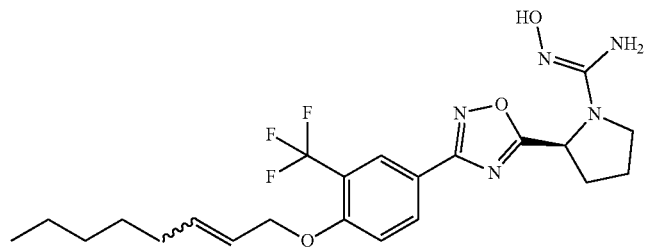 [SMILES: CCCCCC=CCOc1ccc(-c2noc([C@@H]3CCCN3/C(N)=N/O)n2)cc1C(F)(F)F] |
| 83 | 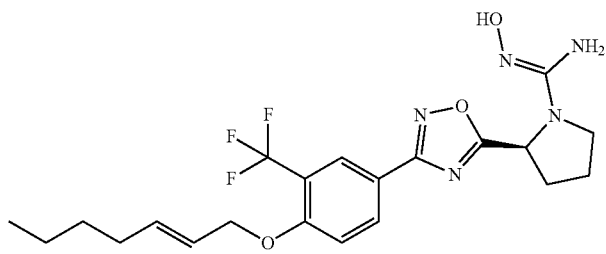 |
| 84 | 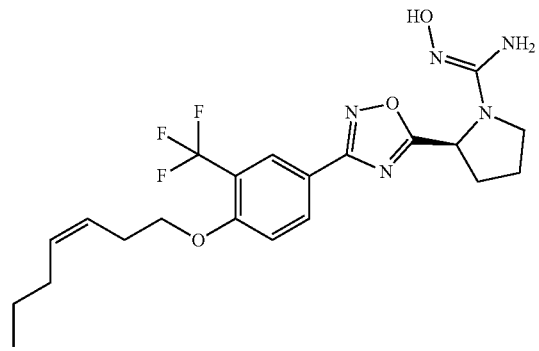 [SMILES: CCC/C=C\CCOc1ccc(-c2noc([C@@H]3CCCN3/C(N)=N/O)n2)cc1C(F)(F)F] |

85
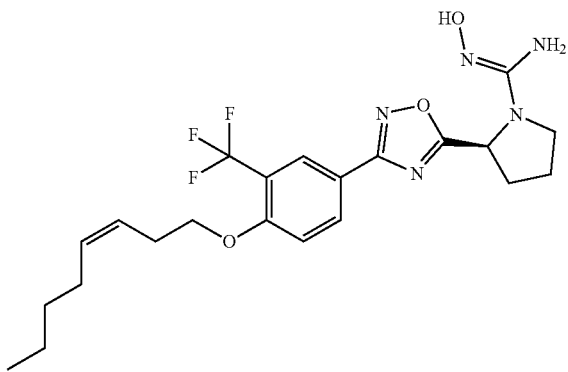 [SMILES: CCCC/C=C\CCOc1ccc(-c2noc([C@@H]3CCCN3/C(N)=N/O)n2)cc1C(F)(F)F]
86
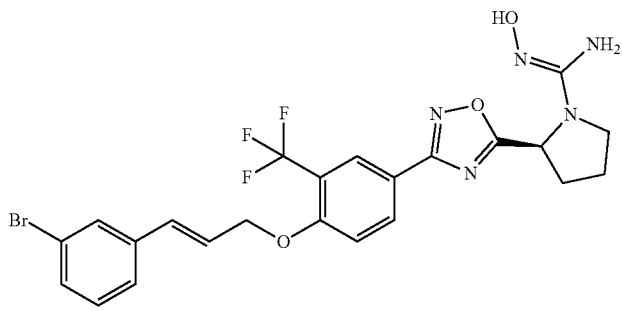 [SMILES: N/C(=N\O)N1CCC[C@H]1c1nc(-c2ccc(OC/C=C/c3cccc(Br)c3)c(C(F)(F)F)c2)no1]
87
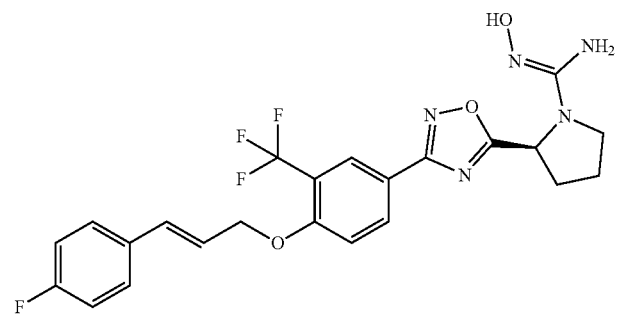 [SMILES: N/C(=N\O)N1CCC[C@H]1c1nc(-c2ccc(OC/C=C/c3ccc(F)cc3)c(C(F)(F)F)c2)no1]
88
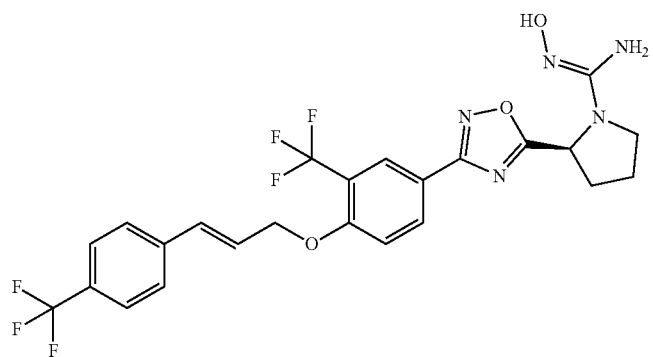 [SMILES: N/C(=N\O)N1CCC[C@H]1c1nc(-c2ccc(OC/C=C/c3ccc(C(F)(F)F)cc3)c(C(F)(F)F)c2)no1]

89
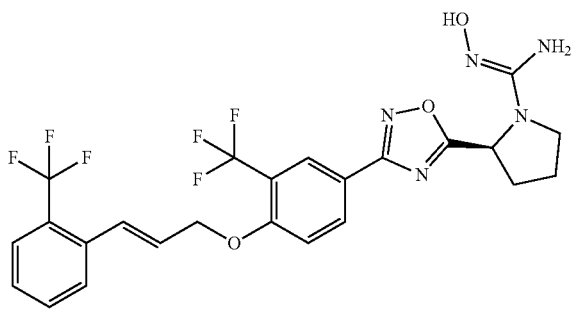 [SMILES: N/C(=N\O)N1CCC[C@H]1c1nc(-c2ccc(OC/C=C/c3ccccc3C(F)(F)F)c(C(F)(F)F)c2)no1]
90
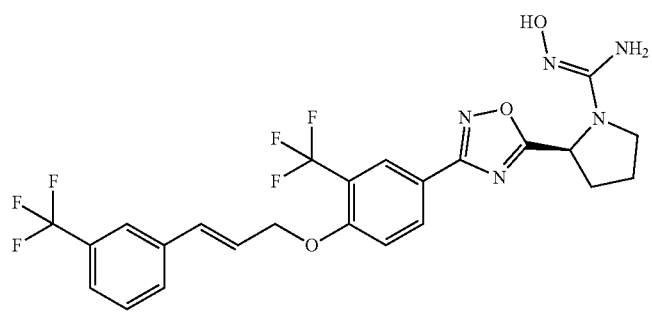 [SMILES: N/C(=N\O)N1CCC[C@H]1c1nc(-c2ccc(OC/C=C/c3cccc(C(F)(F)F)c3)c(C(F)(F)F)c2)no1]
91
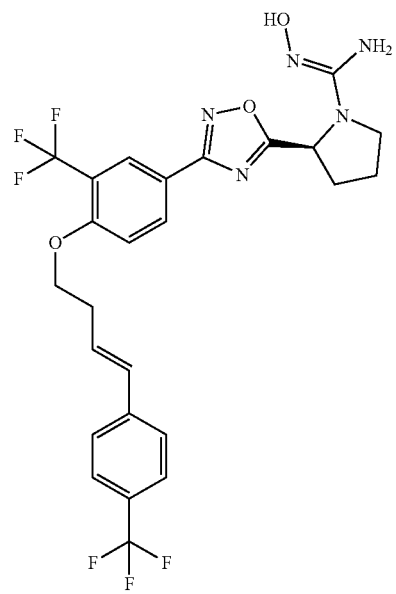 [SMILES: N/C(=N\O)N1CCC[C@H]1c1nc(-c2ccc(OCC/C=C/c3ccc(C(F)(F)F)cc3)c(C(F)(F)F)c2)no1]
92
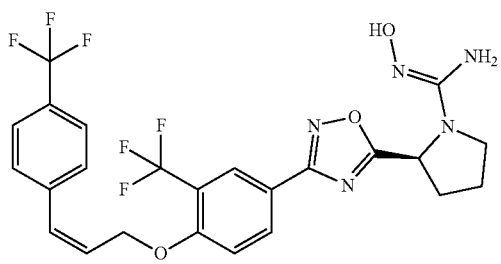 [SMILES: N/C(=N\O)N1CCC[C@H]1c1nc(-c2ccc(OC/C=C\c3ccc(C(F)(F)F)cc3)c(C(F)(F)F)c2)no1]

-continued
93
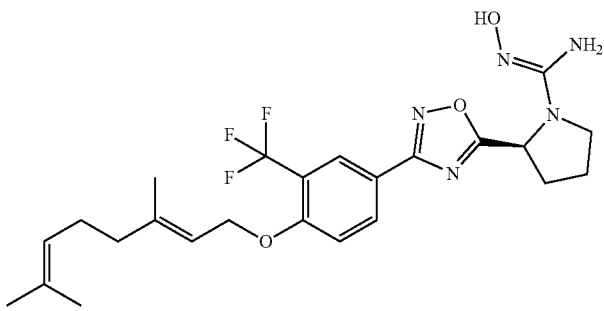 [SMILES: CC(C)=CCC/C(C)=C/COc1ccc(-c2noc([C@@H]3CCCN3/C(N)=N/O)n2)cc1C(F)(F)F]
94
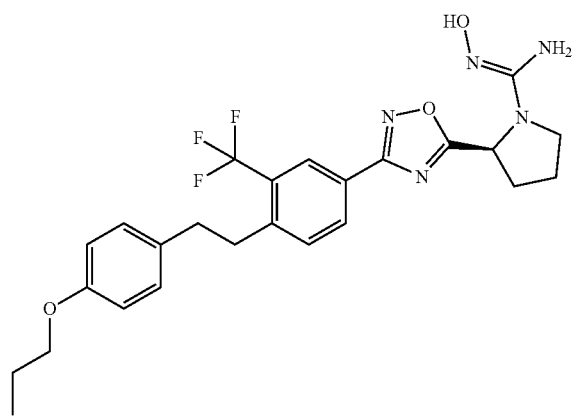 [SMILES: CCCOc1ccc(CCc2ccc(-c3noc([C@@H]4CCCN4/C(N)=N/O)n3)cc2C(F)(F)F)cc1]
95
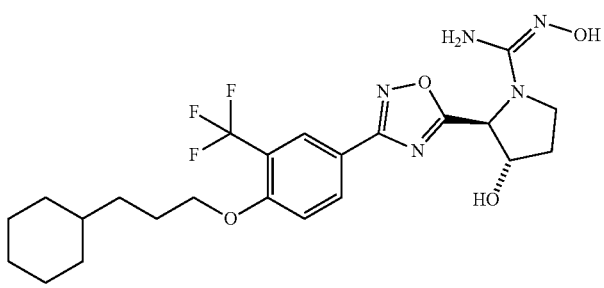 [SMILES: N/C(=N/O)N1CC[C@H](O)[C@H]1c1nc(-c2ccc(OCCCC3CCCCC3)c(C(F)(F)F)c2)no1]
96
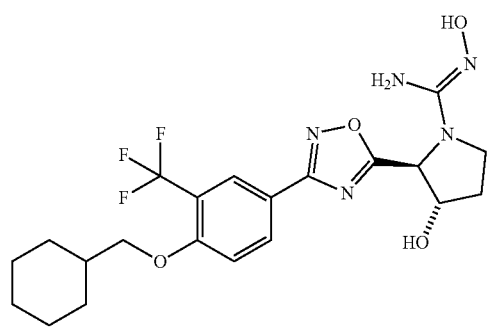 [SMILES: N/C(=N\O)N1CC[C@H](O)[C@H]1c1nc(-c2ccc(OCC3CCCCC3)c(C(F)(F)F)c2)no1]
97
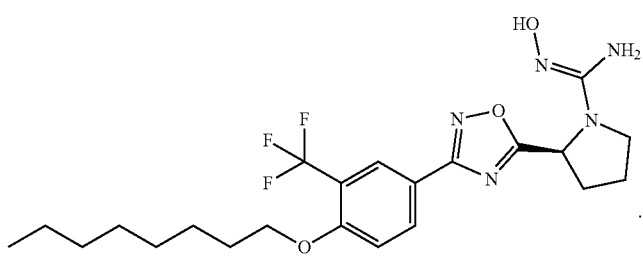 [SMILES: CCCCCCCCOc1ccc(-c2noc([C@@H]3CCCN3/C(N)=N/O)n2)cc1C(F)(F)F]

9. The method according to claim 1, wherein the disease is a fibrotic disease.

10. The method according to claim 9, wherein the fibrotic disease is pulmonary fibrosis, renal fibrosis, cardiac fibrosis, or hepatic fibrosis.

11. The method according to claim 10, wherein the fibrotic disease is renal fibrosis.

12. A method of inhibiting a sphingosine kinase, comprising contacting the sphingosine kinase with an effective amount of a compound according to formula (I)

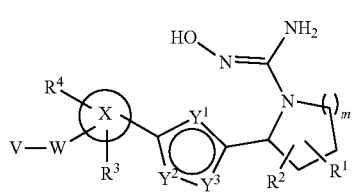

wherein
X is phenyl, indolyl, or naphthyl;
$R^1$ and $R^2$ are independently selected from the group consisting of H, OH, —$(C_1$-$C_6)$alkyl-OH, halo, $NH_2$, NOH, NHOH, and CN;
or $R^1$ and $R^2$, if bound to adjacent carbon atoms, in combination with the existing carbon-carbon bond represent a double bond between the adjacent carbon atoms;
$R^3$ and $R^4$ are independently selected from the group consisting of H, $(C_1$-$C_6)$alkyl, $(C_3$-$C_8)$cycloalkyl, $(C_1$-$C_6)$haloalkyl, CN, and halo;
wherein one of $R^3$ and $R^4$ is —$CF_3$;
m=1;
W is $CH_2$ or O;
V is selected from the group consisting of $(C_1$-$C_{10})$alkyl, $(C_2$-$C_{12})$alkenyl, —$(C_1$-$C_{10})$alkyl-$(C_6$-$C_{10})$aryl, —$(C_2$-$C_{12})$alkenyl-$(C_6$-$C_{10})$aryl, —$(C_1$-$C_{10})$alkyl-$(C_6$-$C_{10})$aryl-$(C_1$-$C_{10})$alkyl, —$(C_1$-$C_{10})$alkyl-$(C_3$-$C_8)$cycloalkyl, —$(C_1$-$C_{10})$alkyl-heterocyclyl containing from 1 to 3 ring heteroatoms selected from N, O, and S;
wherein any aryl is optionally fused to $(C_6$-$C_{10})$aryl, $(C_3$-$C_8)$cycloalkyl, or heterocyclyl containing from 1 to 3 ring heteroatoms selected from N, O, and S
wherein any alkyl, alkenyl, cycloalkyl, heterocyclyl, or aryl is optionally substituted by 1-4 substituents independently selected from the group consisting of F, Cl, Br, $(C_1$-$C_6)$alkyl, —O—$(C_1$-$C_6)$alkyl, $(C_2$-$C_6)$alkenyl, $(C_1$-$C_6)$haloalkyl, $(C_6$-$C_{10})$aryl, and CN;
$Y^1$ is N;
$Y^2$ is N and $Y^3$ is O, or $Y^2$ is O and $Y^3$ is N;
or a pharmaceutically acceptable salt thereof.

13. The method according to claim 12, wherein the sphingosine kinase is sphingosine kinase type 1 or sphingosine kinase type 2, or both.

14. The method according to claim 13, further comprising selectively inhibiting sphingosine kinase type 2 relative to sphingosine kinase type 1.

* * * * *